(12) United States Patent
Ranade et al.

(10) Patent No.: US 7,482,124 B2
(45) Date of Patent: Jan. 27, 2009

(54) METHOD OF IDENTIFYING A PPARGAMMA-AGONIST COMPOUND HAVING A DECREASED LIKELIHOOD OF INDUCING DOSE-DEPENDENT PERIPHERAL EDEMA

(75) Inventors: Koustubh Ranade, Princeton, NJ (US); Terrye Aigeldinger Delmonte, Ewing, NJ (US); William J. Geese, Doylestown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/483,290

(22) Filed: Jul. 7, 2006

(65) Prior Publication Data

US 2007/0009945 A1 Jan. 11, 2007

Related U.S. Application Data

(60) Provisional application No. 60/697,727, filed on Jul. 8, 2005, provisional application No. 60/706,171, filed on Aug. 5, 2005, provisional application No. 60/705,995, filed on Aug. 5, 2005.

(51) Int. Cl.
 *C12Q 1/68* (2006.01)
 *G01N 33/53* (2006.01)

(52) U.S. Cl. .......................... 435/6; 435/7.21

(58) Field of Classification Search ........................ None
 See application file for complete search history.

(56) References Cited

U.S. PATENT DOCUMENTS

| | | | |
|---|---|---|---|
| 4,179,337 A | 12/1979 | Davis et al. |
| 4,376,110 A | 3/1983 | David et al. |
| 4,444,887 A | 4/1984 | Hoffmann |
| 4,474,893 A | 10/1984 | Reading |
| 4,631,211 A | 12/1986 | Houghten |
| 4,676,980 A | 6/1987 | Segal et al. |
| 4,683,195 A | 7/1987 | Mullis et al. |
| 4,714,681 A | 12/1987 | Reading |
| 4,716,111 A | 12/1987 | Osband et al. |
| 4,741,900 A | 5/1988 | Alvarez et al. |
| 4,816,397 A | 3/1989 | Boss et al. |
| 4,816,567 A | 3/1989 | Cabilly et al. |
| 4,925,648 A | 5/1990 | Hansen et al. |
| 4,946,778 A | 8/1990 | Ladner et al. |
| 4,980,286 A | 12/1990 | Morgan et al. |
| 5,073,627 A | 12/1991 | Curtis et al. |
| 5,112,946 A | 5/1992 | Maione |
| 5,122,464 A | 6/1992 | Wilson et al. |
| 5,205,290 A | 4/1993 | Unger |
| 5,223,409 A | 6/1993 | Ladner et al. |
| 5,225,539 A | 7/1993 | Winter |
| 5,258,498 A | 11/1993 | Huston et al. |
| 5,314,995 A | 5/1994 | Fell, Jr. et al. |
| 5,336,603 A | 8/1994 | Capon et al. |
| 5,349,053 A | 9/1994 | Landolfi |
| 5,359,046 A | 10/1994 | Capon et al. |
| 5,403,484 A | 4/1995 | Ladner et al. |
| 5,413,923 A | 5/1995 | Kucherlapati et al. |
| 5,427,908 A | 6/1995 | Dower et al. |
| 5,441,050 A | 8/1995 | Thurston et al. |
| 5,447,851 A | 9/1995 | Beutler et al. |
| 5,474,981 A | 12/1995 | Leder et al. |
| 5,478,925 A | 12/1995 | Wallach et al. |
| 5,516,637 A | 5/1996 | Huang et al. |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |

(Continued)

FOREIGN PATENT DOCUMENTS

| | | |
|---|---|---|
| EP | 232 262 | 2/1987 |
| EP | 0 367 166 | 5/1990 |
| EP | 0 394 827 | 10/1990 |
| EP | 0 307 434 | 9/1993 |
| EP | 0 396 387 | 12/1993 |
| EP | 0 239 400 | 8/1994 |
| EP | 0 401 384 | 3/1996 |
| EP | 0 439 095 | 5/1998 |
| EP | 1 007 712 | 2/1999 |
| EP | 0 592 106 | 11/2004 |

(Continued)

OTHER PUBLICATIONS

Abali, H. et al., "Circulating and Local Bone Marrow Renin-angiotensin System in Leukemic Hematopoiesis: Preliminary Evidences", Hematology, vol. 7, No. 2, pp. 75-82 (2002).

(Continued)

*Primary Examiner*—Robert Landsman
(74) *Attorney, Agent, or Firm*—Stephen C. D'Amico

(57) ABSTRACT

The invention provides novel polynucleotides and polypeptides associated with the incidence of PPAR-agonist induced edema. The invention also provides polynucleotide fragments corresponding to the genomic and/or coding regions of these polynucleotides which comprise at least one polymorphic locus per fragment. Allele-specific primers and probes which hybridize to these regions, and/or which comprise at least one polymorphic locus are also provided. The polynucleotides, primers, and probes of the present invention are useful in phenotype correlations, medicine, and genetic analysis. Also provided are vectors, host cells, antibodies, and recombinant and synthetic methods for producing said polynucleotides and/or polypeptides. The invention further relates to diagnostic and therapeutic methods for applying these novel polynucleotides and polypeptides to the diagnosis, treatment, and/or prevention of various diseases and/or disorders, particularly PPAR-agonist induced edema or related indications. The invention further relates to screening methods for identifying agonists of PPAR proteins with decreased risk of inducing peripheral edema in patients.

17 Claims, 112 Drawing Sheets

U.S. PATENT DOCUMENTS

Figure 11:
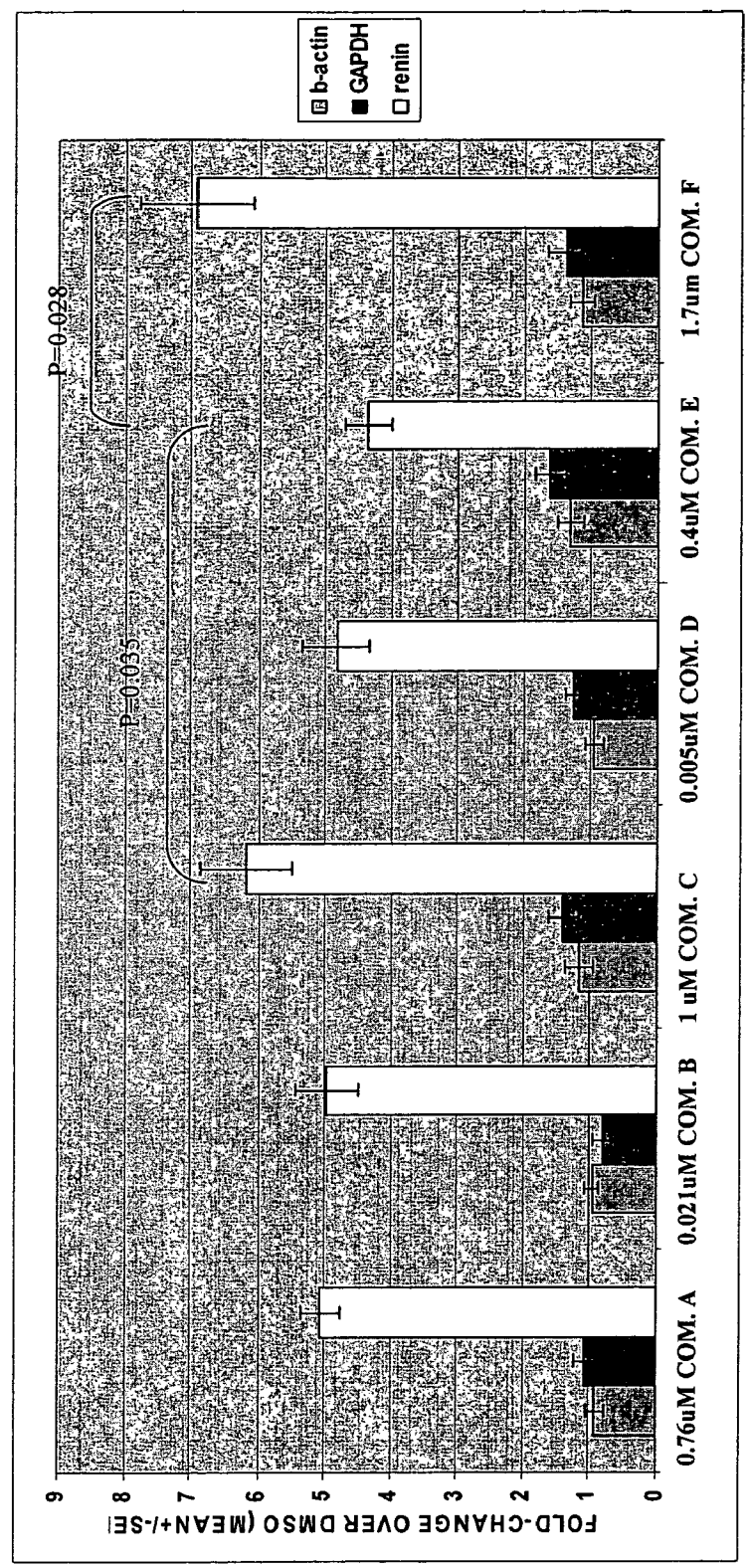

| | | | |
|---|---|---|---|
| 5,571,698 A | 11/1996 | Ladner et al. |
| 5,573,920 A | 11/1996 | Randle |
| 5,580,717 A | 12/1996 | Dower et al. |
| 5,585,089 A | 12/1996 | Queen et al. |
| 5,601,819 A | 2/1997 | Wong et al. |
| 5,622,929 A | 4/1997 | Willner et al. |
| 5,625,126 A | 4/1997 | Lonberg et al. |
| 5,633,425 A | 5/1997 | Lonberg et al. |
| 5,641,670 A | 6/1997 | Treco et al. |
| 5,658,727 A | 8/1997 | Barbas et al. |
| 5,661,016 A | 8/1997 | Lonberg et al. |
| 5,661,106 A | 8/1997 | Baumann et al. |
| 5,698,426 A | 12/1997 | Huse |
| 5,716,805 A | 2/1998 | Srinivasan et al. |
| 5,733,743 A | 3/1998 | Johnson et al. |
| 5,733,761 A | 3/1998 | Treco et al. |
| 5,750,753 A | 5/1998 | Kimae et al. |
| 5,780,225 A | 7/1998 | Wigler et al. |
| 5,807,715 A | 9/1998 | Morrison et al. |
| 5,814,318 A | 9/1998 | Lonberg et al. |
| 5,821,047 A | 10/1998 | Garrard et al. |
| 5,837,832 A | 11/1998 | Chee et al. |
| 5,856,104 A | 1/1999 | Chee et al. |
| 5,856,174 A | 1/1999 | Lipshutz et al. |
| 5,858,659 A | 1/1999 | Sapolsky et al. |
| 5,874,219 A | 2/1999 | Rava et al. |
| 5,885,793 A | 3/1999 | Griffiths et al. |
| 5,916,771 A | 6/1999 | Hori et al. |
| 5,939,598 A | 8/1999 | Kucherlapati et al. |
| 5,969,108 A | 10/1999 | McCafferty et al. |
| 6,028,066 A | 2/2000 | Unger |
| 6,414,002 B1 | 7/2002 | Cheng et al. |
| 2005/0288343 A1 | 12/2005 | Rusowicz et al. |

FOREIGN PATENT DOCUMENTS

| | | |
|---|---|---|
| EP | 0 519 596 | 2/2005 |
| WO | WO 86/05807 | 10/1986 |
| WO | WO 98/01036 | 2/1989 |
| WO | WO 89/12624 | 12/1989 |
| WO | WO 90/02809 | 3/1990 |
| WO | WO 91/00360 | 1/1991 |
| WO | WO 91/06570 | 5/1991 |
| WO | WO 91/09967 | 7/1991 |
| WO | WO 91/10737 | 7/1991 |
| WO | WO 91/10741 | 7/1991 |
| WO | WO 91/14438 | 10/1991 |
| WO | WO 92/01047 | 1/1992 |
| WO | WO 92/05793 | 4/1992 |
| WO | WO 92/08495 | 5/1992 |
| WO | WO 92/08802 | 5/1992 |
| WO | WO 92/18619 | 10/1992 |
| WO | WO 92/20373 | 11/1992 |
| WO | WO 92/22324 | 12/1992 |
| WO | WO 93/08829 | 5/1993 |
| WO | WO 93/11236 | 6/1993 |
| WO | WO 93/17715 | 9/1993 |
| WO | WO 93/21232 | 10/1993 |
| WO | WO 94/10308 | 5/1994 |
| WO | WO 94/12650 | 6/1994 |
| WO | WO 95/15982 | 6/1995 |
| WO | WO 95/20401 | 8/1995 |
| WO | WO 96/04388 | 2/1996 |
| WO | WO 96/22024 | 7/1996 |
| WO | WO 96/29411 | 9/1996 |
| WO | WO 96/33735 | 10/1996 |
| WO | WO 96/34096 | 10/1996 |
| WO | WO 98/16654 | 4/1998 |
| WO | WO 98/24893 | 6/1998 |
| WO | WO 98/46645 | 10/1998 |
| WO | WO 98/49305 | 11/1998 |
| WO | WO 98/50433 | 11/1998 |
| WO | WO 99/04813 | 2/1999 |
| WO | WO 00/22166 | 4/2000 |
| WO | WO 2004/014308 | 2/2004 |
| WO | WO 2004/035822 | 4/2004 |
| WO | WO 2004/100871 | 11/2004 |
| WO | WO 2005/089731 | 9/2005 |

OTHER PUBLICATIONS

Agapitov, A.V. et al., "Role of endothelin in cardiovascular disease", Journal of the Renin-Angiotensin-Aldosterone System, vol. 3, No. 1, pp. 1-15 (2002).

Ahmad, U. et al., "Strong Association of a Renin Intronic Dimorphism with Essential Hypertension", Hypertens. Res., vol. 28, No. 4, pp. 339-344 (2005).

Albertin, G. et al., "Endothelin-1 and adrenomedullin enhance the growth of human adrenocortical carcinoma-derived SW-13 cell line by stimulating proliferation and inhibiting apoptosis", International Journal of Molecular Medicine, vol. 15, pp. 469-474 (2005).

Alberts, G.F. et al., "Constitutive Endothelin-1 Overexpression Promotes Smooth Muscle Cell Proliferation via an External Autocrine Loop", The Journal of Biological Chemistry, vol. 269, No. 13, pp. 10112-10118 (1994).

Altschul, S.F. et al., "Basic Local Alignment Search Tool", J. Mol. Biol., vol. 215, pp. 403-410 (1990).

Ames, R.S. et al., "Conversion of murine Fabs isolated from a combinatorial phage display library to full length immunoglobulins", Journal of Immunological Methods, vol. 184, pp. 177-186 (1995).

Amiri, F. et al., "Endothelium-Restricted Overexpression of Human Endothelin-1 Causes Vascular Remodeling and Endothelial Dysfunction", Circulation, vol. 110, pp. 2233-2240 (2004).

Andersen, U.B. et al., "Left Ventricular Structure and Diastolic Function in Subjects with Two Hypertensive Parents", Blood Pressure, vol. 10, pp. 193-198 (2001).

Arenkov, P. et al., "Protein Microchips: Use for Immunoassay and Enzymatic Reactions", Analytical Biochemistry, vol. 278, pp. 123-131 (2000).

Arinami, T. et al., "Chromosomal Assignments of the Human Endothelin Family Genes: The Endothelin-1 Gene (EDN1) to 6p23-p24, the Endothelin-2 Gene (EDN2) to 1p34, and the Endothelin-3 Gene (EDN3) to 20q13.2-q13.3", Am. J. Hum. Genet., vol. 48, pp. 990-996 (1991).

Arnon, R. et al., "Monoclonal Antibodies for Immunotargeting of Drugs in Cancer Therapy", Monoclonal Antibodies and Cancer Therapy, Alan R. Liss, Inc., publ., Reisfeld, R.A. et al., eds., pp. 243-256 (1985).

Arun, C. et al., "Endothelin-1 is a novel prognostic factor in non-small cell lung cancer", The International Journal of Biological Markers, vol. 19, No. 4, pp. 262-267 (2004).

Asakura, H. et al., "Changes in Plasma Endothelin-1 After Elective Cesarean Section in Women with Preeclampsia and the Relationship to Thrombocytopenia", J. Nippon Med. Sch., vol. 70, No. 6, pp. 480-489 (2003).

Asham, E. et al., "Increased endothelin-1 in colorectal cancer and reduction of tumour growth by $ET_A$ receptor antagonism", British Journal of Cancer, vol. 85, No. 11, pp. 1759-1763 (2001).

Ashkenazi, A. et al., "Protection against endotoxic shock by a tumor necrosis factor receptor immunoadhesin", Proc. Natl. Acad. Sci. USA, vol. 88, pp. 10535-10539 (1991).

Ausubel, F.M. et al., eds., Current Protocols in Molecular Biology, vols. 1, 2, 3 and 4, John Wiley & Sons, Inc., publ., pp. 1-11 (table of contents) (2001).

Ausubel, F.M. et al., eds., Unit 10.8: "Immunoblotting and Immunodetection", Current Protocols in Molecular Biology, vol. 2, John Wiley & Sons, Inc., publ., pp. 10.8.1-10.8.21 (1997).

Ausubel, F.M. et al., eds., Unit 10.16: "Immunoprecipitation", Current Protocols in Molecular Biology, vol. 2, John Wiley & Sons, Inc., publ., pp. 10.16.1-10.16.29 (1999).

Ausubel, F.M. et al., eds., Unit 11.2: "Enzyme-Linked Immunosorbent Assays (ELISA)", Current Protocols in Molecular Biology, vol. 2, John Wiley & Sons, Inc., publ., pp. 11.2.1.-11.2.22 (1991).

Bajora, R. et al., "Brain natriuretic peptide and endothelin-1 in the pathogenesis of polyhydramnios-oligohydramnios in monochorionic twins", Am. J. Obstet. Gynecol., vol. 189, No. 1, pp. 189-194 (2003).

Barish, G.D. et al., "PPARδ: a dagger in the heart of the metabolic syndrome", The Journal of Clinical Investigation, vol. 116, No. 3, pp. 590-597 (2006).

Bartlett, R.J. et al., "In vivo targeted repair of a point mutation in the canine dystrophin gene by a chimeric RNA/DNA oligonucleotide", Nature Biotechnology, vol. 18, pp. 615-622 (2000).

Bebbington, C.R. et al., Chapter 8: "The use of vectors based on gene amplification for the expression of cloned genes in mammalian cells", DNA Cloning, vol. 3: A Practical Approach, IRL Press Limited, publ., Glover, D.M., ed., pp. 163-188 (1987).

Benatti, L. et al., "Two Preproendothelin 1 mRNAs Transcribed by Alternative Promoters", J. Clin. Invest., vol. 91, pp. 1149-1156 (1993).

Bengtsson, K. et al., "Polymorphism in the $\beta_1$-Adrenergic Receptor Gene and Hypertension", Circulation, vol. 104, pp. 187-190 (2001).

Bennett, D. et al., "Kinetic Characterization of the Interaction of Biotinylated Human Interleukin 5 with a Fc Chimera of its Receptor αSubunit and Development of an ELISA Screening Assay using Real-Time Interaction Biosensor Analysis", Journal of Molecular Recognition, vol. 8, pp. 52-58 (1995).

Berg, J.M. et al., "Lessons from Zinc-Binding Peptides", Annu. Rev. Biophys. Biomol. Struct., vol. 26, pp. 357-371 (1997).

Berger, J. et al., "Physiological and Therapeutic Roles of Peroxisome Proliferator-Activated Receptors", Diabetes Technology & Therapeutics, vol. 4, No. 2, pp. 163-174 (2002).

Better, M. et al., "*Escherichia coli* Secretion of an Active Chimeric Antibody Fragment", Science, vol. 240, pp. 1041-1043 (1988).

Bitter, G.A. et al., "Expression and Secretion Vectors for Yeast", Methods in Enzymology, vol. 153, pp. 516-544 (1987).

Bloch, K.D. et al., "Structural Organization and Chromosomal Assignment of the Gene Encoding Endothelin", The Journal of Biological Chemistry, vol. 264, No. 18, pp. 10851-10857 (1989).

Boerner, P. et al., "Production of Antigen-Specific Human Monoclonal Antibodies from In Vitro-Primed Human Splenocytes", The Journal of Immunology, vol. 147, No. 1, pp. 86-95 (1991).

Brewster, U.C. et al., "The Renin-Angiotensin-Aldosterone System: Cardiorenal Effects and Implications for Renal and Cardiovascular Disease States", The American Journal of the Medical Science, vol. 326, No. 1, pp. 15-24 (2003).

Brinkmann, U. et al., "Phage display of disulfide-stabilized Fv fragments", Journal of Immunological Methods, vol. 182, pp. 41-50 (1995).

Brodeur, B.R. et al., Chapter 4: "Mouse-Human Myeloma Partners for the Production of Heterohybridomas", Monoclonal Antibody Production Techniques and Applications, Marcel Dekker, Inc., publ., Schook, L.B., ed., pp. 51-63 (1987).

Bruno, C.M. et al., "Pathophysiology of endothelin and medical emergencies", Panminerva Med., vol. 45, No. 2, pp. 151-154 (2003).

Bruno, C.M. et al., "Plasma endothelin-1 levels and albumin excretion rate in normotensive, microalbuminuric type 2 diabetic patients", Journal of Biological Regulators and Homeostatic Agents, vol. 16, pp. 114-117 (2002).

Buchwald, H. et al., "Long-term, continuous intravenous heparin administration by an implantable infusion pump in ambulatory patients with recurrent venous thrombosis", Surgery, vol. 88, No. 4, pp. 507-516 (1980).

Bullido, M.J. et al., "Polymorphism in genes involved in adrenergic signaling associated with Alzheimer's", Neurobiology of Aging, vol. 25, pp. 853-859 (2004).

Burchiel, S.W. et al., Chapter 13: "Immunopharmacokinetics of Radiolabeled Antibodies and Their Fragments", Tumor Imaging: The Radioimmunochemical Detection of Cancer, Masson Publishing USA, Inc., publ., Burchiel, S.W. et al., eds, pp. 125-139 (1982).

Burt, D.W. et al., "Identification of Negative and Positive Regulatory Elements in the Human Renin Gene", The Journal of Biological Chemistry, vol. 264, No. 13, pp. 7357-7362 (1989).

Burton, D.R. et al., "Human Antibodies from Combinatorial Libraries", Advances in Immunology, vol. 57, pp. 191-280 (1994).

Cambiaggi, C. et al., "Gene Expression of Endothelin-1 (ET-1) and Release of Mature Peptide by Activated Human Neutrophils", Cytokine, vol. 14, No. 4, pp. 230-233 (2001).

Camsari, A. et al., "Endothelin-1 and Nitric Oxide Concentrations and Their Response to Exercise in Patients With Slow Coronary Flow", Circulation Journal, vol. 67, pp. 1022-1028 (2003).

Casares, M.T.G. et al., "Renin Expression in Hematological in Hematological Malignancies and its Role in the Regulation of Hematopoiesis", Leukemia and Lymphoma, vol. 43, No. 12, pp. 2377-2381 (2002).

Casey, M.L. et al., "Endothelin-1 Gene Expression and Regulation of Endothelin mRNA and Protein Biosynthesis in Avascular Human Amnion", The Journal of Biological Chemistry, vol. 266, No. 9, pp. 5762-5768 (1991).

Castellano, M. et al., "The Cardiac β-Adrenoceptor-Mediated Signaling Pathway and Its Alterations in Hypertensive Heart Disease", Hypertension, vol. 29, No. 3, pp. 715-722 (1997).

Cauduro, R.L. et al., "Cyclosporine Increases Endothelin-1 Plasma Levels in Renal Transplant Recipients", Transplantation Proceedings, vol. 36, pp. 880-881 (2004).

Charloux, A. et al., "Circulating endothelin parallels arterial blood pressure during sleep in healthy subjects", Regulatory Peptides, vol. 119, pp. 133-138 (2004).

Chen, H.H. et al., "Angiotensin II $AT_1$ receptor antagonism prevents detrimental renal actions of acute diuretic therapy in human heart failure", Am. J. Physiol. Renal Physiol., vol. 284, pp. F1115-F1119 (2003).

Chen, M.-C. et al., "Increased Circulating Endothelin-1 in Rheumatic Mitral Stenosis: Irrelevance to Left Atrial and Pulmonary Artery Pressures", Chest, vol. 125, No. 2, pp. 390-396 (2004).

Chen, X. et al., "Fluorescence Polarization in Homogeneous Nucleic Acid Analysis", Genome Research, vol. 9, pp. 492-498 (1999).

Cheng, C.-M. et al., "Crucial Role of Extracellular Signal-Regulated Kinase Pathway in Reactive Oxygen Species-Mediated Endothelin-1 Gene Expression Induced by Endothelin-1 in Rat Cardiac Fibroblasts", Molecular Pharmacology, vol. 63, No. 5, pp. 1002-1011 (2003).

Chow, M. et al., "Synthetic peptides from four separate regions of the poliovirus type 1 capsid protein VP1 induce neutralizing antibodies", Proc. Natl. Acad. Sci. USA, vol. 82, pp. 910-914 (1985).

Chruscinski, A. et al., "Differential Distribution of β-Adrenergic Receptor Subtypes in Blood Vessels of Knockout Mice Lacking $\beta_1$- or $\beta_2$-Adrenergic Receptors", Molecular Pharmacology, vol. 60, No. 5, pp. 955-962 (2001).

Chun, T.-H. et al., "Modification of GATA-2 Transcriptional Activity in Endothelial Cells by the SUMO E3 Ligase PIASy", Circulation Research, vol. 92, pp. 1201-1208 (2003).

Clark, A.G., "Inference of Haplotypes from PCR-amplified Samples of Diploid Populations", Mol. Biol. Evol., vol. 7, No. 2, pp. 111-122 (1990).

Clark, A.G. et al., "Haplotype Structure and Population Genetic Inferences from Nucleotide-Sequence Variation in Human Lipoprotein Lipase", Am. J. Hum. Genet., vol. 63, pp. 595-612 (1998).

Cockett, M.I. et al., "High Level Expression of Tissue Inhibitor of Metalloproteinases in Chinese Hamster Ovary Cells Using Glutamine Synthetase Gene Amplification", Bio/Technology, vol. 8, pp. 662-667 (1990).

Colbére-Gerapin, F. et al., "A New Dominant Hybrid Selective Marker for Higher Eukaryotic Cells", J. Mol. Biol., vol. 150, pp. 1-14 (1981).

Cole, S.P.C. et al., "The EBV-Hybridoma Techniques and Its Application to Human Lung Cancer", Monoclonal Antibodies and Cancer Therapy, Alan R. Liss, Inc., publ., Reisfeld, R.A. et al., eds., pp. 77-96 (1985).

Cormack, B., Unit 8.5: "Directed Mutagenesis Using the Polymerase Chain Reaction", Current Protocols in Molecular Biology, vol. 1, Suppl. 37, John Wiley & Sons, Inc., publ. Ausubel, F.M. et al., eds., pp. 8.5.1-8.5.10 (1997).

Costa, C. et al., "Endothelin-1 Plasma Levels in Cyclosporine-Treated Stable Renal Transplant Patients", Transplantation Proceedings, vol. 34, pp. 487-488 (2002).

Cote, R.J. et al., "Generation of human monoclonal antibodies reactive with cellular antigens", Proc. Natl. Acad. Sci. USA, vol. 80, pp. 2026-2030 (1983).

Creighton, T.E., Proteins: Structures and Molecular Properties, Second Edition, W.H. Freeman and Company, publ., pp. v-x (table of contents) (1993).

Crouse, G.F. et al., "Expression and Amplification of Engineered Mouse Dihydrofolate Reductase Minigenes", Molecular and Cellular Biology, vol. 3, No. 2, pp. 257-266 (1983).

Danser, A.H.J. et al., "Prorenin Uptake in the Heart: a Prerequisite for Local Angiotensin Generation?", J. Mol. Cell Cardiol., vol. 34, pp. 1463-1472 (2002).

David, G.S. et al., "Protein Iodination with Solid State Lactoperoxidase", Biochemistry, vol. 13, No. 5, pp. 1014-1021 (1974).

Davis, L.G. et al., Basic Methods in Molecular Biology, Elsevier Science Publishing Co., Inc., publ., pp. v-viii (table of contents) (1986).

De Groote, P. et al., "Association between bata-1 and beta-2 adrenergic receptor gene polymorphisms and the response to beta-blockade in patients with stable congestive heart failure", Pharmacogenetics and Genomics, vol. 15, No. 3, pp. 137-142 (2005).

Delerive, P. et al., "Peroxisome Proliferator-Activated Receptor Activators Inhibit Thrombin-Induced Endothelin-1 Production in Human Vascular Endothelial Cells by Inhibiting the Activator Protein-1 Signaling Pathway", Circulation Research, vol. 85, pp. 394-402 (1999).

Deutscher, M.P., ed., Methods in Enzymology, vol. 182, Academic Press, Inc., publ., pp. v-viii (table of contents) (1990).

Dhanaraj, V. et al., "X-ray analyses of peptide-inhibitor complexes define the structural basis of specificity for human and mouse renins", Nature, vol. 357, pp. 466-472 (1992).

Di Paolo, S. et al., "Increased placental expression of tissue factor is associated with abnormal uterine and umbilical Doppler waveforms in severe preeclampsia with fetal growth restriction", J. Nephrol., vol. 16, pp. 650-657 (2003).

Didier, N. et al., "HIV-1-induced production of endothelin-1 in an in vitro model of the human blood-brain barrier", NeuroReport, vol. 13, No. 9, pp. 1179-1183 (2002).

Diep, Q.N. et al., "Structure, Endothelial Function, Cell Growth, and Inflammation in Blood Vessels of Angiotensin II-Infused Rats: Role of Peroxisome Proliferator-Activated Receptor-$\gamma$", Circulation, vol. 105, pp. 2296-2302 (2002).

Ding, K.-H. et al., "Glucose-dependent insulinotropic peptide stimulates thymidine incorporation in endothelial cells: role of endothelin-1", Am. J. Physiol. Endocrinol. Metab., vol. 285, pp. E390-E396 (2003).

Dionne, I.J. et al., "Association between obesity and a polymorphism in the $\beta_1$-adrenoceptor gene (Gly389Arg ADRB1) in Caucasian women", International Journal of Obesity, vol. 26, pp. 633-639 (2002).

Dong, Y. et al., "Endothelin-1 Gene and Progression of Blood Pressure and Left Ventricular Mass: Longitudinal Findings in Youth", Hypertension, vol. 44, pp. 884-890 (2004).

Dosanjh, A. et al., "Endothelin-1 (ET-1) Decreases Human Bronchial Epithelial Cell Migration and Proliferation: Implications for Airway Remodeling in Asthma", Journal of Asthma, vol. 40, No. 8, pp. 883-886 (2003).

Douglas, M.L. et al., "Endothelin Axis Expression in Markedly Different in the Two Main Subtypes of Renal Cell Carcinoma", Cancer, vol. 100, No. 10, pp. 2118-2124 (2004).

Dracopoli, N.C. et al., eds., Chapter 12: "Vectors for Gene Therapy", Current Protocols in Human Genetics, vol. 3, John Wiley & Sons, Inc., pp. 12.0.1-12.12.15 (1999).

Dracopoli, N.C. et al., eds., Chapter 13: "Delivery Systems for Gene Therapy", Current Protocols in Human Genetics, vol. 3, John Wiley & Sons, Inc., pp. 13.0.1-13.10.7 (2000).

Dunigan, C.D. et al., "Complexity of Agonist- and Cyclic AMP-Mediated Downregulation of the Human $\beta_1$-Adrenergic Receptor: Role of Internalization, Degradation, and mRNA Destabilization", Biochemistry, vol. 41, No. 25, pp. 8019-8030 (2002).

During, M.J. et al., "Controlled Release of Dopamine from a Polymeric Brain Implant: In Vivo Characterization", Annals of Neurology, vol. 25, No. 4, pp. 351-356 (1989).

Dzimiri, N., "Regulation of $\beta$-Adrenoceptor Signaling in Cardiac Function and Disease", Pharmacological Reviews, vol. 51, No. 3, pp. 465-501 (1999).

Eberle, J. et al., "Edothelin-1 Decreases Basic Apoptotic Rates in Human Melanoma Cell Lines", The Journal of Investigative Dermatology, vol. 119, No. 3, pp. 549-555 (2002).

Egholm, E. et al., "PNA hybridizes to complementary oligonucleotides obeying the Watson-Crick hydrogen-bonding rules", Nature, vol. 365, pp. 566-568 (1993).

El-Gamal, Y. et al., "Plasma endothelin-1 immunoreactivity in asthmatic children", Annals of Allergy, Asthma & Immunology, vol. 88, pp. 370-373 (2002).

Elies, R. et al., "Structural and Functional Analysis of the B Cell Epitopes Recognized by Anti-Receptor Autoantibodies in Patients with Chagas' Disease", The Journal of Immunology, vol. 157, pp. 4203-4211 (1996).

Ellis, S.B. et al., "Isolation of Alcohol Oxidase and Two Other Methanol Regulatable Genes from the Yeast Pichia pastoris", Molecular and Cellular Biology, vol. 5, No. 5, pp. 1111-1121 (1985).

El-Sharkawy, I.M.A. et al., "Serum Levels of Endothelin-1 (ET-1), Interleukin-2 (IL-2) and Amino-Terminal Propeptide Type III Procollagen (PIII NP) in Patients with Acute and Chronic Filariasis", Journal of the Egyptian Society of Parasitology, vol. 31, No. 1, pp. 169-176 (2001).

Erdem, M. et al., "Immunohistochemical Localization of Endothelin-1 in Human Placenta from Normal and Growth-Restricted Pregnancies", Pediatric and Developmental Pathology, vol. 6, pp. 307-313 (2003).

Ergul, S. et al., "Vasoactive Factors in Sickle Cell Disease: In Vitro Evidence for Endothelin-1-Mediated Vasoconstriction", American Journal of Hematology, vol. 76, pp. 245-251 (2004).

Erkan, E. et al., "Role of Nitric Oxide, Endothelin-1, and Inflammatory Cytokines in Blood Pressure Regulation in Hemodialysis Patients", American Journal of Kidney Diseases, vol. 40, No. 1, pp. 76-81 (2002).

Erlich, H.A., ed., PCR Tecnology: Principles and Applications for DNA Amplification, Stockton Press, publ., pp. ix-x (table of contents) (1989).

Erlich, H.A. et al., "Recent Advances in the Polymerase Chain Reaction", Science, vol. 252, pp. 1643-1651 (1991).

Evans, J.J. et al., "Effects of endothelin-1 on release of adrenomedullin and C-type natriuretic peptide from individual human vascular endothelial cells", Journal of Endocrinology, vol. 175, pp. 225-232 (2002).

Excoffier, L. et al., "Maximum-Likelihood Estimation of Molecular Haplotype Frequencies in a Diploid Population", Mol. Biol. Evol., vol. 12, No. 5, pp. 921-927 (1995).

Fahimi-Vahid, M. et al., "Distinct Signaling Pathways Mediate Cardiomyocyte Phospholipase D Stimulation by Endothelin-1 and Thrombin", J. Mol. Cell Cardiol., vol. 34, pp. 441-453 (2002).

Fallin, D. et al., "Accuracy of Haplotype Frequency Estimation for Biallelic Loci, via the Expectation-Maximization Algorithm for Unphased Diploid Genotype Data", Am. J. Hum. Genet., vol. 67, pp. 947-959 (2000).

Fell, H.P. et al., "Genetic Construction and Characterization of a Fusion Protein Consisting of a Chimeric F(ab') with Specificity for Carcinomas and Human IL-2", The Journal of Immunology, vol. 146, No. 7, pp. 2446-2452 (1991).

Ferreé, "The Biology of Peroxisome Proliferator-Activated Receptors: Relationship with Lipid Metabolism and Insulin Sensitivity", Diabetes, vol. 53, Suppl. 1, pp. S43-S50 (2004).

Fishwild, D.M. et al., "High-avidity human IgGκ monoclonal antibodies from a novel strain of minilocus trasgenic mice", Nature Biotechnology, vol. 14, pp. 845-851 (1996).

Foecking, M.K. et al., "Powerful and versatile enhancer-promoter unit for mammalian expression vectors", Gene, vol. 45, pp. 101-105 (1986).

Forse, R.A. et al., "The Effect of Escherichia coli Endotoxin on the Adrenergic Control of Lipolysis in the Human Adipocyte", Journal of Surgical Research, vol. 46, No. 1, pp. 41-48 (1989).

Foster, N. et al., "Lysosomal traffic of liganded endothelin B receptor", Biochimica et Biophysica Acta, vol. 1642, pp. 45-52 (2003).

Fountoulakis, M. et al., "Interferon γ Receptor Extracellular Domain Expressed as IgG Fusion Protein in Chinese Hamster Ovary Cells", The Journal of Biological Chemistry, vol. 270, No. 8, pp. 3958-3964 (1995).

Francis, M.J. et al., "Immunological Priming with Synthetic Peptides of Foot-and-Mouth Disease Virus", J. Gen. Virol., vol. 66, pp. 2347-2354 (1985).

Frielle, T. et al., "Cloning of the cDNA for the human $\beta_1$-adrenergic receptor", Proc. Natl. Acad. Sci. USA, vol. 84, pp. 7920-7924 (1987).

Frielle, T. et al., "Human $\beta_1$- and $\beta_2$-adrenergic receptors: structurally and functionally related receptors derived from distinct genes", Trends in Neurosciences, vol. 11, No. 7, pp. 321-324 (1988).

Fuchs, S. et al., "Functionality of two new polymorphisms in the human renin gene enhancer region", Journal of Hypertension, vol. 20, No. 12, pp. 2391-2398 (2002).

Fuchs, S. et al., "Implication of Ref-1 in the repression of renin gene transcription by intracellular calcium", Journal of Hypertension, vol. 21, No. 2, pp. 327-335 (2003).

Fuchsjäger-Mayrl, G. et al., "Ocular hyperperfusion following onset of intensified insulin therapy is inversely correlated with plasma endothelin-1 in Type I diabetes", Diabetologia, vol. 45, pp. 883-889 (2002).

Fukamizu, A. et al., "Human renin gene of renin-secreting tumor", Gene, vol. 49, pp. 139-145 (1986).

Fukunaga, Y. et al., "Thiazolidinediones, peroxisome proliferator-activated receptor γ agonists, regulate endothelial cell growth and secretion of vasoactive peptides", Atherosclerosis, vol. 158, pp. 113-119 (2001).

Fullerton, S.M. et al., "Apolipoprotein E Variation at the Sequence Haplotype Level: Implications for the Origin and Maintenance of a Major Human Polymorphism", Am. J. Hum. Genet., vol. 67, pp. 881-900 (2000).

Funalot, B. et al., "Genes encoding endothelin-converting enzyme-1 and endothelin-1 interact to influence blood pressure in women: The EVA study", Journal of Hypertension, vol. 22, No. 4, pp. 739-743 (2004).

Galindo-Fraga, A. et al., "Elevation of Plasmatic Endothelin in Patients with Heart Failure", Archives of Medical Research, vol. 34, pp. 367-372 (2003).

Gao, J. et al., "Changes in the Protein Expression of Yeast as a Function of Carbon Source," Journal of Proteome Research, vol. 2, No. 6, pp. 643-649 (2003).

Gao, J. et al., "Identification of in vitro protein biomarkers of idiosyncratic liver toxicity", Toxicology in Vitro, vol. 18, pp. 533-541 (2004).

Gardner, L.A. et al., "Role of the Cyclic AMP-dependent Protein Kinase in Homologous Resensitization of the $\beta_1$-Adrenergic Receptor", The Journal of Biological Chemistry, vol. 279, No. 20, pp. 21135-21143 (2004).

Gavi, S. et al., "The 15-Amino Acid Motif of the C Terminus of the $\beta_2$-Adrenergic Receptor is Sufficient to Confer Insulin-Stimulated Counterregulation to the $\beta_1$-Adrenergic Receptor", Endocrinology, vol. 146, No. 1, pp. 450-457 (2005).

Gentz, R. et al., "Bioassay for the trans-activation using purified human immunodeficiency virus tat-encoded protein: Trans-activation requires mRNA synthesis", Proc. Natl. Acad. Sci. USA, vol. 86, pp. 821-824 (1989).

Germain, A.M. et al., "Endothelin receptor mRNAs in human fetal membranes, chorionic vessels, and decidua parietalis", Molecular and Cellular Endocrinology, vol. 132, pp. 161-168 (1997).

Germain, S. et al., "Dissection of silencer elements in first intron controlling the human renin gene", Journal of Hypertension, vol. 17, No. 7, pp. 899-905 (1999).

Germain, S. et al., "New Elements in Human Renin Promoter Involved in Cell-Specific Expression", Clinical and Experimental Pharmacology and Physiology, vol. 28, pp. 1056-1059 (2001).

Germain, S. et al., "Regulation of human renin secretion and gene transcription in Calu-6 cells", FEBS Letters, vol. 407, pp. 177-183 (1997).

Geysen, H.M. et al., "Use of peptide synthesis to probe viral antigens for epitopes to a resolution of a single amino acid", Proc. Natl. Acad. Sci. USA, vol. 81, pp. 3998-4002 (1984).

Giaid, A. et al., "Endothelin 1, an endothelium-derived peptide, is expressed in neurons of the human spinal cord and dorsal root ganglia", Proc. Natl. Acad. Sci. USA, vol. 86, pp. 7634-7638 (1989).

Giannessi, D. et al., "The Role of Endothelins and Their Receptors in Heart Failure", Pharmacological Research, vol. 43, No. 2, pp. 111-126 (2001).

Gillies, S.D. et al., "Antibody-targeted interleukin 2 stimulates T-cell killing of autologous tumor cells", Proc. Natl. Acad. Sci. USA, vol. 89, pp. 1428-1432 (1992).

Gillies, S.D. et al., "High-level expression of chimeric antibodies using adapted cDNA variable region cassettes", Journal of Immunological Methods, vol. 125, pp. 191-202 (1989).

Goding, J.W., Chapter 3: "Production of Monoclonal Antibodies", Monoclonal Antibodies: Principles and Practice, Second Edition, Academic Press Limited, publ., pp. 59-103 (1986).

Goldspiel, B.R. et al., "Human gene therapy", Clinical Pharmacy, vol. 12, pp. 488-505 (1993).

Goodfriend, T.L. et al., "Angiotensin Receptors and Their Antagonists", The New England Journal of Medicine, vol. 334, No. 25, pp. 1649-1654 (1996).

Goodson, J.M., Chapter 6: "Dental Applications", Medical Applications of Controlled Release, vol. II: Applications and Evaluation, CRC Press, Inc., publ., Langer, R.S. et al., eds., pp. 115-138 (1984).

Gordon, D. et al., "Consed: A Graphical Tool for Sequence Finishing", Genome Research, vol. 8, pp. 195-202 (1998).

Greenspan, N.S. et al., "Idiotypes: structure and immunogenicity", The FASEB Journal, vol. 7, pp. 437-444 (1993).

Grubbs, A.L. et al., "Saphenous Vein Endothelin System Expression and Activity in African American Patients", Arterioscler. Thromb. Vasc. Biol., vol. 22, pp. 1122-1127 (2002).

Guan, Y. et al., "Thiazolidinediones expand body fluid volume through PPARγ stimulation of ENaC-mediated renal salt absorption", Nature Medicine, vol. 11, No. 8, pp. 861-866 (2005).

Guruli, G. et al., "Function and survival of dendritic cells depend on endothelin-1 and endothelin receptor autocrine loops", Blood, vol. 104, No. 7, pp. 2107-2115 (2004).

Gusella, J.F., "DNA Polymorphism and Human Disease", Ann. Rev. Biochem., vol. 55, pp. 831-854 (1986).

Hafizi, S. et al., "Profibrotic Effects of Endothelin-1 via the $ET_A$ Receptor in Cultured Human Cardiac Fibroblasts", Cellular Physiology and Biochemistry, vol. 14, pp. 285-292 (2004).

Hämmerling, G.J. et al., eds., "Production of Antibody-Producing Hybridomas in the Rodent Systems", Monoclonal Antibodies and T-Cell Hybridomas: Perspectives and technical advances, Elsevier/North-Holland Biomedical Press, publ., pp. 563-587 (1981).

Hansen, L. et al., "The Pro12Ala Variant of the PPARG Gene is a Risk Factor for Peroxisome Proliferator-Activated Receptor-γ/α Agonist-Induced Edema in Type 2 Diabetic Patients", The Journal of Clinical Endocrinology & Metabolism, vol. 91, No. 9, pp. 3446-3450 (2006).

Hardman, J.A. et al., "Primary Structure of the Human Renin Gene", DNA, vol. 3, No. 6, pp. 457-468 (1984).

Harlow, E. et al., Antibodies: A Laboratory Manual, Cold Spring Harbor Laboratory, publ., pp. iii-ix (table of contents) (1988).

Harrity, T. et al., "Muraglitazar, a Novel Dual (α/γ) Peroxisome Proliferator-Activated Receptor Activator, Improves Diabetes and Other Metabolic Abnormalities and Preseves β-Cell Function in db/db Mice", Diabetes, vol. 55, pp. 240-248 (2006).

He, J. et al., "Glycosylation of $\beta_1$-adrenergic receptors regulates receptor surface expression and dimerization", Biochemical and Biophysical Research Communications, vol. 297, pp. 565-572 (2002).

Hegarty, B.D. et al., "Peroxisome Proliferator-Activated Receptor (PPAR) Activation Induces Tissue-Specific Effects on Fatty Acid Uptake and Metabolism in Vivo—A Study Using the Novel PPARα/γ Agonist Tesaglitazar", Endocrinology, vol. 145, No. 7, pp. 3158-3164 (2004).

Hellström, K.E. et al., Chapter 15: "Antibodies for Drug Delivery", Controlled Drug Delivery: Fundamentals and Applications, Second Edition, Marcel Dekker, Inc., publ., Robinson, J.R. et al., eds., pp. 623-653 (1987).

Hewage, C.M. et al., "Design of $ET_B$ receptor agonists: NMR spectroscopic and conformational studies of ET7-21[Leu7, Aib11, Cys(Acm)15]", Protein Engineering, vol. 15, No. 3, pp. 161-167 (2002).

Higgins, D.R. et al., eds., Methods in Molecular Biology: *Pichia* Protocols, Humana Press Inc., publ., pp. vii-viii (table of contents) (1998).

Hillier, C. et al., "Effect of adrenomedullin on the production of endothelin-1 and on its vasoconstrictor action in resistance arteries: evidence for a receptor-specific functional interaction in patients with heart failure", Clinical Science, vol. 101, pp. 45-51 (2001).

Hobart, P.M. et al., "Human renin gene: Structure and sequence analysis", Proc. Natl. Acad. Sci. USA, vol. 81, pp. 5026-5030 (1984).

Hoehe, M.R. et al., "Genetic mapping of adrenergic receptor genes in humans", J. Mol. Med., vol. 73, pp. 299-306 (1995).

Hoh, F. et al., "High-Resolution X-ray Structure of the Unexpectedly Stable Dimer of the $[Lys^{(-2)}-Arg^{(-1)}-des(17-21)]$Endothelin-1 Peptide", Biochemistry, vol. 43, No. 48, pp. 15154-15168 (2004).

Hollenberg, N.K., "Considerations for Management of Fluid Dynamic Issues Associated with Thiazolidinediones", The American Journal of Medicine, vol. 115, No. 8A, pp. 111S-115S (2003).

Holmer, S.R. et al., "Beta-adrenergic stimulation of renin expression in vivo", Journal of Hypertension, vol. 15, No. 12, Pt. 1, pp. 1471-1479 (1997).

Hoppe, H.-J. et al., "A parallel three stranded α-helical bundle at the nucleation site of collagen triple-helix formation", FEBS Letters, vol. 344, pp. 191-195 (1994).

Hosmer, D.W. et al., Applied Logistic Regression, Second Edition, John Wiley & Sons, Inc., publ., pp. v-vii (table of contents) (2000).

Hotta, J. et al., "Polymorphisms of Renin-Angiotensin System Genes with High-Altitude Pulmonary Edema in Japanese Subjects", Chest, vol. 126, No. 3, pp. 825-830 (2004).

Houghten, R.A., "General method for the rapid solid-phase synthesis of large numbers of peptides: Specificity of antigen-antibody interaction at the level of individual amino acids", Proc. Natl. Acad. Sci. USA, vol. 82, pp. 5131-5135 (1985).

Howard III, M.A. et al., "Intracerebral drug delivery in rats with lesion-induced memory deficits", J. Neurosurg., vol. 71, pp. 105-112 (1989).

Hu, L.A. et al., "$β_1$-Adrenergic Receptor Association with PSD-95", The Journal of Biological Chemistry, vol. 275, No. 49, pp. 38659-38666 (2000).

Hunkapiller, M. et al., "A microchemical facility for the analysis and synthesis of genes and proteins", Nature, vol. 310, pp. 105-111 (1984).

Hunter, W.M. et al., "Preparation of Iodine-131 Labelled Human Growth Hormone of High Specific Activity", Nature, vol. 194, pp. 495-496 (1962).

Huston, J.S. et al., "Protein Engineering of Single-Chain Fv Analogs and Fusion Proteins", Methods in Enzymology, vol. 203, pp. 46-88 (1991).

Iglarz, M. et al., "Effect of Peroxisome Proliferator-Activated Receptor-α and -γ Activators on Vascular Remodeling in Endothelin-Dependent Hypertension", Arterioscler. Thromb. Vasc. Biol., vol. 23, pp. 45-51 (2003).

Imai, T. et al., "Cloning and sequence analysis of cDNA for human renin precursor", Proc. Natl. Acad. Sci. USA, vol. 80, pp. 7405-7409 (1983).

Imokawa, G. et al., "Endothelins Secreted from Human Keratinocytes are Intrinsic Mitogens for Human Melanocytes", The Journal of Biological Chemistry, vol. 267, No. 34, pp. 24675-24680 (1992).

Innis, M.A. et al., eds., PCR Protocols: A Guide to Methods and Applications, Academic Press, Inc., publ., pp. v-x (table of contents) (1990).

Inoue, A. et al., "The Human Preproendothelin-1 Gene", The Journal of Biological Chemistry, vol. 264, No. 25, pp. 14954-14959 (1989).

Inoue, K. et al., "Further Evidence for Endothelin as an Important Mediator of Pancreatic and Intestinal Ischemia in Severe Acute Pancreatitis", Pancreas, vol. 26, No. 3, pp. 218-223 (2003).

Inouye, S. et al., "Up-promoter mutations in the *lpp* gene of *Escherichia coli*", Nucleic Acids Research, vol. 13, No. 9, pp. 3101-3110 (1985).

Itoh, Y. et al., "Cloning and sequence analysis of cDNA encoding the presursor of a human endothelium-derived vasoconstrictor peptide, endothelin: identity of human and porcine endothelin", FEBS Letters, vol. 231, No. 2, pp. 440-444 (1988).

Iwai, C. et al., "Suppressive Effect of the Gly389 Allele of the $β_1$-Adrenergic Receptor Gene on the Occurrence of Ventricular Tachycardia in Dilated Cardiomyopathy", Circulation Journal, vol. 66, pp. 723-728 (2002).

Izzo, Jr., J.L. et al., eds., Hypertension Primer: The Essentials of High Blood Pressure, American Heart Association, publ., pp. v-viii (table of contents) (1993).

Jakoby, W.B., ed., Methods in Enzymology, vol. 104, Academic Press, Inc., publ., pp. v-vii (table of contents) (1984).

Jalkanen, M. et al., "Cell Surface Proteoglycan of Mouse Mammary Epithelial Cells is Shed by Cleavage of Its Matrix-binding Ectodomain from Its Membrane-associated Domain", The Journal of Cell Biology, vol. 105, No. 6, Pt. 2, pp. 3087-3096 (1987).

Jalkanen, M. et al., "Heparan Sulfate Proteoglycans from Mouse Mammary Epithelial Cells: Localization on the Cell Surface with a Monoclonal Antibody", The Journal of Cell Biology, vol. 101, pp. 976-984 (1985).

Jamal, S. et al., "UV-induction of keratinocyte endothelin-1 downregulates E-cadherin in melanocytes and melanoma cells", The Journal of Clinical Investigation, vol. 110, No. 4, pp. 443-452 (2002).

Janknecht, R. et al., "Rapid and efficient purification of native histidine-tagged protein expressed by recombinant vaccinia virus", Proc. Natl. Acad. Sci. USA, vol. 88, pp. 8972-8976 (1991).

Jespers, L.S. et al., "Guiding the Selection of Human Antibodies from Phage Display Repertoires to a Single Epitope of an Antigen", Bio/Technology, vol. 12, pp. 899-903 (1994).

Jin, J.J. et al., "Association of Endothelin-1 Gene Variant with Hypertension", Hypertension, vol. 41, pp. 163-167 (2003).

Johanson, K. et al., "Binding Interactions of Human Interleukin 5 with Its Receptor α Subunit", The Journal of Biological Chemistry, vol. 270, No. 16, pp. 9459-9471 (1995).

Johnson, B.C., ed., Posttranslational Covalent Modifications of Proteins, Academic Press, publ., pp. 1-12 (1983).

Johnson, J.A. et al., "$β_1$-Adrenergic receptor polymorphisms and antihypertensive response to metoprolol", Clinical Pharmacology & Therapeutics, vol. 74, No. 1, pp. 44-52 (2003).

Joliot, A. et al., "Antennapedia homeobox peptide regulates neural morphogenesis", Proc. Natl. Acad. Sci. USA, vol. 88, pp. 1864-1868 (1991).

Jones, P.T. et al., "Replacing the complementarity-determining regions in a human antibody with those from a mouse", Nature, vol. 321, pp. 522-525 (1986).

Kang, J.S. et al., "Zinc Finger Proteins as Designer Transcription Factors", The Journal of Biological Chemistry, vol. 275, No. 12, pp. 8742-8748 (2000).

Kawana, M. et al., "Cooperative Interaction of GATA-2 and AP1 Regulates Transcription of the Endothelin-1 Gene", Molecular and Cellular Biology, vol. 15, No. 8, pp. 4225-4231 (1995).

Kermani, A. et al., "Thiazolidinedione-Associated Congestive Heart Failure and Pulmonary Edema", Mayo Clin. Proc., vol. 78, pp. 1088-1091 (2003).

Kettleborough, C.A. et al., "Isolation of tumor cell-specific single-chain Fv from immunized mice using phage-antibody libraries and the re-construction of whole antibodies from these antibody fragments", Eur. J. Immunol., vol. 24, pp. 952-958 (1994).

Kim. T.H. et al., "β-Catenin activates the growth factor endothelin-1 in colon cancer cells", Oncogene, vol. 24, pp. 597-604 (2005).

Kimmel, C.B. et al., "Endothelin 1-mediated regulation of pharyngeal bone development in zebrafish", Development, vol. 130, pp. 1339-1351 (2003).

Kinugawa, T. et al., "Plasma Endothelin-1 Levels and Clinical Correlates in Patients with Chronic Heart Failure", Journal of Cardiac Failure, vol. 9, No. 4, pp. 318-324 (2003).

Kitamura, A. et al., "Endothelin-1 is a potent stimulator of α1β1 integrin-mediated collagen matrix remodeling by rat mesangial cells", Biochemical and Biophysical Research Communications, vol. 299, pp. 555-561 (2002).

Knapp. M. et al., "The Haplotype-Relative-Risk (HRR) Method for Analysis of Association in Nuclear Families", Am. J. Hum. Genet., vol. 52, pp. 1085-1093 (1993).

Kocik, M. et al., "The effect of cyclosporin A on the level of big endothelin in patients one year after orthotopic heart transplantation", Transpl. Int., vol. 17, pp. 65-70 (2004).

Köhler, G., "Immunoglobulin chain loss in hybridoma lines", Proc. Natl. Acad. Sci. USA, vol. 77, No. 4, pp. 2197-2199 (1980).

Köhler, G. et al., "Continuous cultures of fused cells secreting antibody of predefined specificity", Nature, vol. 256, pp. 495-497 (1975).

Koller, B.H. et al., "Inactivating the $\beta_2$-microglobulin locus in mouse embryonic stem cells by homologous recombination", Proc. Natl. Acad. Sci. USA, vol. 86, pp. 8932-8935 (1989).

Kostelny, S.A. et al., "Formation of a Bispecific Antibody by the Use of Leucine Zippers", The Journal of Immumology, vol. 148, No. 5, pp. 1547-1553 (1992).

Koutz, P. et al., "Structural Comparison of the *Pichia pastoris* Alcohol Oxidase Genes", Yeast, vol. 5, pp. 167-177 (1989).

Kozák, M. et al., "Endothelin-1 gene polymorphism in the identification of patients at risk for malignant ventricular arrhythmia", Med. Sci. Monit., vol. 8, No. 5, pp. BR164-BR167 (2002).

Kozbor, D. et al., "A Human Hybrid Myeloma for Production of Human Monoclonal Antibodies", The Journal of Immunology, vol. 133, No. 6, pp. 3001-3005 (1984).

Kozbor, D. et al., "The production of monoclonal antibodies from human lymphocytes", Immunology Today, vol. 4, No. 3, pp. 72-79 (1983).

Kriegler, M., Gene Transfer and Expression: A Laboratory Manual, Stockton Press, publ., pp. vii-x (table of contents) (1990).

Kumazaki, T. et al., "Aging- and Growth-Dependent Modulation of Endothelin-1 Gene Expression in Human Vascular Endothelial Cells", Experimental Cell Research, vol. 211, pp. 6-11 (1994).

Landschulz, W.H. et al., "The Leucine Zipper: A Hypothetical Structure Common to a New Class of DNA Binding Proteins", Science, vol. 240, pp. 1759-1764 (1988).

Lang, J.A. et al., "Endogenous Human Renin Expression and Promoter Activity in CALU-6, a Pulmonary Carcinoma Cell Line", Hypertension, vol. 25, No. 4, Pt. 2, pp. 704-710 (1995).

Langer, R., "New Methods of Drug Delivery", Science, vol. 249, pp. 1527-1533 (1990).

Langer, R. et al., "Chemical and Physical Structure of Polymers as Carriers for Controlled Release of Bioactive Agents: A Review", JMS—Rev. Macromol. Chem. Phys., vol. C23, No. 1, pp. 61-126 (1983).

Langer, R.S. et al., eds., Medical Applications of Controlled Release, vol. I: Classes of Systems, CRC Press, Inc., publ. (1984) (table of contents).

Langer, R.S. et al., eds., Medical Applications of Controlled Release, vol. II: Applications and Evaluation, CRC Press, Inc., publ. (1984) (table of contents).

Lavoie, C. et al., "$\beta_1/\beta_2$-Adrenergic Receptor Heterodimerization Regulates $\beta_2$-Adrenergic Receptor Internalization and ERK Signaling Efficacy", The Journal of Biological Chemistry, vol. 277, No. 38, pp. 35402-35410 (2002).

Lee-Kirsch, M.A. et al., "Distinct Renin Isoforms Generated by Tissue-Specific Transcription Initiation and Alternative Splicing", Circulation Research, vol. 84, pp. 240-246 (1999).

Leff, T. et al., "The Antidiabetic PPARγ Ligands: An Update on Compounds in Development", Curr. Med. Chem.—Immun., Endoc. & Metab. Agents, vol. 2, No. 1, pp. 33-47 (2002).

Lennon, G. et al., "The I.M.A.G.E. Consortium: An Integrated Molecular Analysis of Genomes and Their Expression", Genomics, vol. 33, pp. 151-152 (1996).

Leon, O. et al., "Zinc fingers: DNA binding and protein-protein interactions", Biol. Res., vol. 33, pp. 21-30 (2000).

Levy, R.J. et al., "Inhibition of Calcification of Bioprosthetic Heart Valves by Local Controlled-Release Diphosphonate", Science, vol. 228, pp. 190-192 (1985).

Li, J.-M. et al., "Endothelin-1 Expression and Quantitative Analysis in Astrocytomas", Ai Zheng (Chinese Journal of Cancer), vol. 21, No. 10, pp. 1109-1111 (2002).

Li, T. et al., "Case-control, haplotype relative risk and transmission disequilibrium analysis of a dopamine D2 receptor functional promoter polymorphism in schizophrenia", Schizophrenia Research, vol. 32, pp. 87-92 (1998).

Liang, W. et al., "Differences in endosomal targeting of human $\beta_1$- and $\beta_2$- adrenergic receptors following clathrin-mediated endocytosis", Journal of Cell Science, vol. 117, No. 5, pp. 723-734 (2003).

Liang, W. et al., "Resistance of the Human $\beta_1$-Adrenergic Receptor to Agonist-induced Ubiquitination", The Journal of Biological Chemistry, vol. 279, No. 45, pp. 46882-46889 (2004).

Link, A.J., "Multidimensional peptide separations in proteomics", Trends in Biotechnology, vol. 20, No. 12 (Suppl.), pp. S8-S13 (2002).

Logan, J. et al., "Adenovirus tripartite leader sequence enhances translation of mRNAs late after infection", Proc. Natl. Acad. Sci. USA, vol. 81, pp. 3655-3659 (1984).

Lohse, M.J. et al., "What is the Role of β-Adrenergic Signaling in Heart Failure?", Circulation Research, vol. 93, pp. 896-906 (2003).

Lonberg, N. et al., "Antigen-specific human antibodies from mice comprising four distinct genetic modifications", Nature, vol. 368, pp. 856-859 (1994).

Lonberg, N. et al., "Human Antibodies from Transgenic Mice", Intern, Rev. Immunol., vol. 13, pp. 65-93 (1995).

Long, J.C. et al., "An E-M Algorithm and Testing Strategy for Multiple-Locus Haplotypes", Am. J. Hum. Genet., vol. 56, pp. 799-810 (1995).

Lopez-Berestein, G., "Treatment of Systemic Fungal Infections with Liposomal-Amphotericin B", Liposomes in the Therapy of Infectious Diseases and Cancer, Alan R. Liss, Inc., publ., Lopez-Berestein, G. et al., eds., pp. 317-327 (1989).

Lowy, I. et al., "Isolation of Transforming DNA: Cloning the Hamster aprt Gene", Cell, vol. 22, pp. 817-823 (1980).

Lüscher, T.F. et al., "Endothelins and Endothelin Receptor Antagonists: Therapeutic Considerations for a Novel Class of Cardiovascular Drugs", Circulation, vol. 102, pp. 2434-2440 (2000).

Maack, C. et al., "Partial Agonist Activity of Bucindolol is Dependent on the Activation State of the Human $\beta_1$-Adrenergic Receptor", Circulation, vol. 108, pp. 348-353 (2003).

Maggi, M. et al., "Expression and Biological Effects of Endothelin-1 in Human Gonadotropin-Releasing Hormone-Secreting Neurons", The Journal of Clinical Endocrinology & Metabolism, vol. 85, No. 4, pp. 1658-1665 (2000).

Malik, F. et al., "Polyethylene Glycol (PEG)-modified Granulocyte-Macrophage Colony-stimulating Factor (GM-CSF) with Conserved Biological Activity", Experimental Hematology, vol. 20, pp. 1028-1035 (1992).

Mangahas, C.R. et al., "Endothelin-1 Upregulates MCAM in Melanocytes", The Journal of Investigative Dermatology, vol. 123, pp. 1135-1139 (2004).

Marinoni, E. et al., "Follicular fluid adrenomedullin concentrations in spontaneous and stimulated cycles: relationship to ovarian function and endothelin-1 and nitric oxide", Regulatory Peptides, vol. 107, pp. 125-128 (2002).

Marks, J.D. et al., "By-Passing Immunization: Building High Affinity Human Antibodies by Chain Shuffling", Bio/Technology, vol. 10, pp. 779-783 (1992).

Marx, N. et al., "PPARγ Activation in Human Endothelial Cells Increases Plasminogen Activator Inhibitor Type-1 Expression: PPARγ as a Potential Mediator in Vascular Disease", Arterioscler, Thromb. Vasc. Biol., vol. 19, pp. 546-551 (1999).

Masharani, U. et al., "MboI RFLP at the human renin (*ren*) gene locus", Nucleic Acids Research, vol. 16, No. 5, p. 2357 (1988).

Mason, D.A. et al., "A Gain-of-function Polymorphism in a G-protein Coupling Domain of the Human $\beta_1$-Adrenergic Receptor", The Journal of Biological Chemistry, vol. 274, No. 18, pp. 12670-12674 (1999).

Massai, L. et al., "Prepro-endothelin-1 mRNA and its mature peptide in human appendix", Am. J. Physiol. Gastrointest.Liver Physiol., vol. 284, pp. G340-G348 (2003).

Matise, T.C., "Genome Scanning for Complex Disease Genes Using the Transmission/Disequilibrium Test and Haplotype-based Haplotype Relative Risk", Genetic Epidemiology, vol. 12, pp. 641-645 (1995).

Mawji, I.A. et al., "Role of the 3'-Untranslated Region of Human Endothelin-1 in Vascular Endothelial Cells", The Journal of Biological Chemistry, vol. 279, No. 10, pp. 8655-8667 (2004).

McColl, D.J. et al., "Structure-based design of an RNA-binding zinc finger", Proc. Natl. Acad. Sci. USA, vol. 96, pp. 9521-9526 (1999).

McDonald, W.H. et al., "Shotgun proteomics and biomarker discovery", Disease Markers, vol. 18, pp. 99-105 (2002).

Medinger, M. et al., "Angiogenesis and the ET-1/ET$_A$ receptor system: Immunohistochemical expression analysis in bone metastases from patients with different primary tumors", Angiogenesis, vol. 6, pp. 225-231 (2003).

Mehta, C.R. et al., "Exact Logistic Regression: Theory and Examples", Statistics in Medicine, vol. 14, pp. 2143-2160 (1995).

Mercier, J.-F. et al., "Quantitative Assessment of $\beta_1$- and $\beta_2$-Adrenergic Receptor Homo- and Heterodimerization by Bioluminescence Resonance Energy Transfer", The Journal of Biological Chemistry, vol. 277, No. 47, pp. 44925-44931 (2002).

Milstein, C. et al., "Hybrid hybridomas and their use in immunohistochemistry", Nature, vol. 305, pp. 537-540 (1983).

Miyazaki, H. et al., "Structure of the human renin gene", Proc. Natl. Acad. Sci. USA, vol. 81, pp. 5999-6003 (1984).

Morgan, R.A. et al., "Human Gene Therapy", Ann. Rev. Biochem., vol. 62, pp. 191-217 (1993).

Morris, B.J., "New possibilities for intracellular renin and inactive renin now that the structure of the human renin gene has been elucidated", Clinical Science, vol. 71, pp. 345-355 (1986).

Morrison, S.L., "Transfectomas Provide Novel Chimeric Antibodies", Science, vol. 229, pp. 1202-1207 (1985).

Mulligan, R.C., "The Basic Science of Gene Therapy", Science, vol. 260, pp. 926-932 (1993).

Mulligan, R.C. et al., "Selection for animal cells that express the *Escherichia coli* gene coding for Exanthine-guanine phosphoribosyltransferase", Proc. Natl. Acad. Sci. USA, vol. 78, No. 4, pp. 2072-2076 (1981).

Mullinax, R.L. et al., "Expression of a Heterodimeric Fab Antibody Protein in One Cloning Step", BioTechniques, vol. 12, No. 6, pp. 864-869 (1992).

Mullis, K. et al., "Specific Enzymatic Amplification of DNA In Vitro: The Polymerase Chain Reaction", Cold Spring Harbor Symposia on Quantitative Biology, vol. 51, pp. 263-273 (1986).

Munson, P.J. et al., "LIGAND: A Versatile Computerized Approach for Characterization of Ligand-Binding Systems", Analytical Biochemistry, vol. 107, pp. 220-239 (1980).

Nagai, M. et al., "Role of Endothelin-1 Induced by Insulin in the Regulation of Vascular Cell Growth", American Journal of Hypertension, vol. 16, No. 3, pp. 223-228 (2003).

Namiki, A. et al., "Endothelin-1 Concentrations in Pericardial Fluid are More Elevated in Patients with Ischemic Heart Disease than in Patients with Nonischemic Heart Disease", Jpn. Heart J., vol. 44, No. 5, pp. 633-644 (2003).

Naramura, M. et al., "Mechanisms of cellular cytotoxicity mediated by a recombinant antibody-IL2 fusion protein against human melanoma cells", Immunology Letters, vol. 39, pp. 91-99 (1994).

Narayan, S. et al., "Endothelin-1 Synthesius and Secretion in Human Retinal Pigment Epithelial Cells (ARPE-19): Differential Regulation by Cholinergics and TNF-α", Invest. Ophthalmol. Vis. Sci., vol. 44, No. 11, pp. 485-4894 (2003).

Nesto, R.W. et al., "Thiazolidinedione Use, Fluid Retention, and Congestive Heart Failure", Ciculation, vol. 108, pp. 2941-2948 (2003).

Neuberger, M., "Generating hihj-avidity human Mabs in mice", Nature Biotechnology, vol. 14, p. 826 (1996).

Ng, T.M.H. et al., "Neurohormonal Activation does not explain Elevated Tissue Factor Expression in Heart Failure", Thromb. Haemost., vol. 87, pp. 176-177 (2002).

Nguyen, G. et al., "Pivotal role of the renin/prorenin receptor in angiotensin II production and cellular responses to renin", The Journal of Clinical Investigation, vol. 109, No. 11, pp. 1417-1427 (2002).

Nicherson, D.A. et al., "PolyPhred: automating the detection and genotyping of single nucleotide substitutions using fluorescence-based resequencing", Nucleic Acids Research, vol. 25, No. 14, pp. 2745-2751 (1997).

Nicolaidou, P. et al., "Urinary excretion of endothelin-1 in children with absorptive idiopathic hypercalciuria", Pediatr. Nephrol., vol. 18, pp. 1157-1160 (2003).

Nielsen, P.E. et al., "Sequence-Selective Recognition of DNA by Strand Displacement with a Thymine-Substitute Polyamide", Science, vol. 254, pp. 1497-1500 (1991).

Nisonoff, A., "Idiotypes: Concepts and Applications", The Journal of Immunology, vol. 147, No. 8, pp. 2429-2438 (1991).

Nygren, H., "Conjugation of Horseradish Peroxidase to Fab Fragments with Different Homobifunctional and Heterobifunctional Cross-Linking Reagents", The Journal of Histochemistry and Cytochemistry, vol. 30, No. 5, pp. 407-412 (1982).

O'Hare, K. et al., "Transformation of mouse fibroblasts to methotrexate resistance by a recombinant plasmid expressing a prokaryotic dihydrofolate reductase", Proc. Natl. Acad. Sci. USA, vol. 78, No. 3, pp. 1527-1531 (1981).

Oi, V.T. et al., "Chimeric Antibodies", BioTechniques, vol. 4, No. 3, pp. 214-221 (1986).

Ong, A.C.M. et al., "Expression and Cellular Localisation of Renal Endothelin-1 and Endothelin Receptor Subtypes in Autosomal-Dominant Polycystic Kidney Disease", Nephron Experimental Nephrology, vol. 93, pp. e80-e86 (2003).

Opgaard, O.S. et al., "Endocradial expression and functional characterization of endothelin-1", Molecular and Cellular Biochemistry, vol. 224, pp. 151-158 (2001).

Order, S.E., Chapter 15: "Analysis, Results, and Future Prospective of the Therapeutic Use of Radiolabeled Antibody in Cancer Therapy", Monoclonal Antibodies for Cancer Detection and Therapy, Academic Press Inc., publ., Baldwin, R.W. et al., eds., pp. 303-316 (1985).

Ott, J., "Statistical Properties of the Haplotype Relative Risk", Genetic Epidemiology, vol. 6, pp. 127-130 (1989).

Padlan, E.A., "A Possible Procedure for Reducing the Immunogenicity of Antibody Variable Domains While Preserving Their Ligand-Binding Properties", Molecular Immunology, vol. 28, No. 4/5, pp. 489-498 (1991).

Padmanabhan, N. et al., "Genetic basis of cardiovascular disease—the renin-angiotensin-aldosterone system as a paradigm", Journal of the Renin-Angiotensin-Aldosterone System, vol. 1, No. 4, pp. 316-324 (2000).

Pain, D. et al., "Preparation of Protein A-Peroxidase Monoconjugate Using a Heterobiofunctional Reagent, and Its Use in Enzyme Immunoassays", Journal of Immunological Methods, vol. 40, pp. 219-230 (1981).

Pak, Y. et al., "Direct Binding of the $\beta$1 Adrenergic Receptor to the Cyclic AMP-Dependent Guanine Nucleotide Exchange Factor CNrasGEF Leads to Ras Activation", Molecular and Cellular Biology, vol. 22, No. 22, pp. 7942-7952 (2002).

Pang, J.X. et al., "Biomarker Discovery in Urine by Proteomics", Journal of Proteome Research, vol. 1, No. 2, pp. 161-169 (2002).

Perez, J.M. et al., "$\beta_1$-adrenergic receptor polymorphisms confer differential function and predisposition to heart failure", Nature Medicine, vol. 9, No. 10, pp. 1300-1305 (2003).

Persic, L. et al., "An integrated vector system for the eukaryotic expression of antibodies or their fragments after selection from phage display libraries", Gene, vol. 187, pp. 9-18 (1997).

Pinto-Sietsma, S.-J. et al., "Role of the Endothelin-1 Gene Locus for Renal Impairment in the General Nondiabetic Population", Journal of the American Society of Nephrology, vol. 14, pp. 2596-2602 (2003).

Podlowski, S. et al., "$\beta_1$-Adrenoceptor gene variations: a role in idiopathic dilated cardiomyopathy?", J. Mol. Med., vol. 78, pp. 87-93 (2000).

Pomerantz, J.L. et al., "Structure-Based Design of a Dimeric Zinc Finger Protein", Biochemistry, vol. 37, No. 4, pp. 965-970 (1998).

Pontiroli, A.E. et al., "Body weight and glucose metabolism have a different effect on circulating levels of ICAM-1, E-selectin, and endothelin-1 in humans", European Journal of Endocrinology, vol. 150, pp. 195-200 (2004).

Presta, L.G., "Antibody engineering", Current Opinion in Structural Biology, vol. 2, pp. 593-596 (1992).

Proudfoot, N.J., "Transcriptional interference and termination between duplicated α-globin gene constructs suggests a novel mechanism for gene regulation", Nature, vol. 322, pp. 562-565 (1986).

Qin, H. et al., "Reassignment of Human Renin Gene to Chromosome 1q32 in Studies of a (1;4)(q42;p16) Translocation", Hum. Hered., vol. 43, pp. 261-264 (1993).

Quehenberger, P. et al., "Leptin Induces Endothelin-1 in Endothelial Cells in Vitro", Circulation Research, vol. 90, pp. 711-718 (2002).

Ranade, K. et al., "A Polymorphism in the β1 Adrenergic Receptor is Associated with Resting Heart Rate", Am. J. Hum. Genet., vol. 70, pp. 935-942 (2002).

Ranade, K. et al., "High-Throughput Genotyping with Single Nucleotide Polymorphisms", Genome Research, vol. 11, pp. 1262-1268 (2001).

Rattan, S.I.S. et al., "Protein Synthesis, Posttranslational Modifications, and Aging", Annals New York Academy of Sciences, vol. 663, pp. 48-62 (1992).

Rebuffat, P. et al., "Signaling pathways involved in the A and B receptor-mediated cortisol secretagogue effect of endothelins in the human adrenal cortex", International Journal of Molecular Medicine, vol. 7, pp. 301-305 (2001).

Ricote, M. et al., "The peroxisome proliferator-activated receptor-γ is a Negative regulator of macrophage activation", Nature, vol. 391, pp. 79-82 (1998).

Riechmann, L. et al., "Reshaping human antibodies for therapy", Nature, vol. 332, pp. 323-327 (1988).

Roguska, M.A. et al., "Humanization of murine monoclonal antibodies through variable domain resurfacing", Proc. Natl. Acad. Sci. USA, vol. 91, pp. 969-973 (1994).

Roy-Beaudry, M. et al., "Endothelin 1 Promotes Osteoarthritic Cartilage Degradation Via Matrix Metalloprotease 1 and Matrix Metalloprotease 13 Induction", Arthritis & Rheumatism, vol. 48, No. 10, pp. 2855-2864 (2003).

Rozen, S. et al., Chapter 20: "Primer3 on the WWW for General Users and for Biologist Programmers", Methods in Molecular Biology, vol. 132: Bioinformatics Methods and Protocols, Humana Press Inc., publ., Misener, S. et al., eds., pp. 365-386 (2000).

Rüther, U. et al., "Easy identification of cDNA clones", The EMBO Journal, vol. 2, No. 10, pp. 1791-1794 (1983).

Ryan, M.J. et al., "Endothelin-1 increase calcium and attenuates renin gene expression in As4.1 cells", Am. J. Physiol. Heart Circ. Physiol., vol. 283, pp. H2458-H2465 (2002).

Saiki, R.K. et al., "Primer-Directed Enzymatic Amplification of DNA with a Thermostable DNA Polymerase", Science, vol. 239, pp. 487-491 (1988).

Sambrook, J. et al., Molecular Cloning: A Laboratory Manual, Second Edition, Books 1, 2 and 3, Cold Spring Harbor Laboratory Press, publ., pp. xi-xxxviii (table of contents) (1989).

Santerre, R.F. et al., "Expression of prokaryotic genes for hygromycin B and G418 resistance as dominant-selection markers in mouse L cells", Gene, vol. 30, pp. 147-156 (1984).

Satoh, H. et al., "Thiazolidinediones Suppress Endothelin-1 Secretion from Bovine Vascular Endothelial Cells: A New Possible Role of PPARγ on Vacular Endothelial Function", Biochemical and Biophysical Research Communications, vol. 254, No. 3, pp. 757-763 (1999).

Saudek, C.D. et al., "A Preliminary Trial of the Programmable Implantable Medication System for Insulin Delivery", The New England Journal of Medicine, vol. 321, No. 9, pp. 574-579 (1989).

Saunders, R. et al., "Ouabain stimulates endothelin release and expression in human endothelial cells without inhibiting the sodium pump", Eur. J. Biochem., vol. 271, pp. 1054-1062 (2004).

Sawai, H. et al., "Direct Production of the Fab Fragment Derived from the Sperm Immobilizing Antibody Using Polymerase Chain Reaction and cDNA Expression Vectors", American Journal of Reproductive Immunology, vol. 34, pp. 26-34 (1995).

Schiffrin, E.L., "Role of Endothelin-1 in Hypertension and Vascular Disease", American Journal of Hypertension, vol. 14, No. 6, Pt. 2, pp. 83S-89S (2001)..

Schiffrin, E.L. et al., "Peroxisome Proliferator-Activated Receptors: Vascular and Cardiac Effects in Hypertension", Hypertension, vol. 42, Pt. 2, pp. 664-668 (2003).

Scopes, R.K., Protein Purification: Principles and Practice, Second Edition, Springer-Verlag New York Inc., publ., pp. xiii-xv (table of contents) (1987).

Sefton, M.V., "Implantable Pumps", CRC Critical Reviews in Biomedical Engineering, vol. 14, No. 3, pp. 201-240 (1987).

Segal, D.J. et al., "Toward controlling gene expression at will: Selection and design of zinc finger domains recognizing each of the 5'-GNN-3'DNA target sequences", Proc. Natl. Acad. Sci. USA, vol. 96, pp. 2758-2763 (1999).

Seifter, S. et al., "Analysis for Protein Modifications and Nonprotein Confactors", Methods in Enzymology, vol. 182, pp. 626-646 (1990).

Shephard, P. et al., "Dissecting the roles of endothelin, TGF-β and GM-CSF on myofibroblast differentiation by keratinocytes", Thromb. Haemost., vol. 92, pp. 262-274 (2004).

Shiina, T. et al., "Interaction with β-Arrestin Determines the Difference in Internalization Behavior between $β_1$-Adrenergic Receptors", The Journal of Biological Chemistry, vol. 275, No. 37, pp. 29082-29090 (2000).

Shine, J. et al., "Structure of the Human Renin Gene", Transactions of the Association of American Physicians, vol. 97, Waverly Press, Inc., publ., pp. 63-69 (1984).

Shioji, K. et al., "Association between Hypertension and the α-Adducin, β1-Adrenoreceptor, and G-Protein β3 Subunit Genes in the Japanese Population; the Suita Study", Hypertens. Res., vol. 27, No. 1, pp. 31-37 (2004).

Shiu, Y.-T. et al., "Sickle erythrocytes increase prostacyclin and endothelin-1 production by cultured human endothelial cells under flow conditions", European Journal of Haematology, vol. 68, pp. 163-169 (2002).

Shi-wen, X. et al., "Endothelin-1 Induces Expression of Matrix-associated Genes in Lung Fibroblasts through MEK/ERK", The Journal of Biological Chemistry, vol. 279, No. 22, pp. 23098-23103 (2004).

Shi-Wen, X. et al., "Endothelin-1 Promotes Myofibroblast Induction through the ETA Receptor via a rac/Phosphoinositide 3-Kinase/Akt-dependent Pathway and is Essential for the Enhanced Contractile Phenotype of Fibrotic Fibroblasts", Molecular Biology of the Cell, vol. 15, pp. 2707-2719 (2004).

Shu, L. et al., "Secretion of a single-gene-encoded immunoglobulin from myeloma cells", Proc. Natl. Acad. Sci. USA, vol. 90, pp. 7995-7999 (1993).

Sielecki, A.R. et al., "Structure of Recombinant Human Renin, a Target for Cardiovascular-Active Drugs, at 2.5 Å Resolution", Science, vol. 243, pp. 1346-1351 (1989).

Skerra, A. et al., "Assembly of a Functional Immunoglobulin $F_v$ Fragment in *Escherichia coli*", Science, vol. 240, pp. 1038-1041 (1988).

Smolen, V.F. et al., eds., Controlled Drug Bioavailability, vol. 1: Drug Product Design and Performance, John Wiley & Sons, Inc., publ., p. xiii (table of contents) (1984).

Sofowora, .G.G. et al., "A common $β_1$-adrenergic receptor polymorphism (Arg389Gly) affects blood pressure response to β-blockade", Clinical Pharmacology & Therapeutics, vol. 73, No. 4, pp. 366-371 (2003).

Soubrier, F. et al., "Molecular cloning and nucleotides sequence of a human renin cDNA fragment", Nucleic Acids Research, vol. 11, No. 20, pp. 7181-7190 (1983).

Soubrier, F. et al., "Segmental homology between the promoter region of the human renin gene and the mouse *ren1* and *ren2* promoter regions", Gene, vol. 41, pp. 85-92 (1986).

Spinella, F. et al., "Endothelin-1 Decreases Gap Junctional Intercellular Communication by Inducing Phosphorylation of Connexin 43 in Human Ovarian Carcinoma Cells", The Journal of Biological Chemistry, vol. 278, No. 42, pp. 41294-41301 (2003).

Spinella, F. et al., "Endothelin-1-induced Prostaglandin E2-EP2, EP4 Signaling Regulates Vascular Endothelial Growth Factor Production and Ovarian Carcinoma Cell Invasion", The Journal of Biological Chemistry, vol. 279, No. 45, pp. 46700-46705 (2004).

Stachon, A. et al., "The Secretion of Endothelin-1 by Microvascular Endothelial Cells from Human Benign Prostatic Hyperplasia is Inhibited by Vascular Endothelial Growth Factor", Growth Factors, vol. 22, No. 4, pp. 281-289 (2004).

Staels, B. et al., "Activation of human aortic smooth-muscle cells is inhibited by PPARα but not by PPARγ activators", Nature, vol. 393, pp. 790-793 (1998).

Stannard, C. et al., "Rapid Changes in the Phosphoproteome Show Diverse Cellular Responses Following Stimulation of Human Lung Fibroblasts with Endothelin-1", Biochemistry, vol. 42, No. 47, pp. 13919-13928 (2003).

Stein, M.B. et al., "A Polymorphism of the $β_1$-Adrenergic Receptor is Associated with Low Extraversion", Biol. Psychiatry, vol. 56, pp. 217-224 (2004).

Stiles, G.L. et al., "The Cardiac β-Adrenergic Receptor", The Journal of Biological Chemistry, vol. 258, No. 13, pp. 8443-8449 (1983).

Studnicka, G.M. et al., "Human-engineered monoclonal antibodies retain full specific binding activity by preserving non-CDR complementarity-modulating residues", Protein Engineering, vol. 7, No. 6, pp. 805-814 (1994).

Sugawara, A. et al., "Transcriptional Suppression of Type 1 Angiotensin II Receptor Gene Expression by Peroxisome Proliferator-Activated Receptor-γ in Vascular Smooth Muscle Cells", Endocrinology, vol. 142, No. 7, pp. 3125-3134 (2001).

Suresh, M.R. et al., "Bispecific Monoclonal Antibodies from Hybrid Hybridomas", Methods in Enzymology, vol. 121, pp. 210-228 (1986).

Sutcliffe, J.G. et al., "Antibodies that React with Predetermined Sites on Proteins", Science, vol. 219, pp. 660-666 (1983).

Suzuki, F. et al., "Human Prorenin Has 'Gate and Handle' Regions for Its Non-proteolytic Activation", The Journal of Biological Chemistry, vol. 278, No. 25, pp. 22217-22222 (2003).

Suzuki, M. et al., "Single-nucleotide polymorphisms in the 17β-hydroxysteroid dehydrogenase genes might predict the risk of side-effects of estramustine phosphate sodium in prostate cancer patients", International Journal of Urology, vol. 12, pp. 166-172 (2005).

Sventek, P. et al., "Vascular and cardiac overexpression of endothelin-1 gene in one-kidney, one clip Goldblatt hypertensive rats but only in the late phase of two-kidney one clip Goldblatt hypertension", Journal of Hypertension, vol. 14, No. 1, pp. 57-64 (1996).

Szybalska, E.H. et al., "Genetics of Human Cell Lines, IV. DNA-Mediated Heritable Transformation of a Biochemical Trait", Proc. Natl. Acad. Sci., vol. 48, pp. 2026-2034 (1962).

Takashima, H. et al., "Hydrophobic Core around Tyrosine for Human Endothelin-1 Investigated by Photochemically Induced Dynamic Nuclear Polarization Nuclear Magnetic Resonance and Matrix-Assisted Laser Desorption Ionization Time-of-Flight Mass Spectrometry", Biochemistry, vol. 43, No. 44, pp. 13932-13936 (2004).

Takeda, K. et al., "Peroxisome Proliferator-Activated Receptor γ Activators Downregulate Angiotensin II Type 1 Receptor in Vascular Smooth Muscle Cells", Circulation, vol. 102, pp. 1834-1839 (2000).

Tamura, K. et al., "Recent Advances in the Study of Renin and Angiotensinogen Genes: From Molecules to the Whole Body", Hypertens. Res., vol. 18, No. 1, pp. 7-18 (1995).

Tanaka, C. et al., "Evaluation of the Lys198Asn and -134delA Genetic Polymorphisms of the Endothelin-1 Gene", Hypertens. Res., vol. 27, No. 5, pp. 367-371 (2004).

Templeton, A.R. et al., "Recombinational and Mutational Hotspots within the Human Lipoprotein Lipase Gene", Am. J. Hum. Genet., vol. 66, pp. 69-83 (2000).

Terwilliger, J.D. et al., "A Haplotype-Based 'Haplotype Relative Risk' Approach to Detecting Allelic Associations", Hum. Hered., vol. 42, pp. 337-346 (1992).

Thorpe, P.E., "Antibody Carriers of Cytotoxic Agents in Cancer Therapy: A Review", Monoclonal Antibodies '84: Biological and Clinical Applications, Editrice Kurtis s.r.l., publ., Pinchera, A. et al., eds., pp. 475-506 (1985).

Thorpe, P.E. et al., "The Preparation and Cytotoxic Properties of Antibody-Toxin Conjugates", Immunological Rev., vol. 62, pp. 119-158 (1982).

Tilly, N. et al., "Endothelin-1 Levels in Patients with Disorders of the Thyroid Gland", Exp. Clin. Endocrinol. Diabetes, vol. 111, pp. 80-84 (2003).

Tiret, L. et al., "The Lys198Asn Polymorphism in the Endothelin-1 Gene is Associated with Blood Pressure in Overweight People", Hypertension, vol. 33, pp. 1169-1174 (1999).

Tolstoshev, P., "Gene Therapy, Concepts, Current Trials and Future Directions", Annu. Rev. Pharmacol. Toxicol., vol. 32, pp. 573-596 (1993).

Traunecker, A. et al., "Bispecific single chain molecules (Janusins) target cytotoxic lymphocytes on HIV infected cells", The EMBO Journal, vol. 10, No. 12, pp. 3655-3659 (1991).

Traunecker, A. et al., "Soluble CD4 molecules neutralize human immunodeficiency virus type 1", Nature, vol. 331, pp. 84-86 (1988).

Treat, J. et al., "Liposome Encapsulated Doxorubicin: Preliminary Results of Phase I and Phase II Trials", Liposomes in the Therapy of Infectious Diseases and Cancer, Alan R. Liss, Inc., publ., Lopez-Berestein, G. et al., eds., pp. 353-365 (1989).

Treiber, F.A. et al., "Endothelin-1 Gene LYS198ASN Polymorphism and Blood Pressure Reactivity", Hypertension, vol. 42, pp. 494-499 (2003).

Trends in Biotechnology, vol. 11, No. 5, pp. 155-215 (1993).

Tschopp, J.F. et al., "Expression of the *lacZ* gene from two methanol-regulated promoters in *Pichia pastoris*", Nucleic Acids Research, vol. 15, No. 9, pp. 3859-3876 (1987).

Tutt, A. et al., "Trispecific F(ab')$_3$ Derivatives that Use Cooperative Signaling via the TCR/CD3 Complex and CD2 to Activate and Redirect Resting Cytotoxic T Cells", The Journal of Immunology, vol. 147, No. 1, pp. 60-69 (1991).

Van Heeke, G. et al., "Expression of Human Asparagine Synthetase in *Escherichia coli*", The Journal of Biological Chemistry, vol. 264, No. 10, pp. 5503-5509 (1989).

Varagic, J. et al., "Local Cardiac Renin-Angiotensin System: Hypertension and Cardiac Failure", J. Mol. Cell Cardiol., vol. 34, pp. 1435-1442 (2002).

Vašků, "The Double Heterozygote of Two Endothelin-1 Gene Polymorphisms (G8002A and -3A/-4A) is Related to Big Endothelin Levels in Chronic Heart Failure", Experimental and Molecular Pathology, vol. 73, pp. 230-233 (2002).

Verhoeyen, M. et al., "Reshaping Human Antibodies: Grafting an Antilysozyme Activity", Science, vol. 239, pp. 1534-1536 (1988).

Vié, H. et al. "Human fusion proteins between interleukin 2 and IgM heavy chain are cytotoxic for cells expressing the interleukin 2 receptor", Proc. Natl. Acad. Sci. USA, vol. 89, pp. 11337-11341 (1992).

Wahl, R.L. et al., "Improved Radioimaging and Tumor Localization with Monoclonal F(ab')$_2$", The Journal of Nuclear Medicine, vol. 24, No. 4, pp. 316-325 (1983).

Wang, B.S. et al., "Dimerization of zinc fingers mediated by peptides evolved in vitro from random sequences", Proc. Natl. Acad. Sci. USA, vol. 96, pp. 9568-9573 (1999).

Wang, G.-X. et al., "Shear-Induced Changes in Endothelin-1 Secretion of Microvascular Endothelial Cells", Microvascular Research, vol. 63, pp. 209-217 (2002).

Wenzel-Seifert, K. et al., "Similarities and differences in the coupling of human $\beta_1$- and $\beta_2$-adrenoceptors to $G_{s\alpha}$ splice variants", Biochemical Parmacology, vol. 64, pp. 9-20 (2002).

Wigler, M. et al., "Transfer of Purified Herpes Virus Thymidine Kinase Gene to Cultured Mouse Cells", Cell, vol. 11, pp. 223-232 (1977).

Wilson, I.A. et al., "The Structure of an Antigenic Determinant in a Protein", Cell, vol. 37, pp. 767-778 (1984).

Wolfe, S.A. et al., "Analysis of Zinc Fingers Optimized via Phage Display: Evaluating the Utility of a Recognition Code", J. Mol. Biol., vol. 285, pp. 1917-1934 (1999).

Wolfe, S.A. et al., "Combining structure-based design with phage display to create new Cys$_2$His$_2$ zinc finger dimers", Structure, vol. 8, No. 7, pp. 739-750 (2000).

Woods, M. et al., "Endothelin-1 is Induced by Cytokines in Human Vascular Smooth Muscle Cells: Evidence for Intracellular Endothelin-Converting Enzyme", Molecular Pharmacology, vol. 55, pp. 902-909 (1999).

Wu, G.Y. et al., "Delivery systems for gene therapy", Biotherapy, vol. 3, pp. 87-95 (1991).

Wu, G.Y. et al., "Receptor-mediated in Vitro Gene Transformation by a Soluble DNA Carrier System", The Journal of Biological Chemistry, vol. 262, No. 10, pp. 4429-4432 (1987).

Wülfing, C. et al., "Expression of endothelin-1 and endothelin-A and -B receptors in invasive bladder cancer", Oncology Reports, vol. 13, pp. 223-228 (2005).

Wülfing, P. et al., "Endothelin-1-, Endothelin-A-, and Endothelin-B-Receptor Expression is Correlated with Vascular Endothelial Growth Factor Expression and Angiogenesis in Breast Cancer", Clinical Cancer Research, vol. 10, pp. 2393-2400 (2004).

Wülfing, P. et al., "Expression of Endothelin-1, Endothelin-A, and Endothelin-B Receptor in Human Breast Cancer and Correlation with Long-Term Follow-Up", Clinical Cancer Research, vol. 9, pp. 4125-4131 (2003).

Wunderlich, K. et al., "Vasospastic persons exhibit differential expression of ABC-transport proteins", Molecular Vision, vol. 9, pp. 756-761 (2003).

Xu, J. et al., "$\beta_1$-Adrenergic Receptor Association with the Synaptic Scaffolding Protein Membrane-associated Guanylate Kinase Inverted-2 (MAGI-2)", The Journal of Biological Chemistry, vol. 276, No. 44, pp. 41310-14317 (2001).

Xu, J. et al., "Heterodimerization of $\alpha_{2A}$- and $\beta_1$-Adrenergic Receptors", The Journal of Biological Chemistry, vol. 278, No. 12, pp. 10770-10777 (2003).

Yang-Feng, T.L. et al., "Chromosomal organization of adrenergic receptor genes", Proc. Natl. Acad. Sci. USA, vol. 87, pp. 1516-1520 (1990).

Yin, J.J. et al., "A causal role for endothelin-1 in the pathogenesis of osteoblastic bone metastases", Proc. Natl. Acad. Sci., vol. 100, No. 19, pp. 10954-10959 (2003).

Yokoyama, Y. et al., "Endothelin Receptor Remodeling Induces the Portal Venous Hyper-Responsive to Endothelin-1 Following Endotoxin Pretreatment", Shock, vol. 17, No. 1, pp. 36-40 (2002).

Zhang, H. et al., "Collecting duct-specific deletion of peroxisome proliferator-activated receptor γ blocks thiazolidinedione-induced fluid retention", Proc. Natl. Acad. Sci., vol. 102, No. 26, pp. 9406-9411 (2005).

Zhang, L. et al., "Expression of local renin and angiotensinogen mRNA in cirrhotic portal hypertensive patient", World J. Gastroenterol., vol. 9, No. 7, pp. 1584-1588 (2003).

Zhao, R.-Z. et al., "TNF-α induces interleukin-8 and endothelin-1 expression in human endothelial cells with different redox pathways", Biochemical and Biophysical Research Communications, vol. 327, pp. 985-992 (2005).

Zheng, X.X. et al., "Administration of Noncytolytic IL-10/Fc in Murine Models of Lipopolysaccharide-Induced Septic Shock and Allogeneic Islet Transplantation", The Journal of Immunology, vol. 154, pp. 5590-5600 (1995).

Zijlstra, M. et al., "Germ-line transmission of a disrupted $\beta_2$-microglobulin gene produced by homologous recombination in embryonic stem cells", Nature, vol. 342, pp. 435-438 (1989).

Zill, P. et al., "Beta-1-Adrenergic Receptor Gene in Major Depression: Influence on Antidepressant Treatment Response", American Journal of Medical Genetics, Part B (Neuropsychiatric Genetics), vol. 120B, pp. 85-89 (2003).

Zola, H., Monoclonal Antibodies: A Manual of Techniques, CRC Press, Inc., publ., pp. 147-158 (1987).

Zurfluh, L.L. et al., "Auxin-induced changes in the patterns of protein synthesis in soybean hypocotyl", Proc. Natl. Acad. Sci. USA, vol. 77, No. 1, pp. 357-361 (1980).

NCBI Entrez Accession No. AL592114 (gi:20386829), Clark, S., Jan. 16, 2007.

NCBI Entrez Accession No. AL592146 (gi:16973122), Tracey, A., Jan. 18, 2007.

NCBI Entrez Accession No. NC_000001 (gi:42406218), International Human Genome Sequencing Consortium, Feb. 20, 2004.

NCBI Entrez Accession No. NM_001955 (gi:21359861), Tamilselvan, S. et al., Apr. 15, 2007.

NCBI Entrez Accession No. NP_000675 (gi:4557265), Hicks, S.W. et al., Apr. 15, 2007.

NCBI Entrez Accession No. NP_001946 (gi:21359862), Tamilselvan, S. et al., Apr. 15, 2007.

NCBI Single Nucleotide Polymorphism No. rs2368564, Sep. 20, 2001.

NCBI Single Nucleotide Polymorphism No. rs6676458, Jun. 27, 2003.

NCBI Single Nucleotide Polymorphism No. rs11571092, Jan. 16, 2004.

FIG. 1A

```
   1  GGTCTTTGTAAAATAATAATTATTCATTTCACAAAAGTGATAATTAAAAGACTTTAATAG    60

61  CAATACAGAAAGTTACATGAATATAAAGACTTAACCTTTCTAAAGCTCAGTTTTCCTAAG   120

121  TAATCAAAAACCTGATAAAGATAACAAGAATGAGGAATTATCTTGAGAAAATGTAAAATC   180

181  TTTCCTTTTATTTTTTGAGACAGGGTCTCACTCTGTCATCCAGGCTAAAGTGCAGTGGCA   240

241  CAATCATAGCTCACTACAGCCTTGAACTCCTGGACTCAAGTGATCCTCCCGCCTCAGCCT   300

301  CCCCAGTAGCTAAGACTACAGGCACGCACCACCACACCCAGCTAATTTTTTCAGAGATG    360

361  GGGTCTTGCTATATTGCCCTGGCTGGTCTTGAACGAGCTTCAAGTGAGCGTGAGCCTCCT   420

421  ACCTCATCCTCCCAAAGCACTAGGATTACAGGCATGAGCCACTGTTTCCCAGCCTAAAAT   480

481  AATTGTTTCTTAGGCCAGCTACCAAAAACGCAAAGAAAAACTTTCTGTAGTGTGATTGCT   540

541  TCTTCTTATGGGAAGCCCATTTAGATAACCTGTAAGTCAAACCTGATGAAAACAATACTT   600

601  GAATGTAATCAGACACAGAAAGACTGTTCAAGGCTATGAGTAGCTGAGTCCAAGCTCGTA   660

661  TCACTTGCCACACAACAGCCAATAAGTCTAGAGACAAGGTATTGTGGCAAGGAAAGCTAC   720

721  CTTATTCAGAGAACCAGAAAACCAAGAAGATGGTGGACCAGCATCATAAAGAACCATCTG   780

781  AAGTCAGCATGAACGTTAGGCTCTTCTTTATGTTAAGGGAAGGGGAAGAAGAAGGGGATT   840

841  GGGATCAAGAGGTGACTGATGACCACAGACACCTGGGTGCCAGCAAGGGTCTGAGGACGT   900

901  TGTAAAACTTCTTTTTTCTAGGTCAGGTCACAATGTTCCTATACATCTTTAACATAACAT   960

961  TGTTATTTGTCTGTATATTTCCTTATCTCCTTGGGGGTTAGTTTGGGGAAAGGAACTGTT  1020

1021  ACCATTTTTTTAAAGTTGAACTGCAAGCTAAACTCCTATAATTAGCTGGTCTATGTACA   1080

1081  GAGCTAAGCAGAAGCTTTTAGCCTAAAGGATAATACCCCTGGGGGTCAGAGGCAAAATGG  1140
```

FIG. 1B

```
1141  AGTCAGTCATGCTAAGTCTCCCTCCACTCTCTTTCTTTTTTGAGATGGAATTTCACTCTT  1200

1201  ATTGCCCAGGCCGGAGTGCAGTGGCATGATCTCAGCTCACTGCAACCTCCGCCTCCTGGG  1260

1261  TTCAAGCAATTCTCTTGCCTCAGCCTCCTGAGTAGCTGAGATTACAGGTGTCCATCACCA  1320

1321  CACCCAGCTAATTTTTGTAGTTTAGTGGAGATGGGGTTTCACCATTGTTGGTCAGGCTGG  1380

1381  TCTGGAACTCCTGACCTCAGGTGATCTACCCACCTTGGCCTCCCAAAGTGCTGGGACAGG  1440

1441  TGTGAGCCACCATGCCTGGCCCCTCTACTCTTATAATTAAACCAGCTGTTGCTTTTCCTG  1500

1501  CCAAGAAACCAGTCATGAAGATTCACCCATGTTCTAGATGGGAAAACTGGGCTGTAGCCT  1560

1561  GGGAGAGGCCAGTCAGGGACAAAGCCAAAGTTAATATAGAGAATGGAGCTTCCAGGGTAT  1620

1621  AGGGGTTGGGTCTGGGCTAGGGAGCTGGAAACCTAGGTTTTACGCTTGTCCCAGTTTTGA  1680

1681  TGTTAGCCCTGAGCAGTGCTGTTTCTCATCAGCCTCTGCCTGCTCCAGGGGTCACAGGGC  1740

1741  CAAGCCAGATAGAGGGCTGCTAGCGTCACTGGACACAAGATTGCTTTCCCACAGCTGTCC  1800

1801  TTCCTCCAGCCCCTCTGCTCCCCATCCGGAAACCTGGGTACCCTTCACCCACCTAGCTCT  1860

1861  GTCCCGCAGTGAGATTTATTGCTGACTGCCCTGCCATCTACCCCAGGGTAATAAATCAGG  1920

1921  GCAGAGCAGAATTGCAATCACCCCATGCATGGAGTGTATAAAAGGGGAAGGGCTAAGGGA  1980

1981  GCCACAGAACCTCAGTGGATCTCAGAGAGAGCCCCAGACTGAGGGAAGCATGGATGGATG  2040

2041  GAGAAGGATGCCTCGCTGGGGACTGCTGCTGCTGCTCTGGGGCTCCTGTACCTTTGGTCT  2100

2101  CCCGACAGACACCACCACCTTTAAACGGTAATTGGTAACTCAGGCAGAGAAGGGGTGGGA  2160

2161  GGGGTGCAGGGTTCCCACCTTCCCAACACCCTGGCTTTTCCACATGCGGTGTCATTCAGT  2220

2221  CCTTACGATCAGCTGGACAGGGAAGTATGGACCTGTTCAGAGAGGTCAAGTGACTTGCCC  2280
```

FIG. 1C

```
2281  AATAAATGACACTAGTAGTCAGGTCTAGAAGCTGTGACTTTTGCTTCCTGCCCAGAGCAC  2340

2341  CATGCTAACTAAGCACTGTAGAGAACTCAGAAGTATTAGGACATGCCCCTTGCACTTGAG  2400

2401  GAGCTCACAGCCTGAATATTAAGAAGGGCATGGGTGGTTGGGCGCGGTGGCTCCTGCCTG  2460

2461  TAATCCCAGCACTTTGGGAGGCTGAGACGGATCACTTGAGGTCAGGAGTTTGAGACCAGC  2520

2521  CTGGCCAACATGGGGAAACCCCATCTCTACTAAAAATACAAAAATTAGCCGGGCATGGTG  2580

2581  GCAGGCACTTGTAATCCCCAGCTACTCGGGAAGCTGAGGCAGGAGAATCGTTTGAGCCCG  2640

2641  GAAGGTGGAGATTGCTGAGCCAAGATCGTGCCACTGCACTCCAGCCTGAGTGACAGAACA  2700

2701  AGACTCCATCTCAAAAAAAAAAAAGACGGGGGTCGGGGCATGGGTACAGTTAACTGTACC  2760

2761  AGGGAAGCAGCTTGATATCGTGGTTAAATGCAAGGCTTATAGAGTTAGATTGCCTTCATT  2820

2821  TAAATTTTGCTTCACTAGCAGAACAAACTAGGTCTGGAATCATGGGCAAGTTATTTAACC  2880

2881  TCTCCAAGTCTCAGTTTATCATTTTAAACAGGTATGATAATAACAGTACCTACTTGATGG  2940

2941  GGCTGCTTTGGGGATTTTAGGAGATAAGGCATAGAAAGCTGGGCACGTTGTAAGAGCCCA  3000

3001  GCTACTGTTAGTACTACAGGATAGATTCTTACAAATATCAAAAGCAAGGTTTGGCCGGGA  3060

3061  GCAGTGGCTCACGCCTATAATCCCAACACTTTGGGAGGCCGAGGGGGGCAGATCACCCGA  3120

3121  GGTCAGGAGTTCAAGACCAGCCTGACCAACATGGAGAAACCCTGTCTCTACTAAAAATAC  3180

3181  AAAATTAGCCGGGCGTGGTGGCACATGCCTGTAATTCCAGCTACTTGGGAGGCTGAGGCA  3240

3241  GGAGAATCGCTTGAACCTGGGAGGCTGAGGTTGCAGTGAGCCGACATAGCGCCATTGCAC  3300

3301  TCCAGCCTGGTCAACAAGAGCAAAACTCAGTCTAAAAAAAAAAAAGAAAGAAAAAAACAA  3360

3361  GGCTTTAGGTAGCCCACAATTAGAAGGAGAAAACCTTAGCATCCCCTAGGTGCCAGGCCT  3420
```

FIG. 1D

| | | |
|---|---|---|
| 3421 | TGTGGGAACAAGTGATTCATTAAGACTGTAGAAGGAAGCTGGGCACGCGGCTCATGCTTG | 3480 |
| 3481 | TAATTCCAGCACTTTGAGAGGCTGAGGTGGGCAGATCGCTTGAGCTCACGAGTTCAAGAC | 3540 |
| 3541 | CAGCCTAGGCAACATGGTGAAACCTTGTCTGTACAAATACAAAAATTAGCTAGGTGTGGT | 3600 |
| 3601 | GGTGCAAATCTGTAGTCCCAGCTACTCGGGAGGCTGAGGTGGGAGCATCACTTCAGCCTG | 3660 |
| 3661 | GGAGGTGGAGGCTGCAGTGAGCAGAGACTGACCCACTGTGCTCTAGCCTGGGTGATAGAG | 3720 |
| 3721 | CCAGACCTTATGTAAAAAAAAAAAAAAAAAAAAAAAGACTGAAGAAGGGGAAGAGACAG | 3780 |
| 3781 | CATTTGAGAAAAGGCCTCACAGAGAAAGGGGTTTTCAATCTGGGACAGCAGATATGACC | 3840 |
| 3841 | AGCAGTCCTGAAGGTAGGGAGGCACACTTTAATAATGGTAATAGTTGCTAAGCCTATAAA | 3900 |
| 3901 | ATGCTTAGGGTGTCACAGGATCTTTTCACATGTCTCATCTCAAGTCATGCCCCCAACAAC | 3960 |
| 3961 | TCAGCATTCCCACTTTGCAGATGAGGACACTGAGGCTCAGGGAGGTGATATGTAAGAGGC | 4020 |
| 4021 | TAAGCCTCAACACACACTGGGCCTTTTGCTTCCGAAACTGCTTTCCCTTGCTCTGAGGCT | 4080 |
| 4081 | CTCGGAGAGTAATTGCTGGGTTGTGAGCACTGGGTAAGAGGATGGGTGCTTCAAAGCAGC | 4140 |
| 4141 | TGCACTCCAGGATAAAGGTAGAGGAAAGTAAAAACATCTTCCCCTGCTGTTATCCAAAAG | 4200 |
| 4201 | AGAAAAAGAATGGAATTGGGCAAGGGGTGGAGGGGGAATCCAGCTTTTGAAACAGTATTA | 4260 |
| 4261 | TAGGAATTTTGCTACCCGCTATGTGCAGAGCATCATGCGAGGCACTTGGGACAGCTGAAT | 4320 |
| 4321 | GAATGAGCTCCATTCTCAAGGTGAACATGTACATATACACACCTACAATTTACATTTATT | 4380 |
| 4381 | GAGCAGTGGTCGCATGGTTTCATCTGCACAGTGACTCTGAGGTAGGTACTACCATTAGGC | 4440 |
| 4441 | CCATTGTTAGAGAGGGGTTAATGGAGACTTAGAAGAGGCCCAGAGAGGTTAGGTAGCTTT | 4500 |
| 4501 | CTCAGAATCACATAAGTGGTAAGGGGATTCAGGCATGCCCCCTGCAACCACTGTCTTCAC | 4560 |

FIG. 1E

```
4561  CACCGTACGGCACCAGTTCCACAAGCTGTACAGTGTGGGCTGTGAGACCCAAGGAAAAAC  4620

4621  AGAGCTGAGGCCCACGGGAAGGTGAGGCCGGTGTGGGCTGGAGGCCTTGGGGTAAGCTTC  4680

4681  CTGGAGGTGGGGGTACATGTTGGGCCTTGGAGGACTAAAGAACTGGGGGGAAAAGGAAGG  4740

4741  GAAGAAGGAAAGGATTTTCTGAAAAGGAAATGGCAAGAAGTAAAGGTCCAAAGCATAGGC  4800

4801  TGTTGTGAGTAAACAGTGGGAAATGCAACCTCTTTGGGGCCAAACCTCTGACCCTCCACG  4860

4861  TTCCCAGCTGTGAAGTGGGAGTAATAAAATCATCCACCTTATGAGAGCAAATAAAATAAT  4920

4921  GATTGTGAAAATATTTTGGTAACAGTAACCTGTGATAGGAAGATAACAAATCATTTCTGT  4980

4981  TACAATACCATGCTGATAGGCATAAAAGTTGCATTCATGTTCATGGGCAAAATGGGGGTA  5040

5041  AGTAGAATGCATGGGACGCAAGAAGGATGTAGGAAGGAAAGGGTAGTGTGAGTATAGGAG  5100

5101  GACTAGCCACTGAGAAGAAAGTAGAAGAAAGAGGGAATCTTTGTGTGTATGGGAAAGTCT  5160

5161  ATTGCAGAGTCAACTTGGGCTTCCATCCTGGGACCTTCCCGTGAACAGCTAGAGACATCT  5220

5221  TCCTCTGGGCTTTGGCAGCCTTTATGTCGGGACCCAGGGGACCCTATATGGGAAATAGGG  5280

5281  CCAGACACATGCTCTGAATCCCTGCTTCAACATTTCTGAGTCACCTTTGTCCCTGTGAGC  5340

5341  CTTCATTTTCTCATCTATAAAATGGATGACAGCTAGCTTGTTGGTGTGATTTCAGTAGC  5400

5401  GGCTCAGTAGAGTCAGTTTCCTAGGTCTCTTTAATTCTGCCTCTCAAAGGTGATGGGAAA  5460

5461  ACATCTAGACAAGAAGCCAAGGGACCGGGACACATCTCTCCAAGGACGAGGTGCATGGCG  5520

5521  CTCTGAAGATGCTGGCATCTCTCTAGGCCCAACCCAGCTCAGGGGTCCACTCCACCACA  5580

5581  GCCCTGGCTGGGTGCCTGTCCCCTGGTATCCTGGAGACCTTGCAGCTGCTGTGGGCATCT  5640

5641  GCTGCCACCTAGCGGCCTCCCATGGCACTGTCTCCCCGCCAGCCCCTAGTTTTGACAGGG  5700
```

FIG. 1F

```
5701  GCACTCCCTGGCATTAATCTCTTCAGAGGGAATGTCTGTGCCTGTTTCCTGTCTGTCCTC  5760

5761  CCGCCAGGTGGAGTTCCTTAAAGGCAGTCATGATCATTATCTTTCTAGCTCCAGTGTCCA  5820

5821  GCACAGTGAGGCACAAAGTAGTTGTTCAGCAGGTGATTACGGAATAAATGAATGAACGGA  5880

5881  CCAATAAACAAATAGCCTTGTCTAATCAAAATTAGGCAACAGAAGGAAGTCACTTCAGGG  5940

5941  TTATTTAATCCCCGGGCAGCTGACTCCTCTAAATTGACTCTTGACAAGAAGTAACTCTTA  6000

6001  TAAATGCTCCAGAGGCCCTCAGCGACAGAGGTGATTTCCAGGTGGCTGGGCTAACGTTAA  6060

6061  AGGTGGTTGTACTAAAAGCAGGGGTTTGGCCTCAGGGACTCCACCACTGTGGTGGAGGTA  6120

6121  CAGCACTTTTCTATTTTTGCTTCCTCCACCCTGGGCCAGGATCTTCCTCAAGAGAATGCC  6180

6181  CTCAATCCGAGAAAGCCTGAAGGAACGAGGTGTGGACATGGCCAGGCTTGGTCCCGAGTG  6240

6241  GAGCCAACCCATGAAGAGGCTGACACTTGGCAACACCACCTCCTCCGTGATCCTCACCAA  6300

6301  CTACATGGACGTGAGTGCTTGGCTCAGCCCCTCGCTCCCTCCCTGTCTCCTTTCCCTCAT  6360

6361  GGACCTAGGGCTTTCTTTGCTGCAAGACTCACCCTTTCCAAGCTGTGTTTGACGAAGGCG  6420

6421  CTGAGTAGCACGTGAGCACCCTAGAAAATTCCCATTTTCCAGCTGGAAAGCCTGAGCACA  6480

6481  GAAGACAGGAAGGCATCCAGGGGCCATTCAGGGGCAGGGTTAGGTTTGGAACTCAGCCCA  6540

6541  GGCCTCAAGCCAGGTGTCACAGGTGGGTGGGAAGGGGTGTGTGACTCAGGTGGGGGTTTC  6600

6601  TGTGACCTGGCCCAGCACAACCTGATGGCTTCCTGCCCCAGAGGATCCTCAAGAGTCAAG  6660

6661  TTTGCTTCCTGCTTCATTCTCAATGTTTTGATTTGCCCTCTTGTCTTACTGAGACTCCC  6720

6721  ACTTTCTGGGATGCCATGGGGAGATGCTAAGCCTCCTACCAGTTCCTGCAGGAAAATGGA  6780

6781  AACCCCGAGAGGCTATAGGACCTCGCCTGGGCCAAGTCTCACACCGAGAGCCAAGAGTGA  6840
```

FIG. 1G

```
6841  AGCCAGGCAAGACCCCAAGACCCAAGGTCCCCTGAGCCCCTCCAGCCCTCTCTTTTTACC  6900

6901  CCCACAGACCCAGTACTATGGCGAGATTGGCATCGGCACCCCACCCCAGACCTTCAAAGT  6960

6961  CGTCTTTGACACTGGTTCGTCCAATGTTTGGGTGCCCTCCTCCAAGTGCAGCCGTCTCTA  7020

7021  CACTGCCTGTGGTGAGACCTAAGACCCACAGTGCCTCTCCTCCATCCCCCTGCCCTACTG  7080

7081  TGCATGAGCAATCCTGCCCAACACCCAGCTCCCATCCCTCTTGCCACCAAGGGAGTGGCT  7140

7141  TCCTCTCTGCCTCTGTGCCCACTGACATGTAGGGGAGAGGGGAAGATGTCTCCCGTTTTT  7200

7201  CTGATACAGCCACCAAGGTTAAAAACAAAAAAAGGTCCAAGAACCCCTGAGCACCCAGAA  7260

7261  GGCCACTTCCCAGTCTTCCTGAGATTGAGACAGGACTGAATTCTCAAACCCATCCCAGGC  7320

7321  ACTCGGAACTCTTCCATCCCTAGTCTTAATCAACAACCTCTTACTAGGCACTTACTCTGT  7380

7381  GCCTGGCATCTTCTCTGGTGTTATCAGTGTTAGTGATTACTTTAAATTCCTTCATTTAGG  7440

7441  ACAAAATTCTCGATGTATGGGCACATTAGGAGAGCCCAAGAAACCCAGTCCTTGATTGAT  7500

7501  GAAGCACATATTCCAAGCCCCCTGACCCTAGGGCCACTCATCCCTGCACCTAAGCTAACC  7560

7561  AGCCATACCCACAATGCACCCTGCCTCTGAGTCCCCCTGTCTGGGCCACTCTTGGACAAA  7620

7621  CCTGAGCCTCTGTCCCCCTGCCAGTGTATCACAAGCTCTTCGATGCTTCGGATTCCTCCA  7680

7681  GCTACAAGCACAATGGAACAGAACTCACCCTCCGCTATTCAACAGGGACAGTCAGTGGCT  7740

7741  TTCTCAGCCAGGACATCATCACCGTAAGTTGGGCCGCCCTAGGTCATCTGCCCCGGACCC  7800

7801  CTTCTGTCCCCAGGCCTCTCCTGACCCTCCAGGGCCCACACCTGCGGGGAGGTACACTGC  7860

7861  AGCCCACTTGGAGCCTGGGGAGCTGAGGAACACCCTACTCTGCCACATCTGGCTGTTGCT  7920

7921  GCAAAGCAGCAGTACCTATGGGGAGCAAGCCTGGGCTACGGGCTCACCGTTGGGTGGTT  7980
```

FIG. 1H

```
7981  TGTGGATGTTTTTGCATCTAACTTGCATGTAGGGCTTGTCCTGAGCCCCGTGGCTGCAGT  8040

8041  CAAGTAACTCGTCCAAGTTCACCAGCTCTGACTGGGCTACACCCTAGACTGAAATCCAGG  8100

8101  GTCAGAGTCAGGCTGAGTTTTAGGGTCAGGCATAGGTTTTAAGGTCACAGTTGAGGTTGA  8160

8161  CTCTGGGACTCAGGTCAAGGCCTGCTTTTCTTTTCCATGTGGCCCATGTCTGACCGTTTC  8220

8221  CTCATCCTGGAGTTTCTCAGGCCCTGCTCCATCAGAGTTAGGGGAGGGGCACACGTGGCA  8280

8281  CCTGAGAGGAAATCAGGGTGATTCCTGCCTCCCTTCCTTTTCTGTGAACTCAGATATAA  8340

8341  AGGAGGGAGAAGGGCAAGCTTGTCTGTGCTAAAGAAACCCTTCGCCCATGATAAGGGTGG  8400

8401  GGGCCAAGACCCAGTCCTGCCAGGCACGAAAGTCTGGCCACTGGGGAGGGGAGGAGCTCT  8460

8461  TGGCAGCTTTTCTTTTGCTGCTTGGCAGGACCACCCTCTCAGCCTCTGCTCTCCGATCCC  8520

8521  TGGTCAACTCTAGCTCTCTCTGGGCTCCGCAGCAGAGATGTGTATTGGCACAGAGTGTGT  8580

8581  GCGTGCAGGGTTGAGGAAATACTCTTACCCCGATTTCTGTACCCTGGAGCATGTGTGCCC  8640

8641  CTGGGATCCCTAGTGTGGAAGCCCAGACCAGACTCCAACCAAGGAGTGGGCAGTGGGCTT  8700

8701  GGTCTCCTCTGGTCCTTCCTCCCACAGGTGGGTGGAATCACGGTGACACAGATGTTTGGA  8760

8761  GAGGTCACGGAGATGCCCGCCTTACCCTTCATGCTGGCCGAGTTTGATGGGGTTGTGGGC  8820

8821  ATGGGCTTCATTGAACAGGCCATTGGCAGGGTCACCCCTATCTTCGACAACATCATCTCC  8880

8881  CAAGGGGTGCTAAAAGAGGACGTCTTCTCTTTCTACTACAACAGGTGGGGACTGGGACTC  8940

8941  CAAGGGCTGAGGTGGGGGGACAGGAGGGGAGAAGAGATGGGGAGTGGAAGGAGAGTCTGG  9000

9001  GCCAGAATTGTAAAGTGTTTGTAATTAGGTGACAGCCAATCAATATCTAGAGCTGTACTA  9060

9061  GCCAATATGGAAGGCACTATTGAAATTTAAATTAATTAAATACAGTTAAGCATCAATTAA  9120
```

FIG. 1I

```
 9121  GCATTCAACTGGTGGCTCTTAGTTGTACTAGCCACACGTCAAATGCCTGGCAGCCACGGT   9180

9181  GGCTAGTAACTACAGTCTTATGACAGTGCAGATAGAGAATATTCCCAGCATGACAGGACA   9240

9241  TTCTAATAGACAGCGCCACTCTGGAGCAAGAGGAGATGCAAGGTGGGGGCGATGGTAAAT   9300

9301  AAGGGATTACTGTGACCTGTAGCCCTGCCTGTTAGGGCCATGGCTCCTCCCACACAGAGA   9360

9361  CAGCCAACTTCAGTCATCCATTAGATCCTTCATTCGTTTGTTTGCTCACTCATCAGTTCA   9420

9421  GTAAATGCTATGTGCCAAGCACTGTGGTAGGCTCTGGGGGTGCAGCAGTGAACACAGTGA   9480

9481  ACAAGGCAGAATCTGTACTCCCCTACCCACATAGAGCTTACAGGCTAACAGGGAAGACAA   9540

9541  GACATATTCCAACATAAAGAGTGTCACAGGCAGGCAGCAAGTGTGGTGCTGAAAACCATG   9600

9601  GATGCTTTTCAATTCTAGGCTGAGCTTATATGCAGCTCAGCCAGCCTTGGGGAAGCTCTT   9660

9661  GAGCAGGGTTGGGCTCTACTCCAAACTGCTGGGCTTAGAAAGATGGCATGAGTTGGAGAC   9720

9721  AAGAGAGCTGGAGGCAAAAGGGGCTGGGTGCAGTGGCTCATGCCTGTAATCCCAGCACTT   9780

9781  TGGGAGGCCAAGGCGAGAGGATCGCATGAGCCCAGGAGTTAAGGCTTCAGTGAGCAGTGA   9840

9841  TTGTGCCACTGCACTCCAGCTAAGGCAACAGAGTGAGATCCAGTCTCAAAAAAAAAAAAA   9900

9901  AAAAAAAAAAGTCACAAGGGTAAGAACATGAGGCCAGTGGCAAAAAGAATAGAGGAGAG   9960

9961  GATCAGAGTTCAGAGAAATCTCACAGTAAAATGGAGAGGAGTCTCCGGTTTGGTGATAGA  10020

10021  AAGTGAGGCCTTGAGAAAAGGCCAATTGGCGGCTCTGCATTCAGGGGTGGTCTTTAGAAG  10080

10081  AACTGTTTTAGAGGAAGTGGGGGCAAGGCCAGATGGCAAGAAGTTAAGAGGTGGACGACG  10140

10141  TGGGTGTCAGGAAGTGGAGGTCATGAGATGTAGGCTGCCCTGGGACATTCAACAGGGAAG  10200

10201  GGAATGGGGGGTGGCGTGGGGGGTGAGATCCAGAAGCAGAAGAGGAAGGGTGGGTGTTTT  10260
```

FIG. 1J

```
10261   TAAATGCTAGAGGATGCTCGAGTGATGCCTGTAGGTGGAGGAAGAAGCCAATGGAAAGAA   10320

10321   AGAGATTAAAAATGTGGAAAGAAGAGGAGCTAAATGGGGCACTGGAGTTTGGAGGCCTT    10380

10381   GAAAGAGATGAGGTTCCAGCAGACAGGAAGAAGCCAGGTTTTGCAGAGGAGAGGGCTGGC   10440

10441   CTCTTCTTTTATCTTGGGATGGGAAGGAGGGAACATCCAGAGAGATACTGAAGTGTTGAG   10500

10501   AGACAGGCAGGAGGGAATTTGTGCTAGCATATACACATACATTCCGAATTTATAAAAACA   10560

10561   CAAGTAGTTTGCAGTTGCACAAAATAACATATGCACACCTACACACCCATGCACACATGT   10620

10621   GCATGTGTGAATTCTAGTATGAATTCTGGAAAAACACATCACACACACAGGCATGCCCTG   10680

10681   GAGACTAGGCCTACAGTAGTCCCTGAGCCAAGTGCAGTGAGGAGGAAAGGAAGGTGAGGG   10740

10741   GAATCAGCTCCAGACGGGGCACCAGGAGCCTGGCTCCAGTCCCCCACTTGTTCACTCATG   10800

10801   GACTGGGTAACTTCAGGCAAGTGACTTCGCCTCTTGGTGACTCCATTGCCTGAAGGGCAA   10860

10861   AGAGAGTACATAACACCCACCCTGCCAAACAGCAGGGCTGATGAGGCTGGCATGAAATGA   10920

10921   AGCTTCCTTTCTGCTGTCTCTCTTTCTCTGCAGAGATTCCGAGTAAGGAGACAAAACCCC   10980

10981   CACATGGCTGTGACCTTCCAGTACTCCCCGAGCACCTGACCTAGAATTACACACGCCACC   11040

11041   GGCCCAAAACTCACATCAGCAAGCCCAGCCTCCGCTAGATGCCGAAGTTCTCTGTCTCTC   11100

11101   CTTCCTGCTCTCTCCATGCCACCTGCCCACCCCATACCCAATAGCCTCCCCAGGGTCCCC   11160

11161   TCCCATGCACCTGCTCAATCAGCAGCAACCCAAGAGTGAGGGTGTCCATTTGTGTCTTG    11220

11221   TTCACATCCACTCACTGTCCTTGTACCTGCTCCTTTTCTGTGACCTCTCTGGGGATGCTT   11280

11281   TTTGGGGGAACAGCTGGACTACCCTGGAACAACCTCTGGTTGGTCTTGGGGAGGGGAAGA   11340

11341   AAGGCAGAGAAGCAGTATGTTCTGCATGCTTCCCAACGACAGCTCCGAGCCTGGCTGTCT   11400
```

FIG. 1K

```
11401  GTCCCACATTCCTCTGCTCTAGAGCCCTCTGTCCTCCCCTGCACCCTTGTGCAACCTTCC  11460

11461  CCAATTGCCTGAGTTGCTGGGTCCTGGAGGTTATGGGTTTCCAAGAGCTTCTGATCTTTC  11520

11521  CTTTAGGAATTCCCAATCGCTGGGAGGACAGATTGTGCTGGGAGGCAGCGACCCCCAGCA  11580

11581  TTACGAAGGGAATTTCCACTATATCAACCTCATCAAGACTGGTGTCTGGCAGATTCAAAT  11640

11641  GAAGGGGTCAGAAATCCTCAACCCTCCCCGGGCTCCAAAAAATGCTGCCGTCACTGGGGT  11700

11701  TGGGCAGGGTGGGGAAGGACTGCATTACCATCCTGCCCTCTTTCCAAATGCAGCCACTTC  11760

11761  TTAAGCACAGCCACCATTTGCTCTCTGCCTGCTCTGTCCAGGCTGGGAACAGAGAAGGG  11820

11821  AGGGGCCTGGGGAGAAGTGGTGGAGGGTGACAGTACCTTCCCTCCTCTACTCACTGCCTC  11880

11881  AACAGGCCACCAGCGTGGCCTCCACCCACCCACCCACACTCAGGAAGGACATGCAGCCTG  11940

11941  GAGGTGCCCCATCAGCCTTCTGTCTGTCTGTCTGTCTGTCTGTCTGACTGTGGCCTCCCC  12000

12001  CAGGGTGTCTGTGGGGTCATCCACCTTGCTCTGTGAAGACGGCTGCCTGGCATTGGTAGA  12060

12061  CACCGGTGCATCCTACATCTCAGGTTCTACCAGCTCCATAGAGAAGCTCATGGAGGCCTT  12120

12121  GGGAGCCAAGAAGAGGCTGTTTGATGTAAGAAGCCAAAGAGGGAAGGTGCTGTGGGTGGG  12180

12181  GGGAGCGCCACCTGGTATCGGCTCACAAATCCCCAGGCAAATGAGGCCATCTCAGGCCT  12240

12241  TCGCTTGTTCACCTCACACTCTCCACACATGTGGCTGGTCACCCATGGGGCGGGGCACTG  12300

12301  TCCCCAGCCCTCTCCAGCAGAGAGACCAGGCCACCAGCGCAGGACTCCTTGTCTGCTGAG  12360

12361  ACGTCTTCCATACTCAAGAAGGCTCTCTTTGCCCCCCACCCCAGTATGTCGTGAAGTGTA  12420

12421  ACGAGGGCCCTACACTCCCCGACATCTCTTTCCACCTGGGAGGCAAAGAATACACGCTCA  12480

12481  CCAGCGCGGACTATGTATTTCAGGTGAGGTTCGAGTCGGCCCCCTCGGTGGCAGGGAGAA  12540
```

FIG. 1L

```
12541  AGGCTGGACAGAGACCCTCAAAGAGTGACAGATTACAATGCACAGgTCATGTTAGAACTG  12600

12601  TAGTTCTCAAACTTGGCTGTGCATGTCACCTGGAGAGCTTTGAAAAATCCTGGTACCTGG  12660

12661  GCCACATCCCATACCTATTAAATCAGAACCTCTAGAAGTGGCACCTGGGGTTCAGTTTCC  12720

12721  CCAGGTGATTCCAATGTGTGGCCATGTTTGGGCATCACTATGCCTGTTCCCTCATCTCCA  12780

12781  TTTTCTCATCAAATACTCCCAAGAATCCTATGCTCCTATATTCTTACCCTCTTTTCATAA  12840

12841  TCAATAGGCTTAGAGAAGTTGAATAACTTGTCTAGGATCAGAAGCTAAGGCAAACTGTAA  12900

12901  GCTCCTGAAGGAAGCACGGTGCCTGATGCATTGTTTGCCTGGGATCTAGCACAGGGGCTA  12960

12961  AACATAGGAGTGGTGCAGTCCACGATGGGGCAAAATGGCCATGATGTGAGGGAGGCCCAG  13020

13021  TGTGGCTAGGGGAGAGATGGGGGCGAGAGGGGGAATGTTGCTGAAGACAGTTGCTGGGGG  13080

13081  TCAGGCAAGGTGAAAGGAGAATGCTCATGTGCTGGGTATGGAGAAACTCTCCCCCTTCCT  13140

13141  GCCAGGAATCCTACAGTAGTAAAAAGCTGTGCACACTGGCCATCCACGCCATGGATATCC  13200

13201  CGCCACCCACTGGACCCACCTGGGCCCTGGGGGCCACCTTCATCCGAAAGTTCTACACAG  13260

13261  AGTTTGATCGGCGTAACAACCGCATTGGCTTCGCCTTGGCCCGCTGAGGCCCTCTGCCAC  13320

13321  CCAGGCAGGCCCTGCCTTCAGCCCTGGCCCAGAGCTGGAACACTCTCTGAGATGCCCCTC  13380

13381  TGCCTGGGCTTATGCCCTCAGATGGAGACATTGGATGTGGAGCTCCTGCTGGATGCGTGC  13440

13441  CCTGACCCCTGCACCAGCCCTTCCCTGCTTTGAGGACAAAGAGAATAAAGACTTCATGTT  13500

13501  CACAGCCTGTTGCATCTGGGTTCACTAGGGTTTAGAACAGAGGGAGGGGCTGCGTGATCA  13560

13561  TGTGTGGACAGGAATGTGACACAGACAAGCTACACATTCGCCTAGCGCACAGGTTCTTGC  13620

13621  GTGCAGGGATGATGCCATCCATCTGCCATCAACGGGACTCAGGTGGAGCTGTTTACACAA  13680
```

FIG. 1M

```
13681  CCTCAGGTGGGAAGTCTGAAAAGAGCCGGAACCAAGCTCCCTCTAGTCCCTCAGGGACCA  13740

13741  AGGCTAATGCTGTGGCAGTAGACTGTGGGTCAGAAAGTTCTCCCAGCTCACAGAAGCCAG  13800

13801  CTCTGAGTTCAGACTCTGCTCTGCTGAGCTAGTCAGCCCTGTCTCTTGTCCCTGCAAAAC  13860

13861  TCCCCTCAGCTGTCCTTATCCACTGCAGATGCCCCCGCCCTGCCCCATGTAGCCATTTAC  13920

13921  ACAGGCATTCTAAGGCACTACCACCTAAAATCATAGAACACCAGAGATCCAGGCAATACT  13980

13981  TCCACTTTACAGGTGGGGAAACTGAGGCCCAGAGAATGGAAGGCCTTGCCCAAGATTACT  14040

14041  CGGTCAAGAATCAAGTAGTGAAGAATACTGAAAGATAGTGAAGAATCAAGACTGGAACCC  14100

14101  AGCCCGTCTGACTTGGGTCCTGGGGGTTTCCACCTTATCATAAGCAGTTGGTACCGTCAT  14160

14161  AAGTACAGTGCTTCACGCACGCTGGTACAGGGCCACGTGCACAAGCACACAGGTGCACAC  14220

14221  ACACACTGCTATCCTCCATCCCATCCACCTGGGACTCGTCAGGCTGAAGTCTCTTCTCCC  14280

14281  ACTCTCACTCCTTGGGCTGTCTTCAGGGCACATGTAACTTGGGGAATGAGAAATTAGCAT  14340

14341  CCACCTGGAGCCACTGAAGCCATCCCTCTTCACCATAGTTGCTCACCTCTCTTTTGACAG  14400

14401  AAAGTCGTGAGGCACTGAATGGCCCAACCAGGCCCTCAGTACCTCTGGGAGCCATCTGCA  14460

14461  AGAGTCCCTGTGTAGCGCCAAGAGCCGGAGCCTGGGCTTCAGG  14503
```

FIG. 2A

```
   1  GGTCTTTGTAAAATAATAATTATTCATTTCACAAAAGTGATAATTAAAAGACTTTAATAG    60

61  CAATACAGAAAGTTACATGAATATAAAGACTTAACCTTTCTAAAGCTCAGTTTTCCTAAG   120

121  TAATCAAAAACCTGATAAAGATAACAAGAATGAGGAATTATCTTGAGAAAATGTAAAATC   180

181  TTTCCTTTTATTTTTTGAGACAGGGTCTCACTCTGTCATCCAGGCTAAAGTGCAGTGGCA   240

241  CAATCATAGCTCACTACAGCCTTGAACTCCTGGACTCAAGTGATCCTCCCGCCTCAGCCT   300

301  CCCCAGTAGCTAAGACTACAGGCACGCACCACCACACCCAGCTAATTTTTTCAGAGATG   360

361  GGGTCTTGCTATATTGCCCTGGCTGGTCTTGAACGAGCTTCAAGTGAGCGTGAGCCTCCT   420

421  ACCTCATCCTCCCAAAGCACTAGGATTACAGGCATGAGCCACTGTTTCCCAGCCTAAAAT   480

481  AATTGTTTCTTAGGCCAGCTACCAAAAACGCAAAGAAAAACTTTCTGTAGTGTGATTGCT   540

541  TCTTCTTATGGGAAGCCCATTTAGATAACCTGTAAGTCAAACCTGATGAAAACAATACTT   600

601  GAATGTAATCAGACACAGAAAGACTGTTCAAGGCTATGAGTAGCTGAGTCCAAGCTCGTA   660

661  TCACTTGCCACACAACAGCCAATAAGTCTAGAGACAAGGTATTGTGGCAAGGAAAGCTAC   720

721  CTTATTCAGAGAACCAGAAAACCAAGAAGATGGTGGACCAGCATCATAAAGAACCATCTG   780

781  AAGTCAGCATGAACGTTAGGCTCTTCTTTATGTTAAGGGAAGGGGAAGAAGAAGGGGATT   840

841  GGGATCAAGAGGTGACTGATGACCACAGACACCTGGGTGCCAGCAAGGGTCTGAGGACGT   900

901  TGTAAAACTTCTTTTTTCTAGGTCAGGTCACAATGTTCCTATACATCTTTAACATAACAT   960

961  TGTTATTTGTCTGTATATTTCCTTATCTCCTTGGGGGTTAGTTTGGGGAAAGGAACTGTT  1020

1021  ACCATTTTTTTTAAAGTTGAACTGCAAGCTAAACTCCTATAATTAGCTGGTCTATGTACA  1080

1081  GAGCTAAGCAGAAGCTTTTAGCCTAAAGGATAATACCCCTGGGGGTCAGAGGCAAAATGG  1140
```

FIG. 2B

```
1141  AGTCAGTCATGCTAAGTCTCCCTCCACTCTCTTTCTTTTTTGAGATGGAATTTCACTCTT  1200

1201  ATTGCCCAGGCCGGAGTGCAGTGGCATGATCTCAGCTCACTGCAACCTCCGCCTCCTGGG  1260

1261  TTCAAGCAATTCTCTTGCCTCAGCCTCCTGAGTAGCTGAGATTACAGGTGTCCATCACCA  1320

1321  CACCCAGCTAATTTTTGTAGTTTAGTGGAGATGGGGTTTCACCATTGTTGGTCAGGCTGG  1380

1381  TCTGGAACTCCTGACCTCAGGTGATCTACCCACCTTGGCCTCCCAAAGTGCTGGGACAGG  1440

1441  TGTGAGCCACCATGCCTGGCCCCTCTACTCTTATAATTAAACCAGCTGTTGCTTTTCCTG  1500

1501  CCAAGAAACCAGTCATGAAGATTCACCCATGTTCTAGATGGGAAAACTGGGCTGTAGCCT  1560

1561  GGGAGAGGCCAGTCAGGGACAAAGCCAAAGTTAATATAGAGAATGGAGCTTCCAGGGTAT  1620

1621  AGGGGTTGGGTCTGGGCTAGGGAGCTGGAAACCTAGGTTTTACGCTTGTCCCAGTTTTGA  1680

1681  TGTTAGCCCTGAGCAGTGCTGTTTCTCATCAGCCTCTGCCTGCTCCAGGGGTCACAGGGC  1740

1741  CAAGCCAGATAGAGGGCTGCTAGCGTCACTGGACACAAGATTGCTTTCCCACAGCTGTCC  1800

1801  TTCCTCCAGCCCCTCTGCTCCCCATCCGGAAACCTGGGTACCCTTCACCCACCTAGCTCT  1860

1861  GTCCCGCAGTGAGATTTATTGCTGACTGCCCTGCCATCTACCCCAGGGTAATAAATCAGG  1920

1921  GCAGAGCAGAATTGCAATCACCCCATGCATGGAGTGTATAAAAGGGGAAGGGCTAAGGGA  1980

1981  GCCACAGAACCTCAGTGGAT<u>CTCAGAGAGAGCCCCAGACTGAGGGAAGCATGGATGGATG</u>  2040

2041  <u>GAGAAGGATGCCTCGCTGGGGACTGCTGCTGCTGCTCTGGGGCTCCTGTACCTTTGGTCT</u>  2100

2101  <u>CCCGACAGACACCACCACCTTTAAAC</u>GGTAATTGGTAACTCAGGCAGAGAAGGGGTGGGA  2160

2161  GGGGTGCAGGGTTCCCACCTTCCCAACACCCTGGCTTTTCCACATGCGGTGTCATTCAGT  2220

2221  CCTTACGATCAGCTGGACAGGGAAGTATGGACCTGTTCAGAGAGGTCAAGTGACTTGCCC  2280
```

FIG. 2C

```
2281  AATAAATGACACTAGTAGTCAGGTCTAGAAGCTGTGACTTTTGCTTCCTGCCCAGAGCAC  2340

2341  CATGCTAACTAAGCACTGTAGAGAACTCAGAAGTATTAGGACATGCCCCTTGCACTTGAG  2400

2401  GAGCTCACAGCCTGAATATTAAGAAGGGCATGGGTGGTTGGGCGCGGTGGCTCCTGCCTG  2460

2461  TAATCCCAGCACTTTGGGAGGCTGAGACGGATCACTTGAGGTCAGGAGTTTGAGACCAGC  2520

2521  CTGGCCAACATGGGGAAACCCCATCTCTACTAAAAATACAAAAATTAGCCGGGCATGGTG  2580

2581  GCAGGCACTTGTAATCCCCAGCTACTCGGGAAGCTGAGGCAGGAGAATCGTTTGAGCCCG  2640

2641  GAAGGTGGAGATTGCTGAGCCAAGATCGTGCCACTGCACTCCAGCCTGAGTGACAGAACA  2700

2701  AGACTCCATCTCAAAAAAAAAAAGACGGGGGTCGGGGCATGGGTACAGTTAACTGTACC  2760

2761  AGGGAAGCAGCTTGATATCGTGGTTAAATGCAAGGCTTATAGAGTTAGATTGCCTTCATT  2820

2821  TAAATTTTGCTTCACTAGCAGAACAAACTAGGTCTGGAATCATGGGCAAGTTATTTAACC  2880

2881  TCTCCAAGTCTCAGTTTATCATTTTAAACAGGTATGATAATAACAGTACCTACTTGATGG  2940

2941  GGCTGCTTTGGGGATTTTAGGAGATAAGGCATAGAAAGCTGGGCACGTTGTAAGAGCCCA  3000

3001  GCTACTGTTAGTACTACAGGATAGATTCTTACAAATATCAAAAGCAAGGTTTGGCCGGGA  3060

3061  GCAGTGGCTCACGCCTATAATCCCAACACTTTGGGAGGCCGAGGGGGGCAGATCACCCGA  3120

3121  GGTCAGGAGTTCAAGACCAGCCTGACCAACATGGAGAAACCCTGTCTCTACTAAAAATAC  3180

3181  AAAATTAGCCGGGCGTGGTGGCACATGCCTGTAATTCCAGCTACTTGGGAGGCTGAGGCA  3240

3241  GGAGAATCGCTTGAACCTGGGAGGCTGAGGTTGCAGTGAGCCGACATAGCGCCATTGCAC  3300

3301  TCCAGCCTGGTCAACAAGAGCAAAACTCAGTCTAAAAAAAAAAAGAAAGAAAAAACAA  3360

3361  GGCTTTAGGTAGCCCACAATTAGAAGGAGAAAACCTTAGCATCCCCTAGGTGCCAGGCCT  3420
```

FIG. 2D

```
3421  TGTGGGAACAAGTGATTCATTAAGACTGTAGAAGGAAGCTGGGCACGCGGCTCATGCTTG  3480

3481  TAATTCCAGCACTTTGAGAGGCTGAGGTGGGCAGATCGCTTGAGCTCACGAGTTCAAGAC  3540

3541  CAGCCTAGGCAACATGGTGAAACCTTGTCTGTACAAATACAAAAATTAGCTAGGTGTGGT  3600

3601  GGTGCAAATCTGTAGTCCCAGCTACTCGGGAGGCTGAGGTGGGAGCATCACTTCAGCCTG  3660

3661  GGAGGTGGAGGCTGCAGTGAGCAGAGACTGACCCACTGTGCTCTAGCCTGGGTGATAGAG  3720

3721  CCAGACCTTATGTAAAAAAAAAAAAAAAAAAAAAGACTGAAGAAGGGGAAGAGACAG     3780

3781  CATTTGAGAAAAGGCCTCACAGAGAAAGGGGTTTTCAATCTGGGGACAGCAGATATGACC  3840

3841  AGCAGTCCTGAAGGTAGGGAGGCACACTTTAATAATGGTAATAGTTGCTAAGCCTATAAA  3900

3901  ATGCTTAGGGTGTCACAGGATCTTTTCACATGTCTCATCTCAAGTCATGCCCCCAACAAC  3960

3961  TCAGCATTCCCACTTTGCAGATGAGGACACTGAGGCTCAGGGAGGTGATATGTAAGAGGC  4020

4021  TAAGCCTCAACACACACTGGGCCTTTTGCTTCCGAAACTGCTTTCCCTTGCTCTGAGGCT  4080

4081  CTCGGAGAGTAATTGCTGGGTTGTGAGCACTGGGTAAGAGGATGGGTGCTTCAAAGCAGC  4140

4141  TGCACTCCAGGATAAAGGTAGAGGAAAGTAAAAACATCTTCCCCTGCTGTTATCCAAAAG  4200

4201  AGAAAAAGAATGGAATTGGGCAAGGGGTGGAGGGGGAATCCAGCTTTTGAAACAGTATTA  4260

4261  TAGGAATTTTGCTACCCGCTATGTGCAGAGCATCATGCGAGGCACTTGGGACAGCTGAAT  4320

4321  GAATGAGCTCCATTCTCAAGGTGAACATGTACATATACACCTACAATTTACATTTATT    4380

4381  GAGCAGTGGTCGCATGGTTTCATCTGCACAGTGACTCTGAGGTAGGTACTACCATTAGGC  4440

4441  CCATTGTTAGAGAGGGGTTAATGGAGACTTAGAAGAGGCCCAGAGAGGTTAGGTAGCTTT  4500

4501  CTCAGAATCACATAAGTGGTAAGGGGATTCAGGCATGCCCCCTGCAACCACTGTCTTCAC  4560
```

FIG. 2E

```
4561  CACCGTACGGCACCAGTTCCACAAGCTGTACAGTGTGGGCTGTGAGACCCAAGGAAAAAC  4620

4621  AGAGCTGAGGCCCACGGGAAGGTGAGGCCGGTGTGGGCTGGAGGCCTTGGGGTAAGCTTC  4680

4681  CTGGAGGTGGGGGTACATGTTGGGCCTTGGAGGACTAAAGAACTGGGGGGAAAAGGAAGG  4740

4741  GAAGAAGGAAAGGATTTTCTGAAAAGGAAATGGCAAGAAGTAAAGGTCCAAAGCATAGGC  4800

4801  TGTTGTGAGTAAACAGTGGGAAATGCAACCTCTTTGGGGCCAAACCTCTGACCCTCCACG  4860

4861  TTCCCAGCTGTGAAGTGGGAGTAATAAAATCATCCACCTTATGAGAGCAAATAAAATAAT  4920

4921  GATTGTGAAAATATTTTGGTAACAGTAACCTGTGATAGGAAGATAACAAATCATTTCTGT  4980

4981  TACAATACCATGCTGATAGGCATAAAAGTTGCATTCATGTTCATGGGCAAAATGGGGGTA  5040

5041  AGTAGAATGCATGGGACGCAAGAAGGATGTAGGAAGGAAAGGGTAGTGTGAGTATAGGAG  5100

5101  GACTAGCCACTGAGAAGAAAGTAGAAGAAAGAGGGAATCTTTGTGTGTATGGGAAAGTCT  5160

5161  ATTGCAGAGTCAACTTGGGCTTCCATCCTGGGACCTTCCCGTGAACAGCTAGAGACATCT  5220

5221  TCCTCTGGGCTTTGGCAGCCTTTATGTCGGGACCCAGGGGACCCTATATGGGAAATAGGG  5280

5281  CCAGACACATGCTCTGAATCCCTGCTTCAACATTTCTGAGTCACCTTTGTCCCTGTGAGC  5340

5341  CTTCATTTTTCTCATCTATAAAATGGATGACAGCTAGCTTGTTGGTGTGATTTCAGTAGC  5400

5401  GGCTCAGTAGAGTCAGTTTCCTAGGTCTCTTTAATTCTGCCTCTCAAAGGTGATGGGAAA  5460

5461  ACATCTAGACAAGAAGCCAAGGGACCGGGACACATCTCTCCAAGGACGAGGTGCATGGCG  5520

5521  CTCTGAAGATGCTGGCATCTCTCTAGGCCCAACCCAGCTCAGGGGTCCACTCCACCACA  5580

5581  GCCCTGGCTGGGTGCCTGTCCCCTGGTATCCTGGAGACCTTGCAGCTGCTGTGGGCATCT  5640

5641  GCTGCCACCTAGCGGCCTCCCATGGCACTGTCTCCCCGCCAGCCCCTAGTTTTGACAGGG  5700
```

FIG. 2F

```
5701  GCACTCCCTGGCATTAATCTCTTCAGAGGGAATGTCTGTGCCTGTTTCCTGTCTGTCCTC  5760

5761  CCGCCAGGTGGAGTTCCTTAAAGGCAGTCATGATCATTATCTTTCTAGCTCCAGTGTCCA  5820

5821  GCACAGTGAGGCACAAAGTAGTTGTTCAGCAGGTGATTACGGAATAAATGAATGAACGGA  5880

5881  CCAATAAACAAATAGCCTTGTCTAATCAAAATTAGGCAACAGAAGGAAGTCACTTCAGGG  5940

5941  TTATTTAATCCCCGGGCAGCTGACTCCTCTAAATTGACTCTTGACAAGAAGTAACTCTTA  6000

6001  TAAATGCTCCAGAGGCCCTCAGCGACAGAGGTGATTTCCAGGTGGCTGGGCTAACGTTAA  6060

6061  AGGTGGTTGTACTAAAAGCAGGGGTTTGGCCTCAGGGACTCCACCACTGTGGTGGAGGTA  6120

6121  CAGCACTTTTCTATTTTTGCTTCCTCCACCCTGGGCCAGGATCTTCCTCAAGAGAATGCC  6180

6181  CTCAATCCGAGAAAGCCTGAAGGAACGAGGTGTGGACATGGCCAGGCTTGGTCCCGAGTG  6240

6241  GAGCCAACCCATGAAGAGGCTGACACTTGGCAACACCACCTCCTCCGTGATCCTCACCAA  6300

6301  CTACATGGACGTGAGTGCTTGGCTCAGCCCCTCGCTCCCTCCCTGTCTCCTTTCCCTCAT  6360

6361  GGACCTAGGGCTTTCTTTGCTGCAAGACTCACCCTTTCCAAGCTGTGTTTGACGAAGGCG  6420

6421  CTGAGTAGCACGTGAGCACCCTAGAAAATTCCCATTTTCCAGCTGGAAAGCCTGAGCACA  6480

6481  GAAGACAGGAAGGCATCCAGGGGCCATTCAGGGGCAGGGTTAGGTTTGGAACTCAGCCCA  6540

6541  GGCCTCAAGCCAGGTGTCACAGGTGGGTGGGAAGGGGTGTGTGACTCAGGTGGGGTTTC  6600

6601  TGTGACCTGGCCCAGCACAACCTGATGGCTTCCTGCCCCAGAGGATCCTCAAGAGTCAAG  6660

6661  TTTGCTTCCTGCTTCATTCTCAATGTTTTGATTTTGCCCTCTTGTCTTACTGAGACTCCC  6720

6721  ACTTTCTGGGATGCCATGGGGAGATGCTAAGCCTCCTACCAGTTCCTGCAGGAAAATGGA  6780

6781  AACCCCGAGAGGCTATAGGACCTCGCCTGGGCCAAGTCTCACACCGAGAGCCAAGAGTGA  6840
```

FIG. 2G

```
6841  AGCCAGGCAAGACCCCAAGACCCAAGGTCCCCTGAGCCCCTCCAGCCCTCTCTTTTTACC  6900

6901  CCCACAGACCCAGTACTATGGCGAGATTGGCATCGGCACCCCACCCCAGACCTTCAAAGT  6960

6961  CGTCTTTGACACTGGTTCGTCCAATGTTTGGGTGCCCTCCTCCAAGTGCAGCCGTCTCTA  7020

7021  CACTGCCTGTGGTGAGACCTAAGACCCACAGTGCCTCTCCTCCATCCCCCTGCCCTACTG  7080

7081  TGCATGAGCAATCCTGCCCAACACCCAGCTCCCATCCCTCTTGCCACCAAGGGAGTGGCT  7140

7141  TCCTCTCTGCCTCTGTGCCCACTGACATGTAGGGGAGAGGGGAAGATGTCTCCCGTTTTT  7200

7201  CTGATACAGCCACCAAGGTTAAAAACAAAAAAGGTCCAAGAACCCCTGAGCACCCAGAA   7260

7261  GGCCACTTCCCAGTCTTCCTGAGATTGAGACAGGACTGAATTCTCAAACCCATCCCAGGC  7320

7321  ACTCGGAACTCTTCCATCCCTAGTCTTAATCAACAACCTCTTACTAGGCACTTACTCTGT  7380

7381  GCCTGGCATCTTCTCTGGTGTTATCAGTGTTAGTGATTACTTTAAATTCCTTCATTTAGG  7440

7441  ACAAAATTCTCGATGTATGGGCACATTAGGAGAGCCCAAGAAACCCAGTCCTTGATTGAT  7500

7501  GAAGCACATATTCCAAGCCCCCTGACCCTAGGGCCACTCATCCCTGCACCTAAGCTAACC  7560

7561  AGCCATACCCACAATGCACCCTGCCTCTGAGTCCCCCTGTCTGGGCCACTCTTGGACAAA  7620

7621  CCTGAGCCTCTGTCCCCCTGCCAGTGTATCACAAGCTCTTCGATGCTTCGGATTCCTCCA  7680

7681  GCTACAAGCACAATGGAACAGAACTCACCCTCCGCTATTCAACAGGGACAGTCAGTGGCT  7740

7741  TTCTCAGCCAGGACATCATCACCGTAAGTTGGGCCGCCCTAGGTCATCTGCCCCGGACCC  7800

7801  CTTCTGTCCCCAGGCCTCTCCTGACCCTCCAGGGCCCACACCTGCGGGGAGGTACACTGC  7860

7861  AGCCCACTTGGAGCCTGGGGAGCTGAGGAACACCCTACTCTGCCACATCTGGCTGTTGCT  7920

7921  GCAAAGCAGCAGTACCTATGGGGAGCAAGCCTGGGCTACGGGCTCACCGTTGGGTGGTT   7980
```

FIG. 2H

```
7981  TGTGGATGTTTTTGCATCTAACTTGCATGTAGGGCTTGTCCTGAGCCCCGTGGCTGCAGT  8040

8041  CAAGTAACTCGTCCAAGTTCACCAGCTCTGACTGGGCTACACCCTAGACTGAAATCCAGG  8100

8101  GTCAGAGTCAGGCTGAGTTTTAGGGTCAGGCATAGGTTTTAAGGTCACAGTTGAGGTTGA  8160

8161  CTCTGGGACTCAGGTCAAGGCCTGCTTTTCTTTTCCATGTGGCCCATGTCTGACCGTTTC  8220

8221  CTCATCCTGGAGTTTCTCAGGCCCTGCTCCATCAGAGTTAGGGGAGGGGCACACGTGGCA  8280

8281  CCTGAGAGGAAATCAGGGTGATTCCTGCCTCCCTTCCTTTTCTGTGAACTCAGATATAA  8340

8341  AGGAGGGAGAAGGGCAAGCTTGTCTGTGCTAAAGAAACCCTTCGCCCATGATAAGGGTGG  8400

8401  GGGCCAAGACCCAGTCCTGCCAGGCACGAAAGTCTGGCCACTGGGGAGGGGAGGAGCTCT  8460

8461  TGGCAGCTTTTCTTTTGCTGCTTGGCAGGACCACCCTCTCAGCCTCTGCTCTCCGATCCC  8520

8521  TGGTCAACTCTAGCTCTCTCTGGGCTCCGCAGCAGAGATGTGTATTGGCACAGAGTGTGT  8580

8581  GCGTGCAGGGTTGAGGAAATACTCTTACCCCGATTTCTGTACCCTGGAGCATGTGTGCCC  8640

8641  CTGGGATCCCTAGTGTGGAAGCCCAGACCAGACTCCAACCAAGGAGTGGGCAGTGGGCTT  8700

8701  GGTCTCCTCTGGTCCTTCCTCCCACAGGTGGGTGGAATCACGGTGACACAGATGTTTGGA  8760

8761  GAGGTCACGGAGATGCCCGCCTTACCCTTCATGCTGGCCGAGTTTGATGGGGTTGTGGGC  8820

8821  ATGGGCTTCATTGAACAGGCCATTGGCAGGGTCACCCCTATCTTCGACAACATCATCTCC  8880

8881  CAAGGGGTGCTAAAAGAGGACGTCTTCTCTTTCTACTACAACAGGTGGGGACTGGGACTC  8940

8941  CAAGGGCTGAGGTGGGGGGACAGGAGGGGAGAAGAGATGGGGAGTGGAAGGAGAGTCTGG  9000

9001  GCCAGAATTGTAAAGTGTTTGTAATTAGGTGACAGCCAATCAATATCTAGAGCTGTACTA  9060

9061  GCCAATATGGAAGGCACTATTGAAATTTAAATTAATTAAATACAGTTAAGCATCAATTAA  9120
```

FIG. 2I

```
 9121  GCATTCAACTGGTGGCTCTTAGTTGTACTAGCCACACGTCAAATGCCTGGCAGCCACGGT   9180

9181  GGCTAGTAACTACAGTCTTATGACAGTGCAGATAGAGAATATTCCCAGCATGACAGGACA   9240

9241  TTCTAATAGACAGCGCCACTCTGGAGCAAGAGGAGATGCAAGGTGGGGGCGATGGTAAAT   9300

9301  AAGGGATTACTGTGACCTGTAGCCCTGCCTGTTAGGGCCATGGCTCCTCCCACACAGAGA   9360

9361  CAGCCAACTTCAGTCATCCATTAGATCCTTCATTCGTTTGTTTGCTCACTCATCAGTTCA   9420

9421  GTAAATGCTATGTGCCAAGCACTGTGGTAGGCTCTGGGGGTGCAGCAGTGAACACAGTGA   9480

9481  ACAAGGCAGAATCTGTACTCCCCTACCCACATAGAGCTTACAGGCTAACAGGGAAGACAA   9540

9541  GACATATTCCAACATAAAGAGTGTCACAGGCAGGCAGCAAGTGTGGTGCTGAAAACCATG   9600

9601  GATGCTTTTCAATTCTAGGCTGAGCTTATATGCAGCTCAGCCAGCCTTGGGGAAGCTCTT   9660

9661  GAGCAGGGTTGGGCTCTACTCCAAACTGCTGGGCTTAGAAAGATGGCATGAGTTGGAGAC   9720

9721  AAGAGAGCTGGAGGCAAAAGGGGCTGGGTGCAGTGGCTCATGCCTGTAATCCCAGCACTT   9780

9781  TGGGAGGCCAAGGCGAGAGGATCGCATGAGCCCAGGAGTTAAGGCTTCAGTGAGCAGTGA   9840

9841  TTGTGCCACTGCACTCCAGCTAAGGCAACAGAGTGAGATCCAGTCTCAAAAAAAAAAAAA   9900

9901  AAAAAAAAAAGTCACAAGGGTAAGAACATGAGGCCAGTGGCAAAAAGAATAGAGGAGAG   9960

9961  GATCAGAGTTCAGAGAAATCTCACAGTAAAATGGAGAGGAGTCTCCGGTTTGGTGATAGA  10020

10021  AAGTGAGGCCTTGAGAAAAGGCCAATTGGCGGCTCTGCATTCAGGGGTGGTCTTTAGAAG  10080

10081  AACTGTTTTAGAGGAAGTGGGGGCAAGGCCAGATGGCAAGAAGTTAAGAGGTGGACGACG  10140

10141  TGGGTGTCAGGAAGTGGAGGTCATGAGATGTAGGCTGCCCTGGGACATTCAACAGGGAAG  10200

10201  GGAATGGGGGGTGGCGTGGGGGGTGAGATCCAGAAGCAGAAGAGGAAGGGTGGGTGTTTT  10260
```

FIG. 2J

```
10261  TAAATGCTAGAGGATGCTCGAGTGATGCCTGTAGGTGGAGGAAGAAGCCAATGGAAAGAA  10320

10321  AGAGATTAAAAATGTGGAAAGAAGAGGAGCTAAATGGGGCACTGGAGTTTGGAGGCCTT   10380

10381  GAAAGAGATGAGGTTCCAGCAGACAGGAAGAAGCCAGGTTTTGCAGAGGAGAGGGCTGGC  10440

10441  CTCTTCTTTTATCTTGGGATGGGAAGGAGGGAACATCCAGAGAGATACTGAAGTGTTGAG  10500

10501  AGACAGGCAGGAGGGAATTTGTGCTAGCATATACACATACATTCCGAATTTATAAAAACA  10560

10561  CAAGTAGTTTGCAGTTGCACAAAATAACATATGCACACCTACACACCCATGCACACATGT  10620

10621  GCATGTGTGAATTCTAGTATGAATTCTGGAAAAACACATCACACACACAGGCATGCCCTG  10680

10681  GAGACTAGGCCTACAGTAGTCCCTGAGCCAAGTGCAGTGAGGAGGAAAGGAAGGTGAGGG  10740

10741  GAATCAGCTCCAGACGGGGCACCAGGAGCCTGGCTCCAGTCCCCCACTTGTTCACTCATG  10800

10801  GACTGGGTAACTTCAGGCAAGTGACTTCGCCTCTTGGTGACTCCATTGCCTGAAGGGCAA  10860

10861  AGAGAGTACATAACACCCACCCTGCCAAACAGCAGGGCTGATGAGGCTGGCATGAAATGA  10920

10921  AGCTTCCTTTCTGCTGTCTCTCTTTCTCTGCAGAGATTCCGAGTAAGGAGACAAAACCCC  10980

10981  CACATGGCTGTGACCTTCCAGTACTCCCCGAGCACCTGACCTAGAATTACACACGCCACC  11040

11041  GGCCCAAAACTCACATCAGCAAGCCCAGCCTCCGCTAGATGCCGAAGTTCTCTGTCTCTC  11100

11101  CTTCCTGCTCTCTCCATGCCACCTGCCCACCCCATACCCAATAGCCTCCCCAGGGTCCCC  11160

11161  TCCCATGCACCTGCTCAATCAGCAGCAACCCAAGAGTGAGGGGTGTCCATTTGTGTCTTG  11220

11221  TTCACATCCACTCACTGTCCTTGTACCTGCTCCTTTTCTGTGACCTCTCTGGGGATGCTT  11280

11281  TTTGGGGGAACAGCTGGACTACCCTGGAACAACCTCTGGTTGGTCTTGGGGAGGGGAAGA  11340

11341  AAGGCAGAGAAGCAGTATGTTCTGCATGCTTCCCAACGACAGCTCCGAGCCTGGCTGTCT  11400
```

FIG. 2K

```
11401   GTCCCACATTCCTCTGCTCTAGAGCCCTCTGTCCTCCCCTGCACCCTTGTGCAACCTTCC   11460

11461   CCAATTGCCTGAGTTGCTGGGTCCTGGAGGTTATGGGTTTCCAAGAGCTTCTGATCTTTC   11520

11521   CTTTAGGAATTCCCAATCGCTGGGAGGACAGATTGTGCTGGGAGGCAGCGACCCCCAGCA   11580

11581   TTACGAAGGGAATTTCCACTATATCAACCTCATCAAGACTGGTGTCTGGCAGATTCAAAT   11640

11641   GAAGGGGTCAGAAATCCTCAACCCTCCCCGGGCTCCAAAAAATGCTGCCGTCACTGGGGT   11700

11701   TGGGGAGGGTGGGGAAGGACTGCATTACCATCCTGCCCTCTTTCCAAATGCAGCCACTTC   11760

11761   TTAAGCACAGCCACCATTTGCTCTCTGCCTGCTCTGTCCAGGCTGGGGAACAGAGAAGGG   11820

11821   AGGGGCCTGGGGAGAAGTGGTGGAGGGTGACAGTACCTTCCCTCCTCTACTCACTGCCTC   11880

11881   AACAGGCCACCAGCGTGGCCTCCACCCACCCACCCACACTCAGGAAGGACATGCAGCCTG   11940

11941   GAGGTGCCCCATCAGCCTTCTGTCTGTCTGTCTGTCTGTCTGTCTGACTGTGGCCTCCCC   12000

12001   CAGGGTGTCTGTGGGGTCATCCACCTTGCTCTGTGAAGACGGCTGCCTGGCATTGGTAGA   12060

12061   CACCGGTGCATCCTACATCTCAGGTTCTACCAGCTCCATAGAGAAGCTCATGGAGGCCTT   12120

12121   GGGAGCCAAGAAGAGGCTGTTTGATGTAAGAAGCCAAAGAGGGAAGGTGCTGTGGGTGGG   12180

12181   GGGAGCGCCACCTGGTATCGGCTCACAAATCCCCCAGGCAAATGAGGCCATCTCAGGCCT   12240

12241   TCGCTTGTTCACCTCACACTCTCCACACATGTGGCTGGTCACCCATGGGGCGGGGCACTG   12300

12301   TCCCCAGCCCTCTCCAGCAGAGAGACCAGGCCACCAGCGCAGGACTCCTTGTCTGCTGAG   12360

12361   ACGTCTTCCATACTCAAGAAGGCTCTCTTTGCCCCCCACCCCAGTATGTCGTGAAGTGTA   12420

12421   ACGAGGGCCCTACACTCCCCGACATCTCTTTCCACCTGGGAGGCAAAGAATACACGCTCA   12480

12481   CCAGCGCGGACTATGTATTTCAGGTGAGGTTCGAGTCGGCCCCCTCGGTGGCAGGGAGAA   12540
```

FIG. 2L

```
12541  AGGCTGGACAGAGACCCTCAAAGAGTGACAGATTACAATGCACAGATCATGTTAGAACTG  12600

12601  TAGTTCTCAAACTTGGCTGTGCATGTCACCTGGAGAGCTTTGAAAAATCCTGGTACCTGG  12660

12661  GCCACATCCCATACCTATTAAATCAGAACCTCTAGAAGTGGCACCTGGGGTTCAGTTTCC  12720

12721  CCAGGTGATTCCAATGTGTGGCCATGTTTGGGCATCACTATGCCTGTTCCCTCATCTCCA  12780

12781  TTTTCTCATCAAATACTCCCAAGAATCCTATGCTCCTATATTCTTACCCTCTTTTCATAA  12840

12841  TCAATAGGCTTAGAGAAGTTGAATAACTTGTCTAGGATCAGAAGCTAAGGCAAACTGTAA  12900

12901  GCTCCTGAAGGAAGCACGGTGCCTGATGCATTGTTTGCCTGGGATCTAGCACAGGGCTA  12960

12961  AACATAGGAGTGGTGCAGTCCACGATGGGGCAAAATGGCCATGATGTGAGGGAGGCCCAG  13020

13021  TGTGGCTAGGGGAGAGATGGGGGCGAGAGGGGGAATGTTGCTGAAGACAGTTGCTGGGGG  13080

13081  TCAGGCAAGGTGAAAGGAGAATGCTCATGTGCTGGGTATGGAGAAACTCTCCCCCTTCCT  13140

13141  GCCAGGAATCCTACAGTAGTAAAAAGCTGTGCACACTGGCCATCCACGCCATGGATATCC  13200

13201  CGCCACCCACTGGACCCACCTGGGCCCTGGGGGCCACCTTCATCCGAAAGTTCTACACAG  13260

13261  AGTTTGATCGGCGTAACAACCGCATTGGCTTCGCCTTGGCCCGCTGAGGCCCTCTGCCAC  13320

13321  CCAGGCAGGCCCTGCCTTCAGCCCTGGCCCAGAGCTGGAACACTCTCTGAGATGCCCCTC  13380

13381  TGCCTGGGCTTATGCCCTCAGATGGAGACATTGGATGTGGAGCTCCTGCTGGATGCGTGC  13440

13441  CCTGACCCCTGCACCAGCCCTTCCCTGCTTTGAGGACAAAGAGAATAAAGACTTCATGTT  13500

13501  CACAGCCTGTTGCATCTGGGTTCACTAGGGTTTAGAACAGAGGGAGGGGCTGCGTGATCA  13560

13561  TGTGTGGACAGGAATGTGACACAGACAAGCTACACATTCGCCTAGCGCACAGGTTCTTGC  13620

13621  GTGCAGGGATGATGCCATCCATCTGCCATCAACGGGACTCAGGTGGAGCTGTTTACACAA  13680
```

FIG. 2M

```
13681  CCTCAGGTGGGAAGTCTGAAAAGAGCCGGAACCAAGCTCCCTCTAGTCCCTCAGGGACCA  13740

13741  AGGCTAATGCTGTGGCAGTAGACTGTGGGTCAGAAAGTTCTCCCAGCTCACAGAAGCCAG  13800

13801  CTCTGAGTTCAGACTCTGCTCTGCTGAGCTAGTCAGCCCTGTCTCTTGTCCCTGCAAAAC  13860

13861  TCCCCTCAGCTGTCCTTATCCACTGCAGATGCCCCCGCCCTGCCCCATGTAGCCATTTAC  13920

13921  ACAGGCATTCTAAGGCACTACCACCTAAAATCATAGAACACCAGAGATCCAGGCAATACT  13980

13981  TCCACTTTACAGGTGGGGAAACTGAGGCCCAGAGAATGGAAGGCCTTGCCCAAGATTACT  14040

14041  CGGTCAAGAATCAAGTAGTGAAGAATACTGAAAGATAGTGAAGAATCAAGACTGGAACCC  14100

14101  AGCCCGTCTGACTTGGGTCCTGGGGGTTTCCACCTTATCATAAGCAGTTGGTACCGTCAT  14160

14161  AAGTACAGTGCTTCACGCACGCTGGTACAGGGCCACGTGCACAAGCACACAGGTGCACAC  14220

14221  ACACACTGCTATCCTCCATCCCATCCACCTGGGACTCGTCAGGCTGAAGTCTCTTCTCCC  14280

14281  ACTCTCACTCCTTGGGCTGTCTTCAGGGCACATGTAACTTGGGGAATGAGAAATTAGCAT  14340

14341  CCACCTGGAGCCACTGAAGCCATCCCTCTTCACCATAGTTGCTCACCTCTCTTTTGACAG  14400

14401  AAAGTCGTGAGGCACTGAATGGCCCAACCAGGCCCTCAGTACCTCTGGGAGCCATCTGCA  14460

14461  AGAGTCCCTGTGTAGCGCCAAGAGCCGGAGCCTGGGCTTCAGG  14503
```

FIG. 3A

```
   1  GGTCTTTGTAAAATAATAATTATTCATTTCACAAAAGTGATAATTAAAAGACTTTAATAG    60

61  CAATACAGAAAGTTACATGAATATAAAGACTTAACCTTTCTAAAGCTCAGTTTTCCTAAG   120

121  TAATCAAAAACCTGATAAAGATAACAAGAATGAGGAATTATCTTGAGAAAATGTAAAATC   180

181  TTTCCTTTTATTTTTTGAGACAGGGTCTCACTCTGTCATCCAGGCTAAAGTGCAGTGGCA   240

241  CAATCATAGCTCACTACAGCCTTGAACTCCTGGACTCAAGTGATCCTCCCGCCTCAGCCT   300

301  CCCCAGTAGCTAAGACTACAGGCACGCACCACCACACCCAGCTAATTTTTTCAGAGATG    360

361  GGGTCTTGCTATATTGCCCTGGCTGGTCTTGAACGAGCTTCAAGTGAGCGTGAGCCTCCT   420

421  ACCTCATCCTCCCAAAGCACTAGGATTACAGGCATGAGCCACTGTTTCCCAGCCTAAAAT   480

481  AATTGTTTCTTAGGCCAGCTACCAAAAACGCAAAGAAAAACTTTCTGTAGTGTGATTGCT   540

541  TCTTCTTATGGGAAGCCCATTTAGATAACCTGTAAGTCAAACCTGATGAAAACAATACTT   600

601  GAATGTAATCAGACACAGAAAGACTGTTCAAGGCTATGAGTAGCTGAGTCCAAGCTCGTA   660

661  TCACTTGCCACACAACAGCCAATAAGTCTAGAGACAAGGTATTGTGGCAAGGAAAGCTAC   720

721  CTTATTCAGAGAACCAGAAAACCAAGAAGATGGTGGACCAGCATCATAAAGAACCATCTG   780

781  AAGTCAGCATGAACGTTAGGCTCTTCTTTATGTTAAGGGAAGGGGAAGAAGAAGGGGATT   840

841  GGGATCAAGAGGTGACTGATGACCACAGACACCTGGGTGCCAGCAAGGGTCTGAGGACGT   900

901  TGTAAAACTTCTTTTTTCTAGGTCAGGTCACAATGTTCCTATACATCTTTAACATAACAT   960

961  TGTTATTTGTCTGTATATTTCCTTATCTCCTTGGGGGTTAGTTTGGGGAAAGGAACTGTT  1020

1021  ACCATTTTTTTTAAAGTTGAACTGCAAGCTAAACTCCTATAATTAGCTGGTCTATGTACA  1080

1081  GAGCTAAGCAGAAGCTTTTAGCCTAAAGGATAATACCCCTGGGGGTCAGAGGCAAAATGG  1140
```

FIG. 3B

```
1141  AGTCAGTCATGCTAAGTCTCCCTCCACTCTCTTTCTTTTTTGAGATGGAATTTCACTCTT  1200

1201  ATTGCCCAGGCCGGAGTGCAGTGGCATGATCTCAGCTCACTGCAACCTCCGCCTCCTGGG  1260

1261  TTCAAGCAATTCTCTTGCCTCAGCCTCCTGAGTAGCTGAGATTACAGGTGTCCATCACCA  1320

1321  CACCCAGCTAATTTTTGTAGTTTAGTGGAGATGGGGTTTCACCATTGTTGGTCAGGCTGG  1380

1381  TCTGGAACTCCTGACCTCAGGTGATCTACCCACCTTGGCCTCCCAAAGTGCTGGGACAGG  1440

1441  TGTGAGCCACCATGCCTGGCCCCTCTACTCTTATAATTAAACCAGCTGTTGCTTTTCCTG  1500

1501  CCAAGAAACCAGTCATGAAGATTCACCCATGTTCTAGATGGGAAAACTGGGCTGTAGCCT  1560

1561  GGGAGAGGCCAGTCAGGGACAAAGCCAAAGTTAATATAGAGAATGGAGCTTCCAGGGTAT  1620

1621  AGGGGTTGGGTCTGGGCTAGGGAGCTGGAAACCTAGGTTTTACGCTTGTCCCAGTTTTGA  1680

1681  TGTTAGCCCTGAGCAGTGCTGTTTCTCATCAGCCTCTGCCTGCTCCAGGGGTCACAGGGC  1740

1741  CAAGCCAGATAGAGGGCTGCTAGCGTCACTGGACACAAGATTGCTTTCCCACAGCTGTCC  1800

1801  TTCCTCCAGCCCCTCTGCTCCCCATCCGGAAACCTGGGTACCCTTCACCCACCTAGCTCT  1860

1861  GTCCCGCAGTGAGATTTATTGCTGACTGCCCTGCCATCTACCCCAGGGTAATAAATCAGG  1920

1921  GCAGAGCAGAATTGCAATCACCCCATGCATGGAGTGTATAAAAGGGGAAGGGCTAAGGGA  1980

1981  GCCACAGAACCTCAGTGGATCTCAGAGAGAGCCCCAGACTGAGGGAAGCATGGATGGATG  2040

2041  GAGAAGGATGCCTCGCTGGGGACTGCTGCTGCTGCTCTGGGGCTCCTGTACCTTTGGTCT  2100

2101  CCCGACAGACACCACCACCTTTAAACGGTAATTGGTAACTCAGGCAGAGAAGGGGTGGGA  2160

2161  GGGGTGCAGGGTTCCCACCTTCCCAACACCCTGGCTTTTCCACATGCGGTGTCATTCAGT  2220

2221  CCTTACGATCAGCTGGACAGGGAAGTATGGACCTGTTCAGAGAGGTCAAGTGACTTGCCC  2280
```

FIG. 3C

```
2281  AATAAATGACACTAGTAGTCAGGTCTAGAAGCTGTGACTTTTGCTTCCTGCCCAGAGCAC  2340

2341  CATGCTAACTAAGCACTGTAGAGAACTCAGAAGTATTAGGACATGCCCCTTGCACTTGAG  2400

2401  GAGCTCACAGCCTGAATATTAAGAAGGGCATGGGTGGTTGGGCGCGGTGGCTCCTGCCTG  2460

2461  TAATCCCAGCACTTTGGGAGGCTGAGACGGATCACTTGAGGTCAGGAGTTTGAGACCAGC  2520

2521  CTGGCCAACATGGGGAAACCCCATCTCTACTAAAAATACAAAAATTAGCCGGGCATGGTG  2580

2581  GCAGGCACTTGTAATCCCCAGCTACTCGGGAAGCTGAGGCAGGAGAATCGTTTGAGCCCG  2640

2641  GAAGGTGGAGATTGCTGAGCCAAGATCGTGCCACTGCACTCCAGCCTGAGTGACAGAACA  2700

2701  AGACTCCATCTCAAAAAAAAAAAGACGGGGGTCGGGGCATGGGTACAGTTAACTGTACC  2760

2761  AGGGAAGCAGCTTGATATCGTGGTTAAATGCAAGGCTTATAGAGTTAGATTGCCTTCATT  2820

2821  TAAATTTTGCTTCACTAGCAGAACAAACTAGGTCTGGAATCATGGGCAAGTTATTTAACC  2880

2881  TCTCCAAGTCTCAGTTTATCATTTTAAACAGGTATGATAATAACAGTACCTACTTGATGG  2940

2941  GGCTGCTTTGGGGATTTTAGGAGATAAGGCATAGAAAGCTGGGCACGTTGTAAGAGCCCA  3000

3001  GCTACTGTTAGTACTACAGGATAGATTCTTACAAATATCAAAAGCAAGGTTTGGCCGGGA  3060

3061  GCAGTGGCTCACGCCTATAATCCCAACACTTTGGGAGGCCGAGGGGGGCAGATCACCCGA  3120

3121  GGTCAGGAGTTCAAGACCAGCCTGACCAACATGGAGAAACCCTGTCTCTACTAAAAATAC  3180

3181  AAAATTAGCCGGGCGTGGTGGCACATGCCTGTAATTCCAGCTACTTGGGAGGCTGAGGCA  3240

3241  GGAGAATCGCTTGAACCTGGGAGGCTGAGGTTGCAGTGAGCCGACATAGCGCCATTGCAC  3300

3301  TCCAGCCTGGTCAACAAGAGCAAAACTCAGTCTAAAAAAAAAAAGAAAGAAAAAAACAA  3360

3361  GGCTTTAGGTAGCCCACAATTAGAAGGAGAAAACCTTAGCATCCCCTAGGTGCCAGGCCT  3420
```

FIG. 3D

```
3421  TGTGGGAACAAGTGATTCATTAAGACTGTAGAAGGAAGCTGGGCACGCGGCTCATGCTTG  3480

3481  TAATTCCAGCACTTTGAGAGGCTGAGGTGGGCAGATCGCTTGAGCTCACGAGTTCAAGAC  3540

3541  CAGCCTAGGCAACATGGTGAAACCTTGTCTGTACAAATACAAAAATTAGCTAGGTGTGGT  3600

3601  GGTGCAAATCTGTAGTCCCAGCTACTCGGGAGGCTGAGGTGGGAGCATCACTTCAGCCTG  3660

3661  GGAGGTGGAGGCTGCAGTGAGCAGAGACTGACCCACTGTGCTCTAGCCTGGGTGATAGAG  3720

3721  CCAGACCTTATGTAAAAAAAAAAAAAAAAAAAAAAAAGACTGAAGAAGGGGAAGAGACAG  3780

3781  CATTTGAGAAAAGGCCTCACAGAGAAAGGGGTTTTCAATCTGGGGACAGCAGATATGACC  3840

3841  AGCAGTCCTGAAGGTAGGGAGGCACACTTTAATAATGGTAATAGTTGCTAAGCCTATAAA  3900

3901  ATGCTTAGGGTGTCACAGGATCTTTTCACATGTCTCATCTCAAGTCATGCCCCCAACAAC  3960

3961  TCAGCATTCCCACTTTGCAGATGAGGACACTGAGGCTCAGGGAGGTGATATGTAAGAGGC  4020

4021  TAAGCCTCAACACACACTGGGCCTTTTGCTTCCGAAACTGCTTTCCCTTGCTCTGAGGCT  4080

4081  CTCGGAGAGTAATTGCTGGGTTGTGAGCACTGGGTAAGAGGATGGGTGCTTCAAAGCAGC  4140

4141  TGCACTCCAGGATAAAGGTAGAGGAAAGTAAAAACATCTTCCCCTGCTGTTATCCAAAAG  4200

4201  AGAAAAAGAATGGAATTGGGCAAGGGGTGGAGGGGGAATCCAGCTTTTGAAACAGTATTA  4260

4261  TAGGAATTTTGCTACCCGCTATGTGCAGAGCATCATGCGAGGCACTTGGGACAGCTGAAT  4320

4321  GAATGAGCTCCATTCTCAAGGTGAACATGTACATATACACACCTACAATTTACATTTATT  4380

4381  GAGCAGTGGTCGCATGGTTTCATCTGCACAGTGACTCTGAGGTAGGTACTACCATTAGGC  4440

4441  CCATTGTTAGAGAGGGGTTAATGGAGACTTAGAAGAGGCCCAGAGAGGTTAGGTAGCTTT  4500

4501  CTCAGAATCACATAAGTGGTAAGGGGATTCAGGCATGCCCCCTGCAACCACTGTCTTCAC  4560
```

FIG. 3E

```
4561  CACCGTACGGCACCAGTTCCACAAGCTGTACAGTGTGGGCTGTGAGACCCAAGGAAAAAC  4620

4621  AGAGCTGAGGCCCACGGGAAGGTGAGGCCGGTGTGGGCTGGAGGCCTTGGGGTAAGCTTC  4680

4681  CTGGAGGTGGGGGTACATGTTGGGCCTTGGAGGACTAAAGAACTGGGGGGAAAAGGAAGG  4740

4741  GAAGAAGGAAAGGATTTTCTGAAAAGGAAATGGCAAGAAGTAAAGGTCCAAAGCATAGGC  4800

4801  TGTTGTGAGTAAACAGTGGGAAATGCAACCTCTTTGGGGCCAAACCTCTGACCCTCCACG  4860

4861  TTCCCAGCTGTGAAGTGGGAGTAATAAAATCATCCACCTTATGAGAGCAAATAAAATAAT  4920

4921  GATTGTGAAAATATTTTGGTAACAGTAACCTGTGATAGGAAGATAACAAATCATTTCTGT  4980

4981  TACAATACCATGCTGATAGGCATAAAAGTTGCATTCATGTTCATGGGCAAAATGGGGGTA  5040

5041  AGTAGAATGCATGGGACGCAAGAAGGATGTAGGAAGGAAAGGGTAGTGTGAGTATAGGAG  5100

5101  GACTAGCCACTGAGAAGAAAGTAGAAGAAAGAGGGAATCTTTGTGTGTATGGGAAAGTCT  5160

5161  ATTGCAGAGTCAACTTGGGCTTCCATCCTGGGACCTTCCCGTGAACAGCTAGAGACATCT  5220

5221  TCCTCTGGGCTTTGGCAGCCTTTATGTCGGGACCCAGGGGACCCTATATGGGAAATAGGG  5280

5281  CCAGACACATGCTCTGAATCCCTGCTTCAACATTTCTGAGTCACCTTTGTCCCTGTGAGC  5340

5341  CTTCATTTTTCTCATCTATAAAATGGATGACAGCTAGCTTGTTGGTGTGATTTCAGTAGC  5400

5401  GGCTCAGTAGAGTCAGTTTCCTAGGTCTCTTTAATTCTGCCTCTCAAAGGTGATGGGAAA  5460

5461  ACATCTAGACAAGAAGCCAAGGGACCGGGACACATCTCTCCAAGGACGAGGTGCATGGCG  5520

5521  CTCTGAAGATGCTGGCATCTCTCTAGGCCCAACCCAGCTCAGGGGGTCCACTCCACCACA  5580

5581  GCCCTGGCTGGGTGCCTGTCCCCTGGTATCCTGGAGACCTTGCAGCTGCTGTGGGCATCT  5640

5641  GCTGCCACCTAGCGGCCTCCCATGGCACTGTCTCCCCGCCAGCCCCTAGTTTTGACAGGG  5700
```

FIG. 3F

```
5701  GCACTCCCTGGCATTAATCTCTTCAGAGGGAATGTCTGTGCCTGTTTCCTGTCTGTCCTC  5760

5761  CCGCCAGGTGGAGTTCCTTAAAGGCAGTCATGATCATTATCTTTCTAGCTCCAGTGTCCA  5820

5821  GCACAGTGAGGCACAAAGTAGTTGTTCAGCAGGTGATTACGGAATAAATGAATGAACGGA  5880

5881  CCAATAAACAAATAGCCTTGTCTAATCAAAATTAGGCAACAGAAGGAAGTCACTTCAGGG  5940

5941  TTATTTAATCCCCGGGCAGCTGACTCCTCTAAATTGACTCTTGACAAGAAGTAACTCTTA  6000

6001  TAAATGCTCCAGAGGCCCTCAGCGACAGAGGTGATTTCCAGGTGGCTGGGCTAACGTTAA  6060

6061  AGGTGGTTGTACTAAAAGCAGGGGTTTGGCCTCAGGGACTCCACCACTGTGGTGGAGGTA  6120

6121  CAGCACTTTTCTATTTTTGCTTCCTCCACCCTGGGCCAGGATCTTCCTCAAGAGAATGCC  6180

6181  CTCAATCCGAGAAAGCCTGAAGGAACGAGGTGTGGACATGGCCAGGCTTGGTCCCGAGTG  6240

6241  GAGCCAACCCATGAAGAGGCTGACACTTGGCAACACCACCTCCTCCGTGATCCTCACCAA  6300

6301  CTACATGGACGTGAGTGCTTGGCTCAGCCCCTCGCTCCCTCCCTGTCTCCTTTCCCTCAT  6360

6361  GGACCTAGGGCTTTCTTTGCTGCAAGACTCACCCTTTCCAAGCTGTGTTTGACGAAGGCG  6420

6421  CTGAGTAGCACGTGAGCACCCTAGAAAATTCCCATTTTCCAGCTGGAAAGCCTGAGCACA  6480

6481  GAAGACAGGAAGGCATCCAGGGGCCATTCAGGGGCAGGGTTAGGTTTGGAACTCAGCCCA  6540

6541  GGCCTCAAGCCAGGTGTCACAGGTGGGTGGGAAGGGGTGTGTGACTCAGGTGGGGGTTTC  6600

6601  TGTGACCTGGCCCAGCACAACCTGATGGCTTCCTGCCCCAGAGGATCCTCAAGAGTCAAG  6660

6661  TTTGCTTCCTGCTTCATTCTCAATGTTTTGATTTTGCCCTCTTGTCTTACTGAGACTCCC  6720

6721  ACTTTCTGGGATGCCATGGGGAGATGCTAAGCCTCCTACCAGTTCCTGCAGGAAAATGGA  6780

6781  AACCCCGAGAGGCTATAGGACCTCGCCTGGGCCAAGTCTCACACCGAGAGCCAAGAGTGA  6840
```

FIG. 3G

```
6841  AGCCAGGCAAGACCCCAAGACCCAAGGTCCCCTGAGCCCCTCCAGCCCTCTCTTTTTACC  6900

6901  CCCACAGACCCAGTACTATGGCGAGATTGGCATCGGCACCCCACCCCAGACCTTCAAAGT  6960

6961  CGTCTTTGACACTGGTTCGTCCAATGTTTGGGTGCCCTCCTCCAAGTGCAGCCGTCTCTA  7020

7021  CACTGCCTGTGGTGAGACCTAAGACCCACAGTGCCTCTCCTCCATCCCCCTGCCCTACTG  7080

7081  TGCATGAGCAATCCTGCCCAACACCCAGCTCCCATCCCTCTTGCCACCAAGGGAGTGGCT  7140

7141  TCCTCTCTGCCTCTGTGCCCACTGACATGTAGGGGAGAGGGGAAGATGTCTCCCGTTTTT  7200

7201  CTGATACAGCCACCAAGGTTAAAAACAAAAAAAGGTCCAAGAACCCCTGAGCACCCAGAA  7260

7261  GGCCACTTCCCAGTCTTCCTGAGATTGAGACAGGACTGAATTCTCAAACCCATCCCAGGC  7320

7321  ACTCGGAACTCTTCCATCCCTAGTCTTAATCAACAACCTCTTACTAGGCACTTACTCTGT  7380

7381  GCCTGGCATCTTCTCTGGTGTTATCAGTGTTAGTGATTACTTTAAATTCCTTCATTTAGG  7440

7441  ACAAAATTCTCGATGTATGGGCACATTAGGAGAGCCCAAGAAACCCAGTCCTTGATTGAT  7500

7501  GAAGCACATATTCCAAGCCCCCTGACCCTAGGGCCACTCATCCCTGCACCTAAGCTAACC  7560

7561  AGCCATACCCACAATGCACCCTGCCTCTGAGTCCCCCTGTCTGGGCCACTCTTGGACAAA  7620

7621  CCTGAGCCTCTGTCCCCCTGCCAGTGTATCACAAGCTCTTCGATGCTTCGGATTCCTCCA  7680

7681  GCTACAAGCACAATGGAACAGAACTCACCCTCCGCTATTCAACAGGGACAGTCAGTGGCT  7740

7741  TTCTCAGCCAGGACATCATCACCGTAAGTTGGGCCGCCCTAGGTCATCTGCCCCGGACCC  7800

7801  CTTCTGTCCCCAGGCCTCTCCTGACCCTCCAGGGCCCACACCTGCGGGGAGGTACACTGC  7860

7861  AGCCCACTTGGAGCCTGGGGAGCTGAGGAACACCCTACTCTGCCACATCTGGCTGTTGCT  7920

7921  GCAAAGCAGCAGTACCTATGGGGGAGCAAGCCTGGGCTACGGGCTCACCGTTGGGTGGTT  7980
```

FIG. 3H

```
7981  TGTGGATGTTTTTGCATCTAACTTGCATGTAGGGCTTGTCCTGAGCCCCGTGGCTGCAGT  8040

8041  CAAGTAACTCGTCCAAGTTCACCAGCTCTGACTGGGCTACACCCTAGACTGAAATCCAGG  8100

8101  GTCAGAGTCAGGCTGAGTTTTAGGGTCAGGCATAGGTTTTAAGGTCACAGTTGAGGTTGA  8160

8161  CTCTGGGACTCAGGTCAAGGCCTGCTTTTCTTTTCCATGTGGCCCATGTCTGACCGTTTC  8220

8221  CTCATCCTGGAGTTTCTCAGGCCCTGCTCCATCAGAGTTAGGGGAGGGGCACACGTGGCA  8280

8281  CCTGAGAGGAAATCAGGGTGATTCCTGCCTCCCTTCCTTTTTCTGTGAACTCAGATATAA  8340

8341  AGGAGGGAGAAGGGCAAGCTTGTCTGTGCTAAAGAAACCCTTCGCCCATGATAAGGGTGG  8400

8401  GGGCCAAGACCCAGTCCTGCCAGGCACGAAAGTCTGGCCACTGGGGAGGGGAGGAGCTCT  8460

8461  TGGCAGCTTTTCTTTTGCTGCTTGGCAGGACCACCCTCTCAGCCTCTGCTCTCCGATCCC  8520

8521  TGGTCAACTCTAGCTCTCTCTGGGCTCCGCAGCAGAGATGTGTATTGGCACAGAGTGTGT  8580

8581  GCGTGCAGGGTTGAGGAAATACTCTTACCCCGATTTCTGTACCCTGGAGCATGTGTGCCC  8640

8641  CTGGGATCCCTAGTGTGGAAGCCCAGACCAGACTCCAACCAAGGAGTGGGCAGTGGGCTT  8700

8701  GGTCTCCTCTGGTCCTTCCTCCCACAGGTGGGTGGAATCACGGTGACACAGATGTTTGGA  8760

8761  GAGGTCACGGAGATGCCCGCCTTACCCTTCATGCTGGCCGAGTTTGATGGGGTTGTGGGC  8820

8821  ATGGGCTTCATTGAACAGGCCATTGGCAGGGTCACCCCTATCTTCGACAACATCATCTCC  8880

8881  CAAGGGTGCTAAAAGAGGACGTCTTCTCTTTCTACTACAACAGGTGGGGACTGGGACTC  8940

8941  CAAGGGCTGAGGTGGGGGGACAGGAGGGGAGAAGAGATGGGGAGTGGAAGGAGAGTCTGG  9000

9001  GCCAGAATTGTAAAGTGTTTGTAATTAGGTGACAGCCAATCAATATCTAGAGCTGTACTA  9060

9061  GCCAATATGGAAGGCACTATTGAAATTTAAATTAATTAAATACAGTTAAGCATCAATTAA  9120
```

FIG. 3I

```
9121  GCATTCAACTGGTGGCTCTTAGTTGTACTAGCCACACGTCAAATGCCTGGCAGCCACGGT  9180

9181  GGCTAGTAACTACAGTCTTATGACAGTGCAGATAGAGAATATTCCCAGCATGACAGGACA  9240

9241  TTCTAATAGACAGCGCCACTCTGGAGCAAGAGGAGATGCAAGGTGGGGCGATGGTAAAT  9300

9301  AAGGGATTACTGTGACCTGTAGCCCTGCCTGTTAGGGCCATGGCTCCTCCCACACAGAGA  9360

9361  CAGCCAACTTCAGTCATCCATTAGATCCTTCATTCGTTTGTTTGCTCACTCATCAGTTCA  9420

9421  GTAAATGCTATGTGCCAAGCACTGTGGTAGGCTCTGGGGGTGCAGCAGTGAACACAGTGA  9480

9481  ACAAGGCAGAATCTGTACTCCCCTACCCACATAGAGCTTACAGGCTAACAGGGAAGACAA  9540

9541  GACATATTCCAACATAAAGAGTGTCACAGGCAGGCAGCAAGTGTGGTGCTGAAAACCATG  9600

9601  GATGCTTTTCAATTCTAGGCTGAGCTTATATGCAGCTCAGCCAGCCTTGGGGAAGCTCTT  9660

9661  GAGCAGGGTTGGGCTCTACTCCAAACTGCTGGGCTTAGAAAGATGGCATGAGTTGGAGAC  9720

9721  AAGAGAGCTGGAGGCAAAAGGGGCTGGGTGCAGTGGCTCATGCCTGTAATCCCAGCACTT  9780

9781  TGGGAGGCCAAGGCGAGAGGATCGCATGAGCCCAGGAGTTAAGGCTTCAGTGAGCAGTGA  9840

9841  TTGTGCCACTGCACTCCAGCTAAGGCAACAGAGTGAGATCCAGTCTCAAAAAAAAAAAAA  9900

9901  AAAAAAAAAAGTCACAAGGGTAAGAACATGAGGCCAGTGGCAAAAAGAATAGAGGAGAG  9960

9961  GATCAGAGTTCAGAGAAATCTCACAGTAAAATGGAGAGGAGTCTCCGGTTTGGTGATAGA  10020

10021 AAGTGAGGCCTTGAGAAAAGGCCAATTGGCGGCTCTGCATTCAGGGGTGGTCTTTAGAAG  10080

10081 AACTGTTTTAGAGGAAGTGGGGGCAAGGCCAGATGGCAAGAAGTTAAGAGGTGGACGACG  10140

10141 TGGGTGTCAGGAAGTGGAGGTCATGAGATGTAGGCTGCCCTGGGACATTCAACAGGGAAG  10200

10201 GGAATGGGGGGTGGCGTGGGGGGTGAGATCCAGAAGCAGAAGAGGAAGGGTGGGTGTTTT  10260
```

FIG. 3J

```
10261  TAAATGCTAGAGGATGCTCGAGTGATGCCTGTAGGTGGAGGAAGAAGCCAATGGAAAGAA  10320

10321  AGAGATTAAAAATGTGGAAAGAAGAGGAGCTAAATGGGGGCACTGGAGTTTGGAGGCCTT  10380

10381  GAAAGAGATGAGGTTCCAGCAGACAGGAAGAAGCCAGGTTTTGCAGAGGAGAGGGCTGGC  10440

10441  CTCTTCTTTTATCTTGGGATGGGAAGGAGGGAACATCCAGAGAGATACTGAAGTGTTGAG  10500

10501  AGACAGGCAGGAGGGAATTTGTGCTAGCATATACACATACATTCCGAATTTATAAAAACA  10560

10561  CAAGTAGTTTGCAGTTGCACAAAATAACATATGCACACCTACACACCCATGCACACATGT  10620

10621  GCATGTGTGAATTCTAGTATGAATTCTGGAAAAACACATCACACACACAGGCATGCCCTG  10680

10681  GAGACTAGGCCTACAGTAGTCCCTGAGCCAAGTGCAGTGAGGAGGAAAGGAAGGTGAGGG  10740

10741  GAATCAGCTCCAGACGGGGCACCAGGAGCCTGGCTCCAGTCCCCCACTTGTTCACTCATG  10800

10801  GACTGGGTAACTTCAGGCAAGTGACTTCGCCTCTTGGTGACTCCATTGCCTGAAGGGCAA  10860

10861  AGAGAGTACATAACACCCACCCTGCCAAACAGCAGGGCTGATGAGGCTGGCATGAAATGA  10920

10921  AGCTTCCTTTCTGCTGTCTCTCTTTCTCTGCAGAGATTCCGAGTAAGGAGACAAAACCCC  10980

10981  CACATGGCTGTGACCTTCCAGTACTCCCCGAGCACCTGACCTAGAATTACACACGCCACC  11040

11041  GGCCCAAAACTCACATCAGCAAGCCCAGCCTCCGCTAGATGCCGAAGTTCTCTGTCTCTC  11100

11101  CTTCCTGCTCTCTCCATGCCACCTGCCCACCCCATACCCAATAGCCTCCCCAGGGTCCCC  11160

11161  TCCCATGCACCTGCTCAATCAGCAGCAACCCAAGAGTGAGGGGTGTCCATTTGTGTCTTG  11220

11221  TTCACATCCACTCACTGTCCTTGTACCTGCTCCTTTTCTGTGACCTCTCTGGGGATGCTT  11280

11281  TTTGGGGGAACAGCTGGACTACCCTGGAACAACCTCTGGTTGGTCTTGGGGAGGGGAAGA  11340

11341  AAGGCAGAGAAGCAGTATGTTCTGCATGCTTCCCAACGACAGCTCCGAGCCTGGCTGTCT  11400
```

FIG. 3K

```
11401  GTCCCACATTCCTCTGCTCTAGAGCCCTCTGTCCTCCCCTGCACCCTTGTGCAACCTTCC  11460
11461  CCAATTGCCTGAGTTGCTGGGTCCTGGAGGTTATGGGTTTCCAAGAGCTTCTGATCTTTC  11520
11521  CTTTAGGAATTCCCAATCGCTGGGAGGACAGATTGTGCTGGGAGGCAGCGACCCCCAGCA  11580
11581  TTACGAAGGGAATTTCCACTATATCAACCTCATCAAGACTGGTGTCTGGCAGATTCAAAT  11640
11641  GAAGGGGTCAGAAATCCTCAACCCTCCCCGGGCTCCAAAAAATGCTGCCGTCACTGGGGT  11700
11701  TGGGGAGGGTGGGGAAGGACTGCATTACCATCCTGCCCTCTTTCCAAATGCAGCCACTTC  11760
11761  TTAAGCACAGCCACCATTTGCTCTCTGCCTGCTCTGTCCAGGCTGGGGAACAGAGAAGGG  11820
11821  AGGGGCCTGGGGAGAAGTGGTGGAGGGTGACAGTACCTTCCCTCCTCTACTCACTGCCTC  11880
11881  AACAGGCCACCAGCGTGGCCTCCACCCACCCACCCACACTCAGGAAGGACATGCAGCCTG  11940
11941  GAGGTGCCCCATCAGCCTTCTGTCTGTCTGTCTGTCTGTCTGACTGTGGCCTCCCC       12000
12001  CAGGGTGTCTGTGGGGTCATCCACCTTGCTCTGTGAAGACGGCTGCCTGGCATTGGTAGA  12060
12061  CACCGGTGCATCCTACATCTCAGGTTCTACCAGCTCCATAGAGAAGCTCATGGAGGCCTT  12120
12121  GGGAGCCAAGAAGAGGCTGTTTGATGTAAGAAGCCAAAGAGGGAAGGTGCTGTGGGTGGG  12180
12181  GGGAGCGCCACCTGGTATCGGCTCACAAATCCCCCAGGCAAATGAGGCCATCTCAGGCCT  12240
12241  TCGCTTGTTCACCTCACACTCTCCACACATGTGGCTGGTCACCCATGGGGCGGGGCACTG  12300
12301  TCCCCAGCCCTCTCCAGCAGAGAGACCAGGCCACCAGCGCAGGACTCCTTGTCTGCTGAG  12360
12361  ACGTCTTCCATACTCAAGAAGGCTCTCTTTGCCCCCCACCCCAGTATGTCGTGAAGTGTA  12420
12421  ACGAGGGCCCTACACTCCCCGACATCTCTTTCCACCTGGGAGGCAAAGAATACACGCTCA  12480
12481  CCAGCGCGGACTATGTATTTCAGGTGAGGTTCGAGTCGGCCCCCTCGGTGGCAGGGAGAA  12540
```

FIG. 3L

```
12541  AGGCTGGACAGAGACCCTCAAAGAGTGACAGATTACAATGCACAGGTCATGTTAGAACTG  12600

12601  TAGTTCTCAAACTTGGCTGTGCATGTCACCTGGAGAGCTTTGAAAAATCCTGGTACCTGG  12660

12661  GCCACATCCCATACCTATTAAATCAGAACCTCTAGAAGTGGCACCTGGGGTTCAGTTTCC  12720

12721  CCAGGTGATTCCAATGTGTGGCCATGTTTGGGCATCACTATGCCTGTTCCCTCATCTCCA  12780

12781  TTTTCTCATCAAATACTCCCAAGAATCCTATGCTCCTATATTCTTACCCTCTTTTCATAA  12840

12841  TCAATAGGCTTAGAGAAGTTGAATAACTTGTCTAGGATCAGAAGCTAAGGCAAACTGTAA  12900

12901  GCTCCTGAAGGAAGCACGGTGCCTGATGCATTGTTTGCCTGGGATCTAGCACAGGGGCTA  12960

12961  AACATAGGAGTGGTGCAGTCCACGATGGGGCAAAATGGCCATGATGTGAGGGAGGCCCAG  13020

13021  TGTGGCTAGGGGAGAGATGGGGGCGAGAGGGGGAATGTTGCTGAAGACAGTTGCTGGGGG  13080

13081  TCAGGCAAGGTGAAAGGAGAATGCTCATGTGCTGGGTATGGAGAAACTCTCCCCCTTCCT  13140

13141  GCCAGGAATCCTACAGTAGTAAAAAGCTGTGCACACTGGCCATCCACGCCATGGATATCC  13200

13201  CGCCACCCACTGGACCCACCTGGGCCCTGGGGGCCACCTTCATCCGAAAGTTCTACACAG  13260

13261  AGTTTGATCGGCGTAACAACCGCATTGGCTTCGCCTTGGCCCGCTGAGGCCCTCTGCCAC  13320

13321  CCAGGCAGGCCCTGCCTTCAGCCCTGGCCCAGAGCTGGAACACTCTCTGAGATGCCCCTC  13380

13381  TGCCTGGGCTTATGCCCTCAGATGGAGACATTGGATGTGGAGCTCCTGCTGGATGCGTGC  13440

13441  CCTGACCCCTGCACCAGCCCTTCCCTGCTTTGAGGACAAAGAGAATAAAGACTTCATGTT  13500

13501  CACAGCCTGTTGCATCTGGGTTCACTAGGGTTTAGAACAGAGGGAGGGGCTGCGTGATCA  13560

13561  TGTGTGGACAGGAATGTGACACAGACAAGCTACACATTCGCCTAGCGCACAGGTTCTTGC  13620

13621  GTGCAGGGATGATGCCATCCATCTGCCATCAACGGGACTCAGGTGGAGCTGTTTACACAA  13680
```

FIG. 3M

```
13681  CCTCAGGTGGGAAGTCTGAAAAGAGCCGGAACCAAGCTCCCTCTAGTCCCTCAGGGACCA  13740

13741  AGGCTAATGCTGTGGCAGTAGACTGTGGGTCAGAAAGTTCTCCCAGCTCACAGAAGCCAG  13800

13801  CTCTGAGTTCAGACTCTGCTCTGCTGAGCTAGTCAGCCCTGTCTCTTGTCCCTGCAAAAC  13860

13861  TCCCCTCAGCTGTCCTTATCCACTGCAGATGCCCCCGCCCTGCCCCATGTAGCCATTTAC  13920

13921  ACAGGCATTCTAAGGCACTACCACCTAAAATCATAGAACACCAGAGATCCAGGCAATACT  13980

13981  TCCACTTTACAGGTGGGGAAACTGAGGCCCAGAGAATGGAAGGCCTTGCCCAAGATTACT  14040

14041  CGGTCAAGAATCAAGTAGTGAAGAATACTGAAAGATAGTGAAGAATCAAGACTGGAACCC  14100

14101  AGCCCGTCTGACTTGGGTCCTGGGGGTTTCCACCTTATCATAAGCAGTTGGTACCGTCAT  14160

14161  AAGTACAGTGCTTCACGCACGCTGGTACAGGGCCACGTGCACAAGCACACAGGTGCACAC  14220

14221  ACACACTGCTATCCTCCATCCCATCCACCTGGGACTCGTCAGGCTGAAGTCTCTTCTCCC  14280

14281  ACTCTCACTCCTTGGGCTGTCTTCAGGGCACATGTAACTTGGGGAATGAGAAATTAGCAT  14340

14341  CCACCTGGAGCCACTGAAGCCATCCCTCTTCACCATAGTTGCTCACCTCTCTTTTGACAG  14400

14401  AAAGTCGTGAGGCACTGAATGGCCCAACCAGGCCCTCAGTACCTCTGGGAGCCATCTGCA  14460

14461  AGAGTCCCTGTGTAGCGCCAAGAGCCGGAGCCTGGGCTTCAGG  14503
```

FIG. 4A

```
   1  GGTCTTTGTAAAATAATAATTATTCATTTCACAAAAGTGATAATTAAAAGACTTTAATAG    60

61  CAATACAGAAAGTTACATGAATATAAAGACTTAACCTTTCTAAAGCTCAGTTTTCCTAAG   120

121  TAATCAAAAACCTGATAAAGATAACAAGAATGAGGAATTATCTTGAGAAAATGTAAAATC   180

181  TTTCCTTTTATTTTTTGAGACAGGGTCTCACTCTGTCATCCAGGCTAAAGTGCAGTGGCA   240

241  CAATCATAGCTCACTACAGCCTTGAACTCCTGGACTCAAGTGATCCTCCCGCCTCAGCCT   300

301  CCCCAGTAGCTAAGACTACAGGCACGCACCACCACACCCAGCTAATTTTTTCAGAGATG    360

361  GGGTCTTGCTATATTGCCCTGGCTGGTCTTGAACGAGCTTCAAGTGAGCGTGAGCCTCCT   420

421  ACCTCATCCTCCCAAAGCACTAGGATTACAGGCATGAGCCACTGTTTCCCAGCCTAAAAT   480

481  AATTGTTTCTTAGGCCAGCTACCAAAAACGCAAAGAAAAACTTTCTGTAGTGTGATTGCT   540

541  TCTTCTTATGGGAAGCCCATTTAGATAACCTGTAAGTCAAACCTGATGAAAACAATACTT   600

601  GAATGTAATCAGACACAGAAAGACTGTTCAAGGCTATGAGTAGCTGAGTCCAAGCTCGTA   660

661  TCACTTGCCACACAACAGCCAATAAGTCTAGAGACAAGGTATTGTGGCAAGGAAAGCTAC   720

721  CTTATTCAGAGAACCAGAAAACCAAGAAGATGGTGGACCAGCATCATAAAGAACCATCTG   780

781  AAGTCAGCATGAACGTTAGGCTCTTCTTTATGTTAAGGGAAGGGGAAGAAGAAGGGGATT   840

841  GGGATCAAGAGGTGACTGATGACCACAGACACCTGGGTGCCAGCAAGGGTCTGAGGACGT   900

901  TGTAAAACTTCTTTTTTCTAGGTCAGGTCACAATGTTCCTATACATCTTTAACATAACAT   960

961  TGTTATTTGTCTGTATATTTCCTTATCTCCTTGGGGGTTAGTTTGGGGAAAGGAACTGTT  1020

1021  ACCATTTTTTTAAAGTTGAACTGCAAGCTAAACTCCTATAATTAGCTGGTCTATGTACA   1080

1081  GAGCTAAGCAGAAGCTTTTAGCCTAAAGGATAATACCCCTGGGGGTCAGAGGCAAAATGG  1140
```

FIG. 4B

```
1141  AGTCAGTCATGCTAAGTCTCCCTCCACTCTCTTTCTTTTTTGAGATGGAATTTCACTCTT  1200

1201  ATTGCCCAGGCCGGAGTGCAGTGGCATGATCTCAGCTCACTGCAACCTCCGCCTCCTGGG  1260

1261  TTCAAGCAATTCTCTTGCCTCAGCCTCCTGAGTAGCTGAGATTACAGGTGTCCATCACCA  1320

1321  CACCCAGCTAATTTTTGTAGTTTAGTGGAGATGGGGTTTCACCATTGTTGGTCAGGCTGG  1380

1381  TCTGGAACTCCTGACCTCAGGTGATCTACCCACCTTGGCCTCCCAAAGTGCTGGGACAGG  1440

1441  TGTGAGCCACCATGCCTGGCCCCTCTACTCTTATAATTAAACCAGCTGTTGCTTTTCCTG  1500

1501  CCAAGAAACCAGTCATGAAGATTCACCCATGTTCTAGATGGGAAAACTGGGCTGTAGCCT  1560

1561  GGGAGAGGCCAGTCAGGGACAAAGCCAAAGTTAATATAGAGAATGGAGCTTCCAGGGTAT  1620

1621  AGGGGTTGGGTCTGGGCTAGGGAGCTGGAAACCTAGGTTTTACGCTTGTCCCAGTTTTGA  1680

1681  TGTTAGCCCTGAGCAGTGCTGTTTCTCATCAGCCTCTGCCTGCTCCAGGGGTCACAGGGC  1740

1741  CAAGCCAGATAGAGGGCTGCTAGCGTCACTGGACACAAGATTGCTTTCCCACAGCTGTCC  1800

1801  TTCCTCCAGCCCCTCTGCTCCCCATCCGGAAACCTGGGTACCCTTCACCCACCTAGCTCT  1860

1861  GTCCCGCAGTGAGATTTATTGCTGACTGCCCTGCCATCTACCCCAGGGTAATAAATCAGG  1920

1921  GCAGAGCAGAATTGCAATCACCCCATGCATGGAGTGTATAAAAGGGGAAGGGCTAAGGGA  1980

1981  GCCACAGAACCTCAGTGGATCTCAGAGAGAGCCCCAGACTGAGGGAAGCATGGATGGATG  2040

2041  GAGAAGGATGCCTCGCTGGGGACTGCTGCTGCTGCTCTGGGGCTCCTGTACCTTTGGTCT  2100

2101  CCCGACAGACACCACCACCTTTAAACGGTAATTGGTAACTCAGGCAGAGAAGGGGTGGGA  2160

2161  GGGGTGCAGGGTTCCCACCTTCCCAACACCCTGGCTTTTCCACATGCGGTGTCATTCAGT  2220

2221  CCTTACGATCAGCTGGACAGGGAAGTATGGACCTGTTCAGAGAGGTCAAGTGACTTGCCC  2280
```

FIG. 4C

```
2281  AATAAATGACACTAGTAGTCAGGTCTAGAAGCTGTGACTTTTGCTTCCTGCCCAGAGCAC  2340

2341  CATGCTAACTAAGCACTGTAGAGAACTCAGAAGTATTAGGACATGCCCCTTGCACTTGAG  2400

2401  GAGCTCACAGCCTGAATATTAAGAAGGGCATGGGTGGTTGGGCGCGGTGGCTCCTGCCTG  2460

2461  TAATCCCAGCACTTTGGGAGGCTGAGACGGATCACTTGAGGTCAGGAGTTTGAGACCAGC  2520

2521  CTGGCCAACATGGGGAAACCCCATCTCTACTAAAAATACAAAAATTAGCCGGGCATGGTG  2580

2581  GCAGGCACTTGTAATCCCCAGCTACTCGGGAAGCTGAGGCAGGAGAATCGTTTGAGCCCG  2640

2641  GAAGGTGGAGATTGCTGAGCCAAGATCGTGCCACTGCACTCCAGCCTGAGTGACAGAACA  2700

2701  AGACTCCATCTCAAAAAAAAAAAGACGGGGGTCGGGGCATGGGTACAGTTAACTGTACC  2760

2761  AGGGAAGCAGCTTGATATCGTGGTTAAATGCAAGGCTTATAGAGTTAGATTGCCTTCATT  2820

2821  TAAATTTTGCTTCACTAGCAGAACAAACTAGGTCTGGAATCATGGGCAAGTTATTTAACC  2880

2881  TCTCCAAGTCTCAGTTTATCATTTTAAACAGGTATGATAATAACAGTACCTACTTGATGG  2940

2941  GGCTGCTTTGGGGATTTTAGGAGATAAGGCATAGAAAGCTGGGCACGTTGTAAGAGCCCA  3000

3001  GCTACTGTTAGTACTACAGGATAGATTCTTACAAATATCAAAAGCAAGGTTTGGCCGGGA  3060

3061  GCAGTGGCTCACGCCTATAATCCCAACACTTTGGGAGGCCGAGGGGGGCAGATCACCCGA  3120

3121  GGTCAGGAGTTCAAGACCAGCCTGACCAACATGGAGAAACCCTGTCTCTACTAAAAATAC  3180

3181  AAAATTAGCCGGGCGTGGTGGCACATGCCTGTAATTCCAGCTACTTGGGAGGCTGAGGCA  3240

3241  GGAGAATCGCTTGAACCTGGGAGGCTGAGGTTGCAGTGAGCCGACATAGCGCCATTGCAC  3300

3301  TCCAGCCTGGTCAACAAGAGCAAAACTCAGTCTAAAAAAAAAAAGAAAGAAAAAAACAA  3360

3361  GGCTTTAGGTAGCCCACAATTAGAAGGAGAAAACCTTAGCATCCCCTAGGTGCCAGGCCT  3420
```

FIG. 4D

```
3421  TGTGGGAACAAGTGATTCATTAAGACTGTAGAAGGAAGCTGGGCACGCGGCTCATGCTTG  3480

3481  TAATTCCAGCACTTTGAGAGGCTGAGGTGGGCAGATCGCTTGAGCTCACGAGTTCAAGAC  3540

3541  CAGCCTAGGCAACATGGTGAAACCTTGTCTGTACAAATACAAAAATTAGCTAGGTGTGGT  3600

3601  GGTGCAAATCTGTAGTCCCAGCTACTCGGGAGGCTGAGGTGGGAGCATCACTTCAGCCTG  3660

3661  GGAGGTGGAGGCTGCAGTGAGCAGAGACTGACCCACTGTGCTCTAGCCTGGGTGATAGAG  3720

3721  CCAGACCTTATGTAAAAAAAAAAAAAAAAAAAAAAAGACTGAAGAAGGGGAAGAGACAG  3780

3781  CATTTGAGAAAAGGCCTCACAGAGAAAGGGGTTTTCAATCTGGGGACAGCAGATATGACC  3840

3841  AGCAGTCCTGAAGGTAGGGAGGCACACTTTAATAATGGTAATAGTTGCTAAGCCTATAAA  3900

3901  ATGCTTAGGGTGTCACAGGATCTTTTCACATGTCTCATCTCAAGTCATGCCCCCAACAAC  3960

3961  TCAGCATTCCCACTTTGCAGATGAGGACACTGAGGCTCAGGGAGGTGATATGTAAGAGGC  4020

4021  TAAGCCTCAACACACACTGGGCCTTTTGCTTCCGAAACTGCTTTCCCTTGCTCTGAGGCT  4080

4081  CTCGGAGAGTAATTGCTGGGTTGTGAGCACTGGGTAAGAGGATGGGTGCTTCAAAGCAGC  4140

4141  TGCACTCCAGGATAAAGGTAGAGGAAAGTAAAAACATCTTCCCCTGCTGTTATCCAAAAG  4200

4201  AGAAAAAGAATGGAATTGGGCAAGGGGTGGAGGGGGAATCCAGCTTTTGAAACAGTATTA  4260

4261  TAGGAATTTTGCTACCCGCTATGTGCAGAGCATCATGCGAGGCACTTGGGACAGCTGAAT  4320

4321  GAATGAGCTCCATTCTCAAGGTGAACATGTACATATACACACCTACAATTTACATTTATT  4380

4381  GAGCAGTGGTCGCATGGTTTCATCTGCACAGTGACTCTGAGGTAGGTACTACCATTAGGC  4440

4441  CCATTGTTAGAGAGGGGTTAATGGAGACTTAGAAGAGCCCAGAGAGGTTAGGTAGCTTT  4500

4501  CTCAGAATCACATAAGTGGTAAGGGGATTCAGGCATGCCCCCTGCAACCACTGTCTTCAC  4560
```

FIG. 4E

```
4561  CACCGTACGGCACCAGTTCCACAAGCTGTACAGTGTGGGCTGTGAGACCCAAGGAAAAAC  4620

4621  AGAGCTGAGGCCCACGGGAAGGTGAGGCCGGTGTGGGCTGGAGGCCTTGGGGTAAGCTTC  4680

4681  CTGGAGGTGGGGGTACATGTTGGGCCTTGGAGGACTAAAGAACTGGGGGGAAAAGGAAGG  4740

4741  GAAGAAGGAAAGGATTTTCTGAAAAGGAAATGGCAAGAAGTAAAGGTCCAAAGCATAGGC  4800

4801  TGTTGTGAGTAAACAGTGGGAAATGCAACCTCTTTGGGGCCAAACCTCTGACCCTCCACG  4860

4861  TTCCCAGCTGTGAAGTGGGAGTAATAAAATCATCCACCTTATGAGAGCAAATAAAATAAT  4920

4921  GATTGTGAAAATATTTTGGTAACAGTAACCTGTGATAGGAAGATAACAAATCATTTCTGT  4980

4981  TACAATACCATGCTGATAGGCATAAAAGTTGCATTCATGTTCATGGGCAAAATGGGGGTA  5040

5041  AGTAGAATGCATGGGACGCAAGAAGGATGTAGGAAGGAAAGGGTAGTGTGAGTATAGGAG  5100

5101  GACTAGCCACTGAGAAGAAAGTAGAAGAAAGAGGGAATCTTTGTGTGTATGGGAAAGTCT  5160

5161  ATTGCAGAGTCAACTTGGGCTTCCATCCTGGGACCTTCCCGTGAACAGCTAGAGACATCT  5220

5221  TCCTCTGGGCTTTGGCAGCCTTTATGTCGGGACCCAGGGGACCCTATATGGGAAATAGGG  5280

5281  CCAGACACATGCTCTGAATCCCTGCTTCAACATTTCTGAGTCACCTTTGTCCCTGTGAGC  5340

5341  CTTCATTTTTCTCATCTATAAAATGGATGACAGCTAGCTTGTTGGTGTGATTTCAGTAGC  5400

5401  GGCTCAGTAGAGTCAGTTTCCTAGGTCTCTTTAATTCTGCCTCTCAAAGGTGATGGGAAA  5460

5461  ACATCTAGACAAGAAGCCAAGGGACCGGGACACATCTCTCCAAGGACGAGGTGCATGGCG  5520

5521  CTCTGAAGATGCTGGCATCTCTCTAGGCCCAACCCAGCTCAGGGGGTCCACTCCACCACA  5580

5581  GCCCTGGCTGGGTGCCTGTCCCCTGGTATCCTGGAGACCTTGCAGCTGCTGTGGGCATCT  5640

5641  GCTGCCACCTAGCGGCCTCCCATGGCACTGTCTCCCCGCCAGCCCCTAGTTTTGACAGGG  5700
```

FIG. 4F

```
5701  GCACTCCCTGGCATTAATCTCTTCAGAGGGAATGTCTGTGCCTGTTTCCTGTCTGTCCTC  5760

5761  CCGCCAGGTGGAGTTCCTTAAAGGCAGTCATGATCATTATCTTTCTAGCTCCAGTGTCCA  5820

5821  GCACAGTGAGGCACAAAGTAGTTGTTCAGCAGGTGATTACGGAATAAATGAATGAACGGA  5880

5881  CCAATAAACAAATAGCCTTGTCTAATCAAAATTAGGCAACAGAAGGAAGTCACTTCAGGG  5940

5941  TTATTTAATCCCCGGGCAGCTGACTCCTCTAAATTGACTCTTGACAAGAAGTAACTCTTA  6000

6001  TAAATGCTCCAGAGGCCCTCAGCGACAGAGGTGATTTCCAGGTGGCTGGGCTAACGTTAA  6060

6061  AGGTGGTTGTACTAAAAGCAGGGGTTTGGCCTCAGGGACTCCACCACTGTGGTGGAGGTA  6120

6121  CAGCACTTTTCTATTTTTGCTTCCTCCACCCTGGGCCAGGATCTTCCTCAAGAGAATGCC  6180

6181  CTCAATCCGAGAAAGCCTGAAGGAACGAGGTGTGGACATGGCCAGGCTTGGTCCCGAGTG  6240

6241  GAGCCAACCCATGAAGAGGCTGACACTTGGCAACACCACCTCCTCCGTGATCCTCACCAA  6300

6301  CTACATGGACGTGAGTGCTTGGCTCAGCCCCTCGCTCCCTCCCTGTCTCCTTTCCCTCAT  6360

6361  GGACCTAGGGCTTTCTTTGCTGCAAGACTCACCCTTTCCAAGCTGTGTTTGACGAAGGCG  6420

6421  CTGAGTAGCACGTGAGCACCCTAGAAAATTCCCATTTTCCAGCTGGAAAGCCTGAGCACA  6480

6481  GAAGACAGGAAGGCATCCAGGGGCCATTCAGGGGCAGGGTTAGGTTTGGAACTCAGCCCA  6540

6541  GGCCTCAAGCCAGGTGTCACAGGTGGGTGGGAAGGGGTGTGTGACTCAGGTGGGGGTTTC  6600

6601  TGTGACCTGGCCCAGCACAACCTGATGGCTTCCTGCCCCAGAGGATCCTCAAGAGTCAAG  6660

6661  TTTGCTTCCTGCTTCATTCTCAATGTTTTGATTTTGCCCTCTTGTCTTACTGAGACTCCC  6720

6721  ACTTTCTGGGATGCCATGGGGAGATGCTAAGCCTCCTACCAGTTCCTGCAGGAAAATGGA  6780

6781  AACCCCGAGAGGCTATAGGACCTCGCCTGGGCCAAGTCTCACACCGAGAGCCAAGAGTGA  6840
```

FIG. 4G

```
6841  AGCCAGGCAAGACCCCAAGACCCAAGGTCCCCTGAGCCCCTCCAGCCCTCTCTTTTTACC  6900

6901  CCCACAGACCCAGTACTATGGCGAGATTGGCATCGGCACCCCACCCCAGACCTTCAAAGT  6960

6961  CGTCTTTGACACTGGTTCGTCCAATGTTTGGGTGCCCTCCTCCAAGTGCAGCCGTCTCTA  7020

7021  CACTGCCTGTGGTGAGACCTAAGACCCACAGTGCCTCTCCTCCATCCCCCTGCCCTACTG  7080

7081  TGCATGAGCAATCCTGCCCAACACCCAGCTCCCATCCCTCTTGCCACCAAGGGAGTGGCT  7140

7141  TCCTCTCTGCCTCTGTGCCCACTGACATGTAGGGGAGAGGGGAAGATGTCTCCCGTTTTT  7200

7201  CTGATACAGCCACCAAGGTTAAAAACAAAAAAAGGTCCAAGAACCCCTGAGCACCCAGAA  7260

7261  GGCCACTTCCCAGTCTTCCTGAGATTGAGACAGGACTGAATTCTCAAACCCATCCCAGGC  7320

7321  ACTCGGAACTCTTCCATCCCTAGTCTTAATCAACAACCTCTTACTAGGCACTTACTCTGT  7380

7381  GCCTGGCATCTTCTCTGGTGTTATCAGTGTTAGTGATTACTTTAAATTCCTTCATTTAGG  7440

7441  ACAAAATTCTCGATGTATGGGCACATTAGGAGAGCCCAAGAAACCCAGTCCTTGATTGAT  7500

7501  GAAGCACATATTCCAAGCCCCCTGACCCTAGGGCCACTCATCCCTGCACCTAAGCTAACC  7560

7561  AGCCATACCCACAATGCACCCTGCCTCTGAGTCCCCCTGTCTGGGCCACTCTTGGACAAA  7620

7621  CCTGAGCCTCTGTCCCCCTGCCAGTGTATCACAAGCTCTTCGATGCTTCGGATTCCTCCA  7680

7681  GCTACAAGCACAATGGAACAGAACTCACCCTCCGCTATTCAACAGGGACAGTCAGTGGCT  7740

7741  TTCTCAGCCAGGACATCATCACCGTAAGTTGGGCCGCCCTAGGTCATCTGCCCCGGACCC  7800

7801  CTTCTGTCCCCAGGCCTCTCCTGACCCTCCAGGGCCCACACCTGCGGGGAGGTACACTGC  7860

7861  AGCCCACTTGGAGCCTGGGGAGCTGAGGAACACCCTACTCTGCCACATCTGGCTGTTGCT  7920

7921  GCAAAGCAGCAGTACCTATGGGGGAGCAAGCCTGGGCTACGGGCTCACCGTTGGGTGGTT  7980
```

FIG. 4H

```
7981   TGTGGATGTTTTTGCATCTAACTTGCATGTAGGGCTTGTCCTGAGCCCCGTGGCTGCAGT   8040

8041   CAAGTAACTCGTCCAAGTTCACCAGCTCTGACTGGGCTACACCCTAGACTGAAATCCAGG   8100

8101   GTCAGAGTCAGGCTGAGTTTTAGGGTCAGGCATAGGTTTTAAGGTCACAGTTGAGGTTGA   8160

8161   CTCTGGGACTCAGGTCAAGGCCTGCTTTTCTTTTCCATGTGGCCCATGTCTGACCGTTTC   8220

8221   CTCATCCTGGAGTTTCTCAGGCCCTGCTCCATCAGAGTTAGGGGAGGGGCACACGTGGCA   8280

8281   CCTGAGAGGAAATCAGGGTGATTCCTGCCTCCCTTCCTTTTTCTGTGAACTCAGATATAA   8340

8341   AGGAGGGAGAAGGGCAAGCTTGTCTGTGCTAAAGAAACCCTTCGCCCATGATAAGGGTGG   8400

8401   GGGCCAAGACCCAGTCCTGCCAGGCACGAAAGTCTGGCCACTGGGGAGGGGAGGAGCTCT   8460

8461   TGGCAGCTTTTCTTTTGCTGCTTGGCAGGACCACCCTCTCAGCCTCTGCTCTCCGATCCC   8520

8521   TGGTCAACTCTAGCTCTCTCTGGGCTCCGCAGCAGAGATGTGTATTGGCACAGAGTGTGT   8580

8581   GCGTGCAGGGTTGAGGAAATACTCTTACCCCGATTTCTGTACCCTGGAGCATGTGTGCCC   8640

8641   CTGGGATCCCTAGTGTGGAAGCCCAGACCAGACTCCAACCAAGGAGTGGGCAGTGGGCTT   8700

8701   GGTCTCCTCTGGTCCTTCCTCCCACAGGTGGGTGGAATCACGGTGACACAGATGTTTGGA   8760

8761   GAGGTCACGGAGATGCCCGCCTTACCCTTCATGCTGGCCGAGTTTGATGGGGTTGTGGGC   8820

8821   ATGGGCTTCATTGAACAGGCCATTGGCAGGGTCACCCCTATCTTCGACAACATCATCTCC   8880

8881   CAAGGGGTGCTAAAAGAGGACGTCTTCTCTTTCTACTACAACAGGTGGGGACTGGGACTC   8940

8941   CAAGGGCTGAGGTGGGGGGACAGGAGGGGAGAAGAGATGGGGAGTGGAAGGAGAGTCTGG   9000

9001   GCCAGAATTGTAAAGTGTTTGTAATTAGGTGACAGCCAATCAATATCTAGAGCTGTACTA   9060

9061   GCCAATATGGAAGGCACTATTGAAATTTAAATTAATTAAATACAGTTAAGCATCAATTAA   9120
```

FIG. 4I

```
 9121  GCATTCAACTGGTGGCTCTTAGTTGTACTAGCCACACGTCAAATGCCTGGCAGCCACGGT   9180

9181  GGCTAGTAACTACAGTCTTATGACAGTGCAGATAGAGAATATTCCCAGCATGACAGGACA   9240

9241  TTCTAATAGACAGCGCCACTCTGGAGCAAGAGGAGATGCAAGGTGGGGGCGATGGTAAAT   9300

9301  AAGGGATTACTGTGACCTGTAGCCCTGCCTGTTAGGGCCATGGCTCCTCCCACACAGAGA   9360

9361  CAGCCAACTTCAGTCATCCATTAGATCCTTCATTCGTTTGTTTGCTCACTCATCAGTTCA   9420

9421  GTAAATGCTATGTGCCAAGCACTGTGGTAGGCTCTGGGGGTGCAGCAGTGAACACAGTGA   9480

9481  ACAAGGCAGAATCTGTACTCCCCTACCCACATAGAGCTTACAGGCTAACAGGGAAGACAA   9540

9541  GACATATTCCAACATAAAGAGTGTCACAGGCAGGCAGCAAGTGTGGTGCTGAAAACCATG   9600

9601  GATGCTTTTCAATTCTAGGCTGAGCTTATATGCAGCTCAGCCAGCCTTGGGGAAGCTCTT   9660

9661  GAGCAGGGTTGGGCTCTACTCCAAACTGCTGGGCTTAGAAAGATGGCATGAGTTGGAGAC   9720

9721  AAGAGAGCTGGAGGCAAAAGGGGCTGGGTGCAGTGGCTCATGCCTGTAATCCCAGCACTT   9780

9781  TGGGAGGCCAAGGCGAGAGGATCGCATGAGCCCAGGAGTTAAGGCTTCAGTGAGCAGTGA   9840

9841  TTGTGCCACTGCACTCCAGCTAAGGCAACAGAGTGAGATCCAGTCTCAAAAAAAAAAAA   9900

9901  AAAAAAAAAAAGTCACAAGGGTAAGAACATGAGGCCAGTGGCAAAAAGAATAGAGGAGAG   9960

9961  GATCAGAGTTCAGAGAAATCTCACAGTAAAATGGAGAGGAGTCTCCGGTTTGGTGATAGA  10020

10021  AAGTGAGGCCTTGAGAAAAGGCCAATTGGCGGCTCTGCATTCAGGGGTGGTCTTTAGAAG  10080

10081  AACTGTTTTAGAGGAGGTGGGGGCAAGGCCAGATGGCAAGAAGTTAAGAGGTGGACGACG  10140

10141  TGGGTGTCAGGAAGTGGAGGTCATGAGATGTAGGCTGCCCTGGGACATTCAACAGGGAAG  10200

10201  GGAATGGGGGGTGGCGTGGGGGGTGAGATCCAGAAGCAGAAGAGGAAGGGTGGGTGTTTT  10260
```

FIG. 4J

```
10261  TAAATGCTAGAGGATGCTCGAGTGATGCCTGTAGGTGGAGGAAGAAGCCAATGGAAAGAA  10320

10321  AGAGATTAAAAATGTGGAAAGAAGAGGAGCTAAATGGGGGCACTGGAGTTTGGAGGCCTT  10380

10381  GAAAGAGATGAGGTTCCAGCAGACAGGAAGAAGCCAGGTTTTGCAGAGGAGAGGGCTGGC  10440

10441  CTCTTCTTTTATCTTGGGATGGGAAGGAGGGAACATCCAGAGAGATACTGAAGTGTTGAG  10500

10501  AGACAGGCAGGAGGGAATTTGTGCTAGCATATACACATACATTCCGAATTTATAAAAACA  10560

10561  CAAGTAGTTTGCAGTTGCACAAAATAACATATGCACACCTACACACCCATGCACACATGT  10620

10621  GCATGTGTGAATTCTAGTATGAATTCTGGAAAAACACATCACACACACAGGCATGCCCTG  10680

10681  GAGACTAGGCCTACAGTAGTCCCTGAGCCAAGTGCAGTGAGGAGGAAAGGAAGGTGAGGG  10740

10741  GAATCAGCTCCAGACGGGGCACCAGGAGCCTGGCTCCAGTCCCCCACTTGTTCACTCATG  10800

10801  GACTGGGTAACTTCAGGCAAGTGACTTCGCCTCTTGGTGACTCCATTGCCTGAAGGGCAA  10860

10861  AGAGAGTACATAACACCCACCCTGCCAAACAGCAGGGCTGATGAGGCTGGCATGAAATGA  10920

10921  AGCTTCCTTTCTGCTGTCTCTCTTTCTCTGCAGAGATTCCGAGTAAGGAGACAAAACCCC  10980

10981  CACATGGCTGTGACCTTCCAGTACTCCCCGAGCACCTGACCTAGAATTACACACGCCACC  11040

11041  GGCCCAAAACTCACATCAGCAAGCCCAGCCTCCGCTAGATGCCGAAGTTCTCTGTCTCTC  11100

11101  CTTCCTGCTCTCTCCATGCCACCTGCCCACCCCATACCCAATAGCCTCCCCAGGGTCCCC  11160

11161  TCCCATGCACCTGCTCAATCAGCAGCAACCCAAGAGTGAGGGGTGTCCATTTGTGTCTTG  11220

11221  TTCACATCCACTCACTGTCCTTGTACCTGCTCCTTTTCTGTGACCTCTCTGGGGATGCTT  11280

11281  TTTGGGGGAACAGCTGGACTACCCTGGAACAACCTCTGGTTGGTCTTGGGGAGGGGAAGA  11340

11341  AAGGCAGAGAAGCAGTATGTTCTGCATGCTTCCCAACGACAGCTCCGAGCCTGGCTGTCT  11400
```

FIG. 4K

```
11401  GTCCCACATTCCTCTGCTCTAGAGCCCTCTGTCCTCCCCTGCACCCTTGTGCAACCTTCC  11460

11461  CCAATTGCCTGAGTTGCTGGGTCCTGGAGGTTATGGGTTTCCAAGAGCTTCTGATCTTTC  11520

11521  CTTTAGGAATTCCCAATCGCTGGGAGGACAGATTGTGCTGGGAGGCAGCGACCCCCAGCA  11580

11581  TTACGAAGGGAATTTCCACTATATCAACCTCATCAAGACTGGTGTCTGGCAGATTCAAAT  11640

11641  GAAGGGGTCAGAAATCCTCAACCCTCCCCGGGCTCCAAAAAATGCTGCCGTCACTGGGGT  11700

11701  TGGGGAGGGTGGGGAAGGACTGCATTACCATCCTGCCCTCTTTCCAAATGCAGCCACTTC  11760

11761  TTAAGCACAGCCACCATTTGCTCTCTGCCTGCTCTGTCCAGGCTGGGGAACAGAGAAGGG  11820

11821  AGGGGCCTGGGGAGAAGTGGTGGAGGGTGACAGTACCTTCCCTCCTCTACTCACTGCCTC  11880

11881  AACAGGCCACCAGCGTGGCCTCCACCCACCCACCCACACTCAGGAAGGACATGCAGCCTG  11940

11941  GAGGTGCCCCATCAGCCTTCTGTCTGTCTGTCTGTCTGTCTGTCTGACTGTGGCCTCCCC  12000

12001  CAGGGTGTCTGTGGGGTCATCCACCTTGCTCTGTGAAGACGGCTGCCTGGCATTGGTAGA  12060

12061  CACCGGTGCATCCTACATCTCAGGTTCTACCAGCTCCATAGAGAAGCTCATGGAGGCCTT  12120

12121  GGGAGCCAAGAAGAGGCTGTTTGATGTAAGAAGCCAAAGAGGGAAGGTGCTGTGGGTGGG  12180

12181  GGGAGCGCCACCTGGTATCGGCTCACAAATCCCCCAGGCAAATGAGGCCATCTCAGGCCT  12240

12241  TCGCTTGTTCACCTCACACTCTCCACACATGTGGCTGGTCACCCATGGGGCGGGGCACTG  12300

12301  TCCCCAGCCCTCTCCAGCAGAGAGACCAGGCCACCAGCGCAGGACTCCTTGTCTGCTGAG  12360

12361  ACGTCTTCCATACTCAAGAAGGCTCTCTTTGCCCCCCACCCCAGTATGTCGTGAAGTGTA  12420

12421  ACGAGGGCCCTACACTCCCCGACATCTCTTTCCACCTGGGAGGCAAAGAATACACGCTCA  12480

12481  CCAGCGCGGACTATGTATTTCAGGTGAGGTTCGAGTCGGCCCCCTCGGTGGCAGGGAGAA  12540
```

FIG. 4L

```
12541  AGGCTGGACAGAGACCCTCAAAGAGTGACAGATTACAATGCACAGGTCATGTTAGAACTG  12600

12601  TAGTTCTCAAACTTGGCTGTGCATGTCACCTGGAGAGCTTTGAAAAATCCTGGTACCTGG  12660

12661  GCCACATCCCATACCTATTAAATCAGAACCTCTAGAAGTGGCACCTGGGGTTCAGTTTCC  12720

12721  CCAGGTGATTCCAATGTGTGGCCATGTTTGGGCATCACTATGCCTGTTCCCTCATCTCCA  12780

12781  TTTTCTCATCAAATACTCCCAAGAATCCTATGCTCCTATATTCTTACCCTCTTTTCATAA  12840

12841  TCAATAGGCTTAGAGAAGTTGAATAACTTGTCTAGGATCAGAAGCTAAGGCAAACTGTAA  12900

12901  GCTCCTGAAGGAAGCACGGTGCCTGATGCATTGTTTGCCTGGGATCTAGCACAGGGGCTA  12960

12961  AACATAGGAGTGGTGCAGTCCACGATGGGGCAAAATGGCCATGATGTGAGGGAGGCCCAG  13020

13021  TGTGGCTAGGGGAGAGATGGGGGCGAGAGGGGGAATGTTGCTGAAGACAGTTGCTGGGGG  13080

13081  TCAGGCAAGGTGAAAGGAGAATGCTCATGTGCTGGGTATGGAGAAACTCTCCCCCTTCCT  13140

13141  GCCAGGAATCCTACAGTAGTAAAAAGCTGTGCACACTGGCCATCCACGCCATGGATATCC  13200

13201  CGCCACCCACTGGACCCACCTGGGCCCTGGGGGCCACCTTCATCCGAAAGTTCTACACAG  13260

13261  AGTTTGATCGGCGTAACAACCGCATTGGCTTCGCCTTGGCCCGCTGAGGCCCTCTGCCAC  13320

13321  CCAGGCAGGCCCTGCCTTCAGCCCTGGCCCAGAGCTGGAACACTCTCTGAGATGCCCCTC  13380

13381  TGCCTGGGCTTATGCCCTCAGATGGAGACATTGGATGTGGAGCTCCTGCTGGATGCGTGC  13440

13441  CCTGACCCCTGCACCAGCCCTTCCCTGCTTTGAGGACAAAGAGAATAAAGACTTCATGTT  13500

13501  CACAGCCTGTTGCATCTGGGTTCACTAGGGTTTAGAACAGAGGGAGGGGCTGCGTGATCA  13560

13561  TGTGTGGACAGGAATGTGACACAGACAAGCTACACATTCGCCTAGCGCACAGGTTCTTGC  13620

13621  GTGCAGGGATGATGCCATCCATCTGCCATCAACGGGACTCAGGTGGAGCTGTTTACACAA  13680
```

FIG. 4M

```
13681  CCTCAGGTGGGAAGTCTGAAAAGAGCCGGAACCAAGCTCCCTCTAGTCCCTCAGGGACCA  13740

13741  AGGCTAATGCTGTGGCAGTAGACTGTGGGTCAGAAAGTTCTCCCAGCTCACAGAAGCCAG  13800

13801  CTCTGAGTTCAGACTCTGCTCTGCTGAGCTAGTCAGCCCTGTCTCTTGTCCCTGCAAAAC  13860

13861  TCCCCTCAGCTGTCCTTATCCACTGCAGATGCCCCCGCCCTGCCCCATGTAGCCATTTAC  13920

13921  ACAGGCATTCTAAGGCACTACCACCTAAAATCATAGAACACCAGAGATCCAGGCAATACT  13980

13981  TCCACTTTACAGGTGGGGAAACTGAGGCCCAGAGAATGGAAGGCCTTGCCCAAGATTACT  14040

14041  CGGTCAAGAATCAAGTAGTGAAGAATACTGAAAGATAGTGAAGAATCAAGACTGGAACCC  14100

14101  AGCCCGTCTGACTTGGGTCCTGGGGGTTTCCACCTTATCATAAGCAGTTGGTACCGTCAT  14160

14161  AAGTACAGTGCTTCACGCACGCTGGTACAGGGCCACGTGCACAAGCACACAGGTGCACAC  14220

14221  ACACACTGCTATCCTCCATCCCATCCACCTGGGACTCGTCAGGCTGAAGTCTCTTCTCCC  14280

14281  ACTCTCACTCCTTGGGCTGTCTTCAGGGCACATGTAACTTGGGGAATGAGAAATTAGCAT  14340

14341  CCACCTGGAGCCACTGAAGCCATCCCTCTTCACCATAGTTGCTCACCTCTCTTTTGACAG  14400

14401  AAAGTCGTGAGGCACTGAATGGCCCAACCAGGCCCTCAGTACCTCTGGGAGCCATCTGCA  14460

14461  AGAGTCCCTGTGTAGCGCCAAGAGCCGGAGCCTGGGCTTCAGG  14503
```

FIG. 5A

```
   1  GGTCTTTGTAAAATAATAATTATTCATTTCACAAAAGTGATAATTAAAAGACTTTAATAG    60

61  CAATACAGAAAGTTACATGAATATAAAGACTTAACCTTTCTAAAGCTCAGTTTTCCTAAG   120

121  TAATCAAAAACCTGATAAAGATAACAAGAATGAGGAATTATCTTGAGAAAATGTAAAATC   180

181  TTTCCTTTTATTTTTTGAGACAGGGTCTCACTCTGTCATCCAGGCTAAAGTGCAGTGGCA   240

241  CAATCATAGCTCACTACAGCCTTGAACTCCTGGACTCAAGTGATCCTCCCGCCTCAGCCT   300

301  CCCCAGTAGCTAAGACTACAGGCACGCACCACCACACCCAGCTAATTTTTTCAGAGATG   360

361  GGGTCTTGCTATATTGCCCTGGCTGGTCTTGAACGAGCTTCAAGTGAGCGTGAGCCTCCT   420

421  ACCTCATCCTCCCAAAGCACTAGGATTACAGGCATGAGCCACTGTTTCCCAGCCTAAAAT   480

481  AATTGTTTCTTAGGCCAGCTACCAAAAACGCAAAGAAAAACTTTCTGTAGTGTGATTGCT   540

541  TCTTCTTATGGGAAGCCCATTTAGATAACCTGTAAGTCAAACCTGATGAAAACAATACTT   600

601  GAATGTAATCAGACACAGAAAGACTGTTCAAGGCTATGAGTAGCTGAGTCCAAGCTCGTA   660

661  TCACTTGCCACACAACAGCCAATAAGTCTAGAGACAAGGTATTGTGGCAAGGAAAGCTAC   720

721  CTTATTCAGAGAACCAGAAAACCAAGAAGATGGTGGACCAGCATCATAAAGAACCATCTG   780

781  AAGTCAGCATGAACGTTAGGCTCTTCTTTATGTTAAGGGAAGGGGAAGAAGAAGGGGATT   840

841  GGGATCAAGAGGTGACTGATGACCACAGACACCTGGGTGCCAGCAAGGGTCTGAGGACGT   900

901  TGTAAAACTTCTTTTTTCTAGGTCAGGTCACAATGTTCCTATACATCTTTAACATAACAT   960

961  TGTTATTTGTCTGTATATTTCCTTATCTCCTTGGGGGTTAGTTTGGGGAAAGGAACTGTT  1020

1021  ACCATTTTTTTAAAGTTGAACTGCAAGCTAAACTCCTATAATTAGCTGGTCTATGTACA  1080

1081  GAGCTAAGCAGAAGCTTTTAGCCTAAAGGATAATACCCCTGGGGGTCAGAGGCAAAATGG  1140
```

FIG. 5B

```
1141  AGTCAGTCATGCTAAGTCTCCCTCCACTCTCTTTCTTTTTTGAGATGGAATTTCACTCTT  1200

1201  ATTGCCCAGGCCGGAGTGCAGTGGCATGATCTCAGCTCACTGCAACCTCCGCCTCCTGGG  1260

1261  TTCAAGCAATTCTCTTGCCTCAGCCTCCTGAGTAGCTGAGATTACAGGTGTCCATCACCA  1320

1321  CACCCAGCTAATTTTTGTAGTTTAGTGGAGATGGGGTTTCACCATTGTTGGTCAGGCTGG  1380

1381  TCTGGAACTCCTGACCTCAGGTGATCTACCCACCTTGGCCTCCCAAAGTGCTGGGACAGG  1440

1441  TGTGAGCCACCATGCCTGGCCCCTCTACTCTTATAATTAAACCAGCTGTTGCTTTTCCTG  1500

1501  CCAAGAAACCAGTCATGAAGATTCACCCATGTTCTAGATGGGAAAACTGGGCTGTAGCCT  1560

1561  GGGAGAGGCCAGTCAGGGACAAAGCCAAAGTTAATATAGAGAATGGAGCTTCCAGGGTAT  1620

1621  AGGGGTTGGGTCTGGGCTAGGGAGCTGGAAACCTAGGTTTTACGCTTGTCCCAGTTTTGA  1680

1681  TGTTAGCCCTGAGCAGTGCTGTTTCTCATCAGCCTCTGCCTGCTCCAGGGGTCACAGGGC  1740

1741  CAAGCCAGATAGAGGGCTGCTAGCGTCACTGGACACAAGATTGCTTTCCCACAGCTGTCC  1800

1801  TTCCTCCAGCCCCTCTGCTCCCCATCCGGAAACCTGGGTACCCTTCACCCACCTAGCTCT  1860

1861  GTCCCGCAGTGAGATTTATTGCTGACTGCCCTGCCATCTACCCCAGGGTAATAAATCAGG  1920

1921  GCAGAGCAGAATTGCAATCACCCCATGCATGGAGTGTATAAAAGGGGAAGGGCTAAGGGA  1980

1981  GCCACAGAACCTCAGTGGATCTCAGAGAGAGCCCCAGACTGAGGGAAGCATGGATGGATG  2040

2041  GAGAAGGATGCCTCGCTGGGGACTGCTGCTGCTGCTCTGGGGCTCCTGTACCTTTGGTCT  2100

2101  CCCGACAGACACCACCACCTTTAAACGGTAATTGGTAACTCAGGCAGAGAAGGGGTGGGA  2160

2161  GGGGTGCAGGGTTCCCACCTTCCCAACACCCTGGCTTTTCCACATGCGGTGTCATTCAGT  2220

2221  CCTTACGATCAGCTGGACAGGGAAGTATGGACCTGTTCAGAGAGGTCAAGTGACTTGCCC  2280
```

FIG. 5C

```
2281  AATAAATGACACTAGTAGTCAGGTCTAGAAGCTGTGACTTTTGCTTCCTGCCCAGAGCAC  2340

2341  CATGCTAACTAAGCACTGTAGAGAACTCAGAAGTATTAGGACATGCCCCTTGCACTTGAG  2400

2401  GAGCTCACAGCCTGAATATTAAGAAGGGCATGGGTGGTTGGGCGCGGTGGCTCCTGCCTG  2460

2461  TAATCCCAGCACTTTGGGAGGCTGAGACGGATCACTTGAGGTCAGGAGTTTGAGACCAGC  2520

2521  CTGGCCAACATGGGGAAACCCCATCTCTACTAAAAATACAAAAATTAGCCGGGCATGGTG  2580

2581  GCAGGCACTTGTAATCCCCAGCTACTCGGGAAGCTGAGGCAGGAGAATCGTTTGAGCCCG  2640

2641  GAAGGTGGAGATTGCTGAGCCAAGATCGTGCCACTGCACTCCAGCCTGAGTGACAGAACA  2700

2701  AGACTCCATCTCAAAAAAAAAAAGACGGGGTCGGGGCATGGGTACAGTTAACTGTACC    2760

2761  AGGGAAGCAGCTTGATATCGTGGTTAAATGCAAGGCTTATAGAGTTAGATTGCCTTCATT  2820

2821  TAAATTTTGCTTCACTAGCAGAACAAACTAGGTCTGGAATCATGGGCAAGTTATTTAACC  2880

2881  TCTCCAAGTCTCAGTTTATCATTTTAAACAGGTATGATAATAACAGTACCTACTTGATGG  2940

2941  GGCTGCTTTGGGGATTTTAGGAGATAAGGCATAGAAAGCTGGGCACGTTGTAAGAGCCCA  3000

3001  GCTACTGTTAGTACTACAGGATAGATTCTTACAAATATCAAAAGCAAGGTTTGGCCGGGA  3060

3061  GCAGTGGCTCACGCCTATAATCCCAACACTTTGGGAGGCCGAGGGGGGCAGATCACCCGA  3120

3121  GGTCAGGAGTTCAAGACCAGCCTGACCAACATGGAGAAACCCTGTCTCTACTAAAAATAC  3180

3181  AAAATTAGCCGGGCGTGGTGGCACATGCCTGTAATTCCAGCTACTTGGGAGGCTGAGGCA  3240

3241  GGAGAATCGCTTGAACCTGGGAGGCTGAGGTTGCAGTGAGCCGACATAGCGCCATTGCAC  3300

3301  TCCAGCCTGGTCAACAAGAGCAAAACTCAGTCTAAAAAAAAAAAGAAAGAAAAAAACAA   3360

3361  GGCTTTAGGTAGCCCACAATTAGAAGGAGAAAACCTTAGCATCCCCTAGGTGCCAGGCCT  3420
```

FIG. 5D

```
3421  TGTGGGAACAAGTGATTCATTAAGACTGTAGAAGGAAGCTGGGCACGCGGCTCATGCTTG  3480

3481  TAATTCCAGCACTTTGAGAGGCTGAGGTGGGCAGATCGCTTGAGCTCACGAGTTCAAGAC  3540

3541  CAGCCTAGGCAACATGGTGAAACCTTGTCTGTACAAATACAAAAATTAGCTAGGTGTGGT  3600

3601  GGTGCAAATCTGTAGTCCCAGCTACTCGGGAGGCTGAGGTGGGAGCATCACTTCAGCCTG  3660

3661  GGAGGTGGAGGCTGCAGTGAGCAGAGACTGACCCACTGTGCTCTAGCCTGGGTGATAGAG  3720

3721  CCAGACCTTATGTAAAAAAAAAAAAAAAAAAAAAAAAGACTGAAGAAGGGGAAGAGACAG  3780

3781  CATTTGAGAAAAGGCCTCACAGAGAAAGGGGTTTTCAATCTGGGGACAGCAGATATGACC  3840

3841  AGCAGTCCTGAAGGTAGGGAGGCACACTTTAATAATGGTAATAGTTGCTAAGCCTATAAA  3900

3901  ATGCTTAGGGTGTCACAGGATCTTTTCACATGTCTCATCTCAAGTCATGCCCCCAACAAC  3960

3961  TCAGCATTCCCACTTTGCAGATGAGGACACTGAGGCTCAGGGAGGTGATATGTAAGAGGC  4020

4021  TAAGCCTCAACACACACTGGGCCTTTTGCTTCCGAAACTGCTTTCCCTTGCTCTGAGGCT  4080

4081  CTCGGAGAGTAATTGCTGGGTTGTGAGCACTGGGTAAGAGGATGGGTGCTTCAAAGCAGC  4140

4141  TGCACTCCAGGATAAAGGTAGAGGAAAGTAAAAACATCTTCCCCTGCTGTTATCCAAAAG  4200

4201  AGAAAAAGAATGGAATTGGGCAAGGGGTGGAGGGGGAATCCAGCTTTTGAAACAGTATTA  4260

4261  TAGGAATTTTGCTACCCGCTATGTGCAGAGCATCATGCGAGGCACTTGGGACAGCTGAAT  4320

4321  GAATGAGCTCCATTCTCAAGGTGAACATGTACATATACACACCTACAATTTACATTTATT  4380

4381  GAGCAGTGGTCGCATGGTTTCATCTGCACAGTGACTCTGAGGTAGGTACTACCATTAGGC  4440

4441  CCATTGTTAGAGAGGGGTTAATGGAGACTTAGAAGAGGCCCAGAGAGGTTAGGTAGCTTT  4500

4501  CTCAGAATCACATAAGTGGTAAGGGGATTCAGGCATGCCCCCTGCAACCACTGTCTTCAC  4560
```

FIG. 5E

```
4561  CACCGTACGGCACCAGTTCCACAAGCTGTACAGTGTGGGCTGTGAGACCCAAGGAAAAAC  4620

4621  AGAGCTGAGGCCCACGGGAAGGTGAGGCCGGTGTGGGCTGGAGGCCTTGGGGTAAGCTTC  4680

4681  CTGGAGGTGGGGGTACATGTTGGGCCTTGGAGGACTAAAGAACTGGGGGGAAAAGGAAGG  4740

4741  GAAGAAGGAAAGGATTTTCTGAAAAGGAAATGGCAAGAAGTAAAGGTCCAAAGCATAGGC  4800

4801  TGTTGTGAGTAAACAGTGGGAAATGCAACCTCTTTGGGGCCAAACCTCTGACCCTCCACG  4860

4861  TTCCCAGCTGTGAAGTGGGAGTAATAAAATCATCCACCTTATGAGAGCAAATAAAATAAT  4920

4921  GATTGTGAAAATATTTTGGTAACAGTAACCTGTGATAGGAAGATAACAAATCATTTCTGT  4980

4981  TACAATACCATGCTGATAGGCATAAAAGTTGCATTCATGTTCATGGGCAAAATGGGGGTA  5040

5041  AGTAGAATGCATGGGACGCAAGAAGGATGTAGGAAGGAAAGGGTAGTGTGAGTATAGGAG  5100

5101  GACTAGCCACTGAGAAGAAAGTAGAAGAAAGAGGGAATCTTTGTGTGTATGGGAAAGTCT  5160

5161  ATTGCAGAGTCAACTTGGGCTTCCATCCTGGGACCTTCCCGTGAACAGCTAGAGACATCT  5220

5221  TCCTCTGGGCTTTGGCAGCCTTTATGTCGGGACCCAGGGGACCCTATATGGGAAATAGGG  5280

5281  CCAGACACATGCTCTGAATCCCTGCTTCAACATTTCTGAGTCACCTTTGTCCCTGTGAGC  5340

5341  CTTCATTTTCTCATCTATAAAATGGATGACAGCTAGCTTGTTGGTGTGATTTCAGTAGC  5400

5401  GGCTCAGTAGAGTCAGTTTCCTAGGTCTCTTTAATTCTGCCTCTCAAAGGTGATGGGAAA  5460

5461  ACATCTAGACAAGAAGCCAAGGGACCGGGACACATCTCTCCAAGGACGAGGTGCATGGCG  5520

5521  CTCTGAAGATGCTGGCATCTCTCTAGGCCCAACCCAGCTCAGGGGTCCACTCCACCACA  5580

5581  GCCCTGGCTGGGTGCCTGTCCCCTGGTATCCTGGAGACCTTGCAGCTGCTGTGGGCATCT  5640

5641  GCTGCCACCTAGCGGCCTCCCATGGCACTGTCTCCCCGCCAGCCCCTAGTTTTGACAGGG  5700
```

FIG. 5F

```
5701  GCACTCCCTGGCATTAATCTCTTCAGAGGGAATGTCTGTGCCTGTTTCCTGTCTGTCCTC  5760

5761  CCGCCAGGTGGAGTTCCTTAAAGGCAGTCATGATCATTATCTTTCTAGCTCCAGTGTCCA  5820

5821  GCACAGTGAGGCACAAAGTAGTTGTTCAGCAGGTGATTACGGAATAAATGAATGAACGGA  5880

5881  CCAATAAACAAATAGCCTTGTCTAATCAAAATTAGGCAACAGAAGGAAGTCACTTCAGGG  5940

5941  TTATTTAATCCCCGGGCAGCTGACTCCTCTAAATTGACTCTTGACAAGAAGTAACTCTTA  6000

6001  TAAATGCTCCAGAGGCCCTCAGCGACAGAGGTGATTTCCAGGTGGCTGGGCTAACGTTAA  6060

6061  AGGTGGTTGTACTAAAAGCAGGGGTTTGGCCTCAGGGACTCCACCACTGTGGTGGAGGTA  6120

6121  CAGCACTTTTCTATTTTTGCTTCCTCCACCCTGGGCCAGGATCTTCCTCAAGAGAATGCC  6180

6181  CTCAATCCGAGAAAGCCTGAAGGAACGAGGTGTGGACATGGCCAGGCTTGGTCCCGAGTG  6240

6241  GAGCCAACCCATGAAGAGGCTGACACTTGGCAACACCACCTCCTCCGTGATCCTCACCAA  6300

6301  CTACATGGACGTGAGTGCTTGGCTCAGCCCCTCGCTCCCTCCCTGTCTCCTTTCCCTCAT  6360

6361  GGACCTAGGGCTTTCTTTGCTGCAAGACTCACCCTTTCCAAGCTGTGTTTGACGAAGGCG  6420

6421  CTGAGTAGCACGTGAGCACCCTAGAAAATTCCCATTTTCCAGCTGGAAAGCCTGAGCACA  6480

6481  GAAGACAGGAAGGCATCCAGGGGCCATTCAGGGGCAGGGTTAGGTTTGGAACTCAGCCCA  6540

6541  GGCCTCAAGCCAGGTGTCACAGGTGGGTGGGAAGGGGTGTGTGACTCAGGTGGGGGTTTC  6600

6601  TGTGACCTGGCCCAGCACAACCTGATGGCTTCCTGCCCCAGAGGATCCTCAAGAGTCAAG  6660

6661  TTTGCTTCCTGCTTCATTCTCAATGTTTTGATTTTGCCCTCTTGTCTTACTGAGACTCCC  6720

6721  ACTTTCTGGGATGCCATGGGGAGATGCTAAGCCTCCTACCAGTTCCTGCAGGAAAATGGA  6780

6781  AACCCCGAGAGGCTATAGGACCTCGCCTGGGCCAAGTCTCACACCGAGAGCCAAGAGTGA  6840
```

FIG. 5G

```
6841  AGCCAGGCAAGACCCCAAGACCCAAGGTCCCCTGAGCCCCTCCAGCCCTCTCTTTTTACC  6900

6901  CCCACAGACCCAGTACTATGGCGAGATTGGCATCGGCACCCCACCCCAGACCTTCAAAGT  6960

6961  CGTCTTTGACACTGGTTCGTCCAATGTTTGGGTGCCCTCCTCCAAGTGCAGCCGTCTCTA  7020

7021  CACTGCCTGTGGTGAGACCTAAGACCCACAGTGCCTCTCCTCCATCCCCCTGCCCTACTG  7080

7081  TGCATGAGCAATCCTGCCCAACACCCAGCTCCCATCCCTCTTGCCACCAAGGGAGTGGCT  7140

7141  TCCTCTCTGCCTCTGTGCCCACTGACATGTAGGGGAGAGGGGAAGATGTCTCCCGTTTTT  7200

7201  CTGATACAGCCACCAAGGTTAAAAACAAAAAAAGGTCCAAGAACCCCTGAGCACCCAGAA  7260

7261  GGCCACTTCCCAGTCTTCCTGAGATTGAGACAGGACTGAATTCTCAAACCCATCCCAGGC  7320

7321  ACTCGGAACTCTTCCATCCCTAGTCTTAATCAACAACCTCTTACTAGGCACTTACTCTGT  7380

7381  GCCTGGCATCTTCTCTGGTGTTATCAGTGTTAGTGATTACTTTAAATTCCTTCATTTAGG  7440

7441  ACAAAATTCTCGATGTATGGGCACATTAGGAGAGCCCAAGAAACCCAGTCCTTGATTGAT  7500

7501  GAAGCACATATTCCAAGCCCCCTGACCCTAGGGCCACTCATCCCTGCACCTAAGCTAACC  7560

7561  AGCCATACCCACAATGCACCCTGCCTCTGAGTCCCCCTGTCTGGGCCACTCTTGGACAAA  7620

7621  CCTGAGCCTCTGTCCCCCTGCCAGTGTATCACAAGCTCTTCGATGCTTCGGATTCCTCCA  7680

7681  GCTACAAGCACAATGGAACAGAACTCACCCTCCGCTATTCAACAGGGACAGTCAGTGGCT  7740

7741  TTCTCAGCCAGGACATCATCACCGTAAGTTGGGCCGCCCTAGGTCATCTGCCCCGGACCC  7800

7801  CTTCTGTCCCCAGGCCTCTCCTGACCCTCCAGGGCCCACACCTGCGGGGAGGTACACTGC  7860

7861  AGCCCACTTGGAGCCTGGGGAGCTGAGGAACACCCTACTCTGCCACATCTGGCTGTTGCT  7920

7921  GCAAAGCAGCAGTACCTATGGGGGAGCAAGCCTGGGCTACGGGCTCACCGTTGGGTGGTT  7980
```

FIG. 5H

```
7981  TGTGGATGTTTTTGCATCTAACTTGCATGTAGGGCTTGTCCTGAGCCCCGTGGCTGCAGT  8040

8041  CAAGTAACTCGTCCAAGTTCACCAGCTCTGACTGGGCTACACCCTAGACTGAAATCCAGG  8100

8101  GTCAGAGTCAGGCTGAGTTTTAGGGTCAGGCATAGGTTTTAAGGTCACAGTTGAGGTTGA  8160

8161  CTCTGGGACTCAGGTCAAGGCCTGCTTTTCTTTTCCATGTGGCCCATGTCTGACCGTTTC  8220

8221  CTCATCCTGGAGTTTCTCAGGCCCTGCTCCATCAGAGTTAGGGGAGGGGCACACGTGGCA  8280

8281  CCTGAGAGGAAATCAGGGTGATTCCTGCCTCCCTTCCTTTTTCTGTGAACTCAGATATAA  8340

8341  AGGAGGGAGAAGGGCAAGCTTGTCTGTGCTAAAGAAACCCTTCGCCCATGATAAGGGTGG  8400

8401  GGGCCAAGACCCAGTCCTGCCAGGCACGAAAGTCTGGCCACTGGGGAGGGGAGGAGCTCT  8460

8461  TGGCAGCTTTTCTTTTGCTGCTTGGCAGGACCACCCTCTCAGCCTCTGCTCTCCGATCCC  8520

8521  TGGTCAACTCTAGCTCTCTCTGGGCTCCGCAGCAGAGATGTGTATTGGCACAGAGTGTGT  8580

8581  GCGTGCAGGGTTGAGGAAATACTCTTACCCCGATTTCTGTACCCTGGAGCATGTGTGCCC  8640

8641  CTGGGATCCCTAGTGTGGAAGCCCAGACCAGACTCCAACCAAGGAGTGGGCAGTGGGCTT  8700

8701  GGTCTCCTCTGGTCCTTCCTCCCACAGGTGGGTGGAATCACGGTGACACAGATGTTTGGA  8760

8761  GAGGTCACGGAGATGCCCGCCTTACCCTTCATGCTGGCCGAGTTTGATGGGGTTGTGGGC  8820

8821  ATGGGCTTCATTGAACAGGCCATTGGCAGGGTCACCCCTATCTTCGACAACATCATCTCC  8880

8881  CAAGGGGTGCTAAAAGAGGACGTCTTCTCTTTCTACTACAACAGGTGGGGACTGGGACTC  8940

8941  CAAGGGCTGAGGTGGGGGGACAGGAGGGGAGAAGAGATGGGGAGTGGAAGGAGAGTCTGG  9000

9001  GCCAGAATTGTAAAGTGTTTGTAATTAGGTGACAGCCAATCAATATCTAGAGCTGTACTA  9060

9061  GCCAATATGGAAGGCACTATTGAAATTTAAATTAATTAAATACAGTTAAGCATCAATTAA  9120
```

FIG. 5I

```
9121   GCATTCAACTGGTGGCTCTTAGTTGTACTAGCCACACGTCAAATGCCTGGCAGCCACGGT   9180

9181   GGCTAGTAACTACAGTCTTATGACAGTGCAGATAGAGAATATTCCCAGCATGACAGGACA   9240

9241   TTCTAATAGACAGCGCCACTCTGGAGCAAGAGGAGATGCAAGGTGGGGCGATGGTAAAT   9300

9301   AAGGGATTACTGTGACCTGTAGCCCTGCCTGTTAGGGCCATGGCTCCTCCCACACAGAGA   9360

9361   CAGCCAACTTCAGTCATCCATTAGATCCTTCATTCGTTTGTTTGCTCACTCATCAGTTCA   9420

9421   GTAAATGCTATGTGCCAAGCACTGTGGTAGGCTCTGGGGGTGCAGCAGTGAACACAGTGA   9480

9481   ACAAGGCAGAATCTGTACTCCCCTACCCACATAGAGCTTACAGGCTAACAGGGAAGACAA   9540

9541   GACATATTCCAACATAAAGAGTGTCACAGGCAGGCAGCAAGTGTGGTGCTGAAAACCATG   9600

9601   GATGCTTTTCAATTCTAGGCTGAGCTTATATGCAGCTCAGCCAGCCTTGGGGAAGCTCTT   9660

9661   GAGCAGGGTTGGGCTCTACTCCAAACTGCTGGGCTTAGAAAGATGGCATGAGTTGGAGAC   9720

9721   AAGAGAGCTGGAGGCAAAAGGGGCTGGGTGCAGTGGCTCATGCCTGTAATCCCAGCACTT   9780

9781   TGGGAGGCCAAGGCGAGAGGATCGCATGAGCCCAGGAGTTAAGGCTTCAGTGAGCAGTGA   9840

9841   TTGTGCCACTGCACTCCAGCTAAGGCAACAGAGTGAGATCCAGTCTCAAAAAAAAAAAA   9900

9901   AAAAAAAAAAGTCACAAGGGTAAGAACATGAGGCCAGTGGCAAAAAGAATAGAGGAGAG   9960

9961   GATCAGAGTTCAGAGAAATCTCACAGTAAAATGGAGAGGAGTCTCCGGTTTGGTGATAGA   10020

10021  AAGTGAGGCCTTGAGAAAAGGCCAATTGGCGGCTCTGCATTCAGGGGTGGTCTTTAGAAG   10080

10081  AACTGTTTTAGAGGAAGTGGGGGCAAGGCCAGATGGCAAGAAGTTAAGAGGTGGACGACG   10140

10141  TGGGTGTCAGGAAGTGGAGGTCATGAGATGTAGGCTGCCCTGGGACATTCAACAGGGAAG   10200

10201  GGAATGGGGGGTGGCGTGGGGGGTGAGATCCAGAAGCAGAAGAGGAAGGGTGGGTGTTTT   10260
```

FIG. 5J

```
10261  TAAATGCTAGAGGATGCTCGAGTGATGCCTGTAGGTGGAGGAAGAAGCCAATGGAAAGAA  10320

10321  AGAGATTAAAAATGTGGAAAGAAGAGGAGCTAAATGGGGCACTGGAGTTTGGAGGCCTT   10380

10381  GAAAGAGATGAGGTTCCAGCAGACAGGAAGAAGCCAGGTTTTGCAGAGGAGAGGGCTGGC  10440

10441  CTCTTCTTTTATCTTGGGATGGGAAGGAGGGAACATCCAGAGAGATACTGAAGTGTTGAG  10500

10501  AGACAGGCAGGAGGGAATTTGTGCTAGCATATACACATACATTCCGAATTTATAAAAACA  10560

10561  CAAGTAGTTTGCAGTTGCACAAAATAACATATGCACACCTACACACCCATGCACACATGT  10620

10621  GCATGTGTGAATTCTAGTATGAATTCTGGAAAAACACATCACACACACAGGCATGCCCTG  10680

10681  GAGACTAGGCCTACAGTAGTCCCTGAGCCAAGTGCAGTGAGGAGGAAAGGAAGGTGAGGG  10740

10741  GAATCAGCTCCAGACGGGGCACCAGGAGCCTGGCTCCAGTCCCCCACTTGTTCACTCATG  10800

10801  GACTGGGTAACTTCAGGCAAGTGACTTCGCCTCTTGGTGACTCCATTGCCTGAAGGGCAA  10860

10861  AGAGAGTACATAACACCCACCCTGCCAAACAGCAGGGCTGATGAGGCTGGCATGAAATGA  10920

10921  AGCTTCCTTTCTGCTGTCTCTCTTTCTCTGCAGAGATTCCGAGTAAGGAGACAAAACCCC  10980

10981  CACATGGCTGTGACCTTCCAGTACTCCCCGAGCACCTGACCTAGAATTACACACGCCACC  11040

11041  GGCCCAAAACTCACATCAGCAAGCCCAGCCTCCGCTAGATGCCGAAGTTCTCTGTCTCTC  11100

11101  CTTCCTGCTCTCTCCATGCCACCTGCCCACCCCATACCCAATAGCCTCCCCAGGGTCCCC  11160

11161  TCCCATGCACCTGCTCAATCAGCAGCAACCCAAGAGTGAGGGGTGTCCATTTGTGTCTTG  11220

11221  TTCACATCCACTCACTGTCCTTGTACCTGCTCCTTTTCTGTGACCTCTCTGGGGATGCTT  11280

11281  TTTGGGGGAACAGCTGGACTACCCTGGAACAACCTCTGGTTGGTCTTGGGGAGGGGAAGA  11340

11341  AAGGCAGAGAAGCAGTATGTTCTGCATGCTTCCCAACGACAGCTCCGAGCCTGGCTGTCT  11400
```

FIG. 5K

```
11401  GTCCCACATTCCTCTGCTCTAGAGCCCTCTGTCCTCCCCTGCACCCTTGTGCAACCTTCC  11460

11461  CCAATTGCCTGAGTTGCTGGGTCCTGGAGGTTATGGGTTTCCAAGAGCTTCTGATCTTTC  11520

11521  CTTTAGGAATTCCCAATCGCTGGGAGGACAGATTGTGCTGGGAGGCAGCGACCCCCAGCA  11580

11581  TTACGAAGGGAATTTCCACTATATCAACCTCATCAAGACTGGTGTCTGGCAGATTCAAAT  11640

11641  GAAGGGGTCAGAAATCCTCAACCCTCCCCGGGCTCCAAAAAATGCTGCCGTCACTGGGGT  11700

11701  TGGGGAGGGTGGGGAAGGACTGCATTACCATCCTGCCCTCTTTCCAAATGCAGCCACTTC  11760

11761  TTAAGCACAGCCACCATTTGCTCTCTGCCTGCTCTGTCCAGGCTGGGGAACAGAGAAGGG  11820

11821  AGGGGCCTGGGGAGAAGTGGTGGAGGGTGACAGTACCTTCCCTCCTCTACTCACTGCCTC  11880

11881  AACAGGCCACCAGCGTGGCCTCCACCCACCCACCCACACTCAGGAAGGACATGCAGCCTG  11940

11941  GAGGTGCCCCATCAGCCTTCTGTCTGTCTGTCTGTCTGTCTGTCTGACTGTGGCCTCCCC  12000

12001  CAGGGTGTCTGTGGGGTCATCCACCTTGCTCTGTGAAGACGGCTGCCTGGCATTGGTAGA  12060

12061  CACCGGTGCATCCTACATCTCAGGTTCTACCAGCTCCATAGAGAAGCTCATGGAGGCCTT  12120

12121  GGGAGCCAAGAAGAGGCTGTTTGATGTAAGAAGCCAAAGAGGGAAGGTGCTGTGGGTGGG  12180

12181  GGGAGCGCCACCTGGTATCGGCTCACAAATCCCCCAGGCAAATGAGGCCATCTCAGGCCT  12240

12241  TCGCTTGTTCACCTCACACTCTCCACACATGTGGCTGGTCACCCATGGGGCGGGGCACTG  12300

12301  TCCCCAGCCCTCTCCAGCAGAGAGACCAGGCCACCAGCGCAGGACTCCTTGTCTGCTGAG  12360

12361  ACGTCTTCCATACTCAAGAAGGCTCTCTTTGCCCCCCACCCCAGTATGTCGTGAAGTGTA  12420

12421  ACGAGGGCCCTACACTCCCCGACATCTCTTTCCACCTGGGAGGCAAAGAATACACGCTCA  12480

12481  CCAGCGCGGACTATGTATTTCAGGTGAGGTTCGAGTCGGCCCCCTCGGTGGCAGGGAGAA  12540
```

FIG. 5L

```
12541  AGGCTGGACAGAGACCCTCAAAGAGTGACAGATTACAATGCACAGGTCATGTTAGAACTG  12600

12601  TAGTTCTCAAACTTGGCTGTGCATGTCACCTGGAGAGCTTTGAAAAATCCTGGTACCTGG  12660

12661  GCCACATCCCATACCTATTAAATCAGAACCTCTAGAAGTGGCACCTGGGGTTCAGTTTCC  12720

12721  CCAGGTGATTCCAATGTGTGGCCATGTTTGGGCATCACTATGCCTGTTCCCTCATCTCCA  12780

12781  TTTTCTCATCAAATACTCCCAAGAATCCTATGCTCCTATATTCTTACCCTCTTTTCATAA  12840

12841  TCAATAGGCTTAGAGAAGTTGAATAACTTGTCTAGGATCAGAAGCTAAGGCAAACTGTAA  12900

12901  GCTCCTGAAGGAAGCACGGTGCCTGATGCATTGTTTGCCTGGGATCTAGCACAGGGGCTA  12960

12961  AACATAGGAGTGGTGCAGTCCACGATGGGGCAAAATGGCCATGATGTGAGGGAGGCCCAG  13020

13021  TGTGGCTAGGGGAGAGATGGGGGCGAGAGGGGGAATGTTGCTGAAGACAGTTGCTGGGGG  13080

13081  TCAGGCAAGGTGAAAGGAGAATGCTCATGTGCTGGGTATGGAGAAACTCTCCCCCTTCCT  13140

13141  GCCAGGAATCCTACAGTAGTAAAAAGCTGTGCACACTGGCCATCCACGCCATGGATATCC  13200

13201  CGCCACCCACTGGACCCACCTGGGCCCTGGGGGCCACCTTCATCCGAAAGTTCTACACAG  13260

13261  AGTTTGATCGGCGTAACAACCGCATTGGCTTCGCCTTGGCCCGCTGAGGCCCTCTGCCAC  13320

13321  CCAGGCAGGCCCTGCCTTCAGCCCTGGCCCAGAGCTGGAACACTCTCTGAGATGCCCCTC  13380

13381  TGCCTGGGCTTATGCCCTCAGATGGAGACATTGGATGTGGAGCTCCTGCTGGATGCGTGC  13440

13441  CCTGACCCCTGCACCAGCCCTTCCCTGCTTTGAGGACAAAGAGAATAAAGACTTCATGTT  13500

13501  CACAGCCTGTTGCATCTGGGTTCACTAGGGTTTAGAACAGAGGGAGGGGCTGCGTGATCA  13560

13561  TGTGTGGACAGGAATGTGACACAGACAAGCTACACATTCGCCTAGCGCACAGGTTCTTGC  13620

13621  GTGCAGGGATGATGCCATCCATCTGCCATCAACGGGACTCAGGTGGAGCTGTTTACACAA  13680
```

FIG. 5M

| | | |
|---|---|---|
| 13681 | CCTCAGGTGGGAAGTCTGAAAAGAGCCGGAACCAAGCTCCCTCTAGTCCCTCAGGGACCA | 13740 |
| 13741 | AGGCTAATGCTGTGGCAGTAGACTGTGGGTCAGAAAGTTCTCCCAGCTCACAGAAGCCAG | 13800 |
| 13801 | CTCTGAGTTCAGACTCTGCTCTGCTGAGCTAGTCAGCCCTGTCTCTTGTCCCTGCAAAAC | 13860 |
| 13861 | TCCCCTCAGCTGTCCTTATCCACTGCAGATGCCCCGCCCTGCCCCATGTAGCCATTTAC | 13920 |
| 13921 | ACAGGCATTCTAAGGCACTACCACCTAAAATCATAGAACACCAGAGATCCAGGCAATACT | 13980 |
| 13981 | TCCACTTTACAGGTGGGGAAACTGAGGCCCAGAGAATGGAAGGCCTTGCCCAAGATTACT | 14040 |
| 14041 | CGGTCAAGAATCAAGTAGTGAAGAATACTGAAAGATAGTGAAGAATCAAGACTGGAACCC | 14100 |
| 14101 | AGCCCGTCTGACTTGGGTCCTGGGGGTTTCCACCTTATCATAAGCAGTTGGTACCGTCAT | 14160 |
| 14161 | AAGTACAGTGCTTCACGCACGCTGGTACAGGGCCACGTGCACAAGCACACAGGTGCACAC | 14220 |
| 14221 | ACACACTGCTATCCTCCATCCCATCCACCTGGGACTCGTCAGGCTGAAGTCTCTTCTCCC | 14280 |
| 14281 | ACTCTCACTCCTTGGGCTGTCTTCAGGGCACATGTAACTTGGGGAATGAGAAATTAGCAT | 14340 |
| 14341 | CCACCTGGAGCCACTGAAGCCATCCCTCTTCACCATAGTTGCTCACCTCTCTTTTGACAG | 14400 |
| 14401 | AAAGTCGTGAGGCACTGAATGGCCCAACCAGGCCCTCAGTACCTCTGGGAGCCATCTGCA | 14460 |
| 14461 | AGAGTCCCTGTGTAGCGCCAAGAGCCGGAGCCTGGGCTTCAGG | 14503 |

FIG. 6A

```
   1  GGTCTTTGTAAAATAATAATTATTCATTTCACAAAAGTGATAATTAAAAGACTTTAATAG    60

61  CAATACAGAAAGTTACATGAATATAAAGACTTAACCTTTCTAAAGCTCAGTTTTCCTAAG   120

121  TAATCAAAAACCTGATAAAGATAACAAGAATGAGGAATTATCTTGAGAAAATGTAAAATC   180

181  TTTCCTTTTATTTTTTGAGACAGGGTCTCACTCTGTCATCCAGGCTAAAGTGCAGTGGCA   240

241  CAATCATAGCTCACTACAGCCTTGAACTCCTGGACTCAAGTGATCCTCCCGCCTCAGCCT   300

301  CCCCAGTAGCTAAGACTACAGGCACGCACCACCACACCCAGCTAATTTTTTCAGAGATG    360

361  GGGTCTTGCTATATTGCCCTGGCTGGTCTTGAACGAGCTTCAAGTGAGCGTGAGCCTCCT   420

421  ACCTCATCCTCCCAAAGCACTAGGATTACAGGCATGAGCCACTGTTTCCCAGCCTAAAAT   480

481  AATTGTTTCTTAGGCCAGCTACCAAAAACGCAAAGAAAAACTTTCTGTAGTGTGATTGCT   540

541  TCTTCTTATGGGAAGCCCATTTAGATAACCTGTAAGTCAAACCTGATGAAAACAATACTT   600

601  GAATGTAATCAGACACAGAAAGACTGTTCAAGGCTATGAGTAGCTGAGTCCAAGCTCGTA   660

661  TCACTTGCCACACAACAGCCAATAAGTCTAGAGACAAGGTATTGTGGCAAGGAAAGCTAC   720

721  CTTATTCAGAGAACCAGAAAACCAAGAAGATGGTGGACCAGCATCATAAAGAACCATCTG   780

781  AAGTCAGCATGAACGTTAGGCTCTTCTTTATGTTAAGGGAAGGGGAAGAAGAAGGGGATT   840

841  GGGATCAAGAGGTGACTGATGACCACAGACACCTGGGTGCCAGCAAGGGTCTGAGGACGT   900

901  TGTAAAACTTCTTTTTTCTAGGTCAGGTCACAATGTTCCTATACATCTTTAACATAACAT   960

961  TGTTATTTGTCTGTATATTTCCTTATCTCCTTGGGGGTTAGTTTGGGGAAAGGAACTGTT  1020

1021  ACCATTTTTTTAAAGTTGAACTGCAAGCTAAACTCCTATAATTAGCTGGTCTATGTACA   1080

1081  GAGCTAAGCAGAAGCTTTTAGCCTAAAGGATAATACCCCTGGGGGTCAGAGGCAAAATGG  1140
```

FIG. 6B

```
1141  AGTCAGTCATGCTAAGTCTCCCTCCACTCTCTTTCTTTTTTGAGATGGAATTTCACTCTT  1200

1201  ATTGCCCAGGCCGGAGTGCAGTGGCATGATCTCAGCTCACTGCAACCTCCGCCTCCTGGG  1260

1261  TTCAAGCAATTCTCTTGCCTCAGCCTCCTGAGTAGCTGAGATTACAGGTGTCCATCACCA  1320

1321  CACCCAGCTAATTTTTGTAGTTTAGTGGAGATGGGGTTTCACCATTGTTGGTCAGGCTGG  1380

1381  TCTGGAACTCCTGACCTCAGGTGATCTACCCACCTTGGCCTCCCAAAGTGCTGGGACAGG  1440

1441  TGTGAGCCACCATGCCTGGCCCCTCTACTCTTATAATTAAACCAGCTGTTGCTTTTCCTG  1500

1501  CCAAGAAACCAGTCATGAAGATTCACCCATGTTCTAGATGGGAAAACTGGGCTGTAGCCT  1560

1561  GGGAGAGGCCAGTCAGGGACAAAGCCAAAGTTAATATAGAGAATGGAGCTTCCAGGGTAT  1620

1621  AGGGGTTGGGTCTGGGCTAGGGAGCTGGAAACCTAGGTTTTACGCTTGTCCCAGTTTTGA  1680

1681  TGTTAGCCCTGAGCAGTGCTGTTTCTCATCAGCCTCTGCCTGCTCCAGGGGTCACAGGGC  1740

1741  CAAGCCAGATAGAGGGCTGCTAGCGTCACTGGACACAAGATTGCTTTCCCACAGCTGTCC  1800

1801  TTCCTCCAGCCCCTCTGCTCCCCATCCGGAAACCTGGGTACCCTTCACCCACCTAGCTCT  1860

1861  GTCCCGCAGTGAGATTTATTGCTGACTGCCCTGCCATCTACCCCAGGGTAATAAATCAGG  1920

1921  GCAGAGCAGAATTGCAATCACCCCATGCATGGAGTGTATAAAAGGGGAAGGGCTAAGGGA  1980

1981  GCCACAGAACCTCAGTGGATCTCAGAGAGAGCCCCAGACTGAGGGAAGCATGGATGGATG  2040

2041  GAGAAGGATGCCTCGCTGGGGACTGCTGCTGCTGCTCTGGGGCTCCTGTACCTTTGGTCT  2100

2101  CCCGACAGACACCACCACCTTTAAACGGTAATTGGTAACTCAGGCAGAGAAGGGGTGGGA  2160

2161  GGGGTGCAGGGTTCCCACCTTCCCAACACCCTGGCTTTTCCACATGCGGTGTCATTCAGT  2220

2221  CCTTACGATCAGCTGGACAGGGAAGTATGGACCTGTTCAGAGAGGTCAAGTGACTTGCCC  2280
```

FIG. 6C

```
2281  AATAAATGACACTAGTAGTCAGGTCTAGAAGCTGTGACTTTTGCTTCCTGCCCAGAGCAC  2340

2341  CATGCTAACTAAGCACTGTAGAGAACTCAGAAGTATTAGGACATGCCCCTTGCACTTGAG  2400

2401  GAGCTCACAGCCTGAATATTAAGAAGGGCATGGGTGGTTGGGCGCGGTGGCTCCTGCCTG  2460

2461  TAATCCCAGCACTTTGGGAGGCTGAGACGGATCACTTGAGGTCAGGAGTTTGAGACCAGC  2520

2521  CTGGCCAACATGGGGAAACCCCATCTCTACTAAAAATACAAAAATTAGCCGGGCATGGTG  2580

2581  GCAGGCACTTGTAATCCCCAGCTACTCGGGAAGCTGAGGCAGGAGAATCGTTTGAGCCCG  2640

2641  GAAGGTGGAGATTGCTGAGCCAAGATCGTGCCACTGCACTCCAGCCTGAGTGACAGAACA  2700

2701  AGACTCCATCTCAAAAAAAAAAAAGACGGGGGTCGGGGCATGGGTACAGTTAACTGTACC  2760

2761  AGGGAAGCAGCTTGATATCGTGGTTAAATGCAAGGCTTATAGAGTTAGATTGCCTTCATT  2820

2821  TAAATTTTGCTTCACTAGCAGAACAAACTAGGTCTGGAATCATGGGCAAGTTATTTAACC  2880

2881  TCTCCAAGTCTCAGTTTATCATTTTAAACAGGTATGATAATAACAGTACCTACTTGATGG  2940

2941  GGCTGCTTTGGGGATTTTAGGAGATAAGGCATAGAAAGCTGGGCACGTTGTAAGAGCCCA  3000

3001  GCTACTGTTAGTACTACAGGATAGATTCTTACAAATATCAAAAGCAAGGTTTGGCCGGGA  3060

3061  GCAGTGGCTCACGCCTATAATCCCAACACTTTGGGAGGCCGAGGGGGGCAGATCACCCGA  3120

3121  GGTCAGGAGTTCAAGACCAGCCTGACCAACATGGAGAAACCCTGTCTCTACTAAAAATAC  3180

3181  AAAATTAGCCGGGCGTGGTGGCACATGCCTGTAATTCCAGCTACTTGGGAGGCTGAGGCA  3240

3241  GGAGAATCGCTTGAACCTGGGAGGCTGAGGTTGCAGTGAGCCGACATAGCGCCATTGCAC  3300

3301  TCCAGCCTGGTCAACAAGAGCAAAACTCAGTCTAAAAAAAAAAAGAAAGAAAAAAACAA  3360

3361  GGCTTTAGGTAGCCCACAATTAGAAGGAGAAAACCTTAGCATCCCCTAGGTGCCAGGCCT  3420
```

FIG. 6D

```
3421  TGTGGGAACAAGTGATTCATTAAGACTGTAGAAGGAAGCTGGGCACGCGGCTCATGCTTG  3480

3481  TAATTCCAGCACTTTGAGAGGCTGAGGTGGGCAGATCGCTTGAGCTCACGAGTTCAAGAC  3540

3541  CAGCCTAGGCAACATGGTGAAACCTTGTCTGTACAAATACAAAAATTAGCTAGGTGTGGT  3600

3601  GGTGCAAATCTGTAGTCCCAGCTACTCGGGAGGCTGAGGTGGGAGCATCACTTCAGCCTG  3660

3661  GGAGGTGGAGGCTGCAGTGAGCAGAGACTGACCCACTGTGCTCTAGCCTGGGTGATAGAG  3720

3721  CCAGACCTTATGTAAAAAAAAAAAAAAAAAAAAAAGACTGAAGAAGGGGAAGAGACAG  3780

3781  CATTTGAGAAAAGGCCTCACAGAGAAAGGGGTTTTCAATCTGGGACAGCAGATATGACC  3840

3841  AGCAGTCCTGAAGGTAGGGAGGCACACTTTAATAATGGTAATAGTTGCTAAGCCTATAAA  3900

3901  ATGCTTAGGGTGTCACAGGATCTTTTCACATGTCTCATCTCAAGTCATGCCCCCAACAAC  3960

3961  TCAGCATTCCCACTTTGCAGATGAGGACACTGAGGCTCAGGGAGGTGATATGTAAGAGGC  4020

4021  TAAGCCTCAACACACACTGGGCCTTTTGCTTCCGAAACTGCTTTCCCTTGCTCTGAGGCT  4080

4081  CTCGGAGAGTAATTGCTGGGTTGTGAGCACTGGGTAAGAGGATGGGTGCTTCAAAGCAGC  4140

4141  TGCACTCCAGGATAAAGGTAGAGGAAAGTAAAAACATCTTCCCCTGCTGTTATCCAAAAG  4200

4201  AGAAAAGAATGGAATTGGGCAAGGGGTGGAGGGGGAATCCAGCTTTTGAAACAGTATTA  4260

4261  TAGGAATTTTGCTACCCGCTATGTGCAGAGCATCATGCGAGGCACTTGGGACAGCTGAAT  4320

4321  GAATGAGCTCCATTCTCAAGGTGAACATGTACATATACACACCTACAATTTACATTTATT  4380

4381  GAGCAGTGGTCGCATGGTTTCATCTGCACAGTGACTCTGAGGTAGGTACTACCATTAGGC  4440

4441  CCATTGTTAGAGAGGGGTTAATGGAGACTTAGAAGAGGCCCAGAGAGGTTAGGTAGCTTT  4500

4501  CTCAGAATCACATAAGTGGTAAGGGGATTCAGGCATGCCCCCTGCAACCACTGTCTTCAC  4560
```

FIG. 6E

```
4561  CACCGTACGGCACCAGTTCCACAAGCTGTACAGTGTGGGCTGTGAGACCCAAGGAAAAAC  4620

4621  AGAGCTGAGGCCCACGGGAAGGTGAGGCCGGTGTGGGCTGGAGGCCTTGGGGTAAGCTTC  4680

4681  CTGGAGGTGGGGGTACATGTTGGGCCTTGGAGGACTAAAGAACTGGGGGGAAAAGGAAGG  4740

4741  GAAGAAGGAAAGGATTTTCTGAAAAGGAAATGGCAAGAAGTAAAGGTCCAAAGCATAGGC  4800

4801  TGTTGTGAGTAAACAGTGGGAAATGCAACCTCTTTGGGGCCAAACCTCTGACCCTCCACG  4860

4861  TTCCCAGCTGTGAAGTGGGAGTAATAAAATCATCCACCTTATGAGAGCAAATAAAATAAT  4920

4921  GATTGTGAAAATATTTTGGTAACAGTAACCTGTGATAGGAAGATAACAAATCATTTCTGT  4980

4981  TACAATACCATGCTGATAGGCATAAAAGTTGCATTCATGTTCATGGGCAAAATGGGGGTA  5040

5041  AGTAGAATGCATGGGACGCAAGAAGGATGTAGGAAGGAAAGGGTAGTGTGAGTATAGGAG  5100

5101  GACTAGCCACTGAGAAGAAAGTAGAAGAAAGAGGGAATCTTTGTGTGTATGGGAAAGTCT  5160

5161  ATTGCAGAGTCAACTTGGGCTTCCATCCTGGGACCTTCCCGTGAACAGCTAGAGACATCT  5220

5221  TCCTCTGGGCTTTGGCAGCCTTTATGTCGGGACCCAGGGGACCCTATATGGGAAATAGGG  5280

5281  CCAGACACATGCTCTGAATCCCTGCTTCAACATTTCTGAGTCACCTTTGTCCCTGTGAGC  5340

5341  CTTCATTTTTCTCATCTATAAAATGGATGACAGCTAGCTTGTTGGTGTGATTTCAGTAGC  5400

5401  GGCTCAGTAGAGTCAGTTTCCTAGGTCTCTTTAATTCTGCCTCTCAAAGGTGATGGGAAA  5460

5461  ACATCTAGACAAGAAGCCAAGGGACCGGGACACATCTCTCCAAGGACGAGGTGCATGGCG  5520

5521  CTCTGAAGATGCTGGCATCTCTCTAGGCCCAACCCAGCTCAGGGGTCCACTCCACCACA  5580

5581  GCCCTGGCTGGGTGCCTGTCCCCTGGTATCCTGGAGACCTTGCAGCTGCTGTGGGCATCT  5640

5641  GCTGCCACCTAGCGGCCTCCCATGGCACTGTCTCCCCGCCAGCCCCTAGTTTTGACAGGG  5700
```

FIG. 6F

```
5701  GCACTCCCTGGCATTAATCTCTTCAGAGGGAATGTCTGTGCCTGTTTCCTGTCTGTCCTC  5760

5761  CCGCCAGGTGGAGTTCCTTAAAGGCAGTCATGATCATTATCTTTCTAGCTCCAGTGTCCA  5820

5821  GCACAGTGAGGCACAAAGTAGTTGTTCAGCAGGTGATTACGGAATAAATGAATGAACGGA  5880

5881  CCAATAAACAAATAGCCTTGTCTAATCAAAATTAGGCAACAGAAGGAAGTCACTTCAGGG  5940

5941  TTATTTAATCCCCGGGCAGCTGACTCCTCTAAATTGACTCTTGACAAGAAGTAACTCTTA  6000

6001  TAAATGCTCCAGAGGCCCTCAGCGACAGAGGTGATTTCCAGGTGGCTGGGCTAACGTTAA  6060

6061  AGGTGGTTGTACTAAAAGCAGGGGTTTGGCCTCAGGGACTCCACCACTGTGGTGGAGGTA  6120

6121  CAGCACTTTTCTATTTTTGCTTCCTCCACCCTGGGCCAGGATCTTCCTCAAGAGAATGCC  6180

6181  CTCAATCCGAGAAAGCCTGAAGGAACGAGGTGTGGACATGGCCAGGCTTGGTCCCGAGTG  6240

6241  GAGCCAACCCATGAAGAGGCTGACACTTGGCAACACCACCTCCTCCGTGATCCTCACCAA  6300

6301  CTACATGGACGTGAGTGCTTGGCTCAGCCCCTCGCTCCCTCCCTGTCTCCTTTCCCTCAT  6360

6361  GGACCTAGGGCTTTCTTTGCTGCAAGACTCACCCTTTCCAAGCTGTGTTTGACGAAGGCG  6420

6421  CTGAGTAGCACGTGAGCACCCTAGAAAATTCCCATTTTCCAGCTGGAAAGCCTGAGCACA  6480

6481  GAAGACAGGAAGGCATCCAGGGGCCATTCAGGGGCAGGGTTAGGTTTGGAACTCAGCCCA  6540

6541  GGCCTCAAGCCAGGTGTCACAGGTGGGTGGGAAGGGGTGTGTGACTCAGGTGGGGGTTTC  6600

6601  TGTGACCTGGCCCAGCACAACCTGATGGCTTCCTGCCCCAGAGGATCCTCAAGAGTCAAG  6660

6661  TTTGCTTCCTGCTTCATTCTCAATGTTTTGATTTTGCCCTCTTGTCTTACTGAGACTCCC  6720

6721  ACTTTCTGGGATGCCATGGGGAGATGCTAAGCCTCCTACCAGTTCCTGCAGGAAAATGGA  6780

6781  AACCCCGAGAGGCTATAGGACCTCGCCTGGGCCAAGTCTCACACCGAGAGCCAAGAGTGA  6840
```

FIG. 6G

```
6841  AGCCAGGCAAGACCCCAAGACCCAAGGTCCCCTGAGCCCCTCCAGCCCTCTCTTTTTACC  6900

6901  CCCACAGACCCAGTACTATGGCGAGATTGGCATCGGCACCCCACCCCAGACCTTCAAAGT  6960

6961  CGTCTTTGACACTGGTTCGTCCAATGTTTGGGTGCCCTCCTCCAAGTGCAGCCGTCTCTA  7020

7021  CACTGCCTGTGGTGAGACCTAAGACCCACAGTGCCTCTCCTCCATCCCCCTGCCCTACTG  7080

7081  TGCATGAGCAATCCTGCCCAACACCCAGCTCCCATCCCTCTTGCCACCAAGGGAGTGGCT  7140

7141  TCCTCTCTGCCTCTGTGCCCACTGACATGTAGGGGAGAGGGGAAGATGTCTCCCGTTTTT  7200

7201  CTGATACAGCCACCAAGGTTAAAAACAAAAAAGGTCCAAGAACCCCTGAGCACCCAGAA  7260

7261  GGCCACTTCCCAGTCTTCCTGAGATTGAGACAGGACTGAATTCTCAAACCCATCCCAGGC  7320

7321  ACTCGGAACTCTTCCATCCCTAGTCTTAATCAACAACCTCTTACTAGGCACTTACTCTGT  7380

7381  GCCTGGCATCTTCTCTGGTGTTATCAGTGTTAGTGATTACTTTAAATTCCTTCATTTAGG  7440

7441  ACAAAATTCTCGATGTATGGGCACATTAGGAGAGCCCAAGAAACCCAGTCCTTGATTGAT  7500

7501  GAAGCACATATTCCAAGCCCCCTGACCCTAGGGCCACTCATCCCTGCACCTAAGCTAACC  7560

7561  AGCCATACCCACAATGCACCCTGCCTCTGAGTCCCCTGTCTGGGCCACTCTTGGACAAA  7620

7621  CCTGAGCCTCTGTCCCCCTGCCAGTGTATCACAAGCTCTTCGATGCTTCGGATTCCTCCA  7680

7681  GCTACAAGCACAATGGAACAGAACTCACCCTCCGCTATTCAACAGGGACAGTCAGTGGCT  7740

7741  TTCTCAGCCAGGACATCATCACCGTAAGTTGGGCCGCCCTAGGTCATCTGCCCCGGACCC  7800

7801  CTTCTGTCCCCAGGCCTCTCCTGACCCTCCAGGGCCCACACCTGCGGGGAGGTACACTGC  7860

7861  AGCCCACTTGGAGCCTGGGGAGCTGAGGAACACCCTACTCTGCCACATCTGGCTGTTGCT  7920

7921  GCAAAGCAGCAGTACCTATGGGGGAGCAAGCCTGGGCTACGGGCTCACCGTTGGGTGGTT  7980
```

FIG. 6H

```
7981  TGTGGATGTTTTTGCATCTAACTTGCATGTAGGGCTTGTCCTGAGCCCCGTGGCTGCAGT  8040

8041  CAAGTAACTCGTCCAAGTTCACCAGCTCTGACTGGGCTACACCCTAGACTGAAATCCAGG  8100

8101  GTCAGAGTCAGGCTGAGTTTTAGGGTCAGGCATAGGTTTTAAGGTCACAGTTGAGGTTGA  8160

8161  CTCTGGGACTCAGGTCAAGGCCTGCTTTTCTTTTCCATGTGGCCCATGTCTGACCGTTTC  8220

8221  CTCATCCTGGAGTTTCTCAGGCCCTGCTCCATCAGAGTTAGGGGAGGGGCACACGTGGCA  8280

8281  CCTGAGAGGAAATCAGGGTGATTCCTGCCTCCCTTCCTTTTCTGTGAACTCAGATATAA  8340

8341  AGGAGGGAGAAGGGCAAGCTTGTCTGTGCTAAAGAAACCCTTCGCCCATGATAAGGGTGG  8400

8401  GGGCCAAGACCCAGTCCTGCCAGGCACGAAAGTCTGGCCACTGGGGAGGGGAGGAGCTCT  8460

8461  TGGCAGCTTTTCTTTTGCTGCTTGGCAGGACCACCCTCTCAGCCTCTGCTCTCCGATCCC  8520

8521  TGGTCAACTCTAGCTCTCTCTGGGCTCCGCAGCAGAGATGTGTATTGGCACAGAGTGTGT  8580

8581  GCGTGCAGGGTTGAGGAAATACTCTTACCCCGATTTCTGTACCCTGGAGCATGTGTGCCC  8640

8641  CTGGGATCCCTAGTGTGGAAGCCCAGACCAGACTCCAACCAAGGAGTGGGCAGTGGGCTT  8700

8701  GGTCTCCTCTGGTCCTTCCTCCCACAGGTGGGTGGAATCACGGTGACACAGATGTTTGGA  8760

8761  GAGGTCACGGAGATGCCCGCCTTACCCTTCATGCTGGCCGAGTTTGATGGGGTTGTGGGC  8820

8821  ATGGGCTTCATTGAACAGGCCATTGGCAGGGTCACCCCTATCTTCGACAACATCATCTCC  8880

8881  CAAGGGGTGCTAAAAGAGGACGTCTTCTCTTTCTACTACAACAGGTGGGGACTGGGACTC  8940

8941  CAAGGGCTGAGGTGGGGGGACAGGAGGGGAGAAGAGATGGGGAGTGGAAGGAGAGTCTGG  9000

9001  GCCAGAATTGTAAAGTGTTTGTAATTAGGTGACAGCCAATCAATATCTAGAGCTGTACTA  9060

9061  GCCAATATGGAAGGCACTATTGAAATTTAAATTAATTAAATACAGTTAAGCATCAATTAA  9120
```

FIG. 6I

```
 9121  GCATTCAACTGGTGGCTCTTAGTTGTACTAGCCACACGTCAAATGCCTGGCAGCCACGGT   9180

9181  GGCTAGTAACTACAGTCTTATGACAGTGCAGATAGAGAATATTCCCAGCATGACAGGACA   9240

9241  TTCTAATAGACAGCGCCACTCTGGAGCAAGAGGAGATGCAAGGTGGGGGCGATGGTAAAT   9300

9301  AAGGGATTACTGTGACCTGTAGCCCTGCCTGTTAGGGCCATGGCTCCTCCCACACAGAGA   9360

9361  CAGCCAACTTCAGTCATCCATTAGATCCTTCATTCGTTTGTTTGCTCACTCATCAGTTCA   9420

9421  GTAAATGCTATGTGCCAAGCACTGTGGTAGGCTCTGGGGGTGCAGCAGTGAACACAGTGA   9480

9481  ACAAGGCAGAATCTGTACTCCCCTACCCACATAGAGCTTACAGGCTAACAGGGAAGACAA   9540

9541  GACATATTCCAACATAAAGAGTGTCACAGGCAGGCAGCAAGTGTGGTGCTGAAAACCATG   9600

9601  GATGCTTTTCAATTCTAGGCTGAGCTTATATGCAGCTCAGCCAGCCTTGGGGAAGCTCTT   9660

9661  GAGCAGGGTTGGGCTCTACTCCAAACTGCTGGGCTTAGAAAGATGGCATGAGTTGGAGAC   9720

9721  AAGAGAGCTGGAGGCAAAAGGGGCTGGGTGCAGTGGCTCATGCCTGTAATCCCAGCACTT   9780

9781  TGGGAGGCCAAGGCGAGAGGATCGCATGAGCCCAGGAGTTAAGGCTTCAGTGAGCAGTGA   9840

9841  TTGTGCCACTGCACTCCAGCTAAGGCAACAGAGTGAGATCCAGTCTCAAAAAAAAAAAA   9900

9901  AAAAAAAAAAAGTCACAAGGGTAAGAACATGAGGCCAGTGGCAAAAAGAATAGAGGAGAG  9960

9961  GATCAGAGTTCAGAGAAATCTCACAGTAAAATGGAGAGGAGTCTCCGGTTTGGTGATAGA  10020

10021  AAGTGAGGCCTTGAGAAAAGGCCAATTGGCGGCTCTGCATTCAGGGGTGGTCTTTAGAAG  10080

10081  AACTGTTTTAGAGGAAGTGGGGGCAAGGCCAGATGGCAAGAAGTTAAGAGGTGGACGACG  10140

10141  TGGGTGTCAGGAAGTGGAGGTCATGAGATGTAGGCTGCCCTGGGACATTCAACAGGGAAG  10200

10201  GGAATGGGGGGTGGCGTGGGGGGTGAGATCCAGAAGCAGAAGAGGAAGGGTGGGTGTTTT  10260
```

FIG. 6J

```
10261  TAAATGCTAGAGGATGCTCGAGTGATGCCTGTAGGTGGAGGAAGAAGCCAATGGAAAGAA  10320

10321  AGAGATTAAAAATGTGGAAAGAAGAGGAGCTAAATGGGGGCACTGGAGTTTGGAGGCCTT  10380

10381  GAAAGAGATGAGGTTCCAGCAGACAGGAAGAAGCCAGGTTTTGCAGAGGAGAGGGCTGGC  10440

10441  CTCTTCTTTTATCTTGGGATGGGAAGGAGGGAACATCCAGAGAGATACTGAAGTGTTGAG  10500

10501  AGACAGGCAGGAGGGAATTTGTGCTAGCATATACACATACATTCCGAATTTATAAAAACA  10560

10561  CAAGTAGTTTGCAGTTGCACAAAATAACATATGCACACCTACACACCCATGCACACATGT  10620

10621  GCATGTGTGAATTCTAGTATGAATTCTGGAAAAACACATCACACACACAGGCATGCCCTG  10680

10681  GAGACTAGGCCTACAGTAGTCCCTGAGCCAAGTGCAGTGAGGAGGAAAGGAAGGTGAGGG  10740

10741  GAATCAGCTCCAGACGGGGCACCAGGAGCCTGGCTCCAGTCCCCCACTTGTTCACTCATG  10800

10801  GACTGGGTAACTTCAGGCAAGTGACTTCGCCTCTTGGTGACTCCATTGCCTGAAGGGCAA  10860

10861  AGAGAGTACATAACACCCACCCTGCCAAACAGCAGGGCTGATGAGGCTGGCATGAAATGA  10920

10921  AGCTTCCTTTCTGCTGTCTCTCTTTCTCTGCAGAGATTCCGAGTAAGGAGACAAAACCCC  10980

10981  CACATGGCTGTGACCTTCCAGTACTCCCCGAGCACCTGACCTAGAATTACACACGCCACC  11040

11041  GGCCCAAAACTCACATCAGCAAGCCCAGCCTCCGCTAGATGCCGAAGTTCTCTGTCTCTC  11100

11101  CTTCCTGCTCTCTCCATGCCACCTGCCCACCCCATACCCAATAGCCTCCCCAGGGTCCCC  11160

11161  TCCCATGCACCTGCTCAATCAGCAGCAACCCAAGAGTGAGGGTGTCCATTTGTGTCTTG  11220

11221  TTCACATCCACTCACTGTCCTTGTACCTGCTCCTTTTCTGTGACCTCTCTGGGGATGCTT  11280

11281  TTTGGGGGAACAGCTGGACTACCCTGGAACAACCTCTGGTTGGTCTTGGGGAGGGGAAGA  11340

11341  AAGGCAGAGAAGCAGTATGTTCTGCATGCTTCCCAACGACAGCTCCGAGCCTGGCTGTCT  11400
```

FIG. 6K

```
11401  GTCCCACATTCCTCTGCTCTAGAGCCCTCTGTCCTCCCCTGCACCCTTGTGCAACCTTCC  11460

11461  CCAATTGCCTGAGTTGCTGGGTCCTGGAGGTTATGGGTTTCCAAGAGCTTCTGATCTTTC  11520

11521  CTTTAGGAATTCCCAATCGCTGGGAGGACAGATTGTGCTGGGAGGCAGCGACCCCCAGCA  11580

11581  TTACGAAGGGAATTTCCACTATATCAACCTCATCAAGACTGGTGTCTGGCAGATTCAAAT  11640

11641  GAAGGGGTCAGAAATCCTCAACCCTCCCCGGGCTCCAAAAAATGCTGCCGTCACTGGGGT  11700

11701  TGGGGAGGGTGGGGAAGGACTGCATTACCATCCTGCCCTCTTTCCAAATGCAGCCACTTC  11760

11761  TTAAGCACAGCCACCATTTGCTCTCTGCCTGCTCTGTCCAGGCTGGGGAACAGAGAAGGG  11820

11821  AGGGGCCTGGGGAGAAGTGGTGGAGGGTGACAGTACCTTCCCTCCTCTACTCACTGCCTC  11880

11881  AACAGGCCACCAGCGTGGCCTCCACCCACCCACCCACACTCAGGAAGGACATGCAGCCTG  11940

11941  GAGGTGCCCCATCAGCCTTCTGTCTGTCTGTCTGTCTGTCTGTCTGACTGTGGCCTCCCC  12000

12001  CAGGGTGTCTGTGGGGTCATCCACCTTGCTCTGTGAAGACGGCTGCCTGGCATTGGTAGA  12060

12061  CACCGGTGCATCCTACATCTCAGGTTCTACCAGCTCCATAGAGAAGCTCATGGAGGCCTT  12120

12121  GGGAGCCAAGAAGAGGCTGTTTGATGTAAGAAGCCAAAGAGGGAAGGTGCTGTGGGTGGG  12180

12181  GGGAGCGCCACCTGGTATCGGCTCACAAATCCCCCAGGCAAATGAGGCCATCTCAGGCCT  12240

12241  TCGCTTGTTCACCTCACACTCTCCACACATGTGGCTGGTCACCCATGGGGCGGGGCACTG  12300

12301  TCCCCAGCCCTCTCCAGCAGAGAGACCAGGCCACCAGCGCAGGACTCCTTGTCTGCTGAG  12360

12361  ACGTCTTCCATACTCAAGAAGGCTCTCTTTGCCCCCCACCCCAGTATGTCGTGAAGTGTA  12420

12421  ACGAGGGCCCTACACTCCCCGACATCTCTTTCCACCTGGGAGGCAAAGAATACACGCTCA  12480

12481  CCAGCGCGGACTATGTATTTCAGGTGAGGTTCGAGTCGGCCCCCTCGGTGGCAGGGAGAA  12540
```

FIG. 6L

```
12541  AGGCTGGACAGAGACCCTCAAAGAGTGACAGATTACAATGCACAGGTCATGTTAGAACTG  12600

12601  TAGTTCTCAAACTTGGCTGTGCATGTCACCTGGAGAGCTTTGAAAAATCCTGGTACCTGG  12660

12661  GCCACATCCCATACCTATTAAATCAGAACCTCTAGAAGTGGCACCTGGGGTTCAGTTTCC  12720

12721  CCAGGTGATTCCAATGTGTGGCCATGTTTGGGCATCACTATGCCTGTTCCCTCATCTCCA  12780

12781  TTTTCTCATCAAATACTCCCAAGAATCCTATGCTCCTATATTCTTACCCTCTTTTCATAA  12840

12841  TCAATAGGCTTAGAGAAGTTGAATAACTTGTCTAGGATCAGAAGCTAAGGCAAACTGTAA  12900

12901  GCTCCTGAAGGAAGCACGGTGCCTGATGCATTGTTTGCCTGGGATCTAGCACAGGGGCTA  12960

12961  AACATAGGAGTGGTGCAGTCCACGATGGGGCAAAATGGCCATGATGTGAGGGAGGCCCAG  13020

13021  TGTGGCTAGGGGAGAGATGGGGGCGAGAGGGGGAATGTTGCTGAAGACAGTTGCTIGGGG  13080

13081  TCAGGCAAGGTGAAAGGAGAATGCTCATGTGCTGGGTATGGAGAAACTCTCCCCCTTCCT  13140

13141  GCCAGGAATCCTACAGTAGTAAAAAGCTGTGCACACTGGCCATCCACGCCATGGATATCC  13200

13201  CGCCACCCACTGGACCCACCTGGGCCCTGGGGGCCACCTTCATCCGAAAGTTCTACACAG  13260

13261  AGTTTGATCGGCGTAACAACCGCATTGGCTTCGCCTTGGCCCGCTGAGGCCCTCTGCCAC  13320

13321  CCAGGCAGGCCCTGCCTTCAGCCCTGGCCCAGAGCTGGAACACTCTCTGAGATGCCCCTC  13380

13381  TGCCTGGGCTTATGCCCTCAGATGGAGACATTGGATGTGGAGCTCCTGCTGGATGCGTGC  13440

13441  CCTGACCCCTGCACCAGCCCTTCCCTGCTTTGAGGACAAAGAGAATAAAGACTTCATGTT  13500

13501  CACAGCCTGTTGCATCTGGGTTCACTAGGGTTTAGAACAGAGGGAGGGGCTGCGTGATCA  13560

13561  TGTGTGGACAGGAATGTGACACAGACAAGCTACACATTCGCCTAGCGCACAGGTTCTTGC  13620

13621  GTGCAGGGATGATGCCATCCATCTGCCATCAACGGGACTCAGGTGGAGCTGTTTACACAA  13680
```

FIG. 6M

```
13681  CCTCAGGTGGGAAGTCTGAAAAGAGCCGGAACCAAGCTCCCTCTAGTCCCTCAGGGACCA  13740

13741  AGGCTAATGCTGTGGCAGTAGACTGTGGGTCAGAAAGTTCTCCCAGCTCACAGAAGCCAG  13800

13801  CTCTGAGTTCAGACTCTGCTCTGCTGAGCTAGTCAGCCCTGTCTCTTGTCCCTGCAAAAC  13860

13861  TCCCCTCAGCTGTCCTTATCCACTGCAGATGCCCCGCCCTGCCCCATGTAGCCATTTAC  13920

13921  ACAGGCATTCTAAGGCACTACCACCTAAAATCATAGAACACCAGAGATCCAGGCAATACT  13980

13981  TCCACTTTACAGGTGGGGAAACTGAGGCCCAGAGAATGGAAGGCCTTGCCCAAGATTACT  14040

14041  CGGTCAAGAATCAAGTAGTGAAGAATACTGAAAGATAGTGAAGAATCAAGACTGGAACCC  14100

14101  AGCCCGTCTGACTTGGGTCCTGGGGGTTTCCACCTTATCATAAGCAGTTGGTACCGTCAT  14160

14161  AAGTACAGTGCTTCACGCACGCTGGTACAGGGCCACGTGCACAAGCACACAGGTGCACAC  14220

14221  ACACACTGCTATCCTCCATCCCATCCACCTGGGACTCGTCAGGCTGAAGTCTCTTCTCCC  14280

14281  ACTCTCACTCCTTGGGCTGTCTTCAGGGCACATGTAACTTGGGGAATGAGAAATTAGCAT  14340

14341  CCACCTGGAGCCACTGAAGCCATCCCTCTTCACCATAGTTGCTCACCTCTCTTTTGACAG  14400

14401  AAAGTCGTGAGGCACTGAATGGCCCAACCAGGCCCTCAGTACCTCTGGGAGCCATCTGCA  14460

14461  AGAGTCCCTGTGTAGCGCCAAGAGCCGGAGCCTGGGCTTCAGG  14503
```

FIG. 7A

```
   1  GGTCTTTGTAAAATAATAATTATTCATTTCACAAAAGTGATAATTAAAAGACTTTAATAG    60

61  CAATACAGAAAGTTACATGAATATAAAGACTTAACCTTTCTAAAGCTCAGTTTTCCTAAG   120

121  TAATCAAAAACCTGATAAAGATAACAAGAATGAGGAATTATCTTGAGAAAATGTAAAATC   180

181  TTTCCTTTTATTTTTTGAGACAGGGTCTCACTCTGTCATCCAGGCTAAAGTGCAGTGGCA   240

241  CAATCATAGCTCACTACAGCCTTGAACTCCTGGACTCAAGTGATCCTCCCGCCTCAGCCT   300

301  CCCCAGTAGCTAAGACTACAGGCACGCACCACCACACCCAGCTAATTTTTTCAGAGATG    360

361  GGGTCTTGCTATATTGCCCTGGCTGGTCTTGAACGAGCTTCAAGTGAGCGTGAGCCTCCT   420

421  ACCTCATCCTCCCAAAGCACTAGGATTACAGGCATGAGCCACTGTTTCCCAGCCTAAAAT   480

481  AATTGTTTCTTAGGCCAGCTACCAAAAACGCAAAGAAAAACTTTCTGTAGTGTGATTGCT   540

541  TCTTCTTATGGGAAGCCCATTTAGATAACCTGTAAGTCAAACCTGATGAAAACAATACTT   600

601  GAATGTAATCAGACACAGAAAGACTGTTCAAGGCTATGAGTAGCTGAGTCCAAGCTCGTA   660

661  TCACTTGCCACACAACAGCCAATAAGTCTAGAGACAAGGTATTGTGGCAAGGAAAGCTAC   720

721  CTTATTCAGAGAACCAGAAAACCAAGAAGATGGTGGACCAGCATCATAAAGAACCATCTG   780

781  AAGTCAGCATGAACGTTAGGCTCTTCTTTATGTTAAGGGAAGGGGAAGAAGAAGGGGATT   840

841  GGGATCAAGAGGTGACTGATGACCACAGACACCTGGGTGCCAGCAAGGGTCTGAGGACGT   900

901  TGTAAAACTTCTTTTTTCTAGGTCAGGTCACAATGTTCCTATACATCTTTAACATAACAT   960

961  TGTTATTTGTCTGTATATTTCCTTATCTCCTTGGGGGTTAGTTTGGGGAAAGGAACTGTT  1020

1021  ACCATTTTTTTAAAGTTGAACTGCAAGCTAAACTCCTATAATTAGCTGGTCTATGTACA   1080

1081  GAGCTAAGCAGAAGCTTTTAGCCTAAAGGATAATACCCCTGGGGGTCAGAGGCAAAATGG  1140
```

FIG. 7B

```
1141  AGTCAGTCATGCTAAGTCTCCCTCCACTCTCTTTCTTTTTTGAGATGGAATTTCACTCTT  1200

1201  ATTGCCCAGGCCGGAGTGCAGTGGCATGATCTCAGCTCACTGCAACCTCCGCCTCCTGGG  1260

1261  TTCAAGCAATTCTCTTGCCTCAGCCTCCTGAGTAGCTGAGATTACAGGTGTCCATCACCA  1320

1321  CACCCAGCTAATTTTTGTAGTTTAGTGGAGATGGGGTTTCACCATTGTTGGTCAGGCTGG  1380

1381  TCTGGAACTCCTGACCTCAGGTGATCTACCCACCTTGGCCTCCCAAAGTGCTGGGACAGG  1440

1441  TGTGAGCCACCATGCCTGGCCCCTCTACTCTTATAATTAAACCAGCTGTTGCTTTTCCTG  1500

1501  CCAAGAAACCAGTCATGAAGATTCACCCATGTTCTAGATGGGAAAACTGGGCTGTAGCCT  1560

1561  GGGAGAGGCCAGTCAGGGACAAAGCCAAAGTTAATATAGAGAATGGAGCTTCCAGGGTAT  1620

1621  AGGGGTTGGGTCTGGGCTAGGGAGCTGGAAACCTAGGTTTTACGCTTGTCCCAGTTTTGA  1680

1681  TGTTAGCCCTGAGCAGTGCTGTTTCTCATCAGCCTCTGCCTGCTCCAGGGGTCACAGGGC  1740

1741  CAAGCCAGATAGAGGGCTGCTAGCGTCACTGGACACAAGATTGCTTTCCACAGCTGTCC  1800

1801  TTCCTCCAGCCCCTCTGCTCCCCATCCGGAAACCTGGGTACCCTTCACCCACCTAGCTCT  1860

1861  GTCCCGCAGTGAGATTTATTGCTGACTGCCCTGCCATCTACCCCAGGGTAATAAATCAGG  1920

1921  GCAGAGCAGAATTGCAATCACCCCATGCATGGAGTGTATAAAAGGGGAAGGGCTAAGGGA  1980

1981  GCCACAGAACCTCAGTGGAT<u>CTCAGAGAGAGCCCCAGACTGAGGGAAGCATGGATGGATG</u>  2040

2041  <u>GAGAAGGATGCCTCGCTGGGGACTGCTGCTGCTGCTCTGGGGCTCCTGTACCTTTGGTCT</u>  2100

2101  <u>CCCGACAGACACCACCACCTTTAAAC</u>GGTAATTGGTAACTCAGGCAGAGAAGGGGTGGGA  2160

2161  GGGGTGCAGGGTTCCCACCTTCCCAACACCCTGGCTTTTCCACATGCGGTGTCATTCAGT  2220

2221  CCTTACGATCAGCTGGACAGGGAAGTATGGACCTGTTCAGAGAGGTCAAGTGACTTGCCC  2280
```

FIG. 7C

```
2281  AATAAATGACACTAGTAGTCAGGTCTAGAAGCTGTGACTTTTGCTTCCTGCCCAGAGCAC  2340

2341  CATGCTAACTAAGCACTGTAGAGAACTCAGAAGTATTAGGACATGCCCCTTGCACTTGAG  2400

2401  GAGCTCACAGCCTGAATATTAAGAAGGGCATGGGTGGTTGGGCGCGGTGGCTCCTGCCTG  2460

2461  TAATCCCAGCACTTTGGGAGGCTGAGACGGATCACTTGAGGTCAGGAGTTTGAGACCAGC  2520

2521  CTGGCCAACATGGGGAAACCCCATCTCTACTAAAAATACAAAAATTAGCCGGGCATGGTG  2580

2581  GCAGGCACTTGTAATCCCCAGCTACTCGGGAAGCTGAGGCAGGAGAATCGTTTGAGCCCG  2640

2641  GAAGGTGGAGATTGCTGAGCCAAGATCGTGCCACTGCACTCCAGCCTGAGTGACAGAACA  2700

2701  AGACTCCATCTCAAAAAAAAAAAGACGGGGGTCGGGGCATGGGTACAGTTAACTGTACC   2760

2761  AGGGAAGCAGCTTGATATCGTGGTTAAATGCAAGGCTTATAGAGTTAGATTGCCTTCATT  2820

2821  TAAATTTTGCTTCACTAGCAGAACAAACTAGGTCTGGAATCATGGGCAAGTTATTTAACC  2880

2881  TCTCCAAGTCTCAGTTTATCATTTTAAACAGGTATGATAATAACAGTACCTACTTGATGG  2940

2941  GGCTGCTTTGGGGATTTTAGGAGATAAGGCATAGAAAGCTGGGCACGTTGTAAGAGCCCA  3000

3001  GCTACTGTTAGTACTACAGGATAGATTCTTACAAATATCAAAAGCAAGGTTTGGCCGGGA  3060

3061  GCAGTGGCTCACGCCTATAATCCCAACACTTTGGGAGGCCGAGGGGGGCAGATCACCCGA  3120

3121  GGTCAGGAGTTCAAGACCAGCCTGACCAACATGGAGAAACCCTGTCTCTACTAAAAATAC  3180

3181  AAAATTAGCCGGGCGTGGTGGCACATGCCTGTAATTCCAGCTACTTGGGAGGCTGAGGCA  3240

3241  GGAGAATCGCTTGAACCTGGGAGGCTGAGGTTGCAGTGAGCCGACATAGCGCCATTGCAC  3300

3301  TCCAGCCTGGTCAACAAGAGCAAAACTCAGTCTAAAAAAAAAAAGAAAGAAAAAAACAA   3360

3361  GGCTTTAGGTAGCCCACAATTAGAAGGAGAAAACCTTAGCATCCCCTAGGTGCCAGGCCT  3420
```

FIG. 7D

```
3421  TGTGGGAACAAGTGATTCATTAAGACTGTAGAAGGAAGCTGGGCACGCGGCTCATGCTTG  3480

3481  TAATTCCAGCACTTTGAGAGGCTGAGGTGGGCAGATCGCTTGAGCTCACGAGTTCAAGAC  3540

3541  CAGCCTAGGCAACATGGTGAAACCTTGTCTGTACAAATACAAAAATTAGCTAGGTGTGGT  3600

3601  GGTGCAAATCTGTAGTCCCAGCTACTCGGGAGGCTGAGGTGGGAGCATCACTTCAGCCTG  3660

3661  GGAGGTGGAGGCTGCAGTGAGCAGAGACTGACCCACTGTGCTCTAGCCTGGGTGATAGAG  3720

3721  CCAGACCTTATGTAAAAAAAAAAAAAAAAAAAAAAAGACTGAAGAAGGGGAAGAGACAG  3780

3781  CATTTGAGAAAAGGCCTCACAGAGAAAGGGGTTTTCAATCTGGGACAGCAGATATGACC  3840

3841  AGCAGTCCTGAAGGTAGGGAGGCACACTTTAATAATGGTAATAGTTGCTAAGCCTATAAA  3900

3901  ATGCTTAGGGTGTCACAGGATCTTTTCACATGTCTCATCTCAAGTCATGCCCCCAACAAC  3960

3961  TCAGCATTCCCACTTTGCAGATGAGGACACTGAGGCTCAGGGAGGTGATATGTAAGAGGC  4020

4021  TAAGCCTCAACACACACTGGGCCTTTTGCTTCCGAAACTGCTTTCCCTTGCTCTGAGGCT  4080

4081  CTCGGAGAGTAATTGCTGGGTTGTGAGCACTGGGTAAGAGGATGGGTGCTTCAAAGCAGC  4140

4141  TGCACTCCAGGATAAAGGTAGAGGAAAGTAAAAACATCTTCCCCTGCTGTTATCCAAAAG  4200

4201  AGAAAAAGAATGGAATTGGGCAAGGGGTGGAGGGGGAATCCAGCTTTTGAAACAGTATTA  4260

4261  TAGGAATTTTGCTACCCGCTATGTGCAGAGCATCATGCGAGGCACTTGGGACAGCTGAAT  4320

4321  GAATGAGCTCCATTCTCAAGGTGAACATGTACATATACACACCTACAATTTACATTTATT  4380

4381  GAGCAGTGGTCGCATGGTTTCATCTGCACAGTGACTCTGAGGTAGGTACTACCATTAGGC  4440

4441  CCATTGTTAGAGAGGGGTTAATGGAGACTTAGAAGAGGCCCAGAGAGGTTAGGTAGCTTT  4500

4501  CTCAGAATCACATAAGTGGTAAGGGGATTCAGGCATGCCCCCTGCAACCACTGTCTTCAC  4560
```

FIG. 7E

```
4561  CACCGTACGGCACCAGTTCCACAAGCTGTACAGTGTGGGCTGTGAGACCCAAGGAAAAAC  4620

4621  AGAGCTGAGGCCCACGGGAAGGTGAGGCCGGTGTGGGCTGGAGGCCTTGGGGTAAGCTTC  4680

4681  CTGGAGGTGGGGGTACATGTTGGGCCTTGGAGGACTAAAGAACTGGGGGGAAAAGGAAGG  4740

4741  GAAGAAGGAAAGGATTTTCTGAAAAGGAAATGGCAAGAAGTAAAGGTCCAAAGCATAGGC  4800

4801  TGTTGTGAGTAAACAGTGGGAAATGCAACCTCTTTGGGGCCAAACCTCTGACCCTCCACG  4860

4861  TTCCCAGCTGTGAAGTGGGAGTAATAAAATCATCCACCTTATGAGAGCAAATAAAATAAT  4920

4921  GATTGTGAAAATATTTTGGTAACAGTAACCTGTGATAGGAAGATAACAAATCATTTCTGT  4980

4981  TACAATACCATGCTGATAGGCATAAAAGTTGCATTCATGTTCATGGGCAAAATGGGGGTA  5040

5041  AGTAGAATGCATGGGACGCAAGAAGGATGTAGGAAGGAAAGGGTAGTGTGAGTATAGGAG  5100

5101  GACTAGCCACTGAGAAGAAAGTAGAAGAAAGAGGGAATCTTTGTGTGTATGGGAAAGTCT  5160

5161  ATTGCAGAGTCAACTTGGGCTTCCATCCTGGGACCTTCCCGTGAACAGCTAGAGACATCT  5220

5221  TCCTCTGGGCTTTGGCAGCCTTTATGTCGGGACCCAGGGGACCCTATATGGGAAATAGGG  5280

5281  CCAGACACATGCTCTGAATCCCTGCTTCAACATTTCTGAGTCACCTTTGTCCCTGTGAGC  5340

5341  CTTCATTTTTCTCATCTATAAAATGGATGACAGCTAGCTTGTTGGTGTGATTTCAGTAGC  5400

5401  GGCTCAGTAGAGTCAGTTTCCTAGGTCTCTTTAATTCTGCCTCTCAAAGGTGATGGGAAA  5460

5461  ACATCTAGACAAGAAGCCAAGGGACCGGGACACATCTCTCCAAGGACGAGGTGCATGGCG  5520

5521  CTCTGAAGATGCTGGCATCTCTCTAGGCCCAACCCAGCTCAGGGGGTCCACTCCACCACA  5580

5581  GCCCTGGCTGGGTGCCTGTCCCCTGGTATCCTGGAGACCTTGCAGCTGCTGTGGGCATCT  5640

5641  GCTGCCACCTAGCGGCCTCCCATGGCACTGTCTCCCCGCCAGCCCCTAGTTTTGACAGGG  5700
```

FIG. 7F

```
5701  GCACTCCCTGGCATTAATCTCTTCAGAGGGAATGTCTGTGCCTGTTTCCTGTCTGTCCTC  5760

5761  CCGCCAGGTGGAGTTCCTTAAAGGCAGTCATGATCATTATCTTTCTAGCTCCAGTGTCCA  5820

5821  GCACAGTGAGGCACAAAGTAGTTGTTCAGCAGGTGATTACGGAATAAATGAATGAACGGA  5880

5881  CCAATAAACAAATAGCCTTGTCTAATCAAAATTAGGCAACAGAAGGAAGTCACTTCAGGG  5940

5941  TTATTTAATCCCCGGGCAGCTGACTCCTCTAAATTGACTCTTGACAAGAAGTAACTCTTA  6000

6001  TAAATGCTCCAGAGGCCCTCAGCGACAGAGGTGATTTCCAGGTGGCTGGGCTAACGTTAA  6060

6061  AGGTGGTTGTACTAAAAGCAGGGGTTTGGCCTCAGGGACTCCACCACTGTGGTGGAGGTA  6120

6121  CAGCACTTTTCTATTTTTGCTTCCTCCACCCTGGGCCAGGATCTTCCTCAAGAGAATGCC  6180

6181  CTCAATCCGAGAAAGCCTGAAGGAACGAGGTGTGGACATGGCCAGGCTTGGTCCCGAGTG  6240

6241  GAGCCAACCCATGAAGAGGCTGACACTTGGCAACACCACCTCCTCCGTGATCCTCACCAA  6300

6301  CTACATGGACGTGAGTGCTTGGCTCAGCCCCTCGCTCCCTCCCTGTCTCCTTTCCCTCAT  6360

6361  GGACCTAGGGCTTTCTTTGCTGCAAGACTCACCCTTTCCAAGCTGTGTTTGACGAAGGCG  6420

6421  CTGAGTAGCACGTGAGCACCCTAGAAAATTCCCATTTTCCAGCTGGAAAGCCTGAGCACA  6480

6481  GAAGACAGGAAGGCATCCAGGGGCCATTCAGGGGCAGGGTTAGGTTTGGAACTCAGCCCA  6540

6541  GGCCTCAAGCCAGGTGTCACAGGTGGGTGGGAAGGGTGTGTGACTCAGGTGGGGGTTTC  6600

6601  TGTGACCTGGCCCAGCACAACCTGATGGCTTCCTGCCCCAGAGGATCCTCAAGAGTCAAG  6660

6661  TTTGCTTCCTGCTTCATTCTCAATGTTTTGATTTTGCCCTCTTGTCTTACTGAGACTCCC  6720

6721  ACTTTCTGGGATGCCATGGGGAGATGCTAAGCCTCCTACCAGTTCCTGCAGGAAAATGGA  6780

6781  AACCCCGAGAGGCTATAGGACCTCGCCTGGGCCAAGTCTCACACCGAGAGCCAAGAGTGA  6840
```

FIG. 7G

```
6841  AGCCAGGCAAGACCCCAAGACCCAAGGTCCCCTGAGCCCCTCCAGCCCTCTCTTTTTACC  6900

6901  CCCACAGACCCAGTACTATGGCGAGATTGGCATCGGCACCCCACCCCAGACCTTCAAAGT  6960

6961  CGTCTTTGACACTGGTTCGTCCAATGTTTGGGTGCCCTCCTCCAAGTGCAGCCGTCTCTA  7020

7021  CACTGCCTGTGGTGAGACCTAAGACCCACAGTGCCTCTCCTCCATCCCCCTGCCCTACTG  7080

7081  TGCATGAGCAATCCTGCCCAACACCCAGCTCCCATCCCTCTTGCCACCAAGGGAGTGGCT  7140

7141  TCCTCTCTGCCTCTGTGCCCACTGACATGTAGGGGAGAGGGGAAGATGTCTCCCGTTTTT  7200

7201  CTGATACAGCCACCAAGGTTAAAAACAAAAAAGGTCCAAGAACCCCTGAGCACCCAGAA  7260

7261  GGCCACTTCCCAGTCTTCCTGAGATTGAGACAGGACTGAATTCTCAAACCCATCCCAGGC  7320

7321  ACTCGGAACTCTTCCATCCCTAGTCTTAATCAACAACCTCTTACTAGGCACTTACTCTGT  7380

7381  GCCTGGCATCTTCTCTGGTGTTATCAGTGTTAGTGATTACTTTAAATTCCTTCATTTAGG  7440

7441  ACAAAATTCTCGATGTATGGGCACATTAGGAGAGCCCAAGAAACCCAGTCCTTGATTGAT  7500

7501  GAAGCACATATTCCAAGCCCCCTGACCCTAGGGCCACTCATCCCTGCACCTAAGCTAACC  7560

7561  AGCCATACCCACAATGCACCCTGCCTCTGAGTCCCCCTGTCTGGGCCACTCTTGGACAAA  7620

7621  CCTGAGCCTCTGTCCCCCTGCCAGTGTATCACAAGCTCTTCGATGCTTCGGATTCCTCCA  7680

7681  GCTACAAGCACAATGGAACAGAACTCACCCTCCGCTATTCAACAGGGACAGTCAGTGGCT  7740

7741  TTCTCAGCCAGGACATCATCACCGTAAGTTGGGCCGCCCTAGGTCATCTGCCCCGGACCC  7800

7801  CTTCTGTCCCCAGGCCTCTCCTGACCCTCCAGGGCCCACACCTGCGGGGAGGTACACTGC  7860

7861  AGCCCACTTGGAGCCTGGGGAGCTGAGGAACACCCTACTCTGCCACATCTGGCTGTTGCT  7920

7921  GCAAAGCAGCAGTACCTATGGGGGAGCAAGCCTGGGCTACGGGCTCACCGTTGGGTGGTT  7980
```

FIG. 7H

```
7981  TGTGGATGTTTTTGCATCTAACTTGCATGTAGGGCTTGTCCTGAGCCCCGTGGCTGCAGT  8040

8041  CAAGTAACTCGTCCAAGTTCACCAGCTCTGACTGGGCTACACCCTAGACTGAAATCCAGG  8100

8101  GTCAGAGTCAGGCTGAGTTTTAGGGTCAGGCATAGGTTTTAAGGTCACAGTTGAGGTTGA  8160

8161  CTCTGGGACTCAGGTCAAGGCCTGCTTTTCTTTTCCATGTGGCCCATGTCTGACCGTTTC  8220

8221  CTCATCCTGGAGTTTCTCAGGCCCTGCTCCATCAGAGTTAGGGGAGGGGCACACGTGGCA  8280

8281  CCTGAGAGGAAATCAGGGTGATTCCTGCCTCCCTTCCTTTTTCTGTGAACTCAGATATAA  8340

8341  AGGAGGGAGAAGGGCAAGCTTGTCTGTGCTAAAGAAACCCTTCGCCCATGATAAGGGTGG  8400

8401  GGGCCAAGACCCAGTCCTGCCAGGCACGAAAGTCTGGCCACTGGGGAGGGGAGGAGCTCT  8460

8461  TGGCAGCTTTTCTTTTGCTGCTTGGCAGGACCACCCTCTCAGCCTCTGCTCTCCGATCCC  8520

8521  TGGTCAACTCTAGCTCTCTCTGGGCTCCGCAGCAGAGATGTGTATTGGCACAGAGTGTGT  8580

8581  GCGTGCAGGGTTGAGGAAATACTCTTACCCCGATTTCTGTACCCTGGAGCATGTGTGCCC  8640

8641  CTGGGATCCCTAGTGTGGAAGCCCAGACCAGACTCCAACCAAGGAGTGGGCAGTGGGCTT  8700

8701  GGTCTCCTCTGGTCCTTCCTCCCACAG<u>GTGGGTGGAATCACGGTGACACAGATGTTTGGA</u>  8760

8761  <u>GAGGTCACGGAGATGCCCGCCTTACCCTTCATGCTGGCCGAGTTTGATGGGGTTGTGGGC</u>  8820

8821  <u>ATGGGCTTCATTGAACAGGCCATTGGCAGGGTCACCCCTATCTTCGACAACATCATCTCC</u>  8880

8881  <u>CAAGGGGTGCTAAAAGAGGACGTCTTCTCTTTCTACTACAACAG</u>GTGGGGACTGGGACTC  8940

8941  CAAGGGCTGAGGTGGGGGGACAGGAGGGGAGAAGAGATGGGGAGTGGAAGGAGAGTCTGG  9000

9001  GCCAGAATTGTAAAGTGTTTGTAATTAGGTGACAGCCAATCAATATCTAGAGCTGTACTA  9060

9061  GCCAATATGGAAGGCACTATTGAAATTTAAATTAATTAAATACAGTTAAGCATCAATTAA  9120
```

FIG. 7I

```
9121  GCATTCAACTGGTGGCTCTTAGTTGTACTAGCCACACGTCAAATGCCTGGCAGCCACGGT  9180

9181  GGCTAGTAACTACAGTCTTATGACAGTGCAGATAGAGAATATTCCCAGCATGACAGGACA  9240

9241  TTCTAATAGACAGCGCCACTCTGGAGCAAGAGGAGATGCAAGGTGGGGGCGATGGTAAAT  9300

9301  AAGGGATTACTGTGACCTGTAGCCCTGCCTGTTAGGGCCATGGCTCCTCCCACACAGAGA  9360

9361  CAGCCAACTTCAGTCATCCATTAGATCCTTCATTCGTTTGTTTGCTCACTCATCAGTTCA  9420

9421  GTAAATGCTATGTGCCAAGCACTGTGGTAGGCTCTGGGGGTGCAGCAGTGAACACAGTGA  9480

9481  ACAAGGCAGAATCTGTACTCCCCTACCCACATAGAGCTTACAGGCTAACAGGGAAGACAA  9540

9541  GACATATTCCAACATAAAGAGTGTCACAGGCAGGCAGCAAGTGTGGTGCTGAAAACCATG  9600

9601  GATGCTTTTCAATTCTAGGCTGAGCTTATATGCAGCTCAGCCAGCCTTGGGGAAGCTCTT  9660

9661  GAGCAGGGTTGGGCTCTACTCCAAACTGCTGGGCTTAGAAAGATGGCATGAGTTGGAGAC  9720

9721  AAGAGAGCTGGAGGCAAAAGGGGCTGGGTGCAGTGGCTCATGCCTGTAATCCCAGCACTT  9780

9781  TGGGAGGCCAAGGCGAGAGGATCGCATGAGCCCAGGAGTTAAGGCTTCAGTGAGCAGTGA  9840

9841  TTGTGCCACTGCACTCCAGCTAAGGCAACAGAGTGAGATCCAGTCTCAAAAAAAAAAAAA  9900

9901  AAAAAAAAAAAGTCACAAGGGTAAGAACATGAGGCCAGTGGCAAAAAGAATAGAGGAGAG  9960

9961  GATCAGAGTTCAGAGAAATCTCACAGTAAAATGGAGAGGAGTCTCCGGTTTGGTGATAGA  10020

10021 AAGTGAGGCCTTGAGAAAAGGCCAATTGGCGGCTCTGCATTCAGGGGTGGTCTTTAGAAG  10080

10081 AACTGTTTTAGAGGA$\underline{N}$GTGGGGGCAAGGCCAGATGGCAAGAAGTTAAGAGGTGGACGACG  10140

10141 TGGGTGTCAGGAAGTGGAGGTCATGAGATGTAGGCTGCCCTGGGACATTCAACAGGGAAG  10200

10201 GGAATGGGGGGTGGCGTGGGGGGTGAGATCCAGAAGCAGAAGAGGAAGGGTGGGTGTTTT  10260
```

FIG. 7J

```
10261  TAAATGCTAGAGGATGCTCGAGTGATGCCTGTAGGTGGAGGAAGAAGCCAATGGAAAGAA  10320

10321  AGAGATTAAAAATGTGGAAAGAAGAGGAGCTAAATGGGGCACTGGAGTTTGGAGGCCTT   10380

10381  GAAAGAGATGAGGTTCCAGCAGACAGGAAGAAGCCAGGTTTTGCAGAGGAGAGGGCTGGC  10440

10441  CTCTTCTTTTATCTTGGGATGGGAAGGAGGGAACATCCAGAGAGATACTGAAGTGTTGAG  10500

10501  AGACAGGCAGGAGGGAATTTGTGCTAGCATATACACATACATTCCGAATTTATAAAAACA  10560

10561  CAAGTAGTTTGCAGTTGCACAAAATAACATATGCACACCTACACACCCATGCACACATGT  10620

10621  GCATGTGTGAATTCTAGTATGAATTCTGGAAAAACACATCACACACACAGGCATGCCCTG  10680

10681  GAGACTAGGCCTACAGTAGTCCCTGAGCCAAGTGCAGTGAGGAGGAAAGGAAGGTGAGGG  10740

10741  GAATCAGCTCCAGACGGGGCACCAGGAGCCTGGCTCCAGTCCCCCACTTGTTCACTCATG  10800

10801  GACTGGGTAACTTCAGGCAAGTGACTTCGCCTCTTGGTGACTCCATTGCCTGAAGGGCAA  10860

10861  AGAGAGTACATAACACCCACCCTGCCAAACAGCAGGGCTGATGAGGCTGGCATGAAATGA  10920

10921  AGCTTCCTTTCTGCTGTCTCTCTTTCTCTGCAGAGATTCCGAGTAAGGAGACAAAACCCC  10980

10981  CACATGGCTGTGACCTTCCAGTACTCCCCGAGCACCTGACCTAGAATTACACACGCCACC  11040

11041  GGCCCAAAACTCACATCAGCAAGCCCAGCCTCCGCTAGATGCCGAAGTTCTCTGTCTCTC  11100

11101  CTTCCTGCTCTCTCCATGCCACCTGCCCACCCCATACCCAATAGCCTCCCCAGGGTCCCC  11160

11161  TCCCATGCACCTGCTCAATCAGCAGCAACCCAAGAGTGAGGGTGTCCATTTGTGTCTTG   11220

11221  TTCACATCCACTCACTGTCCTTGTACCTGCTCCTTTTCTGTGACCTCTCTGGGGATGCTT  11280

11281  TTTGGGGGAACAGCTGGACTACCCTGGAACAACCTCTGGTTGGTCTTGGGGAGGGGAAGA  11340

11341  AAGGCAGAGAAGCAGTATGTTCTGCATGCTTCCCAACGACAGCTCCGAGCCTGGCTGTCT  11400
```

FIG. 7K

| | | |
|---|---|---|
| 11401 | GTCCCACATTCCTCTGCTCTAGAGCCCTCTGTCCTCCCCTGCACCCTTGTGCAACCTTCC | 11460 |
| 11461 | CCAATTGCCTGAGTTGCTGGGTCCTGGAGGTTATGGGTTTCCAAGAGCTTCTGATCTTTC | 11520 |
| 11521 | CTTTAGGAATTCCCAATCGCTGGGAGGACAGATTGTGCTGGGAGGCAGCGACCCCCAGCA | 11580 |
| 11581 | TTACGAAGGGAATTTCCACTATATCAACCTCATCAAGACTGGTGTCTGGCAGATTCAAAT | 11640 |
| 11641 | GAAGGGGTCAGAAATCCTCAACCCTCCCCGGGCTCCAAAAAATGCTGCCGTCACTGGGGT | 11700 |
| 11701 | TGGGGAGGGTGGGGAAGGACTGCATTACCATCCTGCCCTCTTTCCAAATGCAGCCACTTC | 11760 |
| 11761 | TTAAGCACAGCCACCATTTGCTCTCTGCCTGCTCTGTCCAGGCTGGGGAACAGAGAAGGG | 11820 |
| 11821 | AGGGGCCTGGGGAGAAGTGGTGGAGGGTGACAGTACCTTCCCTCCTCTACTCACTGCCTC | 11880 |
| 11881 | AACAGGCCACCAGCGTGGCCTCCACCCACCCACCCACACTCAGGAAGGACATGCAGCCTG | 11940 |
| 11941 | GAGGTGCCCCATCAGCCTTCTGTCTGTCTGTCTGTCTGTCTGACTGTGGCCTCCCC | 12000 |
| 12001 | CAGGGTGTCTGTGGGGTCATCCACCTTGCTCTGTGAAGACGGCTGCCTGGCATTGGTAGA | 12060 |
| 12061 | CACCGGTGCATCCTACATCTCAGGTTCTACCAGCTCCATAGAGAAGCTCATGGAGGCCTT | 12120 |
| 12121 | GGGAGCCAAGAAGAGGCTGTTTGATGTAAGAAGCCAAAGAGGGAAGGTGCTGTGGGTGGG | 12180 |
| 12181 | GGGAGCGCCACCTGGTATCGGCTCACAAATCCCCCAGGCAAATGAGGCCATCTCAGGCCT | 12240 |
| 12241 | TCGCTTGTTCACCTCACACTCTCCACACATGTGGCTGGTCACCCATGGGGCGGGGCACTG | 12300 |
| 12301 | TCCCCAGCCCTCTCCAGCAGAGAGACCAGGCCACCAGCGCAGGACTCCTTGTCTGCTGAG | 12360 |
| 12361 | ACGTCTTCCATACTCAAGAAGGCTCTCTTTGCCCCCCACCCCAGTATGTCGTGAAGTGTA | 12420 |
| 12421 | ACGAGGGCCCTACACTCCCCGACATCTCTTTCCACCTGGGAGGCAAAGAATACACGCTCA | 12480 |
| 12481 | CCAGCGCGGACTATGTATTTCAGGTGAGGTTCGAGTCGGCCCCCTCGGTGGCAGGGAGAA | 12540 |

FIG. 7L

```
12541  AGGCTGGACAGAGACCCTCAAAGAGTGACAGATTACAATGCACAGNTCATGTTAGAACTG  12600
12601  TAGTTCTCAAACTTGGCTGTGCATGTCACCTGGAGAGCTTTGAAAAATCCTGGTACCTGG  12660
12661  GCCACATCCCATACCTATTAAATCAGAACCTCTAGAAGTGGCACCTGGGGTTCAGTTTCC  12720
12721  CCAGGTGATTCCAATGTGTGGCCATGTTTGGGCATCACTATGCCTGTTCCCTCATCTCCA  12780
12781  TTTTCTCATCAAATACTCCCAAGAATCCTATGCTCCTATATTCTTACCCTCTTTTCATAA  12840
12841  TCAATAGGCTTAGAGAAGTTGAATAACTTGTCTAGGATCAGAAGCTAAGGCAAACTGTAA  12900
12901  GCTCCTGAAGGAAGCACGGTGCCTGATGCATTGTTTGCCTGGGATCTAGCACAGGGGCTA  12960
12961  AACATAGGAGTGGTGCAGTCCACGATGGGGCAAAATGGCCATGATGTGAGGGAGGCCCAG  13020
13021  TGTGGCTAGGGGAGAGATGGGGGCGAGAGGGGGAATGTTGCTGAAGACAGTTGCTNGGGG  13080
13081  TCAGGCAAGGTGAAAGGAGAATGCTCATGTGCTGGGTATGGAGAAACTCTCCCCCTTCCT  13140
13141  GCCAGGAATCCTACAGTAGTAAAAAGCTGTGCACACTGGCCATCCACGCCATGGATATCC  13200
13201  CGCCACCCACTGGACCCACCTGGGCCCTGGGGGCCACCTTCATCCGAAAGTTCTACACAG  13260
13261  AGTTTGATCGGCGTAACAACCGCATTGGCTTCGCCTTGGCCCGCTGAGGCCCTCTGCCAC  13320
13321  CCAGGCAGGCCCTGCCTTCAGCCCTGGCCCAGAGCTGGAACACTCTCTGAGATGCCCCTC  13380
13381  TGCCTGGGCTTATGCCCTCAGATGGAGACATTGGATGTGGAGCTCCTGCTGGATGCGTGC  13440
13441  CCTGACCCCTGCACCAGCCCTTCCCTGCTTTGAGGACAAAGAGAATAAAGACTTCATGTT  13500
13501  CACAGCCTGTTGCATCTGGGTTCACTAGGGTTTAGAACAGAGGGAGGGGCTGCGTGATCA  13560
13561  TGTGTGGACAGGAATGTGACACAGACAAGCTACACATTCGCCTAGCGCACAGGTTCTTGC  13620
13621  GTGCAGGGATGATGCCATCCATCTGCCATCAACGGGACTCAGGTGGAGCTGTTTACACAA  13680
```

FIG. 7M

```
13681  CCTCAGGTGGGAAGTCTGAAAAGAGCCGGAACCAAGCTCCCTCTAGTCCCTCAGGGACCA  13740

13741  AGGCTAATGCTGTGGCAGTAGACTGTGGGTCAGAAAGTTCTCCCAGCTCACAGAAGCCAG  13800

13801  CTCTGAGTTCAGACTCTGCTCTGCTGAGCTAGTCAGCCCTGTCTCTTGTCCCTGCAAAAC  13860

13861  TCCCCTCAGCTGTCCTTATCCACTGCAGATGCCCCCGCCCTGCCCCATGTAGCCATTTAC  13920

13921  ACAGGCATTCTAAGGCACTACCACCTAAAATCATAGAACACCAGAGATCCAGGCAATACT  13980

13981  TCCACTTTACAGGTGGGGAAACTGAGGCCCAGAGAATGGAAGGCCTTGCCCAAGATTACT  14040

14041  CGGTCAAGAATCAAGTAGTGAAGAATACTGAAAGATAGTGAAGAATCAAGACTGGAACCC  14100

14101  AGCCCGTCTGACTTGGGTCCTGGGGGTTTCCACCTTATCATAAGCAGTTGGTACCGTCAT  14160

14161  AAGTACAGTGCTTCACGCACGCTGGTACAGGGCCACGTGCACAAGCACACAGGTGCACAC  14220

14221  ACACACTGCTATCCTCCATCCCATCCACCTGGGACTCGTCAGGCTGAAGTCTCTTCTCCC  14280

14281  ACTCTCACTCCTTGGGCTGTCTTCAGGGCACATGTAACTTGGGGAATGAGAAATTAGCAT  14340

14341  CCACCTGGAGCCACTGAAGCCATCCCTCTTCACCATAGTTGCTCACCTCTCTTTTGACAG  14400

14401  AAAGTCGTGAGGCACTGAATGGCCCAACCAGGCCCTCAGTACCTCTGGGAGCCATCTGCA  14460

14461  AGAGTCCCTGTGTAGCGCCAAGAGCCGGAGCCTGGGCTTCAGG  14503
```

FIG. 8

Association between Renin SNP3 and PPAR alpha/gamma
agonist-induced edema

Crosstab

|  |  |  | Edema status | | Total |
|---|---|---|---|---|---|
|  |  |  | No edema at Dose E in 006 & 008 | Edema from all treated groups |  |
| Renin SNP3 | G/G | Count | 52 | 87 | 139 |
|  |  | % within Edema status | 44.4% | 56.9% | 51.5% |
|  | G/A | Count | 50 | 59 | 109 |
|  |  | % within Edema status | 42.7% | 38.6% | 40.4% |
|  | A/A | Count | 15 | 7 | 22 |
|  |  | % within Edema status | 12.8% | 4.6% | 8.1% |
| Total |  | Count | 117 | 153 | 270 |
|  |  | % within Edema status | 100.0% | 100.0% | 100.0% |

Multivariate P value = 0.003 with age, race, body mass index, trial, sex and SNP as predictors.

Odds ratio G/A vs. G/G = 0.72 (95% confidence interval 0.37-1.41)
Odds ratio A/A vs. G/G = 0.12 (95% confidence interval 0.04-0.41)

FIG. 9

Association between Renin SNP5 and PPAR alpha/gamma agonist-induced edema

Crosstab

|  |  |  | Edema status | | Total |
|---|---|---|---|---|---|
|  |  |  | No edema at Dose E in 006 & 008 | Edema from all treated groups | |
| Renin SNP3 | A/A | Count | 62 | 104 | 166 |
|  |  | % within Edema status | 53.0% | 68.0% | 61.5% |
|  | A/G | Count | 49 | 45 | 94 |
|  |  | % within Edema status | 41.9% | 29.4% | 34.8% |
|  | G/G | Count | 6 | 4 | 10 |
|  |  | % within Edema status | 5.1% | 2.6% | 3.7% |
| Total |  | Count | 117 | 153 | 270 |
|  |  | % within Edema status | 100.0% | 100.0% | 100.0% |

Multivariate P value = 0.01 with age, race, body mass index, trial, sex and SNP as predictors.

Odds ratio A/G vs. A/A = 0.51 (95% confidence interval 0.26-0.91)
Odds ratio G/G vs. A/A = 0.13 (95% confidence interval 0.03-0.63)

FIG. 10

Association between Renin SNP7 and PPAR alpha/gamma agonist-induced edema

Crosstab

|  |  |  | Edema status | | Total |
|---|---|---|---|---|---|
|  |  |  | No edema at Dose E in 006 & 008 | Edema from all treated groups |  |
| Renin SNP3 | G/G | Count | 62 | 104 | 169 |
|  |  | % within Edema status | 53.0% | 70.4% | 62.8% |
|  | G/dG | Count | 49 | 41 | 90 |
|  |  | % within Edema status | 41.9% | 27.0% | 33.5% |
|  | d G/dG | Count | 6 | 4 | 10 |
|  |  | % within Edema status | 5.1% | 2.6% | 3.7% |
| Total |  | Count | 117 | 152 | 269 |
|  |  | % within Edema status | 100.0% | 100.0% | 100.0% |

Multivariate P value = 0.004 with age, race, body mass index, trial, sex and SNP as predictors.

Odds ratio G/delG vs. A/A = 0.42 (95% confidence interval 0.21-0.83)
Odds ratio delG/delG vs. G/G = 0.12 (95% confidence interval 0.02-0.60)

FIG. 12A

Quantitative real-time PCR analysis of renin induction by PPAR agonists.

| Treatment | Fold Change (mean ± SEM) n=6 | p-value |
|---|---|---|
| 0.76 µM Compound A | 5.06±0.30 | 3.59E-10 |
| 0.021 µM Compound B | 4.96±0.47 | 2.15E-09 |
| 1 µM Compound C | 6.17±0.68 | 2.28E-09 |
| 0.005 µM Compound D | 4.84±0.50 | 1.08E-08 |
| 0.4 µM Compound E | 4.36±0.36 | 3.44E-09 |
| 1.7 µM Compound F | 6.92±0.84 | 1.17E-09 |

FIG. 12B

Microarray analysis of renin induction by PPAR agonists.

| | Compound A | | Compound B | | Compound E | |
|---|---|---|---|---|---|---|
| Gene | Fold-Change (mean±SEM) n=3 | p-value | Fold-Change (mean±SEM) n=3 | p-value | Fold-Change (mean±SEM) n=3 | p-value |
| RENIN | 3.08±0.33 | 0.004 | 3.29±0.46 | 0.008 | 2.98±0.73 | 0.056 |

FIG. 13A

```
  1 CGCCGCGTGCGCCTGCAGACGCTCCGCTCGCTGCCTTCTCTCCTGGCAGGCGCTGCCTTT   60

61 TCTCCCCGTTAAAGGGCACTTGGGCTGAAGGATCGCTTTGAGATCTGAGGAACCCGCAGC  120

121 GCTTTGAGGGACCTGAAGCTGTTTTTCTTCGTTTTCCTTTGGGTTCAGTTTGAACGGGAG  180

181 GTTTTTGATCCCTTTTTTTCAGAATGGATTATTTGCTCATGATTTTCTCTCTGCTGTTTG  240
  1                           M  D  Y  L  L  M  I  F  S  L  L  F  V   13

241 TGGCTTGCCAAGGAGCTCCAGAAACAGCAGTCTTAGGCGCTGAGCTCAGCGCGGTGGGTG  300
 14  A  C  Q  G  A  P  E  T  A  V  L  G  A  E  L  S  A  V  G  E   33

301 AGAACGGCGGGGAGAAACCCACTCCCAGTCCACCCTGGCGGCTCCGCCGGTCCAAGCGCT  360
 34  N  G  G  E  K  P  T  P  S  P  P  W  R  L  R  R  S  K  R  C   53

361 GCTCCTGCTCGTCCCTGATGGATAAAGAGTGTGTCTACTTCTGCCACCTGGACATCATTT  420
 54  S  C  S  S  L  M  D  K  E  C  V  Y  F  C  H  L  D  I  I  W   73

421 GGGTCAACACTCCCGAGCACGTTGTTCCGTATGGACTTGGAAGCCCTAGGTCCAAGAGAG  480
 74  V  N  T  P  E  H  V  V  P  Y  G  L  G  S  P  R  S  K  R  A   93

481 CCTTGGAGAATTTACTTCCCACAAAGGCAACAGACCGTGAGAATAGATGCCAATGTGCTA  540
 94  L  E  N  L  L  P  T  K  A  T  D  R  E  N  R  C  Q  C  A  S  113

541 GCCAAAAAGACAAGAAGTGCTGGAATTTTTGCCAAGCAGGAAAAGAACTCAGGGCTGAAG  600
114  Q  K  D  K  K  C  W  N  F  C  Q  A  G  K  E  L  R  A  E  D  133

601 ACATTATGGAGAAAGACTGGAATAATCATAAGAAAGGAAAAGACTGTTCCAAGCTTGGGA  660
134  I  M  E  K  D  W  N  N  H  K  K  G  K  D  C  S  K  L  G  K  153

661 AAAAGTGTATTTATCAGCAGTTAGTGAGAGGAAGAAAAATCAGAAGAAGTTCAGAGGAAC  720
154  K  C  I  Y  Q  Q  L  V  R  G  R  K  I  R  R  S  S  E  E  H  173

721 ACCTAAGACAAACCAGGTCGGAGACCATGAGAAACAGCGTCAAATCATCTTTTCATGATC  780
174  L  R  Q  T  R  S  E  T  M  R  N  S  V  K  S  S  F  H  D  P  193

781 CCAAGCTGAAAGGCAAGCCCTCCAGAGAGCGTTATGTGACCCACAACCGAGCACATTGGT  840
194  K  L  K  G  K  P  S  R  E  R  Y  V  T  H  N  R  A  H  W     212

841 GACAGACCTTCGGGGCCTGTCTGAAGCCATAGCCTCCACGGAGAGCCCTGTGGCCGACTC  900

901 TGCACTCTCCACCCTGGCTGGGATCAGAGCAGGAGCATCCTCTGCTGGTTCCTGACTGGC  960
```

FIG. 13B

```
 961  AAAGGACCAGCGTCCTCGTTCAAAACATTCCAAGAAAGGTTAAGGAGTTCCCCCAACCAT  1020

1021  CTTCACTGGCTTCCATCAGTGGTAACTGCTTTGGTCTCTTCTTTCATCTGGGGATGACAA  1080

1081  TGGACCTCTCAGCAGAAACACACAGTCACATTCGAATTCGGGTGGCATCCTCCGGAGAGA  1140

1141  GAGAGAGGAAGGAGATTCCACACAGGGGTGGAGTTTCTGACGAAGGTCCTAAGGGAGTGT  1200

1201  TTGTGTCTGACTCAGGCGCCTGGCACATTTCAGGGAGAAACTCCAAAGTCCACACAAAGA  1260

1261  TTTTCTAAGGAATGCACAAATTGAAAACACACTCAAAAGACAAACATGCAAGTAAAGAAA  1320

1321  AAAAAAAAAAAAAA  1334
```

FIG. 14A

```
  1  CGCCGCGTGCGCCTGCAGACGCTCCGCTCGCTGCCTTCTCTCCTGGCAGGCGCTGCCTTT    60

61  TCTCCCCGTTAAAGGGCACTTGGGCTGAAGGATCGCTTTGAGATCTGAGGAACCCGCAGC   120

121  GCTTTGAGGGACCTGAAGCTGTTTTTCTTCGTTTTCCTTTGGGTTCAGTTTGAACGGGAG   180

181  GTTTTTGATCCCTTTTTTTCAGAATGGATTATTTGCTCATGATTTTCTCTCTGCTGTTTG   240
  1                          M   D   Y   L   L   M   I   F   S   L   L   F   V    13

241  TGGCTTGCCAAGGAGCTCCAGAAACAGCAGTCTTAGGCGCTGAGCTCAGCGCGGTGGGTG   300
 14    A   C   Q   G   A   P   E   T   A   V   L   G   A   E   L   S   A   V   G   E    33

301  AGAACGGCGGGGAGAAACCCACTCCCAGTCCACCCTGGCGGCTCCGCCGGTCCAAGCGCT   360
 34    N   G   G   E   K   P   T   P   S   P   P   W   R   L   R   R   S   K   R   C    53

361  GCTCCTGCTCGTCCCTGATGGATAAAGAGTGTGTCTACTTCTGCCACCTGGACATCATTT   420
 54    S   C   S   S   L   M   D   K   E   C   V   Y   F   C   H   L   D   I   I   W    73

421  GGGTCAACACTCCCGAGCACGTTGTTCCGTATGGACTTGGAAGCCCTAGGTCCAAGAGAG   480
 74    V   N   T   P   E   H   V   V   P   Y   G   L   G   S   P   R   S   K   R   A    93

481  CCTTGGAGAATTTACTTCCCACAAAGGCAACAGACCGTGAGAATAGATGCCAATGTGCTA   540
 94    L   E   N   L   L   P   T   K   A   T   D   R   E   N   R   C   Q   C   A   S   113

541  GCCAAAAAGACAAGAAGTGCTGGAATTTTTGCCAAGCAGGAAAAGAACTCAGGGCTGAAG   600
114    Q   K   D   K   K   C   W   N   F   C   Q   A   G   K   E   L   R   A   E   D   133

601  ACATTATGGAGAAAGACTGGAATAATCATAAGAAAGGAAAAGACTGTTCCAAGCTTGGGA   660
134    I   M   E   K   D   W   N   N   H   K   K   G   K   D   C   S   K   L   G   K   153

661  AAAAGTGTATTTATCAGCAGTTAGTGAGAGGAAGAAAAATCAGAAGAAGTTCAGAGGAAC   720
154    K   C   I   Y   Q   Q   L   V   R   G   R   K   I   R   R   S   S   E   E   H   173

721  ACCTAAGACAAACCAGGTCGGAGACCATGAGAAACAGCGTCAAATCATCTTTTCATGATC   780
174    L   R   Q   T   R   S   E   T   M   R   N   S   V   K   S   S   F   H   D   P   193

781  CCAAGCTGAAAGGCAATCCCTCCAGAGAGCGTTATGTGACCCACAACCGAGCACATTGGT   840
194    K   L   K   G   N   P   S   R   E   R   Y   V   T   H   N   R   A   H   W   212

841  GACAGACCTTCGGGGCCTGTCTGAAGCCATAGCCTCCACGGAGAGCCCTGTGGCCGACTC   900

901  TGCACTCTCCACCCTGGCTGGGATCAGAGCAGGAGCATCCTCTGCTGGTTCCTGACTGGC   960
```

FIG. 14B

```
 961  AAAGGACCAGCGTCCTCGTTCAAAACATTCCAAGAAAGGTTAAGGAGTTCCCCCAACCAT  1020

1021  CTTCACTGGCTTCCATCAGTGGTAACTGCTTTGGTCTCTTCTTTCATCTGGGGATGACAA  1080

1081  TGGACCTCTCAGCAGAAACACACAGTCACATTCGAATTCGGGTGGCATCCTCCGGAGAGA  1140

1141  GAGAGAGGAAGGAGATTCCACACAGGGGTGGAGTTTCTGACGAAGGTCCTAAGGGAGTGT  1200

1201  TTGTGTCTGACTCAGGCGCCTGGCACATTTCAGGGAGAAACTCCAAAGTCCACACAAAGA  1260

1261  TTTTCTAAGGAATGCACAAATTGAAAACACACTCAAAAGACAAACATGCAAGTAAAGAAA  1320

1321  AAAAAAAAAAAAAA  1334
```

FIG. 15

Association between Endothelin SNP1 and PPAR alpha/gamma agonist-induced edema

|  |  |  | Edema status | | Total |
|---|---|---|---|---|---|
|  |  |  | No edema 20 mg 006 & 008 | Edema from all treated groups |  |
| EDN1SNP1 | K/K | Count | 68 | 104 | 172 |
|  |  | % within Edema status | 58.1% | 68.0% | 63.7% |
|  | K/N | Count | 44 | 48 | 92 |
|  |  | % within Edema status | 37.6% | 31.4% | 34.1% |
|  | N/N | Count | 5 | 1 | 6 |
|  |  | % within Edema status | 4.3% | 7% | 2.2% |
| Total |  | Count | 117 | 153 | 270 |
|  |  | % within Edema status | 100.0% | 100.0% | 100.0% |

Multivariate P value = 0.028 with age, race, body mass index, trial, sex and SNP as predictors.

Odds ratio K/N vs. K/K = 0.70 (95% confidence interval 0.36-1.28)
Odds ratio N/N vs. K/K = 0.04 (95% confidence interval 0.004-0.51)

FIG. 17

Quantitative real-time PCR analysis of endothelin induction by PPAR agonists

| Treatment | Fold Change (mean ± SEM) n=6 | p-value |
|---|---|---|
| 0.76 µM Compound A | -3.91 ± 0.25 | 3.62E-11 |
| 0.021 µM Compound B | -4.12 ± 0.21 | 9.10E-12 |
| 1 µM Compound C* | -5.03 ± 0.99* | 4.80E-09 |
| 0.005 µM Compound D* | -4.17 ± 0.38* | 2.50E-10 |
| 0.4 µM Compound E | -3.88 ± 0.17 | 1.19E-11 |
| 1.7 µM Compound F | -3.08 ± 0.47 | 2.76E-06 |

*n=5 for these experiments

FIG. 18A

```
  1 TGCTACCCGCGCCCGGGCTTCTGGGGTGTTCCCCAACCACGGCCCAGCCCTGCCACACCC    60

61 CCCGCCCCCGGCCTCCGCAGCTCGGCATGGGCGCGGGGGTGCTCGTCCTGGGCGCCTCCG   120
  1                           M  G  A  G  V  L  V  L  G  A  S  E    12

121 AGCCCGGTAACCTGTCGTCGGCCGCACCGCTCCCCGACGGCGCGGCCACCGCGGCGCGGC   180
 13  P  G  N  L  S  S  A  A  P  L  P  D  G  A  A  T  A  A  R  L    32

181 TGCTGGTGCCCGCGTCGCCGCCCGCCTCGTTGCTGCCTCCCGCCAGCGAAAGCCCCGAGC   240
 33  L  V  P  A  S  P  P  A  S  L  L  P  P  A  S  E  S  P  E  P    52

241 CGCTGTCTCAGCAGTGGACAGCGGGCATGGGTCTGCTGATGGCGCTCATCGTGCTGCTCA   300
 53  L  S  Q  Q  W  T  A  G  M  G  L  L  M  A  L  I  V  L  L  I    72

301 TCGTGGCGGGCAATGTGCTGGTGATCGTGGCCATCGCCAAGACGCCGCGGCTGCAGACGC   360
 73  V  A  G  N  V  L  V  I  V  A  I  A  K  T  P  R  L  Q  T  L    92

361 TCACCAACCTCTTCATCATGTCCCTGGCCAGCGCCGACCTGGTCATGGGGCTGCTGGTGG   420
 93  T  N  L  F  I  M  S  L  A  S  A  D  L  V  M  G  L  L  V  V   112

421 TGCCGTTCGGGGCCACCATCGTGGTGTGGGGCCGCTGGGAGTACGGCTCCTTCTTCTGCG   480
113  P  F  G  A  T  I  V  V  W  G  R  W  E  Y  G  S  F  F  C  E   132

481 AGCTGTGGACCTCAGTGGACGTGCTGTGCGTGACGGCCAGCATCGAGACCCTGTGTGTCA   540
133  L  W  T  S  V  D  V  L  C  V  T  A  S  I  E  T  L  C  V  I   152

541 TTGCCCTGGACCGCTACCTCGCCATCACCTCGCCCTTCCGCTACCAGAGCCTGCTGACGC   600
153  A  L  D  R  Y  L  A  I  T  S  P  F  R  Y  Q  S  L  L  T  R   172

601 GCGCGCGGGCGCGGGGCCTCGTGTGCACCGTGTGGGCCATCTCGGCCCTGGTGTCCTTCC   660
173  A  R  A  R  G  L  V  C  T  V  W  A  I  S  A  L  V  S  F  L   192

661 TGCCCATCCTCATGCACTGGTGGCGGGCGGAGAGCGACGAGGCGCGCCGCTGCTACAACG   720
193  P  I  L  M  H  W  W  R  A  E  S  D  E  A  R  R  C  Y  N  D   212

721 ACCCCAAGTGCTGCGACTTCGTCACCAACCGGGCCTACGCCATCGCCTCGTCCGTAGTCT   780
213  P  K  C  C  D  F  V  T  N  R  A  Y  A  I  A  S  S  V  V  .S  232

781 CCTTCTACGTGCCCCTGTGCATCATGGCCTTCGTGTACCTGCGGGTGTTCCGCGAGGCCC   840
233  F  Y  V  P  L  C  I  M  A  F  V  Y  L  R  V  F  R  E  A  Q   252

841 AGAAGCAGGTGAAGAAGATCGACAGCTGCGAGCGCCGTTTCCTCGGCGGCCCAGCGCGGC   900
253  K  Q  V  K  K  I  D  S  C  E  R  R  F  L  G  G  P  A  R  P   272
```

FIG. 18B

```
 901  CGCCCTCGCCCTCGCCCTCGCCCGTCCCCGCGCCCGCGCCGCCGCCCGGACCCCCGCGCC   960
 273    P  S  P  S  P  S  P  V  P  A  P  A  P  P  P  G  P  P  R  P    292

961  CCGCCGCCGCCGCCGCCACCGCCCCGCTGGCCAACGGGCGTGCGGGTAAGCGGCGGCCCT  1020
 293    A  A  A  A  T  A  P  L  A  N  G  R  A  G  K  R  R  P  S       312

1021  CGCGCCTCGTGGCCCTACGCGAGCAGAAGGCGCTCAAGACGCTGGGCATCATCATGGGCG  1080
 313    R  L  V  A  L  R  E  Q  K  A  L  K  T  L  G  I  I  M  G  V    332

1081  TCTTCACGCTCTGCTGGCTGCCCTTCTTCCTGGCCAACGTGGTGAAGGCCTTCCACCGCG  1140
 333    F  T  L  C  W  L  P  F  F  L  A  N  V  V  K  A  F  H  R  E    352

1141  AGCTGGTGCCCGACCGCCTCTTCGTCTTCTTCAACTGGCTGGGCTACGCCAACTCGGCCT  1200
 353    L  V  P  D  R  L  F  V  F  F  N  W  L  G  Y  A  N  S  A  F    372

1201  TCAACCCCATCATCTACTGCCGCAGCCCCGACTTCCGCAAGGCCTTCCAGCGACTGCTCT  1260
 373    N  P  I  I  Y  C  R  S  P  D  F  R  K  A  F  Q  R  L  L  C    392

1261  GCTGCGCGCGCAGGGCTGCCCGCCGGCGCCACGCGACCCACGGAGACCGGCCGCGCGCCT  1320
 393    C  A  R  R  A  A  R  R  R  H  A  T  H  G  D  R  P  R  A  S    412

1321  CGGGCTGTCTGGCCCGGCCCGGACCCCCGCCATCGCCCGGGGCCGCCTCGGACGACGACG  1380
 413    G  C  L  A  R  P  G  P  P  P  S  P  G  A  A  S  D  D  D  D    432

1381  ACGACGATGTCGTCGGGGCCACGCCGCCCGCGCGCCTGCTGGAGCCCTGGGCCGGCTGCA  1440
 433    D  D  V  V  G  A  T  P  P  A  R  L  L  E  P  W  A  G  C  N    452

1441  ACGGCGGGGCGGCGGCGGACAGCGACTCGAGCCTGGACGAGCCGTGCCGCCCCGGCTTCG  1500
 453    G  G  A  A  A  D  S  D  S  S  L  D  E  P  C  R  P  G  F  A    472

1501  CCTCGGAATCCAAGGTGTAGGGCCCGGCGCGGGGCGCGGACTCCGGGCACGGCTTCCCAG  1560
 473    S  E  S  K  V                                                  477

1561  GGGAACGAGGAGATCTGTGTTTACTTAAGACCGATAGCAGGTGAACTCGAAGCCCACAAT  1620

1621  CCTCGTCTGAATCATCCGAGGCAAAGAGAAAAGCCACGGACCGTTGCACAAAAAGGAAAG  1680

1681  TTTGGGAAGGGATGGGAGAGTGGCTTGCTGATGTTCCTTGTTG  1723
```

FIG. 19A

```
  1  TGCTACCCGCGCCCGGGCTTCTGGGGTGTTCCCCAACCACGGCCCAGCCCTGCCACACCC   60

61  CCCGCCCCCGGCCTCCGCAGCTCGGCATGGGCGCGGGGGTGCTCGTCCTGGGCGCCTCCG  120
  1                                  M  G  A  G  V  L  V  L  G  A  S  E   12

121  AGCCCGGTAACCTGTCGTCGGCCGCACCGCTCCCCGACGGCGCGGCCACCGCGGCGCGGC  180
 13   P  G  N  L  S  S  A  A  P  L  P  D  G  A  A  T  A  A  R  L   32

181  TGCTGGTGCCCGCGTCGCCGCCCGCCTCGTTGCTGCCTCCCGCCAGCGAAAGCCCCGAGC  240
 33   L  V  P  A  S  P  P  A  S  L  L  P  P  A  S  E  S  P  E  P   52

241  CGCTGTCTCAGCAGTGGACAGCGGGCATGGGTCTGCTGATGGCGCTCATCGTGCTGCTCA  300
 53   L  S  Q  Q  W  T  A  G  M  G  L  L  M  A  L  I  V  L  L  I   72

301  TCGTGGCGGGCAATGTGCTGGTGATCGTGGCCATCGCCAAGACGCCGCGGCTGCAGACGC  360
 73   V  A  G  N  V  L  V  I  V  A  I  A  K  T  P  R  L  Q  T  L   92

361  TCACCAACCTCTTCATCATGTCCCTGGCCAGCGCCGACCTGGTCATGGGGCTGCTGGTGG  420
 93   T  N  L  F  I  M  S  L  A  S  A  D  L  V  M  G  L  L  V  V  112

421  TGCCGTTCGGGGCCACCATCGTGGTGTGGGGCCGCTGGGAGTACGGCTCCTTCTTCTGCG  480
113   P  F  G  A  T  I  V  V  W  G  R  W  E  Y  G  S  F  F  C  E  132

481  AGCTGTGGACCTCAGTGGACGTGCTGTGCGTGACGGCCAGCATCGAGACCCTGTGTGTCA  540
133   L  W  T  S  V  D  V  L  C  V  T  A  S  I  E  T  L  C  V  I  152

541  TTGCCCTGGACCGCTACCTCGCCATCACCTCGCCCTTCCGCTACCAGAGCCTGCTGACGC  600
153   A  L  D  R  Y  L  A  I  T  S  P  F  R  Y  Q  S  L  L  T  R  172

601  GCGCGCGGGCGCGGGGCCTCGTGTGCACCGTGTGGGCCATCTCGGCCCTGGTGTCCTTCC  660
173   A  R  A  R  G  L  V  C  T  V  W  A  I  S  A  L  V  S  F  L  192

661  TGCCCATCCTCATGCACTGGTGGCGGGCGGAGAGCGACGAGGCGCGCCGCTGCTACAACG  720
193   P  I  L  M  H  W  W  R  A  E  S  D  E  A  R  R  C  Y  N  D  212

721  ACCCCAAGTGCTGCGACTTCGTCACCAACCGGGCCTACGCCATCGCCTCGTCCGTAGTCT  780
213   P  K  C  C  D  F  V  T  N  R  A  Y  A  I  A  S  S  V  V  S  232

781  CCTTCTACGTGCCCCTGTGCATCATGGCCTTCGTGTACCTGCGGGTGTTCCGCGAGGCCC  840
233   F  Y  V  P  L  C  I  M  A  F  V  Y  L  R  V  F  R  E  A  Q  252

841  AGAAGCAGGTGAAGAAGATCGACAGCTGCGAGCGCCGTTTCCTCGGCGGCCCAGCGCGGC  900
253   K  Q  V  K  K  I  D  S  C  E  R  R  F  L  G  G  P  A  R  P  272
```

FIG. 19B

```
 901  CGCCCTCGCCCTCGCCCTCGCCCGTCCCCGCGCCCGCGCCGCCGCCCGGACCCCCGCGCC   960
 273    P  S  P  S  P  S  P  V  P  A  P  A  P  P  P  G  P  P  R  P     292

961  CCGCCGCCGCCGCCACCGCCCCGCTGGCCAACGGGCGTGCGGGTAAGCGGCGGCCCT      1020
 293    A  A  A  A  A  T  A  P  L  A  N  G  R  A  G  K  R  R  P  S     312

1021  CGCGCCTCGTGGCCCTACGCGAGCAGAAGGCGCTCAAGACGCTGGGCATCATCATGGGCG   1080
 313    R  L  V  A  L  R  E  Q  K  A  L  K  T  L  G  I  I  M  G  V     332

1081  TCTTCACGCTCTGCTGGCTGCCCTTCTTCCTGGCCAACGTGGTGAAGGCCTTCCACCGCG   1140
 333    F  T  L  C  W  L  P  F  F  L  A  N  V  V  K  A  F  H  R  E     352

1141  AGCTGGTGCCCGACCGCCTCTTCGTCTTCTTCAACTGGCTGGGCTACGCCAACTCGGCCT   1200
 353    L  V  P  D  R  L  F  V  F  F  N  W  L  G  Y  A  N  S  A  F     372

1201  TCAACCCCATCATCTACTGCCGCAGCCCCGACTTCCGCAAGGCCTTCCAGGGACTGCTCT   1260
 373    N  P  I  I  Y  C  R  S  P  D  F  R  K  A  F  Q  G  L  L  C     392

1261  GCTGCGCGCGCAGGGCTGCCCGCCGGCGCCACGCGACCCACGGAGACCGGCCGCGCGCCT   1320
 393    C  A  R  R  A  A  R  R  R  H  A  T  H  G  D  R  P  R  A  S     412

1321  CGGGCTGTCTGGCCCGGCCCGGACCCCCGCCATCGCCCGGGGCCGCCTCGGACGACGACG   1380
 413    G  C  L  A  R  P  G  P  P  P  S  P  G  A  A  S  D  D  D  D     432

1381  ACGACGATGTCGTCGGGGCCACGCCGCCCGCGCGCCTGCTGGAGCCCTGGGCCGGCTGCA   1440
 433    D  D  V  V  G  A  T  P  P  A  R  L  L  E  P  W  A  G  C  N     452

1441  ACGGCGGGGCGGCGGCGGACAGCGACTCGAGCCTGGACGAGCCGTGCCGCCCCGGCTTCG   1500
 453    G  G  A  A  A  D  S  D  S  S  L  D  E  P  C  R  P  G  F  A     472

1501  CCTCGGAATCCAAGGTGTAGGGCCCGGCGCGGGGCGCGGACTCCGGGCACGGCTTCCCAG   1560
 473    S  E  S  K  V                                                  477

1561  GGGAACGAGGAGATCTGTGTTTACTTAAGACCGATAGCAGGTGAACTCGAAGCCCACAAT   1620

1621  CCTCGTCTGAATCATCCGAGGCAAAGAGAAAAGCCACGGACCGTTGCACAAAAAGGAAAG   1680

1681  TTTGGGAAGGGATGGGAGAGTGGCTTGCTGATGTTCCTTGTTG   1723
```

FIG. 20

Association between β1 adrenergic receptor Arg389Gly SNP (R389G)
and peripheral edema Crosstab

|  |  |  | Edema status | | Total |
|---|---|---|---|---|---|
|  |  |  | No edema 20 mg 006 & 008 | Edema from all treated groups |  |
| ADRB1R389G | R/R | Count | 69 | 66 | 135 |
|  |  | % within Edema status | 59.0% | 44.0% | 50.6% |
|  | R/G | Count | 41 | 65 | 106 |
|  |  | % within Edema status | 35.0% | 43.3% | 39.7% |
|  | G/G | Count | 7 | 19 | 26 |
|  |  | % within Edema status | 6.0% | 12.7% | 9.7% |
| Total |  | Count | 117 | 150 | 267 |
|  |  | % within Edema status | 100.0% | 100.0% | 100.0% |

Multivariate P value = 0.03 with age, race, body mass index, trial, sex and SNP as predictors.

Odds ratio R/G vs. R/R = 2.12(95% confidence interval 1.12-4.10)
Odds ratio G/G vs. R/R = 3.08 (95% confidence interval 0.90-10.6)

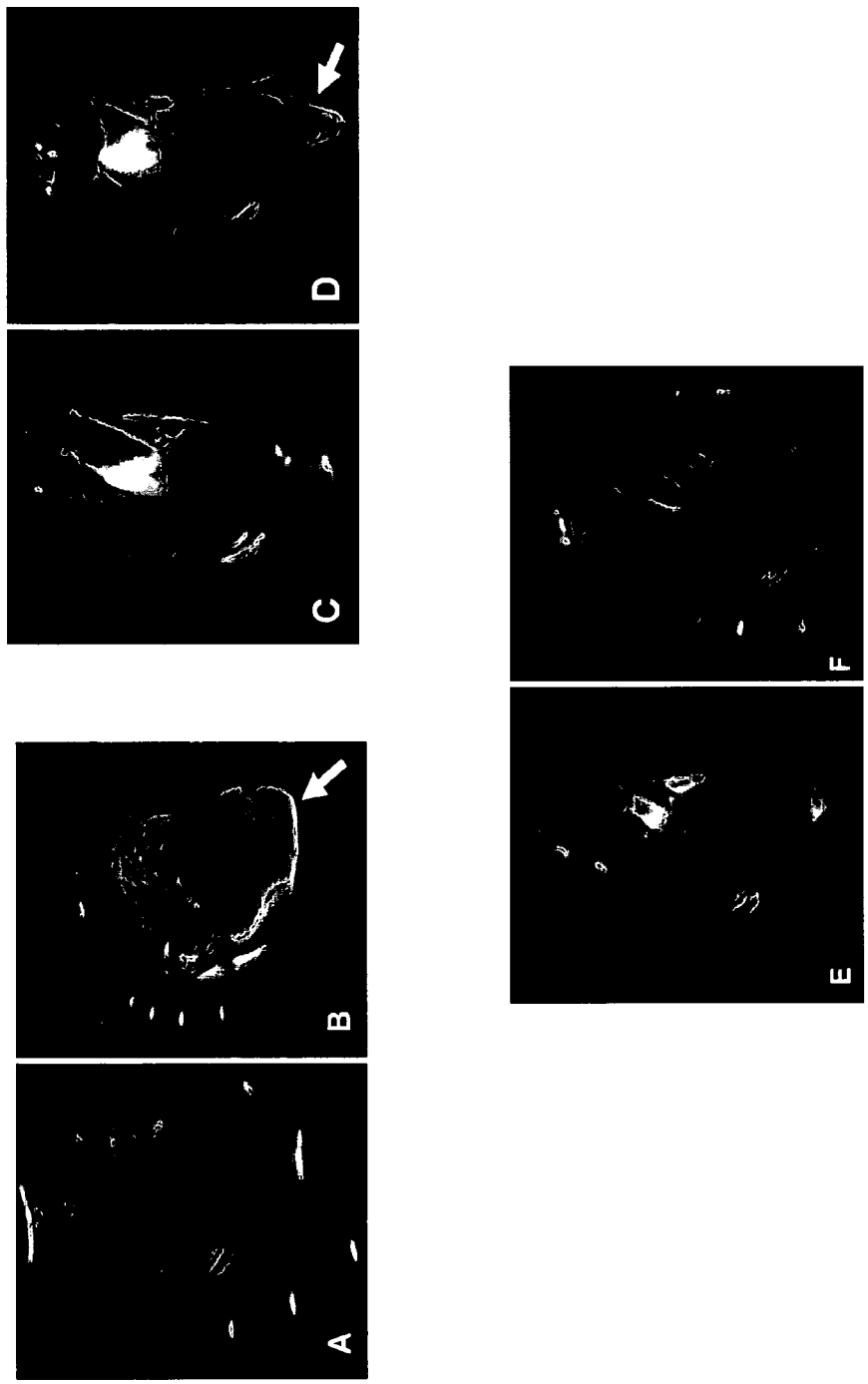
FIG. 22A-F

METHOD OF IDENTIFYING A PPARGAMMA-AGONIST COMPOUND HAVING A DECREASED LIKELIHOOD OF INDUCING DOSE-DEPENDENT PERIPHERAL EDEMA

This application claims benefit to provisional application U.S. Ser. No. 60/697,727 filed Jul. 8, 2005; to provisional application U.S. Ser. No. 60/706,171 filed Aug. 5, 2005; and to provisional application U.S. Ser. No. 60/705,995, filed Aug. 5, 2005; under 35 U.S.C. 119(e). The entire teachings of the referenced applications are incorporated herein by reference.

FIELD OF THE INVENTION

The invention provides novel polynucleotides and polypeptides associated with the incidence of PPAR-agonist induced edema. The invention also provides polynucleotide fragments corresponding to the genomic and/or coding regions of these polynucleotides which comprise at least one polymorphic locus per fragment. Allele-specific primers and probes which hybridize to these regions, and/or which comprise at least one polymorphic locus are also provided. The polynucleotides, primers, and probes of the present invention are useful in phenotype correlations, medicine, and genetic analysis. The invention further relates to diagnostic methods for using these novel polynucleotides in the diagnosis, treatment, and/or prevention of various PPAR-related diseases and/or disorders. The invention further relates to screening methods for identifying agonists of PPAR proteins with decreased risk of inducing peripheral edema in patients.

BACKGROUND OF THE INVENTION

The genomes of all organisms undergo spontaneous mutation in the course of their continuing evolution, generating variant forms of progenitor nucleic acid sequences (Gusella, Ann. Rev. Biochem., 55:831-854 (1986). The variant form may confer an evolutionary advantage or disadvantage relative to a progenitor form, or may be neutral. In some instances, a variant form confers a lethal disadvantage and is not transmitted to subsequent generations of the organism. In other instances, a variant form confers an evolutionary advantage to the species and is eventually incorporated into the DNA of many or most members of the species and effectively becomes the progenitor form. In many instances, both progenitor and variant form(s) survive and co-exist in a species population. The coexistence of multiple forms of a sequence gives rise to polymorphisms.

Several different types of polymorphism have been reported. A restriction fragment length polymorphism (RFLP) is a variation in DNA sequence that alters the length of a restriction fragment. The restriction fragment length polymorphism may create or delete a restriction site, thus changing the length of the restriction fragment. RFLPs have been widely used in human and animal genetic analyses. When a heritable trait can be linked to a particular RFLP, the presence of the RFLP in an individual can be used to predict the likelihood that the animal will also exhibit the trait.

Other polymorphisms take the form of short tandem repeats (STRs) that include tandem di-, tri- and tetra-nucleotide repeated motifs. These tandem repeats are also referred to as variable number tandem repeat (VNTR) polymorphisms. VNTRs have been used in identity and paternity analysis, and in a large number of genetic mapping studies.

Other polymorphisms take the form of single nucleotide variations between individuals of the same species. Such polymorphisms are far more frequent than RFLPs, STRs and VNTRs. Some single nucleotide polymorphisms (SNPs) occur in protein-coding nucleic acid sequences (coding sequence SNP (cSNP)), in which case, one of the polymorphic forms may give rise to the expression of a defective or otherwise variant protein and, potentially, a genetic disease. Examples of genes in which polymorphisms within coding sequences give rise to genetic disease include: globin (sickle cell anemia), apoE4 (Alzheimer's Disease), Factor V Leiden (thrombosis), and CFTR (cystic fibrosis). cSNPs can alter the codon sequence of the gene and therefore specify an alternative amino acid. Such changes are called "missense" when another amino acid is substituted, and "nonsense" when the alternative codon specifies a stop signal in protein translation. When the cSNP does not alter the amino acid specified the cSNP is called "silent".

Other single nucleotide polymorphisms occur in noncoding regions. Some of these polymorphisms may also result in defective protein expression (e.g., as a result of defective splicing). Other single nucleotide polymorphisms have no phenotypic effects. Single nucleotide polymorphisms can be used in the same manner as RFLPs and VNTRs, but offer several advantages.

Single nucleotide polymorphisms occur with greater frequency and are spaced more uniformly throughout the genome than other forms of polymorphism. The greater frequency and uniformity of single nucleotide polymorphisms means that there is a greater probability that such a polymorphism will be found in close proximity to a genetic locus of interest than would be the case for other polymorphisms. The different forms of characterized single nucleotide polymorphisms are often easier to distinguish than other types of polymorphism (e.g., by use of assays employing allele-specific hybridization probes or primers).

Only a small percentage of the total repository of polymorphisms in humans and other organisms has been identified. The limited number of polymorphisms identified to date is due to the large amount of work required for their detection by conventional methods. For example, a conventional approach to identifying polymorphisms might be to sequence the same stretch of DNA in a population of individuals by dideoxy sequencing. In this type of approach, the amount of work increases in proportion to both the length of sequence and the number of individuals in a population and becomes impractical for large stretches of DNA or large numbers of persons.

The renin-angiotensin-aldosterone system (RAAS) represents an endocrine system that plays a fundamental role in cardiovascular function by regulating extracellular fluid volume and sodium balance. Activation of RAAS is triggered with the release of renin from the kidney, resulting in proteolytic cleavage of angiotensinogen to angiotensin I (AT1). AT1 is converted to angiotensin II (AT2) by angiotensin-converting enzyme (ACE). Additional non-renin and non-ACE-dependent mechanisms also exist for the production of AT2 directly from angiotensinogen and from AT1. Binding of AT2 to the angiotensin II receptor type 1 (AT2R1) stimulates the production of the steroid hormone aldosterone which mediates its effects through the mineralocorticoid receptor (MLR), promoting renal sodium retention and potassium loss.

Dysregulation of RAAS is associated with a number of disease states including renal injury and most forms of hypertension. Modulation of RAAS has been achieved clinically with compounds that suppress AT2 and aldosterone production (e.g. ACE inhibitors, AT2R1 blockers) as well as compounds that suppress aldosterone action (e.g. MLR antagonists).

Thiazolidinediones (TZDs) are high affinity PPARγ ligands which induce the expression of genes involved in glucose homeostasis and insulin sensitivity. PPARγ is expressed primarily in adipose tissue, where much of its antidiabetic actions are believed to be manifested. However PPARγ plays a significant role in vascular tissues as well. Expression of PPARγ has been detected in endothelial cells as well as vascular smooth muscle cells. PPARγ also plays a role in macrophages where its induction results in anti-inflammatory responses via inhibition of iNOS, MMP9 and scavenger receptor A genes. PPARγ has also been shown to play significant anti-inflammatory roles in monocytes and in atherosclerotic plaques.

An observed, adverse event associated with PPARγ-agonist treatment is the development of dose-dependent peripheral edema. Although the underlying mechanism is currently unknown, PPAR-agonist induced edema is believed to arise through direct action on the kidney (Hollenberg N K, Am J Med 115(8A):111-115 (2003)). Several lines of evidence have implicated a role for PPARγ agonists in the modulation of RAAS. In vascular smooth muscle cells, treatment with PPARγ agonists was shown to antagonize the transcription of the AT2R1 receptor, resulting in both reduced AT2R1 mRNA and protein levels (Sugawara et al., Endocrinology 142:3125-3134 (2000); Takeda et al., Circulation 102:1834-1839 (2000)). Moreover, animal model studies have shown that treatment with TZDs, including pioglitazone and rosiglitazone, mitigated hypertension in AT2-infused rats, in part, via inhibition of AT2R1 and induction of angiotensin II receptor type 2 (Diep et al., Circulation 105:2296-2302 (2002)). As RAAS plays a fundamental role in fluid volume homeostasis, it is conceivable that modulation of other components of this system, by PPAR agonists, might contribute to agonist-induced edema mechanism of action.

The endothelins (ETs) constitute a family of three separate genes (ET-1, ET-2, ET-3) that encode tissue-specific precursor peptide products (Gianessi et al., 2001). All three ET isoforms are proteolytically processed to generate 21 amino acid vasoactive peptides. ET-1 is the predominant isoform that is secreted by vascular endothelial cells in response to endothelial cell activators such as thrombin, TNF-α and angiotensin II (Gianessi et al., 2001; Delerive et al., 1999).

Endothelin-1 (ET-1) plays a role in a number of biological processes including monocytic chemotaxis, induction of endothelial cell adhesion molecules as well as vascular tone maintenance (Gianessi et al., 2001; Delerive et al., 1999). ET-1 is the most potent vasoconstrictor known and, as such, plays a important role in blood pressure elevation in several animal models of hypertension (Schiffrin, 2001). ET-1 also participates in salt and water homeostasis via cross-talk with the Renin-Angiotensin-Aldosterone-System (RAAS) (Agapitov and Haynes (2002)

Elevated ET-1 secretion is associated with a number of clinical states including hypertension, atherosclerosis, heart failure and renal failure (Luscher and Barton, 2000). Hyperinsulinemia and/or insulin resistance is also associated with increased ET-1 secretion from vascular endothelial cells in vitro and in vivo (Satoh et al., 1999). ET-1 receptor antagonists possess hypotensive effects in animal models of hypertension (Luscher and Barton, 2000) and in patients with essential hypertension (Satoh et al., 1999). Taken together, these observations suggest that elevated ET-1 may play a role in type 2 diabetes-associated hypertension (Satoh et al., 1999).

Recent studies have shown that ET-1 secretion is suppressed by PPARα and -γ agonists in endothelial and vascular smooth muscle cells (Fukunaga et al., 2001; Delerive et al., 1999; Satoh et al., 1999). The underlying mechanism of action is through negative interference of PPARα and -γ with the Activator Protein-1 signaling pathway (Delerive et al., 1999), which regulates ET-1 transcriptional activity (Kawana et al., 1995). This inhibition may contribute to the hypotensive effect observed with PPAR-agonist treatment in diabetic patients (Satoh et al., 1999).

The roles described above for ET-1 in vascular tone maintenance, along with its involvement in numerous cardiovascular disease processes suggest ET-1 may potential be involved in PPAR-agonist induced edema mechanism of action.

Genetic polymorphisms in members of the renin-angiotensin-aldosterone system, in addition to other proteins described herein, may cause alterations in the level of renin or its related peptides, or may affect downstream signal transduction. Genetic polymorphisms in ET-1 may also cause alterations in the level of ET-1 or its related peptides, or may affect downstream signal transduction. Such polymorphisms may genetically predispose certain individuals to an increased risk of developing edema, particularly in response to PPAR-agonist induced therapy. Such polymorphisms are expected to show a significant difference in allele frequency between individuals treated with a high dose of a PPAR-agonist who do not exhibit edema and individuals treated with a PPAR-agonist who do exhibit edema. Genotypes of such polymorphisms can predict each individual's susceptibility to edema, and thus will be useful in identifying a group of high risk individuals that may be subject to modified PPAR-directed treatment regimens. Alternatively, the identification of such a group may preclude one or more individuals within said group from being administered an PPAR-directed agonist or antagonist.

Moreover, the present invention also provides, for the first time, strong supporting evidence that renin expression is specifically upregulated and endothelin-1 expression is specifically downregulated in response to PPAR-agonist treatment and thus serves as an effective predictive marker for PPAR-agonist efficacy in addition to aiding in the identification of individuals at risk of developing PPAR-agonist induced dose-dependent peripheral edema.

The β-adrenergic receptor family consists of three genes ($β_1$, $β_2$, $β_3$) that encode membrane-bound G-protein coupled receptors (Dzimiri et al., 1999). All three receptor subtypes respond to extracellular signals by increasing intracellular cAMP levels via G-protein dependent adenylyl cyclase activation. Increased cAMP levels activate cAMP-dependent protein kinase A (PKA), which, in turn, phosphorylates a variety of target proteins to elicit cellular responses (Castellano and Bohm, 1997; Dzimiri et al., 1999)

In cardiac tissue, β-adrenergic signaling enhances overall cardiac output by increasing heart rate and contractility in response to catecholamine-induced receptor stimulation. These effects are brought about by PKA-dependent phosphorylation of target genes that are essential for cardiac function including L-type calcium channels, phospholambin-a, troponin I and myosin binding protein C. (Lohse et al., 2003; Bengtsson et al., 2001; Dzimiri, 1999). Together, these target proteins mediate their effects through the regulation of calcium activity (e.g. availability and sensitivity) in cardiomyocytes. Although both $β_1$ and $β_2$ contribute to these cardiac effects, most of the functional effects are mediated through $β_1$ subtype (Lohse et al., 2003) $β_1$ also mediates other cellular responses relevant to cardiac function including transient relaxation of blood vessels (Chruscinski et al., 2001) and activation of RAAS by enhancing renin secretion in the kidneys (Dzimiri et al., 1999).

The roles described above for $\beta_1$-adrenergic receptor in regulating cardiac performance directly within cardiomyocytes as well as indirectly via actions on kidney function suggest that the $\beta_1$-adrenergic receptor may be associated with the mechanism of action of PPAR-agonist induced edema.

Genetic polymorphisms in the $\beta_1$-adrenergic receptor may cause alterations in the level of the $\beta_1$-adrenergic receptor or its related peptides, or may affect downstream signal transduction. Such polymorphisms may genetically predispose certain individuals to an increased risk of developing edema, particularly in response to PPAR-agonist induced therapy. Such polymorphisms are expected to show a significant difference in allele frequency between healthy individuals and edema subjects. Genotypes of such polymorphisms can predict each individual's susceptibility to edema, and thus will be useful in identifying a group of high risk individuals that may be subject to modified PPAR-directed treatment regimens. Alternatively, the identification of such a group may preclude one or more individuals within said group from being administered an PPAR-directed agonist or antagonist.

SUMMARY OF THE INVENTION

The invention relates to a nucleic acid molecule which comprises, or alternatively consists of, at least one single nucleotide polymorphism within the renin genomic sequence at a specific polymorphic locus. In a particular embodiment the invention relates to the variant allele of the renin gene or polynucleotide having at least one single nucleotide polymorphism, which variant allele differs from a reference allele by one nucleotide at the site(s) identified in FIGS. 1A-M, FIGS. 2A-M, FIGS. 3A-M, FIGS. 4A-M, FIGS. 5A-M, FIGS. 6A-M, and/or FIGS. 7A-M, or elsewhere herein. The complementary sequence of each of these nucleic acid molecules are also provided. The nucleic acid molecules can be comprised of DNA or RNA, can be double- or single-stranded, and may comprise fragments. Fragments can be, for example, about 5 to about 10, about 5 to about 15, about 10 to about 20, about 15 to about 25, about 10 to about 30, about 10 to about 50, or about 10 to about 100 bases long, and preferably comprise at least one polymorphic allele.

In another embodiment, the invention relates to the reference or wild type allele of the renin gene or polynucleotide having a polymorphic locus, in which said reference or wild type allele differs from a variant allele by one nucleotide at the polymorphic site(s) identified in FIGS. 1A-M, FIGS. 2A-M, FIGS. 3A-M, FIGS. 4A-M, FIGS. 5A-M, FIGS. 6A-M, and/or FIGS. 7A-M, or elsewhere herein. The complementary sequence of each of these nucleic acid molecules are also provided. The nucleic acid molecules can be comprised of DNA or RNA, can be double- or single-stranded, and may comprise fragments. Fragments can be, for example, about 5 to about 10, about 5 to about 15, about 10 to about 20, about 15 to about 25, about 10 to about 30, about 10 to about 50, or about 10 to about 100 bases long, and preferably comprise at least one polymorphic locus.

The invention further provides variant and reference allele-specific oligonucleotides that hybridize to a Renin-SNP3, Renin-SNP5, and/or Renin-SNP7 nucleic acid molecule comprising at least one polymorphic locus, in addition to the complement of said oligonucleotide. These oligonucleotides can be probes or primers.

The invention further provides oligonucleotides that may be used to amplify a portion of either the variant or reference sequences of Renin-SNP3, Renin-SNP5, and/or Renin-SNP7 comprising at least one polymorphic locus of the present invention, in addition to providing oligonucleotides that may be used to sequence said amplified sequence. The invention further provides a method of analyzing a nucleic acid from a DNA sample using said amplification and sequencing primers to assess whether said sample contains the reference or variant nucleotide (allele) at the polymorphic locus, comprising the steps of amplifying a sequence using appropriate oligonucleotide primers for amplifying across a polymorphic locus, and sequencing the resulting amplified product using appropriate sequencing primers to sequence said product to determine whether the variant or reference base is present at the polymorphic locus.

The invention further provides a method of analyzing a nucleic acid from patient sample(s) using said amplification and sequencing primers to assess whether said sample(s) contain the reference or variant nucleotide (allele) at the polymorphic locus of Renin-SNP3, Renin-SNP5, and/or Renin-SNP7 in an effort to identify populations at risk of developing dose-dependent peripheral edema upon administration of a PPAR-agonist, comprising the steps of amplifying a sequence using appropriate oligonucleotide primers for amplifying across a polymorphic locus, and sequencing the resulting amplified product using appropriate sequencing primers to sequence said product to determine whether the variant or reference nucleotide is present at the polymorphic locus.

The invention further provides oligonucleotides that may be used to genotype patient sample(s) to assess whether said sample(s) contain the reference or variant nucleotide (allele) of Renin-SNP3, Renin-SNP5, and/or Renin-SNP7 at the polymorphic site(s). The invention provide a method of using oligonucleotides that may be used to genotype a patient sample to assess whether said sample contains the reference or variant nucleotide (allele) at the polymorphic locus. An embodiment of the method comprises the steps of amplifying a sequence using appropriate oligonucleotide primers for amplifying across a polymorphic locus, and subjecting the product of said amplification to a genetic bit analysis (GBA) reaction.

The invention provides a method of using oligonucleotides that may be used to genotype patient sample(s) to identify individual(s) at risk of developing dose-dependent peripheral edema upon administration of a PPAR-agonist to assess whether said sample(s) contains the reference or variant nucleotide (allele) of Renin-SNP3, Renin-SNP5, and/or Renin-SNP7 at one or more polymorphic loci. An embodiment of the method comprises the steps of amplifying a sequence using appropriate oligonucleotide primers for amplifying across a polymorphic locus, and subjecting the product of said amplification to a genetic bit analysis (GBA) reaction, and optionally determining the statistical association between either the reference or variant allele at the polymorphic site(s) to the incidence of dose-dependent peripheral edema.

The invention provides a method of using oligonucleotides that may be used to genotype patient sample(s) to identify ethnic population(s) that may be at risk of developing dose-dependent peripheral edema upon administration of a PPAR-agonist to assess whether said sample(s) contains the reference or variant nucleotide (allele) of Renin-SNP3, Renin-SNP5, and/or Renin-SNP7 at one or more polymorphic loci comprising the steps of amplifying a sequence using appropriate oligonucleotide primers for amplifying across a polymorphic locus, and subjecting the product of said amplification to a genetic bit analysis (GBA) reaction, and optionally determining the statistical association between either the reference or variant allele at the polymorphic site(s) to the incidence of dose-dependent peripheral edema.

The invention further provides a method of analyzing a nucleic acid from one or more individuals. The method allows the determination of whether the reference or variant base is present at any one, or more, of the polymorphic sites identified FIGS. 1A-M, FIGS. 2A-M, FIGS. 3A-M, FIGS. 4A-M, FIGS. 5A-M, FIGS. 6A-M, and/or FIGS. 7A-M, or elsewhere herein. Optionally, a set of nucleotides occupying a set of the polymorphic loci shown in FIGS. 1A-M, FIGS. 2A-M, FIGS. 3A-M, FIGS. 4A-M, FIGS. 5A-M, FIGS. 6A-M, and/or FIGS. 7A-M, or elsewhere herein, is determined. This type of analysis can be performed on a number of individuals, who are also tested (previously, concurrently or subsequently) for the presence of a dose-dependent edema phenotype or related disorder. The presence or absence of a dose-dependent edema disease phenotype is then correlated with said nucleotide or set of nucleotides present at the polymorphic locus or loci in the individuals tested.

The invention further relates to a method of predicting the presence, absence, likelihood of the presence or absence, or severity of a dose-dependent peripheral edema or related disorder associated with a particular genotype. The method comprises obtaining a nucleic acid sample from an individual and determining the identity of one or more nucleotides at specific polymorphic loci of Renin-SNP3, Renin-SNP5, and/or Renin-SNP7 nucleic acid molecules described herein, wherein the presence of a particular base at that site is correlated with the incidence of dose-dependent peripheral edema or related disorder, thereby predicting the presence, absence, likelihood of the presence or absence, or severity, of the dose-dependent peripheral edema phenotype or related disorder in the individual.

The invention further relates to polynucleotides having one or more polymorphic loci comprising one or more variant alleles of Renin-SNP3, Renin-SNP5, and/or Renin-SNP7. The invention also relates to said polynucleotides lacking a start codon. The invention further relates to polynucleotides of the present invention containing one or more variant alleles wherein said polynucleotides encode a polypeptide of the present invention. The invention relates to polypeptides of the present invention containing one or more variant amino acids encoded by one or more variant alleles.

The present invention relates to antisense oligonucleotides capable of hybridizing to the Renin-SNP3, Renin-SNP5, and/or Renin-SNP7 polynucleotides of the present invention. Preferably, such antisense oligonucleotides are capable of discriminating between the reference or variant allele of the polynucleotide, preferably at one or more polymorphic sites of said polynucleotide.

The present invention relates to siRNA or RNAi oligonucleotides capable of hybridizing to the Renin-SNP3, Renin-SNP5, and/or Renin-SNP7 polynucleotides of the present invention. Preferably, such siRNA or RNAi oligonucleotides are capable of discriminating between the reference or variant allele of the polynucleotide, preferably at one or more polymorphic sites of said polynucleotide.

The present invention also relates to zinc finger proteins capable of binding to the Renin-SNP3, Renin-SNP5, and/or Renin-SNP7 polynucleotides of the present invention. Preferably, such zinc finger proteins are capable of discriminating between the reference or variant allele of the polynucleotide, preferably at one or more polymorphic sites of said polynucleotide.

The present invention also relates to recombinant vectors, which include the isolated Renin-SNP3, Renin-SNP5, and/or Renin-SNP7 nucleic acid molecules of the present invention, and to host cells containing the recombinant vectors, as well as to methods of making such vectors and host cells, in addition to their use in the production of polypeptides or peptides provided herein using recombinant techniques. Synthetic methods for producing the polypeptides and polynucleotides of the present invention are provided. Also provided are diagnostic methods for detecting diseases, disorders, and/or conditions related to the polypeptides and polynucleotides provided herein, and therapeutic methods for treating such diseases, disorders, and/or conditions. The invention further relates to screening methods for identifying binding partners of the polypeptides.

The invention relates to a method of analyzing at least one nucleic acid sample, comprising the step of determining the nucleic acid sequence from one or more samples at one or more polymorphic loci in the human renin gene selected from the group consisting of Renin-SNP3, Renin-SNP5, and/or Renin-SNP7, or any combination thereof, wherein the presence of the reference allele at said one or more polymorphic loci is indicative of an increased risk of developing dose-dependent peripheral edema in a patient receiving PPAR-agonist therapy.

The invention relates to a method of analyzing at least one nucleic acid sample, comprising the step of determining the nucleic acid sequence from one or more samples at one or more polymorphic loci in the human renin gene selected from the group consisting of Renin-SNP3, Renin-SNP5, and/or Renin-SNP7, or any combination thereof, wherein the presence of the variant allele at said one or more polymorphic loci is indicative of a decreased risk of developing dose-dependent peripheral edema in a patient receiving PPAR-agonist therapy.

The invention further relates to a method of constructing haplotypes using the isolated nucleic acids referred to in FIGS. 1A-M, FIGS. 2A-M, FIGS. 3A-M, FIGS. 4A-M, FIGS. 5A-M, FIGS. 6A-M, FIGS. 7A-M, FIGS. 13A-B, FIGS. 14A-B, FIGS. 18A-B, and/or FIGS. 19A-B or elsewhere herein, comprising the step of grouping at least two said nucleic acids.

The invention further relates to a method of constructing haplotypes using the ET1-SNP1, Beta1-SNP1, Renin-SNP3, Renin-SNP5, and/or Renin-SNP7 comprising the step of using said haplotypes to identify an individual for the presence of dose-dependent peripheral edema or related disease phenotype, and correlating the presence of the disease phenotype with said haplotype.

The invention further relates to a library of nucleic acids, each of which comprises one or more polymorphic positions within a gene encoding the human renin protein, wherein said polymorphic positions are selected the polymorphic positions provided in Table I.

The invention further relates to a library of nucleic acids, wherein the sequence at said aforementioned polymorphic position is selected from the group consisting of the polymorphic position identified in FIGS. 1A-M, FIGS. 2A-M, FIGS. 3A-M, FIGS. 4A-M, FIGS. 5A-M, FIGS. 6A-M, and/or FIGS. 7A-M, or elsewhere herein, the complimentary sequence of said sequences, and/or fragments of said sequences.

The invention further relates to a kit for identifying an individual at risk of developing dose-dependent peripheral edema or related disorder upon administration of a pharmaceutically acceptable amount of a PPAR-agonist, wherein said kit comprises oligonucleotide primers capable of identifying the nucleotide residing at one or more polymorphic loci of the human renin gene, wherein the presence of the variant allele at said one or more polymorphic loci is indicative of a decreased risk of developing dose-dependent peripheral edema in a patient receiving PPAR-agonist therapy, while the presence of the reference allele at said one or more polymorphic loci is indicative of an increased risk of developing dose-dependent peripheral edema in a patient receiving PPAR-agonist therapy.

The invention further relates to a kit for identifying an individual at risk of developing dose-dependent peripheral edema or related disorder upon administration of a pharmaceutically acceptable amount of a PPAR-agonist, wherein said kit comprises oligonucleotide primers capable of identifying the nucleotide residing at one or more polymorphic loci of the human renin gene, wherein the presence of the variant allele at said one or more polymorphic loci is indicative of a decreased risk of developing dose-dependent peripheral edema in a patient receiving PPAR-agonist therapy, while the presence of the reference allele at said one or more polymorphic loci is indicative of an increased risk of developing dose-dependent peripheral edema in a patient receiving PPAR-agonist therapy, and wherein said oligonucleotides hybridize immediately adjacent to said one or more polymorphic positions, or wherein said primer(s) hybridizes to said polymorphic positions such that the central position of the primer aligns with the polymorphic position of said gene.

The invention further relates to a method for predicting the likelihood that an individual will be diagnosed as being at risk of developing dose-dependent peripheral edema or related disorder upon administration of a pharmaceutically acceptable amount of a PPAR-agonist comprising the step of determining the nucleotide present within at least one or more nucleic acid sample(s) from an individual to be assessed at one or more polymorphic position(s) of the human renin gene sequence selected from the group consisting of: SEQ ID NOS: 1, 2, 3, 4, 5, 6, and/or 7, wherein the presence of the reference nucleotide at the one or more polymorphic position(s) indicates that the individual has an increased likelihood of being diagnosed as at risk of developing dose-dependent peripheral edema or related disorder upon administration of a pharmaceutically acceptable amount of an PPAR-agonist as compared to an individual having the variant allele at said polymorphic position(s).

The invention further relates to a method for predicting the likelihood that an individual will be diagnosed as being at risk of developing a dose-dependent peripheral edema or related disorder upon administration of a pharmaceutically acceptable amount of a PPAR-agonist comprising the step of determining the nucleotide present within at least one or more nucleic acid sample(s) from an individual to be assessed at one or more polymorphic position(s) of the human renin gene sequence selected from the group consisting of: SEQ ID NOS:1, 2, 3, 4, 5, 6, and/or 7, wherein the presence of the variant nucleotide at the one or more polymorphic position(s) indicates that the individual has an decreased likelihood of being diagnosed as at risk of developing dose-dependent peripheral edema or related disorder upon administration of a pharmaceutically acceptable amount of an PPAR-agonist as compared to an individual having the reference allele at said polymorphic position(s).

The invention further relates to a method for predicting the likelihood that an individual will be diagnosed as being at risk of developing dose-dependent peripheral edema or related disorder upon administration of a pharmaceutically acceptable amount of a PPAR-agonist comprising the step of determining the nucleotide present within at least one or more nucleic acid sample(s) from an individual to be assessed at one or more polymorphic position(s) of the human renin gene sequence selected from the group consisting of: nucleotide position 12586 of SEQ ID NOS:1 or 2; nucleotide position 10096 of SEQ ID NOS: 3 or 4; nucleotide position 13076 of SEQ ID NOS:5 or 6; and nucleotide positions 12586, 10096, and/or 13076 of SEQ ID NO:7, wherein the presence of the reference nucleotide at the one or more polymorphic position(s) indicates that the individual has an increased likelihood of being diagnosed as at risk of developing dose-dependent peripheral edema or related disorder upon administration of a pharmaceutically acceptable amount of a PPAR-agonist as compared to an individual having the variant allele at said polymorphic position(s).

The invention further relates to a method for predicting the likelihood that an individual will be diagnosed as being at risk of developing a dose-dependent peripheral edema or related disorder upon administration of a pharmaceutically acceptable amount of a PPAR-agonist comprising the step of determining the nucleotide present within at least one or more nucleic acid sample(s) from an individual to be assessed at one or more polymorphic position(s) of the human renin gene sequence selected from the group consisting of: nucleotide position 12586 of SEQ ID NOS:1 or 2; nucleotide position 10096 of SEQ ID NOS:3 or 4; nucleotide position 13076 of SEQ ID NOS:5 or 6; and nucleotide positions 12586, 10096, and/or 13076 of SEQ ID NO:7, wherein the presence of the variant nucleotide at the one or more polymorphic position(s) indicates that the individual has a decreased likelihood of being diagnosed as at risk of developing dose-dependent peripheral edema or related disorder upon administration of a pharmaceutically acceptable amount of a PPAR-agonist as compared to an individual having the reference allele at said polymorphic position(s).

The present invention is also directed to methods of predicting whether a patient administered a PPAR-agonist will respond to PPAR-agonist therapy; for predicting whether a patient will respond to specific doses of a PPAR-agonist; whether the level of the administered PPAR-agonist needs to be increased or decreased to achieve the desired level of human renin expression identified as representing a responsive level; whether a patient has an increased risk of developing dose-dependent peripheral edema upon the administration of a pharmaceutically acceptable level of a PPAR-agonist; whether said patient requires a lower level of administered PPAR agonist to limit the risk of developing said dose-dependent peripheral edema; or whether said patient may be administered a higher level of administered PPAR agonist without the risk of developing said dose-dependent peripheral edema, inorder to limit the risk of developing said dose-dependent peripheral edema, comprising the step of assessing the level of renin expression resulting from the administration of a PPAR-agonist relative to a control compound.

The present invention also relates to a method of screening for compounds capable of modulating PPAR-alpha and/or gamma, but are predicted to not increase an individuals likelihood of developing dose-dependent edema upon the administration of the same. In specific embodiments of the invention, such systems may comprise renin expressing cell lines incubated in the presence or absence of one or more drugs, compounds, or other therapeutic agents; followed by the step of measuring the level of induced renin expression attributable to administration of the test PPAR-agonist compounds or combinations of such compounds, and selecting the test compound with a diminished ability to induce renin expression relative to a control compound.

The invention relates to a nucleic acid molecule which comprises, or alternatively consists of, at least one single nucleotide polymorphism within the endothelin-1 genomic sequence at a specific polymorphic locus. In a particular embodiment the invention relates to the variant allele of the endothelin-1 gene or polynucleotide having at least one single nucleotide polymorphism, which variant allele differs from a reference allele by one nucleotide at the site(s) identified in FIGS. 13A-B, and/or FIGS. 14A-B, or elsewhere herein. The complementary sequence of each of these nucleic acid molecules are also provided. The nucleic acid molecules can be comprised of DNA or RNA, can be double- or single-stranded, and may comprise fragments. Fragments can be, for example, about 5 to about 10, about 5 to about 15, about 10 to about 20, about 15 to about 25, about 10 to about 30, about 10 to about 50, or about 10 to about 100 bases long, and preferably comprise at least one polymorphic allele.

In another embodiment, the invention relates to the reference or wild type allele of a gene or polynucleotide having a polymorphic locus, in which said reference or wild type allele differs from a variant allele by one nucleotide at the polymorphic site(s) identified in FIGS. 13A-B, and/or FIGS. 14A-B, or elsewhere herein. The complementary sequence of each of these nucleic acid molecules are also provided. The nucleic acid molecules can be comprised of DNA or RNA, can be double- or single-stranded, and may comprise fragments. Fragments can be, for example, about 5 to about 10, about 5 to about 15, about 10 to about 20, about 15 to about 25, about 10 to about 30, about 10 to about 50, or about 10 to about 100 bases long, and preferably comprise at least one polymorphic locus.

The invention further provides variant and reference allele-specific oligonucleotides that hybridize to an ET1-SNP1 nucleic acid molecule comprising at least one polymorphic locus, in addition to the complement of said oligonucleotide. These oligonucleotides can be probes or primers.

The invention further provides oligonucleotides that may be used to amplify a portion of either the variant or reference ET1-SNP1 sequences comprising at least one polymorphic locus of the present invention, in addition to providing oligonucleotides that may be used to sequence said amplified sequence. The invention further provides a method of analyzing a nucleic acid from a DNA sample using said amplification and sequencing primers to assess whether said sample contains the reference or variant nucleotide (allele) at the polymorphic locus, comprising the steps of amplifying a sequence using appropriate oligonucleotide primers for amplifying across a polymorphic locus, and sequencing the resulting amplified product using appropriate sequencing primers to sequence said product to determine whether the variant or reference base is present at the polymorphic locus.

The invention further provides a method of analyzing a nucleic acid from patient sample(s) using said amplification and sequencing primers to assess whether said sample(s) contain the ET1-SNP1 reference or variant nucleotide (allele) at the polymorphic locus in an effort to identify populations at risk of developing dose-dependent peripheral edema upon administration of a PPAR-agonist, comprising the steps of amplifying a sequence using appropriate oligonucleotide primers for amplifying across a polymorphic locus, and sequencing the resulting amplified product using appropriate sequencing primers to sequence said product to determine whether the variant or reference nucleotide is present at the polymorphic locus.

The invention further provides oligonucleotides that may be used to genotype patient sample(s) to assess whether said sample(s) contain the ET1-SNP1 reference or variant nucleotide (allele) at the polymorphic site(s). The invention provide a method of using oligonucleotides that may be used to genotype a patient sample to assess whether said sample contains the reference or variant nucleotide (allele) at the polymorphic locus. An embodiment of the method comprises the steps of amplifying a sequence using appropriate oligonucleotide primers for amplifying across a polymorphic locus, and subjecting the product of said amplification to a genetic bit analysis (GBA) reaction.

The invention provides a method of using oligonucleotides that may be used to genotype patient sample(s) to identify individual(s) at risk of developing dose-dependent peripheral edema upon administration of a PPAR-agonist to assess whether said sample(s) contains the ET1-SNP1 reference or variant nucleotide (allele) at one or more polymorphic loci. An embodiment of the method comprises the steps of amplifying a sequence using appropriate oligonucleotide primers for amplifying across a polymorphic locus, and subjecting the product of said amplification to a genetic bit analysis (GBA) reaction, and optionally determining the statistical association between either the reference or variant allele at the polymorphic site(s) to the incidence of dose-dependent peripheral edema.

The invention provides a method of using oligonucleotides that may be used to genotype patient sample(s) to identify ethnic population(s) that may be at risk of developing dose-dependent peripheral edema upon administration of a PPAR-agonist to assess whether said sample(s) contains the ET1-SNP1 reference or variant nucleotide (allele) at one or more polymorphic loci comprising the steps of amplifying a sequence using appropriate oligonucleotide primers for amplifying across a polymorphic locus, and subjecting the product of said amplification to a genetic bit analysis (GBA) reaction, and optionally determining the statistical association between either the reference or variant allele at the polymorphic site(s) to the incidence of dose-dependent peripheral edema.

The invention further provides a method of analyzing a nucleic acid from one or more individuals. The method allows the determination of whether the ET1-SNP1 reference or variant base is present at any one, or more, of the polymorphic sites identified in FIGS. 13A-B, and/or FIGS. 14A-B, or elsewhere herein. Optionally, a set of nucleotides occupying a set of the polymorphic loci shown in FIGS. 13A-B, and/or FIGS. 14A-B, or elsewhere herein, is determined. This type of analysis can be performed on a number of individuals, who are also tested (previously, concurrently or subsequently) for the presence of a dose-dependent edema phenotype or related disorder. The presence or absence of a dose-dependent edema disease phenotype is then correlated with said nucleotide or set of nucleotides present at the polymorphic locus or loci in the individuals tested.

The invention further relates to a method of predicting the presence, absence, likelihood of the presence or absence, or severity of a dose-dependent peripheral edema or related disorder associated with a particular genotype. The method comprises obtaining a nucleic acid sample from an individual and determining the identity of one or more nucleotides at specific polymorphic loci of the ET1-SNP1 nucleic acid molecules described herein, wherein the presence of a particular base at that site is correlated with the incidence of dose-dependent peripheral edema or related disorder, thereby predicting the presence, absence, likelihood of the presence or absence, or severity, of the dose-dependent peripheral edema phenotype or related disorder in the individual.

The invention further relates to ET1-SNP1 polynucleotides having one or more polymorphic loci comprising one or more variant alleles. The invention also relates to said polynucleotides lacking a start codon. The invention further relates to polynucleotides of the present invention containing one or more variant alleles wherein said polynucleotides encode a polypeptide of the present invention. The invention relates to polypeptides of the present invention containing one or more variant amino acids encoded by one or more variant alleles.

The present invention relates to antisense oligonucleotides capable of hybridizing to the ET1-SNP1 polynucleotides of the present invention. Preferably, such antisense oligonucleotides are capable of discriminating between the reference or variant allele of the polynucleotide, preferably at one or more polymorphic sites of said polynucleotide.

The present invention relates to siRNA or RNAi oligonucleotides capable of hybridizing to the ET1-SNP1 polynucleotides of the present invention. Preferably, such siRNA or RNAi oligonucleotides are capable of discriminating between the reference or variant allele of the polynucleotide, preferably at one or more polymorphic sites of said polynucleotide.

The present invention also relates to zinc finger proteins capable of binding to the ET1-SNP1 polynucleotides of the present invention. Preferably, such zinc finger proteins are capable of discriminating between the reference or variant allele of the polynucleotide, preferably at one or more polymorphic sites of said polynucleotide.

The present invention relates to antibodies directed against the ET1-SNP1 polypeptides of the present invention. Preferably, such antibodies are capable of discriminating between the reference or variant allele of the polypeptide, preferably at one or more polymorphic sites of said polynucleotide.

The present invention also relates to recombinant vectors, which include the isolated ET1-SNP1 nucleic acid molecules of the present invention, and to host cells containing the recombinant vectors, as well as to methods of making such vectors and host cells, in addition to their use in the production of polypeptides or peptides provided herein using recombinant techniques. Synthetic methods for producing the polypeptides and polynucleotides of the present invention are provided. Also provided are diagnostic methods for detecting diseases, disorders, and/or conditions related to the polypeptides and polynucleotides provided herein, and therapeutic methods for treating such diseases, disorders, and/or conditions. The invention further relates to screening methods for identifying binding partners of the polypeptides.

The invention relates to a method of analyzing at least one nucleic acid sample, comprising the step of determining the nucleic acid sequence from one or more samples at one or more polymorphic loci in the human endothelin-1 gene selected from the group consisting of ET1-SNP1, or any combination thereof, wherein the presence of the variable allele at said one or more polymorphic loci is indicative of a decreased risk of developing dose-dependent peripheral edema in a patient receiving PPAR-agonist therapy.

The invention relates to a method of analyzing at least one nucleic acid sample, comprising the step of determining the nucleic acid sequence from one or more samples at one or more polymorphic loci in the human endothelin-1 gene selected from the group consisting of ET1-SNP1, or any combination thereof, wherein the presence of the variant allele at said one or more polymorphic loci is indicative of a decreased risk of developing dose-dependent peripheral edema in a patient receiving PPAR-agonist therapy.

The invention further relates to a library of nucleic acids, each of which comprises one or more polymorphic positions within a gene encoding the human endothelin-1 protein, wherein said polymorphic positions are selected from a group consisting of the polymorphic positions provided in FIGS. 13A-B, FIGS. 14A-B, and/or Table I.

The invention further relates to a library of nucleic acids, wherein the sequence at said aforementioned polymorphic position is selected from the group consisting of the polymorphic position identified in FIGS. 13A-B, and/or FIGS. 14A-B, or elsewhere herein, the complimentary sequence of said sequences, and/or fragments of said sequences.

The invention further relates to a kit for identifying an individual at risk of developing dose-dependent peripheral edema or related disorder upon administration of a pharmaceutically acceptable amount of a PPAR-agonist, wherein said kit comprises oligonucleotide primers capable of identifying the nucleotide residing at one or more polymorphic loci of the human endothelin-1 gene, wherein the presence of the variant allele at said one or more polymorphic loci is indicative of a decreased risk of developing dose-dependent peripheral edema in a patient receiving PPAR-agonist therapy, while the presence of the reference allele at said one or more polymorphic loci is indicative of an increased risk of developing dose-dependent peripheral edema in a patient receiving PPAR-agonist therapy.

The invention further relates to a kit for identifying an individual at risk of developing dose-dependent peripheral edema or related disorder upon administration of a pharmaceutically acceptable amount of a PPAR-agonist, wherein said kit comprises oligonucleotide primers capable of identifying the nucleotide residing at one or more polymorphic loci of the human endothelin-1 gene, wherein the presence of the variant allele at said one or more polymorphic loci is indicative of a decreased risk of developing dose-dependent peripheral edema in a patient receiving PPAR-agonist therapy, while the presence of the reference allele at said one or more polymorphic loci is indicative of an increased risk of developing dose-dependent peripheral edema in a patient receiving PPAR-agonist therapy, and wherein said oligonucleotides hybridize immediately adjacent to said one or more polymorphic positions, or wherein said primer(s) hybridizes to said polymorphic positions such that the central position of the primer aligns with the polymorphic position of said gene.

The invention further relates to a method for predicting the likelihood that an individual will be diagnosed as being at risk of developing dose-dependent peripheral edema or related disorder upon administration of a pharmaceutically acceptable amount of a PPAR-agonist comprising the step of determining the nucleotide present within at least one or more nucleic acid sample(s) from an individual to be assessed at one or more polymorphic position(s) of the human endothelin-1 gene sequence selected from the group consisting of: SEQ ID NOS:37, and/or 39, wherein the presence of the variable nucleotide at the one or more polymorphic position(s) indicates that the individual has a decreased likelihood of being diagnosed as at risk of developing dose-dependent peripheral edema or related disorder upon administration of a pharmaceutically acceptable amount of an PPAR-agonist as compared to an individual having the reference allele at said polymorphic position(s).

The invention further relates to a method for predicting the likelihood that an individual will be diagnosed as being at risk of developing a dose-dependent peripheral edema or related disorder upon administration of a pharmaceutically acceptable amount of a PPAR-agonist comprising the step of determining the nucleotide present within at least one or more nucleic acid sample(s) from an individual to be assessed at one or more polymorphic position(s) of the human endothelin-1 gene sequence selected from the group consisting of:

SEQ ID NOS:37, and/or 39, wherein the presence of the reference nucleotide at the one or more polymorphic position(s) indicates that the individual has an increased likelihood of being diagnosed as at risk of developing dose-dependent peripheral edema or related disorder upon administration of a pharmaceutically acceptable amount of an PPAR-agonist as compared to an individual having the variable allele at said polymorphic position(s).

The invention further relates to a method for predicting the likelihood that an individual will be diagnosed as being at risk of developing dose-dependent peripheral edema or related disorder upon administration of a pharmaceutically acceptable amount of a PPAR-agonist comprising the step of determining the polypeptide present within at least one or more sample(s) from an individual to be assessed at one or more polymorphic position(s) of the human endothelin-1 polypeptide sequence selected from the group consisting of: SEQ ID NOS:38, and/or 40, wherein the presence of the variable amino acid at the one or more polymorphic position(s) indicates that the individual has a decreased likelihood of being diagnosed as at risk of developing dose-dependent peripheral edema or related disorder upon administration of a pharmaceutically acceptable amount of an PPAR-agonist as compared to an individual having the reference allele at said polymorphic position(s).

The invention further relates to a method for predicting the likelihood that an individual will be diagnosed as being at risk of developing a dose-dependent peripheral edema or related disorder upon administration of a pharmaceutically acceptable amount of a PPAR-agonist comprising the step of determining the nucleotide present within at least one or more sample(s) from an individual to be assessed at one or more polymorphic position(s) of the human endothelin-1 polypeptide sequence selected from the group consisting of: SEQ ID NOS:38, and/or 40, wherein the presence of the reference amino acid at the one or more polymorphic position(s) indicates that the individual has an increased likelihood of being diagnosed as at risk of developing dose-dependent peripheral edema or related disorder upon administration of a pharmaceutically acceptable amount of an PPAR-agonist as compared to an individual having the reference allele at said polymorphic position(s).

The invention further relates to a method for predicting the likelihood that an individual will be diagnosed as being at risk of developing dose-dependent peripheral edema or related disorder upon administration of a pharmaceutically acceptable amount of a PPAR-agonist comprising the step of determining the nucleotide present within at least one or more nucleic acid sample(s) from an individual to be assessed at one or more polymorphic position(s) of the human endothelin-1 gene sequence selected from the group consisting of: nucleotide position 797 of SEQ ID NOS:37 or 39, wherein the presence of the variable nucleotide at the one or more polymorphic position(s) indicates that the individual has a decreased likelihood of being diagnosed as at risk of developing dose-dependent peripheral edema or related disorder upon administration of a pharmaceutically acceptable amount of a PPAR-agonist as compared to an individual having the reference allele at said polymorphic position(s).

The invention further relates to a method for predicting the likelihood that an individual will be diagnosed as being at risk of developing a dose-dependent peripheral edema or related disorder upon administration of a pharmaceutically acceptable amount of a PPAR-agonist comprising the step of determining the nucleotide present within at least one or more nucleic acid sample(s) from an individual to be assessed at one or more polymorphic position(s) of the human endothelin-1 gene sequence selected from the group consisting of: nucleotide position 797 of SEQ ID NOS:37 or 39, wherein the presence of the reference nucleotide at the one or more polymorphic position(s) indicates that the individual has an increased likelihood of being diagnosed as at risk of developing dose-dependent peripheral edema or related disorder upon administration of a pharmaceutically acceptable amount of a PPAR-agonist as compared to an individual having the variable allele at said polymorphic position(s).

The invention further relates to a method for predicting the likelihood that an individual will be diagnosed as being at risk of developing dose-dependent peripheral edema or related disorder upon administration of a pharmaceutically acceptable amount of a PPAR-agonist comprising the step of determining the amino acid present within at least one or more sample(s) from an individual to be assessed at one or more polymorphic position(s) of the human endothelin-1 polypeptide sequence selected from the group consisting of: amino acid position 198 of SEQ ID NOS:38 or 40, wherein the presence of the variable amino acid at the one or more polymorphic position(s) indicates that the individual has a decreased likelihood of being diagnosed as at risk of developing dose-dependent peripheral edema or related disorder upon administration of a pharmaceutically acceptable amount of a PPAR-agonist as compared to an individual having the reference allele at said polymorphic position(s).

The invention further relates to a method for predicting the likelihood that an individual will be diagnosed as being at risk of developing a dose-dependent peripheral edema or related disorder upon administration of a pharmaceutically acceptable amount of a PPAR-agonist comprising the step of determining the amino acid present within at least one or more sample(s) from an individual to be assessed at one or more polymorphic position(s) of the human endothelin-1 polypeptide sequence selected from the group consisting of: amino acid position 198 of SEQ ID NOS:38 or 40, wherein the presence of the reference amino acid at the one or more polymorphic position(s) indicates that the individual has an increased likelihood of being diagnosed as at risk of developing dose-dependent peripheral edema or related disorder upon administration of a pharmaceutically acceptable amount of a PPAR-agonist as compared to an individual having the variable allele at said polymorphic position(s).

The present invention is also directed to methods of predicting whether a patient administered a PPAR-agonist will respond to PPAR-agonist therapy; for predicting whether a patient will respond to specific doses of a PPAR-agonist; whether the level of the administered PPAR-agonist needs to be increased or decreased to achieve the desired level of human endothelin-1 expression identified as representing a responsive level; whether a patient has an increased risk of developing dose-dependent peripheral edema upon the administration of a pharmaceutically acceptable level of a PPAR-agonist; whether said patient requires a lower level of administered PPAR agonist to limit the risk of developing said dose-dependent peripheral edema; or whether said patient may be administered a higher level of administered PPAR agonist without the risk of developing said dose-dependent peripheral edema, inorder to limit the risk of developing said dose-dependent peripheral edema, comprising the step of assessing the level of endothelin-1 expression resulting from the administration of a PPAR-agonist relative to a control compound.

The present invention also relates to a method of screening for compounds capable of modulating PPAR-alpha and/or gamma, but are predicted to not increase an individuals likelihood of developing dose-dependent edema upon the administration of the same. In specific embodiments of the invention, such methods may comprise endothelin-1 expressing cell lines incubated in the presence or absence of one or more drugs, compounds, or other therapeutic agents; followed by the step of measuring the level of repressed endothelin-1 expression attributable to administration of the test PPAR-agonist compounds or combinations of such compounds, and selecting the test compound with a diminished ability to repress endothelin-1 expression relative to a control compound, wherein said selected test compound has a diminished ability to induce dose-dependent peripheral edema relative to a reference compound.

The invention relates to a nucleic acid molecule which comprises, or alternatively consists of, at least one single nucleotide polymorphism within the β1-adrenergic receptor genomic sequence at a specific polymorphic locus. In a particular embodiment the invention relates to the variant allele of the β1-adrenergic receptor gene or polynucleotide having at least one single nucleotide polymorphism, which variant allele differs from a reference allele by one nucleotide at the site(s) identified in FIGS. 18A-B, and/or FIGS. 19A-B, or elsewhere herein. The complementary sequence of each of these nucleic acid molecules are also provided. The nucleic acid molecules can be comprised of DNA or RNA, can be double- or single-stranded, and may comprise fragments. Fragments can be, for example, about 5 to about 10, about 5 to about 15, about 10 to about 20, about 15 to about 25, about 10 to about 30, about 10 to about 50, or about 10 to about 100 bases long, and preferably comprise at least one polymorphic allele.

In another embodiment, the invention relates to the reference or wild type allele of a gene or polynucleotide having a polymorphic locus, in which said reference or wild type allele differs from a variant allele by one nucleotide at the polymorphic site(s) identified in FIGS. 18A-B, and/or FIGS. 19A-B, or elsewhere herein. The complementary sequence of each of these nucleic acid molecules are also provided. The nucleic acid molecules can be comprised of DNA or RNA, can be double- or single-stranded, and may comprise fragments. Fragments can be, for example, about 5 to about 10, about 5 to about 15, about 10 to about 20, about 15 to about 25, about 10 to about 30, about 10 to about 50, or about 10 to about 100 bases long, and preferably comprise at least one polymorphic locus.

The invention further provides variant and reference allele-specific oligonucleotides that hybridize to a Beta1-SNP1 nucleic acid molecule comprising at least one polymorphic locus, in addition to the complement of said oligonucleotide. These oligonucleotides can be probes or primers.

The invention further provides oligonucleotides that may be used to amplify a portion of either the Beta1-SNP1 variant or reference sequences comprising at least one polymorphic locus of the present invention, in addition to providing oligonucleotides that may be used to sequence said amplified sequence. The invention further provides a method of analyzing a nucleic acid from a DNA sample using said amplification and sequencing primers to assess whether said sample contains the reference or variant nucleotide (allele) at the polymorphic locus, comprising the steps of amplifying a sequence using appropriate oligonucleotide primers for amplifying across a polymorphic locus, and sequencing the resulting amplified product using appropriate sequencing primers to sequence said product to determine whether the variant or reference base is present at the polymorphic locus.

The invention further provides a method of analyzing a nucleic acid from patient sample(s) using said Beta1-SNP1 amplification and sequencing primers to assess whether said sample(s) contain the reference or variant nucleotide (allele) at the polymorphic locus in an effort to identify populations at risk of developing dose-dependent peripheral edema upon administration of a PPAR-agonist, comprising the steps of amplifying a sequence using appropriate oligonucleotide primers for amplifying across a polymorphic locus, and sequencing the resulting amplified product using appropriate sequencing primers to sequence said product to determine whether the variant or reference nucleotide is present at the polymorphic locus.

The invention further provides oligonucleotides that may be used to genotype patient sample(s) to assess whether said sample(s) contain the Beta1-SNP1 reference or variant nucleotide (allele) at the polymorphic site(s). The invention provide a method of using oligonucleotides that may be used to genotype a patient sample to assess whether said sample contains the reference or variant nucleotide (allele) at the polymorphic locus. An embodiment of the method comprises the steps of amplifying a sequence using appropriate oligonucleotide primers for amplifying across a polymorphic locus, and subjecting the product of said amplification to a genetic bit analysis (GBA) reaction.

The invention provides a method of using oligonucleotides that may be used to genotype patient sample(s) to identify individual(s) at risk of developing dose-dependent peripheral edema upon administration of a PPAR-agonist to assess whether said sample(s) contains the Beta1-SNP1 reference or variant nucleotide (allele) at one or more polymorphic loci. An embodiment of the method comprises the steps of amplifying a sequence using appropriate oligonucleotide primers for amplifying across a polymorphic locus, and subjecting the product of said amplification to a genetic bit analysis (GBA) reaction, and optionally determining the statistical association between either the reference or variant allele at the polymorphic site(s) to the incidence of dose-dependent peripheral edema.

The invention provides a method of using oligonucleotides that may be used to genotype patient sample(s) to identify ethnic population(s) that may be at risk of developing dose-dependent peripheral edema upon administration of a PPAR-agonist to assess whether said sample(s) contains the Beta1-SNP1 reference or variant nucleotide (allele) at one or more polymorphic loci comprising the steps of amplifying a sequence using appropriate oligonucleotide primers for amplifying across a polymorphic locus, and subjecting the product of said amplification to a genetic bit analysis (GBA) reaction, and optionally determining the statistical association between either the reference or variant allele at the polymorphic site(s) to the incidence of dose-dependent peripheral edema.

The invention further provides a method of analyzing a nucleic acid from one or more individuals. The method allows the determination of whether the reference or variant base is present at any one, or more, of the polymorphic sites identified in FIGS. 18A-B, and/or FIGS. 19A-B, or elsewhere herein. Optionally, a set of nucleotides occupying a set of the polymorphic loci shown in FIGS. 18A-B, and/or FIGS. 19A-B, or elsewhere herein, is determined. This type of analysis can be performed on a number of individuals, who are also tested (previously, concurrently or subsequently) for the presence of a dose-dependent edema phenotype or related disorder. The presence or absence of a dose-dependent edema disease phenotype is then correlated with said nucleotide or set of nucleotides present at the polymorphic locus or loci in the individuals tested.

The invention further relates to a method of predicting the presence, absence, likelihood of the presence or absence, or severity of a dose-dependent peripheral edema or related disorder associated with a particular genotype. The method comprises obtaining a nucleic acid sample from an individual and determining the identity of one or more nucleotides at specific polymorphic loci of the Beta1-SNP1 nucleic acid molecules described herein, wherein the presence of a particular base at that site is correlated with the incidence of dose-dependent peripheral edema or related disorder, thereby predicting the presence, absence, likelihood of the presence or absence, or severity, of the dose-dependent peripheral edema phenotype or related disorder in the individual.

The invention further relates to polynucleotides having one or more polymorphic loci comprising one or more Beta1-SNP1 reference or variant alleles. The invention also relates to said polynucleotides lacking a start codon. The invention further relates to polynucleotides of the present invention containing one or more variant alleles wherein said polynucleotides encode a polypeptide of the present invention. The invention relates to polypeptides of the present invention containing one or more variant amino acids encoded by one or more variant alleles.

The present invention relates to antisense oligonucleotides capable of hybridizing to the Beta1-SNP1 polynucleotides of the present invention. Preferably, such antisense oligonucleotides are capable of discriminating between the reference or variant allele of the polynucleotide, preferably at one or more polymorphic sites of said polynucleotide.

The present invention relates to siRNA or RNAi oligonucleotides capable of hybridizing to the Beta1-SNP1 polynucleotides of the present invention. Preferably, such siRNA or RNAi oligonucleotides are capable of discriminating between the reference or variant allele of the polynucleotide, preferably at one or more polymorphic sites of said polynucleotide.

The present invention also relates to zinc finger proteins capable of binding to the Beta1-SNP1 polynucleotides of the present invention. Preferably, such zinc finger proteins are capable of discriminating between the reference or variant allele of the polynucleotide, preferably at one or more polymorphic sites of said polynucleotide.

The present invention relates to antibodies directed against the Beta1-SNP1 polypeptides of the present invention. Preferably, such antibodies are capable of discriminating between the reference or variant allele of the polypeptide, preferably at one or more polymorphic sites of said polynucleotide.

The present invention also relates to recombinant vectors, which include the isolated Beta1-SNP1 nucleic acid molecules of the present invention, and to host cells containing the recombinant vectors, as well as to methods of making such vectors and host cells, in addition to their use in the production of polypeptides or peptides provided herein using recombinant techniques. Synthetic methods for producing the polypeptides and polynucleotides of the present invention are provided. Also provided are diagnostic methods for detecting diseases, disorders, and/or conditions related to the polypeptides and polynucleotides provided herein, and therapeutic methods for treating such diseases, disorders, and/or conditions. The invention further relates to screening methods for identifying binding partners of the polypeptides.

The invention relates to a method of analyzing at least one nucleic acid sample, comprising the step of determining the nucleic acid sequence from one or more samples at one or more polymorphic loci in the human β1-adrenergic receptor gene selected from the group consisting of Beta1-SNP1, or any combination thereof, wherein the presence of the variable allele at said one or more polymorphic loci is indicative of an increased risk of developing dose-dependent peripheral edema in a patient receiving PPAR-agonist therapy.

The invention relates to a method of analyzing at least one nucleic acid sample, comprising the step of determining the nucleic acid sequence from one or more samples at one or more polymorphic loci in the human β1-adrenergic receptor gene selected from the group consisting of Beta1-SNP1, or any combination thereof, wherein the presence of the reference allele at said one or more polymorphic loci is indicative of a decreased risk of developing dose-dependent peripheral edema in a patient receiving PPAR-agonist therapy.

The invention further relates to a library of nucleic acids, each of which comprises one or more polymorphic positions within a gene encoding the human β1-adrenergic receptor protein, wherein said polymorphic positions are selected from a group consisting of the polymorphic positions provided in FIGS. 18A-B, FIGS. 19A-B, and/or Table I.

The invention further relates to a library of nucleic acids, wherein the sequence at said aforementioned polymorphic position is selected from the group consisting of the polymorphic position identified in FIGS. 18A-B, and/or FIGS. 19A-B, or elsewhere herein, the complimentary sequence of said sequences, and/or fragments of said sequences.

The invention further relates to a kit for identifying an individual at risk of developing dose-dependent peripheral edema or related disorder upon administration of a pharmaceutically acceptable amount of a PPAR-agonist, wherein said kit comprises oligonucleotide primers capable of identifying the nucleotide residing at one or more polymorphic loci of the human β1-adrenergic receptor gene, wherein the presence of the variant allele at said one or more polymorphic loci is indicative of an increased risk of developing dose-dependent peripheral edema in a patient receiving PPAR-agonist therapy, while the presence of the reference allele at said one or more polymorphic loci is indicative of a decreased risk of developing dose-dependent peripheral edema in a patient receiving PPAR-agonist therapy.

The invention further relates to a kit for identifying an individual at risk of developing dose-dependent peripheral edema or related disorder upon administration of a pharmaceutically acceptable amount of a PPAR-agonist, wherein said kit comprises oligonucleotide primers capable of identifying the nucleotide residing at one or more polymorphic loci of the human β1-adrenergic receptor gene, wherein the presence of the variant allele at said one or more polymorphic loci is indicative of an increased risk of developing dose-dependent peripheral edema in a patient receiving PPAR-agonist therapy, while the presence of the reference allele at said one or more polymorphic loci is indicative of a decreased risk of developing dose-dependent peripheral edema in a patient receiving PPAR-agonist therapy, and wherein said oligonucleotides hybridize immediately adjacent to said one or more polymorphic positions, or wherein said primer(s) hybridizes to said polymorphic positions such that the central position of the primer aligns with the polymorphic position of said gene.

The invention further relates to a method for predicting the likelihood that an individual will be diagnosed as being at risk of developing dose-dependent peripheral edema or related disorder upon administration of a pharmaceutically acceptable amount of a PPAR-agonist comprising the step of determining the nucleotide present within at least one or more nucleic acid sample(s) from an individual to be assessed at one or more polymorphic position(s) of the human β1-adrenergic receptor gene sequence selected from the group consisting of: SEQ ID NOS:50, and/or 52, wherein the presence of the variable nucleotide at the one or more polymorphic position(s) indicates that the individual has an increased likelihood of being diagnosed as at risk of developing dose-dependent peripheral edema or related disorder upon administration of a pharmaceutically acceptable amount of an PPAR-agonist as compared to an individual having the reference allele at said polymorphic position(s).

The invention further relates to a method for predicting the likelihood that an individual will be diagnosed as being at risk of developing a dose-dependent peripheral edema or related disorder upon administration of a pharmaceutically acceptable amount of a PPAR-agonist comprising the step of determining the nucleotide present within at least one or more nucleic acid sample(s) from an individual to be assessed at one or more polymorphic position(s) of the human β1-adrenergic receptor gene sequence selected from the group consisting of: SEQ ID NOS:50, and/or 52, wherein the presence of the reference nucleotide at the one or more polymorphic position(s) indicates that the individual has a decreased likelihood of being diagnosed as at risk of developing dose-dependent peripheral edema or related disorder upon administration of a pharmaceutically acceptable amount of an PPAR-agonist as compared to an individual having the variable allele at said polymorphic position(s).

The invention further relates to a method for predicting the likelihood that an individual will be diagnosed as being at risk of developing dose-dependent peripheral edema or related disorder upon administration of a pharmaceutically acceptable amount of a PPAR-agonist comprising the step of determining the polypeptide present within at least one or more sample(s) from an individual to be assessed at one or more polymorphic position(s) of the human β1-adrenergic receptor polypeptide sequence selected from the group consisting of: SEQ ID NOS:51, and/or 53, wherein the presence of the variable amino acid at the one or more polymorphic position(s) indicates that the individual has an increased likelihood of being diagnosed as at risk of developing dose-dependent peripheral edema or related disorder upon administration of a pharmaceutically acceptable amount of an PPAR-agonist as compared to an individual having the reference allele at said polymorphic position(s).

The invention further relates to a method for predicting the likelihood that an individual will be diagnosed as being at risk of developing a dose-dependent peripheral edema or related disorder upon administration of a pharmaceutically acceptable amount of a PPAR-agonist comprising the step of determining the nucleotide present within at least one or more sample(s) from an individual to be assessed at one or more polymorphic position(s) of the human β1-adrenergic receptor polypeptide sequence selected from the group consisting of: SEQ ID NOS:50, and/or 52, wherein the presence of the reference amino acid at the one or more polymorphic position(s) indicates that the individual has a decreased likelihood of being diagnosed as at risk of developing dose-dependent peripheral edema or related disorder upon administration of a pharmaceutically acceptable amount of an PPAR-agonist as compared to an individual having the variable allele at said polymorphic position(s).

The invention further relates to a method for predicting the likelihood that an individual will be diagnosed as being at risk of developing dose-dependent peripheral edema or related disorder upon administration of a pharmaceutically acceptable amount of a PPAR-agonist comprising the step of determining the nucleotide present within at least one or more nucleic acid sample(s) from an individual to be assessed at one or more polymorphic position(s) of the human β1-adrenergic receptor gene sequence selected from the group consisting of: nucleotide position 1251 of SEQ ID NOS:50 or 52, wherein the presence of the variable nucleotide at the one or more polymorphic position(s) indicates that the individual has an increased likelihood of being diagnosed as at risk of developing dose-dependent peripheral edema or related disorder upon administration of a pharmaceutically acceptable amount of a PPAR-agonist as compared to an individual having the reference allele at said polymorphic position(s).

The invention further relates to a method for predicting the likelihood that an individual will be diagnosed as being at risk of developing a dose-dependent peripheral edema or related disorder upon administration of a pharmaceutically acceptable amount of a PPAR-agonist comprising the step of determining the nucleotide present within at least one or more nucleic acid sample(s) from an individual to be assessed at one or more polymorphic position(s) of the human β1-adrenergic receptor gene sequence selected from the group consisting of: nucleotide position 1251 of SEQ ID NOS:50 or 52, wherein the presence of the reference nucleotide at the one or more polymorphic position(s) indicates that the individual has a decreased likelihood of being diagnosed as at risk of developing dose-dependent peripheral edema or related disorder upon administration of a pharmaceutically acceptable amount of a PPAR-agonist as compared to an individual having the variable allele at said polymorphic position(s).

The invention further relates to a method for predicting the likelihood that an individual will be diagnosed as being at risk of developing dose-dependent peripheral edema or related disorder upon administration of a pharmaceutically acceptable amount of a PPAR-agonist comprising the step of determining the amino acid present within at least one or more sample(s) from an individual to be assessed at one or more polymorphic position(s) of the human β1-adrenergic receptor polypeptide sequence selected from the group consisting of: amino acid position 389 of SEQ ID NOS:51 or 53, wherein the presence of the variable amino acid at the one or more polymorphic position(s) indicates that the individual has an increased likelihood of being diagnosed as at risk of developing dose-dependent peripheral edema or related disorder upon administration of a pharmaceutically acceptable amount of a PPAR-agonist as compared to an individual having the reference allele at said polymorphic position(s).

The invention further relates to a method for predicting the likelihood that an individual will be diagnosed as being at risk of developing a dose-dependent peripheral edema or related disorder upon administration of a pharmaceutically acceptable amount of a PPAR-agonist comprising the step of determining the amino acid present within at least one or more sample(s) from an individual to be assessed at one or more polymorphic position(s) of the human β1-adrenergic receptor polypeptide sequence selected from the group consisting of: amino acid position 389 of SEQ ID NOS:51 or 53, wherein the presence of the reference amino acid at the one or more polymorphic position(s) indicates that the individual has a decreased likelihood of being diagnosed as at risk of developing dose-dependent peripheral edema or related disorder upon administration of a pharmaceutically acceptable amount of a PPAR-agonist as compared to an individual having the variable allele at said polymorphic position(s).

The present invention is also directed to methods of predicting whether a patient administered a PPAR-agonist will respond to PPAR-agonist therapy; for predicting whether a patient will respond to specific doses of a PPAR-agonist; whether the level of the administered PPAR-agonist needs to be increased or decreased to achieve the desired level of human β1-adrenergic receptor expression identified as representing a responsive level; whether a patient has an increased risk of developing dose-dependent peripheral edema upon the administration of a pharmaceutically acceptable level of a PPAR-agonist; whether said patient requires a lower level of administered PPAR agonist to limit the risk of developing said dose-dependent peripheral edema; or whether said patient may be administered a higher level of administered PPAR agonist without the risk of developing said dose-dependent peripheral edema, inorder to limit the risk of developing said dose-dependent peripheral edema, comprising the step of assessing the level of endothelin-1 expression resulting from the administration of a PPAR-agonist relative to a control compound.

BRIEF DESCRIPTION OF THE FIGURES/DRAWINGS

FIGS. 1A-M show the polynucleotide sequence (SEQ ID NO:1) of Renin-SNP3 allele G of the human renin genomic sequence comprising, or alternatively consisting of, a predicted polynucleotide polymorphic locus located at nucleotide 12586 of SEQ ID NO:1. The polynucleotide sequence contains a sequence of 14503 nucleotides. The nucleotide at the polymorphic locus within this allele is a "G" and is denoted in bold and double underlining. Exons encoding the renin polypeptide are denoted by single underlining, while non-underlined sequence represents introns.

FIGS. 2A-M show the polynucleotide sequence (SEQ ID NO:2) of Renin-SNP3 allele A of the human renin genomic sequence comprising, or alternatively consisting of, a predicted polynucleotide polymorphic locus located at nucleotide 12586 of SEQ ID NO:2. The polynucleotide sequence contains a sequence of 14503 nucleotides. The nucleotide at the polymorphic locus within this allele is a "A" and is denoted in bold and double underlining. Exons encoding the renin polypeptide are denoted by single underlining, while non-underlined sequence represents introns.

FIGS. 3A-M show the polynucleotide sequence (SEQ ID NO:3) of Renin-SNP5 allele A of the human renin genomic sequence comprising, or alternatively consisting of, a predicted polynucleotide polymorphic locus located at nucleotide 10096 of SEQ ID NO:3. The polynucleotide sequence contains a sequence of 14503 nucleotides. The nucleotide at the polymorphic locus within this allele is a "A" and is denoted in bold and double underlining. Exons encoding the renin polypeptide are denoted by single underlining, while non-underlined sequence represents introns.

FIGS. 4A-M show the polynucleotide sequence (SEQ ID NO:4) of Renin-SNP5 allele G of the human renin genomic sequence comprising, or alternatively consisting of, a predicted polynucleotide polymorphic locus located at nucleotide 10096 of SEQ ID NO:4. The polynucleotide sequence contains a sequence of 14503 nucleotides. The nucleotide at the polymorphic locus within this allele is a "G" and is denoted in bold and double underlining. Exons encoding the renin polypeptide are denoted by single underlining, while non-underlined sequence represents introns.

FIGS. 5A-M show the polynucleotide sequence (SEQ ID NO:5) of Renin-SNP7 allele G of the human renin genomic sequence comprising, or alternatively consisting of, a predicted polynucleotide polymorphic locus located at nucleotide 13076 of SEQ ID NO:5. The polynucleotide sequence contains a sequence of 14503 nucleotides. The nucleotide at the polymorphic locus within this allele is a "G" and is denoted in bold and double underlining. Exons encoding the renin polypeptide are denoted by single underlining, while non-underlined sequence represents introns.

FIGS. 6A-M show the polynucleotide sequence (SEQ ID NO:6) of Renin-SNP7 allele G deletion of the human renin genomic sequence comprising, or alternatively consisting of, a predicted polynucleotide polymorphic locus located at nucleotide 13076 of SEQ ID NO:6. The polynucleotide sequence contains a sequence of 14502 nucleotides. The polymorphic locus for this allele represents a nucleotide deletion and is denoted in bold brackets ("[ ]") and double underlining. Exons encoding the renin polypeptide are denoted by single underlining, while non-underlined sequence represents introns.

FIGS. 7A-M show the polynucleotide sequence (SEQ ID NO:7) of the human renin genomic sequence comprising, or alternatively consisting of, one or more of the predicted polynucleotide polymorphic loci of the present invention, which includes but is not limited to the following polynucleotide polymorphisms: Renin-SNP3, Renin-SNP5, and Renin-SNP7. The polynucleotide sequence contains a sequence of 14503 nucleotides (SEQ ID NO:7). The polynucleotide polymorphic sites are represented by an "N", in bold double underlining. The present invention encompasses the nucleotide at nucleotide position 12586 as being either a "G" or an "A", the nucleotide at nucleotide position 10096 as being either an "A" or a "G", and/or the presence or deletion of nucleotide "G" at nucleotide position 13076, in addition to any combination thereof.

FIG. 8 shows the statistical association between human renin Renin-SNP3 alleles "G" and "A" with the incidence of edema in patients administered a PPAR alpha/gamma agonist. As shown, "G" allele homozygous patients ("G/G") at the Renin-SNP3 locus have the highest incidence of edema; heterozygous patients ("G/A") at the Renin-SNP3 locus have a slighter lower incidence of edema compared to homozygous "G/G" allele patients; while "A" allele homozygous patients ("A/A") at the Renin-SNP3 locus have a significantly lower incidence of edema compared to homozygous "G" and heterozygous ("G/A") allele patients. Dose E is as defined in Table A of Example 3, while 006 and 008 are references to the clinical trials defined in Example 2.

FIG. 9 shows the statistical association between human renin Renin-SNP5 alleles "A" and "G" with the incidence of edema in patients administered a PPAR alpha/gamma agonist. As shown, "A" allele homozygous patients ("A/A") at the Renin-SNP5 locus have the highest incidence of edema; heterozygous patients ("A/G") at the Renin-SNP5 locus have a slighter lower incidence of edema compared to homozygous "A/A" allele patients; while "G" allele homozygous patients ("G/G") at the Renin-SNP5 locus have a significantly lower incidence of edema compared to homozygous "A" and heterozygous ("A/G") allele patients. Dose E is as defined in Table A of Example 3, while 006 and 008 are references to the clinical trials defined in Example 2.

FIG. 10 shows the statistical association between human renin Renin-SNP7 alleles "G" and "dG" (deletion of "G" nucleotide) with the incidence of edema in patients administered a PPAR alpha/gamma agonist. As shown, "G" allele homozygous patients ("G/G") at the Renin-SNP7 locus have the highest incidence of edema; heterozygous patients ("G/dG") at the Renin-SNP7 locus have a slighter lower incidence of edema compared to homozygous "G/G" allele patients; while "dG" allele homozygous patients ("dG/dG") at the Renin-SNP7 locus have a significantly lower incidence of edema compared to homozygous "G" and heterozygous ("G/dG") allele patients. Dose E is as defined in Table A of Example 3, while 006 and 008 are references to the clinical trials defined in Example 2.

FIG. 11 shows the relative expression level of the human renin gene within CALU-6 cells in response to treatment with several PPAR-agonist compounds, denoted "COM. A" thru "COM. F", using quantitative RT-PCR. Expression levels of the PPAR-agonist treated CALU-6 cells are presented as fold-change over DMSO treated CALU-6 cells. B-actin and GAPDH were used as controls. As shown, human renin expression was significantly increased in the presence of each of the PPAR-agonist compounds. Experiments were performed as described in Example 7.

FIGS. 12A-B show the relative expression level of the human renin gene within CALU-6 cells in response to treatment with several PPAR-agonist compounds, denoted "COM. A", "COM. B, and "COM. E", using microarray analysis. Expression levels of the PPAR-agonist treated CALU-6 cells are presented as fold-change over DMSO treated CALU-6 cells. As shown, human renin expression was significantly increased in the presence of each of the PPAR-agonist compounds. Experiments were performed as described in Example 8.

FIGS. 13A-B show the polynucleotide sequence (SEQ ID NO:37) of the ET1-SNP1 allele "g" of the human endothelin-1 genomic sequence comprising, or alternatively consisting of, a predicted polynucleotide polymorphic locus located at nucleotide 797 of SEQ ID NO:37 (GENBANK® Accession No. gi|21359861), and the resulting encoded endothelin-1 polypeptide (SEQ ID NO:38; GENBANK® Accession No. gi|NP_001946.2), comprising, or alternatively consisting of, a predicted sense polymorphic locus located at amino acid 198 of SEQ ID NO:38. The polynucleotide sequence contains a sequence of 1334 nucleotides (SEQ ID NO:37), which encodes a polypeptide containing a sequence of 212 amino acids (SEQ ID NO:38). The nucleotide at the polymorphic locus for this allele is a "g" and is denoted in bold and double underlining, while the amino acid encoded by the "g" allele at the polymorphic locus is a "K" and is also denoted in bold and double underlining.

FIGS. 14A-B show the polynucleotide sequence (SEQ ID NO:39) of the ET1-SNP1 allele "g" of the human endothelin-1 genomic sequence comprising, or alternatively consisting of, a predicted polynucleotide polymorphic locus located at nucleotide 797 of SEQ ID NO:39, and the resulting encoded endothelin-1 polypeptide (SEQ ID NO:40), comprising, or alternatively consisting of, a predicted sense polymorphic locus located at amino acid 198 of SEQ ID NO:40. The polynucleotide sequence contains a sequence of 1334 nucleotides (SEQ ID NO:39), which encodes a polypeptide containing a sequence of 212 amino acids (SEQ ID NO:40). The nucleotide at the polymorphic locus for this allele is a "t" and is denoted in bold and double underlining, while the amino acid encoded by the "t" allele at the polymorphic locus is a "N" and is also denoted in bold and double underlining.

FIG. 15 shows the statistical association between human endothelin-1 ET1-SNP1 alleles "g" and "t" with the incidence of edema in patients administered a PPAR alpha/gamma agonist. As shown, "g" allele homozygous patients ("g/g") at the ET1-SNP1 locus have the highest incidence of edema; heterozygous patients ("g/t") at the ET1-SNP1 locus have a slighter lower incidence of edema compared to homozygous "g/g" allele patients; while "t" allele homozygous patients ("t/t") at the ET1-SNP1 locus have a significantly lower incidence of edema compared to homozygous "g" and heterozygous ("g/t") allele patients. Dose E is as defined in Table A of Example 3, while 006 and 008 are references to the clinical trials defined in Example 10.

Figure 16:
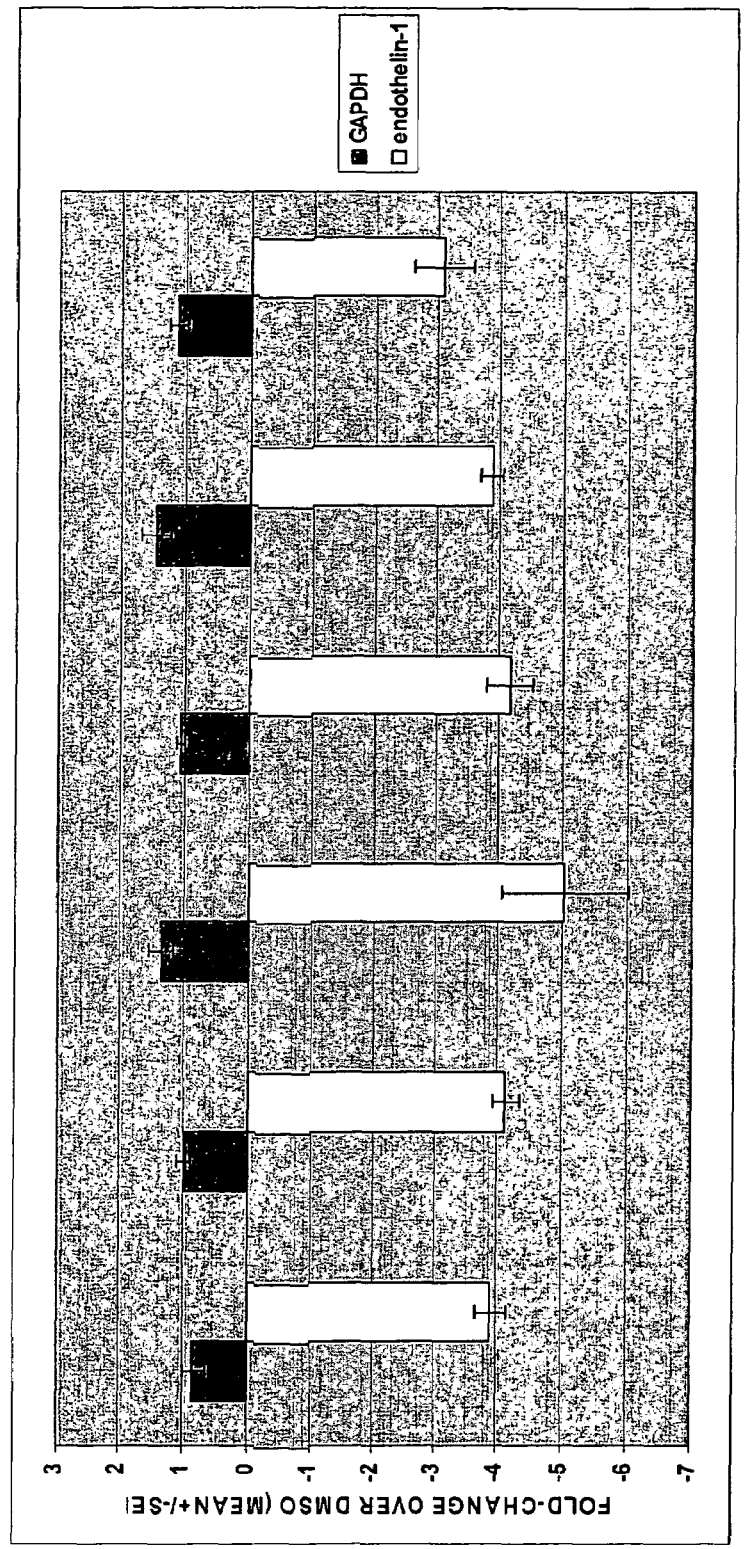

FIG. 16 shows the relative expression level of the human endothelin-1 gene within CALU-6 cells in response to treatment with several PPAR-agonist compounds, denoted "COM. A" thru "COM. F", using quantitative RT-PCR. Expression levels of the PPAR-agonist treated CALU-6 cells are presented as fold-change over DMSO treated CALU-6 cells. GAPDH was used as a control. As shown, human endothelin-1 expression was significantly decreased in the presence of each of the PPAR-agonist compounds. Relative to the GADPH control Experiments were performed as described in Example 15.

FIG. 17 shows the quantitative expression level of the human endothelin-1 gene within CALU-6 cells in response to treatment with several PPAR-agonist compounds, denoted "COM. A", "COM. B, and "COM. E", based upon the results graphically presented in FIG. 16. As shown, human endothelin-1 expression was repressed to similar levels for all of the PPAR agonists tested in accordance with their being used at equivalent effective doses (e.g. 5×EC50). There was no significant difference in the level of endothelin-1 repression when CALU-6 cells treated with Muraglitazar were compared to other PPAR agonist studied. Experiments were performed as described in Example 15.

FIGS. 18A-B show the polynucleotide sequence (SEQ ID NO:50) of the Beta1-SNP1 allele "c" of the human β1-adrenergic receptor genomic sequence comprising, or alternatively consisting of, a predicted polynucleotide polymorphic locus located at nucleotide 1251 of SEQ ID NO:50 (GENBANK® Accession No. gi|NP_000675), and the resulting encoded β1-adrenergic receptor polypeptide (SEQ ID NO:51; GENBANK® Accession No. gi|NP_000675), comprising, or alternatively consisting of, a predicted sense polymorphic locus located at amino acid 389 of SEQ ID NO:51. The polynucleotide sequence contains a sequence of 1723 nucleotides (SEQ ID NO:50), which encodes a polypeptide containing a sequence of 477 amino acids (SEQ ID NO:51). The nucleotide at the polymorphic locus for this allele is a "c" and is denoted in bold and double underlining, while the amino acid encoded by the "c" allele at the polymorphic locus is a "R" and is also denoted in bold and double underlining.

FIGS. 19A-B show the polynucleotide sequence (SEQ ID NO:52) of the Beta1-SNP1 allele "g" of the human β1-adrenergic receptor genomic sequence comprising, or alternatively consisting of, a predicted polynucleotide polymorphic locus located at nucleotide 1251 of SEQ ID NO:52, and the resulting encoded endothelin-1 polypeptide (SEQ ID NO:53), comprising, or alternatively consisting of, a predicted sense polymorphic locus located at amino acid 389 of SEQ ID NO:53. The polynucleotide sequence contains a sequence of 1723 nucleotides (SEQ ID NO:52), which encodes a polypeptide containing a sequence of 477 amino acids (SEQ ID NO:53). The nucleotide at the polymorphic locus for this allele is a "g" and is denoted in bold and double underlining, while the amino acid encoded by the "g" allele at the polymorphic locus is a "G" and is also denoted in bold and double underlining.

FIG. 20 shows the statistical association between human β1-adrenergic receptor Beta1-SNP1 alleles "R" and "G" with the incidence of dose-dependent peripheral edema in patients administered a PPAR alpha/gamma agonist. As shown, "R" allele homozygous patients ("R/R") at the Beta1-SNP1 locus have the lowest incidence of dose-dependent peripheral edema; heterozygous patients ("R/G") at the Beta1-SNP1 locus have a slighter higher incidence of dose-dependent peripheral edema compared to homozygous "R/R" allele patients; while "G" allele homozygous patients ("G/G") at the Beta1-SNP1 locus have the highest incidence of dose-dependent peripheral edema compared to homozygous "R" and heterozygous ("R/G") allele patients. Dose E is as defined in Table A of Example 3, while 006 and 008 are references to the clinical trials defined in Example 17.

Figure 21A:
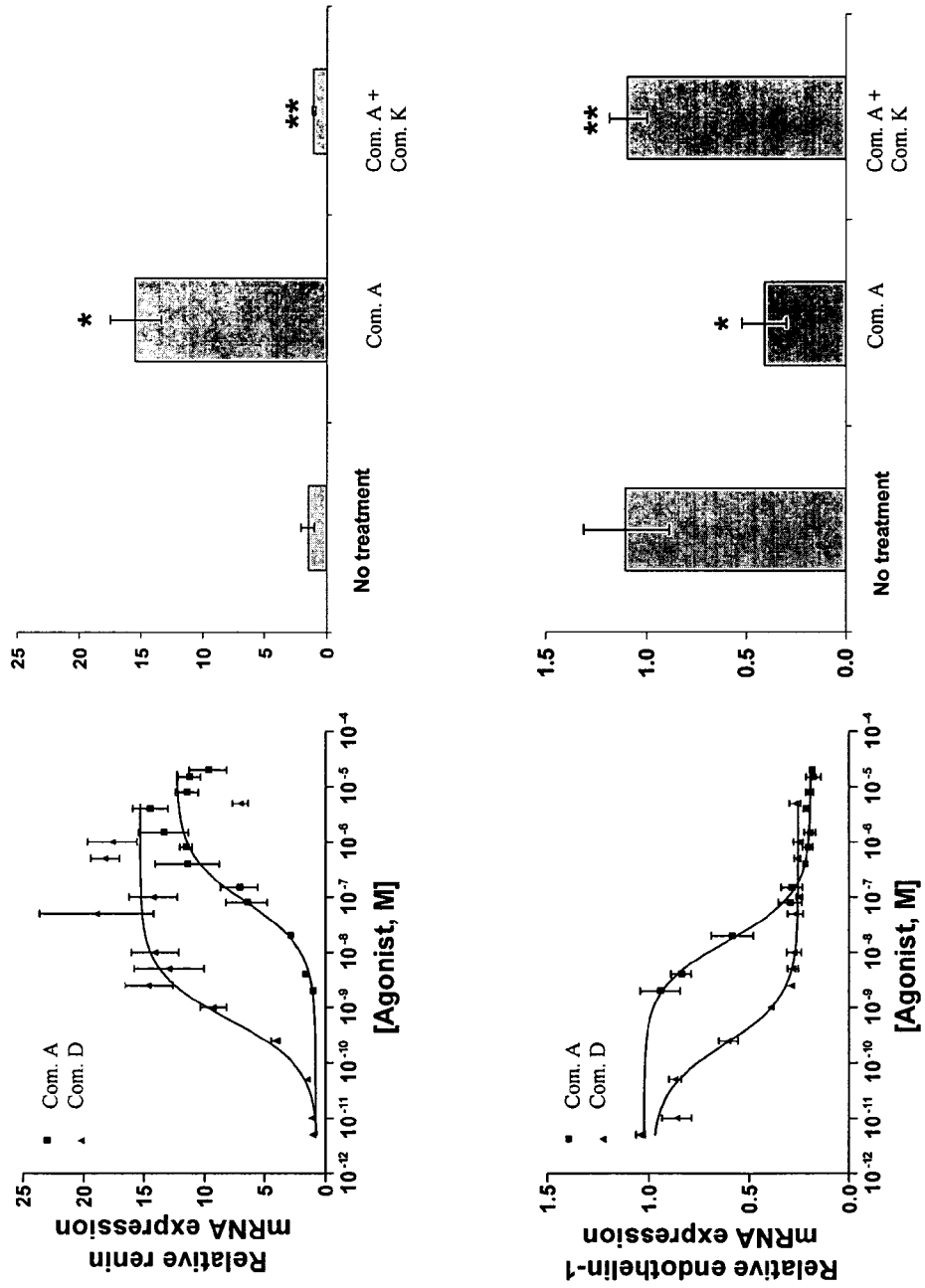
Figure 21B:
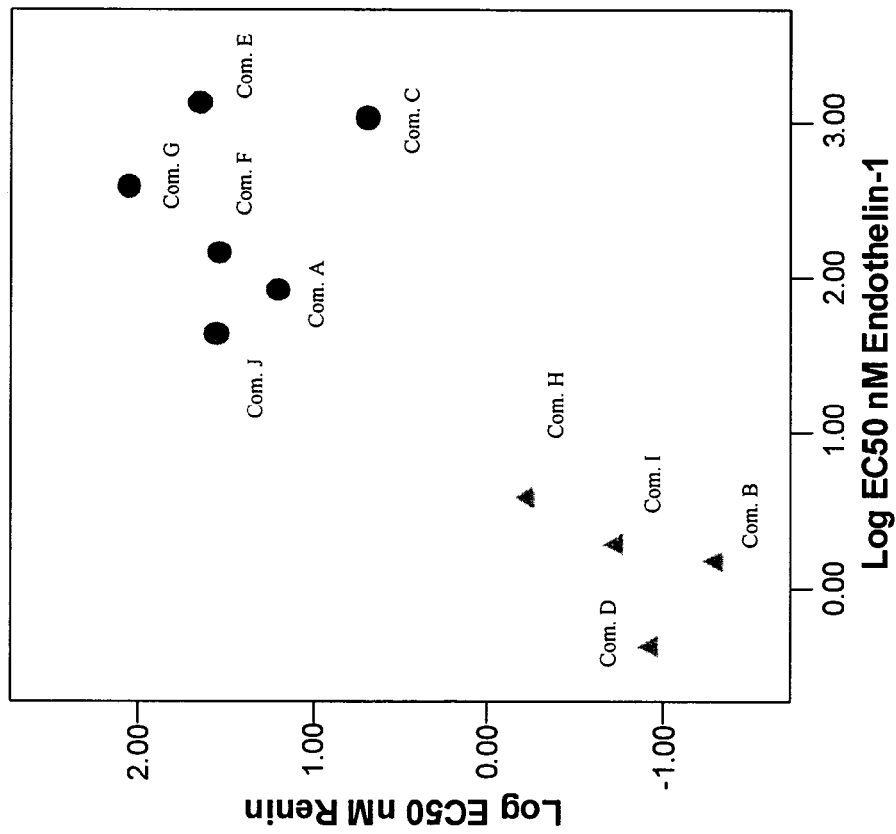

FIGS. 21A-B provides additional data demonstrating that renin and endothelin-1 gene expression are regulated by PPAR agonists. (A) Renin up-regulation and endothelin-1 down-regulation by PPAR agonists is PPARγ-dependent. Left panels, representative quantitative RT-PCR (qRT-PCR) dose-titration induction studies in CALU-6 treated with either Compound A or Compound D. Right panels, qRT-PCR induction studies in CALU-6 treated with 0.76 μM Compound A with or without 5 μM Compound K, a PPARγ antagonist. All data shown represent the mean ±SEM and are normalized to GAPDH expression. (B) PPAR agonist potency tracks with edemagenicity. $EC_{50}$ values derived from experiments similar to dose-titration experiments described in (A) are shown for ten PPAR agonists. K-means clustering of those values identified two distinct clusters of compounds colored orange and blue. Data in (A) are presented relative to DMSO treatment and are normalized to GAPDH expression. Error bars in (A) indicate SEM of triplicate determinations. * P<0.05 compared to vehicle, ** P<0.05 compared to either Compound A or forskolin alone. Experiments were performed as described in Example 24 and elsewhere herein.

FIGS. 22A-F shows fat suppressed diffusion-weighted MR images of scrotal region of a cynomolgus monkey treated with several PPAR-agonists. The hyperintense areas in the images indicated by white arrow depict edematous region. Single sagittal slice image is shown. A, C and E: pre-treatment and B, D and F: post Compound I (4 mg/kg dose), Compound H (10 mg/kg dose), Compound J (3 mg/kg dose). Experiments were performed as described in Example 25 and elsewhere herein.

Figure 23B:
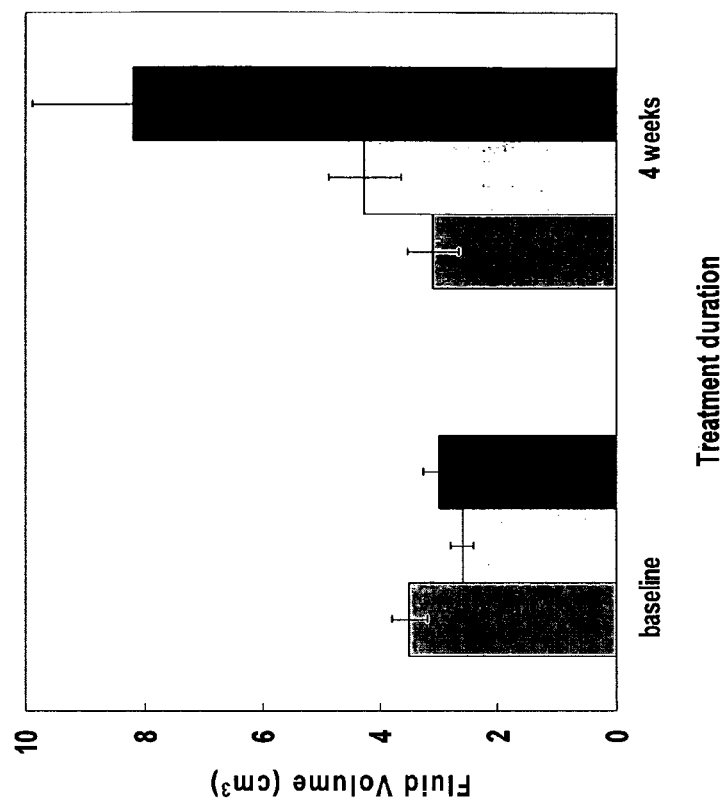
Figure 23A:
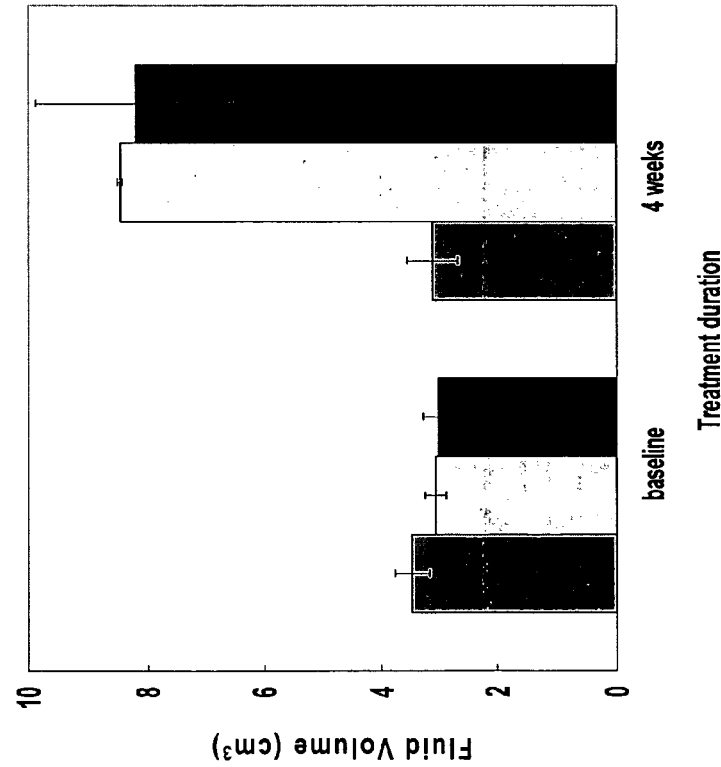

FIGS. 23A-B show the observed fluid retention by administered doses of several PPAR-agonists (panel "A"); and the observed fluid retention adjusted for drug exposure levels for all three PPAR-agonist compounds tested (panel "B"). Fluid retention was quantified in the scrotal region of cynomolgus monkeys after 4 weeks of treatment with Compound J (medium shade), Compound H (light shade) and Compound I (dark shade). Experiments were performed as described in Example 25 and elsewhere herein.

Table A shows the incidence of edema according to various doses of Compound A.

Table B shows the demographic characteristics of subjects used in the genetic analysis used to identify the single nucleotide polymorphisms of the present invention.

Table C shows a multivariate analysis of the associations of Renin-SNP3 (SNP3), Renin-SNP5 (SNP5), Renin-SNP7 (SNP7), ET1-SNP1 (SNP1), and Beta1-SNP1 (SNP1) with edema.

Table D shows the genotype distribution of the ET1-SNP1.

Table E shows a multivariate analysis of the associations of ET1-SNP1 (SNP1) with edema.

Table F shows the genotype distribution of the Beta1-SNP1.

Table G shows a multivariate analysis of the associations of Beta1-SNP1 (SNP1) with edema.

Table H shows the $EC_{50}$ values for PPAR agonists tested for their affect on renin and endothlin-1 expression levels.

Table I provides a summary of the SNPs of the present invention.

DETAILED DESCRIPTION OF THE INVENTION

The present invention relates to a nucleic acid molecule comprising a single nucleotide polymorphism (SNP) at a specific location, referred to herein as the polymorphic locus, and complements thereof. The nucleic acid molecule, which includes the SNP, has at least two alleles, referred to herein as the reference allele and the variant allele. The reference allele (prototypical or wild type allele) typically corresponds to the nucleotide sequence of the native form of the nucleic acid molecule.

The present invention pertains to novel polynucleotides of the human renin gene comprising at least one single nucleotide polymorphism (SNP) which has been shown to be associated with the incidence of dose-dependent peripheral edema in patients administered PPAR-agonists. These renin SNPs were identified by sequencing the renin genomic sequence of a large number of individuals that were subjected to PPAR-agonist therapy, and comparing the renin sequences of those individuals who developed dose-dependent peripheral edema to those individuals who did not develop dose-dependent peripheral edema. Each of the novel renin SNPs were located in non-coding regions of the renin gene and are thought to affect the expression levels of renin in those patients containing one or more of these SNPs.

The present invention also relates to variant alleles of the described renin gene and to complements of the variant alleles. The variant allele differs from the reference allele by one nucleotide at the polymorphic locus identified in the FIGS. 1A-M, FIGS. 2A-M, FIGS. 3A-M, FIGS. 4A-M, FIGS. 5A-M, FIGS. 6A-M, and/or FIGS. 7A-M.

The invention further relates to fragments of the variant renin alleles and portions of complements of the variant alleles which comprise the site of the SNP (e.g., polymorphic locus) and are at least 10 nucleotides in length. Fragments can be, for example, about 5-10, about 5-15, about 10-20, about 5-25, about 10-30, about 10-50 or about 10-100 bases long. For example, a portion of a variant allele which is about 10 nucleotides in length comprises at least one single nucleotide polymorphism (the nucleotide which differs from the reference allele at the polymorphic locus) and nine additional nucleotides which flank the site in the variant allele. These additional nucleotides can be on one or both sides of the polymorphism. Polymorphisms which are the subject of this invention are defined in FIGS. 1A-M, FIGS. 2A-M, FIGS. 3A-M, FIGS. 4A-M, FIGS. 5A-M, FIGS. 6A-M, and/or FIGS. 7A-M herein.

Specifically, the invention relates to the human renin gene having a nucleotide sequence according to FIGS. 1A-M, FIGS. 2A-M, FIGS. 3A-M, FIGS. 4A-M, FIGS. 5A-M, FIGS. 6A-M, or FIGS. 7A-M (SEQ ID NOs:1, 2, 3, 4, 5, 6, or 7) comprising a single nucleotide polymorphism at a polymorphic locus selected from the group consisting of: nucleotide 10096, 12586, and 13076 of SEQ ID NOs: 1, 2, 3, 4, 5, 6, or 7. The reference nucleotide for the polymorphic locus at nucleotide 10096 is "A", the reference nucleotide for the polymorphic locus at nucleotide 12586 is "G", and the reference nucleotide for the polymorphic locus at nucleotide 13076 is "G". The variant nucleotide for the polymorphic locus at nucleotide 10096 is "G", the reference nucleotide for the polymorphic locus at nucleotide 12586 is "A", and the reference nucleotide for the polymorphic locus at nucleotide 13076 is a deletion of the "G" nucleotide. The nucleotide sequences of the present invention can be double- or single-stranded.

The invention further relates to a portion of the human renin gene comprising one or more polymorphic loci selected from the group consisting of: nucleotide 10096, 12586, and 13076 of SEQ ID NOs: 1, 2, 3, 4, 5, 6, or 7.

The single nucleotide polymorphisms described herein derive from the renin gene that have been shown to be associated, for the first time, with the incidence of dose-dependent peripheral edema or related disorders. Specifically, the reference single nucleotide polymorphisms of the human renin gene described herein have been demonstrated to statistically increase an individuals susceptibility to developing dose-dependent peripheral edema or an edema-like event upon the administration of an increased dose of a PPAR-agonist.

The human renin gene was chosen as a candidate gene to investigate the potential of it comprising one or more single nucleotide polymorphisms associated with dose-dependent peripheral edema or related-edema phenotype, and in particular, the potential of identifying a renin SNP associated with the incidence of dose-dependent peripheral edema or related-edema phenotype upon the administration of an increased dose of a PPAR-agonist, based upon the role of renin in regulating extracellular fluid volume and sodium balance.

The invention further provides allele-specific oligonucleotides that hybridize to the human renin gene, or fragments or complements thereof, comprising one or more single nucleotide polymorphisms and/or polymorphic locus. Such oligonucleotides are expected to hybridize to one polymorphic allele of the nucleic acid molecules described herein but not to the other polymorphic allele(s) of the sequence. Thus, such oligonucleotides can be used to determine the presence or absence of particular alleles of the polymorphic sequences described herein and to distinguish between reference and variant allele for each form. These oligonucleotides can be probes or primers.

The invention further provides a method of analyzing a nucleic acid from an individual to identify the presence or absence of a particular nucleotide at a given polymorphic locus and to distinguish between the reference and variant allele at each locus. The method determines which base is present at any one of the renin polymorphic loci shown in FIGS. 1A-M, FIGS. 2A-M, FIGS. 3A-M, FIGS. 4A-M, FIGS. 5A-M, FIGS. 6A-M, or FIGS. 7A-M (SEQ ID NOs:1, 2, 3, 4, 5, 6, or 7), or elsewhere herein. Optionally, a set of bases occupying a set of the polymorphic loci shown in FIGS. 1A-M, FIGS. 2A-M, FIGS. 3A-M, FIGS. 4A-M, FIGS. 5A-M, FIGS. 6A-M, or FIGS. 7A-M (SEQ ID NOs: 1, 2, 3, 4, 5, 6, or 7) is determined. This type of analysis can be performed on a number of individuals, who are also tested (previously, concurrently or subsequently) for the presence of dose-dependent peripheral edema or edema-like phenotype in the presence or absence of a PPAR-agonist. The presence or absence of dose-dependent peripheral edema or edema-like phenotype is then correlated with a base or set of bases present at the polymorphic locus or loci in the patient and/or sample tested.

Thus, the invention further relates to a method of predicting the presence, absence, likelihood of the presence or absence, or severity of a particular dose-dependent peripheral edema or edema-like phenotype associated with a particular genotype in the presence or absence of an increased dose of a PPAR-agonist. The method comprises obtaining a nucleic acid sample from an individual and determining the identity of one or more bases (nucleotides) at on or more polymorphic loci of the nucleic acid molecules described herein, wherein the presence of a particular base is correlated with the incidence of dose-dependent peripheral edema or edema-like phenotype or an increased risk of developing dose-dependent peripheral edema or edema-like phenotype in the presence of a PPAR-agonist, thereby predicting the presence, absence, likelihood of the presence or absence, or severity of dose-dependent peripheral edema or edema-like in the individual or sample. The correlation between a particular polymorphic form of a gene and a phenotype can thus be used in methods of diagnosis of that phenotype, as well as in the development of treatments for the phenotype.

The present invention pertains to novel polynucleotides of the human endothelin-1 gene comprising at least one single nucleotide polymorphism (SNP) which has been shown to be associated with the incidence of dose-dependent peripheral edema in patients administered PPAR-agonists. These endothelin-1 SNPs were identified by sequencing the endothelin-1 genomic sequence of a large number of individuals that were subjected to PPAR-agonist therapy, and comparing the endothelin-1 sequences of those individuals who developed dose-dependent peripheral edema to those individuals who did not develop dose-dependent peripheral edema. Each of the novel endothelin-1 SNPs were located in coding regions of the endothelin-1 gene and are thought to affect the expression levels of endothelin-1 in those patients containing one or more of these SNPs.

The present invention also relates to endothelin-1 variant alleles of the described gene and to complements of the variant alleles. The variant allele differs from the reference allele by one nucleotide at the polymorphic locus identified in the FIGS. 13A-B, and/or FIGS. 14A-B.

The invention further relates to fragments of the endothelin-1 variant alleles and portions of complements of the variant alleles which comprise the site of the SNP (e.g., polymorphic locus) and are at least 10 nucleotides in length. Fragments can be, for example, about 5-10, about 5-15, about 10-20, about 5-25, about 10-30, about 10-50 or about 10-100 bases long. For example, a portion of a variant allele which is about 10 nucleotides in length comprises at least one single nucleotide polymorphism (the nucleotide which differs from the reference allele at the polymorphic locus) and nine additional nucleotides which flank the site in the variant allele. These additional nucleotides can be on one or both sides of the polymorphism. Polymorphisms which are the subject of this invention are defined in FIGS. 13A-B, and/or FIGS. 14A-B herein.

Specifically, the invention relates to the human endothelin-1 gene having a nucleotide sequence according to FIGS. 13A-B, or FIGS. 14A-B (SEQ ID NOs:37, or 39) comprising a single nucleotide polymorphism at a polymorphic locus selected from the group consisting of: nucleotide 797 of SEQ ID NOs:37 or 39. The reference nucleotide for the polymorphic locus at nucleotide 797 is "g". The variant nucleotide for the polymorphic locus at nucleotide 797 is "t". The nucleotide sequences of the present invention can be double- or single-stranded.

The invention also relates to the human endothelin-1 polypeptide having an amino acid sequence according to FIGS. 13A-B, or FIGS. 14A-B (SEQ ID NOs:38, or 40) comprising a polymorphism at a polymorphic locus selected from the group consisting of: amino acid 198 of SEQ ID NOs:38 or 40. The reference amino acid for the polymorphic locus at amino acid 198 is "K". The variant amino acid for the polymorphic locus at amino acid 198 is "N".

The invention further relates to a portion of the human endothelin-1 gene comprising one or more polymorphic loci selected from the group consisting of: nucleotide 797 of SEQ ID NOs:37 or 39.

The single nucleotide polymorphisms described herein derive from the endothelin-1 gene that have been shown to be associated, for the first time, with the incidence of dose-dependent peripheral edema or related disorders. Specifically, the variable single nucleotide polymorphism(s) of the human endothelin-1 gene described herein have been demonstrated to statistically decrease an individuals susceptibility to developing dose-dependent peripheral edema or an edema-like event upon the administration of an increased dose of a PPAR-agonist, while the reference single nucleotide polymorphism(s) of the human endothelin-1 gene described herein have been demonstrated to statistically increase an individuals susceptibility to developing dose-dependent peripheral edema or an edema-like event upon the administration of an increased dose of a PPAR-agonist.

The human endothelin-1 gene was chosen as a candidate gene to investigate the potential of it comprising one or more single nucleotide polymorphisms associated with dose-dependent peripheral edema or related-edema phenotype, and in particular, the potential of identifying a endothelin-1 SNP associated with the incidence of dose-dependent peripheral edema or related-edema phenotype upon the administration of an increased dose of a PPAR-agonist, based upon the role of endothelin-1 in regulating extracellular fluid volume and sodium balance.

The invention further provides allele-specific oligonucleotides that hybridize to the human endothelin-1 gene, or fragments or complements thereof, comprising one or more single nucleotide polymorphisms and/or polymorphic locus. Such oligonucleotides are expected to hybridize to one polymorphic allele of the nucleic acid molecules described herein but not to the other polymorphic allele(s) of the sequence. Thus, such oligonucleotides can be used to determine the presence or absence of particular alleles of the polymorphic sequences described herein and to distinguish between reference and variant allele for each form. These oligonucleotides can be probes or primers.

The invention further provides a method of analyzing a nucleic acid from an individual to identify the presence or absence of a particular nucleotide at a given polymorphic locus and to distinguish between the reference and variant allele at each locus. The method determines which base is present at any one of the endothelin-1 polymorphic loci shown in FIGS. 13A-B, and/or FIGS. 14A-B (SEQ ID NOs: 37, and/or 39), or elsewhere herein. Optionally, a set of bases occupying a set of the polymorphic loci shown in FIGS. 13A-B, and/or FIGS. 14A-B (SEQ ID NOs:37, and/or 39) is determined. This type of analysis can be performed on a number of individuals, who are also tested (previously, concurrently or subsequently) for the presence of dose-dependent peripheral edema or edema-like phenotype in the presence or absence of a PPAR-agonist. The presence or absence of dose-dependent peripheral edema or edema-like phenotype is then correlated with a base or set of bases present at the polymorphic locus or loci in the patient and/or sample tested.

Thus, the invention further relates to a method of predicting the presence, absence, likelihood of the presence or absence, or severity of a particular dose-dependent peripheral edema or edema-like phenotype associated with a particular genotype in the presence or absence of an increased dose of a PPAR-agonist. The method comprises obtaining a nucleic acid sample from an individual and determining the identity of one or more bases (nucleotides) at on or more polymorphic loci of the nucleic acid molecules described herein, wherein the presence of a particular base is correlated with the incidence of dose-dependent peripheral edema or edema-like phenotype or an increased risk of developing dose-dependent peripheral edema or edema-like phenotype in the presence of a PPAR-agonist, thereby predicting the presence, absence, likelihood of the presence or absence, or severity of dose-dependent peripheral edema or edema-like in the individual or sample. The correlation between a particular polymorphic form of a gene and a phenotype can thus be used in methods of diagnosis of that phenotype, as well as in the development of treatments for the phenotype.

The present invention pertains to novel polynucleotides of the human β1-adrenergic receptor gene comprising at least one single nucleotide polymorphism (SNP) which has been shown to be associated with the incidence of dose-dependent peripheral edema in patients administered PPAR-agonists. These endothelin-1 SNPs were identified by sequencing the β1-adrenergic receptor genomic sequence of a large number of individuals that were subjected to PPAR-agonist therapy, and comparing the β1-adrenergic receptor sequences of those individuals who developed dose-dependent peripheral edema to those individuals who did not develop dose-dependent peripheral edema. Each of the novel endothelin-1 SNPs were located in coding regions of the β1-adrenergic receptor gene and are thought to affect the expression levels of endothelin-1 in those patients containing one or more of these SNPs.

The present invention also relates to human β1-adrenergic receptor variant alleles of the described gene and to complements of the variant alleles. The variant allele differs from the reference allele by one nucleotide at the polymorphic locus identified in the FIGS. 18A-B, and/or FIGS. 19A-B.

The invention further relates to fragments of the human β1-adrenergic receptor variant alleles and portions of complements of the variant alleles which comprise the site of the SNP (e.g., polymorphic locus) and are at least 10 nucleotides in length. Fragments can be, for example, about 5-10, about 5-15, about 10-20, about 5-25, about 10-30, about 10-50 or about 10-100 bases long. For example, a portion of a variant allele which is about 10 nucleotides in length comprises at least one single nucleotide polymorphism (the nucleotide which differs from the reference allele at the polymorphic locus) and nine additional nucleotides which flank the site in the variant allele. These additional nucleotides can be on one or both sides of the polymorphism. Polymorphisms which are the subject of this invention are defined in FIGS. 18A-B, and/or FIGS. 19A-B herein.

Specifically, the invention relates to the human β1-adrenergic receptor gene having a nucleotide sequence according to FIGS. 18A-B, or FIGS. 19A-B (SEQ ID NOs:50, or 52) comprising a single nucleotide polymorphism at a polymorphic locus selected from the group consisting of: nucleotide 1251 of SEQ ID NOs:50 or 52. The reference nucleotide for the polymorphic locus at nucleotide 1251 is "g". The variant nucleotide for the polymorphic locus at nucleotide 1251 is "t". The nucleotide sequences of the present invention can be double- or single-stranded.

The invention also relates to the human β1-adrenergic receptor polypeptide having an amino acid sequence according to FIGS. 18A-B, or FIGS. 19A-B (SEQ ID NOs:51, or 53) comprising a polymorphism at a polymorphic locus selected from the group consisting of: amino acid 389 of SEQ ID NOs:51 or 53. The reference amino acid for the polymorphic locus at amino acid 198 is "K". The variant amino acid for the polymorphic locus at amino acid 198 is "N".

The invention further relates to a portion of the human β1-adrenergic receptor gene comprising one or more polymorphic loci selected from the group consisting of: nucleotide 1251 of SEQ ID NOs:50 or 52.

The single nucleotide polymorphisms described herein derive from the β1-adrenergic receptor gene that have been shown to be associated, for the first time, with the incidence of dose-dependent peripheral edema or related disorders. Specifically, the variable single nucleotide polymorphism(s) of the human β1-adrenergic receptor gene described herein have been demonstrated to statistically decrease an individuals susceptibility to developing dose-dependent peripheral edema or an edema-like event upon the administration of an increased dose of a PPAR-agonist, while the reference single nucleotide polymorphism(s) of the human β1-adrenergic receptor gene described herein have been demonstrated to statistically increase an individuals susceptibility to developing dose-dependent peripheral edema or an edema-like event upon the administration of an increased dose of a PPAR-agonist.

The human β1-adrenergic receptor gene was chosen as a candidate gene to investigate the potential of it comprising one or more single nucleotide polymorphisms associated with dose-dependent peripheral edema or related-edema phenotype, and in particular, the potential of identifying a endothelin-1 SNP associated with the incidence of dose-dependent peripheral edema or related-edema phenotype upon the administration of an increased dose of a PPAR-agonist, based upon the role of endothelin-1 in regulating extracellular fluid volume and sodium balance.

The invention further provides allele-specific oligonucleotides that hybridize to the human β1-adrenergic receptor gene, or fragments or complements thereof, comprising one or more single nucleotide polymorphisms and/or polymorphic locus. Such oligonucleotides are expected to hybridize to one polymorphic allele of the nucleic acid molecules described herein but not to the other polymorphic allele(s) of the sequence. Thus, such oligonucleotides can be used to determine the presence or absence of particular alleles of the polymorphic sequences described herein and to distinguish between reference and variant allele for each form. These oligonucleotides can be probes or primers.

The invention further provides a method of analyzing a nucleic acid from an individual to identify the presence or absence of a particular nucleotide at a given polymorphic locus and to distinguish between the reference and variant allele at each locus. The method determines which base is present at any one of the human β1-adrenergic receptor polymorphic loci shown in FIGS. 18A-B, and/or FIGS. 19A-B (SEQ ID NOs:50, and/or 52), or elsewhere herein. Optionally, a set of bases occupying a set of the polymorphic loci shown in FIGS. 18A-B, and/or FIGS. 19A-B (SEQ ID NOs:50, and/or 52) is determined. This type of analysis can be performed on a number of individuals, who are also tested (previously, concurrently or subsequently) for the presence of dose-dependent peripheral edema or edema-like phenotype in the presence or absence of a PPAR-agonist. The presence or absence of dose-dependent peripheral edema or edema-like phenotype is then correlated with a base or set of bases present at the polymorphic locus or loci in the patient and/or sample tested.

Thus, the invention further relates to a method of predicting the presence, absence, likelihood of the presence or absence, or severity of a particular dose-dependent peripheral edema or edema-like phenotype associated with a particular genotype in the presence or absence of an increased dose of a PPAR-agonist. The method comprises obtaining a nucleic acid sample from an individual and determining the identity of one or more bases (nucleotides) at on or more polymorphic loci of the nucleic acid molecules described herein, wherein the presence of a particular base is correlated with the incidence of dose-dependent peripheral edema or edema-like phenotype or an increased risk of developing dose-dependent peripheral edema or edema-like phenotype in the presence of a PPAR-agonist, thereby predicting the presence, absence, likelihood of the presence or absence, or severity of dose-dependent peripheral edema or edema-like in the individual or sample. The correlation between a particular polymorphic form of a gene and a phenotype can thus be used in methods of diagnosis of that phenotype, as well as in the development of treatments for the phenotype.

DEFINITIONS

An "oligonucleotide" can be DNA or RNA, and single- or double-stranded. An oligonucleotide may be used as either a "primer" or a "probe". Oligonucleotides can be naturally occurring or synthetic, but are typically prepared by synthetic means. An oligonucleotide primer, for example, may be designed to hybridize to the complementary sequence of either the sense or antisense strand of a specific target sequence, and may be used alone or as a pair, such as in DNA amplification reactions, and may or may not comprise one or more polymorphic loci of the present invention. An oligonucleotide probe may also be designed to hybridize to the complementary sequence of either the sense or antisense strand of a specific target sequence, and may be used alone or as a pair, such as in DNA amplification reactions, but necessarily will comprise one or more polymorphic loci of the present invention. Preferred oligonucleotides of the invention include fragments of DNA, or their complements thereof, of the human renin gene, and may comprise one or more of the polymorphic loci shown or described in FIGS. 1A-M, FIGS. 2A-M, FIGS. 3A-M, FIGS. 4A-M, FIGS. 5A-M, FIGS. 6A-M, FIGS. 7A-M, FIGS. 13A-B, FIGS. 14A-B, FIGS. 18A-B, and/or FIGS. 19A-B, or as described elsewhere herein. The fragments can be between 10 and 250 bases, and, in specific embodiments, are between about 5 to about 10, about 5 to about 15, about 10 to about 20, about 15 to about 25, about 10 to about 30, about 10 to about 50, or about 10 to about 100 bases in length. For example, the fragment can be 40 bases in length. The polymorphic locus can occur within any nucleotide position of the fragment, including at either terminus or directly in the middle, for example. The fragments can be from any of the allelic forms of DNA shown or described herein.

As used herein, the terms "nucleotide", "base" and "nucleic acid" are intended to be equivalent. The terms "nucleotide sequence", "nucleic acid sequence", "nucleic acid molecule" and "segment" are intended to be equivalent.

Hybridization probes are oligonucleotides which bind in a base-specific manner to a complementary strand of nucleic acid and are designed to identify the allele at one or more polymorphic loci within the renin gene of the present invention. Such probes include peptide nucleic acids, as described in Nielsen et al., Science 254, 1497-1500 (1991). Probes can be any length suitable for specific hybridization to the target nucleic acid sequence. The most appropriate length of the probe may vary depending upon the hybridization method in which it is being used; for example, particular lengths may be more appropriate for use in microfabricated arrays, while other lengths may be more suitable for use in classical hybridization methods. Such optimizations are known to the skilled artisan. Suitable probes can range from about 12 nucleotides to about 25 nucleotides in length. For example, probes and primers can be about 4, 6, 8, 10, 12, 14, 16, 18, 20, 22, 24, 25, 26, or about 40 nucleotides in length. The probe preferably comprises at least one polymorphic locus occupied by any of the possible variant nucleotides. For comparison purposes, the present invention also encompasses probes that comprise the reference nucleotide at least one polymorphic locus. The nucleotide sequence can correspond to the coding sequence of the allele or to the complement of the coding sequence of the allele, where applicable.

As used herein, the term "primer" refers to a single-stranded oligonucleotide which acts as a point of initiation of template-directed DNA synthesis under appropriate conditions. Such DNA synthesis reactions may be carried out in the traditional method of including all four different nucleoside triphosphates (e.g., in the form of phosphoramidates, for example) corresponding to adenine, guanine, cytosine and thymine or uracil nucleotides, and an agent for polymerization, such as DNA or RNA polymerase or reverse transcriptase in an appropriate buffer and at a suitable temperature. Alternatively, such a DNA synthesis reaction may utilize only a single nucleoside (e.g., for single base-pair extension assays). The appropriate length of a primer depends on the intended use of the primer, but typically ranges from about 10 to about 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term primer pair refers to a set of primers including a 5' (upstream) primer that hybridizes with the 5' end of the DNA sequence to be amplified and a 3' (downstream) primer that hybridizes with the complement of the 3' end of the sequence to be amplified.

As used herein, "linkage" describes the tendency of genes, alleles, loci or genetic markers to be inherited together as a result of their location on the same chromosome. It can be measured by percent recombination between the two genes, alleles, loci or genetic markers.

As used herein, "polymorphism" refers to the occurrence of two or more genetically determined alternative sequences or alleles in a population. A "polymorphic locus" is a marker or site at which divergence from a reference allele occurs. The phrase "polymorphic loci" is meant to refer to two or more markers or sites at which divergence from two or more reference alleles occurs. Preferred markers have at least two alleles, each occurring at frequency of greater than 1%, and more preferably greater than 10% or 20% of a selected population. A polymorphic locus may be as small as one base pair. Polymorphic loci include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the "reference form" or "reference allele" and other allelic forms are designated as alternative forms or "variant alleles". The allelic form occurring most frequently in a selected population is sometimes referred to as the wild type form. Diploid organisms may be homozygous or heterozygous for allelic forms. A diallelic or biallelic polymorphism has two forms. A triallelic polymorphism has three forms.

As used herein, the term "genotype" is meant to encompass the particular allele present at a polymorphic locus of a DNA sample, a gene, and/or chromosome.

As used herein, the term "haplotype" is meant to encompass the combination of genotypes across two or more polymorphic loci of a DNA sample, a gene, and/or chromosome, wherein the genotypes are closely linked, may be inherited together as a unit, and may be in linkage disequilibrium relative to other haplotypes and/or genotypes of other DNA samples, genes, and/or chromosomes.

As used herein, the term "linkage disequilibrium" refers to a measure of the degree of association between two alleles in a population. For example, when alleles at two distinctive loci occur in a sample more frequently than expected given the known allele frequencies and recombination fraction between the two loci, the two alleles may be described as being in "linkage disequilibrium".

As used herein, the terms "genotype assay" and "genotype determination", and the phrase "to genotype" or the verb usage of the term "genotype" are intended to be equivalent and refer to assays designed to identify the allele or alleles at a particular polymorphic locus or loci in a DNA sample, a gene, and/or chromosome. Such assays may employ single base extension reactions, DNA amplification reactions that amplify across one or more polymorphic loci, or may be as simple as sequencing across one or more polymorphic loci. A number of methods are known in the art for genotyping, with many of these assays being described herein or referred to herein.

Work described herein pertains to the resequencing of the human renin gene in a large number of individuals to identify polymorphisms associated with the incidence of dose-dependent peripheral edema or edema-like disorders upon the administration of a PPAR-agonist, which may predispose individuals to developing such a disorder. For example, polymorphisms in the renin gene described herein are associated with the incidence of dose-dependent peripheral edema or edema-like disorders and are useful for predicting the likelihood that an individual will be susceptible to such a disorder, or that such an individual may have an increased susceptibility to such a disorder, upon the administration of a PPAR-agonist.

By altering amino acid sequence, SNPs may alter the function of the encoded proteins. The discovery of the SNP facilitates biochemical analysis of the variants and the development of assays to characterize the variants and to screen for pharmaceutical compounds that would interact directly with one or another form of the protein. SNPs (including silent SNPs) may also alter the regulation of the gene at the transcriptional or post-transcriptional level. SNPs (including silent SNPs) also enable the development of specific DNA, RNA, or protein-based diagnostics that detect the presence or absence of the polymorphism in particular conditions.

Some SNPs that alter the amino acid sequence of an encoded protein may alter the function of said proteins. The discovery of the SNP facilitates biochemical analysis of the variants and the development of assays to characterize the variants and to screen for pharmaceutical compounds that would interact directly with one or another form of the protein. SNPs (including silent SNPs) may also alter the regulation of the gene at the transcriptional or post-transcriptional level. SNPs (including silent SNPs) also enable the development of specific DNA, RNA, or protein-based diagnostics that detect the presence or absence of the polymorphism in particular conditions.

The phrase "PPAR-agonist" is meant to encompass compounds, including small molecules, antibodies, RNAi reagents, siRNA reagents, antisense compounds, or any compound in general capable of increasing the activity or expression of one or more peroxisome proliferator activator receptors (PPAR), including but not limited to, PPAR-alpha agonists, PPAR-beta agonists, PPAR-gamma agonists, and PPAR-delta agonists, including mono-PPAR-alpha agonists, mono-PPAR-beta agonists, mono-PPAR-gamma agonists, mono-PPAR-delta agonists, dual PPAR-alpha and gamma agonists, and any combination of the same. In addition, such PPAR-agonists are necessarily meant to encompass the following, non-limiting compounds: Muraglitazar, peliglitazar, Farglitazar, thiazolidinediones class of PPAR-agonists, Troglitazone, Pioglitazone, Rosiglitazone, MCC555, KRP297, JTT-501, BM 17.0744, L764486, GW501516, NN622, bezafibrate, gemfibrozil, fibrate class of PPAR—agonists, DRF 2725, WY 14,643, SB 213068, Tesaglitazar (AZ 242), Avandaryl, Naveglitazar, Ragaglitazar (NN622), PLX 204, PLX 134, PLX 203, CS 7017, DRF 10945, AVE 0847, AVE 8134, 641597 (GSK), 590735 (GSK), MK 767, AA 10090, LY 674, LY 929, T 131, DRF 4158, CLX 0921, NS 220, LY 293111, DRF 4832, GW 7282, 501516 (GSK), LG 100754, GW 544, AR H049020, AK-109, E-3030 (Eisai), CS-7017 (Sankyo), DRF-10945, KRP-101, ONO-5129, TY-51501, GSK-677954, LSN-862, LY-518674, GW-590735, KT6-207, K-111 (Roche), Bay-54-9801 (GSK), R-483 (Roche), EMD-336340 (Merck KGaA), LR-90 (Merck KGaA), CLX-0940, CLX-0921, LG-100754, GW409890, SB-219994, NIP-223, T-174 (Tanabe Seiyaku), balaglitazone (DRF-2593), VDO-52, GW-1929, NC-2100, netoglitazone, ciglitazone, LGD 1268, LG 101506, LGD 1324, GW 9578, Englitazone, and/or Darglitazone.

A single nucleotide polymorphism occurs at a polymorphic locus occupied by a single nucleotide, which is the site of variation between allelic sequences. The site is usually preceded by and followed by highly conserved sequences of the allele (e.g., sequences that vary in less than 1/100 or 1/1000 members of the populations).

A single nucleotide polymorphism usually arises due to substitution of one nucleotide for another at the polymorphic locus. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele. Typically the polymorphic locus is occupied by a base other than the reference base. For example, where the reference allele contains the base "T" at the polymorphic site, the altered allele can contain a "C", "G" or "A" at the polymorphic locus.

For the purposes of the present invention the terms "polymorphic position", "polymorphic site", "polymorphic locus", and "polymorphic allele" shall be construed to be equivalent and are defined as the location of a sequence identified as having more than one nucleotide represented at that location in a population comprising at least one or more individuals, and/or chromosomes.

Probe hybridizations are usually performed under stringent conditions, for example, at a salt concentration of no more than 1 M and a temperature of at least 25° C. For example, conditions of 5×SSPE (750 mM NaCl, mM NaPhosphate, mM EDT A, pH 7.4) and a temperature of 25-30° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

Wherever the terms "compound A", "Com. A" are used herein, it is understood (unless otherwise indicated) that the compound 'N-[(4-methoxyphenoxy)carbonyl]-N-[[4-[2-(5-methyl-2-phenyl-4-oxazolyl)ethoxy]phenyl]methyl] glycine having the following structure (I):

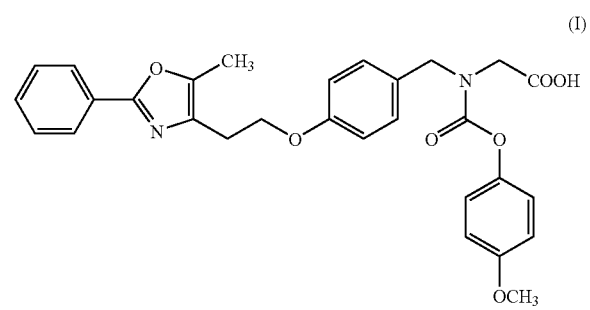

(I)

is intended (also referred hereinafter as "((4-methoxy-phenoxycarbonyl)-{4-[2-(5-methyl-2-phenyl-oxazol-4-yl)-ethoxy]-benzyl}-amino)-acetic acid)", "muraglitazar", or PARGLUVA®), as well as all pharmaceutically acceptable salts thereof. Use of the term encompasses (unless otherwise indicated) solvates (including hydrates), crystal structures (including polymorphic forms of such structures) and salts of the compound (I). Pharmaceutical compositions of Com. A include all pharmaceutically acceptable Dompositions comprising Corn. A and one or more diluents, vehicles and/or excipients, such as those compositions described in U.S. Pat. No. 6,414,002 (described in Example 230) and U.S. Ser. No. 11/130,048, filed May 16, 2005, incorporated herein by reference.

The term "isolated" is used herein to indicate that the material in question exists in a physical milieu distinct from that in which it occurs in nature, and thus is altered "by the hand of man" from its natural state.

On one hand, and in specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, and may comprise all or a portion of an intron. In another embodiment, the polynucleotides preferentially do not contain the genomic sequence of the gene or genes flanking the human renin (i.e., 5' or 3' to the renin gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

On the other hand, and in specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, comprise a portion of non-coding sequences, comprise a portion of an intron sequence, etc., or any combination of the latter, as disclosed herein. Alternatively, the polynucleotides of the invention may comprise the entire coding sequence, the entire 5' non-coding sequence, the entire 3' non-coding sequence, an entire intron sequence, an entire exon sequence, or any combination of the latter, as disclosed herein. In another embodiment, the polynucleotides may correspond to a genomic sequence flanking a gene (i.e., 5' or 3' to the gene of interest in the genome). In other embodiments, the polynucleotides of the invention may contain the non-coding sequence of more than 1000, 500, 250, 100, 50, 25, 20, 15, 10, 5, 4, 3, 2, or 1 genomic flanking gene(s).

As used herein, a "polynucleotide" refers to a molecule comprising a nucleic acid of SEQ ID NO:1, 2, 3, 4, 5, 6, 7, 37, 39, 50, or 52. For example, the polynucleotide can contain the nucleotide sequence of the full length cDNA sequence, including the 5' and 3' untranslated sequences, the coding region, with or without a signal sequence, the secreted protein coding region, and the genomic sequence with or without the accompanying promoter and transcriptional termination sequences, as well as fragments, epitopes, domains, and variants of the nucleic acid sequence. Moreover, as used herein, a "polypeptide" refers to a molecule having the translated amino acid sequence generated from the polynucleotide as defined.

Unless otherwise indicated, all nucleotide sequences determined by sequencing a DNA molecule herein were determined using an automated DNA sequencer (such as the Model 3730-XL from Applied Biosystems, Inc., and/or ther PE 9700 from Perkin Elmer), and all amino acid sequences of polypeptides encoded by DNA molecules determined herein were predicted by translation of a DNA sequence determined above. The nucleotide sequence can also be determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion. Since the present relates to the identification of single nucleotide polymorphisms whereby the novel sequence differs by as few as a single nucleotide from a reference sequence, identified SNPs were multiply verified to ensure each novel sequence represented a true SNP.

Using the information provided herein, a nucleic acid molecule of the present invention encoding a polypeptide of the present invention may be obtained using standard cloning and screening procedures, such as those for cloning cDNAs using mRNA as starting material.

A "polynucleotide" of the present invention also includes those polynucleotides capable of hybridizing, under stringent hybridization conditions, to sequences described herein, or the complement thereof. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65 degree C.

The polynucleotide of the present invention can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W.H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

The term "organism" as referred to herein is meant to encompass any organism referenced herein, though preferably to eukaryotic organisms, more preferably to mammals, and most preferably to humans.

As used herein the terms "modulate" or "modulates" refer to an increase or decrease in the amount, quality or effect of a particular activity, DNA, RNA, or protein. The definition of "modulate" or "modulates" as used herein is meant to encompass agonists and/or antagonists of a particular activity, DNA, RNA, or protein.

Polynucleotides and Polypeptides of the Invention
Features of Gene No:1

The present invention relates to isolated nucleic acid molecules comprising, or alternatively consisting of, all or a portion of one or more alleles of Renin-SNP3 of the human renin gene, as provided in FIGS. 1A-M (SEQ ID NO:1) comprising at least one polymorphic locus. The allele described for Renin-SNP3 in FIGS. 1A-M (SEQ ID NO:1) represents the reference allele for this SNP and is exemplified by a "G" at nucleotide position 12586. Fragments of this polynucleotide are at least about 10, at least about 20, at least about 40, or at least about 100, contiguous nucleotides and comprise one or more reference alleles at the nucleotide position(s) provided in FIGS. 1A-M (SEQ ID NO:1).

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the nucleotide present at nucleotide position 12586 of SEQ ID NO:1, from a DNA sample to be assessed, or the corresponding nucleotide at this position if only a fragment of the sequence provided as SEQ ID NO:1 is assessed. The presence of the reference allele at said position indicates that the individual from whom said DNA sample or fragment was obtained has an increased likelihood of developing dose-dependent peripheral edema or an edema-like disorder upon the administration of a pharmaceutically acceptable amount of a PPAR-agonist, comprising the step of identifying the nucleotide present at nucleotide position 12586 of SEQ ID NO:2, from a DNA sample to be assessed, or the corresponding nucleotide at this position if only a fragment of the sequence provided as SEQ ID NO:2 is assessed. The presence of the variable allele at said position indicates that the individual from whom said DNA sample or fragment was obtained has a decreased likelihood of developing dose-dependent peripheral edema or an edema-like disorder upon the administration of a pharmaceutically acceptable amount of a PPAR-agonist than an individual having the reference allele(s) at said position(s); or an decreased likelihood of developing more severe peripheral edema symptoms upon administration of the same.

Importantly, the presence of the reference allele at said position in a DNA sample provided by an individual indicates that said individual should be monitored more closely if an increased dosage of a PPAR-agonist is contemplated in order to avoid the potential of increasing the likelihood of developing dose-dependent peripheral edema or an edema-like disorder relative to another individual having the variant allele(s) at said position.

Representative disorders which may be detected, diagnosed, identified, treated, prevented, and/or ameliorated by the SNPs and methods of the present invention include, the following, non-limiting diseases and disorders: dose-dependent peripheral edema, edema, susceptibility to developing dose-dependent peripheral edema or an edema-like disorder upon the administration of a pharmaceutically acceptable amount of a PPAR-agonist, susceptibility to developing dose-dependent peripheral edema or an edema-like disorder upon the administration of an increased level of a PPAR-agonist, adverse reactions associated with PPAR-agonist, disorders associated with aberrant renin expression, disorders associated with aberrant renin regulation, disorders associated with aberrant renin activity, disorders associated with aberrant regulation of renin by aldosterone, disorders associated with aberrant angiotensin II peptide levels, disorders associated with aberrant adrenal and renal vascular responses to angiotensin II, disorders associated with refractory responses to angiotensin II antagonists, hypertension, high blood pressure, hypotension, low-renin essential hypertension, high-renin essential hypertension, atherosclerosis, congestive heart failure, pulmonary edema, beta blocker induced edema, and beta-1 blocker induced edema.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

Features of Gene No:2

The present invention relates to isolated nucleic acid molecules comprising, or alternatively consisting of, all or a portion of one or more alleles of Renin-SNP3 of the human renin gene, as provided in FIGS. 2A-M (SEQ ID NO:2) comprising at least one polymorphic locus. The allele described for Renin-SNP3 in FIGS. 2A-M (SEQ ID NO:2) represents the variable allele for this SNP and is exemplified by an "A" at nucleotide position 12586. Fragments of this polynucleotide are at least about 10, at least about 20, at least about 40, at least about 100, contiguous nucleotides and comprise one or more variable alleles at the nucleotide position(s) provided in FIGS. 2A-M (SEQ ID NO:2).

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the nucleotide present at nucleotide position 12586 of SEQ ID NO:2, from a DNA sample to be assessed, or the corresponding nucleotide at this position if only a fragment of the sequence provided as SEQ ID NO:2 is assessed. The presence of the variable allele at said position indicates that the individual from whom said DNA sample or fragment was obtained has a decreased likelihood of developing dose-dependent peripheral edema or an edema-like disorder upon the administration of a pharmaceutically acceptable amount of a PPAR-agonist than an individual having the reference allele(s) at said position(s); or an decreased likelihood of developing more severe peripheral edema symptoms upon administration of the same.

Importantly, the presence of the variable allele at said position in a nucleic acid sample provided by an individual, indicates that said individual may be administered a correspondingly higher amount of a PPAR-agonist without increasing the likelihood of developing dose-dependent peripheral edema or an edema-like disorder relative to another individual having the reference allele(s) at said position. Therefore, such individuals may have the level of administered PPAR-agonist "titrated-up" in a safe manner.

Representative disorders which may be detected, diagnosed, identified, treated, prevented, and/or ameliorated by the SNPs and methods of the present invention include, the following, non-limiting diseases and disorders: dose-dependent peripheral edema, edema, susceptibility to acquiring a peripheral edema or an edema-like disorder upon the administration of a pharmaceutically acceptable amount of a PPAR-agonist, adverse reactions associated with PPAR-agonist, disorders associated with aberrant renin expression, disorders associated with aberrant renin regulation, disorders associated with aberrant renin activity, disorders associated with aberrant regulation of renin by aldosterone, disorders associated with aberrant angiotensin II peptide levels, disorders associated with aberrant adrenal and renal vascular responses to angiotensin II, disorders associated with refractory responses to angiotensin II antagonists, hypertension, high blood pressure, hypotension, low-renin essential hypertension, high-renin essential hypertension, atherosclerosis, congestive heart failure, pulmonary edema, beta blocker induced edema, and beta-1 blocker induced edema.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

Features of Gene No:3

The present invention relates to isolated nucleic acid molecules comprising, or alternatively consisting of, all or a portion of one or more alleles of Renin-SNP5 of the human renin gene, as provided in FIGS. 3A-M (SEQ ID NO:3) comprising at least one polymorphic locus. The allele described for Renin-SNP5 in FIGS. 3A-M (SEQ ID NO:3) represents the reference allele for this SNP and is exemplified by a "A" at nucleotide position 10096. Fragments of this polynucleotide are at least about 10, at least about 20, at least about 40, or at least about 100, contiguous nucleotides and comprise one or more reference alleles at the nucleotide position(s) provided in FIGS. 3A-M (SEQ ID NO:3).

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the nucleotide present at nucleotide position 10096 of SEQ ID NO:3, from a DNA sample to be assessed, or the corresponding nucleotide at this position if only a fragment of the sequence provided as SEQ ID NO:3 is assessed. The presence of the reference allele at said position indicates that the individual from whom said DNA sample or fragment was obtained has an increased likelihood of developing dose-dependent peripheral edema or an edema-like disorder upon the administration of a pharmaceutically acceptable amount of a PPAR-agonist than an individual having the alternate (variant) allele(s) at said position(s), or an increased likelihood of developing more severe peripheral edema symptoms upon administration of the same.

Importantly, the presence of the reference allele at said position indicates that said individual should be monitored more closely if an increase in dosage of a PPAR-agonist is contemplated in order to avoid the potential of increasing the likelihood of developing dose-dependent peripheral edema or an edema-like disorder relative to another individual having the variable allele(s) at said position.

Representative disorders which may be detected, diagnosed, identified, treated, prevented, and/or ameliorated by the SNPs and methods of the present invention include, the following, non-limiting diseases and disorders: dose-dependent peripheral edema, edema, susceptibility to developing dose-dependent a peripheral edema or an edema-like disorder upon the administration of a pharmaceutically acceptable amount of a PPAR-agonist, adverse reactions associated with a PPAR-agonist, disorders associated with aberrant renin expression, disorders associated with aberrant renin regulation, disorders associated with aberrant renin activity, disorders associated with aberrant regulation of renin by aldosterone, disorders associated with aberrant angiotensin II peptide levels, disorders associated with aberrant adrenal and renal vascular responses to angiotensin II, disorders associated with refractory responses to angiotensin II antagonists, hypertension, high blood pressure, hypotension, low-renin essential hypertension, high-renin essential hypertension, atherosclerosis, congestive heart failure, pulmonary edema, beta blocker induced edema, and beta-1 blocker induced edema.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

Features of Gene No:4

The present invention relates to isolated nucleic acid molecules comprising, or alternatively consisting of, all or a portion of one or more alleles of Renin-SNP5 of the human renin gene, as provided in FIGS. 4A-M (SEQ ID NO:4) comprising at least one polymorphic locus. The allele described for Renin-SNP5 in FIGS. 4A-M (SEQ ID NO:4) represents the variable allele for this SNP and is exemplified by a "G" at nucleotide position 10096. Fragments of this polynucleotide are at least about 10, at least about 20, at least about 40, or at least about 100, contiguous nucleotides and comprise one or more variable alleles at the nucleotide position(s) provided in FIGS. 4A-M (SEQ ID NO:4).

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of PPAR-agonist, comprising the step of identifying the nucleotide present at nucleotide position 10096 of SEQ ID NO:4, from a DNA sample to be assessed, or the corresponding nucleotide at this position if only a fragment of the sequence provided as SEQ ID NO:4 is assessed. The presence of the variable allele at said position indicates that the individual from whom said DNA sample or fragment was obtained has a decreased likelihood of developing dose-dependent peripheral edema or an edema-like disorder upon the administration of a pharmaceutically acceptable amount of a PPAR-agonist than an individual having the reference allele(s) at said position(s), or an decreased likelihood of developing more severe peripheral edema symptoms upon administration of the same.

Importantly, the presence of the variable allele at said position indicates that an individual may be administered a correspondingly higher amount of a PPAR-agonist without increasing the likelihood of developing dose-dependent peripheral edema or an edema-like disorder relative to another individual having the reference allele(s) at said position. Such patients may have their dosages "titrated-up" in a safe manner.

Representative disorders which may be detected, diagnosed, identified, treated, prevented, and/or ameliorated by the SNPs and methods of the present invention include, the following, non-limiting diseases and disorders: dose-dependent peripheral edema, edema, susceptibility to developing dose-dependent peripheral edema or an edema-like disorder upon the administration of a pharmaceutically acceptable amount of a PPAR-agonist, adverse reactions associated with a PPAR-agonist, disorders associated with aberrant renin expression, disorders associated with aberrant renin regulation, disorders associated with aberrant renin activity, disorders associated with aberrant regulation of renin by aldosterone, disorders associated with aberrant angiotensin II peptide levels, disorders associated with aberrant adrenal and renal vascular responses to angiotensin II, disorders associated with refractory responses to angiotensin II antagonists, hypertension, high blood pressure, hypotension, low-renin essential hypertension, high-renin essential hypertension, atherosclerosis, congestive heart failure, pulmonary edema, beta blocker induced edema, and beta-1 blocker induced edema.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

Features of Gene No:5

The present invention relates to isolated nucleic acid molecules comprising, or alternatively consisting of, all or a portion of one or more alleles of Renin-SNP7 of the human renin gene, as provided in FIGS. 5A-M (SEQ ID NO:5) comprising at least one polymorphic locus. The allele described for Renin-SNP7 in FIGS. 5A-M (SEQ ID NO:5) represents the reference allele for this SNP and is exemplified by a "G" at nucleotide position 13076. Fragments of this polynucleotide are at least about 10, at least about 20, at least about 40, or at least about 100, contiguous nucleotides and comprise one or more reference alleles at the nucleotide position(s) provided in FIGS. 5A-M (SEQ ID NO:5).

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the nucleotide present at nucleotide position 13076 of SEQ ID NO:5, from a DNA sample to be assessed, or the corresponding nucleotide at this position if only a fragment of the sequence provided as SEQ ID NO:5 is assessed. The presence of the reference allele at said position indicates that the individual from whom said DNA sample or fragment was obtained has an increased likelihood of developing dose-dependent peripheral edema or an edema-like disorder upon the administration of a pharmaceutically acceptable amount of PPAR-agonist than an individual having the alternate (variant) allele(s) at said position(s), or an increased likelihood of developing more severe peripheral edema symptoms upon administration of the same.

Importantly, the presence of the reference allele at said position indicates that an individual should be monitored more closely if an increase in dosage of a PPAR-agonist is contemplated in order to avoid the potential of increasing the likelihood of developing dose-dependent peripheral edema or an edema-like disorder relative to another individual having the variant allele(s) at said position.

Representative disorders which may be detected, diagnosed, identified, treated, prevented, and/or ameliorated by the SNPs and methods of the present invention include, the following, non-limiting diseases and disorders: dose-dependent peripheral edema, edema, susceptibility to developing dose-dependent peripheral edema or an edema-like disorder upon the administration of a pharmaceutically acceptable amount of a PPAR-agonist, adverse reactions associated with a PPAR-agonist, disorders associated with aberrant renin expression, disorders associated with aberrant renin regulation, disorders associated with aberrant renin activity, disorders associated with aberrant regulation of renin by aldosterone, disorders associated with aberrant angiotensin II peptide levels, disorders associated with aberrant adrenal and renal vascular responses to angiotensin II, disorders associated with refractory responses to angiotensin II antagonists, hypertension, high blood pressure, hypotension, low-renin essential hypertension, high-renin essential hypertension, atherosclerosis, congestive heart failure, pulmonary edema, beta blocker induced edema, and beta-1 blocker induced edema.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

Features of Gene No:6

The present invention relates to isolated nucleic acid molecules comprising, or alternatively consisting of, all or a portion of one or more alleles of Renin-SNP7 of the human renin gene, as provided in FIGS. 6A-M (SEQ ID NO:6) comprising at least one polymorphic locus. The allele described for Renin-SNP7 in FIGS. 6A-M (SEQ ID NO:6) represents the variable allele for this SNP and is exemplified by the deletion of the "G" nucleotide at nucleotide position 13076. Fragments of this polynucleotide are at least about 10, at least about 20, at least about 40, or at least about 100, contiguous nucleotides and comprise one or more variable alleles at the nucleotide position(s) provided in FIGS. 6A-M (SEQ ID NO:6).

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the nucleotide present at nucleotide position 13076 of SEQ ID NO:6, from a DNA sample to be assessed, or the corresponding nucleotide at this position if only a fragment of the sequence provided as SEQ ID NO:6 is assessed. The presence of the variable allele at said position indicates that the individual from whom said DNA sample or fragment was obtained has a decreased likelihood of developing dose-dependent peripheral edema or an edema-like disorder upon the administration of a pharmaceutically acceptable amount of a PPAR-agonist than an individual having the reference allele(s) at said position(s), or a decreased likelihood of developing more severe peripheral edema symptoms upon administration of the same.

Importantly, the presence of the variable allele at said position indicates that said individual may be administered a correspondingly higher amount of a PPAR-agonist without increasing the likelihood of developing dose-dependent peripheral edema or an edema-like disorder relative to another individual having the reference allele(s) at said position. Such patients may have their dosages "titrated-up" in a safe manner.

Representative disorders which may be detected, diagnosed, identified, treated, prevented, and/or ameliorated by the SNPs and methods of the present invention include, the following, non-limiting diseases and disorders: dose-dependent peripheral edema, edema, susceptibility to developing dose-dependent peripheral edema or an edema-like disorder upon the administration of a pharmaceutically acceptable amount of a PPAR-agonist, adverse reactions associated with a PPAR-agonist, disorders associated with aberrant renin expression, disorders associated with aberrant renin regulation, disorders associated with aberrant renin activity, disorders associated with aberrant regulation of renin by aldosterone, disorders associated with aberrant angiotensin II peptide levels, disorders associated with aberrant adrenal and renal vascular responses to angiotensin II, disorders associated with refractory responses to angiotensin II antagonists, hypertension, high blood pressure, hypotension, low-renin essential hypertension, high-renin essential hypertension, atherosclerosis, congestive heart failure, pulmonary edema, beta blocker induced edema, and beta-1 blocker induced edema.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

Features of Gene No:7

The present invention relates to isolated nucleic acid molecules comprising, or alternatively consisting of, all or a portion of one or more alleles of the human renin gene, as provided in FIGS. 7A-M (SEQ ID NO:7) comprising at least one polymorphic locus. The polynucleotide sequence provided in FIGS. 7A-M (SEQ ID NO:7) comprises, or alternatively consists of, the polymorphic loci of Renin-SNP3, Renin-SNP5, and/or Renin-SNP7, and may contain the reference or variable allele at each polymorphic locus, in addition to any combination thereof. The reference allele(s) at loci 12586, 10096, and 13076 of SEQ ID NO:7 are exemplified by a "G", an "A", and a "G", respectively; while the variable allele at these loci are exemplified by an "A", a "G", and a deletion of the "G" nucleotide, respectively. Fragments of this polynucleotide are at least about 10, at least about 20, at least about 40, or at least about 100, contiguous nucleotides and comprise one or more reference or variable alleles at the nucleotide position(s) provided in FIGS. 7A-M (SEQ ID NO:7).

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the nucleotides present at nucleotide position 12586, 10096, and/or 13076 of SEQ ID NO:7, from a DNA sample to be assessed, or the corresponding nucleotide at these positions if only a fragment of the sequence provided as SEQ ID NO:7 is assessed. The presence of one or more variable alleles at said position(s) indicates that the individual from whom said DNA sample or fragment was obtained has a decreased likelihood of developing dose-dependent peripheral edema or an edema-like disorder upon the administration of a pharmaceutically acceptable amount of a PPAR-agonist than an individual having one or more reference allele(s) at said position(s), or a decreased likelihood of developing more severe peripheral edema symptoms upon administration of the same. The presence of one or more reference alleles at said position(s) indicates that the individual from whom said DNA sample or fragment was obtained has an increased likelihood of developing dose-dependent peripheral edema or an edema-like disorder upon the administration of a pharmaceutically acceptable amount of PPAR-agonist than an individual having the alternate (variant) allele(s) at said position(s), or an increased likelihood of developing more severe peripheral edema symptoms upon administration of the same.

Importantly, the presence of the reference allele at said one or more positions indicates that said individual should be monitored more closely if an increase in dosage of a PPAR-agonist is contemplated in order to avoid the potential of increasing the likelihood of developing dose-dependent peripheral edema or an edema-like disorder relative to another individual having the variable allele(s) at said position; while the presence of the variable allele at said position indicates that said individual may be administered a correspondingly higher amount of a PPAR-agonist without increasing the likelihood of developing dose-dependent peripheral edema or an edema-like disorder relative to another individual having the reference allele(s) at said position. Such patients may have their dosages "titrated-up" in a safe manner.

Representative disorders which may be detected, diagnosed, identified, treated, prevented, and/or ameliorated by the SNPs and methods of the present invention include, the following, non-limiting diseases and disorders: dose-dependent peripheral edema, edema, susceptibility to developing dose-dependent peripheral edema or an edema-like disorder upon the administration of a pharmaceutically acceptable amount of a PPAR-agonist, adverse reactions associated with a PPAR-agonist, disorders associated with aberrant renin expression, disorders associated with aberrant renin regulation, disorders associated with aberrant renin activity, disorders associated with aberrant regulation of renin by aldosterone, disorders associated with aberrant angiotensin II peptide levels, disorders associated with aberrant adrenal and renal vascular responses to angiotensin II, disorders associated with refractory responses to angiotensin II antagonists, hypertension, high blood pressure, hypotension, low-renin essential hypertension, high-renin essential hypertension, atherosclerosis, congestive heart failure, pulmonary edema, beta blocker induced edema, and beta-1 blocker induced edema.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

Features of Gene No:8

The present invention relates to isolated nucleic acid molecules comprising, or alternatively consisting of, all or a portion of one or more alleles of ET1-SNP1 of the human endothelin-1 gene, as provided in FIGS. 13A-B (SEQ ID NO:37) comprising at least one polymorphic locus. The allele described for ET1-SNP1 in FIGS. 13A-B (SEQ ID NO:37) represents the reference allele for this SNP and is exemplified by a "G" at nucleotide position 797. Fragments of this polynucleotide are at least about 10, at least about 20, at least about 40, or at least about 100, contiguous nucleotides and comprise one or more reference alleles at the nucleotide position(s) provided in FIGS. 13A-B (SEQ ID NO:37).

The present invention further relates to isolated proteins or polypeptides comprising, or alternatively, consisting of all or a portion of the encoded variant amino acid sequence of human endothelin-1 (e.g., wherein reference to wildtype or reference endothelin-1 polypeptide is exemplified by SEQ ID NO:38). Preferred portions are at least 10, preferably at least 20, preferably at least 40, preferably at least 100, contiguous polypeptides and comprises a "K" at the amino acid position corresponding to amino acid 198 of the endothelin-1 polypeptide, or a portion of SEQ ID NO:38. The invention further relates to isolated nucleic acid molecules encoding such polypeptides or proteins, as well as to antibodies that bind to such proteins or polypeptides.

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the nucleotide present at nucleotide position 797 of SEQ ID NO:37, from a DNA sample to be assessed, or the corresponding nucleotide at this position if only a fragment of the sequence provided as SEQ ID NO:37 is assessed. The presence of the reference allele at said position indicates that the individual from whom said DNA sample or fragment was obtained has an increased likelihood of developing dose-dependent peripheral edema or an edema-like disorder upon the administration of a pharmaceutically acceptable amount of a PPAR-agonist, compared to an individual having the alternate (variant) allele(s) at said position(s); or at least an increased likelihood of developing more severe peripheral edema symptoms upon administration of the same.

Importantly, the presence of the reference allele at said position in a DNA sample provided by an individual indicates that said individual should be monitored more closely if an increased dosage of a PPAR-agonist is contemplated in order to avoid the potential of increasing the likelihood of developing dose-dependent peripheral edema or an edema-like disorder relative to another individual having the variant allele(s) at said position.

Representative disorders which may be detected, diagnosed, identified, treated, prevented, and/or ameliorated by the SNPs and methods of the present invention include, the following, non-limiting diseases and disorders: dose-dependent peripheral edema, edema, susceptibility to developing dose-dependent peripheral edema or an edema-like disorder upon the administration of a pharmaceutically acceptable amount of a PPAR-agonist, susceptibility to developing dose-dependent peripheral edema or an edema-like disorder upon the administration of an increased level of a PPAR-agonist, adverse reactions associated with PPAR-agonist, disorders associated with aberrant endothelin-1 expression, disorders associated with aberrant endothelin-1 regulation, disorders associated with aberrant endothelin-1 activity, disorders associated with aberrant regulation of endothelin-1 by aldosterone, disorders associated with aberrant angiotensin II peptide levels, disorders associated with aberrant adrenal and renal vascular responses to angiotensin II, disorders associated with refractory responses to angiotensin II antagonists, hypertension, high blood pressure, hypotension, low-endothelin-1 essential hypertension, high-endothelin-1 essential hypertension, atherosclerosis, congestive heart failure, pulmonary edema, beta blocker induced edema, and beta-1 blocker induced edema.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the amino acid present at amino acid position 198 of SEQ ID NO:38, from a sample to be assessed, or the corresponding amino acid at this position if only a fragment of the sequence provided as SEQ ID NO:38 is assessed. The presence of the reference allele (e.g., "K") at said position indicates that the individual from whom said sample or fragment was obtained has an increased likelihood of developing dose-dependent peripheral edema or an edema-like disorder upon the administration of a pharmaceutically acceptable amount of a PPAR-agonist, compared to an individual having the alternate (variant) allele(s) at said position(s); or at least an increased likelihood of developing more severe peripheral edema symptoms upon administration of the same.

Importantly, the presence of the reference allele at said amino acid position in a sample provided by an individual indicates that said individual should be monitored more closely if an increased dosage of a PPAR-agonist is contemplated in order to avoid the potential of increasing the likelihood of developing dose-dependent peripheral edema or an edema-like disorder relative to another individual having the variable allele(s) at said position.

In preferred embodiments, the following N-terminal reference allele endothelin-1 deletion polypeptides are encompassed by the present invention: M1-W212, D2-W212, Y3-W212, L4-W212, L5-W212, M6-W212, 17-W212, F8-W212, S9-W212, L10-W212, L11-W212, F12-W212, V13-W212, A14-W212, C15-W212, Q16-W212, G17-W212, A18-W212, P19-W212, E20-W212, T21-W212, A22-W212, V23-W212, L24-W212, G25-W212, A26-W212, E27-W212, L28-W212, S29-W212, A30-W212, V31-W212, G32-W212, E33-W212, N34-W212, G35-W212, G36-W212, E37-W212, K38-W212, P39-W212, T40-W212, P41-W212, S42-W212, P43-W212, P44-W212, W45-W212, R46-W212, L47-W212, R48-W212, R49-W212, S50-W212, K51-W212, R52-W212, C53-W212, S54-W212, C55-W212, S56-W212, S57-W212, L58-W212, M59-W212, D60-W212, K61-W212, E62-W212, C63-W212, V64-W212, Y65-W212, F66-W212, C67-W212, H68-W212, L69-W212, D70-W212, 171-W212, 172-W212, W73-W212, V74-W212, N75-W212, T76-W212, P77-W212, E78-W212, H79-W212, V80-W212, V81-W212, P82-W212, Y83-W212, G84-W212, L85-W212, G86-W212, S87-W212, P88-W212, R89-W212, S90-W212, K91-W212, R92-W212, A93-W212, L94-W212, E95-W212, N96-W212, L97-W212, L98-W212, P99-W212, T100-W212, K101-W212, A102-W212, T103-W212, D104-W212, R105-W212, E106-W212, N107-W212, R108-W212, C109-W212, Q110-W212, C111-W212, A112-W212, S113-W212, Q114-W212, K115-W212, D116-W212, K117-W212, K118-W212, C119-W212, W120-W212, N121-W212, F122-W212, C123-W212, Q124-W212, A125-W212, G126-W212, K127-W212, E128-W212, L129-W212, R130-W212, A131-W212, E132-W212, D133-W212, I134-W212, M135-W212, E136-W212, K137-W212, D138-W212, W139-W212, N140-W212, N141-W212, H142-W212, K143-W212, K144-W212, G145-W212, K146-W212, D147-W212, C148-W212, S149-W212, K150-W212, L151-W212, G152-W212, K153-W212, K154-W212, C155-W212, I156-W212, Y157-W212, Q158-W212, Q159-W212, L160-W212, V161-W212, R162-W212, G163-W212, R164-W212, K165-W212, I166-W212, R167-W212, R168-W212, S169-W212, S170-W212, E171-W212, E172-W212, H173-

W212, L174-W212, R175-W212, Q176-W212, T177-W212, R178-W212, S179-W212, E180-W212, T181-W212, M182-W212, R183-W212, N184-W212, S185-W212, V186-W212, K187-W212, S188-W212, S189-W212, F190-W212, H191-W212, D192-W212, P193-W212, K194-W212, L195-W212, K196-W212, G197-W212, K198-W212, P199-W212, S200-W212, R201-W212, E202-W212, R203-W212, Y204-W212, V205-W212, and/or T206-W212 of SEQ ID NO:38. Polynucleotide sequences encoding these polypeptides are also provided. The present invention also encompasses the use of these N-terminal reference allele endothelin-1 deletion polypeptides as immunogenic and/or antigenic epitopes as described elsewhere herein.

In preferred embodiments, the following C-terminal reference allele endothelin-1 deletion polypeptides are encompassed by the present invention: M1-W212, M1-H211, M1-A210, M1-R209, M1-N208, M1-H207, M1-T206, M1-V205, M1-Y204, M1-R203, M1-E202, M1-R201, M1-S200, M1-P199, and/or M1-K198 of SEQ ID NO:38. Polynucleotide sequences encoding these polypeptides are also provided. The present invention also encompasses the use of these C-terminal reference allele endothelin-1 deletion polypeptides as immunogenic and/or antigenic epitopes as described elsewhere herein.

Alternatively, preferred polypeptides of the present invention may comprise polypeptide sequences corresponding to, for example, internal regions of the endothelin-1 polypeptide (e.g., any combination of both N- and C-terminal endothelin-1 polypeptide deletions) of SEQ ID NO:38. For example, internal regions could be defined by the equation: amino acid NX to amino acid CX, wherein NX refers to any N-terminal deletion polypeptide amino acid of endothelin-1 (SEQ ID NO:38), and where CX refers to any C-terminal deletion polypeptide amino acid of endothelin-1 (SEQ ID NO:38). Polynucleotides encoding these polypeptides are also provided. The present invention also encompasses the use of these polypeptides as an immunogenic and/or antigenic epitope as described elsewhere herein and are useful for creating allele-specific antibodies to discriminate between the reference and variable allele in a given sample, among other uses described herein. In addition such fragments may also be useful in designing allele-specific hybridization or other means probes to identify the allele to discriminate between the reference and variable allele in a given sample, among other uses described herein.

Features of Gene No:9

The present invention relates to isolated nucleic acid molecules comprising, or alternatively consisting of, all or a portion of one or more alleles of ET 1-SNP 1 of the human endothelin-1 gene, as provided in FIGS. 14A-B (SEQ ID NO:39) comprising at least one polymorphic locus. The allele described for ET1-SNP1 in FIGS. 14A-B (SEQ ID NO:39) represents the variable allele for this SNP and is exemplified by a "t" at nucleotide position 797. Fragments of this polynucleotide are at least about 10, at least about 20, at least about 40, at least about 100, contiguous nucleotides and comprise one or more variable alleles at the nucleotide position(s) provided in FIGS. 14A-B (SEQ ID NO:39).

The present invention further relates to isolated proteins or polypeptides comprising, or alternatively, consisting of all or a portion of the encoded variant amino acid sequence of human endothelin-1 (e.g., wherein reference to variant or variable human endothelin-1 polypeptide is exemplified by SEQ ID NO:40). Preferred portions are at least 10, preferably at least 20, preferably at least 40, preferably at least 100, contiguous polypeptides and comprises a "N" at the amino acid position corresponding to amino acid 198 of the endothelin-1 polypeptide, or a portion of SEQ ID NO:40. The invention further relates to isolated nucleic acid molecules encoding such polypeptides or proteins, as well as to antibodies that bind to such proteins or polypeptides.

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the nucleotide present at nucleotide position 797 of SEQ ID NO:39, from a DNA sample to be assessed, or the corresponding nucleotide at this position if only a fragment of the sequence provided as SEQ ID NO:39 is assessed. The presence of the variable allele at said position indicates that the individual from whom said DNA sample or fragment was obtained has a decreased likelihood of developing dose-dependent peripheral edema or an edema-like disorder upon the administration of a pharmaceutically acceptable amount of a PPAR-agonist than an individual having the reference allele(s) at said position(s); or a decreased likelihood of developing more severe peripheral edema symptoms upon administration of the same.

Importantly, the presence of the reference allele at said nucleic acid position in a sample provided by an individual, indicates that said individual may be administered a correspondingly higher amount of a PPAR-agonist without increasing the likelihood of developing dose-dependent peripheral edema or an edema-like disorder relative to another individual having the reference allele(s) at said position. Therefore, such individuals may have the level of administered PPAR-agonist "titrated-up" in a safe manner.

Representative disorders which may be detected, diagnosed, identified, treated, prevented, and/or ameliorated by the SNPs and methods of the present invention include, the following, non-limiting diseases and disorders: dose-dependent peripheral edema, edema, susceptibility to acquiring a peripheral edema or an edema-like disorder upon the administration of a pharmaceutically acceptable amount of a PPAR-agonist, adverse reactions associated with PPAR-agonist, disorders associated with aberrant endothelin-1 expression, disorders associated with aberrant endothelin-1 regulation, disorders associated with aberrant endothelin-1 activity, disorders associated with aberrant regulation of endothelin-1 by aldosterone, disorders associated with aberrant angiotensin II peptide levels, disorders associated with aberrant adrenal and renal vascular responses to angiotensin II, disorders associated with refractory responses to angiotensin II antagonists, hypertension, high blood pressure, hypotension, low-endothelin-1 essential hypertension, high-endothelin-1 essential hypertension, atherosclerosis, congestive heart failure, pulmonary edema, beta blocker induced edema, and beta-1 blocker induced edema.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the amino acid present at amino acid position 198 of SEQ ID NO:40, from a sample to be assessed, or the corresponding amino acid at this position if only a fragment of the sequence provided as SEQ ID NO:40 is assessed. The presence of the reference allele (e.g., "N") at said position indicates that the individual from whom said sample or fragment was obtained has a decreased likelihood of developing dose-dependent peripheral edema or an edema-like disorder upon the administration of a pharmaceutically acceptable amount of a PPAR-agonist, compared to an individual having the reference allele(s) at said position(s); or at least a decreased likelihood of developing more severe peripheral edema symptoms upon administration of the same.

Importantly, the presence of the variable allele at said amino acid position in a sample provided by an individual indicates that said individual may be administered a correspondingly higher amount of a PPAR-agonist without increasing the likelihood of developing dose-dependent peripheral edema or an edema-like disorder relative to another individual having the reference allele(s) at said position. Therefore, such individuals may have the level of administered PPAR-agonist "titrated-up" in a safe manner.

In preferred embodiments, the following N-terminal variable allele endothelin-1 deletion polypeptides are encompassed by the present invention: M1-W212, D2-W212, Y3-W212, L4-W212, L5-W212, M6-W212, I7-W212, F8-W212, S9-W212, L10-W212, L11-W212, F12-W212, V13-W212, A14-W212, C15-W212, Q16-W212, G17-W212, A18-W212, P19-W212, E20-W212, T21-W212, A22-W212, V23-W212, L24-W212, G25-W212, A26-W212, E27-W212, L28-W212, S29-W212, A30-W212, V31-W212, G32-W212, E33-W212, N34-W212, G35-W212, G36-W212, E37-W212, K38-W212, P39-W212, T40-W212, P41-W212, S42-W212, P43-W212, P44-W212, W45-W212, R46-W212, L47-W212, R48-W212, R49-W212, S50-W212, K51-W212, R52-W212, C53-W212, S54-W212, C55-W212, S56-W212, S57-W212, L58-W212, M59-W212, D60-W212, K61-W212, E62-W212, C63-W212, V64-W212, Y65-W212, F66-W212, C67-W212, H68-W212, L69-W212, D70-W212, I71-W212, I72-W212, W73-W212, V74-W212, N75-W212, T76-W212, P77-W212, E78-W212, H79-W212, V80-W212, V81-W212, P82-W212, Y83-W212, G84-W212, L85-W212, G86-W212, S87-W212, P88-W212, R89-W212, S90-W212, K91-W212, R92-W212, A93-W212, L94-W212, E95-W212, N96-W212, L97-W212, L98-W212, P99-W212, T100-W212, K101-W212, A102-W212, T103-W212, D104-W212, R105-W212, E106-W212, N107-W212, R108-W212, C109-W212, Q110-W212, C111-W212, A112-W212, S113-W212, Q114-W212, K115-W212, D116-W212, K117-W212, K118-W212, C119-W212, W120-W212, N121-W212, F122-W212, C123-W212, Q124-W212, A125-W212, G126-W212, K127-W212, E128-W212, L129-W212, R130-W212, A131-W212, E132-W212, D133-W212, I134-W212, M135-W212, E136-W212, K137-W212, D138-W212, W139-W212, N140-W212, N141-W212, H142-W212, K143-W212, K144-W212, G145-W212, K146-W212, D147-W212, C148-W212, S149-W212, K150-W212, L151-W212, G152-W212, K153-W212, K154-W212, C155-W212, I156-W212, Y157-W212, Q158-W212, Q159-W212, L160-W212, V161-W212, R162-W212, G163-W212, R164-W212, K165-W212, I166-W212, R167-W212, R168-W212, S169-W212, S170-W212, E171-W212, E172-W212, H173-W212, L174-W212, R175-W212, Q176-W212, T177-W212, R178-W212, S179-W212, E180-W212, T181-W212, M182-W212, R183-W212, N184-W212, S185-W212, V186-W212, K187-W212, S188-W212, S189-W212, F190-W212, H191-W212, D192-W212, P193-W212, K194-W212, L195-W212, K196-W212, G197-W212, N198-W212, P199-W212, S200-W212, R201-W212, E202-W212, R203-W212, Y204-W212, V205-W212, and/or T206-W212 of SEQ ID NO:40. Polynucleotide sequences encoding these polypeptides are also provided. The present invention also encompasses the use of these N-terminal endothelin-1 deletion polypeptides as immunogenic and/or antigenic epitopes as described elsewhere herein.

In preferred embodiments, the following C-terminal endothelin-1 deletion polypeptides are encompassed by the present invention: M1-W212, M1-H211, M1-A210, M1-R209, M1-N208, M1-H207, M1-T206, M1-V205, M1-Y204, M1-R203, M1-E202, M1-R201, M1-S200, M1-P199, and/or M1-N198 of SEQ ID NO:40. Polynucleotide sequences encoding these polypeptides are also provided. The present invention also encompasses the use of these C-terminal variable allele endothelin-1 deletion polypeptides as immunogenic and/or antigenic epitopes as described elsewhere herein.

Alternatively, preferred polypeptides of the present invention may comprise polypeptide sequences corresponding to, for example, internal regions of the endothelin-1 polypeptide (e.g., any combination of both N- and C-terminal endothelin-1 polypeptide deletions) of SEQ ID NO:40. For example, internal regions could be defined by the equation: amino acid NX to amino acid CX, wherein NX refers to any N-terminal deletion polypeptide amino acid of endothelin-1 (SEQ ID NO:40), and where CX refers to any C-terminal deletion polypeptide amino acid of endothelin-1 (SEQ ID NO:40). Polynucleotides encoding these polypeptides are also provided. The present invention also encompasses the use of these polypeptides as an immunogenic and/or antigenic epitope as described elsewhere herein and are useful for creating allele-specific antibodies to discriminate between the reference and variable allele in a given sample, among other uses described herein. In addition such fragments may also be useful in designing allele-specific hybridization or other means probes to identify the allele to discriminate between the reference and variable allele in a given sample, among other uses described herein.

Features of Gene No:10

The present invention relates to isolated nucleic acid molecules comprising, or alternatively consisting of, all or a portion of one or more alleles of Beta1-SNP1 of the human β1-adrenergic receptor gene, as provided in FIGS. 18A-B (SEQ ID NO:50) comprising at least one polymorphic locus. The allele described for Beta1-SNP1 in FIGS. 18A-B (SEQ ID NO:50) represents the reference allele for this SNP and is exemplified by a "c" at nucleotide position 1251. Fragments of this polynucleotide are at least about 10, at least about 20, at least about 40, or at least about 100, contiguous nucleotides and comprise one or more reference alleles at the nucleotide position(s) provided in FIGS. 18A-B (SEQ ID NO:50).

The present invention further relates to isolated proteins or polypeptides comprising, or alternatively, consisting of all or a portion of the encoded variant amino acid sequence of human β1-adrenergic receptor (e.g., wherein reference to wildtype or reference endothelin-1 polypeptide is exemplified by SEQ ID NO:51). Preferred portions are at least 10, preferably at least 20, preferably at least 40, preferably at least 100, contiguous polypeptides and comprises a "R" at the amino acid position corresponding to amino acid 389 of the β1-adrenergic receptor polypeptide, or a portion of SEQ ID NO:51. The invention further relates to isolated nucleic acid molecules encoding such polypeptides or proteins, as well as to antibodies that bind to such proteins or polypeptides.

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the nucleotide present at nucleotide position 1251 of SEQ ID NO:50, from a DNA sample to be assessed, or the corresponding nucleotide at this position if only a fragment of the sequence provided as SEQ ID NO:50 is assessed. The presence of the reference allele at said position indicates that the individual from whom said DNA sample or fragment was obtained has a decreased likelihood of developing dose-dependent peripheral edema or an edema-like disorder upon the administration of a pharmaceutically acceptable amount of a PPAR-agonist, compared to an individual having the alternate (variant) allele(s) at said position(s); or at least a decreased likelihood of developing more severe peripheral edema symptoms upon administration of the same.

Importantly, the presence of the reference allele at said nucleic acid position in a sample provided by an individual, indicates that said individual may be administered a correspondingly higher amount of a PPAR-agonist without increasing the likelihood of developing dose-dependent peripheral edema or an edema-like disorder relative to another individual having the variable allele(s) at said position. Therefore, such individuals may have the level of administered PPAR-agonist "titrated-up" in a safe manner.

Representative disorders which may be detected, diagnosed, identified, treated, prevented, and/or ameliorated by the SNPs and methods of the present invention include, the following, non-limiting diseases and disorders: dose-dependent peripheral edema, edema, susceptibility to developing dose-dependent peripheral edema or an edema-like disorder upon the administration of a pharmaceutically acceptable amount of a PPAR-agonist, susceptibility to developing dose-dependent peripheral edema or an edema-like disorder upon the administration of an increased level of a PPAR-agonist, adverse reactions associated with PPAR-agonist, disorders associated with aberrant endothelin-1 expression, disorders associated with aberrant endothelin-1 regulation, disorders associated with aberrant endothelin-1 activity, disorders associated with aberrant regulation of endothelin-1 by aldosterone, disorders associated with aberrant angiotensin II peptide levels, disorders associated with aberrant adrenal and renal vascular responses to angiotensin II, disorders associated with refractory responses to angiotensin II antagonists, hypertension, high blood pressure, hypotension, low-endothelin-1 essential hypertension, high-endothelin-1 essential hypertension, atherosclerosis, congestive heart failure, pulmonary edema, beta blocker induced edema, and beta-1 blocker induced edema.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the amino acid present at amino acid position 389 of SEQ ID NO:51, from a sample to be assessed, or the corresponding amino acid at this position if only a fragment of the sequence provided as SEQ ID NO:51 is assessed. The presence of the reference allele (e.g., "R") at said position indicates that the individual from whom said sample or fragment was obtained has a decreased likelihood of developing dose-dependent peripheral edema or an edema-like disorder upon the administration of a pharmaceutically acceptable amount of a PPAR-agonist, compared to an individual having the alternate (variant) allele(s) at said position(s); or at least a decreased likelihood of developing more severe peripheral edema symptoms upon administration of the same.

Importantly, the presence of the reference allele at said amino acid position in a sample provided by an individual, indicates that said individual may be administered a correspondingly higher amount of a PPAR-agonist without increasing the likelihood of developing dose-dependent peripheral edema or an edema-like disorder relative to another individual having the variable allele(s) at said position. Therefore, such individuals may have the level of administered PPAR-agonist "titrated-up" in a safe manner.

In preferred embodiments, the following N-terminal beta1-adrenergic receptor deletion polypeptides are encompassed by the present invention: M1-V477, G2-V477, A3-V477, G4-V477, V5-V477, L6-V477, V7-V477, L8-V477, G9-V477, A10-V477, S11-V477, E12-V477, P13-V477, G14-V477, N15-V477, L16-V477, S17-V477, S18-V477, A19-V477, A20-V477, P21-V477, L22-V477, P23-V477, D24-V477, G25-V477, A26-V477, A27-V477, T28-V477, A29-V477, A30-V477, R31-V477, L32-V477, L33-V477, V34-V477, P35-V477, A36-V477, S37-V477, P38-V477, P39-V477, A40-V477, S41-V477, L42-V477, L43-V477, P44-V477, P45-V477, A46-V477, S47-V477, E48-V477, S49-V477, P50-V477, E51-V477, P52-V477, L53-V477, S54-V477, Q55-V477, Q56-V477, W57-V477, T58-V477, A59-V477, G60-V477, M61-V477, G62-V477, L63-V477, L64-V477, M65-V477, A66-V477, L67-V477, I68-V477, V69-V477, L70-V477, L71-V477, I72-V477, V73-V477, A74-V477, G75-V477, N76-V477, V77-V477, L78-V477, V79-V477, I80-V477, V81-V477, A82-V477, I83-V477, A84-V477, K85-V477, T86-V477, P87-V477, R88-V477, L89-V477, Q90-V477, T91-V477, L92-V477, T93-V477, N94-V477, L95-V477, F96-V477, I97-V477, M98-V477, S99-V477, L100-V477, A101-V477, S102-V477, A103-V477, D104-V477, L105-V477, V106-V477, M107-V477, G108-V477, L109-V477, L110-V477, V111-V477, V112-V477, P113-V477, F114-V477, G115-V477, A116-V477, T117-V477, I118-V477, V119-V477, V120-V477, W121-V477, G122-V477, R123-V477, W124-V477, E125-V477, Y126-V477, G127-V477, S128-V477, F129-V477, F130-V477, C131-V477, E132-V477, L133-V477, W134-V477, T135-V477, S136-V477, V137-V477, D138-V477, V139-V477, L140-V477, C141-V477, V142-V477, T143-V477, A144-V477, S145-V477, I146-V477, E147-V477, T148-V477, L149-V477, C150-V477, V151-V477, I152-V477, A153-V477, L154-V477, D155-V477, R156-V477, Y157-V477, L158-V477, A159-V477, I160-V477, T161-

V477, S162-V477, P163-V477, F164-V477, R165-V477, Y166-V477, Q167-V477, S168-V477, L169-V477, L170-V477, T171-V477, R172-V477, A173-V477, R174-V477, A175-V477, R176-V477, G177-V477, L178-V477, V179-V477, C180-V477, T181-V477, V182-V477, W183-V477, A184-V477, I185-V477, S186-V477, A187-V477, L188-V477, V189-V477, S190-V477, F191-V477, L192-V477, P193-V477, I194-V477, L195-V477, M196-V477, H197-V477, W198-V477, W199-V477, R200-V477, A201-V477, E202-V477, S203-V477, D204-V477, E205-V477, A206-V477, R207-V477, R208-V477, C209-V477, Y210-V477, N211-V477, D212-V477, P213-V477, K214-V477, C215-V477, C216-V477, D217-V477, F218-V477, V219-V477, T220-V477, N221-V477, R222-V477, A223-V477, Y224-V477, A225-V477, I226-V477, A227-V477, S228-V477, S229-V477, V230-V477, V231-V477, S232-V477, F233-V477, Y234-V477, V235-V477, P236-V477, L237-V477, C238-V477, I239-V477, M240-V477, A241-V477, F242-V477, V243-V477, Y244-V477, L245-V477, R246-V477, V247-V477, F248-V477, R249-V477, E250-V477, A251-V477, Q252-V477, K253-V477, Q254-V477, V255-V477, K256-V477, K257-V477, I258-V477, D259-V477, S260-V477, C261-V477, E262-V477, R263-V477, R264-V477, F265-V477, L266-V477, G267-V477, G268-V477, P269-V477, A270-V477, R271-V477, P272-V477, P273-V477, S274-V477, P275-V477, S276-V477, P277-V477, S278-V477, P279-V477, V280-V477, P281-V477, A282-V477, P283-V477, A284-V477, P285-V477, P286-V477, P287-V477, G288-V477, P289-V477, P290-V477, R291-V477, P292-V477, A293-V477, A294-V477, A295-V477, A296-V477, A297-V477, T298-V477, A299-V477, P300-V477, L301-V477, A302-V477, N303-V477, G304-V477, R305-V477, A306-V477, G307-V477, K308-V477, R309-V477, R3110-V477, P311-V477, S312-V477, R313-V477, L314-V477, V315-V477, A316-V477, L317-V477, R318-V477, E319-V477, Q320-V477, K321-V477, A322-V477, L323-V477, K324-V477, T325-V477, L326-V477, G327-V477, I328-V477, I329-V477, M330-V477, G331-V477, V332-V477, F333-V477, T334-V477, L335-V477, C336-V477, W337-V477, L338-V477, P339-V477, F340-V477, F341-V477, L342-V477, A343-V477, N344-V477, V345-V477, V346-V477, K347-V477, A348-V477, F349-V477, H350-V477, R351-V477, E352-V477, L353-V477, V354-V477, P355-V477, D356-V477, R357-V477, L358-V477, F359-V477, V360-V477, F361-V477, F362-V477, N363-V477, W364-V477, L365-V477, G366-V477, Y367-V477, A368-V477, N369-V477, S370-V477, A371-V477, F372-V477, N373-V477, P374-V477, I375-V477, I376-V477, Y377-V477, C378-V477, R379-V477, S380-V477, P381-V477, D382-V477, F383-V477, R384-V477, K385-V477, A386-V477, F387-V477, Q388-V477, and/or R389-V477 of SEQ ID NO:51. Polynucleotide sequences encoding these polypeptides are also provided. The present invention also encompasses the use of these N-terminal beta1-adrenergic receptor deletion polypeptides as immunogenic and/or antigenic epitopes as described elsewhere herein.

In preferred embodiments, the following C-terminal beta1-adrenergic receptor deletion polypeptides are encompassed by the present invention: M1-V477, M1-K476, M1-S475, M1-E474, M1-S473, M1-A472, M1-F471, M1-G470, M1-P469, M1-R468, M1-C467, M1-P466, M1-E465, M1-D464, M1-L463, M1-S462, M1-S461, M1-D460, M1-S459, M1-D458, M1-A457, M1-A456, M1-A455, M1-G454, M1-G453, M1-N452, M1-C451, M1-G450, M1-A449, M1-W448, M1-P447, M1-E446, M1-L445, M1-L444, M1-R443, M1-A442, M1-P441, M1-P440, M1-T439, M1-A438, M1-G437, M1-V436, M1-V435, M1-D434, M1-D433, M1-D432, M1-D431, M1-D430, M1-D429, M1-S428, M1-A427, M1-A426, M1-G425, M1-P424, M1-S423, M1-P422, M1-P421, M1-P420, M1-G419, M1-P418, M1-R417, M1-A416, M1-L415, M1-C414, M1-G413, M1-S412, M1-A411, M1-R410, M1-P409, M1—R408, M1-D407, M1-G406, M1-H405, M1-T404, M1-A403, M1-H402, M1-R401, M1-R400, M1-R399, M1-A398, M1-A397, M1-R396, M1-R395, M1-A394, M1-C393, M1-C392, M1-L391, M1-L390, and/or M1-R389 of SEQ ID NO:51. Polynucleotide sequences encoding these polypeptides are also provided. The present invention also encompasses the use of these C-terminal beta1-adrenergic receptor deletion polypeptides as immunogenic and/or antigenic epitopes as described elsewhere herein.

Alternatively, preferred polypeptides of the present invention may comprise polypeptide sequences corresponding to, for example, internal regions of the 01-adrenergic receptor polypeptide (e.g., any combination of both N- and C-terminal endothelin-1 polypeptide deletions) of SEQ ID NO:51. For example, internal regions could be defined by the equation: amino acid NX to amino acid CX, wherein NX refers to any N-terminal deletion polypeptide amino acid of endothelin-1 (SEQ ID NO:51), and where CX refers to any C-terminal deletion polypeptide amino acid of endothelin-1 (SEQ ID NO:51). Polynucleotides encoding these polypeptides are also provided. The present invention also encompasses the use of these polypeptides as an immunogenic and/or antigenic epitope as described elsewhere herein and are useful for creating allele-specific antibodies to discriminate between the reference and variable allele in a given sample, among other uses described herein. In addition such fragments may also be useful in designing allele-specific hybridization or other means probes to identify the allele to discriminate between the reference and variable allele in a given sample, among other uses described herein.

Features of Gene No:11

The present invention relates to isolated nucleic acid molecules comprising, or alternatively consisting of, all or a portion of one or more alleles of Beta1-SNP1 of the human β1-adrenergic receptor gene, as provided in FIGS. 19A-B (SEQ ID NO:52) comprising at least one polymorphic locus. The allele described for Beta1-SNP1 in FIGS. 19A-B (SEQ ID NO:52) represents the variable allele for this SNP and is exemplified by a "g" at nucleotide position 1251. Fragments of this polynucleotide are at least about 10, at least about 20, at least about 40, at least about 100, contiguous nucleotides and comprise one or more variable alleles at the nucleotide position(s) provided in FIGS. 19A-B (SEQ ID NO:52).

The present invention further relates to isolated proteins or polypeptides comprising, or alternatively, consisting of all or a portion of the encoded variant amino acid sequence of human β1-adrenergic receptor (e.g., wherein reference to variant or variable human β1-adrenergic receptor polypeptide is exemplified by SEQ ID NO:53). Preferred portions are at least 10, preferably at least 20, preferably at least 40, preferably at least 100, contiguous polypeptides and comprises a "G" at the amino acid position corresponding to amino acid 389 of the β1-adrenergic receptor polypeptide, or a portion of SEQ ID NO:53. The invention further relates to isolated nucleic acid molecules encoding such polypeptides or proteins, as well as to antibodies that bind to such proteins or polypeptides.

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the nucleotide present at nucleotide position 1251 of SEQ ID NO:52, from a DNA sample to be assessed, or the corresponding nucleotide at this position if only a fragment of the sequence provided as SEQ ID NO:52 is assessed. The presence of the variable allele at said position indicates that the individual from whom said DNA sample or fragment was obtained has an increased likelihood of developing dose-dependent peripheral edema or an edema-like disorder upon the administration of a pharmaceutically acceptable amount of a PPAR-agonist than an individual having the reference allele(s) at said position(s); or an increased likelihood of developing more severe peripheral edema symptoms upon administration of the same.

Importantly, the presence of the variable allele at said polynucleotide position in a sample provided by an individual indicates that said individual should be monitored more closely if an increased dosage of a PPAR-agonist is contemplated in order to avoid the potential of increasing the likelihood of developing dose-dependent congestive heart failure or a congestive heart failure-like disorder relative to another individual having the reference allele(s) at said position.

Representative disorders which may be detected, diagnosed, identified, treated, prevented, and/or ameliorated by the SNPs and methods of the present invention include, the following, non-limiting diseases and disorders: dose-dependent peripheral edema, edema, susceptibility to acquiring a peripheral edema or an edema-like disorder upon the administration of a pharmaceutically acceptable amount of a PPAR-agonist, adverse reactions associated with PPAR-agonist, disorders associated with aberrant endothelin-1 expression, disorders associated with aberrant endothelin-1 regulation, disorders associated with aberrant endothelin-1 activity, disorders associated with aberrant regulation of endothelin-1 by aldosterone, disorders associated with aberrant angiotensin II peptide levels, disorders associated with aberrant adrenal and renal vascular responses to angiotensin II, disorders associated with refractory responses to angiotensin II antagonists, hypertension, high blood pressure, hypotension, low-endothelin-1 essential hypertension, high-endothelin-1 essential hypertension, atherosclerosis, congestive heart failure, pulmonary edema, beta blocker induced edema, and beta-1 blocker induced edema.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

In one embodiment, the invention relates to a method for predicting the likelihood that an individual will have a disorder, particularly dose-dependent peripheral edema or an edema-like disorder, or be susceptible to developing dose-dependent peripheral edema or an edema-like disorder upon the administration of a pharmaceutically acceptable amount of a PPAR-agonist, comprising the step of identifying the amino acid present at amino acid position 389 of SEQ ID NO:53, from a sample to be assessed, or the corresponding amino acid at this position if only a fragment of the sequence provided as SEQ ID NO:53 is assessed. The presence of the variable allele (e.g., "G") at said position indicates that the individual from whom said sample or fragment was obtained has an increased likelihood of developing dose-dependent peripheral edema or an edema-like disorder upon the administration of a pharmaceutically acceptable amount of a PPAR-agonist, compared to an individual having the reference allele(s) at said position(s); or at least an increased likelihood of developing more severe peripheral edema symptoms upon administration of the same.

Importantly, the presence of the variable allele at said amino acid position in a sample provided by an individual indicates that said individual should be monitored more closely if an increased dosage of a PPAR-agonist is contemplated in order to avoid the potential of increasing the likelihood of developing dose-dependent congestive heart failure or a congestive heart failure-like disorder relative to another individual having the reference allele(s) at said position.

In preferred embodiments, the following N-terminal beta1-adrenergic receptor deletion polypeptides are encompassed by the present invention: M1-V477, G2-V477, A3-V477, G4-V477, V5-V477, L6-V477, V7-V477, L8-V477, G9-V477, A10-V477, S11-V477, E12-V477, P13-V477, G14-V477, N15-V477, L16-V477, S17-V477, S18-V477, A19-V477, A20-V477, P21-V477, L22-V477, P23-V477, D24-V477, G25-V477, A26-V477, A27-V477, T28-V477, A29-V477, A30-V477, R31-V477, L32-V477, L33-V477, V34-V477, P35-V477, A36-V477, S37-V477, P38-V477, P39-V477, A40-V477, S41-V477, L42-V477, L43-V477, P44-V477, P45-V477, A46-V477, S47-V477, E48-V477, S49-V477, P50-V477, E51-V477, P52-V477, L53-V477, S54-V477, Q55-V477, Q56-V477, W57-V477, T58-V477, A59-V477, G60-V477, M61-V477, G62-V477, L63-V477, L64-V477, M65-V477, A66-V477, L67-V477, I68-V477, V69-V477, L70-V477, L71-V477, I72-V477, V73-V477, A74-V477, G75-V477, N76-V477, V77-V477, L78-V477, V79-V477, I80-V477, V81-V477, A82-V477, I83-V477, A84-V477, K85-V477, T86-V477, P87-V477, R88-V477, L89-V477, Q90-V477, T91-V477, L92-V477, T93-V477, N94-V477, L95-V477, F96-V477, I97-V477, M98-V477, S99-V477, L100-V477, A101-V477, S102-V477, A103-V477, D104-V477, L105-V477, V106-V477, M107-V477, G108-V477, L109-V477, L110-V477, V111-V477, V112-V477, P113-V477, F114-V477, G115-V477, A116-V477, T117-V477, I118-V477, V119-V477, V120-V477, W121-V477, G122-V477, R123-V477, W124-V477, E125-V477, Y126-V477, G127-V477, S128-V477, F129-V477, F130-V477, C131-V477, E132-V477, L133-V477, W134-V477, T135-V477, S1136-V477, V137-V477, D138-V477, V139-V477, L140-V477, C141-V477, V142-V477, T143-V477, A144-V477, S145-V477, I146-V477, E147-V477, T148-V477, L149-V477, C150-V477, V151-V477, I152-V477, A153-V477, L154-V477, D155-V477, R156-V477, Y157-V477, L158-V477, A159-V477, I160-V477, T161-V477, S162-V477, P163-V477, F164-V477, R165-V477, Y166-V477, Q167-V477, S168-V477, L169-V477, L170-V477, T171-V477, R172-V477, A173-V477, R174-V477, A175-V477, R176-V477, G177-V477, L178-V477, V179-V477, C180-V477, T181-V477, V182-V477, W183-V477, A184-V477, I185-V477, S186-V477, A187-V477, L188-V477, V189-V477, S190-V477, F191-V477, L 192-V477, P193-V477, I194-V477, L 195-V477, M 196-V477, H197-V477, W198-V477, W199-V477, R200-V477, A201-V477, E202-V477, S203-V477, D204-V477, E205-V477, A206-V477, R207-V477, R208-V477, C209-V477, Y210-V477, N211-V477, D212-V477, P213-V477, K214-V477, C215-V477, C216-V477, D217-V477, F218-V477, V219-V477, T220-V477, N221-V477, R222-V477, A223-V477, Y224-

V477, A225-V477, I226-V477, A227-V477, S228-V477, S229-V477, V230-V477, V231-V477, S232-V477, F233-V477, Y234-V477, V235-V477, P236-V477, L237-V477, C238-V477, I239-V477, M240-V477, A241-V477, F242-V477, V243-V477, Y244-V477, L245-V477, R246-V477, V247-V477, F248-V477, R249-V477, E250-V477, A251-V477, Q252-V477, K253-V477, Q254-V477, V255-V477, K256-V477, K257-V477, I258-V477, D259-V477, S260-V477, C261-V477, E262-V477, R263-V477, R264-V477, F265-V477, L266-V477, G267-V477, G268-V477, P269-V477, A270-V477, R271-V477, P272-V477, P273-V477, S274-V477, P275-V477, S276-V477, P277-V477, S278-V477, P279-V477, V280-V477, P281-V477, A282-V477, P283-V477, A284-V477, P285-V477, P286-V477, P287-V477, G288-V477, P289-V477, P290-V477, R291-V477, P292-V477, A293-V477, A294-V477, A295-V477, A296-V477, A297-V477, T298-V477, A299-V477, P300-V477, L301-V477, A302-V477, N303-V477, G304-V477, R305-V477, A306-V477, G307-V477, K308-V477, R309-V477, R310-V477, P311-V477, S312-V477, R313-V477, L314-V477, V315-V477, A316-V477, L317-V477, R318-V477, E319-V477, Q320-V477, K321-V477, A322-V477, L323-V477, K324-V477, T325-V477, L326-V477, G327-V477, I328-V477, I329-V477, M330-V477, G331-V477, V332-V477, F333-V477, T334-V477, L335-V477, C336-V477, W337-V477, L338-V477, P339-V477, F340-V477, F341-V477, L342-V477, A343-V477, N344-V477, V345-V477, V346-V477, K347-V477, A348-V477, F349-V477, H350-V477, R351-V477, E352-V477, L353-V477, V354-V477, P355-V477, D356-V477, R357-V477, L358-V477, F359-V477, V360-V477, F361-V477, F362-V477, N363-V477, W364-V477, L365-V477, G366-V477, Y367-V477, A368-V477, N369-V477, S370-V477, A371-V477, F372-V477, N373-V477, P374-V477, I375-V477, I376-V477, Y377-V477, C378-V477, R379-V477, S380-V477, P381-V477, D382-V477, F383-V477, R384-V477, K385-V477, A386-V477, F387-V477, Q388-V477, and/or G389-V477 of SEQ ID NO:53. Polynucleotide sequences encoding these polypeptides are also provided. The present invention also encompasses the use of these N-terminal beta1-adrenergic receptor deletion polypeptides as immunogenic and/or antigenic epitopes as described elsewhere herein.

In preferred embodiments, the following C-terminal beta1-adrenergic receptor deletion polypeptides are encompassed by the present invention: M1-V477, M1-K476, M1-S475, M1-E474, M1-S473, M1-A472, M1-F471, M1-G470, M1-P469, M1-R468, M1-C467, M1-P466, M1-E465, M1-D464, M1-L463, M1-S462, M1-S461, M1-D460, M1-S459, M1-D458, M1-A457, M1-A456, M1-A455, M1-G454, M1-G453, M1-N452, M1-C451, M1-G450, M1-A449, M1-W448, M1-P447, M1-E446, M1-L445, M1-L444, M1-R443, M1-A442, M1-P441, M1-P440, M1-T439, M1-A438, M1-G437, M1-V436, M1-V435, M1-D434, M1-D433, M1-D432, M1-D431, M1-D430, M1-D429, M1-S428, M1-A427, M1-A426, M1-G425, M1-P424, M1-S423, M1-P422, M1-P421, M1-P420, M1-G419, M1-P418, M1-R417, M1-A416, M1-L415, M1-C414, M1-G413, M1-S412, M1-A411, M1-R410, M1-P409, M1—R408, M1-D407, M1-G406, M1-H405, M1-T404, M1-A403, M1-H402, M1-R401, M1-R400, M1-R399, M1-A398, M1-A397, M1-R396, M1-R395, M1-A394, M1-C393, M1-C392, M1-L391, M1-L390, and/or M1-G389 of SEQ ID NO:53. Polynucleotide sequences encoding these polypeptides are also provided. The present invention also encompasses the use of these C-terminal beta1-adrenergic receptor deletion polypeptides as immunogenic and/or antigenic epitopes as described elsewhere herein.

Alternatively, preferred polypeptides of the present invention may comprise polypeptide sequences corresponding to, for example, internal regions of the β1-adrenergic receptor polypeptide (e.g., any combination of both N- and C-terminal endothelin-1 polypeptide deletions) of SEQ ID NO:53. For example, internal regions could be defined by the equation: amino acid NX to amino acid CX, wherein NX refers to any N-terminal deletion polypeptide amino acid of endothelin-1 (SEQ ID NO:53), and where CX refers to any C-terminal deletion polypeptide amino acid of endothelin-1 (SEQ ID NO:53). Polynucleotides encoding these polypeptides are also provided. The present invention also encompasses the use of these polypeptides as an immunogenic and/or antigenic epitope as described elsewhere herein and are useful for creating allele-specific antibodies to discriminate between the reference and variable allele in a given sample, among other uses described herein. In addition such fragments may also be useful in designing allele-specific hybridization or other means probes to identify the allele to discriminate between the reference and variable allele in a given sample, among other uses described herein.

TABLE I

| Polynucleotide No. | SNP | Allele | Number of Polymorphic Loci | Nucleotide Position of Polymorphic Locus | Nucleotide at Polymorphic Locus | DNA SEQ ID NO: | Amino Acid Position of Polymorphic Locus | Amino Acid at Polymorphic Locus | AA SEQ ID NO: |
|---|---|---|---|---|---|---|---|---|---|
| 1 | Renin-SNP3 | Reference | 1 | 12586 | G | 1 | N/A | N/A | N/A |
| 2 | Renin-SNP3 | Variable | 1 | 12586 | A | 2 | N/A | N/A | N/A |
| 3 | Renin-SNP5 | Reference | 1 | 10096 | A | 3 | N/A | N/A | N/A |
| 4 | Renin-SNP5 | Variable | 1 | 10096 | G | 4 | N/A | N/A | N/A |
| 5 | Renin-SNP7 | Reference | 1 | 13076 | G | 5 | N/A | N/A | N/A |
| 6 | Renin-SNP7 | Variable | 1 | 13076 | G deletion | 6 | N/A | N/A | N/A |

TABLE I-continued

| Polynucleotide No. | SNP | Allele | Number of Polymorphic Loci | Nucleotide Position of Polymorphic Locus | Nucleotide at Polymorphic Locus | DNA SEQ ID NO: | Amino Acid Position of Polymorphic Locus | Amino Acid at Polymorphic Locus | AA SEQ ID NO: |
|---|---|---|---|---|---|---|---|---|---|
| 7 | Renin Polymorphic | N/A | 3 | 12586, 10096, and 13076 | G, A, or G deletion | 7 | N/A | N/A | N/A |
| 8 | ET1-SNP1 | Reference | 1 | 797 | G | 37 | 198 | K | 38 |
| 9 | ET1-SNP1 | Variable | 1 | 797 | T | 39 | 198 | N | 40 |
| 10 | Beta1-SNP1 | Reference | 1 | 1251 | C | 50 | 389 | R | 51 |
| 11 | Beta1-SNP1 | Variable | 1 | 1251 | G | 52 | 389 | G | 53 |

The present invention provides a polynucleotide comprising, or alternatively consisting of, the sequence identified as SEQ ID NO:1, 2, 3, 4, 5, 6, 7, 37, 39, 50, and/or 52; or a fragment containing the polymorphic allele, wherein said fragment comprises at least 10 contiguous nucleotides of SEQ ID NO:1, 2, 3, 4, 5, 6, 7, 37, 39, 50, and/or 52.

Preferably, the present invention is directed to a polynucleotide comprising, or alternatively consisting of, the sequence identified as SEQ ID NO:1, 2, 3, 4, 5, 6, 7, 37, 39, 50, and/or 52, that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:1, 2, 3, 4, 5, 6, 7, 37, 39, 50, and/or 52, and/or the nucleic acid sequence encoding the sequence disclosed as SEQ ID NO:9, 38, 40, 51, or 53.

The invention encompasses the application of PCR methodology to the polynucleotide sequences of the present invention, and/or the cDNA encoding the polypeptides of the present invention. PCR techniques for the amplification of nucleic acids are described in U.S. Pat. No. 4,683,195 and Saiki et al., Science, 239:487-491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643-1650, (1991); and "PCR Protocols, A Guide to Methods and Applications", Eds., Innis et al., Academic Press, New York, (1990).

Polynucleotide Variants

The present invention also encompasses variants (e.g., allelic variants, orthologs, etc.) of the polynucleotide sequence disclosed herein in SEQ ID NO:1, 2, 3, 4, 5, 6, 7, 37, 39, 50, and/or 52, and the complementary strand thereto.

The present invention also encompasses variants of the polypeptide sequence, and/or fragments therein, disclosed in SEQ ID NO:9, 38, 40, 51, or 53, a polypeptide encoded by the polynucleotide sequence in SEQ ID NO:1, 2, 3, 4, 5, 6, 7, 37, 39, 50, and/or 52.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), or (d), above. Polynucleotides which hybridize to the complement of these nucleic acid molecules under stringent hybridization conditions or alternatively, under lower stringency conditions, are also encompassed by the invention, as are polypeptides encoded by these polypeptides.

Polynucleotide Fragments

The present invention is directed to polynucleotide fragments of the polynucleotides of the invention, and polynucleotide sequences that hybridize thereto.

In the present invention, a "polynucleotide fragment" refers to a short polynucleotide having a nucleic acid sequence which: is a portion of that shown in SEQ ID NO: 1, 2, 3, 4, 5, 6, 7, 37, 39, 50, and/or 52 or the complementary strand thereto, or is a portion of a polynucleotide sequence encoding the polypeptide of SEQ ID NO:9, 38, 40, 51, or 53. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length, and comprise at least one polymorphic locus. A fragment "at least 20 nt in length," for example, is intended to include 20 or more contiguous bases from the cDNA sequence shown in SEQ ID NO:1, 2, 3, 4, 5, 6, 7, 37, 39, 50, and/or 52. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, isolated fragments comprising, or alternatively consisting of, a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:1, 2, 3, 4, 5, 6, 7, 37, 39, 50, and/or 52 or the complementary strand thereto. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NOs:9, 38, 40, 51, and/or 53. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 21-40, 41-60, 61-80, 81-100, 102-120, 121-140, 141-160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1-60, can be deleted from the amino terminus of the full-length polypeptide. Similarly, any number of amino acids, ranging from 1-30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NOs:9, 38, 40, 51, and/or 53 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NOs:9, 38, 40, 51, and/or 53, or encoded by a polynucleotide that hybridizes to the complement of the sequence of SEQ ID NOs:9, 38, 40, 51, and/or 53 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NOs:9, 38, 40, 51, and/or 53), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length, or longer. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394, 827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Antibodies

Further polypeptides of the invention relate to antibodies and T-cell antigen receptors (TCR) which immunospecifically bind a polypeptide, polypeptide fragment, or variant of SEQ ID NOs:9, 38, 40, 51, and/or 53, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F (ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F (ab')2 fragments) which are capable of specifically binding to protein. Fab and F (ab')2 fragments lack the Fc fragment of intact antibody, clear more rapidly from the circulation of the animal or plant, and may have less non-specific tissue binding than an intact antibody (Wahl et al., J. Nucl. Med. 24:316-325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F (ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. Preferably the antibodies of the present invention are specific for a single nucleotide polymorphism of any one of the angioedema candidate gene polypeptides of the present invention. More preferred are antibodies that are capable of specifically distinguishing between the variant and reference forms of a polypeptide of the present invention. Such antibodies are primarily useful in a kit to identify variant or normal forms of a polypeptide, and hence determining whether a particular individual is at a higher or lower risk of being susceptible to edema or an edema-like disorder upon the administration of a PPAR-agonist.

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387 B1.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988), which is hereby incorporated herein by reference in its entirety). For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivatizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, $2^{nd}$ ed. (1988), by Hammerling, et al., Monoclonal Antibodies and T-Cell Hybridomas (Elsevier, N.Y., (1981)), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suiTable Dulture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. As inferred throughout the specification, human myeloma and mouse-human heteromyeloma cell lines also have been described for the production of human monoclonal antibodies (Kozbor, J. Immunol., 133:3001

(1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoadsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra). SuiTable Dulture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC®. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F (ab')2 fragments of the invention may be produced by proteolytic cleavage of immunoglobulin molecules, using enzymes such as papain (to produce Fab fragments) or pepsin (to produce F (ab')2 fragments). F (ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F (ab')$_2$ fragments can also be employed using methods known in the art such as those disclosed in PCT publication WO 92/22324; Mullinax et al., BioTechniques 12 (6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240: 1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.)

Antibodies can be humanized using a variety of techniques known in the art including, for example, CDR-grafting (EP 239,400B1; PCT publication WO 91/09967; U.S. Pat. Nos. 5,225,539; 5,530,101; and 5,585,089), veneering or resurfacing (EP 592,106B1; EP 519,596B1; Padlan, Molecular Immunology 28 (4/5):489-498 (1991); Studnicka et al., Protein Engineering 7 (6):805-814 (1994); Roguska. et al., PNAS 91:969-973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239:1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature 332:323-329 (1988) and Presta, Curr. Op. Struct. Biol., 2:593-596 (1992).

Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boerner et al., J. Immunol., 147 (1):86-95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779-783 (1992); Lonberg et al., Nature 368:856-859 (1994); Fishwild et al., Nature Biotechnol., 14:845-51 (1996); Neuberger, Nature Biotechnol., 14:826 (1996); Lonberg and Huszer, Intern. Rev. Immunol., 13:65-93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7 (5):437-444; (1989) and Nissinoff, J. Immunol. 147 (8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The antibodies of the present invention may be bispecific antibodies. Bispecific antibodies are monoclonal, preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art.

Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. . . . 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk–, hgprt– or aprt– cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11 (5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in vitro immunoassays and purification methods using methods known in the art. See e.g., Harbor et al., supra, and PCT publication WO 93/21232; EP 439,095B1; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434B1; EP 367,166; PCT publications WO 96/04388; WO 91/06570; Ashkenazi et al., Proc. Natl. Acad. Sci. USA 88:10535-10539 (1991); Zheng et al., J.

Immunol. 154:5590-5600 (1995); and Vil et al., Proc. Natl. Acad. Sci. USA 89:11337-11341 (1992) (said references incorporated by reference in their entireties).

As discussed, supra, the polypeptides corresponding to a polypeptide, polypeptide fragment, or a variant of SEQ ID NOs:9, 38, 40, 51, and/or 53 may be fused or conjugated to the above antibody portions to increase the in vivo half life of the polypeptides or for use in immunoassays using methods known in the art. Further, the polypeptides corresponding to SEQ ID NOs:9, 38, 40, 51, and/or 53 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232, 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270: 9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Uses for Antibodies Directed Against Polypeptides of the Invention

The antibodies of the present invention have various utilities. For example, such antibodies may be used in diagnostic assays to detect the presence or quantification of a variant or reference form of a polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278 (2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147-158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219 (1981); and Nygren, J. Histochem. And Cytochem., 30:407 (1982).

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% TRASYLOL®) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detecTable Dompound such as an enzymatic substrate (e.g., horseradish peroxidase or alkaline phosphatase) to the well and incubating for a period of time, and detecting the presence of the antigen. In ELISAs the antibody of interest does not have to be conjugated to a detecTable Dompound; instead, a second antibody (which recognizes the antibody of interest) conjugated to a detecTable Dompound may be added to the well. Further, instead of coating the well with the antigen, the antibody may be coated to the well. In this case, a second antibody conjugated to a detecTable Dompound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic/Prophylactic Administration and Compositions

The invention provides methods of treatment, inhibition and prophylaxis by administration to a subject of an effective amount of a compound or pharmaceutical composition of the invention, including an antibody, antisense reagent, RNAi reagent, and/or a zinc-finger protein of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically accepTable Darrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging with Antibodies

Labeled antibodies, and derivatives and analogs thereof, which specifically bind to a variant or reference allele of a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising: (a) assaying the expression of the polypeptide of interest in cells or body fluid of an individual using one or more antibodies specific to the polypeptide interest; and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising: (a) assaying the expression of the polypeptide of interest in cells or body fluid of an individual using one or more antibodies specific to the polypeptide interest; and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: (a) administering (for example, parenterally, subcutaneously, or intraperitoneally) to a subject an effective amount of a labeled molecule which specifically binds to the polypeptide of interest; (b) waiting for a time interval following the administering for permitting the labeled molecule to preferentially concentrate at sites in the subject where the polypeptide is expressed (and for unbound labeled molecule to be cleared to background level); (c) determining background level; and (d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Kits

The invention further provides kits comprising at least one agent for identifying which alleleic form of the SNPs identified herein is present in a sample. For example, suitable kits can comprise at least one antibody specific for a particular protein or peptide encoded by one alleleic form of the gene, or allele-specific oligonucleotide as described herein. Often, the kits contain one or more pairs of allele-specific oligonucleotides hybridizing to different forms of a polymorphism. In some kits, the allele-specific oligonucleotides are provided immobilized to a substrate. For example, the same substrate can comprise allele-specific oligonucleotide probes for detecting at least 1, 10, 100 or all of the polymorphisms shown in Table I. Optional additional components of the kit include, for example, reagents, buffers, restriction enzymes, reverse-transcriptase or polymerase, the substrate nucleoside triphosphates, means used to label (for example, an avidin-enzyme conjugate and enzyme substrate and chromogen if the label is biotin, fluophores, and others as described herein), and the appropriate buffers for reverse transcription, PCR, or hybridization reactions. Usually, the kit also contains instructions for carrying out the methods.

The present invention provides kits that can be used in the methods described herein. In one embodiment, a kit comprises a single primer or probe of the invention comprising a means to detect at least one polymorphic locus, said means preferably comprises a purified primer or probe, in one or more containers. Such a primer or probe may further comprise a detectable label such as a fluorescent compound, an enzymatic substrate, a radioactive compound, a luminescent compound, a fluorophore, and/or a fluorophore linked to a terminator contained therein. Such a kit may further comprise reagents required to enable adequate hybridization of said single primer or probe to a DNA test sample, such that under suitable conditions, the primer or probe is capable of binding to said DNA test sample and signaling whether the variant or reference allele at the polymorphic locus is present in said DNA test sample.

In one example, the kit comprises a means method for detecting the presence of a polymorphic locus comprising one specific allele of at least one polynucleotide in a DNA test sample which serves as a template nucleic acid comprising: (a) forming an oligonucleotide bound to the polymorphic locus wherein the oligonucleotide comprises a fluorophore linked to a terminator contained therein; and (b) detecting fluorescence polarization of the fluorophore of the fluorescently-labeled oligonucleotide, wherein the oligonucleotide is formed from a primer bound to said DNA sample immediately 3' to the polymorphic locus and a terminator covalently linked to a fluorophore, and wherein said terminator-linked fluorophore binds to the polymorphic locus and reacts with the primer to produce an extended primer which is said fluorescently labeled oligonucleotide, wherein an increase in fluorescence polarization indicates the presence of the specific allele at the polymorphic locus, thereby detecting the presence of the specific allele at the polymorphic locus by said increase in fluorescence polarization.

The kit of the present invention may comprise the following non-limiting examples of fluorophores linked to a primer or probe of the present invention: 5-carboxyfluorescein (FAM-ddNTPs); 6-carboxy-X-rhodamine (ROX-ddNTPs); N,N,N',N'-tetramethyl-6-carboxyrhodamine (TMR-ddNTPs); and BODIPY-Texas Red (BTR-ddNTPs).

The present invention is also directed towards a kit comprising a solid support to which oligonucleotides comprising at least 10 contiguous nucleotides of SEQ ID NO:1, 2, 3, 4, 5, 6, 7, 37, 39, 50, or 52 wherein said oligonucleotide further comprises at least one polymorphic locus of SEQ ID NO:1, 2, 3, 4, 5, 6, 7, 37, 39, 50, or 52, are affixed. In such an embodiment, detection of a polynucleotide within a sample comprising the same or similar sequence to said oligonucleotide can be detected by hybridization.

The solid surface reagent in the above assay is prepared by known techniques for attaching protein material to solid support material, such as polymeric beads, dip sticks, 96-well plate or filter material. These attachment methods generally include non-specific adsorption of the oligonucleotide to the support or covalent attachment of the oligonucleotide to a chemically reactive group on the solid support. Alternatively, streptavidin coated plates can be used in conjunction with biotinylated oligonucleotide(s).

Thus, the invention provides an assay system or kit for carrying out this diagnostic method. The kit generally includes a support with surface-bound oligonucleotides, and a reporter for detecting hybridization of said oligonucleotide to a test polynucleotide.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC® Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; PBLUESCRIPT® vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., Mol. Cell. Biol. 5:1111-21 (1985); Koutz, P. J, et al., Yeast 5:167-77 (1989); Tschopp, J. F., et al., Nucl. Acids Res. 15:3859-76 (1987). Thus, a heterologous coding sequence, such as, for example, a polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a polypeptide of the invention, as set forth herein, in a Pichea yeast system essentially as described in "*Pichia* Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105-111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly (vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly (ethylene glycol) (PEG), poly (vinylpyrrolidine), polyoxomers, polysorbate and poly (vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384B1, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as PLURONIC®, commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NOs:9, 38, 40, 51, and/or 53 (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the Sequence Listing). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between FLAG® polypeptide sequence contained in fusion proteins of the invention containing FLAG® polypeptide sequence. In a further embodiment, associations proteins of the invention are associated by interactions between heterologous polypeptide sequence contained in FLAG® fusion proteins of the invention and anti-FLAG® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Methods of Use of the Allelic Polynucleotides of the Present Invention

The determination of the polymorphic form(s) present in an individual at one or more polymorphic sites defined herein can be used in a number of methods.

In preferred embodiments, the polynucleotides and polypeptides of the present invention, including allelic and variant forms thereof, have uses which include, but are not limited to diagnosing individuals to identify whether a given individual has increased susceptibility or risk for developing dose-dependent peripheral edema or edema-like disorder using the genotype assays of the present invention. In addition, the polynucleotides and polypeptides of the present invention, including allelic and variant forms thereof, have uses which include, but are not limited to, diagnosing individuals to identify whether a given individual, upon administration of an increased dose of a PPAR-agonist, has increased susceptibility or risk for developing dose-dependent peripheral edema or edema-like disorder using the genotype assays of the present invention.

In preferred embodiments, the polynucleotides and polypeptides of the present invention, including allelic and variant forms thereof, have uses which include, but are not limited to diagnosing individuals to identify whether a given individual is at a higher risk of developing dose-dependent peripheral edema. An acceptable higher level of a pharmaceutically acceptable dose of a PPAR-agonist for a patient identified as being at low risk of developing dose-dependent peripheral edema may be 5%, 10%, 15%, 20%, 25%, 30%, 35%, 40%, 45%, 50%, 55%, 60%, 65%, 75%, 80%, 85%, 90%, or 95% higher than the prescribed or typical dose, as may be the case.

In another preferred embodiment, the polynucleotides and polypeptides of the present invention, including allelic and variant forms thereof, have uses which include, but are not limited to diagnosing individuals to identify whether a given individual should be administered a correspondingly higher dose of a PPAR-agonist in order to ameliorate an individuals susceptibility or risk for developing dose-dependent peripheral edema or edema-like disorder using the genotype assays of the present invention.

In preferred embodiments, the polynucleotides and polypeptides of the present invention, including allelic and variant forms thereof, have uses which include, but are not limited to use in methods of screening to identify compounds, particularly PPAR-agonist compounds, that have a lower risk of inducing dose-dependent peripheral edema or related disorder in a patient. Such identified compounds would be expected to retain all the benefits of a PPAR-agonist but would have diminished ability of inducing increased renin expression and/or function, or alternatively, capable of increasing renin expression and/or function to a lesser extent than a reference compound known to be capable of inducing dose-dependent peripheral edema. Such compounds would be expected to be less likely to result in the development of dose-dependent peripheral edema or related edema-like disorder.

In another embodiment, the polynucleotides and polypeptides of the present invention, including allelic and variant forms thereof, either alone, or in combination with other polymorphic polynucleotides (haplotypes) are useful as genetic markers for predicting an individuals susceptibility to develop dose-dependent peripheral edema or edema-like disorder, and particularly to predicting an individuals susceptibility to develop dose-dependent peripheral edema or edema-like disorder upon the administration of an increased dose of a PPAR-agonist.

Additionally, the polynucleotides and polypeptides of the present invention, including allelic and/or variant forms thereof, are useful for creating additional antagonists directed against these polynucleotides and polypeptides, which include, but are not limited to the design of antisense RNA, ribozymes, PNAs, recombinant zinc finger proteins (Wolfe, S A., Ramm, E I., Pabo, C O, Structure, Fold, Des., 8 (7):739-50, (2000); Kang, J S., Kim, J S, J. Biol, Chem., 275 (12): 8742-8, (2000); Wang, B S., Pabo, C O, Proc, Natt, Acad, Sci, U, S, A., 96 (17):9568-73, (1999); McColl, D J., Honchell, C D., Frankel, A D, Proc, Natl, Acad, Sci, U.S.A., 96 (17):9521-6, (1999); Segal, D J., Dreier, B., Beerli, R R., Barbas, CF-3rd, Proc, Natl, Acad, Sci, U, S, A., 96 (6):2758-63, (1999); Wolfe, S A., Greisman, H A., Ramm, E I., Pabo, C O, J. Mol, Biol., 285 (5):1917-34, (1999); Pomerantz, J L., Wolfe, S A., Pabo, C O, Biochemistry., 37 (4):965-70, (1998); Leon, O., Roth, M., Biol. Res. 33 (1):21-30 (2000); Berg, J M., Godwin, H A, Ann. Rev. Biophys. Biomol. Struct., 26:357-71 (1997)), in addition to other types of antagonists which are either described elsewhere herein, or known in the art.

The polynucleotides and polypeptides of the present invention, including allelic and/or variant forms thereof, are useful for identifying small molecule antagonists directed against the variant forms of these polynucleotides and polypeptides, preferably wherein such small molecules are useful as therapeutic and/or pharmaceutical compounds for the treatment, detection, prognosis, and/or prevention of the following, non-limiting diseases and/or disorders, peripheral edema, edema, susceptibility to acquiring a peripheral edema or an edema-like disorder upon the administration of a pharmaceutically acceptable amount of a PPAR-agonist, adverse reactions associated with PPAR-agonist, disorders associated with aberrant renin expression, disorders associated with aberrant renin regulation, disorders associated with aberrant renin activity, disorders associated with aberrant regulation of renin by aldosterone, disorders associated with aberrant angiotensin II peptide levels, disorders associated with aberrant adrenal and renal vascular responses to angiotensin II, disorders associated with refractory responses to angiotensin II antagonists, hypertension, high blood pressure, hypotension, low-renin essential hypertension, high-renin essential hypertension, atherosclerosis, congestive heart failure, pulmonary edema, beta blocker induced edema, and beta-1 blocker induced edema.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

The polynucleotides and polypeptides of the present invention, including allelic and/or variant forms thereof, are useful for the treatment of angioedema, hypertension, and congestive heart failure, in addition to other diseases and/or conditions referenced elsewhere herein, through the application of gene therapy based regimens.

Additional uses of the polynucleotides and polypeptides of the present invention are provided herein.

Modified Polypeptides and Gene Sequences

The invention further provides variant forms of nucleic acids and corresponding proteins. The nucleic acids comprise one of the sequences described in Table I, in which the polymorphic position is occupied by one of the alternative bases for that position. Some nucleic acids encode full-length variant forms of proteins. Variant genes can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide. Processing includes glycosylation, ubiquitination, disulfide bond formation, general post-translational modification, and the like. As used herein, "gene product" includes mRNA, peptide and protein products.

The protein may be isolated by conventional means of protein biochemistry and purification to obtain a substantially pure product, i.e., 80, 95 or 99% free of cell component contaminants, as described in Jacoby, Methods in Enzymology Volume 104, Academic Press, New York (1984); Scopes, Protein Purification, Principles and Practice, 2nd Edition, Springer-Verlag, New York (1987); and Deutscher (ed), Guide to Protein Purification, Methods in Enzymology, Vol. 182 (1990). If the protein is secreted, it can be isolated from the supernatant in which the host cell is grown. If not secreted, the protein can be isolated from a lysate of the host cells.

Haplotype Based Genetic Analysis

The invention further provides methods of applying the polynucleotides of the present invention to the elucidation of haplotypes. Such haplotypes may be associated with any one or more of the disease conditions referenced elsewhere herein. A "haplotype" is defined as the pattern of a set of alleles of single nucleotide polymorphisms along a chromosome. For example, consider the case of three single nucleotide polymorphisms (SNP1, SNP2, and Renin-SNP3) in one chromosome region, of which SNP1 is an A/G polymorphism, SNP2 is a G/C polymorphism, and Renin-SNP3 is an A/C polymorphism. A and G are the alleles for the first, G and C for the second and A and C for the third SNP. Given two alleles for each SNP, there are three possible genotypes for individuals at each SNP. For example, for the first SNP, A/A, A/G and G/G are the possible genotypes for individuals. When an individual has a genotype for a SNP in which the alleles are not the same, for example A/G for the first SNP, then the individual is a heterozygote. When an individual has an A/G genotype at SNP1, G/C genotype at SNP2, and A/C genotype at Renin-SNP3, there are four possible combinations of haplotypes (A, B, C, and D) for this individual. The set of SNP genotypes of this individual alone would not provide sufficient information to resolve which combination of haplotypes this individual possesses. However, when this individual's parents' genotypes are available, haplotypes could then be assigned unambiguously. For example, if one parent had an A/A genotype at SNP1, a G/C genotype at SNP2, and an A/A genotype at Renin-SNP3, and the other parent had an A/G genotype at SNP1, C/C genotype at SNP2, and C/C genotype at Renin-SNP3, while the child was a heterozygote at all three SNPs, there is only one possible haplotype combination, assuming there was no crossing over in this region during meiosis.

When the genotype information of relatives is not available, haplotype assignment can be done using the long range-PCR method (Clark, A. G. Mol Biol Evol 7 (2): 111-22 (1990); Clark, A. G., K. M. Weiss, et al. Am J Hum Genet. 63 (2): 595-612 (1998); Fullerton, S. M., A. G. Clark, et al., Am J. Hum. Genet. 67 (4): 881-900 (2000); Templeton, A. R., A. G. Clark, et al., Am J Hum Genet. 66 (1): 69-83 (2000)). When the genotyping result of the SNPs of interest are available from general population samples, the most likely haplotypes can also be assigned using statistical methods (Excoffier, L. and M. Slatkin. Mol Biol Evol 12 (5): 921-7 (1995); Fallin, D. and N. J. Schork, Am J Hum Genet. 67 (4): 947-59 (2000); Long, J. C., R. C. Williams, et al., Am J Hum Genet. 56 (3): 799-810 (1995)).

Once an individual's haplotype in a certain chromosome region (i.e., locus) has been determined, it can be used as a tool for genetic association studies using different methods, which include, for example, haplotype relative risk analysis (Knapp, M., S. A. Seuchter, et al., Am J Hum Genet. 52 (6): 1085-93 (1993); Li, T., M. Arranz, et al., Schizophr Res 32 (2): 87-92 (1998); Matise, T. C., Genet Epidemiol 12 (6): 641-5 (1995); Ott, J., Genet Epidemiol 6 (1): 127-30 (1989); Terwilliger, J. D. and J. Ott, Hum Hered 42 (6): 33746 (1992)). Haplotype based genetic analysis, using a combination of SNPs, provides increased detection sensitivity, and hence statistical significance, for genetic associations of diseases, as compared to analyses using individual SNPs as markers. Multiple SNPs present in a single gene or a continuous chromosomal region are useful for such haplotype-based analyses.

Uses of the Polynucleotides

Each of the polynucleotides identified herein can be used in numerous ways as reagents. The following description should be considered exemplary and utilizes known techniques.

Increased or decreased expression of the gene in affected organisms as compared to unaffected organisms can be assessed using polynucleotides of the present invention. Any of these alterations, including altered expression, or the presence of at least one SNP of the present invention within the gene, can be used as a diagnostic or prognostic marker.

The invention provides a diagnostic method useful during diagnosis of a disorder, involving measuring the presence or expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may Preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The US patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point (T.sub.m) by 8°-20° C., vs. 4°-16° C. for the DNA/DNA 15-mer duplex. Also, the absence of charge groups in PNA means that hybridization can be done at low ionic strengths and reduce possible interference by salt during the analysis.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615-622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

Methods of Use of the Human Renin Biomarker Polypeptide

In accordance with the present invention, the expression level of human renin was determined to be significantly induced in the presence of a PPAR-agonist as shown in FIGS. 11 and 12, indicating that human renin is useful as a biomarker for predicting whether a patient administered a PPAR-agonist will respond to PPAR-agonist therapy; for predicting whether a patient will respond to specific doses of a PPAR-agonist and whether the level of the administered PPAR-agonist needs to be increased or decreased to achieve the desired level of human renin expression identified as representing a responsive level; in addition to predicting whether a patient has an increased risk of developing dose-dependent peripheral edema upon the administration of a pharmaceutically acceptable level of a PPAR-agonist; predicting whether said patient should be monitored more closely prior to increasing the level of administered PPAR agonist to limit the risk of developing said dose-dependent peripheral edema; and predicting whether said patient may be administered a higher level of administered PPAR agonist without the risk of developing said dose-dependent peripheral edema.

In another embodiment of the present invention, human renin is useful as a biomarker for pre- or post-clinical screening to identify PPAR-agonist compounds or combinations of such compounds that are likely to increase the risk of a patient developing dose-dependent peripheral edema in response to the administration of PPAR-agonist compounds or combinations of such compounds, and thus to prevent or diminish the likelihood of a patient developing dose-dependent peripheral edema by either advising patients be monitored more closely if such a compound or combination of compounds are administered at a corresponding higher dose, or by changing the PPAR-agonist combination administered.

Cells endogenously expressing human renin can be treated with at least one test substance, and extracellular and/or intracellular levels of the biomarker renin polypeptide in the presence and absence of the test substance(s) can be compared. The observation of high levels of the renin biomarker polypeptide in the presence of the substance(s) can be used to predict which compounds are likely to increase the risk of a patient developing dose-dependent peripheral edema in response to the administration of PPAR-agonist compounds or combinations of such compounds, and thus to prevent or diminish the likelihood of a patient developing dose-dependent peripheral edema by not selecting such a test compound in the screen. In an additional aspect, the assays of the invention are automated for high throughput screening. The results of such screening may be used to determine the need to modify or discontinue an existing treatment.

The present invention also encompasses microarrays, e.g., protein, antibody, or cell-based microarrays, which can be used in conjunction with the disclosed screening assays for measuring the renin biomarker polypeptide. The protein, antibody, and cell-based microarrays can be used in the manual or automated screening assays of the invention as disclosed herein to test one or more drugs, compounds, or other therapeutic agents. For protein microarrays, polypeptides obtained from renin expression cells (e.g., from extracellular media or cell lysates) incubated in the presence and absence of at least one test substance can be affixed to a support, and then contacted with antibodies that specifically bind to the renin biomarker polypeptide. For antibody microarrays, one or more anti-biomarker antibodies can be affixed to a support, and then contacted with extracellular media or cell lysates obtained from renin expressing cells incubated in the presence and absence of at least one test substance. For cell-based microarrays, one or more cells can be affixed to a support, and then incubated in the presence and absence of at least one test substance. The microarrays can then be analyzed (e.g., by immunoassay) to determine elevated levels of at least one biomarker polypeptide in the presence of the test substance(s), which can be used to predict which compound are likely to increase the risk of a patient developing dose-dependent peripheral edema in response to the administration of PPAR-agonist compounds or combinations of such compounds, and thus to prevent or diminish the likelihood of a patient developing dose-dependent peripheral edema by either decreasing the level of the administered PPAR-agonist compounds or combinations of such compounds, or by changing the PPAR-agonist combination administered.

The present invention additionally encompasses kits comprising one or more biomarker polypeptides, and/or anti-biomarker antibodies, which can be used to predict the likelihood of dose-dependent peripheral edema or edema like effects, of one or more drugs, compounds, or other therapeutic agents. Such kits can be used in clinical or pre-clinical settings, and can include one or more biomarker polypeptides and anti-biomarker antibodies. In specific aspects of the invention, the kits can include one or more microarrays comprising antibodies that specifically bind with these biomarker polypeptides. The kits can be employed in conjunction with the manual and automated screening methods of the invention. In various aspects, the kits can include instructions for use, and reagents and materials for measuring levels of the biomarker polypeptides e.g., in immunoassays, such as enzyme linked immunosorbent assays (ELISAs); Western blotting; direct or indirect immunofluorescence, immunohistochemistry, and the like.

The present invention further encompasses cell culture systems for the identification of polypeptides, in addition to the specified biomarker polypeptides, whose levels (e.g., extracellular, intracellular, or cell lysate levels) correlate with increased risk of developing dose-dependent peripheral edema upon the administration of a PPAR-agonist. In specific aspects of the invention, such systems can comprise renin expressing cell lines, which can be incubated in the presence or absence of one or more drugs, compounds, or other therapeutic agents. The biomarker polypeptides identified from these systems can be useful for identifying test substances (or combinations of test substances) that may directly or indirectly increase the risk of a patient developing dose-dependent peripheral edema in response to the administration of PPAR-agonist compounds or combinations of such compounds, and thus to prevent or diminish the likelihood of a patient developing dose-dependent peripheral edema by either decreasing the level of the administered PPAR-agonist compounds or combinations of such compounds, or by changing the PPAR-agonist combination administered.

The present invention encompasses methods of measuring the levels of polypeptides (e.g., extracellular polypeptides in the media) using mass spectrometer data to determine the number of peptide "hits" for each polypeptide, and comparing the results obtained in the presence and absence of a test substance.

Also encompassed by the invention are nucleic acids encoding the disclosed renin biomarker polypeptide (SEQ ID NO:9), and fragments, variants, and derivatives thereof, as well as screening assays, kits, microarrays, and cell culture systems employing these nucleic acids. In one aspect of the invention, screening assays (e.g., RT-PCR or in situ assays) that measure levels of one or more biomarker nucleic acids are used to predict which compound are likely to increase the risk of a patient developing dose-dependent peripheral edema in response to the administration of PPAR-agonist compounds or combinations of such compounds, and thus to prevent or diminish the likelihood of a patient developing dose-dependent peripheral edema by either decreasing the level of the administered PPAR-agonist compounds or combinations of such compounds, or by changing the PPAR-agonist combination administered. Elevated levels of one or more biomarker nucleic acids in the presence of the test substance(s) can be used to predict which patients have an increased risk of developing dose-dependent peripheral edema in response to the administration of PPAR-agonist compounds or combinations of such compounds, and thus to identify those patients that require monitoring more closely if an increased dosage of a PPAR-agonist is contemplated in order to avoid the potential of increasing the likelihood of developing dose-dependent peripheral edema or an edema-like disorder. Alternatively, low levels of one or more biomarker nucleic acids in the presence of the test substance(s) can be used to predict which patients have a decreased risk of developing dose-dependent peripheral edema in response to the administration of PPAR-agonist compounds or combinations of such compounds, and thus identify which patients may be admininstered a correspondingly higher amount of a PPAR-agonist without increasing the likelihood of developing dose-dependent peripheral edema or an edema-like disorder.

The present invention also encompasses a method of predicting the risk that compound may increase the risk of a patient developing dose-dependent peripheral edema of a test substance comprising the steps of: (a) incubating a renin expressing cell in the presence and absence of a test substance; and (b) comparing levels of at least one biomarker polypeptide, in the presence and absence of said test substance; wherein an elevated level of said biomarker polypeptide(s) in the presence of the test substance indicates that the substance is predicted to increase the risk of a patient developing dose-dependent peripheral edema in response to the administration of PPAR-agonist compounds or combinations of such compounds, and wherein the level of said biomarker polypeptide(s) is measured using single or multi dimensional high performance liquid chromatography coupled to tandem mass spectrometry wherein the number of peptide hits from each protein identification are used to determine the abundance of said biomarker polypeptide(s) in the presence and absence of said test substance.

Publications and other materials setting forth such the proteomics methodologies include the following: McDonald W H, Yates J R 3rd., 2002, Shotgun proteomics and biomarker discovery, *Dis. Markers*. 18(2):99-105; Link A J, 2002, Multidimensional peptide separations in proteomics, *Trends Biotechnol. December;* 20(12 Suppl):S8-13. Additional publications outlining the application of such proteomic methods is set forth in the following: J. Gao et al, "Identification of In Vitro Protein Biomarkers of Idiosyncratic Liver Toxicity," Toxicology In Vitro, 18(4), 533-541 (2004); J. Gao et al, "Changes in the Protein Expression of Yeast as a Function of Carbon Source," Journal of Proteome Research, 2(6), 643-649 (2003); J. X. Pang et al, "Biomarker Discovery in Urine by Proteomics," Journal of Proteome Research, 1(2), 161-169 (2002). All of these publications are incorporated by reference herein in their entirety.

Methods of Use of the Human Endoethelin-1 Biomarker Polypeptide

As shown in FIGS. 16 and 17, Treatment with compounds A thru E all resulted in a significant down-regulation of endothelin-1 gene expression whereas no significant change in GAPDH expression was observed. Down-regulation of endothelin-1 by compound C and D is consistent with published literature (Satoh et al., 1999; Iglarz et al., 2003). In this induction study, all PPAR agonists repressed endothelin-1 expression to similar levels in accordance with their being used at equivalent effective doses (e.g. 5×EC50). There was no significant difference in the level of endothelin-1 repression when comparing CALU-6 cells treated with compound A and any other PPAR agonist studied.

In accordance with the present invention, the expression level of human endothelin-1 was determined to be significantly repressed in the presence of a PPAR-agonist, indicating that human endothelin-1 is useful as a biomarker for predicting whether a patient administered a PPAR-agonist will respond to PPAR-agonist therapy; for predicting whether a patient will respond to specific doses of a PPAR-agonist; whether the level of the administered PPAR-agonist needs to be increased or decreased to achieve the desired level of human endothelin-1 expression identified as representing a responsive level; in addition to predicting whether a patient has an increased risk of developing dose-dependent peripheral edema upon the administration of a pharmaceutically acceptable level of a PPAR-agonist; predicting whether said patient should be monitored more closely prior to increasing the level of administered PPAR agonist to limit the risk of developing said dose-dependent peripheral edema; and predicting whether said patient may be administered a higher level of administered PPAR agonist without the risk of developing said dose-dependent peripheral edema.

In another embodiment of the present invention, human endothelin-1 is useful as a biomarker for pre- or post-clinical screening to identify PPAR-agonist compounds or combinations of such compounds that are likely to increase the risk of a patient developing dose-dependent peripheral edema in response to the administration of PPAR-agonist compounds or combinations of such compounds, and thus to prevent or diminish the likelihood of a patient developing dose-dependent peripheral edema by either advising patients be monitored more closely if such a compound or combination of compounds are administered at a corresponding higher dose, or by changing the PPAR-agonist combination administered.

Cells endogenously expressing human endothelin-1 can be treated with at least one test substance, and extracellular and/or intracellular levels of the biomarker endothelin-1 polypeptide in the presence and absence of the test substance(s) can be compared. The observation of repressed levels of the endothelin-1 biomarker polypeptide in the presence of the substance(s) can be used to predict which compounds are likely to increase the risk of a patient developing dose-dependent peripheral edema in response to the administration of PPAR-agonist compounds or combinations of such compounds, and thus to prevent or diminish the likelihood of a patient developing dose-dependent peripheral edema by not selecting such a test compound in the screen, wherein the induction of a repressed level of endotholin-1 in response to said test compound would be indicative of a compound that may increase the risk of a patient developing dose-dependent peripheral edema in response to the administration of PPAR-agonist compounds or combinations of such compounds. In an additional aspect, the assays of the invention are automated for high throughput screening. The results of such screening may be used to determine the need to modify or discontinue an existing treatment.

The present invention also encompasses microarrays, e.g., protein, antibody, or cell-based microarrays, which can be used in conjunction with the disclosed screening assays for measuring the endothelin-1 biomarker polypeptide. The protein, antibody, and cell-based microarrays can be used in the manual or automated screening assays of the invention as disclosed herein to test one or more drugs, compounds, or other therapeutic agents. For protein microarrays, polypeptides obtained from endothelin-1 expression cells (e.g., from extracellular media or cell lysates) incubated in the presence and absence of at least one test substance can be affixed to a support, and then contacted with antibodies that specifically bind to the endothelin-1 biomarker polypeptide. For antibody microarrays, one or more anti-biomarker antibodies can be affixed to a support, and then contacted with extracellular media or cell lysates obtained from endothelin-1 expressing cells incubated in the presence and absence of at least one test substance. For cell-based microarrays, one or more cells can be affixed to a support, and then incubated in the presence and absence of at least one test substance. The microarrays can then be analyzed (e.g., by immunoassay) to determine elevated levels of at least one biomarker polypeptide in the presence of the test substance(s), which can be used to predict which compound are likely to increase the risk of a patient developing dose-dependent peripheral edema in response to the administration of PPAR-agonist compounds or combinations of such compounds, and thus to prevent or diminish the likelihood of a patient developing dose-dependent peripheral edema by either decreasing the level of the administered PPAR-agonist compounds or combinations of such compounds, or by changing the PPAR-agonist combination administered.

The present invention additionally encompasses kits comprising one or more biomarker polypeptides, and/or anti-biomarker antibodies, particularly endothelin-1 and endothelin-1 directed antibodies, respectively, which can be used to predict the likelihood of dose-dependent peripheral edema or edema like effects, of one or more drugs, compounds, or other therapeutic agents based upon whether the level of biomarker polypeptide observed in a sample relative to the expression level observed for a reference compound is indicative of an increased or decreased risk of a patient developing dose-dependent edema. Such kits can be used in clinical or pre-clinical settings, and can include one or more biomarker polypeptides and anti-biomarker antibodies. In specific aspects of the invention, the kits can include one or more microarrays comprising antibodies that specifically bind with these biomarker polypeptides. The kits can be employed in conjunction with the manual and automated screening methods of the invention. In various aspects, the kits can include instructions for use, and reagents and materials for measuring levels of the biomarker polypeptides e.g., in immunoassays, such as enzyme linked immunosorbent assays (ELISAs); Western blotting; direct or indirect immunofluorescence, immunohistochemistry, and the like.

The present invention further encompasses cell culture systems for the identification of polypeptides, in addition to the specified biomarker polypeptides, whose levels (e.g., extracellular, intracellular, or cell lysate levels) correlate with increased risk of developing dose-dependent peripheral edema upon the administration of a PPAR-agonist. In specific aspects of the invention, such systems can comprise endothelin-1 expressing cell lines, which can be incubated in the presence or absence of one or more drugs, compounds, or other therapeutic agents. The biomarker polypeptides identified from these systems can be useful for identifying test substances (or combinations of test substances) that may directly or indirectly increase the risk of a patient developing dose-dependent peripheral edema in response to the administration of PPAR-agonist compounds or combinations of such compounds, and thus to prevent or diminish the likelihood of a patient developing dose-dependent peripheral edema by either decreasing the level of the administered PPAR-agonist compounds or combinations of such compounds, or by changing the PPAR-agonist combination administered.

The present invention encompasses methods of measuring the levels of polypeptides (e.g., extracellular polypeptides in the media) using mass spectrometer data to determine the number of peptide "hits" for each polypeptide, and comparing the results obtained in the presence and absence of a test substance.

Also encompassed by the invention are nucleic acids encoding the disclosed endothelin-1 biomarker polypeptide (SEQ ID NOs:38 and/or 40), and fragments, variants, and derivatives thereof, as well as screening assays, kits, microarrays, and cell culture systems employing these nucleic acids. In one aspect of the invention, screening assays (e.g., RT-PCR or in situ assays) that measure levels of one or more biomarker nucleic acids, particularly directed to endothlin-1 nucleotides, are used to predict which compound are likely to increase the risk of a patient developing dose-dependent peripheral edema in response to the administration of PPAR-agonist compounds or combinations of such compounds, and thus to prevent or diminish the likelihood of a patient developing dose-dependent peripheral edema by either decreasing the level of the administered PPAR-agonist compounds or combinations of such compounds, or by changing the PPAR-agonist combination administered. Elevated or depressed levels of one or more biomarker nucleic acids in the presence of the test substance(s) can be used to predict which patients have an increased risk of developing dose-dependent peripheral edema in response to the administration of PPAR-agonist compounds or combinations of such compounds, and thus to identify those patients that require monitoring more closely if an increased dosage of a PPAR-agonist is contemplated in order to avoid the potential of increasing the likelihood of developing dose-dependent peripheral edema or an edema-like disorder. In the case of endoethelin-1, a test compound that repressed endothlin-1 expression would be predicted to increase a patients risk of developing dose-dependent edema upon administration of the same. Alternatively, increased levels of one or more biomarker nucleic acids, particularly endothelin-1 directed nucleotides, in the presence of the test substance(s) can be used to predict which patients have a decreased risk of developing dose-dependent peripheral edema in response to the administration of PPAR-agonist compounds or combinations of such compounds, and thus identify which patients may be administered a correspondingly higher amount of a PPAR-agonist without increasing the likelihood of developing dose-dependent peripheral edema or an edema-like disorder.

The present invention also encompasses a method of predicting the risk that compound may increase the risk of a patient developing dose-dependent peripheral edema of a test substance comprising the steps of: (a) incubating a endothelin-1 expressing cell in the presence and absence of a test substance; and (b) comparing levels of at least one biomarker polypeptide, in the presence and absence of said test substance; wherein a repressed level of said biomarker polypeptide(s) in the presence of the test substance indicates that the substance is predicted to increase the risk of a patient developing dose-dependent peripheral edema in response to the administration of PPAR-agonist compounds or combinations of such compounds, and wherein the level of said biomarker polypeptide(s) is measured using single or multi dimensional high performance liquid chromatography coupled to tandem mass spectrometry wherein the number of peptide hits from each protein identification are used to determine the abundance of said biomarker polypeptide(s) in the presence and absence of said test substance.

Publications and other materials setting forth such the proteomics methodologies include the following: McDonald W H, Yates J R 3rd., 2002, Shotgun proteomics and biomarker discovery, *Dis. Markers*. 18(2):99-105; Link A J, 2002, Multidimensional peptide separations in proteomics, *Trends Biotechnol*. December; 20(12 Suppl):S8-13. Additional publications outlining the application of such proteomic methods is set forth in the following: J. Gao et al, "Identification of In Vitro Protein Biomarkers of Idiosyncratic Liver Toxicity," Toxicology In Vitro, 18(4), 533-541 (2004); J. Gao et al, "Changes in the Protein Expression of Yeast as a Function of Carbon Source," Journal of Proteome Research, 2(6), 643-649 (2003); J. X. Pang et al, "Biomarker Discovery in Urine by Proteomics," Journal of Proteome Research, 1(2), 161-169 (2002). All of these publications are incorporated by reference herein in their entirety.

In Vitro and In Vivo Confirmation of Use of Renin and Endothelin-1 Expression Levels as Biomarkers for Predicting Compound Edemagenicity In an effort to further confirm the association between renin and endothelin-1 expression levels to the incidence of edema for PPAR-agonists, an expended number of in vitro experiments as well as in vivo experiments were performed.

The endothelin-1 gene has been shown to be down-regulated by a PPARγ agonist via activating protein 1 (P. Delerive et al., *Circ. Res.* 85, 394 (1999)). However, whether expression of renin and β1 adrenergic receptor expression is affected by a PPARγ agonist was previously unknown. For this reason, the mRNA expression levels of these genes was measured using quantitative RT-PCR in CALU-6 cells, a lung carcinoma cell line that has been used to study renin gene regulation (J. A. Lang et al., *Hypertension*. 25, 704 (1995); S. Germain et al., *Febs Lett*. 407, 177 (1997)). Consistent with expectation, two PPARγ agonists COM. D and COM. A down-regulated endothelin-1 gene expression by a factor of four to five (FIG. 21A). In contrast, both PPARγ agonists increased renin mRNA by a factor of fifteen to twenty (FIG. 21A). This effect was dependent on PPARγ because pretreatment of CALU-6 cells with COM. K, a PPARγ antagonist, prevented induction of renin gene expression and down-regulation of endothelin-1 by COM. A (FIG. 21A). Expression of the β1 adrenergic receptor gene was not affected by any PPARγ agonist tested and was not investigated further (data not shown).

The potencies of ten different PPARγ agonists with regard to induction of renin and down-regulation of endothelin-1 gene expression was then determined. All PPARγ agonists that were tested substantially and statistically significantly induced renin and repressed endothelin-1 gene expression in CALU-6 cells (Table H).

TABLE H $EC_{50}$ values for PPAR agonists tested for affect on Renin and Endothlin-1 Expression Levels

| PPAR agonist | Renin $EC_{50}$ (nM) | Endothelin-1 $IC_{50}$ (nM) |
|---|---|---|
| COM. A | 96.30 ± 32.00 | 17.99 ± 6.07 |
| COM. B | 0.95 ± 0.44 | 0.06 ± 0.008 |
| COM. D | 1.05 ± 0.15 | 0.37 ± 0.05 |
| COM. E | 3082.97 ± 2320.72 | 49.75 ± 12.23 |
| COM. C | 1223.97 ± 505.02 | 6.18 ± 2.39 |
| COM. G | 428.33 ± 71.68 | 120.32 ± 26.64 |
| COM. F | 171.33 ± 57.59 | 35.62 ± 12.13 |
| COM. H | 3.94 ± 0.83 | 1.03 ± 0.23 |
| COM. I | 2.83 ± 0.73 | 0.47 ± 0.11 |
| COM. J | 50.68 ± 13.90 | 34.45 ± 8.26 |

Shown are mean ± SEM $EC_{50}$ values for renin up-regulation and mean ± SEM $IC_{50}$ values for endothelin-1 down-regulation derived from dose-titration experiments (n = 3 to n = 18) described in FIG. 21A.
NA: none available.

Examination of the $EC_{50}$ values (concentration of drug required to achieve half-maximal induction of renin and repression of endothelin-1) revealed that the compounds could be classified into two distinct clusters (FIG. 21B). One cluster was comprised of the very potent PPARγ agonists COM. B and COM. D. Because COM. D is known to be a potent inducer of edema (T. Leff and J. E. Reed. *Curr. Med.*

Chem.-Imm., Endoc. & Metab. Agents, 2, 33 (2002)), this cluster was labeled "more edemagenic". The second cluster, comprised of COM. A, COM. C, COM. E, COM. G and COM. F, was labeled as "less edemagenic" because several of the compounds, including muraglitazar, COM. E and COM. C, have an acceptable incidence and severity of edema at doses that are used to treat diabetics and in Phase III studies (R. W. Nesto et al., Circulation 108, 2941 (2003)). These observations further confirmed the hypothesis that compounds that are potent inducers of renin and repressors of endothelin-1 expression are likely to be more edemagenic than less potent compounds.

To test this hypothesis further, three other investigational PPARα/γ dual agonists, COM. I, COM. J, and COM. H, that were indistinguishable from one another with regard to efficacy in animal models of diabetes were evaluated in the CALU-6 model. Compared to COM.I and COM.H, COM. J was less potent at both inducing renin expression and repressing endothelin-1 expression, clustered with the less edemagenic group of compounds and was therefore classified as less likely to cause edema, whereas the other two compounds clustered with compounds more likely to cause edema (FIG. 21B).

A monkey model of PPARγ agonist-induced edema was used to test the prediction that COM. J may cause less edema than COM. H and COM. I. Pilot studies showed that cynomolgus monkeys were sensitive to PPARγ agonist-induced edema, with the most prominent swelling observed around the eyes, scrotum, and abdomen (unpublished data). To compare the edemagenicity of COM. I, COM. J, and COM. H, monkeys were orally administered each compound once daily for 1 month at doses predicted to yield similar plasma exposures for all 3 compounds. Edema was assessed qualitatively by visual observations performed daily and quantitatively using magnetic resonance imaging (MRI) performed prior to dosing, at the mid-point of the study, and at the end of dosing. Consistent with the prediction from the gene expression assay, on an exposure-related basis, COM. J was the least edemagenic of the three compounds and COM. I the most edemagenic based on both visual observations and quantitative MRI evaluation of fluid retention (FIGS. 22A-F). It is worth noting, however, that while the clustering of $EC_{50}$ values with respect to renin and endothelin-1 expression placed COM. H and COM. I in the same cluster, the monkey experiment permitted a finer distinction between these compounds, with COM. H appearing less edemagenic than COM. I (FIGS. 22G-H). A likely explanation for this observation is that the CALU-6 in vitro model is not affected by pharmacokinetic parameters of a drug. The shorter half-life of COM. H in monkeys (approximately 50% compared to the other 2 compounds) could potentially account for its being less edemagenic than COM. J in vivo.

REFERENCES

Agapitov A V and Haynes W G (2002) Role of endothelin in cardiovascular disease. J Renin Angiotensin Aldosterone Syst 3(1):1-15.

Ahmed, U. et al. *Hyperten. Res.* 28, 339 (2005).

Altschul S F, G. W., Miller W, Myers E W, Lipman D J (1990). "Basic local alignment search tool." J Mol Biol 215 (3): 403-410.

Barish, G. D., et al., *J. Clin. Invest.* 116, 590 (2006).

Bengtsson J, Melander O, Orho-Melander M, Lindblad U, Ranstam J, Rastam L, Groop L. (2001) Polymorphism in the b1-adrenergic receptor gene and hypertension. Circulation 104:187-190.

Berger J, Wagner J A (2002) Physiological and therapeutic roles of peroxisome proliferator-activated receptors. Diabetes Technology & Therapeutics 4(2):163-174.

Brewster U C, Setaro J F, Perazella M A (2003) The renin-angiotensin-aldosterone system: cardiorenal effects and implications for renal and cardiovascular disease states Am J Med Sci 326(1):15-24.

Castellano M and Bohm M (1997) The cardiac b-adrenoceptor-mediated signaling pathway and its alterations in hypertensive heart disease. Hypertension 29(3):715-735.

Chen X, L. L., Kwok P Y. (1999). "Fluorescence polarization in homogeneous nucleic acid analysis." Genome Res. 1999 May; 9 (5):492-8. 9 (5): 492-498.

Chen H H, Redfield M M, Nordstrom L J, Cataliotti A, Burnett J C (2003) Angiotensin II AT1 receptor antagonism prevents detrimental renal actions of acute diuretic therapy in human heart failure Am J Physiol Renal Physiol 284: F1115-F1119.

Chruscinski A, Brede M E, Meinel L, Lohse M J, Kobilka B K, Hein L. (2001) Differential distribution of b-adrenergic receptor subtypes in blood vessels of knockout mice lacking b1- or b2-adrenergic receptors. Mol Pharmacol 60:955-962.

Cormack, B. (2000). Directed Mutagenesis Using the Polymerase Chain Reaction. Current Protocols in Molecular Biology, John Wiley & Sons, Inc. Supplement 37: 8.5.1-8.5.10.

Delerive P, Martin-Nizard F, Chinetti G, Trottein F, Fruchart J C, Najib J, Duriez P, Staels B (1999) Peroxisome proliferator-activated receptor activators inhibit thrombin-induced endothelin-1 production in human vascular endothelial cells by inhibiting the activator protein-1 signaling pathway Circ Res 85(5):394-402.

Diep Q N, Mabrouk M, Cohn J S, Endemann D, Amiri F, Virdis A, Fritsch-Neves M, Schiffrin E L (2002) Structure, endothelial function, cell growth and inflammation in blood vessels of angiotensin II-infused rats—role of peroxisome proliferator-activated receptor gamma Circulation 105:2296-2302.

Dzimiri N. (1999) Regulation of b-adrenoceptor signaling in cardiac function and disease Pharmacological Reviews 51(3):465-501.

Ferre, P., *Diabetes* 53, S43 (2004).

Fukunaga Y, Itoh H, Doi K, Tanaka T, Yamashita J, Chun T H, Inoue M, Masatsugu K, Sawada N, Saito T, Hosoda K, Kook H, Ueda M, Nakao K. (2001) Thiazolidinediones, peroxisome proliferator-activated receptor gamma agonists, regulate endothelial cell growth and secretion of vasoactive peptides. Atherosclerosis' 158(1): 113-119.

Germain S, Philippe J, Fuchs S, Armelle L, Corvol P, Pinet F. (1997) Regulation of human renin secretion and gene transcription in Calu-6 cells. FEBS Letters 407:177-183.

Germain S, Bonnet F, Fuchs S, Phillippe J, Corvol P, Pinet F. (1999) Dissection of silencer elements in first intron controlling the human renin gene. J Hypertens 17(7):899-905.

Gianessi D, Del Ry S, Vitale R L (2001) The role of endothelins and their receptors in heart failure Pharmacolog Res 43(2):111-126

Goodfriend T L, Elliot M E, Catt K J (1996) Angiotensin receptors and their antagonists NEJM 334(25):1649-1654.

Guan, Y. et al. *Nature Med.* 11, 861 (2005). H. Zhang et al. *PNAS* 102, 9406 (2005).

Harrity, T. et al., *Diabetes* 55, 240 (2006).

Hegarty, B. D., et al., *Endocrinology* 145, 3158 (2004).

Hollenberg N K (2003) Considerations for management of fluid dynamic issues associated with thiazolidinediones Am J Med 115(8A): 111-115.

Holmer, S. R. et al., *J. Hypertens.* 15, 1471 (1997).

Hosmer, D. W., and S. Lemeshow, 2000 Applied logistic regression. John Wiley & Sons, New York.

Iglarz M, Touyz R M, Amiri F, Lavoie M F, Diep Q N, Schiffrin E L. (2003) Effect of peroxisome proliferator-activated receptor-alpha and -gamma activators on vascular remodeling in endothelin-dependent hypertension. Arterioscler Thromb Vasc Biol. 23(1):45-51.

Izzo, J. and Black, H. R. eds. *Hypertension Primer* pubs. Lippincott Williams & Williams (1993).

Johnson, J. et al., *Clin. Pharm. Therap.* 74, 44 (2003).

Kawana M, Lee M E, Quertermous E E, Quertermous T (1995) Cooperative interaction of GATA-2 and AP1 regulates transcription of the endothelin-1 gene. Mol Cell Biol. 15(8):4225-4231.

Kermani, A. et al., *Mayo Clin. Proc.* 78, 1088 (2003).

Lang J A, Yang G, Kern J A, Sigmund C D (1995) Endogenous human renin expression and promoter activity in CALU-6, a pulmonary carcinoma cell line. Hypertension 25(4):704-710)

Leff, T. et al., Curr. Med. Chem.-1 mm., Endoc. & Metab. Agents, 2, 33 (2002).

Lennon G, A. C., Polymeropoulos M, Soares M B (1996). "The I.M.A.G.E. Consortium: an integrated molecular analysis of genomes and their expression." Genomics 33 (1): 151-152.

Lohse M J, Engelhardt S, Eschenhagen T. (2003) What is the role of b-adrenergic signaling in heart failure? Circ Res 93:896-906.

Luscher T F and Barton M (2000) Endothelins and Endothelin Receptor Antagonists—therapeutic considerations for a novel class of cardiovascular drugs. Circulation 102:2434-2440.

Marx N, Bourcier T, Sukhova G K, Libby P, Plutzky J. (1999) PPARgamma activation in human endothelial cells increases plasminogen activator inhibitor type-1 expression: PPARgamma as a potential mediator in vascular disease. Arterioscler Thromb Vasc Biol 19(3):546-51.

Mason, D. A. et al. *J. Biol. Chem.* 274, 12670 (1999).

Mehta, C., and N. Patel, 2000 LOGXACT-4® for Windows, pp. Cytel Software Corporation, Cambridge.

Mehta, C. R., and N. R. Patel, 1995 Exact logistic regression: theory and examples. Stat Med 14: 2143-60.

Nesto, R. W. et al., *Circulation* 108, 2941 (2003).

Nickerson D A, T. V., Taylor S L. (1997). "PolyPhred: automating the detection and genotyping of single nucleotide substitutions using fluorescence-based resequencing." Nucleic Acids Res 25 (14): 2745-2751.

Ricote M, Li A C, Willson T M, Kelly C J, Glass C K (1998) The peroxisome proliferator-activated receptor-gamma is a negative regulator of macrophage activation Nature 391 (6662):79-82.

Rozen S, S. H. (2000). "Primer3 on the WWW for general users and for biologist programmers." Methods Mol Biol 132: 365-386.

Ryan, M. J. et al. Am. J. Physiol. Heart Circ. Physiol. 283, H2458 (2002).

Satoh H, Tsukamoto K, Hashimoto Y, Hashimoto N, Togo M, Hara M, Maekawa H, Isoo N, Kimura S, Watanabe T. (1999) Thiazolidinediones suppress endothelin-1 secretion from bovine vascular endothelial cells: a new possible role of PPARgamma on vascular endothelial function. Biochem Biophys Res Commun 254(3):757-763.

Sambrook, J., E. Fritsch, et al. (1989). Molecular Cloning, Cold Spring Harbor Laboratory Press.

Schiffrin E L (2001) Role of endothelin-1 in hypertension and vascular disease Am J Hypertens 14:83-89.

Schiffrin E L, Amiri F, Benkirane K, Iglarz M, Diep Q N (2003) Peroxisome prolifterator-activated receptors—vascular and cardiac effects in hypertension Hypertension 42(2): 1-5.

Sofowara et al. *Clin. Pharm. Therap.* 73, 366 (2003).

Staels B, Koenig W, Habib A, Merval R, Lebret M, Torra I P, Delerive P, Fadel A, Chinetti G, Fruchart J C, Najib J, Maclouf J, Tedgui A. (1998) Activation of human aortic smooth-muscle cells is inhibited by PPARalpha but not by PPARgamma activators. Nature 393(6687):790-793.

Sugawara A, Takeuchi K, Uruno A, Ikeda Y, Arima S, Kudo M, Sato K, Taniyama Y, Ito S (2000) Transcriptional suppression of type I angiotensin II receptor gene expression by peroxisome proliferator-activated receptor gamma in vascular smooth muscle cells. Endocrinology 142:3125-3134.

Takeda K, Ichiki T, Tokunou T, Funakoshi Y, Ino N, Hirano K, Kanaide H, Takeshita A (2000) Peroxisome proliferator-activated receptor gamma activators downregulate angiotensin II type 1 receptor in vascular smooth muscle cells Circulation 102:1834-1839.

Tiret, L. et al., *Hypertension.* 33, 1169 (1999).

EXAMPLES

Example 1

Method of Discovering the Renin Single Nucleotide Polymorphisms (SNPs) of the Present Invention SNP discovery was based on comparative DNA sequencing of PCR products directed to the human renin gene derived from genomic DNA from multiple individuals. All genomic DNA samples for SNP discovery were obtained from a panel of thirty-two human subjects obtained from the Coriell Institute (Camden, N.J.), panel # M44PDR. A total of 50 SNPs within the human renin gene were identified. Of these 50, 3 were found to be associated with the incidence of dose-dependent peripheral edema:

Renin-SNP3: G/A at nucleotide 12586 of SEQ ID NO:1 and 2 in the MBO 1 restriction site (Reference: Renin-SNP3 has been described by Masharani U et al, Nucleic Acids Res. 1988 Mar. 25; 16(5):2357)

Renin-SNP5: A/G at nucleotide 10096 of SEQ ID NO:3 and 4 near the ARE7 motif

Renin-SNP7: G/deletion of G allele at nucleotide 13076 of SEQ ID NO:5 near PPRE motif Renin-SNP3, Renin-SNP5, and Renin-SNP7 were identified using the following protocol. Briefly, portions of the human renin genomic sequence were PCR amplified using the standard PLATINUM® Taq DNA protocol (Invitrogen, Product #10966-083):

The following sequencing primers (20 uM each) were used to find the above SNPs, as well as to sequence across the PCR amplicons:

| SNP | Forward Primer | Reverse Primer |
|---|---|---|
| Renin-SNP3 | TGTAAAACGACGGCCAGTttcgcttgttcacctc acac (SEQ ID NO:11) | CAGGAAACAGCTATGACCgcccaggtac caggattttt (SEQ ID NO:12) |
| Renin-SNP5 | TGTAAAACGACGGCCAGTgggtaagaacatga ggccagt (SEQ ID NO:13) | CAGGAAACAGCTATGACCaaaaacaccc acccttcctc (SEQ ID NO:14) |
| Renin-SNP7 | TGTAAAACGACGGCCAGTttgtttgcctgggatc tagc (SEQ ID NO:15) | CAGGAAACAGCTATGACCggggcatctca gagagtgtt (SEQ ID NO:16) |

All the samples amplified from genomic DNA (50 ng) in reactions (50 ul) containing 50 mM Tris-Acetate pH 8.4, 75 mM KAcetate, 8 mM MgAcetate, 200 uM dNTPs, 0.2 uM of each PCR primer, and 2.5 U PLATINUM® Taq DNA polymerase (Invitrogen).

PCR amplification was performed in Perkin Elmer 9700 machines under the following cycling conditions: 1.) 94 degrees Celsius for 2 minutes; 2.) 94 degrees Celsius for 30 seconds; 3.) 59 degrees Celsius for 1 minute; 4.) 72 degrees Celsius for 30 seconds; 5.) 72 degrees Celsius for 5 minutes; and 6.) 4 degrees Celsius on hold. Steps 2 to 4 were cycled 35 times.

PCR products were sequenced using ABI BigDye Terminator v3.1 Cycle Sequencing chemistry on the 3730-XL capillary sequencers using the same primers used for identifying the SNPs, as described above.

Sequence editing and contig assembly was performed using CONSED software (Genome Res. 1998 March; 8(3): 195-202). Chromatograms were visually inspected for each Coriell DNA and SNPs identified by comparing sequence traces to the reference renin genomic DNA sequence provided as GENBANK® Accession No. gi|42406218 (SEQ ID NO:10; RefSeq No. NC_000001.7, nucleotides 201301381 to 201312898). Nucleotide 1 of SEQ ID NO:10 corresponds to nucleotide 1986 of SEQ ID NO:1, 2, 3, 4, 5, 6, and 7; while nucleotide 11518 of SEQ ID NO:10 corresponds to nucleotide 13503 of SEQ ID NO:1, 2, 3, 4, 5, and 7, and nucleotide 13502 of SEQ ID NO:6.

The nucleotide sequence of the renin gene containing the reference allele ("G") for Renin-SNP3 at nucleotide 12586 is provided in FIGS. 1A-M (SEQ ID NO:1); while the nucleotide sequence of the renin gene containing the variable allele ("A") for Renin-SNP3 at nucleotide 12586 is provided in FIGS. 2A-M (SEQ ID NO:2).

The nucleotide sequence of the renin gene containing the reference allele ("A") for Renin-SNP5 at nucleotide 10096 is provided in FIGS. 3A-M (SEQ ID NO:3); while the nucleotide sequence of the renin gene containing the variable allele ("G") for Renin-SNP5 at nucleotide 10096 is provided in FIGS. 4A-M (SEQ ID NO:4).

The nucleotide sequence of the renin gene containing the reference allele ("G") for Renin-SNP7 at nucleotide 13076 is provided in FIGS. 5A-M (SEQ ID NO:5); while the nucleotide sequence of the renin gene containing the variable allele ("G-deletion") for Renin-SNP7 at nucleotide 13076 is provided in FIGS. 6A-M (SEQ ID NO:6).

Example 2

Method of Genotyping Each SNP of the Present Invention

Genomic DNA samples from patients enrolled in two Bristol-Myers Squibb Company Phase II clinical trials CV168-006 and CV168-008 trials were genotyped for 50 SNPs identified in the human renin gene (see Example 1) and evaluated for association with edema.

498 subjects enrolled in the CV168-006 trial and 232 subjects from the CV168-008 trial were analyzed in this study. All analyses were based on data collected up to 24 weeks, which was the duration of the short-term phase of the trials. DNA was extracted from frozen blood by a third-party (Genaissance Inc, North Carolina) using a salting-out method (Gentra Systems). All subjects gave written informed consent.

Genotyping was performed using the 5' nuclease assay, essentially as described (Ranade K et al., Genome Research 11: 1262-1268 (2001); which is hereby incorporated by reference herein in its entirety), with the following modifications: six nanograms of genomic DNA were used in a 8 ul reaction. All PCR reactions were performed in an ABI 9700 machine and fluorescence was measured using an ABI 7900 machine.

Genotyping of the SNPs of the present invention was performed using sets of TAQMAN® probes (100 uM each) and primers (100 uM each) specific to the SNP. Each probe/primer set was manually designed using ABI Primer Express software (Applied Biosystems). Genomic samples were prepared as described in Example 1. The following TAQMAN® probes and primers were utilized:

| SNP | TAQMAN® Forward Primer | TAQMAN® Reverse Primer | Reference TAQMAN® Probe | Variable TAQMAN® Probe |
|---|---|---|---|---|
| Renin-SNP3 | ACAGAGACCCTCA AAGAGTGACAGA (SEQ ID NO:17) | ACATGCACAGCC AAGTTTGAGA (SEQ ID NO:18) | TTCTAACATGAC CTGTGCATT (SEQ ID NO:19) | CTAACATGATCT GTGCATTGT (SEQ ID NO:20) |
| Renin-SNP5 | TGATAGAAAGTGA GGCCTTGAGAAA (SEQ ID NO:21) | CACGTCGTCCAC CTCTTAACTTCT (SEQ ID NO:22) | CCTTGCCCCCAC TTCCTCTAAAAC AGTT (SEQ ID NO:23) | CCTTGCCCCCAC CTCCTCTAAAAC AGT (SEQ ID NO:24) |

-continued

| SNP | TAQMAN® Forward Primer | TAQMAN® Reverse Primer | Reference TAQMAN® Probe | Variable TAQMAN® Probe |
|---|---|---|---|---|
| Renin-SNP7 | AATGGCCATGATG TGAGGGA (SEQ ID NO:25) | CCATACCCAGCA CATGAGCAT (SEQ ID NO:26) | TTGCCTGACCCC CAGCAACTGTC T (SEQ ID NO:27) | CCTTGCCTGACC CC[ǁ]AGCAACTG TC (SEQ ID NO:28) |

** The allelic nucleotide in each probe sequence is shown in bold and underlined.

The genotype assay conditions are provided below.

| Components | Final Concentration |
|---|---|
| 2x PE Master Mix (#4318157) | 1X |
| 100 uM FAM labeled probe | 200 nmol |
| 100 uM VIC labeled probe | 200 nmol |
| Forward PCR primer | 600 nmol |
| Reverse PCR primer | 600 nmol |
| 6 ng template DNA | as required |
| ddH20 | volume to 8 ul |

TAQMAN® thermo-cycling was performed on Perkin Elmer PE 9700 machines using the following cycling conditions below:
1) 50C for 2 minutes
2) 95C for 10 seconds*
3) 94C for 15 seconds
4) 62C for 1 minute
5) 4C hold

*Steps 2-4 were cycled 40 times

Analysis of genotypes was performed by using the Applied Biosystems ABI 7900 HT sequence detection system.

Example 3

Statistical Analysis of the Association Between Dose-Dependent Peripheral Edema and the Renin SNPs of the Present Invention The association between peripheral edema and the renin single nucleotide polymorphisms of the present invention were investigated by applying statistical analysis to the results of the genotyping assays described elsewhere herein. The central hypothesis of this analysis is that a predisposition to develop dose-dependent peripheral edema may be conferred by specific genomic factors. The analysis attempted to identify one or more of these factors in genomic DNA samples from index cases and matched control subjects who were exposed to Compound A in two Bristol-Myers Squibb (BMS) clinical studies (see Example 2).

SNPs of the present invention were examined for association with edema using 3 (genotypes)×2 (edema and no edema) contingency tables. Significant results for edema (P<0.05) were followed up by logistic regression analysis including baseline body mass index, age, trial, sex, race and SNP as covariates. Because the frequency of renin Renin-SNP3 was significantly different between whites (allele frequency 0.26) and blacks (allele frequency 0.56), this SNP was analyzed by including and excluding blacks from the model. Analyses were performed using S-PLUS® (version 6.0; Insightful Corp. Seattle, Wash.) or SPSS® (version 12.0; SPSS Inc. Chicago, Ill.).

Methods

Sample. Investigators in the BMS clinical trials diagnosed dose-dependent peripheral edema in some subjects.

Measures. Single nucleotide polymorphisms (SNPs) in human renin were genotyped on all subjects essentially as described in Example 2 herein. The SNPs that are genotyped likely represent a sample of the polymorphic variation in each gene and are not exhaustive with regard to coverage of the total genetic variation that may be present in each gene. Specifically, only those 50 SNPs referenced herein were genotyped and statistically analyzed, as described. The SNPs for which a statistical association to angioedema susceptibility was confirmed are provided referred to as Renin-SNP3, Renin-SNP5, and Renin-SNP7.

Statistical Analyses. Conditional logistic regression (HOSMER and LEMESHOW 2000) was used to examine the associations between genotypes of renin gene SNPs and the development of dose-dependent peripheral edema. All SNPs are bi-allelic with three possible genotypes. For each SNP, in the overall sample and each subgroup, allele frequencies are estimated. For consistency in SNP genotype parameter coding in the logistic regression models, the less frequent allele of each SNP was designated as the rare allele and the number of copies of that allele that each subject carried, either 0, 1, or 2, was then determined. Three possible genotypes for each SNP leaves two degrees of freedom for parameters in the conditional logistic regression model representing the information contained in these three genotype categories. Two dummy variables are therefore created based on the copies of the rare allele for each subject for use in the conditional logistic regression model, $x_1 = 1$ if copies of rare allele=1, 0 otherwise and
$x_2 = 1$ if copies of rare allele=2, 0 otherwise.

The full conditional logistic regression model used was $$\pi_k(x) = \frac{e^{\alpha_k + \beta_1' x_1 + \beta_2' x_2}}{1 + e^{\alpha_k + \beta_1' x_1 + \beta_2' x_2}},$$

where x in $\pi_k(X)$ is the vector of dummy variables representing the SNP genotypes described above, k is the matching stratum index specific to each matched case-control set of subjects, $\pi_k(X)$ is the matching stratum-specific expected probability that a subject is a case given x, $\alpha_k$ is the matching stratum-specific contribution to $\pi_k(X)$ of all the matching variables constant within the kth stratum and each β' represents the contribution of the respective dummy variable to $\pi_k(X)$.

For each SNP, the null hypothesis was that the vector of β' are all equal to 0 and was tested using the scores test (HOSMER and LEMESHOW 2000). The degrees of freedom for the scores test statistic was equal to one less than the number of genotypes. Exponentiation of each slope coefficient, β', provided an estimate of the ratio of the odds of an adverse event (e.g., dose-dependent peripheral edema) in subjects carrying the specified copies of the rare allele represented in the definition of the coefficient, relative to controls matched for body mass index, age, trial, sex, race, and SNP as covariates, over the odds of such an adverse event for similarly matched subjects not carrying any copies of the rare allele. 95% confidence interval limits are estimated for each odds ratio based on the standard error estimate of the respective slope coefficient.

Since the SNP coverage within the human renin gene was not exhaustive of the genetic variation that may be present and possibly related to event susceptibility in this gene, inferences about these SNP associations with dose-dependent peripheral edema events for renin are therefore related to the hypothesis that genetic variation in this gene may be involved in susceptibility to such events.

Selection of Affected and Unaffected Subjects for Genetic Analysis of Dose-Dependent Peripheral Edema Table A provides a distribution of the frequency of dose-dependent peripheral edema by treatment arm. The frequency of edema increased as the dose of Compound A increased from 0.5 mg to 20 mg.

TABLE A

Frequency of dose-dependent peripheral edema by treatment

| Treatment arm (number of subjects) | Number of edema cases (%) |
|---|---|
| Placebo (41) | 2 (5) |
| Dose A (79) | 16 (20) |
| Dose B (90) | 14 (16) |
| Dose C (125) | 13 (10) |
| Dose D (129) | 27 (21) |
| Dose E (133) | 54 (41) |

* Dose of Compound A increased gradually from Dose A to Dose E with the latter representing a 40 fold increase in dosage relative to the former.

When compared to the overall trial populations, the Dose A and Dose B doses appeared to have a higher frequency of edema than expected, suggesting that there may have been some inadvertent bias in the collection of samples for genetic analysis.

To increase the likelihood of finding genetic associations, subjects who did not develop dose-dependent peripheral edema at the maximum dose of Compound A, i.e. Dose E, were considered "unaffected" and compared to subjects who developed edema at any dose of Compound A. The characteristics of these two groups are provided in Table B below. To see the reasoning behind this approach, compare the frequency of edema in the Dose C group (10%) and the Dose E group (40%). Thus, if subjects without edema in the Dose C group were considered unaffected, a significant number of individuals (30% of 125 or 38) who might be genetically susceptible to edema when exposed to a high dose of Compound A would be mis-classified, thereby reducing the genetic signal or power of the study. This approach is analogous to the use of extreme discordant sibpairs for detecting genes underlying quantitative traits.

TABLE B

Demographic characteristics of subjects used in the genetic analysis

| Trait | No Edema (N = 117) | Edema (N = 155) |
|---|---|---|
| Sex, Male/Female (% female)[a] | 79/38 (33%) | 56/99 (64%) |
| Age (mean ± sd)[a] | 51.8 ± 9.5 | 56.3 ± 8.3 |
| Baseline body mass index, kg/m$^2$[a] | 30.1 ± 4.3 | 32.4 ± 4.8 |
| Trial, 006/008 (% 006)[a] | 45/72 (39%) | 119/36 (77%) |
| Caucasian | 106 (91%) | 140 (90%) |
| Smokers | 65 (56%) | 85 (55%) |

[a]Significant difference P < 0.05 between subjects with and without edema

As shown in Table B, subjects who developed dose-dependent peripheral edema after exposure to Compound A were more likely to be female, older and heavier. Race and smoking status were not significant predictors of edema.

Genetic Associations with Edema

All subjects for whom sufficient DNA was available were genotyped for 218 SNPs in 65 candidate genes with 50 of these SNPs being specific for the human renin gene. Of these 218 SNPs, subjects enrolled in these trials were polymorphic for 153 SNPs (minor allele frequency >0.1%). In 3×2 contingency table analysis, SNPs in the renin genes were significantly associated with edema status (P<0.05). The distribution of genotypes between the two groups for each SNP is provided in FIGS. 8, 9, and 10 for Renin-SNP3, Renin-SNP5, and Renin-SNP7.

The genotype distributions for all three SNPs were in Hardy-Weinberg equilibrium. These univariate analyses were followed-up by multivariate logistic regression analyses including other covariates such as age and sex (Table C).

TABLE C

Multivariate analysis of SNP associations with edema

| Trait/SNP | Odds ratio (95% C.I.) | P value |
|---|---|---|
| Age | 1.08 (1.04-1.11) | <0.001 |
| Sex (Male vs. Female) | 0.17 (0.09-0.32) | <0.001 |
| Trial (−008 vs. −006) | 0.13 (0.06-0.26) | <0.001 |
| Body mass index | 1.12 (1.04-1.20) | 0.001 |
| Race | | 0.23 |
| Renin Renin-SNP3[a] | | 0.003 |
| C/T vs. C/C | 0.72 (0.37-1.41) | 0.72 |
| T/T vs. C/C | 0.12 (0.04-0.41) | 0.001 |
| Renin Renin-SNP5 | | 0.01 |
| A/G vs. A/A | 0.51 (0.26-0.99) | 0.05 |
| G/G vs. A/A | 0.13 (0.03-0.63) | 0.01 |
| Renin Renin-SNP7 | | 0.004 |
| Δ[b]/G vs. G/G | 0.42 (0.21-0.83) | 0.01 |
| Δ/Δ vs. G/G | 0.12 (0.02-0.60) | 0.01 |

[a]Because the allele frequency of this SNP was significantly different between blacks and whites, this SNP was also analyzed after excluding blacks. The P value for this analysis was 0.006, and the odds ratios were 0.69 (0.34-1.38) and 0.11 (0.03-0.43) for the C/T vs C/C and the T/T vs. C/C comparisons respectively.
[b]Denotes a 1 base-pair deletion.

Consistent with demographic data presented in Table B age, sex, body mass index, and trial were significant predictors of edema status. In contrast, race was not significantly associated with edema.

To explore further the association between the renin gene and edema, additional SNPs were identified by sequencing (see Example 1). Subjects were genotyped for nine of these newly identified SNPs. As shown in Table C, two of these SNPs, Renin Renin-SNP5 and Renin Renin-SNP7, showed evidence of association with edema. The distribution of genotypes for these SNPs is provided in Table C, in addition to FIGS. 8, 9, and 10. Both SNPs were in Hardy-Weinberg equilibrium. Renin-SNP5 is an A/G transition in the intron between exons five and six and Renin-SNP7 is a single base deletion in the intron between exons nine and ten. Like renin Renin-SNP3, the less common alleles of both SNPs reduced risk of edema. However, these SNPs are not in complete linkage disequilibrium with Renin-SNP3. Renin-SNP5 and Renin-SNP7 are in almost complete linkage disequilibrium with each other. Nonetheless, Renin-SNP3 still is statistically associated with the incidence of edema and has been disclosed herewith.

These results suggest that polymorphisms in the renin gene contributes to differences in susceptibility to dose-dependent peripheral edema independent of other significant predictors such as age, sex and body mass index.

The utility, in general, of each of these significant SNP-dose-dependent peripheral edema event associations is that they suggest: (1) such SNPs may be causally involved, alone or in combination with other SNPs in the respective gene regions with susceptibility to dose-dependent peripheral edema events resulting from exposure to a PPAR-agonist; (2) such SNPs, if not directly causally involved, are reflective of an association because of linkage disequilibrium with one or more other SNPs that may be causally involved, alone or in combination with other SNPs in the respective gene regions with susceptibility to dose-dependent peripheral edema resulting from exposure to a PPAR-agonist; (3) such SNPs may be useful in establishing haplotypes that may be used to narrow the search for and identify polymorphisms or combinations of polymorphisms that may be causally, alone or in combination with other SNPs in the respective gene regions with susceptibility to dose-dependent peripheral edema resulting from exposure to a PPAR-agonist; and (4) such SNPs, if used to establish haplotypes that are identified as causally involved in such event susceptibility, may be used to predict which subjects are most likely to experience such events when exposed to a dose-dependent peripheral edema resulting from exposure to a PPAR-agonist. The term "respective gene regions" shall be construed to refer to those regions of each gene which have been used to identify the SNPs of the present invention.

Example 4

Method of Isolating the Native Forms of the Human Renin Gene

A number of methods have been described in the art that may be utilized in isolating the native forms of the human renin gene. Specific methods are referenced below and are hereby incorporated by reference herein in their entireties. The artisan, skilled in the molecular biology arts, would be able to isolate the native form of human renin based upon the methods and information contained, and/or referenced, therein.

Human Renin (gi| 42406218; SEQ ID NO:10; RefSeq No. NC_000001.7, nucleotides 201301381 to 201312898; and gi_NM_000537)

1) Zhang, L., Yang, Z., Shi, B. M., Li, D. P., Fang, C. Y. and Qiu, F. Z., "Expression of local renin and angiotensinogen mRNA in cirrhotic portal hypertensive patient"; World J. Gastroenterol. 9 (7), 1584-1588 (2003).
2) Suzuki, F., Hayakawa, M., Nakagawa, T., Nasir, U. M., Ebihara, A., Iwasawa, A., Ishida, Y., Nakamura, Y. and Murakami, K., "Human prorenin has 'gate and handle' regions for its non-proteolytic activation"; J. Biol. Chem. 278 (25), 22217-22222 (2003).
3) Fuchs, S., Philippe, J., Corvol, P. and Pinet, F., "Implication of Ref-1 in the repression of renin gene transcription by intracellular calcium", J. Hypertens. 21 (2), 327-335 (2003).
4) Lemes, A., Campo, C., Gonzalez San Miguel, J. D., Bosch, J. M., Suarez, A., Guerra, L., Rodriguez-Perez, J. C. and Molero, T., "Renin expression in hematological malignancies and its role in the regulation of hematopoiesis", Leuk. Lymphoma 43 (12), 2377-2381 (2002).
5) Fuchs, S., Philippe, J., Germain, S., Mathieu, F., Jeunemaitre, X., Corvol, P. and Pinet, F., "Functionality of two new polymorphisms in the human renin gene"; J. Hypertens. 20 (12), 2391-2398 (2002).
6) Jan Danser, A. H. and Saris, J. J., "Prorenin uptake in the heart: a prerequisite for local angiotensin generation?"; J. Mol. Cell. Cardiol. 34 (11), 1463-1472 (2002).
7) Varagic, J. and Frohlich, E. D., "Local cardiac renin-angiotensin system: hypertension and cardiac failure"; J. Mol. Cell. Cardiol. 34 (11), 1435-1442 (2002).
8) Nguyen, G., Delarue, F., Burckle, C., Bouzhir, L., Giller, T. and Sraer, J. D., "Pivotal role of the renin/prorenin receptor in angiotensin II production and cellular responses to renin"; J. Clin. Invest. 109 (11), 1417-1427 (2002).
9) Abali, H., Haznedaroglu, I. C., Goker, H., Celik, I., Ozatli, D., Koray, Z. and Caglar, M., "Circulating and local bone marrow renin-angiotensin system in leukemic hematopoiesis: preliminary evidences"; Hematology 7 (2), 75-82 (2002).
10) Germain, S., Fuchs, S., Philippe, J., Corvol, P. and Pinet, F., "New elements in human renin promoter involved in cell-specific expression"; Clin. Exp. Pharmacol. Physiol. 28 (12), 1056-1059 (2001).
11) Andersen, U. B., Steensgaard-Hansen, F., Rokkedal, J., Ibsen, H. and Dige-Petersen, H., "Left ventricular structure and diastolic function in subjects with two hypertensive parents"; Blood Press. 10 (4), 193-198 (2001).
12) Padmanabhan, N., Padmanabhan, S, and Connell, J. M., "Genetic basis of cardiovascular disease—the renin-angiotensin-aldosterone system as a paradigm"; J Renin Angiotensin Aldosterone Syst 1 (4), 316-324 (2000).
13) Lee-Kirsch, M. A., Gaudet, F., Cardoso, M. C. and Lindpaintner, K., "Distinct renin isoforms generated by tissue-specific transcription initiation and alternative splicing"; Circ. Res. 84 (2), 240-246 (1999).
14) Tamura, K., Umemura, S., Fukamizu, A., Ishii, M. and Murakami, K., "Recent advances in the study of renin and angiotensinogen genes:from molecules to the whole body"; Hypertens. Res. 18 (1), 7-18 (1995).
15) Qin, H., Chen, Y. H., Yip, M. Y., Lam-Po-Tang, P. R. and Morris, B. J., "Reassignment of human renin gene to chromosome 1q32 in studies of a (1;4)(q42;p16) translocation"; Hum. Hered. 43 (4), 261-264 (1993).
16) Dhanaraj, V., Dealwis, C. G., Frazao, C., Badasso, M., Sibanda, B. L., Tickle, I. J., Cooper, J. B., Driessen, H. P., Newman, M., Aguilar, C. et al., "X-ray analyses of peptide-inhibitor complexes define the structural basis of specificity for human and mouse renins"; Nature 357 (6378), 466-472 (1992).
17) Burt, D. W., Nakamura, N., Kelley, P. and Dzau, V. J., "Identification of negative and positive regulatory elements in the human renin gene"; J. Biol. Chem. 264 (13), 7357-7362 (1989).
18) Sielecki, A. R., Hayakawa, K., Fujinaga, M., Murphy, M. E., Fraser, M., Muir, A. K., Carilli, C. T., Lewicki, J. A., Baxter, J. D. and James, M. N., "Structure of recombinant human renin, a target for cardiovascular-active drugs, at 2.5 A resolution"; Science 243 (4896), 1346-1351 (1989).

19) Morris, B. J., "New possibilities for intracellular renin and inactive renin now that the structure of the human renin gene has been elucidated"; Clin. Sci. 71 (4), 345-355 (1986).

20) Soubrier, F., Panthier, J. J., Houot, A. M., Rougeon, F. and Corvol, P., "Segmental homology between the promoter region of the human renin gene and the mouse ren1 and ren2 promoter regions"; Gene 41 (1), 85-92 (1986).

21) Fukamizu, A., Nishi, K., Nishimatsu, S., Miyazaki, H., Hirose, S, and Murakami, K., "Human renin gene of renin-secreting tumor"; Gene 49 (1), 139-145 (1986).

22) Hardman, J. A., Hort, Y. J., Catanzaro, D. F., Tellam, J. T., Baxter, J. D., Morris, B. J. and Shine, J., "Primary structure of the human renin gene"; DNA 3 (6), 457-468 (1984).

23) Miyazaki, H., Fukamizu, A., Hirose, S., Hayashi, T., Hori, H., Ohkubo, H., Nakanishi, S. and Murakami, K., "Structure of the human renin gene"; Proc. Natl. Acad. Sci. U.S.A. 81 (19), 5999-6003 (1984).

24) Hobart, P. M., Fogliano, M., O'Connor, B. A., Schaefer, I. M. and Chirgwin, J. M., "Human renin gene: structure and sequence analysis"; Proc. Natl. Acad. Sci. U.S.A. 81 (16), 5026-5030 (1984).

25) Shine, J., Hardman, J. A., Hort, Y. J., Tellam, J. T., Catanzaro, D. F., Morris, B. J. and Baxter, J. D., "Structure of the human renin gene"; Trans. Assoc. Am. Physicians 97, 63-69 (1984).

26) Imai, T., Miyazaki, H., Hirose, S., Hori, H., Hayashi, T., Kageyama, R., Ohkubo, H., Nakanishi, S, and Murakami, K., "Cloning and sequence analysis of cDNA for human renin precursor"; Proc. Natl. Acad. Sci. U.S.A. 80 (24), 7405-7409 (1983).

27) Soubrier, F., Panthier, J. J., Corvol, P. and Rougeon, F., "Molecular cloning and nucleotide sequence of a human renin cDNA fragment"; Nucleic Acids Res. 11 (20), 7181-7190 (1983).

Methods of isolation for the human renin gene of the present invention may also be found in reference to the references cited in the GENBANK® accession nos. for each gene provided herein which are hereby incorporated by reference herein.

Example 5

Method of Isolating the Polymorphic Forms of the Human Renin Gene of the Present Invention Since the allelic genes of the present invention represent genes present within at least a subset of the human population, these genes may be isolated using the methods provided in Example 4 above. For example, the source DNA used to isolate the allelic gene may be obtained through a random sampling of the human population and repeated until the allelic form of the gene is obtained. Preferably, random samples of source DNA from the human population are screened using the SNPs and methods of the present invention to identify those sources that comprise the allelic form of the gene. Once identified, such a source may be used to isolate the allelic form of the gene(s). The invention encompasses the isolation of such allelic genes from both genomic and/or cDNA libraries created from such source(s).

In reference to the specific methods provided in Example 4 above, it is expected that isolating the polymorphic alleles of the human renin gene would be within the skill of an artisan trained in the molecular biology arts. Nonetheless, a detailed exemplary method of isolating at least one of the renin polymorphic alleles, in this case the variant form of Renin-SNP3 ("A" nucleotide at 12586 of SEQ ID NO:1) is provided. Briefly, First, the individuals with the G12586A variation are identified by genotyping the genomic DNA samples using the method outlined in Example 2 herein. Other methods of genotyping may be employed, such as the FP-SBE method (Chen et al., Genome Res., 9(5):492-498 (1999)), or other methods described herein. DNA samples publicly available (e.g., from the Coriell Institute (Collingswood, N.J.) or from the Bristol-Myers Squibb clinical samples described herein may be used. Oligonucleotide primers that are used for this genotyping assay are provided in Example 2.

By analyzing genomic DNA samples, individuals with the G12586A form of the Renin-SNP3 variant may be identified. Once identified, clones comprising the genomic sequence may be obtained using methods well known in the art (see Sambrook, J., E. F. Fritsch, and T. Maniatis, 1989, Molecular Cloning: A Laboratory Manual, Cold Spring Harbor Laboratory Press, Cold Spring Harbor, N.Y.; and Current Protocols in Molecular Biology, 1995, F. M., Ausubel et al., eds, John Wiley and Sons, Inc., which are hereby incorporated by reference herein.).

If cDNA clones of the coding sequence of this allele of the gene are of interest, such clones may be obtained in accordance with the following steps. Next, Lymphoblastoid cell lines from these individuals may be obtained from the Coriell Institute. These cells can be grown in RPMI-1640 medium with L-glutamine plus 10% FCS at 37 degrees. PolyA+ RNA are then isolated from these cells using OLIGOTEX® Direct Kit (Life Technologies).

First strand cDNA (complementary DNA) is produced using SUPERSCRIPT® Preamplification System for First Strand cDNA Synthesis (Life Technologies, Cat No 18089-011) using these polyA+ RNA as templates, as specified in the users manual which is hereby incorporated herein by reference in its entirety. Specific cDNA encoding the human renin protein is amplified by polymerase chain reaction (PCR) using a forward primer which hybridizes to the 5'-UTR region, a reverse primer which hybridizes to the 3'-UTR region, and these first strand cDNA as templates (Sambrook, Fritsch et al. 1989). Alternatively, these primers may be designed using Primer3 program (Rozen S 2000). Restriction enzyme sites (example: SalI for the forward primer, and NotI for reverse primer) are added to the 5'-end of these primer sequences to facilitate cloning into expression vectors after PCR amplification. PCR amplification may be performed essentially as described in the owner's manual of the Expand Long Template PCR System (Roche Molecular Biochemicals) following manufacturer's standard protocol, which is hereby incorporated herein by reference in its entirety.

PCR amplification products are digested with restriction enzymes (such as SalI and NotI, for example) and ligated with expression vector DNA cut with the same set of restriction enzymes. pSPORT (Invitrogen) is one example of such an expression vector. After ligated DNA is introduced into *E. coli* cells (Sambrook, Fritsch et al. 1989), plasmid DNA is isolated from these bacterial cells. This plasmid DNA is sequenced to confirm the presence an intact (full-length) coding region of the human renin protein with the variation, if the variation results in changes in the encoded amino acid sequence, using methods well known in the art and described elsewhere herein.

The skilled artisan would appreciate that the above method may be applied to isolating the other novel human renin genes of the present invention through the simple substitution of applicable PCR and sequencing primers. Such primers may be selected from any one of the applicable primers provided in herein, or may be designed using the Primer3 program (Rozen S 2000) as described. Such primers may preferably comprise at least a portion of any one of the polynucleotide sequences of the present invention.

Example 6

Method of Engineering the Allelic Forms of the Human Renin Gene of the Present Invention Aside from isolating the allelic genes of the present invention from DNA samples obtained from the human population, Bristol-Myers Squibb Company clinical trials, and/or the Coriell Institute, as described in Example 5 above, the invention also encompasses methods of engineering the allelic genes of the present invention through the application of site-directed mutagenesis to the isolated native forms of the genes. Such methodology could be applied to synthesize allelic forms of the genes comprising at least one, or more, of the encoding SNPs of the present invention (e.g., silent, missense)-preferably at least 1, 2, 3, or 4 encoding SNPs for each gene.

In reference to the specific methods provided in Example 5 above, it is expected that isolating the novel polymorphic renin genes of the present invention would be within the skill of an artisan trained in the molecular biology arts. Nonetheless, a detailed exemplary method of engineering at least one of the renin polymorphic alleles to comprise the encoding and/or non-coding polymorphic nucleic acid sequence, in this case the variant form (G12856A) of Renin-SNP3 (SEQ ID NO:2) is provided. Briefly,.

cDNA clones encoding the human renin protein may be identified by homology searches with the BLASTN program (Altschul SF 1990) against the GENBANK® non-redundant nucleotide sequence database using the published human renin cDNA sequence (GENBANK® Accession No.: NM_000537). Alternatively, the genomic sequence of the human renin gene may be obtained as described herein. After obtaining these clones, they are sequenced to confirm the validity of the DNA sequences.

However, in the case of the variant form (G12856A) of Renin-SNP3, genomic clones would need to be obtained and may be identified by homology searches with the BLASTN program (Altschul SF 1990) against the GENBANK® non-redundant nucleotide sequence database using the published human renin genomic sequence (GENBANK® Accession No.: NC_000001.7, nucleotides 201301381 to 201312898). Alternatively, the genomic sequence of the human renin gene may be obtained as described herein. After obtaining these clones, they are sequenced to confirm the validity of the DNA sequences.

Once these clones are confirmed to contain the intact wild type cDNA or genomic sequence of the human renin coding and/or non-coding region, the G12856A polymorphism (mutation) may be introduced into the native sequence using PCR directed in vitro mutagenesis (Cormack, B., Directed Mutagenesis Using the Polymerase Chain Reaction. Current Protocols in Molecular Biology, John Wiley & Sons, Inc. Supplement 37: 8.5.1-8.5.10, (2000)). In this method, synthetic oligonucleotides are designed to incorporate a point mutation at one end of an amplified fragment. Following PCR, the amplified fragments are made blunt-ended by treatment with Klenow Fragment. These fragments are then ligated and subcloned into a vector to facilitate sequence analysis. This method consists of the following steps:

1. Subcloning of cDNA or genomic insert into a plasmid vector, or BAC sequence if the clone is a genomic sequence, containing multiple cloning sites and M13 flanking sequences, such as pUC19 (Sambrook, Fritsch et al. 1989), in the forward orientation. The skilled artisan would appreciate that other plasmids could be equally substituted, and may be desirable in certain circumstances.

2. Introduction of a mutation by PCR amplification of the cDNA region downstream of the mutation site using a primer including the mutation. (FIG. 8.5.2 in Cormack 2000)). In the case of introducing the G12856A mutation into the human renin protein, the following two primers may be used.

M13 reverse sequencing primer:
   5'-AGCGGATAACAATTTCACACAGGA-3' (SEQ ID NO:30).

Mutation primer:
   5'-GACAGATTACAATGCACAG
      ATCATGTTAGAACTGTAGTTC-3' (SEQ ID NO:31)

Mutation primer contains the mutation (G12856A) at the 5' end (in bold and underlined) and a portion of its flanking sequence. M13 reverse sequencing primer hybridizes to the pUC19 vector. Subcloned cDNA or genomic clone comprising the human renin cDNA or genomic sequence is used as a template (described in Step 1). A 100 ul PCR reaction mixture is prepared using 10 ng of the template DNA, 200 uM 4dNTPs, 1 uM primers, 0.25U Taq DNA polymerase (PE), and standard Taq DNA polymerase buffer. Typical PCR cycling condition are as follows:

| | |
|---|---|
| 20-25 cycles: | 45 sec, 93 degrees |
| | 2 min, 50 degrees |
| | 2 min, 72 degrees |
| 1 cycle: | 10 min, 72 degrees |

After the final extension step of PCR, 5U Klenow Fragment is added and incubated for 15 min at 30 degrees. The PCR product is then digested with the restriction enzyme, EcoRI.

3. PCR amplification of the upstream region is then performed, using subcloned cDNA or genomic clone as a template (the product of Step 1). This PCR is done using the following two primers:

M13 forward sequencing primer:
   5'-CGCCAGGGTTTTCCCAGTCACGAC-3' (SEQ ID NO:29).

Flanking primer:
   5'-GAACTACAGTTCTAACA
      TGATCTGTGCATTGTAATCTGTC-3' (SEQ ID NO:32).

Flanking primer is complimentary to the upstream flanking sequence and mutation locus of the G12856A mutation (in bold and underlined). M13 forward sequencing primer hybridizes to the pUC19 vector. PCR conditions and Klenow treatments follow the same procedures as provided in Step 2, above. The PCR product is then digested with the restriction enzyme, HindIII.

4. Prepare the pUC19 vector for cloning the cDNA or genomic clone comprising the polymorphic locus. Digest pUC19 plasmid DNA with EcoRI and HindIII. The resulting digested vector fragment may then be purified using techniques well known in the art, such as gel purification, for example.

5. Combine the products from Step 2 (PCR product containing mutation), Step 3 (PCR product containing the upstream region), and Step 4 (digested vector), and ligate them together using standard blunt-end ligation conditions (Sambrook, Fritsch et al. 1989).

6. Transform the resulting recombinant plasmid from Step 5 into *E. coli* competent cells using methods known in the art, such as, for example, the transformation methods described in Sambrook, Fritsch et al. 1989.

7. Analyze the amplified fragment portion of the plasmid DNA by DNA sequencing to confirm the point mutation, and absence of any other mutations introduced during PCR. The method of sequencing the insert DNA, including the primers utilized, are described herein or are otherwise known in the art.

The skilled artisan would appreciate that the above method may be applied to engineering the other polymorphic bradykinin associated genes of the present invention through the simple substitution of applicable mutation, flanking, PCR, and sequencing primers for each specific gene and/or polymorphism. Some of these primers may be selected from any one of the applicable primers provided elsewhere herein, or may be designed using the Primer3 program (Rozen S 2000), or designed manually, as described. Such primers may preferably comprise at least a portion of any one of the polynucleotide sequences of the present invention. Nonetheless, exemplary mutagenic forward and reverse primers are provided below with the polymorphic locus highlighted in bold and underlined (Renin-SNP7 polymorphism is represented by bold brackets since it represents a deletion).

| SNP | Forward Mutagenic Primer | Reverse Mutagenic Primer |
|---|---|---|
| Renin-SNP5 | GTCTTTAGAAGAACTGTTTTAGAGGAGG TGGGGGCAAGGCCAGATGG (SEQ ID NO:33) | CCATCTGGCCTTGCCCCCACCTCC TCTAAAACAGTTCTTCTAAAGAC (SEQ ID NO:34) |
| Renin-SNP7 | GTTGCTGAAGACAGTTGCT[]GGGGTCAG GCAAGGTGAAAGG (SEQ ID NO:35) | CCTTTCACCTTGCCTGACCCC[]AG CAACTGTCTTCAGCAAC (SEQ ID NO:36) |

Moreover, the skilled artisan would appreciate that the above method may be applied to engineering more than one polymorphic nucleic acid sequence of the present invention into the novel renin genes of the present invention. Such an engineered gene could be created through successive rounds of site-directed mutagenesis, as described in Steps 1 thru 7 above, or consolidated into a single round of mutagenesis. For example, Step 2 above could be performed for each mutation, then the products of both mutation amplifications could be combined with the product of Step 3 and 4, and the procedure followed as described.

Example 7

Method of Assessing the Expression Profile of Human Renin in Response to Treatment with PPAR-Agonists in CALU-6 Cells Using Quantitative RT-PCR Since RAAS plays a fundamental role in fluid volume homeostasis, the possibility that PPAR agonists may contribute to agonist-induced edema mechanism of action through the modulation of other components of this system, specifically renin, was investigated using quantitative RT-PCR. Briefly, gene expression studies were performed using a cell line that was previously shown to express endogenous renin mRNA, CALU-6 (Lang et al., 1995).

Selection and Maintenance of Cell Line for the Invention

The human lung carcinoma cell line, CALU-6, was chosen on account of it being previously shown to endogenously express renin. Furthermore, additional studies demonstrated that renin expression is inducible in CALU-6 (Lang et al., 1995). Over the past several years, CALU-6 has served as a model cell line to study renin transcriptional regulation (Lang et al., 1995; Germain et al., 1997; Germain et al., 1999).

Cell lines and growth media were obtained from the ATCC®. CALU-6 cells were recovered and expanded in complete growth media (Minimal Essential Media+Earle's Balanced Salt Solution, 1% penicillin/streptomycin, 10% Fetal Bovine Serum). CALU-6 cells were passaged after the cells reached 80-90% confluency. Cells were typically split 1:4, twice weekly.

PPAR Agonist Compounds

Compounds A, B, C, D, and F were synthesized at Bristol-Myers Squibb Co. Compound E was purified by reverse phase high-performance liquid chromatography from commercial pharmaceutical preparations. Compounds A, B, and F are dual PPAR alpha and gamma agonists; while compounds C, D, and E are single PPAR gamma agonists. Compounds A and B are disclosed in U.S. Pat. No. 6,414,002; which is hereby incorporated by reference herein in its entirety. All compounds were reconstituted in DMSO such that their working concentrations were 500× the final concentration used in the induction studies. The final concentration of each PPAR-agonist used in the induction studies was 5×EC50 as determined from pre-adipocyte differentiation studies (data not shown). The final concentration of DMSO in all treatments was 0.2%.

Induction Experiments

CALU-6 cells were seeded on day 0 in replicates of six (or twelve for DMSO control), at $5 \times 10^5$ cells/well, in 6-well tissue culture plates. Cells were incubated at 37° C. under 5% CO2. The growth media was removed on day 1 and cells were re-fed with growth media containing 0.2% DMSO (vehicle control), 0.76 µM Compound A, 0.021 µM Compound B, 1 µM Compound C, 0.4 µM Compound D, 0.005 µM Compound E and 1.7 µM Compound F. After 24 hr incubation at 37° C. under 5% $CO_2$, cells were lysed and total RNA was prepared using the RNAeasy mini kit (Qiagen) following the manufacturer's recommendations. RNA quantities were determined spectrophotometrically using a SPECTRA-MAX® 384 spectrophotometer (Molecular Devices). RNA quality was assessed using an Agilent 2100 Bioanalyzer (Agilent Technologies) following the manufacturer's recommendations. All total RNA preparations were adjusted to a final concentration of 83.3 ng/μl.

Quantitative Real-Time PCR Study

All cDNA synthesis and subsequent PCR experiments were performed following the Applied Biosystems TAQMAN® Assay protocol (Applied Biosystems). 250 ng of total RNA was used in the reverse transcription reaction. 10 ng of total RNA converted to cDNA was used as template for real-time PCR experiments. On-Demand TAQMAN® Assays for renin (part number, Hs00166915), GAPDH (part number, Hs99999905) and β-actin (part number, Hs99999903) were obtained from Applied Biosystems. Each On-Demand assay included the required reagents to quantify expression levels of each gene as well as the recommended cycling conditions.

Quantitative Real-Time PCR Data Analysis

Sequence Detection System Software v.2.1 (Applied Biosystems) was used to analyze the quality of each amplification reaction as well as to calculate Ct values for each sample. All data was further analyzed using Microsoft Excel.

To determine if gene expression significantly varied over all treatments (including DMSO control) single-factor ANOVA was performed on Ct values for each gene studied, followed by pair-wise 2-tail Student's t-tests where appropriate.

To quantify gene expression change upon treatment with compound, deltaCt values were calculated by subtracting individual Ct values of each replicate (n=6) from the mean Ct value of the DMSO control (n=12). Gene expression fold-change was then calculated by expressing the mean deltaCt value of each treatment group as a factor of 2.

The results of the RT-PCR expression profile for human renin is provided in FIG. 11.

Example 8

Method of Assessing the Expression Profile of Human Renin in Response to Treatment with PPAR-Agonists in CALU-6 Cells Using Microarray Analysis As an independent measurement of the renin induction by PPAR agonists observed using RT-PCR (see Example 7 and FIG. 11), four of the experimental treatment groups described under the "Induction Experiments" section in Example 7, were analyzed on AFFYMETRIX® genechips, including; DMSO, Compound A, Compound B, and Compound E. Triplicate samples from each treatment group were analyzed.

Microarray Analysis

All cDNA and cRNA synthesis as well as all hybridizations and subsequent washing steps were performed following the GENECHIP® Expression Analysis Technical Manual (Affymetrix). AFFYMETRIX® HG-U133A gene chips were used for all expression profiling studies in this invention.

Micro Array Suite (MAS) 5.0 (Affymetrix) software was used to pre-process all micro-array data. Each treated sample (including DMSO control) was first scaled to an average intensity value of 1500. The data was further analyzed in Excel '97 (Microsoft).

All treated samples were compiled into one Excel spreadsheet such that each compound treated sample (and DMSO control) was aligned for all 22283 genes on the HG-U133A GENECHIP®. Gene fold-change values were calculated by dividing the mean signal intensity of each treatment group by the mean signal intensity of the DMSO control. Pair-wise 2-tailed Student's t-tests were performed for each treatment group.

The results of the microarray expression analysis for human renin is provided in FIG. 12.

Example 9

Method of Discovering the ET-1 Single Nucleotide Polymorphisms (SNPs) of the Present Invention SNP discovery is based on comparative DNA sequencing of PCR products directed to the human endothelin-1 gene derived from genomic DNA from multiple individuals. In the present case, the ET1-SNP1 was publicly known. Nonetheless, studies were performed to confirm the existence of this SNP in the patient cohorts described herein. All genomic DNA samples for SNP discovery were obtained from a panel of thirty-two human subjects obtained from the Coriell Institute (Camden, N.J.), panel # M44PDR.

ET1-SNP1: G/T at Nucleotide 797 of SEQ ID NO:37 and 39

Endothelin-1 ET1-SNP1 was confirmed using the following protocol. Briefly, portions of the human endothelin-1 genomic sequence were PCR amplified using the standard PLATINUM® Taq DNA protocol (Invitrogen, Product #10966-083):

The following sequencing primers (20 uM each) were used to confirm the above SNP, as well as to sequence across the PCR amplicons:

| SNP | Forward Primer | Reverse Primer |
|---|---|---|
| ET1 ET1-SNP1 | ACAGCGTCAAATCATCTTTT CATGAT (SEQ ID NO:41) | TCTGTCACCAATGTGCTCGGTT (SEQ ID NO:42) |

All the samples amplified from genomic DNA (50 ng) in reactions (50 ul) containing 50 mM Tris-Acetate pH 8.4, 75 mM KAcetate, 8 mM MgAcetate, 200 uM dNTPs, 0.2 uM of each PCR primer, and 2.5 U PLATINUM® Taq DNA polymerase (Invitrogen).

PCR amplification was performed in Perkin Elmer 9700 machines under the following cycling conditions: 1.) 94 degrees Celsius for 2 minutes; 2.) 94 degrees Celsius for 30 seconds; 3.) 59 degrees Celsius for 1 minute; 4.) 72 degrees Celsius for 30 seconds; 5.) 72 degrees Celsius for 5 minutes; and 6.) 4 degrees Celsius on hold. Steps 2 to 4 were cycled 35 times.

PCR products were sequenced using ABI BigDye Terminator v3.1 Cycle Sequencing chemistry on the 3730-XL capillary sequencers using the same primers used for identifying the SNPs, as described above.

Sequence editing and contig assembly was performed using CONSED software (Genome Res. 1998 March; 8(3): 195-202). Chromatograms were visually inspected for each Coriell DNA and SNPs identified by comparing sequence traces to the reference endothelin-1 genomic DNA sequence provided as GENBANK® Accession No. gi| NM_001955.2 (SEQ ID NO:49; nucleotides 12398645-12404761). The coding region of the reference endothelin-1 is provided as SEQ ID NO:37 (GENBANK® Accession No. gi/21359861), encoding the reference endothelin-1 polypeptide sequence provided as SEQ ID NO:38 (GENBANK® Accession No. gi|NP_001946.2).

The nucleotide sequence of the endothelin-1 gene containing the reference allele ("g") for ET1-SNP1 at nucleotide 797 is provided in FIGS. 13A-B (SEQ ID NO:37); while the nucleotide sequence of the endothelin-1 gene containing the variable allele ("t") for ET1-SNP1 at nucleotide 797 is provided in FIGS. 14A-B (SEQ ID NO:39).

The polypeptide sequence of endothelin-1 containing the reference allele ("K") for ET1-SNP1 at amino acid 198 is provided in FIGS. 13A-B (SEQ ID NO:38); while the polypeptide sequence of endothelin-1 containing the variable allele ("N") for ET1-SNP1 at amino acid 198 is provided in FIGS. 14A-B (SEQ ID NO:40).

Example 10

Method of Genotyping Each SNP of the Present Invention

Genomic DNA samples from patients enrolled in two Bristol-Myers Squibb Company Phase II clinical trials CV168-006 and CV168-008 trials were genotyped for ET1-SNP1 of the human endothelin-1 gene (see Example 9) and evaluated for association with edema.

498 subjects enrolled in the CV168-006 trial and 232 subjects from the CV168-008 trial were analyzed in this study. All analyses were based on data collected up to 24 weeks, which was the duration of the short-term phase of the trials. DNA was extracted from frozen blood by a third-party (Genaissance Inc, North Carolina) using a salting-out method (Gentra Systems). All subjects gave written informed consent.

Genotyping was performed using the 5' nuclease assay, essentially as described (Ranade K et al., Genome Research 11: 1262-1268 (2001); which is hereby incorporated by reference herein in its entirety), with the following modifications: six nanograms of genomic DNA were used in a 8 ul reaction. All PCR reactions were performed in an ABI 9700 machine and fluorescence was measured using an ABI 7900 machine.

Genotyping of the SNPs of the present invention was performed using sets of TAQMAN® probes (100 uM each) and primers (100 uM each) specific to the SNP. Each probe/primer set was manually designed using ABI Primer Express software (Applied Biosystems). Genomic samples were prepared as described in Example 9. The following TAQMAN® probes and primers were utilized:

The genotype assay conditions are provided below.

| Components | Final Concentration |
| --- | --- |
| 2x PE Master Mix (#4318157) | 1X |
| 100 uM FAM labeled probe | 200 nmol |
| 100 uM VIC labeled probe | 200 nmol |
| Forward PCR primer | 600 nmol |
| Reverse PCR primer | 600 nmol |
| 6 ng template DNA | as required |
| ddH2O | volume to 8 ul |

TAQMAN® thermo-cycling was performed on Perkin Elmer PE 9700 machines using the following cycling conditions below:
1) 50C for 2 minutes
2) 95C for 10 seconds*
3) 94C for 15 seconds
4) 62C for 1 minute
5) 4C hold

*Steps 2-4 were cycled 40 times

Analysis of genotypes was performed by using the Applied Biosystems ABI 7900 HT sequence detection system.

Example 11

Statistical Analysis of the Association Between Dose-Dependent Peripheral Edema and the SNPs of the Present Invention The association between peripheral edema and the single nucleotide polymorphisms of the present invention were investigated by applying statistical analysis to the results of the genotyping assays described elsewhere herein. The central hypothesis of this analysis is that a predisposition to develop dose-dependent peripheral edema may be conferred by specific genomic factors. The analysis attempted to identify one or more of these factors in genomic DNA samples from index cases and matched control subjects who were exposed to Compound A in two Bristol-Myers Squibb (BMS) clinical studies (see Example 10).

SNPs of the present invention were examined for association with edema using 3 (genotypes)×2 (edema and no edema) contingency tables. Significant results for edema (P<0.05) were followed up by logistic regression analysis including baseline body mass index, age, trial, sex, race and SNP as covariates. Analyses were performed using S-PLUS® (version 6.0; Insightful Corp. Seattle, Wash.) or SPSS® (version 12.0; SPSS Inc. Chicago, Ill.).

Methods

Sample. Investigators in the BMS clinical trials diagnosed dose-dependent peripheral edema in some subjects.

| SNP | TAQMAN® Forward Primer | TAQMAN® Reverse Primer | Reference TAQMAN® Probe | Variable TAQMAN® Probe |
| --- | --- | --- | --- | --- |
| ET1-SNP1 | ACAGCGTCAAATC ATCTTTTCATGAT (SEQ ID NO:41) | TCTGTCACCAATG TGCTCGGTT (SEQ ID NO:42) | CTGAAAGGCAA GCCCTCCAGAG AGC (SEQ ID NO:43) | TGAAAGGCAAT CCCTCCAGAGA GCG (SEQ ID NO:44) |

** The allelic nucleotide in each probe sequence is shown in bold and underlined.

Measures. Single nucleotide polymorphisms (SNPs) in human endothelin-1 were genotyped on all subjects essentially as described in Example 10 herein. The SNPs that are genotyped likely represent a sample of the polymorphic variation in each gene and are not exhaustive with regard to coverage of the total genetic variation that may be present in each gene. Specifically, only the ET1 ET1-SNP1 referenced herein was genotyped and statistically analyzed, as described. The SNPs for which a statistical association to peripheral edema susceptibility was confirmed are provided and referred to as ET1-SNP1.

Statistical Analyses. Conditional logistic regression (HOSMER and LEMESHOW 2000) was used to examine the associations between genotypes of endothelin-1 gene SNPs and the development of dose-dependent peripheral edema. All SNPs are bi-allelic with three possible genotypes. For each SNP, in the overall sample and each subgroup, allele frequencies are estimated. For consistency in SNP genotype parameter coding in the logistic regression models, the less frequent allele of each SNP was designated as the rare allele and the number of copies of that allele that each subject carried, either 0, 1, or 2, was then determined. Three possible genotypes for each SNP leaves two degrees of freedom for parameters in the conditional logistic regression model representing the information contained in these three genotype categories. Two dummy variables are therefore created based on the copies of the rare allele for each subject for use in the conditional logistic regression model, $x_1=1$ if copies of rare allele=1, 0 otherwise and
$x_2=1$ if copies of rare allele=2, 0 otherwise.

The full conditional logistic regression model used was $$\pi_k(x) = \frac{e^{\alpha_k+\beta_1' x_1+\beta_2' x_2}}{1+e^{\alpha_k+\beta_1' x_1+\beta_2' x_2}},$$

where x in $\pi_k(X)$ is the vector of dummy variables representing the SNP genotypes described above, k is the matching stratum index specific to each matched case-control set of subjects, $\pi_k(X)$ is the matching stratum-specific expected probability that a subject is a case given x, $\alpha_k$ is the matching stratum-specific contribution to $\pi_k(x)$ of all the matching variables constant within the kth stratum and each $\beta'$ represents the contribution of the respective dummy variable to $\pi_k(X)$.

For each SNP, the null hypothesis was that the vector of $\beta'$ are all equal to 0 and was tested using the scores test (HOSMER and LEMESHOW 2000). The degrees of freedom for the scores test statistic was equal to one less than the number of genotypes. Exponentiation of each slope coefficient, $\beta'$, provided an estimate of the ratio of the odds of an adverse event (e.g., dose-dependent peripheral edema) in subjects carrying the specified copies of the rare allele represented in the definition of the coefficient, relative to controls matched for body mass index, age, trial, sex, race, and SNP as covariates, over the odds of such an adverse event for similarly matched subjects not carrying any copies of the rare allele. 95% confidence interval limits are estimated for each odds ratio based on the standard error estimate of the respective slope coefficient.

Since the SNP coverage within the human endothelin-1 gene was not exhaustive of the genetic variation that may be present and possibly related to event susceptibility in this gene, inferences about these SNP associations with dose-dependent peripheral edema events for endothelin-1 are therefore related to the hypothesis that genetic variation in this gene may be involved in susceptibility to such events.

Selection of Affected and Unaffected Subjects for Genetic Analysis of Dose-Dependent Peripheral Edema Table A provides a distribution of the frequency of dose-dependent peripheral edema by treatment arm. The frequency of edema increased as the dose of Compound A increased from 0.5 mg to 20 mg. Table A is provided in Example 3 above.

To increase the likelihood of finding genetic associations, subjects who did not develop dose-dependent peripheral edema at the maximum dose of Compound A, i.e. Dose E, were considered "unaffected" and compared to subjects who developed edema at any dose of Compound A. The characteristics of these two groups are provided in Table B provided in Example 3. To see the reasoning behind this approach, compare the frequency of edema in the Dose C group (10%) and the Dose E group (40%). Thus, if subjects without edema in the Dose C group were considered unaffected, a significant number of individuals (30% of 125 or 38) who might be genetically susceptible to edema when exposed to a high dose of Compound A would be mis-classified, thereby reducing the genetic signal or power of the study. This approach is analogous to the use of extreme discordant sibpairs for detecting genes underlying quantitative traits.

As shown in Table B in Example 3, subjects who developed dose-dependent peripheral edema after exposure to Compound A were more likely to be female, older and heavier. Race and smoking status were not significant predictors of edema.

Genetic Associations with Edema

All subjects for whom sufficient DNA was available were genotyped for 218 SNPs in 65 candidate genes with 1 of these SNPs being specific for the human endothelin-1 gene (ET1 ET1-SNP1). Of these 218 SNPs, subjects enrolled in these trials were polymorphic for 153 SNPs (minor allele frequency >0.1%). In 3×2 contingency table analysis, SNPs in the endothelin-1 genes were significantly associated with edema status (P<0.05). The distribution of genotypes between the two groups for each SNP is provided in Table D for ET1-SNP1.

TABLE D

| Genotype distribution of β1-adrenergic receptor SNPs | | |
|---|---|---|
| Trait/SNP | Odds ratio (95% C.I.) | P value |
| Endothelin-1/Asn198Lys | | |
| Asn/Asn | 68 (58%) | 104 (68%) |
| Asn/Lys | 44 (38%) | 48 (31%) |
| Lys/Lys | 5 (4%) | 1 (0.7%) |

The genotype distributions for all three SNPs were in Hardy-Weinberg equilibrium. These univariate analyses were followed-up by multivariate logistic regression analyses including other covariates such as age and sex (Table E).

TABLE E

Multivariate analysis of SNP associations with edema

| Trait/SNP | Odds ratio (95% C.I.) | P value |
|---|---|---|
| Age | 1.08 (1.04-1.11) | <0.001 |
| Sex (Male vs. Female) | 0.17 (0.09-0.32) | <0.001 |
| Trial (−008 vs. −006) | 0.13 (0.06-0.26) | <0.001 |
| Body mass index | 1.12 (1.04-1.20) | 0.001 |
| Race | | 0.23 |
| Endothelin-1 ET1-SNP1 | | 0.028 |
| Asn/Lys vs. Asn/Asn | 0.68 (0.36-1.28) | 0.23 |
| Lys/Lys vs. Asn/Asn | 0.04 (0.004-0.51) | 0.012 |

Consistent with demographic data presented in Table B in Example 3, age, sex, body mass index, and trial were significant predictors of edema status. In contrast, race was not significantly associated with edema.

The endothelin-1 ET1-SNP1 was determined to be in Hardy-Weinberg equilibrium. These results suggest that polymorphisms in the endothelin-1 gene contributes to differences in susceptibility to dose-dependent peripheral edema independent of other significant predictors such as age, sex and body mass index.

The utility, in general, of each of these significant SNP-dose-dependent peripheral edema event associations is that they suggest: (1) such SNPs may be causally involved, alone or in combination with other SNPs in the respective gene regions with susceptibility to dose-dependent peripheral edema events resulting from exposure to a PPAR-agonist; (2) such SNPs, if not directly causally involved, are reflective of an association because of linkage disequilibrium with one or more other SNPs that may be causally involved, alone or in combination with other SNPs in the respective gene regions with susceptibility to dose-dependent peripheral edema resulting from exposure to a PPAR-agonist; (3) such SNPs may be useful in establishing haplotypes that may be used to narrow the search for and identify polymorphisms or combinations of polymorphisms that may be causally, alone or in combination with other SNPs in the respective gene regions with susceptibility to dose-dependent peripheral edema resulting from exposure to a PPAR-agonist; and (4) such SNPs, if used to establish haplotypes that are identified as causally involved in such event susceptibility, may be used to predict which subjects are most likely to experience such events when exposed to a dose-dependent peripheral edema resulting from exposure to a PPAR-agonist. The term "respective gene regions" shall be construed to refer to those regions of each gene which have been used to identify the SNPs of the present invention.

Example 12

Method of Isolating the Native Forms of the Human Endothelin-1 Gene

A number of methods have been described in the art that may be utilized in isolating the native forms of the human endothelin-1 gene. Specific methods are referenced below and are hereby incorporated by reference herein in their entireties. The artisan, skilled in the molecular biology arts, would be able to isolate the native form of human endothelin-1 based upon the methods and information contained, and/or referenced, therein.

Human Endothelin-1 (gi| 21359861; SEQ ID NO:37; RefSeq No. NM_001955.2; gi| 21359862; SEQ ID NO:38; RefSeq No. NP_001946.2)

1) Albertin, G. et al, Int. J. Mol. Med. 15 (3), 469-474 (2005).
2) Zhao, R. Z. et al, Biochem. Biophys. Res. Commun. 327 (4), 985-992 (2005)
3) Wulfing, C. et al, Oncol. Rep. 13 (2), 223-228 (2005).
4) Kim, T. H. et al, Oncogene 24 (4), 597-604 (2005).
5) Hoh, F. et al, Biochemistry 43 (48), 15154-15168 (2004).
6) Stachon, A. et al, Growth Factors 22 (4), 281-289 (2004).
7) Mangahas, C. R. et al, J. Invest. Dermatol. 123 (6), 1135-1139 (2004).
8) Dong, Y. et al, Hypertension 44 (6), 884-890 (2004).
9) Takashima, H. et al, Biochemistry 43 (44), 13932-13936 (2004).
10) Spinella, F. et al, J. Biol. Chem. 279 (45), 46700-46705 (2004).
11) Amiri, F. et al, Circulation 110 (15), 2233-2240 (2004).
12) Guruli, G. et al, Blood 104 (7), 2107-2115 (2004).
13) Arun, C. et al, Int. J. Biol. Markers 19 (4), 262-267 (2004).
14) Shephard, P. et al, Thromb. Haemost. 92 (2), 262-274 (2004).
15) Ergul, S. et al, Am. J. Hematol. 76 (3), 245-251 (2004).
16) Charloux, A. et al, Regul. Pept. 119 (1-2), 133-138 (2004).
17) Shi-Wen, X. et al, Mol. Biol. Cell 15 (6), 2707-2719 (2004).
18) Xu, S. W. et al, J. Biol. Chem. 279 (22), 23098-23103 (2004).
19) Douglas, M. L. et al, Cancer 100 (10), 2118-2124 (2004).
20) Tanaka, C. et al, Hypertens. Res. 27 (5), 367-371 (2004).
21) Cauduro, R. L. et al, Transplant. Proc. 36 (4), 880-881 (2004).
22) Wulfing, P. et al, Clin. Cancer Res. 10 (7), 2393-2400 (2004).
23) Funalot, B. et al, J. Hypertens. 22 (4), 739-743 (2004).
24) Mawji, I. A. et al, J. Biol. Chem. 279 (10), 8655-8667 (2004).
25) Saunders, R. et al, Eur. J. Biochem. 271 (5), 1054-1062 (2004).
26) Chen, M. C. et al, Chest 125 (2), 390-396 (2004).
27) Pontiroli, A. E. et al, Eur. J. Endocrinol. 150 (2), 195-200 (2004).
28) Kocik, M. et al, Transpl. Int. 17 (2), 65-70 (2004).
29) Hafizi, S. et al, Cell. Physiol. Biochem. 14 (4-6), 285-292 (2004).
30) Wunderlich, K. et al, Mol. Vis. 9, 756-761 (2003).
31) Stannard, C. et al, Biochemistry 42 (47), 13919-13928 (2003).
32) Dosanjh, A. et al, Mol. Vis. 40 (8), 883-886 (2003).
33) Asakura, H. et al, Invest. Opthalmol. Vis. Sci. 70 (6), 480-489 (2003).
34) Camsarl, A. et al, Circ. J. 67 (12), 1022-1028 (2003).
35) Narayan, S. et al, Invest. Opthalmol. Vis. Sci. 44 (11), 48854894 (2003).
36) Nicolaidou, P. et al, Pediatr. Nephrol. 18 (11), 1157-1160 (2003).
37) Spinella, F. et al, J. Biol. Chem. 278 (42), 41294-41301 (2003).
38) Roy-Beaudry, M. et al, Rheum. 48 (10), 2855-2864 (2003).
39) Pinto-Sietsma, S. J. et al, J. Am. Soc. Nephrol. 14 (10), 2596-2602 (2003).
40) Treiber, F. A. et al, Hypertension 42 (4), 494-499 (2003).
41) Foster, N. et al, Biochim. Biophys. Acta 1642 (1-2), 45-52 (2003).
42) Yin, J. J. et al, Proc. Natl. Acad. Sci. U.S.A. 100 (19), 10954-10959 (2003).
43) Wulfing, P. et al, Clin. Cancer Res. 9 (11), 4125-4131 (2003).

44) Di Paolo, S. et al, J. Nephrol. 16 (5), 650-657 (2003).
45) Galindo-Fraga, A. et al, Arch. Med. Res. 34 (5), 367-372 (2003).
46) Namiki, A. et at, Invest. Opthalmol. Vis. Sci. 44 (5), 633-644 (2003).
47) Kinugawa, T. et al, J. Card. Fail. 9 (4), 318-324 (2003).
48) Ding, K. H. et al, Am. J. Physiol. Endocrinol. Metab. 285 (2), E390-E396 (2003).
49) Erdem, M. et al, Eur. J. Biochem. 6 (4), 307-313 (2003).
50) Bajoria, R. et al, Am. J. Obstet. Gynecol. 189 (1), 189-194 (2003).
51) Chun, T. H. et al, Circ. Res. 92 (11), 1201-1208 (2003).
52) Bruno, C. M. et al, Endocrinol. Metab. 45 (2), 151-154 (2003).
53) Cheng, C. M. et al, Mol. Pharmacol. 63 (5), 1002-1011 (2003).
54) Tilly, N. et al, Exp. Clin. Endocrinol. Diabetes 111 (2), 80-84 (2003).
55) Inoue, K. et al, Pancreas 26 (3), 218-223 (2003).
56) Kimmel, C. B. et al, Development 130 (7), 1339-1351 (2003).
57) Nagai, M. Et at, Am. J. Hypertens. 16 (3), 223-228 (2003).
58) Massai, L. et al, Am. J. Physiol. Gastrointest. Liver Physiol. 284 (2), G340-G348 (2003).
59) Jin, J. J. et al, Hypertension 41 (1), 163-167 (2003).
60) Medinger, M. Et al., J. Biol. Chem. 6 (3), 225-231 (2003).
61) Ong, A. C. et al, Nephron Exp. Nephrol. 93 (2), E80 (2003).
62) Kitamura, A. et al, Biochem. Biophys. Res. Commun. 299 (4), 555-561 (2002).
63) Vasku, A. et al, Exp. Mol. Pathol. 73 (3), 230-233 (2002).
64) Li, J. M. et al, Ai Zheng 21 (10), 1109-1111 (2002).
65) Evans, J. J. et al, J. Endocrinol. 175 (1), 225-232 (2002).
66) Eberle, J. et al, J. Invest. Dermatol. 119 (3), 549-555 (2002).
67) Jamal, S. et al., J. Clin. Invest. 110 (4), 443-452 (2002).
68) Marinoni, E. et al, Regul. Pept. 107 (1-3), 125-128 (2002).
69) Didier, N. et al, Neuroreport 13 (9), 1179-1183 (2002).
70) Grubbs, A. L. et al, Arterioscler. Thromb. Vasc. Biol. 22 (7), 1122-1127 (2002).
71) Erkan, E. et al, Am. J. Kidney Dis. 40 (1), 76-81 (2002).
72) Fuchsjager-Mayrl, G. et al, Diabetologia 45 (6), 883-889 (2002).
73) Kozak, M. Et at, Med. Sci. Monit. 8 (5), BR164-BR167 (2002).
74) Quehenberger, P. Et at, Circ. Res. 90 (6), 711-718 (2002).
75) Bruno, C. M. et al, J. Biol. Regul. Homeost. Agents 16 (2), 114-117 (2002).
76) Fahimi-Vahid, M. et al, J. Mol. Cell. Cardiol. 34 (4), 441-453 (2002).
77) El-Gamal, Y. et al, Ann. Allergy Asthma Immunol. 88 (4), 370-373 (2002).
78) Shiu, Y. T. et al, Eur. J. Haematol. 68 (3), 163-169 (2002).
79) Costa, C. et al, Transplant. Proc. 34 (2), 487-488 (2002).
80) Hewage, C. M. et al, Protein Eng. 15 (3), 161-167 (2002).
81) Wang, G. X. et al, Microvasc. Res. 63 (2), 209-217 (2002).
82) Ng, T. M. et al, Thromb. Haemost. 87 (1), 176-177 (2002).
83) Yokoyama, Y. Et al, Shock 17 (1), 3640 (2002).
84) Asham, E. et al, Br. J. Cancer 85 (11), 1759-1763 (2001).
85) Saetrum Opgaard, O. et al, Mol. Cell. Biochem. 224 (1-2), 151-158 (2001).
86) Hillier, C. et al, Clin. Sci. 101 (1), 45-51 (2001).
87) Cambiaggi, C. et al, Cytokine 14 (4), 230-233 (2001).
88) el-Sharkawy, I. M. et al, Development 31 (1), 169-176 (2001).
89) Rebuffat, P. et al, Int. J. Mol. Med. 7 (3), 301-305 (2001).
90) Maggi, M. et al, J. Clin. Endocrinol. Metab. 85 (4), 1658-1665 (2000).
91) Woods, M. et al, Mol. Pharmacol. 55 (5), 902-909 (1999).
92) Germain, A. M. et al, Mol. Cell. Endocrinol. 132 (1-2), 161-168 (1997).
93) Sventek, P. et al, J. Hypertens. 14 (1), 57-64 (1996).
94) Alberts, G. F. et al, J. Biol. Chem. 269 (13), 10112-10118 (1994).
95) Kumazaki, T. et al, Exp. Cell Res. 211 (1), 6-11 (1994).
96) Benatti, L. et al, J. Clin. Invest. 91 (3), 1149-1156 (1993).
97) Imokawa, G. et al, J. Biol. Chem. 267 (34), 24675-24680 (1992).
98) Arinami, T. Et al, Am. J. Hum. Genet. 48 (5), 990-996 (1991).
99) Casey, M. L. et al, J. Biol. Chem. 266 (9), 5762-5768 (1991).
100) Giaid, A. et al, Proc. Natl. Acad. Sci. U.S.A. 86 (19), 7634-7638 (1989).
101) Inoue, A. et al, J. Biol. Chem. 264 (25), 14954-14959 (1989).
102) Bloch, K. D. et al, J. Biol. Chem. 264 (18), 10851-10857 (1989).
103) Itoh, Y. et al, FEBS Lett. 231 (2), 440-444 (1988).

Methods of isolation for the human endothelin-1 gene of the present invention may also be found in reference to the references cited in the GENBANK® accession nos. for each gene provided herein which are hereby incorporated by reference herein.

Example 13

Method of Isolating the Polymorphic Forms of the Human Endothelin-1 Gene of the Present Invention Since the allelic genes of the present invention represent genes present within at least a subset of the human population, these genes may be isolated using the methods provided in Example 12 above. For example, the source DNA used to isolate the allelic gene may be obtained through a random sampling of the human population and repeated until the allelic form of the gene is obtained. Preferably, random samples of source DNA from the human population are screened using the SNPs and methods of the present invention to identify those sources that comprise the allelic form of the gene. Once identified, such a source may be used to isolate the allelic form of the gene(s). The invention encompasses the isolation of such allelic genes from both genomic and/or cDNA libraries created from such source(s).

In reference to the specific methods provided in Example 12 above, it is expected that isolating the polymorphic alleles of the human endothelin-1 gene would be within the skill of an artisan trained in the molecular biology arts. Nonetheless, a detailed exemplary method of isolating at least one of the endothelin-1 polymorphic alleles, in this case the variant form of ET1-SNP1 ("t" nucleotide at 797 of SEQ ID NO:39) is provided. Briefly, First, the individuals with the G797T variation are identified by genotyping the genomic DNA samples using the method outlined in Example 10 herein. Other methods of genotyping may be employed, such as the FP-SBE method (Chen et al., Genome Res., 9(5):492-498 (1999)), or other methods described herein. DNA samples publicly available (e.g., from the Coriell Institute (Collingswood, N.J.) or from the Bristol-Myers Squibb clinical samples described herein may be used. Oligonucleotide primers that are used for this genotyping assay are provided in Example 10.

By analyzing genomic DNA samples, individuals with the G797T form of the ET1-SNP1 variant may be identified. Once identified, clones comprising the genomic sequence may be obtained using methods well known in the art (see Sambrook, J., E. F. Fritsch, and T. Maniatis, 1989, Molecular Cloning: A Laboratory Manual, Cold Spring Harbor Laboratory Press, Cold Spring Harbor, N.Y.; and Current Protocols in Molecular Biology, 1995, F. M., Ausubel et al., eds, John Wiley and Sons, Inc., which are hereby incorporated by reference herein.).

If cDNA clones of the coding sequence of this allele of the gene are of interest, such clones may be obtained in accordance with the following steps. Next, Lymphoblastoid cell lines from these individuals may be obtained from the Coriell Institute. These cells can be grown in RPMI-1640 medium with L-glutamine plus 10% FCS at 37 degrees. PolyA+ RNA are then isolated from these cells using OLIGOTEX® Direct Kit (Life Technologies).

First strand cDNA (complementary DNA) is produced using SUPERSCRIPT® Preamplification System for First Strand cDNA Synthesis (Life Technologies, Cat No 18089-011) using these polyA+ RNA as templates, as specified in the users manual which is hereby incorporated herein by reference in its entirety. Specific cDNA encoding the human endothelin-1 protein is amplified by polymerase chain reaction (PCR) using a forward primer which hybridizes to the 5'-UTR region, a reverse primer which hybridizes to the 3'-UTR region, and these first strand cDNA as templates (Sambrook, Fritsch et al. 1989). Alternatively, these primers may be designed using Primer3 program (Rozen S 2000). Restriction enzyme sites (example: SalI for the forward primer, and NotI for reverse primer) are added to the 5'-end of these primer sequences to facilitate cloning into expression vectors after PCR amplification. PCR amplification may be performed essentially as described in the owner's manual of the Expand Long Template PCR System (Roche Molecular Biochemicals) following manufacturer's standard protocol, which is hereby incorporated herein by reference in its entirety.

PCR amplification products are digested with restriction enzymes (such as SalI and NotI, for example) and ligated with expression vector DNA cut with the same set of restriction enzymes. pSPORT (Invitrogen) is one example of such an expression vector. After ligated DNA is introduced into *E. coli* cells (Sambrook, Fritsch et al. 1989), plasmid DNA is isolated from these bacterial cells. This plasmid DNA is sequenced to confirm the presence an intact (full-length) coding region of the human endothelin-1 protein with the variation, if the variation results in changes in the encoded amino acid sequence, using methods well known in the art and described elsewhere herein.

The skilled artisan would appreciate that the above method may be applied to isolating the other novel human endothelin-1 genes of the present invention through the simple substitution of applicable PCR and sequencing primers. Such primers may be selected from any one of the applicable primers provided in herein, or may be designed using the Primer3 program (Rozen S 2000) as described. Such primers may preferably comprise at least a portion of any one of the polynucleotide sequences of the present invention.

Example 14

Method of Engineering the Allelic Forms of the Human Endothelin-1 Gene of the Present Invention Aside from isolating the allelic genes of the present invention from DNA samples obtained from the human population, Bristol-Myers Squibb Company clinical trials, and/or the Coriell Institute, as described in Example 13 above, the invention also encompasses methods of engineering the allelic genes of the present invention through the application of site-directed mutagenesis to the isolated native forms of the genes. Such methodology could be applied to synthesize allelic forms of the genes comprising at least one, or more, of the encoding SNPs of the present invention (e.g., silent, missense)—preferably at least 1, 2, 3, or 4 encoding SNPs for each gene.

In reference to the specific methods provided in Example 13 above, it is expected that isolating the novel polymorphic endothelin-1 genes of the present invention would be within the skill of an artisan trained in the molecular biology arts. Nonetheless, a detailed exemplary method of engineering at least one of the endothelin-1 polymorphic alleles to comprise the encoding and/or non-coding polymorphic nucleic acid sequence, in this case the variant form (G797T) of ET1-SNP1 (SEQ ID NO:39) is provided. Briefly, cDNA clones encoding the human endothelin-1 protein may be identified by homology searches with the BLASTN program (Altschul SF 1990) against the GENBANK® non-redundant nucleotide sequence database using the published human endothelin-1 cDNA sequence (GENBANK® Accession No.: gi|21359861). Alternatively, the genomic sequence of the human endothelin-1 gene may be obtained as described herein. After obtaining these clones, they are sequenced to confirm the validity of the DNA sequences.

However, in the case of the variant form (G797T) of ET1-SNP 1, genomic clones would need to be obtained and may be identified by homology searches with the BLASTN program (Altschul SF 1990) against the GENBANK® non-redundant nucleotide sequence database using the published human endothelin-1 cDNA sequence (GENBANK® Accession No.: gi|21359861). Alternatively, the genomic sequence of the human endothelin-1 gene may be obtained as described herein. After obtaining these clones, they are sequenced to confirm the validity of the DNA sequences.

Once these clones are confirmed to contain the intact wild type cDNA or genomic sequence of the human endothelin-1 coding and/or non-coding region, the G797T polymorphism (mutation) may be introduced into the native sequence using PCR directed in vitro mutagenesis (Cormack, B., Directed Mutagenesis Using the Polymerase Chain Reaction. Current Protocols in Molecular Biology, John Wiley & Sons, Inc. Supplement 37: 8.5.1-8.5.10, (2000)). In this method, synthetic oligonucleotides are designed to incorporate a point mutation at one end of an amplified fragment. Following PCR, the amplified fragments are made blunt-ended by treatment with Klenow Fragment. These fragments are then ligated and subcloned into a vector to facilitate sequence analysis. This method consists of the following steps.

1. Subcloning of cDNA or genomic insert into a plasmid vector, or BAC sequence if the clone is a genomic sequence, containing multiple cloning sites and M13 flanking sequences, such as pUC19 (Sambrook, Fritsch et al. 1989), in the forward orientation. The skilled artisan would appreciate that other plasmids could be equally substituted, and may be desirable in certain circumstances.

2. Introduction of a mutation by PCR amplification of the cDNA region downstream of the mutation site using a primer including the mutation. (FIG. 8.5.2 in Cormack 2000)). In the case of introducing the G797T (i.e., K198N) mutation into the human endothelin-1 protein, the following two primers may be used.

M13 reverse sequencing primer:

5'-AGCGGATAACAATTTCACACAGGA-3' (SEQ ID NO:46).

Mutation primer:
  5'-GATCCCAAGCTGAAAGGCAA
  TCCCTCCAGAGAGCGTTATG-3' (SEQ ID NO:47)

Mutation primer contains the mutation (G797T) at the center (in bold and underlined) and a portion of its flanking sequence. M13 reverse sequencing primer hybridizes to the pUC19 vector. Subcloned cDNA or genomic clone comprising the human endothelin-1 cDNA or genomic sequence is used as a template (described in Step 1). A 100 ul PCR reaction mixture is prepared using 10 ng of the template DNA, 200 uM 4dNTPs, 1 uM primers, 0.25U Taq DNA polymerase (PE), and standard Taq DNA polymerase buffer. Typical PCR cycling condition are as follows:

| 20-25 cycles: | 45 sec, 93 degrees |
| --- | --- |
|  | 2 min, 50 degrees |
|  | 2 min, 72 degrees |
| 1 cycle: | 10 min, 72 degrees |

After the final extension step of PCR, 5U Klenow Fragment is added and incubated for 15 min at 30 degrees. The PCR product is then digested with the restriction enzyme, EcoRI.

3. PCR amplification of the upstream region is then performed, using subcloned cDNA or genomic clone as a template (the product of Step 1). This PCR is done using the following two primers:

M 13 forward sequencing primer:
  5'-CGCCAGGGTTTTCCCAGTCACGAC-3' (SEQ ID NO:45).

Flanking primer:
  5'-CATAACGCTCTCTGGAGGG
  ATTGCCTTTCAGCTTGGGATC-3' (SEQ ID NO:48).

Flanking primer is complimentary to the upstream flanking sequence and mutation locus of the G797T mutation (in bold and underlined). M13 forward sequencing primer hybridizes to the pUC19 vector. PCR conditions and Klenow treatments follow the same procedures as provided in Step 2, above. The PCR product is then digested with the restriction enzyme, HindIII.

4. Prepare the pUC19 vector for cloning the cDNA or genomic clone comprising the polymorphic locus. Digest pUC19 plasmid DNA with EcoRI and HindIII. The resulting digested vector fragment may then be purified using techniques well known in the art, such as gel purification, for example.

5. Combine the products from Step 2 (PCR product containing mutation), Step 3 (PCR product containing the upstream region), and Step 4 (digested vector), and ligate them together using standard blunt-end ligation conditions (Sambrook, Fritsch et al. 1989).

6. Transform the resulting recombinant plasmid from Step 5 into E. coli competent cells using methods known in the art, such as, for example, the transformation methods described in Sambrook, Fritsch et al. 1989.

7. Analyze the amplified fragment portion of the plasmid DNA by DNA sequencing to confirm the point mutation, and absence of any other mutations introduced during PCR. The method of sequencing the insert DNA, including the primers utilized, are described herein or are otherwise known in the art.

Moreover, the skilled artisan would appreciate that the above method may be applied to engineering more than one polymorphic nucleic acid sequence of the present invention into the novel endothelin-1 genes of the present invention. Such an engineered gene could be created through successive rounds of site-directed mutagenesis, as described in Steps 1 thru 7 above, or consolidated into a single round of mutagenesis. For example, Step 2 above could be performed for each mutation, then the products of both mutation amplifications could be combined with the product of Step 3 and 4, and the procedure followed as described.

Example 15

Method of Assessing the Expression Profile of Human Endothelin-1 in Response to Treatment with PPAR-Agonists in CALU-6 Cells Using Quantitative RT-PCR On account of the involvement of ET-1 in vascular tone maintenance, along with its involvement in numerous cardiovascular disease processes, the possibility that PPAR agonists may contribute to an agonist-induced edema mechanism of action through the modulation of endoethelin-1, was investigated using quantitative RT-PCR. Briefly, gene expression studies were performed using a cell line that was previously shown to express endogenous endothelin mRNA, CALU-6 (Lang et al., 1995).

Maintenance of Cell Line for the Invention

The human lung carcinoma cell line, CALU-6, was obtained from ATCC®. Cells were recovered and expanded in complete growth media (Minimal Essential Media+Earle's Balanced Salt Solution, 1% penicillin/streptomycin, 10% Fetal Bovine Serum) and were passaged after the cells reached 80-90% confluency. Cells were typically split 1:4, twice weekly.

PPAR Agonist Compounds

Compounds A, B, C, D, and F were synthesized at Bristol-Myers Squibb Co. Compound E was purified by reverse phase high-performance liquid chromatography from commercial pharmaceutical preparations. Compounds A, B, and F are dual PPAR alpha and gamma agonists; while compounds C, D, and E are single PPAR gamma agonists. Compounds A and B are disclosed in U.S. Pat. No. 6,414,002; which is hereby incorporated by reference herein in its entirety. All compounds were reconstituted in DMSO such that their working concentrations were 500× the final concentration used in the induction studies. The final concentration of each PPAR-agonist used in the induction studies was 5×EC50 as determined from pre-adipocyte differentiation studies (data not shown). The final concentration of DMSO in all treatments was 0.2%.

Induction Experiments

CALU-6 cells were seeded on day 0 in replicates of six (or twelve for DMSO control), at $5\times10^5$ cells/well, in 6-well tissue culture plates. Cells were incubated at 37° C. under 5% CO2. The growth media was removed on day 1 and cells were re-fed with growth media containing 0.2% DMSO (vehicle control), 0.76 μM Compound A, 0.021 μM Compound B, 1 μM Compound C, 0.4 μM Compound D, 0.005 μM Compound E and 1.7 μM Compound F. After 24 hr incubation at 37° C. under 5% $CO_2$, cells were lysed and total RNA was prepared using the RNAeasy mini kit (Qiagen) following the manufacturer's recommendations. RNA quantities were determined spectrophotometrically using a SPECTRA-MAX® 384 spectrophotometer (Molecular Devices). RNA quality was assessed using an Agilent 2100 Bioanalyzer (Agilent Technologies) following the manufacturer's recommendations. All total RNA preparations were adjusted to a final concentration of 83.3 ng/µl.

Quantitative Real-Time PCR Study

All cDNA synthesis and subsequent PCR experiments were performed following the Applied Biosystems TAQ-MAN® Assay protocol (Applied Biosystems). 250 ng of total RNA was used in the reverse transcription reaction. 10 ng of total RNA converted to cDNA was used as template for real-time PCR experiments. On-Demand TAQMAN® Assays for endothelin-1, GAPDH (part number, Hs99999905) and m-actin (part number, Hs99999903) were obtained from Applied Biosystems. Each On-Demand assay included the required reagents to quantify expression levels of each gene as well as the recommended cycling conditions.

Quantitative Real-Time PCR Data Analysis

Sequence Detection System Software v.2.1 (Applied Biosystems) was used to analyze the quality of each amplification reaction as well as to calculate Ct values for each sample. All data was further analyzed using Microsoft Excel.

To determine if gene expression significantly varied over all treatments (including DMSO control) single-factor ANOVA was performed on Ct values for each gene studied, followed by pair-wise 2-tail Student's t-tests where appropriate.

To quantify gene expression change upon treatment with compound, deltaCt values were calculated by subtracting individual Ct values of each replicate (n=6) from the mean Ct value of the DMSO control (n=12). Gene expression fold-change was then calculated by expressing the mean deltaCt value of each treatment group as a factor of 2.

The results of the RT-PCR expression profile for human endothelin-1 are provided in FIGS. 16 and 17.

Example 16

Method of Discovering the β1-Adrenergic Receptor Single Nucleotide Polymorphisms (SNPs) of the Present Invention SNP discovery is based on comparative DNA sequencing of PCR products directed to the human β1-adrenergic receptor gene derived from genomic DNA from multiple individuals. In the present case, the β1-adrenergic receptor Beta1-SNP1 was publicly known. Nonetheless, studies were performed to confirm the existence of this SNP in the patient cohorts described herein. All genomic DNA samples for SNP discovery were obtained from a panel of thirty-two human subjects obtained from the Coriell Institute (Camden, N.J.), panel # M44PDR.

β1-Adrenergic Receptor-Beta1-SNP1: c/g at Nucleotide 1251 of SEQ ID NO:50 and 52

β1-adrenergic receptor Beta1-SNP1 was confirmed using the following protocol. Briefly, portions of the human β1-adrenergic receptor genomic sequence were PCR amplified using the standard PLATINUM® Taq DNA protocol (Invitrogen, Product #10966-083):

The following sequencing primers (20 uM each) were used to confirm the above SNP, as well as to sequence across the PCR amplicons:

| SNP | Forward Primer | Reverse Primer |
|---|---|---|
| β1-adrenergic receptor Beta1-SNP1 | GGCCTTCAACCCCATCATCTA (SEQ ID NO:54) | CCGGTCTCCGTGGGTCGCGT (SEQ ID NO:55) |

All the samples amplified from genomic DNA (50 ng) in reactions (50 ul) containing 50 mM Tris-Acetate pH 8.4, 75 mM KAcetate, 8 mM MgAcetate, 200 uM dNTPs, 0.2 uM of each PCR primer, and 2.5 U PLATINUM® Taq DNA polymerase (Invitrogen).

PCR amplification was performed in Perkin Elmer 9700 machines under the following cycling conditions: 1.) 94 degrees Celsius for 2 minutes; 2.) 94 degrees Celsius for 30 seconds; 3.) 59 degrees Celsius for 1 minute; 4.) 72 degrees Celsius for 30 seconds; 5.) 72 degrees Celsius for 5 minutes; and 6.) 4 degrees Celsius on hold. Steps 2 to 4 were cycled 35 times.

PCR products were sequenced using ABI BigDye Terminator v3.1 Cycle Sequencing chemistry on the 3730-XL capillary sequencers using the same primers used for identifying the SNPs, as described above.

Sequence editing and contig assembly was performed using CONSED software (Genome Res. 1998 March; 8(3): 195-202). Chromatograms were visually inspected for each Coriell DNA and SNPs identified by comparing sequence traces to the reference β1-adrenergic receptor genomic DNA sequence provided as GENBANK® Accession No. gi| NP_000675. The coding region of the reference endothelin-1 is provided as SEQ ID NO:50 (GENBANK® Accession No. gi| NP_000675), encoding the reference β1-adrenergic polypeptide sequence provided as SEQ ID NO:51 (GENBANK® Accession No. gi| NP_000675).

The nucleotide sequence of the β1'-adrenergic receptor gene containing the reference allele ("c") for Beta1-SNP1 at nucleotide 1251 is provided in FIGS. 18A-B (SEQ ID NO:50); while the nucleotide sequence of the β1-adrenergic receptor gene containing the variable allele ("g") for Beta1-SNP1 at nucleotide 1251 is provided in FIGS. 19A-B (SEQ ID NO:52).

The polypeptide sequence of β1-adrenergic receptor containing the reference allele ("R") for Beta1-SNP1 at amino acid 389 is provided in FIGS. 18A-B (SEQ ID NO:51); while the polypeptide sequence of β1-adrenergic receptor containing the variable allele ("G") for Beta1-SNP1 at amino acid 389 is provided in FIGS. 19A-B (SEQ ID NO:53).

Example 17

Method of Genotyping Each SNP of the Present Invention

Genomic DNA samples from patients enrolled in two Bristol-Myers Squibb Company Phase II clinical trials CV168-006 and CV168-008 trials were genotyped for Beta1-SNP1 of the human β1-adrenergic receptor gene (see Example 16) and evaluated for association with edema.

498 subjects enrolled in the CV168-006 trial and 232 subjects from the CV168-008 trial were analyzed in this study. All analyses were based on data collected up to 24 weeks, which was the duration of the short-term phase of the trials.

DNA was extracted from frozen blood by a third-party (Genaissance Inc, North Carolina) using a salting-out method (Gentra Systems). All subjects gave written informed consent.

Genotyping was performed using the 5' nuclease assay, essentially as described (Ranade K et al., Genome Research 11: 1262-1268 (2001); which is hereby incorporated by reference herein in its entirety), with the following modifications: six nanograms of genomic DNA were used in a 8 ul reaction. All PCR reactions were performed in an ABI 9700 machine and fluorescence was measured using an ABI 7900 machine.

Genotyping of the SNPs of the present invention was performed using sets of TAQMAN® probes (100 uM each) and primers (100 uM each) specific to the SNP. Each probe/primer set was manually designed using ABI Primer Express software (Applied Biosystems). Genomic samples were prepared as described in Example 16. The following TAQ-MAN® probes and primers were utilized:

| SNP | TAQMAN® Forward Primer | TAQMAN® Reverse Primer | Reference TAQMAN® Probe | Variable TAQMAN® Probe |
|---|---|---|---|---|
| Beta1-SNP1 | GGCCTTCAACCCCA TCATCTA (SEQ ID NO:54) | CCGGTCTCCGTGGG TCGCGT (SEQ ID NO:55) | AGGCCTTCCAGBGA CTGCTCTGC (SEQ ID NO:56) | AGGCCTTCCAGGG ACTGCTCTGCT (SEQ ID NO:57) |

** The allelic nucleotide in each probe sequence is shown in bold and underlined.

The genotype assay conditions are provided below.

| Components: | Final Concentration |
|---|---|
| 2x PE Master Mix (#4318157) | 1X |
| 100 uM FAM labeled probe | 200 nmol |
| 100 uM VIC labeled probe | 200 nmol |
| Forward PCR primer | 600 nmol |
| Reverse PCR primer | 600 nmol |
| 6 ng template DNA | as required |
| ddH2O | volume to 8 ul |

TAQMAN® thermo-cycling was performed on Perkin Elmer PE 9700 machines using the following cycling conditions below:
1) 50C for 2 minutes
2) 95C for 10 seconds*
3) 94C for 15 seconds
4) 62C for 1 minute
5) 4C hold

*Steps 24 were cycled 40 times

Analysis of genotypes was performed by using the Applied Biosystems ABI 7900 HT sequence detection system.

Example 18

Statistical Analysis of the Association Between Dose-Dependent Peripheral Edema and the β1-Adrenergic Receptor SNPs of the Present Invention The association between peripheral edema and the β1-adrenergic receptor single nucleotide polymorphisms of the present invention were investigated by applying statistical analysis to the results of the genotyping assays described elsewhere herein. The central hypothesis of this analysis is that a predisposition to develop dose-dependent peripheral edema may be conferred by specific genomic factors. The analysis attempted to identify one or more of these factors in genomic DNA samples from index cases and matched control subjects who were exposed to Compound A in two Bristol-Myers Squibb (BMS) clinical studies (see Example 17).

SNPs of the present invention were examined for association with edema using 3 (genotypes)×2 (edema and no edema) contingency tables. Significant results for edema (P<0.05) were followed up by logistic regression analysis including baseline body mass index, age, trial, sex, race and SNP as covariates. Analyses were performed using S-PLUS® (version 6.0; Insightful Corp. Seattle, Wash.) or SPSS® (version 12.0; SPSS Inc. Chicago, Ill.).

Methods

Sample. Investigators in the BMS clinical trials diagnosed dose-dependent peripheral edema in some subjects.

Measures. Single nucleotide polymorphisms (SNPs) in human β1-adrenergic receptor were genotyped on all subjects essentially as described in Example 17 herein. The SNPs that are genotyped likely represent a sample of the polymorphic variation in each gene and are not exhaustive with regard to coverage of the total genetic variation that may be present in each gene. Specifically, only the β1-adrenergic receptor Beta1-SNP1 referenced herein was genotyped and statistically analyzed, as described. The SNPs for which a statistical association to peripheral edema susceptibility was confirmed are provided and referred to as Beta1-SNP1.

Statistical Analyses. Conditional logistic regression (HOSMER and LEMESHOW 2000) was used to examine the associations between genotypes of endothelin-1 gene SNPs and the development of dose-dependent peripheral edema. All SNPs are bi-allelic with three possible genotypes. For each SNP, in the overall sample and each subgroup, allele frequencies are estimated. For consistency in SNP genotype parameter coding in the logistic regression models, the less frequent allele of each SNP was designated as the rare allele and the number of copies of that allele that each subject carried, either 0, 1, or 2, was then determined. Three possible genotypes for each SNP leaves two degrees of freedom for parameters in the conditional logistic regression model representing the information contained in these three genotype categories. Two dummy variables are therefore created based on the copies of the rare allele for each subject for use in the conditional logistic regression model, $x_1=1$ if copies of rare allele=1, 0 otherwise and $x_2=1$ if copies of rare allele=2, 0 otherwise.

The full conditional logistic regression model used was $$\pi_k(x) = \frac{e^{\alpha_k + \beta_1' x_1 + \beta_2' x_2}}{1 + e^{\alpha_k + \beta_1' x_1 + \beta_2' x_2}},$$

where x in $\pi_k(X)$ is the vector of dummy variables representing the SNP genotypes described above, k is the matching stratum index specific to each matched case-control set of subjects, $\pi_k(X)$ is the matching stratum-specific expected probability that a subject is a case given x, $\alpha_k$ is the matching stratum-specific contribution to $\pi_k(x)$ of all the matching variables constant within the kth stratum and each β' represents the contribution of the respective dummy variable to $\pi_k(X)$.

For each SNP, the null hypothesis was that the vector of β' are all equal to 0 and was tested using the scores test (HOSMER and LEMESHOW 2000). The degrees of freedom for the scores test statistic was equal to one less than the number of genotypes. Exponentiation of each slope coefficient, β', provided an estimate of the ratio of the odds of an adverse event (e.g., dose-dependent peripheral edema) in subjects carrying the specified copies of the rare allele represented in the definition of the coefficient, relative to controls matched for body mass index, age, trial, sex, race, and SNP as covariates, over the odds of such an adverse event for similarly matched subjects not carrying any copies of the rare allele. 95% confidence interval limits are estimated for each odds ratio based on the standard error estimate of the respective slope coefficient.

Since the SNP coverage within the human β1-adrenergic receptor gene was not exhaustive of the genetic variation that may be present and possibly related to event susceptibility in this gene, inferences about these SNP associations with dose-dependent peripheral edema events for β1-adrenergic receptor are therefore related to the hypothesis that genetic variation in this gene may be involved in susceptibility to such events.

Selection of Affected and Unaffected Subjects for Genetic Analysis of Dose-Dependent Peripheral Edema Table A provides a distribution of the frequency of dose-dependent peripheral edema by treatment arm. The frequency of edema increased as the dose of Compound A increased from 0.5 mg to 20 mg. Table A is provided in Example 3 above.

To increase the likelihood of finding genetic associations, subjects who did not develop dose-dependent peripheral edema at the maximum dose of Compound A, i.e. Dose E, were considered "unaffected" and compared to subjects who developed edema at any dose of Compound A. The characteristics of these two groups are provided in Table B in Example 3. To see the reasoning behind this approach, compare the frequency of edema in the Dose C group (10%) and the Dose E group (40%). Thus, if subjects without edema in the Dose C group were considered unaffected, a significant number of individuals (30% of 125 or 38) who might be genetically susceptible to edema when exposed to a high dose of Compound A would be mis-classified, thereby reducing the genetic signal or power of the study. This approach is analogous to the use of extreme discordant sibpairs for detecting genes underlying quantitative traits.

As shown in Table B in Example 3, subjects who developed dose-dependent peripheral edema after exposure to Compound A were more likely to be female, older and heavier. Race and smoking status were not significant predictors of edema.

Genetic Associations with Edema

All subjects for whom sufficient DNA was available were genotyped for 218 SNPs in 65 candidate genes with 1 of these SNPs being specific for the human β1-adrenergic receptor gene (Beta1-SNP1). Of these 218 SNPs, subjects enrolled in these trials were polymorphic for 153 SNPs (minor allele frequency >0.1%). In 3×2 contingency table analysis, SNPs in the β1-adrenergic receptor genes were significantly associated with edema status (P<0.05). The distribution of genotypes between the two groups for each SNP is provided in Table F for Beta1-SNP1.

TABLE F

Genotype distribution of β1-adrenergic receptor SNPs

| Trait/SNP | Odds ratio (95% C.I.) | P value |
|---|---|---|
| β1 adrenergic receptor/Arg389Gly | | |
| Arg/Arg | 69 (59%) | 66 (44%) |
| Arg/Gly | 41 (35%) | 65 (43%) |
| Gly/Gly | 7 (6%) | 19 (13%) |

The genotype distributions for Beta1-SNP1 was in Hardy-Weinberg equilibrium. These univariate analyses were followed-up by multivariate logistic regression analyses including other covariates such as age and sex (Table G).

TABLE G

Multivariate analysis of β1-adrenergic receptor SNP associations with edema

| Trait/SNP | Odds ratio (95% C.I.) | P value |
|---|---|---|
| Age | 1.08 (1.04-1.11) | <0.001 |
| Sex (Male vs. Female) | 0.17 (0.09-0.32) | <0.001 |
| Trial (−008 vs. −006) | 0.13 (0.06-0.26) | <0.001 |
| Body mass index | 1.12 (1.04-1.20) | 0.001 |
| Race | | 0.23 |
| β1-adrenergic receptor Beta1-SNP1 | | 0.028 |
| Arg/Gly vs. Arg/Arg | 2.12 (1.11-4.02) | 0.02 |
| Gly/Gly vs. Arg/Arg | 3.08 (0.90-10.61) | 0.07 |

Consistent with demographic data presented in Table B in Example 3, age, sex, body mass index, and trial were significant predictors of edema status. In contrast, race was not significantly associated with edema.

The β1-adrenergic Beta1-SNP1 was determined to be in Hardy-Weinberg equilibrium. These results suggest that polymorphisms in the β1-adrenergic receptor gene contributes to differences in susceptibility to dose-dependent peripheral edema independent of other significant predictors such as age, sex and body mass index.

The utility, in general, of each of these significant SNP-dose-dependent peripheral edema event associations is that they suggest: (1) such SNPs may be causally involved, alone or in combination with other SNPs in the respective gene regions with susceptibility to dose-dependent peripheral edema events resulting from exposure to a PPAR-agonist; (2) such SNPs, if not directly causally involved, are reflective of an association because of linkage disequilibrium with one or more other SNPs that may be causally involved, alone or in combination with other SNPs in the respective gene regions with susceptibility to dose-dependent peripheral edema resulting from exposure to a PPAR-agonist; (3) such SNPs may be useful in establishing haplotypes that may be used to narrow the search for and identify polymorphisms or combinations of polymorphisms that may be causally, alone or in combination with other SNPs in the respective gene regions with susceptibility to dose-dependent peripheral edema resulting from exposure to a PPAR-agonist; and (4) such SNPs, if used to establish haplotypes that are identified as causally involved in such event susceptibility, may be used to predict which subjects are most likely to experience such events when exposed to a dose-dependent peripheral edema resulting from exposure to a PPAR-agonist. The term "respective gene regions" shall be construed to refer to those regions of each gene which have been used to identify the SNPs of the present invention.

Example 19

Method of Isolating the Native Forms of the Human β1-Adrenergic Gene

A number of methods have been described in the art that may be utilized in isolating the native forms of the human β1-adrenergic receptor gene. Specific methods are referenced below and are hereby incorporated by reference herein in their entireties. The artisan, skilled in the molecular biology arts, would be able to isolate the native form of human β1-adrenergic receptor based upon the methods and information contained, and/or referenced, therein.

Human β1-adrenergic receptor (gi| NP_000675; SEQ ID NO:50 and 51)

1) de Groote, P. et al, Pharmacogenet Genomics 15 (3), 137-142 (2005).
2) Gavi, S. et al, Endocrinology 146 (1), 450-457 (2005).
3) Liang, W. et al, J. Biol. Chem. 279 (45), 46882-46889 (2004).
4) Stein, M. B. et al, Biol. Psychiatry 56 (4), 217-224 (2004).
5) Bullido, M. J. et al, Neurobiol. Aging 25 (7), 853-859 (2004).
6) Gardner, L. A. et al, J. Biol. Chem. 279 (20), 21135-21143 (2004).
7) Liang, W. et al, J. Cell. Sci. 117 (PT 5), 723-734 (2004).
8) Shioji, K. et al, Hypertens. Res. 27 (1), 31-37 (2004).
9) Mialet Perez, J. et al, Nat. Med. 9 (10), 1300-1305 (2003).
10) Maack, C. et al, Circulation 108 (3), 348-353 (2003).
11) Zill, P. Et al, Am. J. Med. Genet. B Neuropsychiatr. Genet. 120 (1), 85-89 (2003).
12) Xu, J. et al, J. Biol. Chem. 278 (12), 10770-10777 (2003).
13) Mercier, J. F. et al, J. Biol. Chem. 277 (47), 44925-44931 (2002).
14) Pak, Y. et al, Mol. Cell. Biol. 22 (22), 7942-7952 (2002).
15) He, J. et al, Biochem. Biophys. Res. Commun. 297 (3), 565-572 (2002).
16) Lavoie, C. et al, J. Biol. Chem. 277 (38), 35402-35410 (2002).
17) Iwai, C. et al, Circ. J. 66 (8), 723-728 (2002).
18) Wenzel-Seifert, K. Et al, Biochem. Pharmacol. 64 (1), 9-20 (2002).
19) Dunigan, C. D. et al, Biochemistry 41 (25), 8019-8030 (2002).
20) Dionne, I. J. et al, Int. J. Obes. Relat. Metab. Disord. 26 (5), 633-639 (2002).
21) Ranade, K. Et al, Am. J. Hum. Genet. 70 (4), 935-942 (2002).
22) Xu, J. et al, J. Biol. Chem. 276 (44), 41310-41317 (2001).
23) Hu, L. A. et al, J. Biol. Chem. 275 (49), 38659-38666 (2000).
24) Shiina, T. et al, J. Biol. Chem. 275 (37), 29082-29090 (2000).
25) Podlowski, S. Et al, J. Mol. Med. 78 (2), 87-93 (2000).
26) Mason, D. A. et al, J. Biol. Chem. 274 (18), 12670-12674 (1999).
27) Elies, R. et al, J. Immunol. 157 (9), 4203-4211 (1996).
28) Hoehe, M. R. et al, J. Mol. Med. 73 (6), 299-306 (1995).
29) Yang-Feng, T. L. et al, Proc. Natl. Acad. Sci. U.S.A. 87 (4), 1516-1520 (1990).
30) Forse, R. A. et al, J. Surg. Res. 46 (1), 41-48 (1989).
31) Frielle, T. et al, Trends Neurosci. 11 (7), 321-324 (1988).
32) Frielle, T. et al, Proc. Natl. Acad. Sci. U.S.A. 84 (22), 7920-7924 (1987).
33) Stiles, G. L. et al, J. Biol. Chem. 258 (13), 8443-8449 (1983).

Methods of isolation for the human β1-adrenergic receptor gene of the present invention may also be found in reference to the references cited in the GENBANK® accession nos. for each gene provided herein which are hereby incorporated by reference herein.

Example 20

Method of Isolating the Polymorphic Forms of the Human β1-Adrenergic Gene of the Present Invention Since the allelic genes of the present invention represent genes present within at least a subset of the human population, these genes may be isolated using the methods provided in Example 19 above. For example, the source DNA used to isolate the allelic gene may be obtained through a random sampling of the human population and repeated until the allelic form of the gene is obtained. Preferably, random samples of source DNA from the human population are screened using the SNPs and methods of the present invention to identify those sources that comprise the allelic form of the gene. Once identified, such a source may be used to isolate the allelic form of the gene(s). The invention encompasses the isolation of such allelic genes from both genomic and/or cDNA libraries created from such source(s).

In reference to the specific methods provided in Example 19 above, it is expected that isolating the polymorphic alleles of the human β1-adrenergic receptor gene would be within the skill of an artisan trained in the molecular biology arts. Nonetheless, a detailed exemplary method of isolating at least one of the β1-adrenergic receptor polymorphic alleles, in this case the variant form of Beta1-SNP1 ("g" nucleotide at 1251 of SEQ ID NO:52) is provided. Briefly, First, the individuals with the c1251g variation are identified by genotyping the genomic DNA samples using the method outlined in Example 17 herein. Other methods of genotyping may be employed, such as the FP-SBE method (Chen et al., Genome Res., 9(5):492-498 (1999)), or other methods described herein. DNA samples publicly available (e.g., from the Coriell Institute (Collingswood, N.J.) or from the Bristol-Myers Squibb clinical samples described herein may be used. Oligonucleotide primers that are used for this genotyping assay are provided in Example 17.

By analyzing genomic DNA samples, individuals with the c1251g form of the Beta1-SNP1 variant may be identified. Once identified, clones comprising the genomic sequence may be obtained using methods well known in the art (see Sambrook, J., E. F. Fritsch, and T. Maniatis, 1989, Molecular Cloning: A Laboratory Manual, Cold Spring Harbor Laboratory Press, Cold Spring Harbor, N.Y.; and Current Protocols in Molecular Biology, 1995, F. M., Ausubel et al., eds, John Wiley and Sons, Inc., which are hereby incorporated by reference herein.).

If cDNA clones of the coding sequence of this allele of the gene are of interest, such clones may be obtained in accordance with the following steps. Next, Lymphoblastoid cell lines from these individuals may be obtained from the Coriell Institute. These cells can be grown in RPMI-1640 medium with L-glutamine plus 10% FCS at 37 degrees. PolyA+ RNA are then isolated from these cells using OLIGOTEX® Direct Kit (Life Technologies).

First strand cDNA (complementary DNA) is produced using SUPERSCRIPT® Preamplification System for First Strand cDNA Synthesis (Life Technologies, Cat No 18089-011) using these polyA+ RNA as templates, as specified in the users manual which is hereby incorporated herein by reference in its entirety. Specific cDNA encoding the human β1-adrenergic receptor protein is amplified by polymerase chain reaction (PCR) using a forward primer which hybridizes to the 5'-UTR region, a reverse primer which hybridizes to the 3'-UTR region, and these first strand cDNA as templates (Sambrook, Fritsch et al. 1989). Alternatively, these primers may be designed using Primer3 program (Rozen S 2000). Restriction enzyme sites (example: SalI for the forward primer, and NotI for reverse primer) are added to the 5'-end of these primer sequences to facilitate cloning into expression vectors after PCR amplification. PCR amplification may be performed essentially as described in the owner's manual of the Expand Long Template PCR System (Roche Molecular Biochemicals) following manufacturer's standard protocol, which is hereby incorporated herein by reference in its entirety.

PCR amplification products are digested with restriction enzymes (such as SalI and NotI, for example) and ligated with expression vector DNA cut with the same set of restriction enzymes. pSPORT (Invitrogen) is one example of such an expression vector. After ligated DNA is introduced into *E. coli* cells (Sambrook, Fritsch et al. 1989), plasmid DNA is isolated from these bacterial cells. This plasmid DNA is sequenced to confirm the presence an intact (full-length) coding region of the human β1-adrenergic receptor protein with the variation, if the variation results in changes in the encoded amino acid sequence, using methods well known in the art and described elsewhere herein.

The skilled artisan would appreciate that the above method may be applied to isolating the other novel human β1-adrenergic receptor genes of the present invention through the simple substitution of applicable PCR and sequencing primers. Such primers may be selected from any one of the applicable primers provided in herein, or may be designed using the Primer3 program (Rozen S 2000) as described. Such primers may preferably comprise at least a portion of any one of the polynucleotide sequences of the present invention.

Example 21

Method of Engineering the Allelic Forms of the Human β1-Adrenergic Gene of the Present Invention Aside from isolating the allelic genes of the present invention from DNA samples obtained from the human population, Bristol-Myers Squibb Company clinical trials, and/or the Coriell Institute, as described in Example 20 above, the invention also encompasses methods of engineering the allelic genes of the present invention through the application of site-directed mutagenesis to the isolated native forms of the genes. Such methodology could be applied to synthesize allelic forms of the genes comprising at least one, or more, of the encoding SNPs of the present invention (e.g., silent, missense)-preferably at least 1, 2, 3, or 4 encoding SNPs for each gene.

In reference to the specific methods provided in Example 20 above, it is expected that isolating the novel polymorphic β1-adrenergic gene of the present invention would be within the skill of an artisan trained in the molecular biology arts.

Nonetheless, a detailed exemplary method of engineering at least one of the β1-adrenergic receptor polymorphic alleles to comprise the encoding and/or non-coding polymorphic nucleic acid sequence, in this case the variant form (c1251g) of Beta1-SNP1 (SEQ ID NO:52) is provided. Briefly, cDNA clones encoding the human β1-adrenergic receptor protein may be identified by homology searches with the BLASTN program (Altschul SF 1990) against the GEN-BANK® non-redundant nucleotide sequence database using the published human β1-adrenergic receptor cDNA sequence (GENBANK® Accession No.: gi/21359861). Alternatively, the genomic sequence of the human β1-adrenergic receptor gene may be obtained as described herein. After obtaining these clones, they are sequenced to confirm the validity of the DNA sequences.

However, in the case of the variant form (c1251g) of Beta1-SNP1, genomic clones would need to be obtained and may be identified by homology searches with the BLASTN program (Altschul SF 1990) against the GENBANK® non-redundant nucleotide sequence database using the published human β1-adrenergic receptor cDNA sequence (GENBANK® Accession No.: gi|NP_000675). Alternatively, the genomic sequence of the human β1-adrenergic receptor gene may be obtained as described herein. After obtaining these clones, they are sequenced to confirm the validity of the DNA sequences.

Once these clones are confirmed to contain the intact wild type cDNA or genomic sequence of the human β1-adrenergic receptor coding and/or non-coding region, the C1251G polymorphism (mutation) may be introduced into the native sequence using PCR directed in vitro mutagenesis (Cormack, B., Directed Mutagenesis Using the Polymerase Chain Reaction. Current Protocols in Molecular Biology, John Wiley & Sons, Inc. Supplement 37: 8.5.1-8.5.10, (2000)). In this method, synthetic oligonucleotides are designed to incorporate a point mutation at one end of an amplified fragment. Following PCR, the amplified fragments are made blunt-ended by treatment with Klenow Fragment. These fragments are then ligated and subcloned into a vector to facilitate sequence analysis. This method consists of the following steps.

1. Subcloning of cDNA or genomic insert into a plasmid vector, or BAC sequence if the clone is a genomic sequence, containing multiple cloning sites and M13 flanking sequences, such as pUC19 (Sambrook, Fritsch et al. 1989), in the forward orientation. The skilled artisan would appreciate that other plasmids could be equally substituted, and may be desirable in certain circumstances.

2. Introduction of a mutation by PCR amplification of the cDNA region downstream of the mutation site using a primer including the mutation. (FIG. 8.5.2 in Cormack 2000)). In the case of introducing the C1251G (i.e., R389G) mutation into the human β1-adrenergic receptor protein, the following two primers may be used.

M13 reverse sequencing primer:
   5'-AGCGGATAACAATTTCACACAGGA-3' (SEQ ID NO:58).

Mutation primer:
   5'-CCGACTTCCGCAAGGCCTTCAG GGACTGCTCTGCTGCGCGC-3' (SEQ ID NO:60)

Mutation primer contains the mutation (C1251G) at the center (in bold and underlined) and a portion of its flanking sequence. M13 reverse sequencing primer hybridizes to the pUC19 vector. Subcloned cDNA or genomic clone comprising the human β1-adrenergic receptor cDNA or genomic sequence is used as a template (described in Step 1). A 100 ul PCR reaction mixture is prepared using 10 ng of the template DNA, 200 uM 4dNTPs, 1 uM primers, 0.25U Taq DNA polymerase (PE), and standard Taq DNA polymerase buffer. Typical PCR cycling condition are as follows:

| 20-25 cycles: | 45 sec, 93 degrees |
| --- | --- |
|  | 2 min, 50 degrees |
|  | 2 min, 72 degrees |
| 1 cycle: | 10 min, 72 degrees |

After the final extension step of PCR, 5U Klenow Fragment is added and incubated for 15 min at 30 degrees. The PCR product is then digested with the restriction enzyme, EcoRI.

3. PCR amplification of the upstream region is then performed, using subcloned cDNA or genomic clone as a template (the product of Step 1). This PCR is done using the following two primers:

M13 forward sequencing primer:
5'-CGCCAGGGTTTTCCCAGTCACGAC-3' (SEQ ID NO:59).

Flanking primer:
5'-GCGCGCGCAGCAGAGCAGTC
<u>C</u>CTGGAAGGCCTTGCGGAA GTCGG-3' (SEQ ID NO:61).

Flanking primer is complimentary to the upstream flanking sequence and mutation locus of the C1251G mutation (in bold and underlined). M13 forward sequencing primer hybridizes to the pUC19 vector. PCR conditions and Klenow treatments follow the same procedures as provided in Step 2, above. The PCR product is then digested with the restriction enzyme, HindIII.

4. Prepare the pUC19 vector for cloning the cDNA or genomic clone comprising the polymorphic locus. Digest pUC19 plasmid DNA with EcoRI and HindIII. The resulting digested vector fragment may then be purified using techniques well known in the art, such as gel purification, for example.

5. Combine the products from Step 2 (PCR product containing mutation), Step 3 (PCR product containing the upstream region), and Step 4 (digested vector), and ligate them together using standard blunt-end ligation conditions (Sambrook, Fritsch et al. 1989).

6. Transform the resulting recombinant plasmid from Step 5 into E. coli competent cells using methods known in the art, such as, for example, the transformation methods described in Sambrook, Fritsch et al. 1989.

7. Analyze the amplified fragment portion of the plasmid DNA by DNA sequencing to confirm the point mutation, and absence of any other mutations introduced during PCR. The method of sequencing the insert DNA, including the primers utilized, are described herein or are otherwise known in the art.

Moreover, the skilled artisan would appreciate that the above method may be applied to engineering more than one polymorphic nucleic acid sequence of the present invention into the novel β1-adrenergic receptor gene of the present invention. Such an engineered gene could be created through successive rounds of site-directed mutagenesis, as described in Steps 1 thru 7 above, or consolidated into a single round of mutagenesis. For example, Step 2 above could be performed for each mutation, then the products of both mutation amplifications could be combined with the product of Step 3 and 4, and the procedure followed as described.

Example 22

Method of Identifying a Compound Predicted to Have a Decreased Risk of Inducing Edema in a Patient In Vitro As described herein, PPAR-agonists have been shown to significantly elevate human renin expression in patients (see FIGS. 11 and 12). This effect appears to be representative of PPAR-agonists as a class (Compounds A, B, C, D, E, and F), and is not specific to any single PPAR-agonist. As a consequence of the involvement of renin in regulating extracellular fluid volume and sodium balance, it is plausible to associate increased renin expression with an increased susceptibility to a patient in developing dose-dependent peripheral edema or related disorder upon the administration of a PPAR-agonist. Therefore, the present invention encompasses the use of assays designed to measure renin expression in response to PPAR-agonist exposure in cell lines in vitro to identify PPAR-agonist compounds that induce renin expression levels to a lesser extent relative to a control or reference compound, and thus identifying those compounds that have a lower likelihood of inducing dose-dependent peripheral edema or related disorder in a patient.

One example of such an assay is essentially described in Example 7 and/or 8. Generally, any method capable of measuring the expression of renin in a cell would constitute a suitable method for predicting a compounds likelihood of inducing dose-dependent peripheral edema or related disorder. The relative level of expression of renin amongst one or more PPAR-agonist compounds may be determined by comparing the level of renin expression observed in a control cell line not exposed to a PPAR-agonist compound and a cell line that has been exposed to a PPAR-agonist compound. The lower the level of renin expression induction observed for each compound relative to the control, the lower the likelihood that a patient will acquire edema with that compound.

Such an assay would also be useful for identifying levels of a given PPAR-agonist compound in vitro that has a lower likelihood of inducing dose-dependent peripheral edema or related disorder in a patient. For example, it would be possible to identify a dose of a PPAR-agonist compound using the above mentioned assay that induces lower levels of renin expression, but that still has an acceptable level of efficacy.

Example 23

Additional Method of Identifying a Compound Predicted to have a Decreased Risk of Inducing Edema in a Patient In Vitro As described herein, PPAR-agonists have been shown to significantly decrease human endothelin-1 expression in patients (see FIGS. 16 and 17). This effect appears to be representative of PPAR-agonists as a class (Compounds A, B, C, D, E, and F), and is not specific to any single PPAR-agonist. As a consequence of the involvement of endothelin-1 in regulating vascular tone maintenance, it is plausible to associate decreased endothelin-1 expression with a decreased susceptibility to a patient in developing dose-dependent peripheral edema or related disorder upon the administration of a PPAR-agonist. Therefore, the present invention encompasses the use of assays designed to measure endothelin-1 expression in response to PPAR-agonist exposure in cell lines in vitro to identify PPAR-agonist compounds that reduce endothelin-1 expression levels to a greater extent relative to a control or reference compound, and thus identifying those compounds that have a lower likelihood of inducing dose-dependent peripheral edema or related disorder in a patient.

One example of such an assay is essentially described in Example 15. Generally, any method capable of measuring the expression of endothelin-1 in a cell would constitute a suitable method for predicting a compounds likelihood of inducing dose-dependent peripheral edema or related disorder. The relative level of expression of endothelin-1 amongst one or more PPAR-agonist compounds may be determined by comparing the level of endothelin-1 expression observed in a control cell line not exposed to a PPAR-agonist compound and a cell line that has been exposed to a PPAR-agonist compound. The greater the level of endothelin-1 expression repression observed for each compound relative to the control, the lower the likelihood that a patient will acquire edema with that compound.

Such an assay would also be useful for identifying levels of a given PPAR-agonist compound in vitro that has a lower likelihood of inducing dose-dependent peripheral edema or related disorder in a patient. For example, it would be possible to identify a dose of a PPAR-agonist compound using the above mentioned assay that induces lower levels of endothelin-1 expression, but that still has an acceptable level of efficacy.

Example 24

Further In Vitro Methods of Assessing the Expression Profile of Human Renin and Endothelin-1 in Response to Treatment with PPAR-Agonists in CALU-6 Cells Using Quantitative RT-PCR Additional in vitro experiments were performed to confirm the association of renin and endothelin-1 expression to the level of edema induced in response to a PPAR-agonist. The experiments were performed essentially as described below. Briefly:

Gene Expression Studies with CALU-6 Cells

Cell line maintenance: CALU-6 cells and growth media were obtained from ATCC® (Manassas, Va.). CALU-6 cells were recovered and expanded in complete growth media (Minimal Essential Media+Earle's Balanced Salt Solution, 1% penicillin/streptomycin, 10% Fetal Bovine Serum). Antibiotics and FBS were purchased from Invitrogen.

Compounds: Compound A, Compound B, Compound D, Compound C, Compound G, Compound F, Compound H, Compound I, Compound J and Compound K were synthesized at Bristol-Myers Squibb Co. Compound E was purified by reverse phase high-performance liquid chromatography from commercial pharmaceutical preparations. Compounds A, B, F, and G are dual PPAR alpha and gamma agonists; while compounds C, D, and E are single PPAR gamma agonists. Fenofibrate and DMSO were purchased from Sigma. All PPAR agonists were reconstituted in DMSO such that their working concentrations were 500× the final concentration used in the induction studies. Compound K and fenofibrate were reconstituted in DMSO at 2000× the final concentration. The final concentration of DMSO in all treatments was 0.2%.

Quantitative RT-PCR experiments: CALU-6 cells were seeded on day 0 in at $5 \times 10^5$ cells/well, in 6-well tissue culture plates. Cells were incubated at 37° C. under 5% $CO_2$. The growth media was removed on day 1 and cells were re-fed with growth media containing 0.2% DMSO (vehicle control) or PPAR agonist. For experiments including Compound K or fenofibrate, CALU-6 cells were pre-incubated with 5 µM Compound K or 50 µM fenofibrate for 2 hr prior to the addition of PPAR agonist. After 24 hr incubation with PPAR agonist at 37° C. under 5% $CO_2$, cells were lysed and total RNA was prepared using the RNAeasy mini kit (Qiagen) following the manufacturer's recommendations. RNA quantities were determined spectrophotometrically using a SPECTRAMAX® 384 spectrophotometer (Molecular Devices). All cDNA synthesis and subsequent PCR experiments were performed following the Applied Biosystems TAQMAN® Assay protocol (Applied Biosystems). 1 µg of total RNA was used in the reverse transcription reaction. 40 ng of total RNA converted to cDNA was used as template for real-time PCR experiments. On-Demand TAQMAN® Assays for renin, endothelin-1 and GAPDH were obtained from Applied Biosystems. Sequence Detection System Software v.2.1 (Applied Biosystems) was used to analyze the quality of each amplification reaction as well as to calculate Ct values for each sample. All data were further analyzed using Microsoft Excel. Fold-change in gene expression upon treatment with compound was expressed as $2^{66 \ \Delta Ct}$, where $\Delta\Delta Ct = (Ct_{renin, \ endothelin-1} - Ct_{GAPDH})_{DMSO} - (Ct_{renin, \ endothelin-1} - Ct_{GAPDH})_{treatment}$. There was no significant change in GAPDH expression on treatment with any compound used in this study and TAQMAN® efficiencies were equivalent for all genes profiled (data not shown). Dose-titration experiments were further analyzed using GraphPad Prism Software (GraphPad Inc) to derive $EC_{50}$ values. K-means clustering was performed using SPSS® (v. 12, Chicago, Ill.).

As shown in FIGS. 21A-B, the additional experiments confirmed the ability of renin and endothelin-1 expression patterns to predict PPAR-agonist compounds most likely to have increased incidence of edema.

Example 25

Further In Vivo Methods of Assessing the Expression Profile of Human Renin and Endothelin-1 in Response to Treatment with PPAR-Agonists in Cynomolgus Monkeys In an effort to confirm the in vivo predictive capacity of the in vitro experiments used to identify PPAR-agonist compounds with a decreased likelihood of inducing edema, several experiments were performed in cynomolgus monkeys essentially as described. Briefly:

In Vivo Edema Evaluations

Male cynomolgus monkeys (3/dose/compound) were administered solutions of Com. I, Com. J, or Com. H in polyethylene glycol 400 (PEG 400) orally by gavage once daily for 28 days. Three monkeys administered PEG 400 alone served as controls. The monkeys were visually observed twice daily for evidence of swelling, particular in the scrotum, abdomen/thorax, and around the eyes. To quantitatively measure fluid retention, magnetic resonance imaging (MRI) was used to obtain a series of $T_2$- and diffusion-weighted images with and without fat suppression in the scrotal and periocular regions. MR images were obtained using a 4.7T/40 cm MRI system (Bruker Instruments, Billerica, Mass.) equipped with a 26 cm gradient coil and 20 cm volume resonator. MRI evaluations were performed on all monkeys pretest to obtain baseline data. During the study, 2 monkeys per dose group were imaged after 14 and 28 days of dosing. For all imaging experiments, the monkeys were kept under isoflurane anesthesia during the course of imaging. Body temperature was maintained at 38±0.5° C. by placement on an automated temperature controlled surface and monitored with a rectal probe. Anesthesia depth is monitored by measuring blood pressure and heart rate using a non-invasive tail/foot cuff method and a pulse oximeter, respectively. All procedures were performed by trained personnel according to methods approved by the Institutional Animal Care and Use Committee.

$T_2$-weighted and diffusion-weighted spin echo images with and without fat suppression of the scrotal and periocular regions were obtained with the following parameters.

For $T_2$-weighted spin echo imaging, a repetition time (TR) of 1800 msec, an echo time (TE) of 15 msec, a 256×256 matrix and 2 averages were used. For diffusion-weighted spin echo imaging, a repetition time (TR) of 1800 msec, $\Delta$=20 msec and $\delta$=6 msec, a diffusion gradient of 45 mT, a 130×130 matrix (zero filled to 256×256 matrix) and 2 averages were used.

Image analyses were performed using Bruker PARAVISION® software. Regions of hyperintensities in the scrotal and periocular regions were compared between fat suppressed and non-fat suppressed $T_2$- and diffusion-weighted images to delineate the regions of edema from the hyperintense fat regions. These regions of interest with the edema were then manually drawn, and the hyperintensity and the area of the edema were quantified using known saline calibration curve to obtain the volume of edema.

As shown in FIGS. 22A-F and FIGS. 23A-B, the ability of renin and endothelin-1 expression patterns to predict which PPAR-agonist compounds would most likely have an increased incidence of inducing edema., as predicted using the in vitro methods described herein, was confirmed in vivo Example 26

Alternative Methods of Genotyping Polymorphisms Encompassed by the Present Invention Preparation of Samples Polymorphisms are detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed. For example, if the target nucleic acid is a cytochrome P450, the liver is a suitable source.

Many of the methods described below require amplification of DNA from target samples. This can be accomplished by e.g., PCR. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, (1991); PCR (eds. McPherson et al., IRL Press, Oxford); and U.S. Pat. No. 4,683,202.

Other suitable amplification methods include the ligase chain reaction (LCR) (see Wu and Wallace, Genomics 4:560 (1989), Landegren et al., Science 241:1077 (1988), transcription amplification (Kwoh et al., Proc. Natl. Acad. Sci. USA 86, 1173 (1989), and self-sustained sequence replication (Guatelli et al., Proc. Nat. Acad. Sci. USA, 87:1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Additional methods of amplification are known in the art or are described elsewhere herein.

Detection of Polymorphisms in Target DNA

There are two distinct types of analysis of target DNA for detecting polymorphisms. The first type of analysis, sometimes referred to as de novo characterization, is carried out to identify polymorphic sites not previously characterized (i.e., to identify new polymorphisms). This analysis compares target sequences in different individuals to identify points of variation, i.e., polymorphic sites. By analyzing groups of individuals representing the greatest ethnic diversity among humans and greatest breed and species variety in plants and animals, patterns characteristic of the most common alleles/haplotypes of the locus can be identified, and the frequencies of such alleles/haplotypes in the population can be determined. Additional allelic frequencies can be determined for subpopulations characterized by criteria such as geography, race, or gender. The de novo identification of polymorphisms of the invention is described in the Examples section.

The second type of analysis determines which form(s) of a characterized (known) polymorphism are present in individuals under test. Additional methods of analysis are known in the art or are described elsewhere herein.

Allele-Specific Probes

The design and use of allele-specific probes for analyzing polymorphisms is described by e.g., Saiki et al., Nature 324, 163-166 (1986); Dattagupta, EP 235,726B1, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic locus aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

Tiling Arrays

The polymorphisms can also be identified by hybridization to nucleic acid arrays, some examples of which are described in WO 95/11995. The same arrays or different arrays can be used for analysis of characterized polymorphisms. WO 95/11995 also describes sub arrays that are optimized for detection of a variant form of a precharacterized polymorphism. Such a sub array contains probes designed to be complementary to a second reference sequence, which is an allelic variant of the first reference sequence. The second group of probes is designed by the same principles as described, except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to bases).

Allele-Specific Primers

An allele-specific primer hybridizes to a site on target DNA overlapping a polymorphism and only primes amplification of an allelic form to which the primer exhibits perfect complementarity. See Gibbs, Nucleic Acid Res. 17, 2427-2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic locus and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing elongation from the primer (see, e.g., WO 93/22456).

Direct-Sequencing

The direct analysis of the sequence of polymorphisms of the present invention can be accomplished using either the dideoxy chain termination method or the Maxam—Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., PCR Technology. Principles and Applications for DNA Amplification, (W.H. Freeman and Co, New York, 1992), Chapter 7.

Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., Proc. Nat. Acad. Sci. 86, 2766-2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

Single Base Extension

An alternative method for identifying and analyzing polymorphisms is based on single-base extension (SBE) of a fluorescently-labeled primer coupled with fluorescence resonance energy transfer (FRET) between the label of the added base and the label of the primer. Typically, the method, such as that described by Chen et al., (PNAS 94:10756-61 (1997), uses a locus-specific oligonucleotide primer labeled on the 5' terminus with 5-carboxyfluorescein (F AM). This labeled primer is designed so that the 3' end is immediately adjacent to the polymorphic locus of interest. The labeled primer is hybridized to the locus, and single base extension of the labeled primer is performed with fluorescently-labeled dideoxyribonucleotides (ddNTPs) in dye-terminator sequencing fashion. An increase in fluorescence of the added ddNTP in response to excitation at the wavelength of the labeled primer is used to infer the identity of the added nucleotide.

Example 27

Additional Methods of Genotyping the SNPs of the Present Invention

The skilled artisan would acknowledge that there are a number of methods that may be employed for genotyping a SNP of the present invention, aside from the preferred methods described herein. The present invention encompasses the following non-limiting types of genotype assays: PCR-free genotyping methods, Single-step homogeneous methods, Homogeneous detection with fluorescence polarization, Pyrosequencing, "Tag" based DNA chip system, Bead-based methods, fluorescent dye chemistry, Mass spectrometry based genotyping assays, TAQMAN® genotype assays, Invader genotype assays, and microfluidic genotype assays, among others.

Specifically encompassed by the present invention are the following, non-limiting genotyping methods: Landegren, U., Nilsson, M. & Kwok, P. Genome Res 8, 769-776 (1998); Kwok, P., Pharmacogenomics 1, 95-100 (2000); Gut, I., Hum Mutat 17, 475-492 (2001); Whitcombe, D., Newton, C. & Little, S., Curr Opin Biotechnol 9, 602-608 (1998); Tillib, S. & Mirzabekov, A., Curr Opin Biotechnol 12, 53-58 (2001); Winzeler, E. et al., Science 281, 1194-1197 (1998); Lyamichev, V. et al., Nat Biotechnol 17, 292-296 (1999); Hall, J. et al., Proc Natl Acad Sci USA 97, 8272-8277 (2000); Mein, C. et al., Genome Res 10, 333-343 (2000); Ohnishi, Y. et al., J Hum Genet. 46, 471-477 (2001); Nilsson, M. et al., Science 265, 2085-2088 (1994); Baner, J., Nilsson, M., Mendel-Hartvig, M. & Landegren, U., Nucleic Acids Res 26, 5073-5078 (1998); Baner, J. et al., Curr Opin Biotechnol 12, 11-15 (2001); Hatch, A., Sano, T., Misasi, J. & Smith, C., Genet Anal 15, 3540 (1999); Lizardi, P. et al., Nat Genet. 19, 225-232 (1998); Zhong, X., Lizardi, P., Huang, X., Bray-Ward, P. & Ward, D., Proc Natl Acad Sci USA 98, 3940-3945 (2001); Faruqi, F. et al. BMC Genomics 2, 4 (2001); Livak, K., Gnet Anal 14, 143-149 (1999); Marras, S., Kramer, F. & Tyagi, S., Genet Anal 14, 151-156 (1999); Ranade, K. et al., Genome Res 11, 1262-1268 (2001); Myakishev, M., Khripin, Y., Hu, S. & Hamer, D., Genome Res 11, 163-169 (2001); Beaudet, L., Bedard, J., Breton, B., Mercuri, R. & Budarf, M., Genome Res 11, 600-608 (2001); Chen, X., Levine, L. & PY, K., Genome Res 9, 492-498 (1999); Gibson, N. et al., Clin Chem 43, 1336-1341 (1997); Latif, S., Bauer-Sardina, I., Ranade, K., Livak, K. & PY, K., Genome Res 11, 436-440 (2001); Hsu, T., Law, S., Duan, S., Neri, B. & Kwok, P., Clin Chem 47, 1373-1377 (2001); Alderborn, A., Kristofferson, A. & Hammerling, U., Genome Res 10, 1249-1258 (2000); Ronaghi, M., Uhlen, M. & Nyren, P., Science 281, 363, 365 (1998); Ronaghi, M., Genome Res 11, 3-11 (2001); Pease, A. et al., Proc Natl Acad Sci USA 91, 5022-5026 (1994); Southern, E., Maskos, U. & Elder, J., Genomics 13, 1008-1017 (1993); Wang, D. et al., Science 280, 1077-1082 (1998); Brown, P. & Botstein, D., Nat Genet. 21, 33-37 (1999); Cargill, M. et al. Nat Genet. 22, 231-238 (1999); Dong, S. et al., Genome Res 11, 1418-1424 (2001); Halushka, M. et al., Nat Genet. 22, 239-247 (1999); Hacia, J., Nat Genet. 21, 42-47 (1999); Lipshutz, R., Fodor, S., Gingeras, T. & Lockhart, D., Nat Genet. 21, 20-24 (1999); Sapolsky, R. et al., Genet Anal 14, 187-192 (1999); Tsuchihashi, Z. & Brown, P., J Virol 68, 5863 (1994); Herschlag, D., J Biol Chem 270, 20871-20874 (1995); Head, S. et al., Nucleic Acids Res 25, 5065-5071 (1997); Nikiforov, T. et al., Nucleic Acids Res 22, 41674175 (1994); Syvanen, A. et al., Genomics 12, 590-595 (1992); Shumaker, J., Metspalu, A. & Caskey, C., Hum Mutat 7, 346-354 (1996); Lindroos, K., Liljedahl, U., Raitio, M. & Syvanen, A., Nucleic Acids Res 29, E69-9 (2001); Lindblad-Toh, K. et al., Nat Genet. 24, 381-386 (2000); Pastinen, T. et al., Genome Res 10, 1031-1042 (2000); Fan, J. et al., Genome Res 10, 853-860 (2000); Hirschhorn, J. et al., Proc Natl Acad Sci USA 97, 12164-12169 (2000); Bouchie, A., Nat Biotechnol 19, 704 (2001); Hensel, M. et al., Science 269, 400-403 (1995); Shoemaker, D., Lashkari, D., Morris, D., Mittmann, M. & Davis, R. Nat Genet. 14, 450-456 (1996); Gerry, N. et al., J Mol Biol 292, 251-262 (1999); Ladner, D. et al., Lab Invest 81, 1079-1086 (2001); Iannone, M. et al. Cytometry 39, 131-140 (2000); Fulton, R., McDade, R., Smith, P., Kienker, L. & Kettman, J. J., Clin Chem 43, 1749-1756 (1997); Armstrong, B., Stewart, M. & Mazumder, A., Cytometry 40, 102-108 (2000); Cai, H. et al., Genomics 69, 395 (2000); Chen, J. et al., Genome Res 10, 549-557 (2000); Ye, F. et al. Hum Mutat 17, 305-316 (2001); Michael, K., Taylor, L., Schultz, S. & Walt, D., Anal Chem 70, 1242-1248 (1998); Steemers, F., Ferguson, J. & Walt, D., Nat Biotechnol 18, 91-94 (2000); Chan, W. & Nie, S., Science 281, 2016-2018 (1998); Han, M., Gao, X., Su, J. & Nie, S., Nat Biotechnol 19, 631-635 (2001); Griffin, T. & Smith, L., Trends Biotechnol 18, 77-84 (2000); Jackson, P., Scholl, P. & Groopman, J., Mol Med Today 6, 271-276 (2000); Haff, L. & Smirnov, I., Genome Res 7, 378-388 (1997); Ross, P., Hall, L., Smirnov, I. & Haff, L., Nat Biotechnol 16, 1347-1351 (1998); Bray, M., Boerwinkle, E. & Doris, P. Hum Mutat 17, 296-304 (2001); Sauer, S. et al., Nucleic Acids Res 28, E13 (2000); Sauer, S. et al., Nucleic Acids Res 28, E100 (2000); Sun, X., Ding, H., Hung, K. & Guo, B., Nucleic Acids Res 28, E68 (2000); Tang, K. et al., Proc Natl Acad Sci USA 91, 10016-10020 (1999); Li, J. et al., Electrophoresis 20, 1258-1265 (1999); Little, D., Braun, A., O'Donnell, M. & Koster, H., Nat Med 3, 1413-1416 (1997); Little, D. et al. Anal Chem 69, 45404546 (1997); Griffin, T., Tang, W. & Smith, L., Nat Biotechnol 15, 1368-1372 (1997); Ross, P., Lee, K. & Belgrader, P., Anal Chem 69, 41974202 (1997); Jiang-Baucom, P., Girard, J., Butler, J. & Belgrader, P., Anal Chem 69, 489-44898 (1997); Griffin, T., Hall, J., Prudent, J. & Smith, L., Proc Natl Acad Sci USA 96, 6301-6306 (1999); Kokoris, M. et al., Mol Diagn 5, 329-340 (2000); Jurinke, C., van den Boom, D., Cantor, C. & Koster, H. (2001); and/or Taranenko, N. et al., Genet Anal 13, 87-94 (1996).

The following additional genotyping methods are also encompassed by the present invention: the methods described and/or claimed in U.S. Pat. No. 6,458,540; and the methods described and/or claimed in U.S. Pat. No. 6,440,707.

Example 28

Bacterial Expression of a Polypeptide

A polynucleotide encoding a polypeptide of the present invention is amplified using PCR oligonucleotide primers corresponding to the 5' and 3' ends of the DNA sequence, as outlined in the Examples above or otherwise known in the art, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3-4 hours at 4 degree C. The cell debris is removed by centrifugation, and the supernatant containing the polypeptide is loaded onto a nickel-nitrilo-triacetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 29

Purification of a Polypeptide from an Inclusion Body

The following alternative method can be used to purify a polypeptide expressed in *E. coli* when it is present in the form of inclusion bodies. Unless otherwise specified, all of the following steps are conducted at 4-10 degree C.

Upon completion of the production phase of the *E. coli* fermentation, the cell culture is cooled to 4-10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 24 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., POROS® HS-50, Perceptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (POROS® HQ-50, Perceptive Biosystems) and weak anion (POROS® CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 30

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

A polynucleotide encoding a polypeptide of the present invention is amplified using PCR oligonucleotide primers corresponding to the 5' and 3' ends of the DNA sequence, as outlined in the Examples above or otherwise known in the art, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described herein. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures" Texas Agricultural Experimental Station Bulletin No. 1555 (1987).

The amplified fragment is isolated from a 1% agarose gel using a commercially available kit ("GENECLEAN®" BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("GENECLEAN®" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BACULOGOLD® baculovirus DNA", Pharmingen, San Diego, Calif.), using the lipofection method described by Felgner et al., Proc. Natl. Acad. Sci. USA 84:7413-7417 (1987). One ug of BACULOGOLD® virus DNA and 5 ug of the plasmid are mixed in a sterile well of a microtiter plate containing 50 ul of serum-free Grace's medium (Life Technologies Inc., Gaithersburg, Md.). Afterwards, 10 ul LIPOFECTIN® plus 90 ul Grace's medium are added, mixed and incubated for 15 minutes at room temperature. Then the transfection mixture is added drop-wise to Sf9 insect cells (ATCC® CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 31

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC® 37152), pSV2dhfr (ATCC® 37146), pBC12MI (ATCC® 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. . . . 253:1357-1370 (1978); Hamlin, J. L. and Ma, C., Biochem. et Biophys. Acta, 1097:107-143 (1990); Page, M. J. and Sydenham, M. A., Biotechnology 9:64-68 (1991).) Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("GENECLEAN®" BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five μg of an expression plasmid is cotransformed with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100-200 uM. Expression of the desired gene product is analyzed, for instance, by SDS-PAGE and Western blot or by reversed phase HPLC analysis.

Example 32

Production of an Antibody from a Polypeptide

The antibodies of the present invention can be prepared by a variety of methods. (See, Current Protocols, Chapter 2.) As one example of such methods, cells expressing a polypeptide of the present invention are administered to an animal to induce the production of sera containing polyclonal antibodies. In a preferred method, a preparation of the protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Kbhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563-681 (1981).) In general, such procedures involve immunizing an animal (preferably a mouse) with polypeptide or, more preferably, with a polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC®. After fusion, the resulting hybridoma cells are selectively maintained in HAT medium, and then cloned by limiting dilution as described by Wands et al. (Gastroenterology 80:225-232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F (ab')2 and other fragments of the antibodies of the present invention may be used according to the methods disclosed herein. Such fragments are typically produced by proteolytic cleavage, using enzymes such as papain (to produce Fab fragments) or pepsin (to produce F (ab')2 fragments). Alternatively, protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494B1; Neuberger et al., WO 8601533; Robinson et al., WO 8702671; Boulianne et al., Nature 312:643 (1984); Neuberger et al., Nature 314:268 (1985).)

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the Sequence Listing submitted herewith and the corresponding computer readable form are both incorporated herein by reference in their entireties.

While this invention has been particularly shown and described with references to preferred embodiments thereof, it will be understood by those skilled in the art that various changes in form and details may be made therein without departing from the scope of the invention encompassed by the appended claims.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the Sequence Listing submitted herewith and the corresponding computer readable form are both incorporated herein by reference in their entireties.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying a PPARgamma-agonist compound having a decreased likelihood of inducing dose-dependent peripheral edema in a patient comprising the step of:
   (a) incubating mammalian cells that endogenously express renin with a test compound; and
   (b) measuring the level of induced expression of renin mRNA in response to said test compound;
wherein a decreased level of induced renin mRNA expression by said test compound relative to a reference compound is indicative of a decreased risk of said test compound inducing dose-dependent peripheral edema in a patient.

2. The method according to claim 1, wherein said cells are human CALU-6 cells.

3. The method according to claim 1, further comprising the step of measuring the level of induced expression of endothelin-1 mRNA in response to said test compound wherein said cells endogenously express endothelin-1; and
   wherein an increased level of induced endothelin-1 expression by the test compound relative to a reference compound is indicative of a decreased risk of said compound inducing dose-dependent peripheral edema in a patient.

4. The method according to claim 3, wherein said cells are human CALU-6 cells.

5. The method according to claim 1, wherein the measurement of human renin mRNA expression is performed using the polymerase chain reaction.

6. The method according to claim 1, wherein the measurement of human renin mRNA expression is performed using the quantitative polymerase chain reaction.

7. The method according to claim 1, wherein the measurement of human renin mRNA expression is performed using the reverse-transcribed polymerase chain reaction.

8. The method according to claim 1, wherein the measurement of human renin mRNA expression is performed using microarrays.

9. The method according to claim 1, wherein the measurement of human renin mRNA expression is performed using mass spectrometry.

10. A method according to claim 1, wherein said renin mRNA encodes the renin polypeptide with one amino acid substitution.

11. A method according to claim 3, wherein said endothelin-1 mRNA encodes the endothelin-1 polypeptide with one amino acid substitution.

12. A method of identifying whether a PPARgamma-agonist compound has an increased likelihood of inducing dose-dependent peripheral edema in a patient comprising the step of:
  (a) incubating mammalian cells that endogenously express renin with a test compound; and
  (b) measuring the level of induced expression of renin mRNA in response to said test compound;
wherein an increased level of induced renin mRNA expression by said test compound relative to a reference compound is indicative of an increased risk of said test compound inducing dose-dependent peripheral edema in a patient, whereas a decreased level of induced renin mRNA expression by said test compound relative to a reference compound is indicative of a decreased risk of said test compound inducing dose-dependent peripheral edema in a patient.

13. The method according to claim 12, wherein said cells are human CALU-6 cells.

14. The method according to claim 12, further comprising the step of measuring the level of induced expression of endothelin-1 mRNA in response to said test compound, wherein said cells endogenously express endothelin-1;
  wherein a decreased level of induced endothelin-1 expression by the test compound relative to a reference compound is indicative of an increased risk of said compound inducing dose-dependent peripheral edema in a patient, whereas an increased level of induced endothelin-1 expression by the test compound relative to a reference compound is indicative of a decreased risk of said compound inducing dose-dependent peripheral edema in a patient.

15. The method according to claim 14, wherein said cells are human CALU-6 cells.

16. A kit for identifying a PPAR gamma-agonist compound having a decreased likelihood of inducing dose-dependent peripheral edema in a patient comprising:
  (a) a test compound;
  (b) a means for incubating mammalian cells that endogenously express renin with said test compound;
  (c) a means for measuring the level of induced expression of renin mRNA in response to said test compound;
wherein a decreased level of induced renin mRNA expression by said test compound relative to a reference compound is indicative of a decreased risk of said test compound inducing dose-dependent peripheral edema in a patient.

17. The kit according to claim 16, further comprising a means for measuring the level of induced expression of endothelin-1 mRNA in response to said test compound, wherein said cells endogenously express endothelin-1; and
  wherein an increased level of induced endothelin-1 expression by the test compound relative to a reference compound is indicative of a decreased risk of said compound inducing dose-dependent peripheral edema in a patient.

* * * * *

UNITED STATES PATENT AND TRADEMARK OFFICE
CERTIFICATE OF CORRECTION

PATENT NO. : 7,482,124 B2 Page 1 of 1
APPLICATION NO. : 11/483290
DATED : January 27, 2009
INVENTOR(S) : Koustubh Ranade, Terrye Aigeldinger Delmonte and William J. Geese It is certified that error appears in the above-identified patent and that said Letters Patent is hereby corrected as shown below:

Column 25 - Line 11
  After the word "using" add "quantitative RT-PCR (A) and"

Column 25 - Line 12
  After the word "analysis" add "B"

Column 133 - Line 37
  After "FIG. 11" add "and FIG. 12A"

Column 134 - Line 8
  After "FIG. 12" add "B"

Signed and Sealed this

Twenty-second Day of June, 2010

David J. Kappos
*Director of the United States Patent and Trademark Office*

SEQUENCE LISTING

<160> NUMBER OF SEQ ID NOS: 61

<210> SEQ ID NO 1
<211> LENGTH: 14503
<212> TYPE: DNA
<213> ORGANISM: Homo sapiens

<400> SEQUENCE: 1

```
ggtctttgta aaataataat tattcatttc acaaaagtga taattaaaag actttaatag      60
caatacagaa agttacatga atataaagac ttaacctttc taaagctcag ttttcctaag     120
taatcaaaaa cctgataaag ataacaagaa tgaggaatta tcttgagaaa atgtaaaatc     180
tttcctttta tttttgaga cagggtctca ctctgtcatc caggctaaag tgcagtggca      240
caatcatagc tcactacagc cttgaactcc tggactcaag tgatcctccc gcctcagcct     300
ccccagtagc taagactaca ggcacgcacc accacaccca gctaattttt ttcagagatg     360
gggtcttgct atattgccct ggctggtctt gaacgagctt caagtgagcg tgagcctcct     420
acctcatcct cccaaagcac taggattaca ggcatgagcc actgtttccc agcctaaaat     480
aattgtttct taggccagct accaaaaacg caaagaaaaa ctttctgtag tgtgattgct     540
tcttcttatg ggaagcccat ttagataacc tgtaagtcaa acctgatgaa aacaatactt     600
gaatgtaatc agacacagaa agactgttca aggctatgag tagctgagtc caagctcgta     660
tcacttgcca cacaacagcc aataagtcta gagacaaggt attgtggcaa ggaaagctac     720
cttattcaga gaaccagaaa accaagaaga tggtggacca gcatcataaa gaaccatctg     780
aagtcagcat gaacgttagg ctcttcttta tgttaaggga aggggaagaa gaagggggatt    840 gggatcaaga ggtgactgat gaccacagac acctgggtgc cagcaagggt ctgaggacgt     900
tgtaaaactt cttttttcta ggtcaggtca caatgttcct atacatcttt aacataacat     960
tgttatttgt ctgtatattt ccttatctcc ttgggggtta gtttggggaa aggaactgtt    1020 accattttttt ttaaagttga actgcaagct aaactcctat aattagctgg tctatgtaca    1080
gagctaagca gaagcttta gcctaaagga taataccct gggggtcaga ggcaaaatgg      1140
agtcagtcat gctaagtctc cctccactct ctttcttttt tgagatggaa tttcactctt    1200
attgcccagg ccggagtgca gtgcatgat ctcagctcac tgcaacctcc gcctcctggg     1260
ttcaagcaat tctcttgcct cagcctcctg agtagctgag attacaggtg tccatcacca    1320
cacccagcta attttgtag tttagtggag atggggtttc accattgttg gtcaggctgg     1380
tctggaactc ctgacctcag gtgatctacc caccttggcc tcccaaagtg ctgggacagg    1440
tgtgagccac catgcctggc ccctctactc ttataattaa accagctgtt gcttttcctg    1500
ccaagaaacc agtcatgaag attcacccat gttctagatg ggaaaactgg gctgtagcct    1560
```

```
gggagaggcc agtcagggac aaagccaaag ttaatataga gaatggagct tccagggtat    1620
aggggttggg tctgggctag ggagctggaa acctaggttt tacgcttgtc ccagttttga    1680
tgttagccct gagcagtgct gtttctcatc agcctctgcc tgctccaggg gtcacagggc    1740
caagccagat agagggctgc tagcgtcact ggacacaaga ttgctttccc acagctgtcc    1800
ttcctccagc ccctctgctc cccatccgga aacctgggta cccttcaccc acctagctct    1860
gtcccgcagt gagatttatt gctgactgcc ctgccatcta ccccagggta ataaatcagg    1920
gcagagcaga attgcaatca ccccatgcat ggagtgtata aaaggggaag ggctaaggga    1980
gccacagaac ctcagtggat ctcagagaga gccccagact gagggaagca tggatggatg    2040
gagaaggatg cctcgctggg gactgctgct gctgctctgg ggctcctgta cctttggtct    2100
cccgacagac accaccacct ttaaacggta attggtaact caggcagaga aggggtggga    2160
ggggtgcagg gttcccacct tcccaacacc ctggcttttc cacatgcggt gtcattcagt    2220
ccttacgatc agctggacag ggaagtatgg acctgttcag agaggtcaag tgacttgccc    2280
aataaatgac actagtagtc aggtctagaa gctgtgactt ttgcttcctg cccagagcac    2340
catgctaact aagcactgta gagaactcag aagtattagg acatgcccct tgcacttgag    2400
gagctcacag cctgaatatt aagaagggca tgggtggttg ggcgcggtgg ctcctgcctg    2460
taatcccagc actttgggag gctgagacgg atcacttgag gtcaggagtt tgagaccagc    2520
ctggccaaca tggggaaacc ccatctctac taaaaataca aaaattagcc gggcatggtg    2580
gcaggcactt gtaatcccca gctactcggg aagctgaggc aggagaatcg tttgagcccg    2640
gaaggtggag attgctgagc caagatcgtg ccactgcact ccagcctgag tgacagaaca    2700
agactccatc tcaaaaaaaa aaaagacggg ggtcggggca tgggtacagt taactgtacc    2760
agggaagcag cttgatatcg tggttaaatg caaggcttat agagttagat tgccttcatt    2820
taaattttgc ttcactagca gaacaaacta ggtctggaat catgggcaag ttatttaacc    2880
tctccaagtc tcagtttatc attttaaaca ggtatgataa taacagtacc tacttgatgg    2940
ggctgctttg gggattttag gagataaggc atagaaagct gggcacgttg taagagccca    3000
gctactgtta gtactacagg atagattctt acaaatatca aaagcaaggt ttggccggga    3060
gcagtggctc acgcctataa tcccaacact ttgggaggcc gaggggggca gatcacccga    3120
ggtcaggagt tcaagaccag cctgaccaac atggagaaac cctgtctcta ctaaaaatac    3180 aaaaattagcc gggcgtggtg gcacatgcct gtaattccag ctacttggga ggctgaggca    3240
ggagaatcgc ttgaacctgg gaggctgagg ttgcagtgag ccgacatagc gccattgcac    3300
tccagcctgg tcaacaagag caaaactcag tctaaaaaaa aaaagaaag aaaaaacaa     3360 ggctttaggt agcccacaat tagaaggaga aaaccttagc atcccctagg tgccaggcct    3420
tgtgggaaca agtgattcat taagactgta gaaggaagct gggcacgcgg ctcatgcttg    3480
taattccagc actttgagag gctgaggtgg gcagatcgct tgagctcacg agttcaagac    3540
cagcctaggc aacatggtga aaccttgtct gtacaaatac aaaaattagc taggtgtggt    3600
ggtgcaaatc tgtagtccca gctactcggg aggctgaggt gggagcatca cttcagcctg    3660
ggaggtggag gctgcagtga gcagagactg acccactgtg ctctagcctg ggtgatagag    3720
ccagacctta tgtaaaaaaa aaaaaaaaaa aaaaaagac tgaagaaggg gaagagacag    3780
catttgagaa aaggcctcac agagaaaggg gttttcaatc tggggacagc agatatgacc    3840
agcagtcctg aaggtaggga ggcacacttt aataatggta atagttgcta agcctataaa    3900
atgcttaggg tgtcacagga tcttttcaca tgtctcatct caagtcatgc ccccaacaac    3960
```

```
tcagcattcc cactttgcag atgaggacac tgaggctcag ggaggtgata tgtaagaggc    4020
taagcctcaa cacacactgg gccttttgct tccgaaactg ctttcccttg ctctgaggct    4080
ctcggagagt aattgctggg ttgtgagcac tgggtaagag gatgggtgct tcaaagcagc    4140
tgcactccag gataaaggta gaggaaagta aaaacatctt cccctgctgt tatccaaaag    4200
agaaaaagaa tggaattggg caaggggtgg aggggaatc cagcttttga aacagtatta    4260
taggaatttt gctacccgct atgtgcagag catcatgcga ggcacttggg acagctgaat    4320
gaatgagctc cattctcaag gtgaacatgt acatatacac acctacaatt tacatttatt    4380
gagcagtggt cgcatggttt catctgcaca gtgactctga ggtaggtact accattaggc    4440
ccattgttag agagggggtta atggagactt agaagaggcc cagagaggtt aggtagcttt    4500
ctcagaatca cataagtggt aaggggattc aggcatgccc cctgcaacca ctgtcttcac    4560
caccgtacgg caccagttcc acaagctgta cagtgtgggc tgtgagaccc aaggaaaaac    4620
agagctgagg cccacgggaa ggtgaggccg gtgtgggctg gaggccttgg ggtaagcttc    4680
ctggaggtgg gggtacatgt tgggccttgg aggactaaag aactgggggg aaaaggaagg    4740
gaagaaggaa aggattttct gaaaaggaaa tggcaagaag taaaggtcca aagcataggc    4800
tgttgtgagt aaacagtggg aaatgcaacc tctttgggc caaacctctg accctccacg    4860
ttcccagctg tgaagtggga gtaataaaat catccacctt atgagagcaa ataaaataat    4920
gattgtgaaa atattttggt aacagtaacc tgtgatagga agataacaaa tcatttctgt    4980
tacaatacca tgctgatagg cataaaagtt gcattcatgt tcatgggcaa aatgggggta    5040
agtagaatgc atgggacgca agaaggatgt aggaaggaaa gggtagtgtg agtataggag    5100
gactagccac tgagaagaaa gtagaagaaa gagggaatct ttgtgtgtat gggaaagtct    5160
attgcagagt caacttgggc ttccatcctg ggaccttccc gtgaacagct agagacatct    5220
tcctctgggc tttggcagcc tttatgtcgg gacccagggg accctatatg ggaaataggg    5280
ccagacacat gctctgaatc cctgcttcaa catttctgag tcacctttgt ccctgtgagc    5340
cttcattttt ctcatctata aaatggatga cagctagctt gttggtgtga tttcagtagc    5400
ggctcagtag agtcagtttc ctaggtctct ttaattctgc ctctcaaagg tgatgggaaa    5460
acatctagac aagaagccaa gggaccggga cacatctctc caaggacgag gtgcatggcg    5520
ctctgaagat gctggcatct ctctaggccc aacccagctc aggggggtcca ctccaccaca    5580 gccctggctg ggtgcctgtc ccctggtatc ctggagacct tgcagctgct gtgggcatct    5640
gctgccacct agcggcctcc catggcactg tctccccgcc agccctagt tttgacaggg    5700 gcactccctg gcattaatct cttcagaggg aatgtctgtg cctgtttcct gtctgtcctc    5760
ccgccaggtg gagttcctta aaggcagtca tgatcattat ctttctagct ccagtgtcca    5820
gcacagtgag gcacaaagta gttgttcagc aggtgattac ggaataaatg aatgaacgga    5880
ccaataaaca aatagccttg tctaatcaaa attaggcaac agaaggaagt cacttcaggg    5940
ttatttaatc cccgggcagc tgactcctct aaattgactc ttgacaagaa gtaactctta    6000
taaatgctcc agaggccctc agcgacagag gtgatttcca ggtggctggg ctaacgttaa    6060
aggtggttgt actaaaagca gggggtttggc ctcagggact ccaccactgt ggtggaggta    6120
cagcactttt ctattttgc ttcctccacc ctgggcagg atcttcctca agagaatgcc    6180
ctcaatccga gaaagcctga aggaacgagg tgtggacatg gccaggcttg gtcccgagtg    6240
gagccaaccc atgaagaggc tgacacttgg caacaccacc tcctccgtga tcctcaccaa    6300
ctacatggac gtgagtgctt ggctcagccc ctcgctccct ccctgtctcc tttcccctcat    6360
```

```
ggacctaggg ctttctttgc tgcaagactc acccttttcca agctgtgttt gacgaaggcg   6420
ctgagtagca cgtgagcacc ctagaaaatt cccattttcc agctggaaag cctgagcaca   6480
gaagacagga aggcatccag gggccattca ggggcagggt taggtttgga actcagccca   6540
ggcctcaagc caggtgtcac aggtgggtgg aaggggtgt gtgactcagg tgggggtttc   6600
tgtgacctgg cccagcacaa cctgatggct tcctgcccca gaggatcctc aagagtcaag   6660
tttgcttcct gcttcattct caatgttttg attttgccct cttgtcttac tgagactccc   6720
actttctggg atgccatggg gagatgctaa gcctcctacc agttcctgca ggaaaatgga   6780
aaccccgaga ggctatagga cctcgcctgg gccaagtctc acaccgagag ccaagagtga   6840
agccaggcaa gaccccaaga cccaaggtcc cctgagcccc tccagccctc tcttttttacc   6900
cccacagacc cagtactatg gcgagattgg catcggcacc ccaccccaga ccttcaaagt   6960
cgtctttgac actggttcgt ccaatgtttg ggtgccctcc tccaagtgca gccgtctcta   7020
cactgcctgt ggtgagacct aagacccaca gtgcctctcc tccatccccc tgccctactg   7080
tgcatgagca atcctgccca cacccagct cccatccctc ttgccaccaa gggagtggct   7140
tcctctctgc ctctgtgccc actgacatgt aggggagagg ggaagatgtc tcccgttttt   7200
ctgatacagc caccaaggtt aaaaacaaaa aaggtccaa gaaccctga gcacccagaa   7260
ggccacttcc cagtcttcct gagattgaga caggactgaa ttctcaaacc catcccaggc   7320
actcggaact cttccatccc tagtcttaat caacaacctc ttactaggca cttactctgt   7380
gcctggcatc ttctctggtg ttatcagtgt tagtgattac tttaaattcc ttcatttagg   7440
acaaaattct cgatgtatgg gcacattagg agagcccaag aaacccagtc cttgattgat   7500
gaagcacata ttccaagccc cctgacccta gggccactca tccctgcacc taagctaacc   7560
agccataccc acaatgcacc ctgcctctga gtcccctgt ctgggccact cttggacaaa   7620
cctgagcctc tgtcccctg ccagtgtatc acaagctctt cgatgcttcg gattcctcca   7680
gctacaagca caatggaaca gaactcaccc tccgctattc aacagggaca gtcagtggct   7740
ttctcagcca ggacatcatc accgtaagtt gggccgccct aggtcatctg ccccggaccc   7800
cttctgtccc caggcctctc ctgaccctcc agggcccaca cctgcgggga ggtacactgc   7860
agcccacttg gagcctgggg agctgaggaa caccctactc tgccacatct ggctgttgct   7920
gcaaagcagc agtacctatg ggggagcaag cctgggctac gggctcaccg ttgggtggtt   7980
tgtggatgtt tttgcatcta acttgcatgt agggcttgtc ctgagccccg tggctgcagt   8040
caagtaactc gtccaagttc accagctctg actgggctac accctagact gaaatccagg   8100
gtcagagtca ggctgagttt tagggtcagg cataggtttt aaggtcacag ttgaggttga   8160
ctctgggact caggtcaagg cctgcttttc ttttccatgt ggcccatgtc tgaccgtttc   8220
ctcatcctgg agtttctcag gccctgctcc atcagagtta ggggaggggc acacgtggca   8280
cctgagagga aatcagggtg attcctgcct cccttccttt ttctgtgaac tcagatataa   8340
aggagggaga agggcaagct tgtctgtgct aaagaaaccc ttcgcccatg ataagggtgg   8400
gggccaagac ccagtcctgc caggcacgaa agtctggcca ctggggaggg gaggagctct   8460
tggcagcttt tcttttgctg cttggcagga ccaccctctc agcctctgct ctccgatccc   8520
tggtcaactc tagctctctc tgggctccgc agcagagatg tgtattggca cagagtgtgt   8580
gcgtgcaggg ttgaggaaat actcttaccc cgatttctgt accctggagc atgtgtgccc   8640
ctgggatccc tagtgtggaa gcccagacca gactccaacc aaggagtggg cagtgggctt   8700
ggtctcctct ggtccttcct cccacaggtg ggtggaatca cggtgacaca gatgtttgga   8760
```

```
gaggtcacgg agatgcccgc cttacccttc atgctggccg agtttgatgg ggttgtgggc    8820
atgggcttca ttgaacaggc cattggcagg gtcacccta tcttcgacaa catcatctcc     8880
caagggtgc taaaagagga cgtcttctct ttctactaca acaggtgggg actgggactc     8940
caagggctga ggtgggggga caggagggga gaagagatgg ggagtggaag gagagtctgg    9000
gccagaattg taaagtgttt gtaattaggt gacagccaat caatatctag agctgtacta    9060
gccaatatgg aaggcactat tgaaatttaa attaattaaa tacagttaag catcaattaa    9120
gcattcaact ggtggctctt agttgtacta gccacacgtc aaatgcctgg cagccacggt    9180
ggctagtaac tacagtctta tgacagtgca gatagagaat attcccagca tgacaggaca    9240
ttctaataga cagcgccact ctggagcaag aggagatgca aggtggggc gatggtaaat     9300
aagggattac tgtgacctgt agccctgcct gttaggggcca tggctcctcc cacacagaga   9360
cagccaactt cagtcatcca ttagatcctt cattcgtttg tttgctcact catcagttca    9420
gtaaatgcta tgtgccaagc actgtggtag gctctggggg tgcagcagtg aacacagtga    9480
acaaggcaga atctgtactc ccctacccac atagagctta caggctaaca gggaagacaa    9540
gacatattcc aacataaga gtgtcacagg caggcagcaa gtgtggtgct gaaaaccatg     9600
gatgcttttc aattctaggc tgagcttata tgcagctcag ccagccttgg ggaagctctt    9660
gagcagggtt gggctctact ccaaactgct gggcttagaa agatggcatg agttggagac    9720
aagagagctg gaggcaaaag gggctgggtg cagtggctca tgcctgtaat cccagcactt    9780
tgggaggcca aggcgagagg atcgcatgag cccaggagtt aaggcttcag tgagcagtga    9840
ttgtgccact gcactccagc taaggcaaca gagtgagatc cagtctcaaa aaaaaaaaa    9900
aaaaaaaaa agtcacaagg gtaagaacat gaggccagtg gcaaaagaa tagaggagag      9960
gatcagagtt cagagaaatc tcacagtaaa atggagagga gtctccggtt tggtgataga   10020
aagtgaggcc ttgagaaaag gccaattggc ggctctgcat tcaggggtgg tctttagaag   10080
aactgtttta gaggaagtgg gggcaaggcc agatggcaag aagttaagag gtggacgacg   10140
tgggtgtcag gaagtggagg tcatgagatg taggctgccc tgggacattc aacagggaag   10200
ggaatggggg gtggcgtggg gggtgagatc cagaagcaga agaggaaggg tgggtgtttt   10260
taaatgctag aggatgctcg agtgatgcct gtaggtggag gaagaagcca atggaaagaa   10320
agagattaaa aatgtggaaa gaagaggagc taaatggggg cactggagtt tggaggcctt   10380
gaaagagatg aggttccagc agacaggaag aagccaggtt ttgcagagga gagggctggc   10440
ctcttctttt atcttgggat gggaaggagg gaacatccag agagatactg aagtgttgag   10500
agacaggcag gagggaattt gtgctagcat atacacatac attccgaatt tataaaaaca   10560
caagtagttt gcagttgcac aaaataacat atgcacacct acacacccat gcacacatgt   10620
gcatgtgtga attctagtat gaattctgga aaaacacatc acacacacag gcatgccctg   10680
gagactaggc ctacagtagt ccctgagcca agtgcagtga ggaggaaagg aaggtgaggg   10740
gaatcagctc cagacggggc accaggagcc tggctccagt cccccacttg ttcactcatg   10800
gactgggtaa cttcaggcaa gtgacttcgc ctcttggtga ctccattgcc tgaagggcaa   10860
agagagtaca taacacccac cctgccaaac agcagggctg atgaggctgg catgaaatga   10920
agcttccttt ctgctgtctc tctttctctg cagagattcc gagtaaggag acaaaaccc    10980
cacatggctg tgaccttcca gtactcccg agcacctgac ctagaattac acgccacc     11040
ggcccaaaac tcacatcagc aagcccagcc tccgctagat gccgaagttc tctgtctctc   11100
cttcctgctc tctccatgcc acctgcccac cccatacccca atagcctccc cagggtcccc  11160
```

```
tcccatgcac ctgctcaatc agcagcaacc caagagtgag gggtgtccat ttgtgtcttg   11220
ttcacatcca ctcactgtcc ttgtacctgc tccttttctg tgacctctct ggggatgctt   11280
tttgggggaa cagctggact accctggaac aacctctggt tggtcttggg gaggggaaga   11340
aaggcagaga agcagtatgt tctgcatgct tcccaacgac agctccgagc ctggctgtct   11400
gtcccacatt cctctgctct agagccctct gtcctcccct gcaccttgt gcaaccttcc    11460 ccaattgcct gagttgctgg gtcctggagg ttatgggttt ccaagagctt ctgatctttc   11520
ctttaggaat tcccaatcgc tgggaggaca gattgtgctg ggaggcagcg accccagca    11580 ttacgaaggg aatttccact atatcaacct catcaagact ggtgtctggc agattcaaat   11640 gaagggtca gaaatcctca accctccccg ggctccaaaa aatgctgccg tcactggggt    11700
tggggagggt ggggaaggac tgcattacca tcctgccctc tttccaaatg cagccacttc   11760
ttaagcacag ccaccatttg ctctctgcct gctctgtcca ggctgggaa cagagaaggg    11820 aggggcctgg ggagaagtgg tggagggtga cagtaccttc cctcctctac tcactgcctc   11880
aacaggccac cagcgtggcc tccacccacc cacccacact caggaaggac atgcagcctg   11940
gaggtgcccc atcagccttc tgtctgtctg tctgtctgtc tgtctgactg tggcctcccc   12000
cagggtgtct gtggggtcat ccaccttgct ctgtgaagac ggctgcctgg cattggtaga   12060
caccggtgca tcctacatct caggttctac cagctcccata gagaagctca tggaggcctt   12120
gggagccaag aagaggctgt ttgatgtaag aagccaaaga gggaaggtgc tgtgggtggg   12180
gggagcgcca cctggtatcg gctcacaaat cccccaggca aatgaggcca tctcaggcct   12240
tcgcttgttc acctcacact ctccacacat gtggctggtc acccatgggg cggggcactg   12300
tccccagccc tctccagcag agagaccagg ccaccagcgc aggactcctt gtctgctgag   12360
acgtcttcca tactcaagaa ggctctcttt gccccccacc ccagtatgtc gtgaagtgta   12420
acgagggccc tacactcccc gacatctctt tccacctggg aggcaaagaa tacacgctca   12480
ccagcgcgga ctatgtattt caggtgaggt tcgagtcggc ccctcggtg gcagggagaa    12540 aggctggaca gagaccctca aagagtgaca gattacaatg cacaggtcat gttagaactg   12600
tagttctcaa acttggctgt gcatgtcacc tggagagctt tgaaaaatcc tggtacctgg   12660
gccacatccc atacctatta aatcagaacc tctagaagtg gcacctgggg ttcagtttcc   12720
ccaggtgatt ccaatgtgtg gccatgtttg ggcatcacta tgcctgttcc ctcatctcca   12780
ttttctcatc aaatactccc aagaatccta tgctcctata ttcttaccct cttttcataa   12840
tcaataggct tagagaagtt gaataacttg tctaggatca gaagctaagg caaactgtaa   12900
gctcctgaag gaagcacggt gcctgatgca ttgtttgcct gggatctagc acaggggcta   12960
aacatagaag tggtgcagtc cacgatgggg caaaatggcc atgatgtgag ggaggcccag   13020
tgtggctagg ggagagatgg gggcgagagg gggaatgttg ctgaagacag ttgctggggg   13080
tcaggcaagg tgaaaggaga atgctcatgt gctgggtatg gagaaactct cccccttcct   13140
gccaggaatc ctacagtagt aaaaagctgt gcacactggc catccacgcc atggatatcc   13200
cgccacccac tggacccacc tgggccctgg ggccacctt catccgaaag ttctacacag    13260
agtttgatcg gcgtaacaac cgcattggct tcgccttggc ccgctgaggc cctctgccac   13320
ccaggcaggc cctgccttca gccctggccc agagctggaa cactctctga tgcccctc     13380 tgcctgggct tatgccctca gatggagaca ttggatgtgg agctcctgct ggatgcgtgc   13440 cctgaccccct gcaccagccc ttccctgctt tgaggacaaa gagaataaag acttcatgtt   13500
cacagcctgt tgcatctggg ttcactaggg tttagaacag agggaggggc tgcgtgatca   13560
```

-continued

```
tgtgtggaca ggaatgtgac acagacaagc tacacattcg cctagcgcac aggttcttgc    13620
gtgcagggat gatgccatcc atctgccatc aacgggactc aggtggagct gtttacacaa    13680
cctcaggtgg gaagtctgaa aagagccgga accaagctcc ctctagtccc tcagggacca    13740
aggctaatgc tgtggcagta gactgtgggt cagaaagttc tcccagctca cagaagccag    13800
ctctgagttc agactctgct ctgctgagct agtcagccct gtctcttgtc cctgcaaaac    13860
tcccctcagc tgtccttatc cactgcagat gccccgccc tgcccatgt agccatttac     13920 acaggcattc taaggcacta ccacctaaaa tcatagaaca ccagagatcc aggcaatact    13980
tccactttac aggtggggaa actgaggccc agagaatgga aggccttgcc caagattact    14040
cggtcaagaa tcaagtagtg aagaatactg aaagatagtg aagaatcaag actggaaccc    14100
agcccgtctg acttgggtcc tggggtttc caccttatca taagcagttg gtaccgtcat     14160
aagtacagtg cttcacgcac gctggtacag ggccacgtgc acaagcacac aggtgcacac    14220
acacactgct atcctccatc ccatccacct gggactcgtc aggctgaagt ctcttctccc    14280
actctcactc cttgggctgt cttcagggca catgtaactt ggggaatgag aaattagcat    14340
ccacctggag ccactgaagc catccctctt caccatagtt gctcacctct cttttgacag    14400
aaagtcgtga ggcactgaat ggcccaacca ggccctcagt acctctggga gccatctgca    14460
agagtccctg tgtagcgcca agagccggag cctgggcttc agg                       14503
```

<210> SEQ ID NO 2
<211> LENGTH: 14503
<212> TYPE: DNA
<213> ORGANISM: Homo sapiens

<400> SEQUENCE: 2

```
ggtctttgta aaataataat tattcatttc acaaaagtga taattaaaag actttaatag       60
caatacagaa agttacatga atataaagac ttaacctttc taaagctcag ttttcctaag     120
taatcaaaaa cctgataaag ataacaagaa tgaggaatta tcttgagaaa atgtaaaatc     180 tttccttta ttttttgaga cagggtctca ctctgtcatc caggctaaag tgcagtggca     240
caatcatagc tcactacagc cttgaactcc tggactcaag tgatcctccc gcctcagcct     300
ccccagtagc taagactaca ggcacgcacc accacaccca gctaattttt ttcagagatg     360
gggtcttgct atattgccct ggctggtctt gaacgagctt caagtgagcg tgagcctcct     420
acctcatcct cccaaagcac taggattaca ggcatgagcc actgtttccc agcctaaaat     480
aattgtttct taggccagct accaaaaacg caaagaaaaa ctttctgtag tgtgattgct     540
tcttcttatg ggaagcccat ttagataacc tgtaagtcaa acctgatgaa acaatactt     600 gaatgtaatc agacacagaa agactgttca aggctatgag tagctgagtc caagctcgta     660
tcacttgcca cacaacagcc aataagtcta gagacaaggt attgtggcaa ggaaagctac     720
cttattcaga gaaccagaaa accaagaaga tggtggacca gcatcataaa gaaccatctg     780
aagtcagcat gaacgttagg ctcttcttta tgttaaggga aggggaagaa gaagggggatt     840 gggatcaaga ggtgactgat gaccacagac acctgggtgc cagcaagggt ctgaggacgt     900
tgtaaaactt ctttttctcta ggtcaggtca caatgttcct atacatcttt aacataacat    960
tgttatttgt ctgtatattt ccttatctcc ttggggggtta gttgggggaa aggaactgtt    1020
accatttttt ttaaagttga actgcaagct aaactcctat aattagctgg tctatgtaca    1080
gagctaagca gaagctttta gcctaaagga taatacccct gggggtcaga ggcaaaatgg    1140
agtcagtcat gctaagtctc cctccactct cttttcttttt tgagatggaa tttcactctt    1200
```

-continued

```
attgcccagg ccggagtgca gtggcatgat ctcagctcac tgcaacctcc gcctcctggg   1260
ttcaagcaat tctcttgcct cagcctcctg agtagctgag attacaggtg tccatcacca   1320
cacccagcta attttttgtag tttagtggag atggggtttc accattgttg gtcaggctgg   1380
tctggaactc ctgacctcag gtgatctacc caccttggcc tcccaaagtg ctgggacagg   1440
tgtgagccac catgcctggc ccctctactc ttataattaa accagctgtt gcttttcctg   1500
ccaagaaacc agtcatgaag attcacccat gttctagatg ggaaaactgg gctgtagcct   1560
gggagaggcc agtcagggac aaagccaaag ttaatataga aatggagct tccagggtat    1620
aggggttggg tctgggctag ggagctggaa acctaggttt tacgcttgtc ccagttttga   1680
tgttagccct gagcagtgct gtttctcatc agcctctgcc tgctccaggg gtcacagggc   1740
caagccagat agagggctgc tagcgtcact ggacacaaga ttgctttccc acagctgtcc   1800
ttcctccagc ccctctgctc ccatccggaa aacctgggta cccttcaccc acctagctct   1860
gtcccgcagt gagatttatt gctgactgcc ctgccatcta ccccagggta ataaatcagg   1920
gcagagcaga attgcaatca ccccatgcat ggagtgtata aaaggggaag gctaaggga    1980
gccacagaac ctcagtggat ctcagagaga gccccagact gagggaagca tggatggatg   2040
gagaaggatg cctcgctggg gactgctgct gctgctctgg ggctcctgta cctttggtct   2100
cccgacagac accaccacct ttaaacggta attggtaact caggcagaga aggggtggga   2160
ggggtgcagg gttcccacct tcccaacacc ctggcttttc cacatgcggt gtcattcagt   2220
ccttacgatc agctggacag ggaagtatgg acctgttcag agaggtcaag tgacttgccc   2280
aataaatgac actagtagtc aggtctagaa gctgtgactt ttgcttcctg cccagagcac   2340
catgctaact aagcactgta gagaactcag aagtattagg acatgcccct tgcacttgag   2400
gagctcacag cctgaatatt aagaagggca tgggtggttg ggcgcggtgg ctcctgcctg   2460
taatcccagc actttgggag gctgagacgg atcacttgag gtcaggagtt tgagaccagc   2520
ctggccaaca tggggaaacc ccatctctac taaaaataca aaaattagcc gggcatggtg   2580
gcaggcactt gtaatcccca gctactcggg aagctgaggc aggagaatcg tttgagcccg   2640
gaaggtggag attgctgagc caagatcgtg ccactgcact ccagcctgag tgacagaaca   2700
agactccatc tcaaaaaaaa aaaagacggg ggtcggggca tgggtacagt taactgtacc   2760
agggaagcag cttgatatcg tggttaaatg caaggcttat agagttagat tgccttcatt   2820
taaattttgc ttcactagca gaacaaacta ggtctggaat catgggcaag ttatttaacc   2880
tctccaagtc tcagtttatc attttaaaca ggtatgataa taacagtacc tacttgatgg   2940
ggctgctttg gggattttag gagataaggc atagaaagct gggcacgttg taagagccca   3000
gctactgtta gtactacagg atagattctt acaaatatca aaagcaaggt ttggccggga   3060
gcagtggctc acgcctataa tcccaacact ttgggaggcc gagggggca gatcacccga    3120
ggtcaggagt tcaagaccag cctgaccaac atggagaaac cctgtctcta ctaaaaatac   3180
aaaattagcc gggcgtggtg gcacatgcct gtaattccag ctacttggga ggctgaggca   3240
ggagaatcgc ttgaacctgg gaggctgagg ttgcagtgag ccgacatagc gccattgcac   3300
tccagcctgg tcaacaagag caaaactcag tctaaaaaaa aaaagaaag aaaaaaacaa    3360
ggctttaggt agcccacaat tagaaggaga aaaccttagc atcccctagg tgccaggcct   3420
tgtgggaaca agtgattcat taagactgta gaaggaagct gggcacgcgg ctcatgcttg   3480
taattccagc actttgagag gctgaggtgg cagatcgctt tgagctcacg agttcaagac   3540
cagcctaggc aacatggtga aaccttgtct gtacaaatac aaaaattagc taggtgtggt   3600
```

```
ggtgcaaatc tgtagtccca gctactcggg aggctgaggt gggagcatca cttcagcctg    3660
ggaggtggag gctgcagtga gcagagactg acccactgtg ctctagcctg ggtgatagag    3720
ccagacctta tgtaaaaaaa aaaaaaaaaa aaaaaagac tgaagaaggg gaagagacag     3780
catttgagaa aaggcctcac agagaaaggg gttttcaatc tggggacagc agatatgacc    3840
agcagtcctg aaggtaggga ggcacacttt aataatggta atagttgcta agcctataaa    3900
atgcttaggg tgtcacagga tcttttcaca tgtctcatct caagtcatgc ccccaacaac    3960
tcagcattcc cactttgcag atgaggacac tgaggctcag ggaggtgata tgtaagaggc    4020
taagcctcaa cacacactgg gccttttgct tccgaaactg ctttcccttg ctctgaggct    4080
ctcggagagt aattgctggg ttgtgagcac tgggtaagag gatgggtgct tcaaagcagc    4140
tgcactccag gataaaggta gaggaaagta aaaacatctt cccctgctgt tatccaaaag    4200
agaaaaagaa tggaattggg caaggggtgg aggggaatc cagcttttga aacagtatta     4260
taggaatttt gctacccgct atgtgcagag catcatgcga ggcacttggg acagctgaat    4320
gaatgagctc cattctcaag gtgaacatgt acatatacac acctacaatt tacatttatt    4380
gagcagtggt cgcatggttt catctgcaca gtgactctga ggtaggtact accattaggc    4440
ccattgttag agaggggtta atggagactt agaagaggcc cagagaggtt aggtagcttt    4500
ctcagaatca cataagtggt aaggggattc aggcatgccc cctgcaacca ctgtcttcac    4560
caccgtacgg caccagttcc acaagctgta cagtgtgggc tgtgagaccc aaggaaaaac    4620
agagctgagg cccacgggaa ggtgaggccg gtgtgggctg gaggcttgg ggtaagcttc     4680 ctggaggtgg gggtacatgt tgggccttgg aggactaaag aactgggggg aaaaggaagg    4740
gaagaaggaa aggattttct gaaaaggaaa tggcaagaag taaaggtcca agcataggc     4800 tgttgtgagt aaacagtggg aaatgcaacc tctttgggc caaacctctg accctccacg     4860
ttcccagctg tgaagtggga gtaataaaat catccacctt atgagagcaa ataaaataat    4920
gattgtgaaa atattttggt aacagtaacc tgtgatagga agataacaaa tcatttctgt    4980
tacaatacca tgctgatagg cataaaagtt gcattcatgt tcatgggcaa aatgggggta    5040
agtagaatgc atgggacgca agaaggatgt aggaaggaaa gggtagtgtg agtataggag    5100
gactagccac tgagaagaaa gtagaagaaa gagggaatct ttgtgtgtat gggaaagtct    5160
attgcagagt caacttgggc ttccatcctg ggaccttccc gtgaacagct agagacatct    5220
tcctctgggc tttggcagcc tttatgtcgg gacccagggg acccctatatg ggaaatagg    5280 ccagacacat gctctgaatc cctgcttcaa catttctgag tcacctttgt ccctgtgagc    5340
cttcattttt ctcatctata aaatggatga cagctagctt gttggtgtga tttcagtagc    5400
ggctcagtag agtcagtttc ctaggtctct ttaattctgc ctctcaaagg tgatgggaaa    5460
acatctagac aagaagccaa gggaccggga cacatctctc caaggacgag gtgcatggcg    5520
ctctgaagat gctggcatct ctctaggccc aacccagctc aggggtcca ctccaccaca     5580 gccctggctg ggtgcctgtc ccctggtatc ctggagacct tgcagctgct gtgggcatct    5640
gctgccacct agcggcctcc catggcactg tctccccgcc agccctagt tttgacaggg     5700 gcactccctg gcattaatct cttcagaggg aatgtctgtg cctgtttcct gtctgtcctc    5760
ccgccaggtg gagttcctta aaggcagtca tgatcattat ctttctagct ccagtgtcca    5820
gcacagtgag gcacaaagta gttgttcagc aggtgattac ggaataaatg aatgaacgga    5880
ccaataaaca aatagccttg tctaatcaaa attaggcaac agaaggaagt cacttcaggg    5940
ttatttaatc cccgggcagc tgactcctct aaattgactc ttgacaagaa gtaactctta    6000
```

-continued

```
taaatgctcc agaggccctc agcgacagag gtgatttcca ggtggctggg ctaacgttaa     6060
aggtggttgt actaaaagca gggtttggc ctcagggact ccaccactgt ggtggaggta      6120
cagcactttt ctatttttgc ttcctccacc ctgggccagg atcttcctca agagaatgcc    6180
ctcaatccga gaaagcctga aggaacgagg tgtggacatg gccaggcttg gtcccgagtg    6240
gagccaaccc atgaagaggc tgacacttgg caacaccacc tcctccgtga tcctcaccaa    6300
ctacatggac gtgagtgctt ggctcagccc ctcgctccct ccctgtctcc tttccctcat    6360
ggacctaggg cttttcttgc tgcaagactc acccttccaa agctgtgttt gacgaaggcg    6420
ctgagtagca cgtgagcacc ctagaaaatt cccattttcc agctggaaag cctgagcaca    6480
gaagacagga aggcatccag gggccattca ggggcagggt taggtttgga actcagccca    6540
ggcctcaagc caggtgtcac aggtgggtgg aagggggtgt gtgactcagg tgggggtttc    6600
tgtgacctgg cccagcacaa cctgatggct tcctgcccca gaggatcctc aagagtcaag    6660
tttgcttcct gcttcattct caatgttttg attttgccct cttgtcttac tgagactccc    6720
actttctggg atgccatggg gagatgctaa gcctcctacc agttcctgca ggaaaatgga    6780
aacccccgaga ggctatagga cctcgcctgg gccaagtctc acaccgagag ccaagagtga    6840
agccaggcaa gaccccaaga cccaaggtcc cctgagcccc tccagccctc tcttttacc      6900
cccacagacc cagtactatg gcgagattgg catcggcacc ccaccccaga ccttcaaagt    6960
cgtctttgac actggttcgt ccaatgtttg ggtgccctcc tccaagtgca gccgtctcta   7020
cactgcctgt ggtgagacct aagacccaca gtgcctctcc tccatccccc tgccctactg    7080
tgcatgagca atcctgccca cacccagct cccatccctc ttgccaccaa gggagtggct     7140
tcctctctgc ctctgtgccc actgacatgt aggggagagg ggaagatgtc tcccgttttt    7200
ctgatacagc caccaaggtt aaaaacaaaa aaggtccaa gaaccctga gcacccagaa      7260
ggccacttcc cagtcttcct gagattgaga caggactgaa ttctcaaacc catcccaggc    7320
actcggaact cttccatccc tagtcttaat caacaacctc ttactaggca cttactctgt    7380
gcctggcatc ttctctggtg ttatcagtgt tagtgattac tttaaattcc ttcatttagg    7440
acaaaattct cgatgtatgg gcacattagg agagcccaag aaacccagtc cttgattgat    7500
gaagcacata ttccaagccc cctgacccta gggccactca tccctgcacc taagctaacc    7560
agccataccc acaatgcacc ctgcctctga gtcccctgt ctgggccact cttggacaaa     7620
cctgagcctc tgtcccctg ccagtgtatc acaagctctt cgatgcttcg gattcctcca    7680
gctacaagca caatggaaca gaactcaccc tccgctattc aacagggaca gtcagtggct    7740
ttctcagcca ggacatcatc accgtaagtt gggccgccct aggtcatctg ccccggaccc    7800
cttctgtccc caggcctctc ctgaccctcc agggcccaca cctgcgggga ggtacactgc    7860
agcccacttg gagcctgggg agctgaggaa caccctactc tgccacatct ggctgttgct    7920
gcaaagcagc agtacctatg ggggagcaag cctgggctac gggctcaccg ttgggtggtt    7980
tgtggatgtt tttgcatcta acttgcatgt agggcttgtc ctgagccccg tggctgcagt    8040
caagtaactc gtccaagttc accagctctg actgggctac accctagact gaaatccagg    8100
gtcagagtca ggctgagttt tagggtcagg cataggtttt aaggtcacag ttgaggttga    8160
ctctgggact caggtcaagg cctgcttttc ttttccatgt ggcccatgtc tgaccgtttc    8220
ctcatcctgg agtttctcag gcccctgctcc atcagagtta ggggaggggc acacgtggca   8280
cctgagagga aatcagggtg attcctgcct cccttccttt ttctgtgaac tcagatataa    8340
aggagggaga agggcaagct tgtctgtgct aaagaaaccc ttcgcccatg ataagggtgg    8400
```

```
gggccaagac ccagtcctgc caggcacgaa agtctggcca ctggggaggg gaggagctct   8460
tggcagcttt tcttttgctg cttggcagga ccaccctctc agcctctgct ctccgatccc   8520
tggtcaactc tagctctctc tgggctccgc agcagagatg tgtattggca cagagtgtgt   8580
gcgtgcaggg ttgaggaaat actcttaccc cgatttctgt accctggagc atgtgtgccc   8640
ctgggatccc tagtgtggaa gcccagacca gactccaacc aaggagtggg cagtgggctt   8700
ggtctcctct ggtccttcct cccacaggtg ggtggaatca cggtgacaca gatgtttgga   8760
gaggtcacgg agatgcccgc cttacccttc atgctggccg agtttgatgg ggttgtgggc   8820
atgggcttca ttgaacaggc cattggcagg gtcacccccta tcttcgacaa catcatctcc   8880
caaggggtgc taaaagagga cgtcttctct ttctactaca acaggtgggg actgggactc   8940
caagggctga ggtgggggga caggagggga aagagatgg ggagtggaag gagagtctgg   9000
gccagaattg taaagtgttt gtaattaggt gacagccaat caatatctag agctgtacta   9060
gccaatatgg aaggcactat tgaaatttaa attaattaaa tacagttaag catcaattaa   9120
gcattcaact ggtggctctt agttgtacta gccacacgtc aaatgcctgg cagccacggt   9180
ggctagtaac tacagtctta tgacagtgca gatagagaat attcccagca tgacaggaca   9240
ttctaataga cagcgccact ctggagcaag aggagatgca aggtgggggc gatggtaaat   9300
aagggattac tgtgacctgt agccctgcct gttaggccca tggctcctcc cacacagaga   9360
cagccaactt cagtcatcca ttagatcctt cattcgtttg tttgctcact catcagttca   9420
gtaaatgcta tgtgccaagc actgtggtag gctctggggg tgcagcagtg aacacagtga   9480
acaaggcaga atctgtactc ccctacccac atagagctta caggctaaca gggaagacaa   9540
gacatattcc aacataaaga gtgtcacagg caggcagcaa gtgtggtgct gaaaaccatg   9600
gatgcttttc aattctaggc tgagcttata tgcagctcag ccagccttgg ggaagctctt   9660
gagcagggtt gggctctact ccaaactgct gggcttagaa agatggcatg agttggagac   9720
aagagagctg gaggcaaaag gggctgggtg cagtggctca tgcctgtaat cccagcactt   9780
tgggaggcca aggcgagagg atcgcatgag cccaggagtt aaggcttcag tgagcagtga   9840
ttgtgccact gcactccagc taaggcaaca gagtgagatc cagtctcaaa aaaaaaaaaa   9900
aaaaaaaaaa agtcacaagg gtaagaacat gaggccagtg gcaaaaagaa tagaggagag   9960
gatcagagtt cagagaaatc tcacagtaaa atggagagga gtctccggtt tggtgataga  10020
aagtgaggcc ttgagaaaag gccaattggc ggctctgcat tcaggggtgg tctttagaag  10080
aactgtttta gaggaagtgg gggcaaggcc agatggcaag aagttaagag gtggacgacg  10140
tgggtgtcag gaagtggagg tcatgagatg taggctgccc tgggacattc aacagggaag  10200
ggaatggggg gtggcgtggg gggtgagatc cagaagcaga agaggaaggg tggtgtgtttt 10260
taaatgctag aggatgctcg agtgatgcct gtaggtggag gaagaagcca atggaaagaa  10320
agagattaaa aatgtggaaa gaagaggagc taaatggggg cactggagtt tggaggcctt  10380
gaaagagatg aggttccagc agacaggaag aagccaggtt ttgcagagga gagggctggc  10440
ctcttctttt atcttgggat gggaaggagg gaacatccag agagatactg aagtgttgag  10500
agacaggcag gagggaattt gtgctagcat atacacatac attccgaatt tataaaaaca  10560
caagtagttt gcagttgcac aaaataacat atgcacacct acacacccat gcacacatgt  10620
gcatgtgtga attctagtat gaattctgga aaaacacatc acacacacag gcatgccctg  10680
gagactaggc ctacagtagt ccctgagcca agtgcagtga ggaggaaagg aaggtgaggg  10740
gaatcagctc cagacggggc accaggagcc tggctccagt cccccacttg ttcactcatg  10800
```

```
gactgggtaa cttcaggcaa gtgacttcgc ctcttggtga ctccattgcc tgaagggcaa    10860
agagagtaca taacacccac cctgccaaac agcagggctg atgaggctgg catgaaatga    10920
agcttccttt ctgctgtctc tctttctctg cagagattcc gagtaaggag acaaaacccc    10980
cacatggctg tgaccttcca gtactccccg agcacctgac ctagaattac acacgccacc    11040
ggcccaaaac tcacatcagc aagcccagcc tccgctagat gccgaagttc tctgtctctc    11100
cttcctgctc tctccatgcc acctgccac cccatacccca atagcctccc cagggtcccc    11160
tcccatgcac ctgctcaatc agcagcaacc caagagtgag gggtgtccat ttgtgtcttg    11220
ttcacatcca ctcactgtcc ttgtacctgc tccttttctg tgacctctct ggggatgctt    11280
tttgggggaa cagctggact accctggaac aacctctggt tggtcttggg gaggggaaga    11340
aaggcagaga agcagtatgt tctgcatgct tcccaacgac agctccgagc ctggctgtct    11400
gtcccacatt cctctgctct agagccctct gtcctcccct gcaccttgt gcaaccttcc    11460 ccaattgcct gagttgctgg gtcctggagg ttatgggttt ccaagagctt ctgatctttc    11520
ctttaggaat tcccaatcgc tgggaggaca gattgtgctg ggaggcagcg accccagca    11580 ttacgaaggg aatttccact atatcaacct catcaagact ggtgtctggc agattcaaat    11640
gaaggggtca gaaatcctca accctccccg ggctccaaaa aatgctgccg tcactggggt    11700
tggggagggt ggggaaggac tgcattacca tcctgccctc tttccaaatg cagccacttc    11760
ttaagcacag ccaccatttg ctctctgcct gctctgtcca ggctggggaa cagagaaggg    11820
aggggcctgg ggagaagtgg tggagggtga cagtaccttc cctcctctac tcactgcctc    11880
aacaggccac cagcgtggcc tccacccacc cacccacact caggaaggac atgcagcctg    11940
gaggtgcccc atcagccttc tgtctgtctg tctgtctgtc tgtctgactg tggcctcccc    12000
cagggtgtct gtggggtcat ccaccttgct ctgtgaagac ggctgcctgg cattggtaga    12060
caccggtgca tcctacatct caggttctac cagctccata gagaagctca tggaggcctt    12120
gggagccaag aagaggctgt ttgatgtaag aagccaaaga gggaaggtgc tgtgggtggg    12180
gggagcgcca cctggtatcg gctcacaaat cccccaggca aatgaggcca tctcaggcct    12240
tcgcttgttc acctcacact ctccacacat gtggctggtc acccatgggg cggggcactg    12300
tccccagccc tctccagcag agagaccagg ccaccagcgc aggactcctt gtctgctgag    12360
acgtcttcca tactcaagaa ggctctcttt gcccccacc ccagtatgtc gtgaagtgta    12420
acgagggccc tacactcccc gacatctctt tccacctggg aggcaaagaa tacacgctca    12480
ccagcgcgga ctatgtattt caggtgaggt tcgagtcggc cccctcggtg gcagggagaa    12540
aggctggaca gagaccctca aagagtgaca gattacaatg cacagatcat gttagaactg    12600
tagttctcaa acttggctgt gcatgtcacc tggagagctt tgaaaaatcc tggtacctgg    12660
gccacatccc ataccctatta aatcagaacc tctagaagtg gcacctgggg ttcagtttcc    12720
ccaggtgatt ccaatgtgtg gccatgtttg ggcatcacta tgcctgttcc ctcatctcca    12780 tttttctcatc aaatactccc aagaatccta tgctcctata ttcttaccct cttttcataa    12840
tcaataggct tagagaagtt gaataacttg tctaggatca gaagctaagg caaactgtaa    12900
gctcctgaag gaagcacggt gcctgatgca ttgtttgcct gggatctagc acaggggcta    12960 aacatagag tggtgcagtc cacgatgggg caaaatggcc atgatgtgag ggaggcccag    13020
tgtggctagg ggagagatgg gggcgagagg gggaatgttg ctgaagacag ttgctggggg    13080
tcaggcaagg tgaaaggaga atgctcatgt gctgggtatg gagaaactct cccccttcct    13140
gccaggaatc ctacagtagt aaaaagctgt gcacactggc catccacgcc atggatatcc    13200
```

```
cgccacccac tggacccacc tgggccctgg gggccacctt catccgaaag ttctacacag    13260
agtttgatcg gcgtaacaac cgcattggct tcgccttggc ccgctgaggc cctctgccac    13320
ccaggcaggc cctgccttca gccctggccc agagctggaa cactctctga gatgcccctc    13380
tgcctgggct tatgccctca gatggagaca ttggatgtgg agctcctgct ggatgcgtgc    13440
cctgacccct gcaccagccc ttccctgctt tgaggacaaa gagaataaag acttcatgtt    13500
cacagcctgt tgcatctggg ttcactaggg tttagaacag agggagggc tgcgtgatca    13560 tgtgtggaca ggaatgtgac acagacaagc tacacattcg cctagcgcac aggttcttgc    13620
gtgcagggat gatgccatcc atctgccatc aacgggactc aggtggagct gtttacacaa    13680
cctcaggtgg gaagtctgaa aagagccgga accaagctcc ctctagtccc tcagggacca    13740
aggctaatgc tgtggcagta gactgtgggt cagaaagttc tcccagctca cagaagccag    13800
ctctgagttc agactctgct ctgctgagct agtcagccct gtctcttgtc cctgcaaaac    13860
tcccctcagc tgtccttatc cactgcagat gccccgccc tgcccatgt agccatttac    13920 acaggcattc taaggcacta ccacctaaaa tcatagaaca ccagagatcc aggcaatact    13980
tccactttac aggtggggaa actgaggccc agagaatgga aggccttgcc caagattact    14040
cggtcaagaa tcaagtagtg aagaatactg aaagatagtg aagaatcaag actggaaccc    14100
agcccgtctg acttgggtcc tgggggtttc caccttatca taagcagttg gtaccgtcat    14160
aagtacagtg cttcacgcac gctggtacag ggccacgtgc acaagcacac aggtgcacac    14220
acacactgct atcctccatc ccatccacct gggactcgtc aggctgaagt ctcttctccc    14280
actctcactc cttgggctgt cttcagggca catgtaactt ggggaatgag aaattagcat    14340
ccacctggag ccactgaagc catccctctt caccatagtt gctcacctct cttttgacag    14400
aaagtcgtga ggcactgaat ggcccaacca ggccctcagt acctctggga gccatctgca    14460
agagtccctg tgtagcgcca agagccggag cctgggcttc agg                      14503
```

<210> SEQ ID NO 3
<211> LENGTH: 14503
<212> TYPE: DNA
<213> ORGANISM: Homo sapiens

<400> SEQUENCE: 3

```
ggtctttgta aataataat tattcatttc acaaaagtga taattaaaag actttaatag      60
caatacagaa agttacatga atataaagac ttaacctttc taaagctcag ttttcctaag    120
taatcaaaaa cctgataaag ataacaagaa tgaggaatta tcttgagaaa atgtaaaatc    180
tttcctttta ttttttgaga cagggtctca ctctgtcatc caggctaaag tgcagtggca    240
caatcatagc tcactacagc cttgaactcc tggactcaag tgatcctccc gcctcagcct    300
ccccagtagc taagactaca ggcacgcacc accacaccca gctaatttt ttcagagatg    360 gggtcttgct atattgccct ggctggtctt gaacgagctt caagtgagcg tgagcctcct    420
acctcatcct cccaaagcac taggattaca ggcatgagcc actgtttccc agcctaaaat    480
aattgtttct taggccagct accaaaaacg caaagaaaaa cttctgtag tgtgattgct    540 tcttcttatg ggaagcccat ttagataacc tgtaagtcaa acctgatgaa acaatactt    600 gaatgtaatc agacacagaa agactgttca aggctatgag tagctgagtc caagctcgta    660
tcacttgcca cacaacagcc aataagtcta gagacaaggt attgtggcaa ggaaagctac    720
cttattcaga gaaccagaaa accaagaaga tggtggacca gcatcataaa gaaccatctg    780
aagtcagcat gaacgttagg ctcttcttta tgttaaggga aggggaagaa gaaggggatt    840
```

```
gggatcaaga ggtgactgat gaccacagac acctgggtgc cagcaagggt ctgaggacgt      900
tgtaaaactt cttttttcta ggtcaggtca caatgttcct atacatcttt aacataacat      960
tgttatttgt ctgtatattt ccttatctcc ttgggggtta gtttgggaa aggaactgtt      1020 accatttttt ttaaagttga actgcaagct aaactcctat aattagctgg tctatgtaca     1080
gagctaagca gaagcttta gcctaaagga taatacccct gggggtcaga ggcaaaatgg      1140
agtcagtcat gctaagtctc cctccactct ctttcttttt tgagatggaa tttcactctt     1200
attgcccagg ccggagtgca gtggcatgat ctcagctcac tgcaacctcc gcctcctggg     1260
ttcaagcaat tctcttgcct cagcctcctg agtagctgag attacaggtg tccatcacca     1320
cacccagcta attttgtag tttagtggag atggggtttc accattgttg gtcaggctgg      1380
tctggaactc ctgacctcag gtgatctacc caccttggcc tcccaaagtg ctgggacagg     1440
tgtgagccac catgcctggc ccctctactc ttataattaa accagctgtt gctttcctg      1500 ccaagaaacc agtcatgaag attcacccat gttctagatg gaaaactgg gctgtagcct     1560 gggagaggcc agtcagggac aaagccaaag ttaatataga gaatggagct tccagggtat     1620
aggggttggg tctgggctag ggagctggaa acctaggttt tacgcttgtc ccagttttga     1680
tgttagccct gagcagtgct gtttctcatc agcctctgcc tgctccaggg gtcacagggc     1740
caagccagat agagggctgc tagcgtcact ggacacaaga ttgctttccc acagctgtcc     1800
ttcctccagc ccctctgctc cccatccgga aacctgggta cccttcaccc acctagctct     1860
gtcccgcagt gagatttatt gctgactgcc ctgccatcta ccccagggta ataaatcagg     1920
gcagagcaga attgcaatca ccccatgcat ggagtgtata aaaggggaag ggctaaggga     1980
gccacagaac ctcagtggat ctcagagaga gccccagact gagggaagca tggatggatg     2040
gagaaggatg cctcgctggg gactgctgct gctgctctgg ggctcctgta cctttggtct     2100
cccgacagac accaccacct ttaaacggta attggtaact caggcagaga aggggtggga     2160
ggggtgcagg gttcccacct tcccaacacc ctggcttttc cacatgcggt gtcattcagt     2220
ccttacgatc agctggacag ggaagtatgg acctgttcag agaggtcaag tgacttgccc     2280
aataaatgac actagtagtc aggtctagaa gctgtgactt ttgcttcctg cccagagcac     2340
catgctaact aagcactgta gagaactcag aagtattagg acatgcccct tgcacttgag     2400
gagctcacag cctgaatatt aagaagggca tgggtggttg ggcgcggtgg ctcctgcctg     2460
taatcccagc actttgggag gctgagacgg atcacttgag gtcaggagtt tgagaccagc     2520
ctggccaaca tggggaaacc ccatctctac taaaaataca aaaattagcc gggcatggtg     2580
gcaggcactt gtaatcccca gctactcggg aagctgaggc aggagaatcg tttgagcccg     2640
gaaggtggag attgctgagc caagatcgtg ccactgcact ccagcctgag tgacagaaca     2700
agactccatc tcaaaaaaaa aaaagacggg ggtcggggca tgggtacagt taactgtacc     2760
agggaagcag cttgatatcg tggttaaatg caaggcttat agagttagat tgccttcatt     2820
taaattttgc ttcactagca gaacaaacta ggtctggaat catgggcaag ttatttaacc     2880
tctccaagtc tcagtttatc attttaaaca ggtatgataa taacagtacc tacttgatgg     2940
ggctgctttg gggattttag gagataaggc atagaaagct gggcacgttg taagagccca     3000
gctactgtta gtactacagg atagattctt acaaatatca aaagcaaggt ttggccggga     3060
gcagtggctc acgcctataa tcccaacact ttgggaggcc gagggggca gatcacccga     3120 ggtcaggagt tcaagaccag cctgaccaac atggagaaac cctgtctcta ctaaaaatac     3180
aaaattagcc gggcgtggtg gcacatgcct gtaattccag ctacttggga ggctgaggca     3240
```

-continued

```
ggagaatcgc ttgaacctgg gaggctgagg ttgcagtgag ccgacatagc gccattgcac    3300
tccagcctgg tcaacaagag caaaactcag tctaaaaaaa aaaagaaag aaaaaaacaa     3360
ggctttaggt agcccacaat tagaaggaga aaaccttagc atcccctagg tgccaggcct    3420
tgtgggaaca agtgattcat taagactgta gaaggaagct gggcacgcgg ctcatgcttg    3480
taattccagc actttgagag gctgaggtgg gcagatcgct tgagctcacg agttcaagac    3540
cagcctaggc aacatggtga aaccttgtct gtacaaatac aaaaattagc taggtgtggt    3600
ggtgcaaatc tgtagtccca gctactcggg aggctgaggt gggagcatca cttcagcctg    3660
ggaggtggag gctgcagtga gcagagactg acccactgtg ctctagcctg ggtgatagag    3720
ccagacctta tgtaaaaaaa aaaaaaaaa aaaaaagac tgaagaaggg gaagagacag      3780
catttgagaa aaggcctcac agagaaaggg gttttcaatc tggggacagc agatatgacc    3840
agcagtcctg aaggtaggga ggcacacttt aataatggta atagttgcta agcctataaa    3900
atgcttaggg tgtcacagga tcttttcaca tgtctcatct caagtcatgc cccaacaac    3960
tcagcattcc cactttgcag atgaggacac tgaggctcag ggaggtgata tgtaagaggc    4020
taagcctcaa cacacactgg ccttttgct tccgaaactg ctttcccttg ctctgaggct     4080
ctcggagagt aattgctggg ttgtgagcac tgggtaagag gatgggtgct caaagcagc    4140
tgcactccag gataaaggta gaggaaagta aaaacatctt cccctgctgt tatccaaaag   4200
agaaaagaa tggaattggg caaggggtgg aggggaatc cagcttttga aacagtatta    4260
taggaatttt gctacccgct atgtgcagag catcatgcga ggcacttggg acagctgaat   4320
gaatgagctc cattctcaag gtgaacatgt acatatacac acctacaatt tacatttatt   4380
gagcagtggt cgcatggttt catctgcaca gtgactctga ggtaggtact accattaggc   4440
ccattgttag agaggggtta atggagactt agaagaggcc cagagaggtt aggtagcttt   4500
ctcagaatca cataagtggt aaggggattc aggcatgccc cctgcaacca ctgtcttcac   4560
caccgtacgg caccagttcc acaagctgta cagtgtgggc tgtgagaccc aaggaaaaac   4620
agagctgagg cccacgggaa ggtgaggccg gtgtgggctg gaggcttgg ggtaagcttc    4680
ctggaggtgg gggtacatgt tgggccttgg aggactaaag aactgggggg aaaaggaagg   4740
gaagaaggaa aggattttct gaaaaggaaa tggcaagaag taaaggtcca agcataggc    4800
tgttgtgagt aaacagtggg aaatgcaacc tctttgggc caaacctctg accctccacg    4860
ttcccagctg tgaagtggga gtaataaaat catccacctt atgagagcaa ataaaataat   4920
gattgtgaaa atattttggt aacagtaacc tgtgatagga agataacaaa tcatttctgt   4980
tacaatacca tgctgatagg cataaaagtt gcattcatgt tcatgggcaa aatgggggta   5040
agtagaatgc atgggacgca agaaggatgt aggaaggaaa gggtagtgtg agtataggag   5100
gactagccac tgagaagaaa gtagaagaaa gagggaatct tgtgtgtat gggaaagtct     5160
attgcagagt caacttgggc ttccatcctg ggaccttccc gtgaacagct agagacatct   5220
tcctctgggc tttggcagcc tttatgtcgg acccagggg accctatatg ggaaataggg    5280
ccagacacat gctctgaatc cctgcttcaa catttctgag tcacctttgt ccctgtgagc   5340
cttcattttt ctcatctata aaatggatga cagctagctt gttggtgtga tttcagtagc   5400
ggctcagtag agtcagtttc ctaggtctct ttaattctgc ctctcaaagg tgatgggaaa   5460
acatctagac aagaagccaa gggaccggga cacatctctc caaggacgag gtgcatggcg   5520
ctctgaagat gctggcatct ctctaggccc aacccagctc agggggtcca ctccaccaca   5580
gccctggctg ggtgcctgtc ccctggtatc ctggagacct tgcagctgct gtgggcatct   5640
```

```
gctgccacct agcggcctcc catggcactg tctccccgcc agccctagt tttgacaggg    5700 gcactccctg gcattaatct cttcagaggg aatgtctgtg cctgtttcct gtctgtcctc    5760
ccgccaggtg gagttcctta aaggcagtca tgatcattat ctttctagct ccagtgtcca    5820
gcacagtgag gcacaaagta gttgttcagc aggtgattac ggaataaatg aatgaacgga    5880
ccaataaaca aatagccttg tctaatcaaa attaggcaac agaaggaagt cacttcaggg    5940
ttatttaatc cccgggcagc tgactcctct aaattgactc ttgacaagaa gtaactctta    6000
taaatgctcc agaggccctc agcgacagag gtgatttcca ggtggctggg ctaacgttaa    6060
aggtggttgt actaaaagca ggggtttggc ctcaggact ccaccactgt ggtggaggta    6120
cagcactttt ctattttgc ttcctccacc ctgggccagg atcttcctca agagaatgcc    6180
ctcaatccga gaaagcctga aggaacgagg tgtggacatg gccaggcttg tcccgagtg    6240 gagccaaccc atgaagaggc tgacacttgg caacaccacc tcctcgtga tcctcaccaa    6300 ctacatggac gtgagtgctt ggctcagccc ctcgctccct ccctgtctcc tttccctcat    6360
ggacctaggg cttctttgc tgcaagactc acccttcca agctgtgttt gacgaaggcg    6420
ctgagtagca cgtgagcacc ctagaaaatt cccattttcc agctggaaag cctgagcaca    6480
gaagacagga aggcatccag gggccattca ggggcagggt taggtttgga actcagccca    6540
ggcctcaagc caggtgtcac aggtgggtgg aaggggtgt gtgactcagg tgggggtttc    6600
tgtgacctgg cccagcacaa cctgatggct tcctgcccca aggatcctc aagagtcaag    6660 tttgcttcct gcttcattct caatgttttg attttgccct cttgtcttac tgagactccc    6720
actttctggg atgccatggg gagatgctaa gcctcctacc agttcctgca ggaaaatgga    6780
aaccccgaga ggctatagga cctcgcctgg gccaagtctc acaccgagag ccaagagtga    6840
agccaggcaa gaccccaaga cccaaggtcc cctgagcccc tccagccctc tctttttacc    6900
cccacagacc cagtactatg gcgagattgg catcggcacc ccaccccaga ccttcaaagt    6960
cgtctttgac actggttcgt ccaatgtttg ggtgccctcc tccaagtgca gccgtctcta    7020
cactgcctgt ggtgagacct aagacccaca gtgcctctcc tccatccccc tgccctactg    7080
tgcatgagca atcctgccca acacccagct cccatccctc ttgccaccaa gggagtggct    7140
tcctctctgc ctctgtgccc actgacatgt aggggagagg ggaagatgtc tcccgttttt    7200
ctgatacagc caccaaggtt aaaaacaaaa aaggtccaa gaaccctga gcacccagaa    7260 ggccacttcc cagtcttcct gagattgaga caggactgaa ttctcaaacc catcccaggc    7320
actcggaact cttccatccc tagtcttaat caacaacctc ttactaggca cttactctgt    7380
gcctggcatc ttctctggtg ttatcagtgt tagtgattac tttaaattcc ttcatttagg    7440
acaaaattct cgatgtatgg gcacattagg agagcccaag aaaccagtc cttgattgat    7500 gaagcacata ttccaagccc cctgacccta gggccactca tccctgcacc taagctaacc    7560 agccatacccc acaatgcacc ctgcctctga gtccccctgt ctgggccact cttggacaaa    7620
cctgagcctc tgtcccctg ccagtgtatc acaagctctt cgatgcttcg gattcctcca    7680
gctacaagca caatggaaca gaactcaccc tccgctattc aacagggaca gtcagtggct    7740
ttctcagcca ggacatcatc accgtaagtt gggccgccct aggtcatctg cccggaccc    7800 cttctgtccc caggcctctc ctgacccctcc agggcccaca cctgcgggga ggtacactgc    7860
agcccacttg gagcctgggg agctgaggaa caccctactc tgccacatct ggctgttgct    7920
gcaaagcagc agtaccctatg ggggagcaag cctgggctac gggctcaccg ttgggtggtt    7980
tgtggatgtt tttgcatcta acttgcatgt agggcttgtc ctgagccccg tggctgcagt    8040
```

```
caagtaactc gtccaagttc accagctctg actgggctac accctagact gaaatccagg    8100
gtcagagtca ggctgagttt tagggtcagg cataggtttt aaggtcacag ttgaggttga    8160
ctctgggact caggtcaagg cctgcttttc ttttccatgt ggcccatgtc tgaccgtttc    8220
ctcatcctgg agtttctcag gccctgctcc atcagagtta ggggaggggc acacgtggca    8280
cctgagagga aatcagggtg attcctgcct cccttccttt ttctgtgaac tcagatataa    8340
aggagggaga agggcaagct tgtctgtgct aaagaaaccc ttcgcccatg ataagggtgg    8400
gggccaagac ccagtcctgc caggcacgaa agtctggcca ctggggaggg gaggagctct    8460
tggcagcttt tcttttgctg cttggcagga ccaccctctc agcctctgct ctccgatccc    8520
tggtcaactc tagctctctc tgggctccgc agcagagatg tgtattggca cagagtgtgt    8580
gcgtgcaggg ttgaggaaat actcttaccc cgatttctgt accctggagc atgtgtgccc    8640
ctgggatccc tagtgtggaa gcccagacca gactccaacc aaggagtggg cagtgggctt    8700
ggtctcctct ggtccttcct cccacaggtg ggtggaatca cggtgacaca gatgtttgga    8760
gaggtcacgg agatgcccgc cttacccttc atgctggccg agtttgatgg ggttgtgggc    8820
atgggcttca ttgaacaggc cattggcagg gtcaccccta tcttcgacaa catcatctcc    8880
caaggggtgc taaaagagga cgtcttctct ttctactaca caggtggggg actgggactc    8940
caagggctga ggtgggggga caggagggga aagagatgg ggagtggaag gagagtctgg    9000
gccagaattg taaagtgttt gtaattaggt gacagccaat caatatctag agctgtacta    9060
gccaatatgg aaggcactat tgaaatttaa attaattaaa tacagttaag catcaattaa    9120
gcattcaact ggtggctctt agttgtacta gccacacgtc aaatgcctgg cagccacggt    9180
ggctagtaac tacagtctta tgacagtgca gatagagaat attcccagca tgacaggaca    9240
ttctaataga cagcgccact ctggagcaag aggagatgca aggtgggggc gatggtaaat    9300
aagggattac tgtgacctgt agccctgcct gttagggcca tggctcctcc cacacagaga    9360
cagccaactt cagtcatcca ttagatcctt cattcgtttg tttgctcact catcagttca    9420
gtaaatgcta tgtgccaagc actgtggtag gctctggggg tgcagcagtg aacacagtga    9480
acaaggcaga atctgtactc ccctacccac atagagctta caggctaaca gggaagacaa    9540
gacatattcc aacataaaga gtgtcacagg caggcagcaa gtgtggtgct gaaaaccatg    9600
gatgcttttc aattctaggc tgagcttata tgcagctcag ccagccttgg ggaagctctt    9660
gagcagggtt gggctctact ccaaactgct gggcttagaa agatggcatg agttggagac    9720
aagagagctg gaggcaaaag gggctgggtg cagtggctca tgcctgtaat cccagcactt    9780
tgggaggcca aggcgagagg atcgcatgag cccaggagtt aaggcttcag tgagcagtga    9840
ttgtgccact gcactccagc taaggcaaca gagtgagatc cagtctcaaa aaaaaaaaa    9900
aaaaaaaaaa agtcacaagg gtaagaacat gaggccagtg gcaaaaagaa tagaggagag    9960
gatcagagtt cagagaaatc tcacagtaaa atggagagga gtctccggtt tggtgataga   10020
aagtgaggcc ttgagaaaag gccaattggc ggctctgcat tcaggggtgg tctttagaag   10080
aactgtttta gaggaagtgg gggcaaggcc agatggcaag aagttaagag gtggacgacg   10140
tgggtgtcag gaagtggagg tcatgagatg taggctgccc tgggacattc aacagggaag   10200
ggaatggggg gtgcgtggg gggtgagatc cagaagcaga agaggaaggg tggtgttttt   10260
taaatgctag aggatgctcg agtgatgcct gtaggtggag gaagaagcca atggaaagaa   10320
agagattaaa aatgtggaaa gaagaggagc taaatggggg cactggagtt tggaggcctt   10380
gaaagagatg aggttccagc agacaggaag aagccaggtt ttgcagagga gagggctggc   10440
```

```
ctcttctttt atcttgggat gggaaggagg gaacatccag agagatactg aagtgttgag   10500
agacaggcag gagggaattt gtgctagcat atacacatac attccgaatt tataaaaaca   10560
caagtagttt gcagttgcac aaaataacat atgcacacct acacacccat gcacacatgt   10620
gcatgtgtga attctagtat gaattctgga aaaacacatc acacacacag gcatgccctg   10680
gagactaggc ctacagtagt ccctgagcca agtgcagtga ggaggaaagg aaggtgaggg   10740
gaatcagctc cagacggggc accaggagcc tggctccagt cccccacttg ttcactcatg   10800
gactgggtaa cttcaggcaa gtgacttcgc ctcttggtga ctccattgcc tgaagggcaa   10860
agagagtaca taacacccac cctgccaaac agcagggctg atgaggctgg catgaaatga   10920
agcttccttt ctgctgtctc tctttctctg cagagattcc gagtaaggag acaaaacccc   10980
cacatggctg tgaccttcca gtactccccg agcacctgac ctagaattac acgccacc    11040
ggcccaaaac tcacatcagc aagcccagcc tccgctagat gccgaagttc tctgtctctc   11100
cttcctgctc tctccatgcc acctgcccac cccataccca atagcctccc cagggtcccc   11160
tcccatgcac ctgctcaatc agcagcaacc caagagtgag gggtgtccat ttgtgtcttg   11220
ttcacatcca ctcactgtcc ttgtacctgc tccttttctg tgacctctct ggggatgctt   11280
tttgggggaa cagctggact accctggaac aacctctggt tggtcttggg gaggggaaga   11340
aaggcagaga agcagtatgt tctgcatgct tcccaacgac agctccgagc ctggctgtct   11400
gtcccacatt cctctgctct agagccctct gtcctcccct gcacccttgt gcaaccttcc   11460
ccaattgcct gagttgctgg gtcctggagg ttatgggttt caagagctt ctgatctttc    11520
ctttaggaat tcccaatcgc tgggaggaca gattgtgctg ggaggcagcg acccccagca   11580
ttacgaaggg aatttccact atatcaacct catcaagact ggtgtctggc agattcaaat   11640
gaagggtca gaaatcctca accctccccg ggctccaaaa aatgctgccg tcactggggt    11700
tggggagggt ggggaaggac tgcattacca tcctgccctc tttccaaatg cagccacttc   11760
ttaagcacag ccaccatttg ctctctgcct gctctgtcca ggctggggaa cagagaaggg   11820
aggggcctgg ggagaagtgg tggagggtga cagtaccttc cctcctctac tcactgcctc   11880
aacaggccac cagcgtggcc tccacccacc cacccacact caggaaggac atgcagcctg   11940
gaggtgcccc atcagccttc tgtctgtctg tctgtctgtc tgtctgactg tggcctcccc   12000
cagggtgtct gtggggtcat ccaccttgct ctgtgaagac ggctgcctgg cattggtaga   12060
caccggtgca tcctacatct caggttctac cagctccata gagaagctca tggaggcctt   12120
gggagccaag aagaggctgt ttgatgtaag aagccaaaga gggaaggtgc tgtgggtggg   12180
gggagcgcca cctggtatcg gctcacaaat cccccaggca aatgaggcca tctcaggcct   12240
tcgcttgttc acctcacact ctccacacat gtggctggtc acccatgggg cggggcactg   12300
tccccagccc tctccagcag agagaccagg ccaccagcgc aggactcctt gtctgctgag   12360
acgtcttcca tactcaagaa ggctctcttt gccccccacc ccagtatgtc gtgaagtgta   12420
acgagggccc tacactcccc gacatctctt tccacctggg aggcaaagaa tacacgctca   12480
ccagcgcgga ctatgtattt caggtgaggt tcgagtcggc cccctcggtg gcagggagaa   12540
aggctggaca gagaccctca aagagtgaca gattacaatg cacaggtcat gttagaactg   12600
tagttctcaa acttggctgt gcatgtcacc tggagagctt tgaaaaatcc tggtacctgg   12660
gccacatccc atacctatta aatcagaacc tctagaagtg gcacctgggg ttcagtttcc   12720
ccaggtgatt ccaatgtgtg gccatgtttg ggcatcacta tgcctgttcc ctcatctcca   12780
ttttctcatc aaatactccc aagaatccta tgctcctata ttcttaccct cttttcataa   12840
```

```
tcaataggct tagagaagtt gaataacttg tctaggatca gaagctaagg caaactgtaa    12900
gctcctgaag gaagcacggt gcctgatgca ttgtttgcct gggatctagc acaggggcta    12960
aacataggag tggtgcagtc cacgatgggg caaaatggcc atgatgtgag ggaggcccag    13020
tgtggctagg ggagagatgg gggcgagagg gggaatgttg ctgaagacag ttgctggggg    13080
tcaggcaagg tgaaaggaga atgctcatgt gctgggtatg gagaaactct ccccttcct    13140 gccaggaatc ctacagtagt aaaaagctgt gcacactggc catccacgcc atggatatcc    13200
cgccacccac tggacccacc tgggccctgg gggccacctt catccgaaag ttctacacag    13260
agtttgatcg gcgtaacaac cgcattggct tcgccttggc ccgctgaggc cctctgccac    13320
ccaggcaggc cctgccttca gccctggccc agagctggaa cactctctga tgcccctc     13380 tgcctgggct tatgccctca gatggagaca ttggatgtgg agctcctgct ggatgcgtgc    13440
cctgacccct gcaccagccc ttccctgctt tgaggacaaa gagaataaag acttcatgtt    13500
cacagcctgt tgcatctggg ttcactaggg tttagaacag agggaggggc tgcgtgatca    13560
tgtgtggaca ggaatgtgac acagacaagc tacacattcg cctagcgcac aggttcttgc    13620
gtgcagggat gatgccatcc atctgccatc aacgggactc aggtggagct gtttacacaa    13680
cctcaggtgg gaagtctgaa aagagccgga accaagctcc ctctagtccc tcagggacca    13740
aggctaatgc tgtggcagta gactgtgggt cagaaagttc tcccagctca cagaagccag    13800
ctctgagttc agactctgct ctgctgagct agtcagccct gtctcttgtc cctgcaaaac    13860 tccctcagc tgtccttatc cactgcagat gcccccgccc tgcccatgt agccatttac     13920 acaggcattc taaggcacta ccacctaaaa tcatagaaca ccagagatcc aggcaatact    13980
tccactttac aggtggggaa actgaggccc agagaatgga aggccttgcc caagattact    14040
cggtcaagaa tcaagtagtg aagaatactg aaagatagtg aagaatcaag actggaaccc    14100
agcccgtctg acttgggtcc tggggggttc caccttatca taagcagttg gtaccgtcat    14160
aagtacagtg cttcacgcac gctggtacag ggccacgtgc acaagcacac aggtgcacac    14220
acacactgct atcctccatc ccatccacct gggactcgtc aggctgaagt ctcttctccc    14280
actctcactc cttgggctgt cttcagggca catgtaactt ggggaatgag aaattagcat    14340
ccacctggag ccactgaagc catccctctt caccatagtt gctcacctct cttttgacag    14400
aaagtcgtga ggcactgaat ggcccaacca ggccctcagt acctctggga gccatctgca    14460
agagtccctg tgtagcgcca agagccggag cctgggcttc agg                      14503

<210> SEQ ID NO 4
<211> LENGTH: 14503
<212> TYPE: DNA
<213> ORGANISM: Homo sapiens

<400> SEQUENCE: 4
ggtctttgta aaataataat tattcatttc acaaaagtga taattaaaag actttaatag      60
caatacagaa agttacatga atataaagac ttaacctttc taaagctcag ttttcctaag    120
taatcaaaaa cctgataaag ataacaagaa tgaggaatta tcttgagaaa atgtaaaatc    180 tttccttta ttttttgaga cagggtctca ctctgtcatc caggctaaag tgcagtggca    240
caatcatagc tcactacagc cttgaactcc tggactcaag tgatcctccc gcctcagcct    300
ccccagtagc taagactaca ggcacgcacc accacaccca gctaatttt ttcagagatg    360 gggtcttgct atattgccct ggctggtctt gaacagagctt caagtgagcg tgagcctcct    420
acctcatcct cccaaagcac taggattaca ggcatgagcc actgtttccc agcctaaaat    480
```

-continued

| | |
|---|---|
| aattgtttct taggccagct accaaaaacg caaagaaaaa ctttctgtag tgtgattgct | 540 |
| tcttcttatg ggaagcccat ttagataacc tgtaagtcaa acctgatgaa aacaatactt | 600 |
| gaatgtaatc agacacagaa agactgttca aggctatgag tagctgagtc caagctcgta | 660 |
| tcacttgcca cacaacagcc aataagtcta gagacaaggt attgtggcaa ggaaagctac | 720 |
| cttattcaga gaaccagaaa accaagaaga tggtggacca gcatcataaa gaaccatctg | 780 |
| aagtcagcat gaacgttagg ctcttcttta tgttaaggga aggggaagaa gaagggatt | 840 |
| gggatcaaga ggtgactgat gaccacagac acctgggtgc cagcaagggt ctgaggacgt | 900 |
| tgtaaaactt cttttttcta ggtcaggtca caatgttcct atacatcttt aacataacat | 960 |
| tgttatttgt ctgtatattt ccttatctcc ttggggtta gtttggggaa aggaactgtt | 1020 |
| accatttttt ttaaagttga actgcaagct aaactcctat aattagctgg tctatgtaca | 1080 |
| gagctaagca gaagctttta gcctaaagga taatacccct gggggtcaga ggcaaaatgg | 1140 |
| agtcagtcat gctaagtctc cctccactct ctttctttt tgagatggaa tttcactctt | 1200 |
| attgcccagg ccggagtgca gtggcatgat ctcagctcac tgcaacctcc gcctcctggg | 1260 |
| ttcaagcaat tctcttgcct cagcctcctg agtagctgag attacaggtg tccatcacca | 1320 |
| cacccagcta attttgtag tttagtggag atggggtttc accattgttg gtcaggctgg | 1380 |
| tctggaactc ctgacctcag gtgatctacc caccttggcc tcccaaagtg ctgggacagg | 1440 |
| tgtgagccac catgcctggc cctctactc ttataattaa accagctgtt gcttttcctg | 1500 |
| ccaagaaacc agtcatgaag attcacccat gttctagatg ggaaaactgg gctgtagcct | 1560 |
| gggagaggcc agtcagggac aaagccaaag ttaatataga gaatggagct tccagggtat | 1620 |
| aggggttggg tctgggctag ggagctggaa acctaggttt tacgcttgtc ccagttttga | 1680 |
| tgttagccct gagcagtgct gtttctcatc agcctctgcc tgctccaggg gtcacagggc | 1740 |
| caagccagat agagggctgc tagcgtcact ggacacaaga ttgctttccc acagctgtcc | 1800 |
| ttcctccagc ccctctgctc cccatccgga aacctgggta cccttcaccc acctagctct | 1860 |
| gtcccgcagt gagatttatt gctgactgcc ctgccatcta ccccagggta ataaatcagg | 1920 |
| gcagagcaga attgcaatca ccccatgcat ggagtgtata aaaggggaag ggctaaggga | 1980 |
| gccacagaac ctcagtggat ctcagagaga gccccagact gagggaagca tggatggatg | 2040 |
| gagaaggatg cctcgctggg gactgctgct gctgctctgg ggctcctgta cctttggtct | 2100 |
| cccgacagac accaccacct ttaaacggta attggtaact caggcagaga aggggtggga | 2160 |
| ggggtgcagg gttcccacct tcccaacacc ctggcttttc cacatgcggt gtcattcagt | 2220 |
| ccttacgatc agctggacag ggaagtatgg acctgttcag agaggtcaag tgacttgccc | 2280 |
| aataaatgac actagtagtc aggtctagaa gctgtgactt ttgcttcctg cccagagcac | 2340 |
| catgctaact aagcactgta gagaactcag aagtattagg acatgcccct tgcacttgag | 2400 |
| gagctcacag cctgaatatt aagaagggca tgggtggttg ggcgcggtgg ctcctgcctg | 2460 |
| taatcccagc actttgggag gctgagacgg atcacttgag gtcaggagtt tgagaccagc | 2520 |
| ctggccaaca tggggaaacc ccatctctac taaaaataca aaaattagcc gggcatggtg | 2580 |
| gcaggcactt gtaatcccca gctactcggg aagctgaggc aggagaatcg tttgagcccg | 2640 |
| gaaggtggag attgctgagc caagatcgtg ccactgcact ccagcctgag tgacagaaca | 2700 |
| agactccatc tcaaaaaaaa aaaagacggg ggtcggggca tgggtacagt taactgtacc | 2760 |
| agggaagcag cttgatatcg tggttaaatg caaggcttat agagttagat tgccttcatt | 2820 |
| taaattttgc ttcactagca gaacaaacta ggtctggaat catgggcaag ttatttaacc | 2880 |

```
tctccaagtc tcagtttatc attttaaaca ggtatgataa taacagtacc tacttgatgg    2940
ggctgctttg gggattttag gagataaggc atagaaagtc gggcacgttg taagagccca    3000
gctactgtta gtactacagg atagattctt acaaatatca aaagcaaggt ttggccggga    3060
gcagtggctc acgcctataa tcccaacact ttgggaggcc gagggggca gatcacccga     3120 ggtcaggagt tcaagaccag cctgaccaac atggagaaac cctgtctcta ctaaaaatac    3180
aaaattagcc gggcgtggtg gcacatgcct gtaattccag ctacttggga ggctgaggca    3240
ggagaatcgc ttgaacctgg gaggctgagg ttgcagtgag ccgacatagc gccattgcac    3300
tccagcctgg tcaacaagag caaaactcag tctaaaaaaa aaaagaaag aaaaaaacaa     3360 ggctttaggt agcccacaat tagaaggaga aaaccttagc atcccctagg tgccaggcct    3420
tgtgggaaca agtgattcat taagactgta gaaggaagct gggcacgcgg ctcatgcttg    3480
taattccagc actttgagag gctgaggtgg gcagatcgct tgagctcacg agttcaagac    3540
cagcctaggc aacatggtga accttgtct gtacaaatac aaaaattagc taggtgtggt     3600
ggtgcaaatc tgtagtccca gctactcggg aggctgaggt gggagcatca cttcagcctg    3660
ggaggtggag gctgcagtga gcagagactg acccactgtg ctctagcctg gtgatagag     3720 ccagacctta tgtaaaaaaa aaaaaaaaa aaaaaagac tgaagaaggg gaagagacag      3780
catttgagaa aaggcctcac agagaaaggg gttttcaatc tggggacagc agatatgacc    3840
agcagtcctg aaggtaggga ggcacacttt aataatggta atagttgcta agcctataaa    3900
atgcttaggg tgtcacagga tcttttcaca tgtctcatct caagtcatgc ccccaacaac    3960
tcagcattcc cactttgcag atgaggacac tgaggctcag ggaggtgata tgtaagaggc    4020
taagcctcaa cacacactgg gccttttgct tccgaaactg cttttcccttg ctctgaggct   4080 ctcggagagt aattgctggg ttgtgagcac tgggtaagag gatgggtgct tcaaagcagc    4140
tgcactccag gataaaggta gaggaaagta aaaacatctt cccctgctgt tatccaaaag    4200
agaaaaagaa tggaattggg caaggggtgg aggggaatc cagcttttga aacagtatta     4260
taggaatttt gctacccgct atgtgcagag catcatgcga ggcacttggg acagctgaat    4320
gaatgagctc cattctcaag gtgaacatgt acatatacac acctacaatt tacatttatt    4380
gagcagtggt cgcatggttt catctgcaca gtgactctga ggtaggtact accattaggc    4440
ccattgttag agaggggtta atggagactt agaagaggcc cagagaggtt aggtagcttt    4500
ctcagaatca cataagtggt aagggggattc aggcatgccc cctgcaacca ctgtcttcac   4560
caccgtacgg caccagttcc acaagctgta cagtgtgggc tgtgagaccc aaggaaaaac    4620
agagctgagg cccacgggaa ggtgaggccg gtgtgggctg gaggccttgg ggtaagcttc    4680
ctggaggtgg gggtacatgt tgggccttgg aggactaaag aactgggggg aaaaggaagg    4740
gaagaaggaa aggattttct gaaaaggaaa tggcaagaag taaaggtcca agcataggc     4800 tgttgtgagt aaacagtggg aaatgcaacc tctttgggc caaacctctg accctccacg     4860
ttcccagctg tgaagtggga gtaataaaat catccacctt atgagagcaa ataaaataat    4920
gattgtgaaa atattttggt aacagtaacc tgtgatagga agataacaaa tcatttctgt    4980
tacaatacca tgctgatagg cataaaagtt gcattcatgt tcatgggcaa aatggggta    5040 agtagaatgc atgggacgca agaaggatgt aggaaggaaa gggtagtgtg agtataggag    5100
gactagccac tgagaagaaa gtagaagaaa gagggaatct tgtgtgtat gggaaagtct     5160 attgcagagt caacttgggc ttccatcctg ggaccttccc gtgaacagct agagacatct    5220
tcctctgggc tttggcagcc tttatgtcgg gacccagggg accctatatg ggaaataggg    5280
```

```
ccagacacat gctctgaatc cctgcttcaa catttctgag tcacctttgt ccctgtgagc   5340
cttcattttt ctcatctata aaatggatga cagctagctt gttggtgtga tttcagtagc   5400
ggctcagtag agtcagtttc ctaggtctct ttaattctgc ctctcaaagg tgatgggaaa   5460
acatctagac aagaagccaa gggaccggga cacatctctc caaggacgag gtgcatggcg   5520
ctctgaagat gctggcatct ctctaggccc aacccagctc aggggtcca ctccaccaca    5580 gccctggctg ggtgcctgtc ccctggtatc ctggagacct tgcagctgct gtgggcatct   5640
gctgccacct agcggcctcc catggcactg tctccccgcc agccctagt tttgacaggg    5700 gcactccctg gcattaatct cttcagaggg aatgtctgtg cctgtttcct gtctgtcctc   5760
ccgccaggtg gagttcctta aaggcagtca tgatcattat ctttctagct ccagtgtcca   5820
gcacagtgag gcacaaagta gttgttcagc aggtgattac ggaataaatg aatgaacgga   5880
ccaataaaca aatagccttg tctaatcaaa attaggcaac agaaggaagt cacttcaggg   5940
ttatttaatc cccgggcagc tgactcctct aaattgactc ttgacaagaa gtaactctta   6000
taaatgctcc agaggccctc agcgacagag gtgatttcca ggtggctggg ctaacgttaa   6060
aggtggttgt actaaaagca ggggtttggc ctcaggact ccaccactgt ggtggaggta    6120
cagcactttt ctattttgc ttcctccacc ctgggccagg atcttcctca agagaatgcc    6180
ctcaatccga gaaagcctga aggaacgagg tgtggacatg gccaggcttg gtcccgagtg   6240
gagccaaccc atgaagaggc tgacacttgg caacaccacc tcctccgtga tcctcaccaa   6300
ctacatggac gtgagtgctt ggctcagccc ctcgctccct ccctgtctcc tttccctcat   6360
ggacctaggg cttctttgc tgcaagactc acccttcca agctgtgttt gacgaaggcg     6420
ctgagtagca cgtgagcacc ctagaaaatt cccattttcc agctggaaag cctgagcaca   6480
gaagacagga aggcatccag gggccattca ggggcagggt taggtttgga actcagccca   6540
ggcctcaagc caggtgtcac aggtgggtgg aaggggtgt gtgactcagg tgggggtttc    6600
tgtgacctgg cccagcacaa cctgatggct tcctgcccca gaggatcctc aagagtcaag   6660
tttgcttcct gcttcattct caatgttttg attttgccct cttgtcttac tgagactccc   6720
actttctggg atgccatggg gagatgctaa gcctcctacc agttcctgca ggaaaatgga   6780
aaccccgaga ggctatagga cctcgcctgg gccaagtctc acaccgagag ccaagagtga   6840
agccaggcaa gaccccaaga cccaaggtcc cctgagcccc tccagccctc tcttttacc    6900 cccacagacc cagtactatg gcgagattgg catcggcacc ccaccccaga ccttcaaagt   6960
cgtctttgac actggttcgt ccaatgtttg ggtgccctcc tccaagtgca gccgtctcta   7020
cactgcctgt ggtgagacct aagacccaca gtgcctctcc tccatccccc tgccctactg   7080
tgcatgagca atcctgccca acacccagct cccatccctc ttgccaccaa gggagtggct   7140
tcctctctgc ctctgtgccc actgacatgt aggggagagg ggaagatgtc tcccgttttt   7200
ctgatacagc caccaaggtt aaaaacaaaa aaggtccaa gaaccctga gcacccagaa     7260 ggccacttcc cagtcttcct gagattgaga caggactgaa ttctcaaacc catcccaggc   7320
actcggaact cttccatccc tagtcttaat caacaacctc ttactaggca cttactctgt   7380
gcctggcatc ttctctggtg ttatcagtgt tagtgattac tttaaattcc ttcatttagg   7440
acaaaattct cgatgtatgg gcacattagg agagcccaag aaaccagtc cttgattgat    7500 gaagcacata ttccaagccc cctgaccta gggccactca tccctgcacc taagctaacc    7560
agccataccc acaatgcacc ctgcctctga gtccccctgt ctgggccact cttggacaaa   7620
cctgagcctc tgtcccctg ccagtgtatc acaagctctt cgatgcttcg gattcctcca    7680
```

```
gctacaagca caatggaaca gaactcaccc tccgctattc aacagggaca gtcagtggct    7740
ttctcagcca ggacatcatc accgtaagtt gggccgccct aggtcatctg ccccggaccc    7800
cttctgtccc caggcctctc ctgaccctcc agggcccaca cctgcgggga ggtacactgc    7860
agcccacttg gagcctgggg agctgaggaa caccctactc tgccacatct ggctgttgct    7920
gcaaagcagc agtacctatg ggggagcaag cctgggctac gggctcaccg ttgggtggtt    7980
tgtggatgtt tttgcatcta acttgcatgt agggcttgtc ctgagcccg tggctgcagt     8040 caagtaactc gtccaagttc accagctctg actgggctac accctagact gaaatccagg    8100
gtcagagtca ggctgagttt tagggtcagg cataggtttt aaggtcacag ttgaggttga    8160
ctctgggact caggtcaagg cctgctttc ttttccatgt ggcccatgtc tgaccgtttc      8220
ctcatcctgg agtttctcag gccctgctcc atcagagtta ggggaggggc acacgtggca    8280
cctgagagga aatcagggtg attcctgcct cccttccttt ttctgtgaac tcagatataa    8340
aggagggaga agggcaagct tgtctgtgct aaagaaaccc ttcgcccatg ataagggtgg    8400
gggccaagac ccagtcctgc caggcacgaa agtctggcca ctggggaggg gaggagctct    8460 tggcagctt tcttttgctg cttggcagga ccaccctctc agcctctgct ctccgatccc     8520
tggtcaactc tagctctctc tgggctccgc agcagagatg tgtattggca cagagtgtgt    8580
gcgtgcaggg ttgaggaaat actcttaccc cgatttctgt accctggagc atgtgtgccc    8640
ctgggatccc tagtgtggaa gcccagacca gactccaacc aaggagtggg cagtgggctt    8700
ggtctcctct ggtccttcct cccacaggtg ggtggaatca cggtgacaca gatgtttgga    8760
gaggtcacgg agatgcccgc cttacccttc atgctggccg agtttgatgg ggttgtgggc    8820
atgggcttca ttgaacaggc cattggcagg gtcaccccta tcttcgacaa catcatctcc    8880 caagggtgc taaaagagga cgtcttctct ttctactaca caggtgggg actgggactc      8940 caagggctga ggtgggggga caggagggga aagagatgg ggagtggaag gagagtctgg     9000
gccagaattg taaagtgttt gtaattaggt gacagccaat caatatctag agctgtacta    9060
gccaatatgg aaggcactat tgaaattaa attaattaaa tacagttaag catcaattaa     9120
gcattcaact ggtggctctt agttgtacta gccacacgtc aaatgcctgg cagccacggt    9180
ggctagtaac tacagtctta tgacagtgca gatagagaat attcccagca tgacaggaca    9240
ttctaataga cagcgccact ctggagcaag aggagatgca aggtgggggc gatggtaaat    9300
aagggattac tgtgacctgt agccctgcct gttagggcca tggctcctcc cacacagaga    9360
cagccaactt cagtcatcca ttagatcctt cattcgtttg tttgctcact catcagttca    9420
gtaaatgcta tgtgccaagc actgtggtag ctctgggggg tgcagcagtg aacacagtga    9480
acaaggcaga atctgtactc ccctacccac atagagctta caggctaaca gggaagacaa    9540
gacatattcc aacataaaga gtgtcacagg caggcagcaa gtgtggtgct gaaaaccatg    9600
gatgcttttc aattctaggc tgagcttata tgcagctcag ccagccttgg ggaagctctt    9660
gagcagggtt gggctctact ccaaactgct gggcttagaa agatggcatg agttggagac    9720
aagagagctg gaggcaaaag gggctgggtg cagtggctca tgcctgtaat cccagcactt    9780
tgggaggcca aggcgagagg atcgcatgag cccaggagtt aaggcttcag tgagcagtga    9840
ttgtgccact gcactccagc taaggcaaca gagtgagatc cagtctcaaa aaaaaaaaa     9900 aaaaaaaaaa agtcacaagg gtaagaacat gaggccagtg gcaaaaagaa tagaggagag    9960
gatcagagtt cagagaaatc tcacagtaaa atggagagga gtctccggtt tggtgataga   10020
aagtgaggcc ttgagaaaag gccaattggc ggctctgcat tcagggtgg tctttagaag    10080
```

```
aactgttttta gaggaggtgg gggcaaggcc agatggcaag aagttaagag gtggacgacg   10140
tgggtgtcag gaagtggagg tcatgagatg taggctgccc tgggacattc aacagggaag   10200
ggaatggggg gtggcgtggg gggtgagatc cagaagcaga agaggaaggg tgggtgtttt   10260
taaatgctag aggatgctcg agtgatgcct gtaggtggag gaagaagcca atggaaagaa   10320
agagattaaa aatgtggaaa gaagaggagc taaatggggg cactggagtt tggaggcctt   10380
gaaagagatg aggttccagc agacaggaag aagccaggtt ttgcagagga gagggctggc   10440
ctcttctttt atcttgggat gggaaggagg gaacatccag agagatactg aagtgttgag   10500
agacaggcag gagggaattt gtgctagcat atacacatac attccgaatt tataaaaaca   10560
caagtagttt gcagttgcac aaaataacat atgcacacct acacacccat gcacacatgt   10620
gcatgtgtga attctagtat gaattctgga aaaacacatc acacacacag gcatgccctg   10680
gagactaggc ctacagtagt ccctgagcca agtgcagtga ggaggaaagg aaggtgaggg   10740
gaatcagctc cagacggggc accaggagcc tggctccagt cccccacttg ttcactcatg   10800
gactgggtaa cttcaggcaa gtgacttcgc ctcttggtga ctccattgcc tgaagggcaa   10860
agagagtaca taacacccac cctgccaaac agcagggctg atgaggctgg catgaaatga   10920
agcttccttt ctgctgtctc tctttctctg cagagattcc gagtaaggag acaaaacccc   10980
cacatggctg tgaccttcca gtactccccg agcacctgac ctagaattac acacgccacc   11040
ggcccaaaac tcacatcagc aagcccagcc tccgctagat gccgaagttc tctgtctctc   11100
cttcctgctc tctccatgcc acctgccac cccatacca atagcctccc cagggtcccc   11160
tcccatgcac ctgctcaatc agcagcaacc caagagtgag gggtgtccat ttgtgtcttg   11220
ttcacatcca ctcactgtcc ttgtacctgc tccttttctg tgacctctct ggggatgctt   11280 tttggggga cagctggact accctggaac aacctctggt tggtcttggg gagggaaga   11340 aaggcagaga agcagtatgt tctgcatgct tcccaacgac agctccgagc ctggctgtct   11400
gtcccacatt cctctgctct agagccctct gtcctcccct gcaccttgt gcaaccttcc   11460 ccaattgcct gagttgctgg gtcctggagg ttatgggttt ccaagagctt ctgatctttc   11520
ctttaggaat tcccaatcgc tgggaggaca gattgtgctg ggaggcagcg acccccagca   11580
ttacgaaggg aatttccact atatcaacct catcaagact ggtgtctggc agattcaaat   11640 gaagggtca gaaatcctca accctccccg ggctccaaaa aatgctgccg tcactggggt   11700 tgggagggt ggggaaggac tgcattacca tcctgccctc tttccaaatg cagccacttc   11760
ttaagcacag ccaccatttg ctctctgcct gctctgtcca ggctggggaa cagagaaggg   11820 agggggcctgg ggagaagtgg tggagggtga cagtaccttc cctcctctac tcactgcctc   11880
aacaggccac cagcgtggcc tccacccacc cacccacact caggaaggac atgcagcctg   11940
gaggtgcccc atcagccttc tgtctgtctg tctgtctgtc tgtctgactg tggcctcccc   12000
cagggtgtct gtggggtcat ccaccttgct ctgtgaagac ggctgcctgg cattggtaga   12060
caccggtgca tcctacatct caggttctac cagctccata gagaagctca tggaggcctt   12120
gggagccaag aagaggctgt ttgatgtaag aagccaaaga gggaaggtgc tgtgggtggg   12180
gggagcgcca cctggtatcg gctcacaaat cccccaggca aatgaggcca tctcaggcct   12240
tcgcttgttc acctcacact ctccacacat gtggctggtc acccatgggg cggggcactg   12300
tccccagccc tctccagcag agagaccagg ccaccagcgc aggactcctt gtctgctgag   12360
acgtcttcca tactcaagaa ggctctcttt gccccccacc ccagtatgtc gtgaagtgta   12420
acgagggccc tacactcccc gacatctctt tccacctggg aggcaaagaa tacacgctca   12480
```

```
ccagcgcgga ctatgtattt caggtgaggt tcgagtcggc cccctcggtg gcagggagaa    12540
aggctggaca gagaccctca aagagtgaca gattacaatg cacaggtcat gttagaactg    12600
tagttctcaa acttggctgt gcatgtcacc tggagagctt tgaaaaatcc tggtacctgg    12660
gccacatccc atacctatta aatcagaacc tctagaagtg gcacctgggg ttcagtttcc    12720
ccaggtgatt ccaatgtgtg gccatgtttg gcatcacta tgcctgttcc ctcatctcca     12780
ttttctcatc aaatactccc aagaatccta tgctcctata ttcttaccct cttttcataa    12840
tcaataggct tagagaagtt gaataacttg tctaggatca gaagctaagg caaactgtaa    12900
gctcctgaag gaagcacggt gcctgatgca ttgtttgcct gggatctagc acggggcta    12960 aacataggag tggtgcagtc cacgatgggg caaaatggcc atgatgtgag ggaggcccag    13020
tgtggctagg ggagagatgg gggcgagagg gggaatgttg ctgaagacag ttgctggggg    13080
tcaggcaagg tgaaaggaga atgctcatgt gctgggtatg gagaaactct cccccttcct    13140
gccaggaatc ctacagtagt aaaaagctgt gcacactggc catccacgcc atggatatcc    13200
cgccacccac tggacccacc tgggccctgg gggccacctt catccgaaag ttctacacag    13260
agtttgatcg gcgtaacaac cgcattggct tcgccttggc ccgctgaggc cctctgccac    13320 ccagcaggc cctgccttca gccctggccc agagctggaa cactctctga gatgcccctc     13380
tgcctgggct tatgccctca gatggagaca ttggatgtgg agctcctgct ggatgcgtgc    13440
cctgacccct gcaccagccc ttccctgctt tgaggacaaa gagaataaag acttcatgtt    13500
cacagcctgt tgcatctggg ttcactaggg tttagaacag agggaggggc tgcgtgatca    13560
tgtgtggaca ggaatgtgac acagacaagc tacacattcg cctagcgcac aggttcttgc    13620
gtgcagggat gatgccatcc atctgccatc aacgggactc aggtggagct gtttacacaa    13680
cctcaggtgg gaagtctgaa aagagccgga accaagctcc ctctagtccc tcagggacca    13740
aggctaatgc tgtggcagta gactgtgggt cagaaagttc tcccagctca cagaagccag    13800
ctctgagttc agactctgct ctgctgagct agtcagccct gtctcttgtc cctgcaaaac    13860
tcccctcagc tgtccttatc cactgcagat gcccccgccc tgcccatgt agccatttac     13920 acaggcattc taaggcacta ccacctaaaa tcatagaaca ccagagatcc aggcaatact    13980
tccactttac aggtggggaa actgaggccc agagaatgga aggccttgcc caagattact    14040
cggtcaagaa tcaagtagtg aagaatactg aaagatagtg aagaatcaag actggaaccc    14100
agcccgtctg acttgggtcc tgggggtttc caccttatca taagcagttg gtaccgtcat    14160
aagtacagtg cttcacgcac gctggtacag gccacgtgc acaagcacac aggtgcacac     14220
acacactgct atcctccatc ccatccacct gggactcgtc aggctgaagt ctcttctccc    14280
actctcactc cttgggctgt cttcaggcca catgtaactt ggggaatgag aaattagcat    14340
ccacctggag ccactgaagc catccctctt caccatagtt gctcacctct cttttgacag    14400
aaagtcgtga ggcactgaat ggcccaacca ggccctcagt acctctggga gccatctgca    14460
agagtccctg tgtagcgcca agagccggag cctgggcttc agg                      14503
```

<210> SEQ ID NO 5
<211> LENGTH: 14503
<212> TYPE: DNA
<213> ORGANISM: Homo sapiens

<400> SEQUENCE: 5

```
ggtctttgta aaataataat tattcatttc acaaaagtga taattaaaag actttaatag      60
caatacagaa agttacatga atataaagac ttaacctttc taaagctcag ttttcctaag    120
```

-continued

```
taatcaaaaa cctgataaag ataacaagaa tgaggaatta tcttgagaaa atgtaaaatc     180 tttccttta ttttttgaga cagggtctca ctctgtcatc caggctaaag tgcagtggca      240
caatcatagc tcactacagc cttgaactcc tggactcaag tgatcctccc gcctcagcct     300
ccccagtagc taagactaca ggcacgcacc accacaccca gctaattttt ttcagagatg    360
gggtcttgct atattgccct ggctggtctt gaacgagctt caagtgagcg tgagcctcct    420
acctcatcct cccaaagcac taggattaca ggcatgagcc actgtttccc agcctaaaat    480
aattgtttct taggccagct accaaaaacg caaagaaaaa ctttctgtag tgtgattgct    540
tcttcttatg ggaagcccat ttagataacc tgtaagtcaa acctgatgaa acaatactt     600 gaatgtaatc agacacagaa agactgttca aggctatgag tagctgagtc caagctcgta    660
tcacttgcca cacaacagcc aataagtcta gagacaaggt attgtggcaa ggaaagctac    720
cttattcaga gaaccagaaa accaagaaga tggtggacca gcatcataaa gaaccatctg    780
aagtcagcat gaacgttagg ctcttcttta tgttaaggga aggggaagaa gaagggatt     840 gggatcaaga ggtgactgat gaccacagac acctgggtgc cagcaagggt ctgaggacgt    900
tgtaaaactt cttttttcta ggtcaggtca caatgttcct atacatcttt aacataacat    960
tgttatttgt ctgtatattt ccttatctcc ttggggtta gtttgggaa aggaactgtt     1020 accatttttt ttaaagttga actgcaagct aaactcctat aattagctgg tctatgtaca    1080
gagctaagca gaagctttta gcctaaagga taatacccct gggggtcaga ggcaaaatgg    1140
agtcagtcat gctaagtctc cctccactct cttttctttt tgagatggaa tttcactctt    1200
attgcccagg ccggagtgca gtggcatgat ctcagctcac tgcaacctcc gcctcctggg    1260
ttcaagcaat tctcttgcct cagcctcctg agtagctgag attacaggtg tccatcacca    1320
cacccagcta attttgtag tttagtggag atggggtttc accattgttg gtcaggctgg    1380
tctggaactc ctgacctcag gtgatctacc caccttggcc tcccaaagtg ctgggacagg    1440
tgtgagccac catgcctggc ccctctactc ttataattaa accagctgtt gcttttcctg    1500
ccaagaaacc agtcatgaag attcacccat gttctagatg gaaaactgg gctgtagcct     1560 gggagaggcc agtcagggac aaagccaaag ttaatataga gaatggagct tccagggtat    1620
aggggttggg tctgggctag ggagctggaa acctaggttt tacgcttgtc ccagttttga    1680
tgttagccct gagcagtgct gtttctcatc agcctctgcc tgctccaggg gtcacagggc    1740
caagccagat agagggctgc tagcgtcact ggacacaaga ttgctttccc acagctgtcc    1800
ttcctccagc ccctctgctc cccatccgga aacctgggta cccttcaccc acctagctct    1860
gtcccgcagt gagatttatt gctgactgcc ctgccatcta ccccagggta ataaatcagg    1920
gcagagcaga attgcaatca ccccatgcat ggagtgtata aaaggggaag gctaaggga    1980 gccacagaac ctcagtggat ctcagagaga gccccagact gagggaagca tggatggatg    2040
gagaaggatg cctcgctggg gactgctgct gctgctctgg ggctcctgta cctttggtct    2100
cccgacagac accaccacct ttaaacggta attggtaact caggcagaga aggggtggga    2160
ggggtgcagg gttcccacct tcccaacacc ctggcttttc cacatgcggt gtcattcagt    2220
ccttacgatc agctggacag ggaagtatgg acctgttcag agaggtcaag tgacttgccc    2280
aataaatgac actagtagtc aggtctagaa gctgtgactt ttgcttcctg cccagagcac    2340
catgctaact aagcactgta gagaactcag aagtattagg acatgcccct tgcacttgag    2400
gagctcacag cctgaatatt aagaagggca tgggtggttg ggcgcggtgg ctcctgcctg    2460
taatcccagc actttgggag gctgagacgg atcacttgag gtcaggagtt tgagaccagc    2520
```

-continued

```
ctggccaaca tggggaaacc ccatctctac taaaaataca aaaattagcc gggcatggtg    2580
gcaggcactt gtaatcccca gctactcggg aagctgaggc aggagaatcg tttgagcccg    2640
gaaggtggag attgctgagc caagatcgtg ccactgcact ccagcctgag tgacagaaca    2700
agactccatc tcaaaaaaaa aaaagacggg ggtcggggca tgggtacagt taactgtacc    2760
agggaagcag cttgatatcg tggttaaatg caaggcttat agagttagat tgccttcatt    2820
taaattttgc ttcactagca gaacaaacta ggtctggaat catgggcaag ttatttaacc    2880
tctccaagtc tcagtttatc attttaaaca ggtatgataa taacagtacc tacttgatgg    2940
ggctgctttg gggattttag gagataaggc atagaaagct gggcacgttg taagagccca    3000
gctactgtta gtactacagg atagattctt acaaatatca aaagcaaggt ttggccggga    3060
gcagtggctc acgcctataa tcccaacact ttgggaggcc gagggggggca gatcacccga    3120 ggtcaggagt tcaagaccag cctgaccaac atggagaaac cctgtctcta ctaaaaatac    3180
aaaattagcc gggcgtggtg gcacatgcct gtaattccag ctacttggga ggctgaggca    3240
ggagaatcgc ttgaacctgg gaggctgagg ttgcagtgag ccgacatagc gccattgcac    3300
tccagcctgg tcaacaagag caaaactcag tctaaaaaaa aaaagaaag aaaaaaacaa    3360 ggctttaggt agcccacaat tagaaggaga aaaccttagc atccctagg tgccaggcct    3420 tgtgggaaca agtgattcat taagactgta gaaggaagct gggcacgcgg ctcatgcttg    3480
taattccagc actttgagag gctgaggtgg gcagatcgct tgagctcacg agttcaagac    3540
cagcctaggc aacatggtga aaccttgtct gtacaaatac aaaaattagc taggtgtggt    3600
ggtgcaaatc tgtagtccca gctactcggg aggctgaggt gggagcatca cttcagcctg    3660
ggaggtggag gctgcagtga gcagagactg acccactgtg ctctagcctg ggtgatagag    3720
ccagacctta tgtaaaaaaa aaaaaaaaa aaaaaagac tgaagaaggg gaagagacag    3780
catttgagaa aaggcctcac agagaaaggg gttttcaatc tggggacagc agatatgacc    3840
agcagtcctg aaggtaggga ggcacacttt aataatggta atagttgcta agcctataaa    3900
atgcttaggg tgtcacagga tcttttcaca tgtctcatct caagtcatgc ccccaacaac    3960
tcagcattcc cactttgcag atgaggacac tgaggctcag ggaggtgata tgtaagaggc    4020
taagcctcaa cacacactgg gccttttgct tccgaaactg ctttcccttg ctctgaggct    4080
ctcggagagt aattgctggg ttgtgagcac tgggtaagag gatgggtgct tcaaagcagc    4140
tgcactccag gataaggta gaggaaagta aaaacatctt cccctgctgt tatccaaaag    4200 agaaaagaa tggaattggg caaggggtgg aggggaatc cagcttttga aacagtatta    4260
taggaatttt gctacccgct atgtgcagag catcatgcga ggcacttggg acagctgaat    4320
gaatgagctc cattctcaag gtgaacatgt acatatacac acctacaatt tacatttatt    4380
gagcagtggt cgcatggttt catctgcaca gtgactctga ggtaggtact accattaggc    4440
ccattgttag agaggggtta atggagactt agaagaggcc cagagaggtt aggtagcttt    4500
ctcagaatca cataagtggt aagggggattc aggcatgccc cctgcaacca ctgtcttcac    4560
caccgtacgg caccagttcc acaagctgta cagtgtgggc tgtgagaccc aaggaaaaac    4620
agagctgagg cccacgggaa ggtgaggccg gtgtgggctg gaggccttgg ggtaagcttc    4680
ctggaggtgg gggtacatgt tgggccttgg aggactaaag aactgggggg aaaaggaagg    4740
gaagaaggaa aggatttcct gaaaaggaaa tggcaagaag taaaggtcca agcataggc    4800 tgttgtgagt aaacagtggg aaatgcaacc tctttgggc caaacctctg accctccacg    4860
ttcccagctg tgaagtggga gtaataaaat catccacctt atgagagcaa ataaaataat    4920
```

```
gattgtgaaa atattttggt aacagtaacc tgtgatagga agataacaaa tcatttctgt   4980
tacaatacca tgctgatagg cataaaagtt gcattcatgt tcatgggcaa aatgggggta   5040
agtagaatgc atgggacgca agaaggatgt aggaaggaaa gggtagtgtg agtataggag   5100
gactagccac tgagaagaaa gtagaagaaa gagggaatct tgtgtgtat ggaaagtct    5160 attgcagagt caacttgggc ttccatcctg ggaccttccc gtgaacagct agagacatct   5220
tcctctgggc tttggcagcc tttatgtcgg gacccagggg accctatatg ggaaataggg   5280
ccagacacat gctctgaatc cctgcttcaa catttctgag tcacctttgt ccctgtgagc   5340
cttcattttt ctcatctata aaatggatga cagctagctt gttggtgtga tttcagtagc   5400
ggctcagtag agtcagtttc ctaggtctct ttaattctgc ctctcaaagg tgatgggaaa   5460
acatctagac aagaagccaa gggaccggga cacatctctc caaggacgag gtgcatggcg   5520
ctctgaagat gctggcatct ctctaggccc aacccagctc aggggtcca ctccaccaca   5580 gccctggctg ggtgcctgtc ccctggtatc ctggagacct tgcagctgct gtgggcatct   5640
gctgccacct agcggcctcc catggcactg tctccccgcc agccctagt tttgacaggg   5700 gcactccctg gcattaatct cttcagaggg aatgtctgtg cctgtttcct gtctgtcctc   5760
ccgccaggtg gagttcctta aaggcagtca tgatcattat cttctagct ccagtgtcca    5820 gcacagtgag gcacaaagta gttgttcagc aggtgattac ggaataaatg aatgaacgga   5880
ccaataaaca aatagccttg tctaatcaaa attaggcaac agaaggaagt cacttcaggg   5940
ttatttaatc cccgggcagc tgactcctct aaattgactc ttgacaagaa gtaactctta   6000
taaatgctcc agaggccctc agcgacagag gtgatttcca ggtggctggg ctaacgttaa   6060
aggtggttgt actaaaagca ggggtttggc ctcaggact ccaccactgt ggtggaggta    6120
cagcactttt ctattttgc ttcctccacc ctgggccagg atcttcctca agagaatgcc    6180
ctcaatccga gaaagcctga aggaacgagg tgtggacatg gccaggcttg gtcccgagtg   6240
gagccaaccc atgaagaggc tgacacttgg caacaccacc tcctcgtga tcctcaccaa    6300 ctacatggac gtgagtgctt ggctcagccc ctcgctccct ccctgtctcc tttccctcat   6360
ggacctaggg cttttctttgc tgcaagactc acccttcca agctgtgttt gacgaaggcg    6420
ctgagtagca cgtgagcacc ctagaaaatt cccatttcc agctggaaag cctgagcaca    6480
gaagacagga aggcatccag gggccattca ggggcagggt taggtttgga actcagccca   6540
ggcctcaagc caggtgtcac aggtgggtgg gaagggtgt gtgactcagg tgggggtttc    6600
tgtgacctgg cccagcacaa cctgatggct tcctgcccca gaggatcctc aagagtcaag   6660
tttgcttcct gcttcattct caatgttttg attttgccct cttgtcttac tgagactccc   6720
actttctggg atgccatggg gagatgctaa gcctcctacc agttcctgca ggaaaatgga   6780
aaccccgaga ggctatagga cctcgcctgg gccaagtctc acaccgagag ccaagagtga   6840
agccaggcaa gaccccaaga cccaaggtcc cctgagcccc tccagccctc tctttttacc   6900
cccacagacc cagtactatg gcgagattgg catcggcacc ccaccccaga ccttcaaagt   6960
cgtctttgac actggttcgt ccaatgtttg ggtgccctcc tccaagtgca gccgtctcta   7020
cactgcctgt ggtgagacct aagacccaca gtgcctctcc tccatccccc tgccctactg   7080
tgcatgagca atcctgccca acacccagct cccatccctc ttgccaccaa gggagtggct   7140
tcctctctgc ctctgtgccc actgacatgt aggggagagg ggaagatgtc tcccgttttt   7200
ctgatacagc caccaaggtt aaaaacaaaa aaggtccaa gaaccctga gcacccagaa     7260 ggccacttcc cagtcttcct gagattgaga caggactgaa ttctcaaacc catcccaggc   7320
```

```
actcggaact cttccatccc tagtcttaat caacaacctc ttactaggca cttactctgt    7380
gcctggcatc ttctctggtg ttatcagtgt tagtgattac tttaaattcc ttcatttagg    7440
acaaaattct cgatgtatgg gcacattagg agagcccaag aaacccagtc cttgattgat    7500
gaagcacata ttccaagccc cctgacccta gggccactca tccctgcacc taagctaacc    7560
agccatcccc acaatgcacc ctgcctctga gtcccctgt ctgggccact cttggacaaa    7620
cctgagcctc tgtcccctg ccagtgtatc acaagctctt cgatgcttcg gattcctcca    7680
gctacaagca caatggaaca gaactcaccc tccgctattc aacagggaca gtcagtggct    7740
ttctcagcca ggacatcatc accgtaagtt gggccgccct aggtcatctg ccccggaccc    7800
cttctgtccc caggcctctc ctgaccctcc agggcccaca cctgcgggga gtacactgc    7860
agcccacttg gagcctgggg agctgaggaa caccctactc tgccacatct ggctgttgct    7920
gcaaagcagc agtacctatg ggggagcaag cctgggctac gggctcaccg ttgggtggtt    7980
tgtgatgtt tttgcatcta acttgcatgt agggcttgtc ctgagcccg tggctgcagt    8040
caagtaactc gtccaagttc accagctctg actgggctac accctagact gaaatccagg    8100
gtcagagtca ggctgagttt tagggtcagg cataggtttt aaggtcacag ttgaggttga    8160
ctctgggact caggtcaagg cctgcttttc ttttccatgt ggcccatgtc tgaccgtttc    8220
ctcatcctgg agtttctcag gcccctgctcc atcagagtta ggggaggggc acacgtggca    8280
cctgagagga aatcagggtg attcctgcct cccttccttt ttctgtgaac tcagatataa    8340
aggagggaga agggcaagct tgtctgtgct aaagaaaccc ttcgcccatg ataagggtgg    8400
gggccaagac ccagtcctgc caggcacgaa agtctggcca ctggggaggg gaggagctct    8460
tggcagcttt tcttttgctg cttggcagga ccaccctctc agcctctgct ctccgatccc    8520
tggtcaactc tagctctctc tgggctccgc agcagagatg tgtattggca cagagtgtgt    8580
gcgtgcaggt ttgaggaaat actcttaccc cgatttctgt accctggagc atgtgtgccc    8640
ctgggatccc tagtgtggaa gcccagacca gactccaacc aaggagtggg cagtgggctt    8700
ggtctcctct ggtccttcct cccacaggtg ggtggaatca cggtgacaca gatgtttgga    8760
gaggtcacgg agatgcccgc cttacccttc atgctggccg agtttgatgg ggttgtgggc    8820
atgggcttca ttgaacaggc cattggcagg gtcaccccta tcttcgacaa catcatctcc    8880
caagggtgc taaaagagga cgtcttctct ttctactaca acaggtgggg actgggactc    8940
caagggctga ggtgggggga caggagggga gaagagatgg ggagtggaag gagagtctgg    9000
gccagaattg taaagtgttt gtaattaggt gacagccaat caatatctag agctgtacta    9060
gccaatatgg aaggcactat tgaaatttaa attaattaaa tacagttaag catcaattaa    9120
gcattcaact ggtggctctt agttgtacta gccacacgtc aaatgcctgg cagccacggt    9180
ggctagtaac tacagtctta tgacagtgca gatagagaat attcccagca tgacaggaca    9240
ttctaataga cagcgccact ctggagcaag aggagatgca aggtggggc gatggtaaat    9300
aagggattac tgtgacctgt agccctgcct gttagggcca tggctcctcc cacacagaga    9360
cagccaactt cagtcatcca ttagatcctt cattcgtttg tttgctcact catcagttca    9420
gtaaatgcta tgtgccaagc actgtggtag gctctggggg tgcagcagtg aacacagtga    9480
acaaggcaga atctgtactc ccctacccac atagagctta caggctaaca gggaagacaa    9540
gacatattcc aacataaaga gtgtcacagg caggcagcaa gtgtggtgct gaaaaccatg    9600
gatgcttttc aattctaggc tgagcttata tgcagctcag ccagccttgg ggaagctctt    9660
gagcagggtt gggctctact ccaaactgct gggcttagaa agatggcatg agttggagac    9720
```

```
aagagagctg gaggcaaaag gggctgggtg cagtggctca tgcctgtaat cccagcactt    9780
tgggaggcca aggcgagagg atcgcatgag cccaggagtt aaggcttcag tgagcagtga    9840
ttgtgccact gcactccagc taaggcaaca gagtgagatc cagtctcaaa aaaaaaaaa     9900 aaaaaaaaa agtcacaagg gtaagaacat gaggccagtg gcaaaagaa tagaggagag      9960 gatcagagtt cagagaaatc tcacagtaaa atggagagga gtctccggtt tggtgataga    10020
aagtgaggcc ttgagaaaag gccaattggc ggctctgcat tcaggggtgg tctttagaag    10080
aactgtttta gaggaagtgg gggcaaggcc agatggcaag aagttaagag gtggacgacg    10140
tgggtgtcag gaagtggagg tcatgagatg taggctgccc tggacattc aacagggaag     10200 ggaatggggg gtggcgtggg gggtgagatc cagaagcaga agaggaaggg tgggtgtttt    10260
taaatgctag aggatgctcg agtgatgcct gtaggtggag gaagaagcca atggaaagaa    10320
agagattaaa aatgtggaaa gaagaggagc taaatggggg cactggagtt tggaggcctt    10380
gaaagagatg aggttccagc agacaggaag aagccaggtt ttgcagagga gagggctggc    10440
ctcttctttt atcttgggat gggaaggagg gaacatccag agagatactg aagtgttgag    10500
agacaggcag gagggaattt gtgctagcat atacacatac attccgaatt tataaaaaca    10560
caagtagttt gcagttgcac aaaataacat atgcacacct acacacccat gcacacatgt    10620
gcatgtgtga attctagtat gaattctgga aaaacacatc acacacacag gcatgccctg    10680
gagactaggc ctacagtagt ccctgagcca agtgcagtga ggaggaaagg aaggtgaggg    10740
gaatcagctc cagacggggc accaggagcc tggctccagt cccccacttg ttcactcatg    10800
gactgggtaa cttcaggcaa gtgacttcgc ctcttggtga ctccattgcc tgaagggcaa    10860
agagagtaca taacacccac cctgccaaac agcagggctg atgaggctgg catgaaatga    10920
agcttccttt ctgctgtctc tctttctctg cagagattcc gagtaaggag acaaaacccc    10980
cacatggctg tgaccttcca gtactccccg agcacctgac ctagaattac acacgccacc    11040
ggcccaaaac tcacatcagc aagcccagcc tccgctagat gccgaagttc tctgtctctc    11100
cttcctgctc tctccatgcc acctgcccac cccatacca atagcctccc cagggtcccc     11160
tcccatgcac ctgctcaatc agcagcaacc caagagtgag gggtgtccat ttgtgtcttg    11220
ttcacatcca ctcactgtcc ttgtacctgc tcctttctg tgacctctct ggggatgctt     11280 tttggggaa cagctggact accctggaac aacctctggt tggtcttggg gaggggaaga    11340
aaggcagaga agcagtatgt tctgcatgct tcccaacgac agctccgagc ctggctgtct    11400
gtcccacatt cctctgctct agagccctct gtcctcccct gcacccttgt gcaaccttcc    11460
ccaattgcct gagttgctgg gtcctggagg ttatgggttt ccaagagctt ctgatctttc    11520
ctttaggaat tcccaatcgc tgggaggaca gattgtgctg ggaggcagcg acccccagca    11580
ttacgaaggg aatttccact atatcaacct catcaagact ggtgtctggc agattcaaat    11640
gaaggggtca gaaatcctca accctccccg ggctccaaaa aatgctgccg tcactggggt    11700
tggggagggt ggggaaggac tgcattacca tcctgccctc tttccaaatg cagccacttc    11760
ttaagcacag ccaccatttg ctctctgcct gctctgtcca ggctggggaa cagagaaggg    11820
aggggcctgg ggagaagtgg tggagggtga cagtaccttc cctcctctac tcactgcctc    11880
aacaggccac cagcgtggcc tccacccacc cacccacact caggaaggac atgcagcctg    11940
gaggtgcccc atcagccttc tgtctgtctg tctgtctgtc tgtctgactg tggcctcccc    12000
cagggtgtct gtggggtcat ccaccttgct ctgtgaagac ggctgcctgg cattggtaga    12060
caccggtgca tcctacatct caggttctac cagctccata gagaagctca tggaggcctt    12120
```

```
gggagccaag aagaggctgt ttgatgtaag aagccaaaga gggaaggtgc tgtgggtggg    12180
gggagcgcca cctggtatcg gctcacaaat cccccaggca aatgaggcca tctcaggcct    12240
tcgcttgttc acctcacact ctccacacat gtggctggtc acccatgggg cggggcactg    12300
tccccagccc tctccagcag agagaccagg ccaccagcgc aggactcctt gtctgctgag    12360
acgtcttcca tactcaagaa ggctctcttt gcccccacc ccagtatgtc gtgaagtgta     12420
acgagggccc tacactcccc gacatctctt tccacctggg aggcaaagaa tacacgctca    12480
ccagcgcgga ctatgtattt caggtgaggt tcgagtcggc ccctcggtg gcagggagaa     12540 aggctggaca gagaccctca aagagtgaca gattacaatg cacaggtcat gttagaactg    12600
tagttctcaa acttggctgt gcatgtcacc tggagagctt tgaaaaatcc tggtacctgg    12660
gccacatccc atacctatta aatcagaacc tctagaagtg gcacctgggg ttcagtttcc    12720
ccaggtgatt ccaatgtgtg gccatgtttg ggcatcacta tgcctgttcc ctcatctcca    12780 tttttctcatc aaatactccc aagaatccta tgctcctata ttcttaccct cttttcataa   12840
tcaataggct tagagaagtt gaataacttg tctaggatca gaagctaagg caaactgtaa    12900
gctcctgaag gaagcacggt gcctgatgca ttgtttgcct gggatctagc acaggggcta    12960
aacataggag tggtgcagtc cacgatgggg caaaatggcc atgatgtgag ggaggcccag    13020
tgtggctagg ggagagatgg gggcgagagg ggaatgttg ctgaagacag ttgctgggggg     13080 tcaggcaagg tgaaaggaga atgctcatgt gctgggtatg gagaaactct ccccctccct    13140
gccaggaatc ctacagtagt aaaaagctgt gcacactggc catccacgcc atggatatcc    13200
cgccacccac tggacccacc tgggccctgg gggccacctt catccgaaag ttctacacag    13260
agtttgatcg gcgtaacaac cgcattggct tcgccttggc ccgctgaggc cctctgccac    13320
ccaggcaggc cctgccttca gccctggccc agagctggaa cactctctga gatgcccctc    13380
tgcctgggct tatgccctca gatggagaca ttggatgtgg agctcctgct ggatgcgtgc    13440 cctgaccct gcaccagccc ttccctgctt tgaggacaaa gagaataaag acttcatgtt      13500
cacagcctgt tgcatctggg ttcactaggg tttagaacag agggagggc tgcgtgatca     13560 tgtgtggaca ggaatgtgac acagacaagc tacacattcg cctagcgcac aggttcttgc    13620
gtgcagggat gatgccatcc atctgccatc aacgggactc aggtggagct gtttacacaa    13680
cctcaggtgg gaagtctgaa aagagccgga accaagctcc ctctagtccc tcagggacca    13740
aggctaatgc tgtggcagta gactgtgggt cagaaagttc tcccagctca cagaagccag    13800
ctctgagttc agactctgct ctgctgagct agtcagccct gtctcttgtc cctgcaaaac    13860 tccctcagc tgtccttatc cactgcagat gccccgccc tgcccatgt agccatttac       13920 acaggcattc taaggcacta ccacctaaaa tcatagaaca ccagagatcc aggcaatact    13980
tccactttac aggtggggaa actgaggccc agagaatgga aggccttgcc caagattact    14040
cggtcaagaa tcaagtagtg aagaatactg aaagatagtg aagaatcaag actgaaccc     14100 agcccgtctg acttgggtcc tgggggtttc caccttatca taagcagttg gtaccgtcat    14160
aagtacagtg cttcacgcac gctggtacag ggccacgtgc acaagcacac aggtgcacac    14220
acacactgct atcctccatc ccatccacct gggactcgtc aggctgaagt ctcttctccc    14280
actctcactc cttgggctgt cttcaggca catgtaactt ggggaatgag aaattagcat     14340
ccacctggag ccactgaagc catccctctt caccatagtt gctcacctct cttttgacag    14400
aaagtcgtga ggcactgaat ggcccaacca ggccctcagt acctctggga gccatctgca    14460
agagtccctg tgtagcgcca agagccggag cctgggcttc agg                      14503
```

```
<210> SEQ ID NO 6
<211> LENGTH: 14502
<212> TYPE: DNA
<213> ORGANISM: Homo sapiens

<400> SEQUENCE: 6
ggtctttgta aaataataat tattcatttc acaaaagtga taattaaaag actttaatag      60
caatacagaa agttacatga atataaagac ttaacctttc taaagctcag ttttcctaag     120
taatcaaaaa cctgataaag ataacaagaa tgaggaatta tcttgagaaa atgtaaaatc     180
tttcctttta ttttttgaga cagggtctca ctctgtcatc caggctaaag tgcagtggca     240
caatcatagc tcactacagc cttgaactcc tggactcaag tgatcctccc gcctcagcct     300
ccccagtagc taagactaca ggcacgcacc accacaccca gctaattttt ttcagagatg     360
gggtcttgct atattgccct ggctggtctt gaacgagctt caagtgagcg tgagcctcct     420
acctcatcct cccaaagcac taggattaca ggcatgagcc actgtttccc agcctaaaat     480
aattgtttct taggccagct accaaaaacg caaagaaaaa ctttctgtag tgtgattgct     540
tcttcttatg ggaagcccat ttagataacc tgtaagtcaa acctgatgaa acaatactt     600 gaatgtaatc agacacagaa agactgttca aggctatgag tagctgagtc caagctcgta     660
tcacttgcca cacaacagcc aataagtcta gagacaaggt attgtggcaa ggaaagctac     720
cttattcaga gaaccagaaa accaagaaga tggtggacca gcatcataaa gaaccatctg     780
aagtcagcat gaacgttagg ctcttcttta tgttaaggga aggggaagaa gaagggatt     840 gggatcaaga ggtgactgat gaccacagac acctgggtgc cagcaagggt ctgaggacgt     900
tgtaaaactt cttttttcta ggtcaggtca caatgttcct atacatcttt aacataacat     960 tgttattgt ctgtatattt ccttatctcc ttgggggtta gttgggaa aggaactgtt    1020 accatttttt ttaaagttga actgcaagct aaactcctat aattagctgg tctatgtaca    1080
gagctaagca gaagctttta gcctaaagga taatacccct gggggtcaga ggcaaaatgg    1140
agtcagtcat gctaagtctc cctccactct ctttctttttt tgagatggaa tttcactctt    1200
attgcccagg ccgagtgca gtggcatgat ctcagctcac tgcaacctcc gcctcctggg    1260
ttcaagcaat tctcttgcct cagcctcctg agtagctgag attacaggtg tccatcacca    1320
cacccagcta atttttgtag tttagtggag atggggtttc accattgttg gtcaggctgg    1380
tctggaactc ctgacctcag gtgatctacc caccttggcc tcccaaagtg ctgggacagg    1440
tgtgagccac catgcctggc ccctctactc ttataattaa accagctgtt gcttttcctg    1500
ccaagaaacc agtcatgaag attcacccat gttctagatg ggaaaactgg gctgtagcct    1560
gggagaggcc agtcagggac aaagccaaag ttaatataga gaatggagct tccagggtat    1620
aggggttggg tctgggctag ggagctggaa acctaggttt tacgcttgtc ccagttttga    1680
tgttagccct gagcagtgct gtttctcatc agcctctgcc tgctccaggg gtcacagggc    1740
caagccagat agagggctgc tagcgtcact ggacacaaga ttgctttccc acagctgtcc    1800
ttcctccagc ccctctgctc cccatccgga aacctgggta cccttcaccc acctagctct    1860
gtcccgcagt gagattttat gctgactgcc ctgccatcta ccccagggta ataaatcagg    1920
gcagagcaga attgcaatca ccccatgcat ggagtgtata aaggggaag ggctaaggga    1980 gccacagaac ctcagtggat ctcagagaga gccccagact gagggaagca tggatggatg    2040
gagaaggatg cctcgctggg gactgctgct gctgctctgg ggctcctgta cctttggtct    2100
cccgacagac accaccacct ttaaacggta attggtaact caggcagaga aggggtggga    2160
```

```
ggggtgcagg gttcccacct tcccaacacc ctggcttttc cacatgcggt gtcattcagt   2220
ccttacgatc agctggacag ggaagtatgg acctgttcag agaggtcaag tgacttgccc   2280
aataaatgac actagtagtc aggtctagaa gctgtgactt ttgcttcctg cccagagcac   2340
catgctaact aagcactgta gagaactcag aagtattagg acatgcccct tgcacttgag   2400
gagctcacag cctgaatatt aagaagggca tgggtggttg ggcgcggtgg ctcctgcctg   2460
taatcccagc actttgggag gctgagacgg atcacttgag gtcaggagtt tgagaccagc   2520
ctggccaaca tggggaaacc ccatctctac taaaaataca aaaattagcc gggcatggtg   2580
gcaggcactt gtaatcccca gctactcggg aagctgaggc aggagaatcg tttgagcccg   2640
gaaggtggag attgctgagc caagatcgtg ccactgcact ccagcctgag tgacagaaca   2700
agactccatc tcaaaaaaaa aaaagacggg ggtcggggca tgggtacagt taactgtacc   2760
agggaagcag cttgatatcg tggttaaatg caaggcttat agagttagat tgccttcatt   2820
taaattttgc ttcactagca gaacaaacta ggtctggaat catgggcaag ttatttaacc   2880
tctccaagtc tcagtttatc attttaaaca ggtatgataa taacagtacc tacttgatgg   2940
ggctgctttg gggattttag gagataaggc atagaaagct gggcacgttg taagagccca   3000
gctactgtta gtactacagg atagattctt acaaatatca aaagcaaggt ttggccggga   3060
gcagtggctc acgcctataa tcccaacact ttgggaggcc gagggggca gatcacccga   3120 ggtcaggagt tcaagaccag cctgaccaac atggagaaac cctgtctcta ctaaaaatac   3180
aaaattagcc gggcgtggtg gcacatgcct gtaattccag ctacttggga ggctgaggca   3240
ggagaatcgc ttgaacctgg gaggctgagg ttgcagtgag ccgacatagc gccattgcac   3300
tccagcctgg tcaacaagag caaaactcag tctaaaaaaa aaaagaaag aaaaaaacaa   3360 ggctttaggt agcccacaat tagaaggaga aaaccttagc atccctagg tgccaggcct   3420 tgtgggaaca agtgattcat taagactgta aaggaagct gggcacgcgg ctcatgcttg   3480
taattccagc actttgagag gctgaggtgg gcagatcgct tgagctcacg agttcaagac   3540
cagcctaggc aacatggtga aaccttgtct gtacaaatac aaaaattagc taggtgtggt   3600
ggtgcaaatc tgtagtccca gctactcggg aggctgaggt gggagcatca cttcagcctg   3660
ggaggtggag gctgcagtga gcagagactg acccactgtg ctctagcctg ggtgatagag   3720
ccagacctta tgtaaaaaaa aaaaaaaaa aaaaaagac tgaagaaggg gaagagacag   3780
catttgagaa aaggcctcac agagaaaggg gtttcaatc tggggacagc agatatgacc   3840
agcagtcctg aaggtaggga ggcacacttt aataatggta atagttgcta agcctataaa   3900
atgcttaggg tgtcacagga tcttttcaca tgtctcatct caagtcatgc cccaacaac    3960 tcagcattcc cactttgcag atgaggacac tgaggctcag ggaggtgata tgtaagaggc    4020
taagcctcaa cacacactgg gccttttgct tccgaaactg ctttcccttg ctctgaggct    4080 ctcgagagt aattgctggg ttgtgagcac tgggtaagag gatgggtgct tcaaagcagc    4140
tgcactccag gataaaggta gaggaaagta aaacatcttc ccctgctgt tatccaaaag    4200 agaaaaagaa tggaattggg caaggggtgg aggggaatc cagctttga aacagtatta    4260 taggaatttt gctacccgct atgtgcagag catcatgcga ggcacttggg acagctgaat    4320
gaatgagctc cattctcaag gtgaacatgt acatatacac acctacaatt tacatttatt    4380
gagcagtggt cgcatggttt catctgcaca gtgactctga ggtaggtact accattaggc    4440
ccattgttag agagggggtta atggagactt agaagaggcc cagagaggtt aggtagcttt    4500
ctcagaatca cataagtggt aaggggattc aggcatgccc cctgcaacca ctgtcttcac    4560
```

```
caccgtacgg caccagttcc acaagctgta cagtgtgggc tgtgagaccc aaggaaaaac   4620
agagctgagg cccacgggaa ggtgaggccg gtgtgggctg gaggccttgg ggtaagcttc   4680
ctggaggtgg gggtacatgt tgggccttgg aggactaaag aactgggggg aaaaggaagg   4740
gaagaaggaa aggattttct gaaaaggaaa tggcaagaag taaaggtcca aagcataggc   4800
tgttgtgagt aaacagtggg aaatgcaacc tctttgggc caaacctctg accctccacg    4860
ttcccagctg tgaagtggga gtaataaaat catccacctt atgagagcaa ataaataat    4920 gattgtgaaa atattttggt aacagtaacc tgtgatagga agataacaaa tcatttctgt   4980
tacaatacca tgctgatagg cataaaagtt gcattcatgt tcatgggcaa aatgggggta   5040
agtagaatgc atgggacgca agaaggatgt aggaaggaaa gggtagtgtg agtataggag   5100
gactagccac tgagaagaaa gtagaagaaa gagggaatct ttgtgtgtat gggaaagtct   5160
attgcagagt caacttgggc ttccatcctg ggaccttccc gtgaacagct agagacatct   5220
tcctctgggc tttggcagcc tttatgtcgg gacccagggg accctatatg ggaaataggg   5280
ccagacacat gctctgaatc cctgcttcaa catttctgag tcacctttgt ccctgtgagc   5340 cttcatttt ctcatctata aaatggatga cagctagctt gttggtgtga tttcagtagc    5400
ggctcagtag agtcagtttc ctaggtctct ttaattctgc ctctcaaagg tgatgggaaa   5460
acatctagac aagaagccaa gggaccggga cacatctctc caaggacgag gtgcatggcg   5520
ctctgaagat gctggcatct ctctaggccc aacccagctc agggggtcca ctccaccaca   5580
gccctggctg ggtgcctgtc ccctggtatc ctggagacct tgcagctgct gtgggcatct   5640
gctgccacct agcggcctcc catggcactg tctccccgcc agccctagt tttgacaggg    5700 gcactccctg gcattaatct cttcagaggg aatgtctgtg cctgtttcct gtctgtcctc   5760
ccgccaggtg gagttcctta aaggcagtca tgatcattat ctttctagct ccagtgtcca   5820
gcacagtgag gcacaaagta gttgttcagc aggtgattac ggaataaatg aatgaacgga   5880
ccaataaaca aatagccttg tctaatcaaa attaggcaac agaaggaagt cacttcaggg   5940
ttatttaatc cccgggcagc tgactcctct aaattgactc ttgacaagaa gtaactctta   6000
taaatgctcc agaggccctc agcgacagag gtgatttcca ggtggctggg ctaacgttaa   6060
aggtggttgt actaaaagca ggggtttggc ctcaggact ccaccactgt ggtggaggta    6120 cagcacttt ctattttgc ttcctccacc ctgggccagg atcttcctca agagaatgcc     6180
ctcaatccga gaaagcctga aggaacgagg tgtggacatg gccaggcttg gtcccgagtg   6240
gagccaaccc atgaagaggc tgacacttgg caacaccacc tcctccgtga tcctcaccaa   6300
ctacatggac gtgagtgctt ggctcagccc ctcgctccct ccctgtctcc tttccctcat   6360
ggacctaggg cttttctttgc tgcaagactc accctttcca agctgtgttt gacgaaggcg   6420
ctgagtagca cgtgagcacc ctagaaaatt cccattttcc agctggaaag cctgagcaca   6480
gaagacagga aggcatccag gggccattca ggggcaggg taggtttgga actcagccca    6540
ggcctcaagc caggtgtcac aggtgggtgg aaggggtgt gtgactcagg tgggggtttc    6600
tgtgacctgg cccagcacaa cctgatggct tcctgcccca gaggatcctc aagagtcaag   6660
tttgcttcct gcttcattct caatgttttg attttgccct cttgtcttac tgagactccc   6720
actttctggg atgccatggg gagatgctaa gcctcctacc agttcctgca ggaaaatgga   6780
aaccccgaga ggctatagga cctcgcctgg gccaagtctc acaccgagag ccaagagtga   6840
agccaggcaa gaccccaaga cccaaggtcc cctgagcccc tccagccctc tcttttacc    6900 cccacagacc cagtactatg gcgagattgg catcggcacc ccaccccaga ccttcaaagt   6960
```

```
cgtctttgac actggttcgt ccaatgtttg ggtgccctcc tccaagtgca gccgtctcta    7020
cactgcctgt ggtgagacct aagacccaca gtgcctctcc tccatccccc tgccctactg    7080
tgcatgagca atcctgccca cacccagct cccatccctc ttgccaccaa gggagtggct     7140
tcctctctgc ctctgtgccc actgacatgt aggggagagg ggaagatgtc tcccgttttt    7200
ctgatacagc caccaaggtt aaaaacaaaa aaaggtccaa gaaccsctga gcacccagaa    7260
ggccacttcc cagtcttcct gagattgaga caggactgaa ttctcaaacc catcccaggc    7320
actcggaact cttccatccc tagtcttaat caacaacctc ttactaggca cttactctgt    7380
gcctggcatc ttctctggtg ttatcagtgt tagtgattac tttaaattcc ttcatttagg    7440
acaaaattct cgatgtatgg gcacattagg agagcccaag aaacccagtc cttgattgat    7500
gaagcacata ttccaagccc cctgacccta gggccactca tccctgcacc taagctaacc    7560
agccataccc acaatgcacc ctgcctctga gtccccctgt ctgggccact cttggacaaa    7620
cctgagcctc tgtcccctg ccagtgtatc acaagctctt cgatgcttcg gattcctcca     7680
gctacaagca caatggaaca gaactcaccc tccgctattc aacagggaca gtcagtggct    7740
ttctcagcca ggacatcatc accgtaagtt gggccgccct aggtcatctg ccccggaccc    7800
cttctgtccc caggcctctc ctgacccctcc agggcccaca cctgcgggga ggtacactgc   7860
agcccacttg gagcctgggg agctgaggaa caccctactc tgccacatct ggctgttgct    7920
gcaaagcagc agtacctatg ggggagcaag cctgggctac gggctcaccg ttgggtggtt    7980
tgtggatgtt tttgcatcta acttgcatgt agggcttgtc ctgagcccccg tggctgcagt   8040
caagtaactc gtccaagttc accagctctg actgggctac accctagact gaaatccagg    8100
gtcagagtca ggctgagttt tagggtcagg cataggtttt aaggtcacag ttgaggttga    8160
ctctgggact caggtcaagg cctgcttttc ttttccatgt ggcccatgtc tgaccgtttc    8220
ctcatcctgg agtttctcag gccctgctcc atcagagtta ggggagggc acacgtggca    8280
cctgagagga aatcagggtg attcctgcct cccttccttt ttctgtgaac tcagatataa    8340
aggagggaga agggcaagct tgtctgtgct aaagaaaccc ttcgcccatg ataagggtgg    8400
gggccaagac ccagtcctgc caggcacgaa agtctggcca ctggggaggg gaggagctct    8460
tggcagcttt tcttttgctg cttggcagga ccaccctctc agcctctgct ctccgatccc    8520
tggtcaactc tagctctctc tgggctccgc agcagagatg tgtattggca cagagtgtgt    8580
gcgtgcaggg ttgaggaaat actcttaccc cgatttctgt accctggagc atgtgtgccc    8640
ctgggatccc tagtgtggaa gcccagacca gactccaacc aaggagtggg cagtgggctt    8700
ggtctcctct ggtccttcct cccacaggtg ggtggaatca cggtgacaca gatgtttgga    8760
gaggtcacgg agatgcccgc cttacccttc atgctggccg agtttgatgg ggttgtgggc    8820
atgggcttca ttgaacaggc cattggcagg gtcacccccta tcttcgacaa catcatctcc    8880
caaggggtgc taaaagagga cgtcttctct ttctactaca caggtggggg actgggactc    8940
caagggctga ggtgggggga caggagggga gaagagatgg ggagtggaag gagagtctgg    9000
gccagaattg taaagtgttt gtaattaggt gacagccaat caatatctag agctgtacta    9060
gccaatatgg aaggcactat tgaaatttaa attaattaaa tacagttaag catcaattaa    9120
gcattcaact ggtggctctt agttgtacta gccacacgtc aaatgcctgg cagccacggt    9180
ggctagtaac tacagtctta tgacagtgca gatagagaat attcccagca tgacaggaca    9240
ttctaataga cagcgccact ctggagcaag aggagatgca aggtggggc gatggtaaat     9300
aagggattac tgtgaccctgt agccctgcct gttagggcca tggctcctcc cacacagaga   9360
```

```
cagccaactt cagtcatcca ttagatcctt cattcgtttg tttgctcact catcagttca   9420
gtaaatgcta tgtgccaagc actgtggtag gctctggggg tgcagcagtg aacacagtga   9480
acaaggcaga atctgtactc ccctacccac atagagctta caggctaaca gggaagacaa   9540
gacatattcc aacataaaga gtgtcacagg caggcagcaa gtgtggtgct gaaaaccatg   9600
gatgcttttc aattctaggc tgagcttata tgcagctcag ccagccttgg ggaagctctt   9660
gagcagggtt gggctctact ccaaactgct gggcttagaa agatggcatg agttggagac   9720
aagagagctg gaggcaaaag gggctgggtg cagtggctca tgcctgtaat cccagcactt   9780
tgggaggcca aggcgagagg atcgcatgag cccaggagtt aaggcttcag tgagcagtga   9840
ttgtgccact gcactccagc taaggcaaca gagtgagatc cagtctcaaa aaaaaaaaa   9900 aaaaaaaaa agtcacaagg gtaagaacat gaggccagtg gcaaaagaa tagaggagag   9960 gatcagagtt cagagaaatc tcacagtaaa atggagagga gtctccggtt tggtgataga  10020
aagtgaggcc ttgagaaaag gccaattggc ggctctgcat tcaggggtgg tctttagaag  10080
aactgtttta gaggaagtgg gggcaaggcc agatggcaag aagttaagag gtggacgacg  10140
tgggtgtcag gaagtggagg tcatgagatg taggctgccc tgggacattc aacagggaag  10200
ggaatggggg gtggcgtggg gggtgagatc cagaagcaga agaggaaggg tgggtgtttt  10260
taaatgctag aggatgctcg agtgatgcct gtaggtggag gaagaagcca atggaaagaa  10320
agagattaaa aatgtggaaa gaagaggagc taaatggggg cactggagtt tggaggcctt  10380
gaaagagatg aggttccagc agacaggaag aagccaggtt ttgcagagga gagggctggc  10440
ctcttctttt atcttgggat gggaaggagg gaacatccag agagatactg aagtgttgag  10500
agacaggcag gagggaattt gtgctagcat atacacatac attccgaatt tataaaaaca  10560
caagtagttt gcagttgcac aaaataacat atgcacacct acacacccat gcacacatgt  10620
gcatgtgtga attctagtat gaattctgga aaaacacatc acacacacag gcatgccctg  10680
gagactaggc ctacagtagt ccctgagcca agtgcagtga ggaggaaagg aaggtgaggg  10740
gaatcagctc cagacggggc accaggagcc tggctccagt cccccacttg ttcactcatg  10800
gactgggtaa cttcaggcaa gtgacttcgc ctcttggtga ctccattgcc tgaagggcaa  10860
agagagtaca taacacccac cctgccaaac agcagggctg atgaggctgg catgaaatga  10920
agcttccttt ctgctgtctc tctttctctg cagagattcc gagtaaggag acaaaacccc  10980
cacatggctg tgaccttcca gtactcccg agcacctgac ctagaattac acacgccacc  11040
ggcccaaaac tcacatcagc aagcccagcc tccgctagat gccgaagttc tctgtctctc  11100
cttcctgctc tctccatgcc acctgccac cccatacca atagcctccc cagggtcccc  11160
tcccatgcac ctgctcaatc agcagcaacc caagagtgag gggtgtccat ttgtgtcttg  11220
ttcacatcca ctcactgtcc ttgtacctgc tccttttctg tgacctctct ggggatgctt  11280
tttgggggaa cagctggact accctggaac aacctctggt tggtcttggg gagggaaga  11340 aaggcagaga agcagtatgt tctgcatgct tcccaacgac agctccgagc ctggctgtct  11400
gtcccacatt cctctgctct agagccctct gtcctcccct gcacccttgt gcaaccttcc  11460
ccaattgcct gagttgctgg gtcctggagg ttatgggttt ccaagagctt ctgatctttc  11520
ctttaggaat tcccaatcgc tgggaggaca gattgtgctg ggaggcagcg acccccagca  11580
ttacgaaggg aatttccact atatcaacct catcaagact ggtgtctggc agattcaaat  11640
gaaggggtca gaaatcctca accctccccg ggctccaaaa aatgctgccg tcactgggt  11700 tggggagggt gggaaggac tgcattacca tcctgccctc tttccaaatg cagccacttc  11760
```

-continued

```
ttaagcacag ccaccatttg ctctctgcct gctctgtcca ggctgggaa cagagaaggg     11820 aggggcctgg ggagaagtgg tggagggtga cagtaccttc cctcctctac tcactgcctc    11880
aacaggccac cagcgtggcc tccacccacc cacccacact caggaaggac atgcagcctg    11940
gaggtgcccc atcagccttc tgtctgtctg tctgtctgtc tgtctgactg tggcctcccc    12000
cagggtgtct gtgggtcat ccaccttgct ctgtgaagac ggctgcctgg cattggtaga    12060
caccggtgca tcctacatct caggttctac cagctccata gagaagctca tggaggcctt    12120
gggagccaag aagaggctgt ttgatgtaag aagccaaaga gggaaggtgc tgtgggtggg    12180
gggagcgcca cctggtatcg gctcacaaat cccccaggca aatgaggcca tctcaggcct    12240
tcgcttgttc acctcacact ctccacacat gtggctggtc acccatgggg cggggcactg    12300
tccccagccc tctccagcag agagaccagg ccaccagcgc aggactcctt gtctgctgag    12360
acgtcttcca tactcaagaa ggctctcttt gccccccacc ccagtatgtc gtgaagtgta    12420
acgagggccc tacactcccc gacatctctt tccacctggg aggcaaagaa tacacgctca    12480
ccagcgcgga ctatgtattt caggtgaggt tcgagtcggc cccctcggtg gcagggagaa    12540
aggctggaca gagacccctca aagagtgaca gattacaatg cacaggtcat gttagaactg    12600
tagttctcaa acttggctgt gcatgtcacc tggagagctt tgaaaaatcc tggtacctgg    12660
gccacatccc atacctatta aatcagaacc tctagaagtg gcacctgggg ttcagtttcc    12720
ccaggtgatt ccaatgtgtg gccatgtttg gcatcacta tgcctgttcc ctcatctcca    12780
ttttctcatc aaatactccc aagaatccta tgctcctata ttcttacccct cttttcataa    12840 tcaataggct tagagaagtt gaataacttg tctaggatca gaagctaagg caaactgtaa    12900
gctcctgaag gaagcacggt gcctgatgca ttgtttgcct gggatctagc acaggggcta    12960
aacataggag tggtgcagtc cacgatgggg caaaatggcc atgatgtgag ggaggcccag    13020
tgtggctagg ggagagatgg gggcgagagg ggaatgttg ctgaagacag ttgctggggt    13080
caggcaaggt gaaaggagaa tgctcatgtg ctgggtatgg agaaactctc ccccttcctg    13140
ccaggaatcc tacagtagta aaaagctgtg cacactggcc atccacgcca tggatatccc    13200
gccacccact ggacccacct gggccctggg ggccaccttc atccgaaagt tctacacaga    13260
gtttgatcgg cgtaacaacc gcattggctt cgccttggcc cgctgaggcc ctctgccacc    13320
caggcaggcc ctgccttcag ccctggccca gagctggaac actctctgag atgcccctct    13380
gcctgggctt atgccctcag atggagacat tggatgtgga gctcctgctg gatgcgtgcc    13440 ctgaccctg caccagccct tccctgcttt gaggacaaag agaataaaga cttcatgttc    13500
acagcctgtt gcatctgggt tcactagggt ttagaacaga gggaggggct gcgtgatcat    13560
gtgtggacag gaatgtgaca cagacaagct acacattcgc ctagcgcaca ggttcttgcg    13620
tgcagggatg atgccatcca tctgccatca acgggactca ggtggagctg tttacacaac    13680
ctcaggtggg aagtctgaaa agagccggaa ccaagctccc tctagtccct cagggaccaa    13740
ggctaatgct gtggcagtag actgtgggtc agaaagttct cccagctcac agaagccagc    13800
tctgagttca gactctgctc tgctgagcta gtcagccctg tctcttgtcc ctgcaaaact    13860 ccctcagct gtccttatcc actgcagatg cccccgccct gccccatgta gccatttaca    13920
caggcattct aaggcactac cacctaaaat catagaacac cagagatcca ggcaatactt    13980
ccactttaca ggtggggaaa ctgaggccca gagaatggaa ggccttgccc aagattactc    14040
ggtcaagaat caagtagtga agaatactga aagatagtga agaatcaaga ctggaaccca    14100
gcccgtctga cttgggtcct gggggtttcc accttatcat aagcagttgg taccgtcata    14160
```

-continued

```
agtacagtgc ttcacgcacg ctggtacagg gccacgtgca caagcacaca ggtgcacaca    14220
cacactgcta tcctccatcc catccacctg ggactcgtca ggctgaagtc tcttctccca    14280
ctctcactcc ttgggctgtc ttcagggcac atgtaacttg gggaatgaga aattagcatc    14340
cacctggagc cactgaagcc atccctcttc accatagttc ctcacctctc ttttgacaga    14400
aagtcgtgag gcactgaatg gcccaaccag gccctcagta cctctgggag ccatctgcaa    14460
gagtccctgt gtagcgccaa gagccggagc ctgggcttca gg                      14502
```

<210> SEQ ID NO 7
<211> LENGTH: 14503
<212> TYPE: DNA
<213> ORGANISM: Homo sapiens
<220> FEATURE:
<221> NAME/KEY: misc_feature
<222> LOCATION: (10096)..(10096)
<223> OTHER INFORMATION: wherein "n" equals either an "A" or "G".
<220> FEATURE:
<221> NAME/KEY: misc_feature
<222> LOCATION: (12586)..(12586)
<223> OTHER INFORMATION: wherein "n" equals either a "G" or an "A".
<220> FEATURE:
<221> NAME/KEY: misc_feature
<222> LOCATION: (13076)..(13076)
<223> OTHER INFORMATION: wherein "n" equals either a "G" or wherein the
      nucleotide at this position is deleted.

<400> SEQUENCE: 7

```
ggtctttgta aaataataat tattcatttc acaaaagtga taattaaaag actttaatag      60
caatacagaa agttacatga atataaagac ttaacctttc taaagctcag ttttcctaag     120
taatcaaaaa cctgataaag ataacaagaa tgaggaatta tcttgagaaa atgtaaaatc     180 tttccttta ttttttgaga cagggtctca ctctgtcatc caggctaaag tgcagtggca     240
caatcatagc tcactacagc cttgaactcc tggactcaag tgatcctccc gcctcagcct     300
ccccagtagc taagactaca ggcacgcacc accacaccca gctaattttt ttcagagatg     360
gggtcttgct atattgccct ggctggtctt gaacgagctt caagtgagcg tgagcctcct     420
acctcatcct cccaaagcac taggattaca ggcatgagcc actgtttccc agcctaaaat     480
aattgtttct taggccagct accaaaaacg caaagaaaaa cttctctgtag tgtgattgct     540 tcttcttatg ggaagcccat ttagataacc tgtaagtcaa acctgatgaa acaatactt      600 gaatgtaatc agacacagaa agactgttca aggctatgag tagctgagtc caagctcgta     660
tcacttgcca cacaacagcc aataagtcta gagacaaggt attgtggcaa ggaaagctac     720
cttattcaga gaaccagaaa accaagaaga tggtggacca gcatcataaa gaaccatctg     780
aagtcagcat gaacgttagg ctcttcttta tgttaaggga aggggaagaa gaagggggatt     840 gggatcaaga ggtgactgat gaccacagac acctgggtgc cagcaagggt ctgaggacgt     900
tgtaaaactt cttttttcta ggtcaggtca caatgttcct atacatcttt aacataacat     960
tgttatttgt ctgtatattt ccttatctcc ttggggggtta gtttggggaa aggaactgtt    1020
accatttttt ttaaagttga actgcaagct aaactcctat aattagctgg tctatgtaca    1080
gagctaagca gaagctttta gcctaaagga taatacccct gggggtcaga ggcaaaatgg    1140
agtcagtcat gctaagtctc cctccactct cttttctttt tgagatggaa tttcactctt    1200
attgcccagg ccggagtgca gtggcatgat ctcagctcac tgcaacctcc gcctcctggg    1260
ttcaagcaat tctcttgcct cagcctcctg agtagctgag attacaggtg tccatcacca    1320 caccccagcta atttttgtag tttagtggag atggggtttc accattgttg gtcaggctgg    1380
```

```
tctggaactc ctgacctcag gtgatctacc caccttggcc tcccaaagtg ctgggacagg    1440
tgtgagccac catgcctggc ccctctactc ttataattaa accagctgtt gcttttcctg    1500
ccaagaaacc agtcatgaag attcacccat gttctagatg ggaaaactgg gctgtagcct    1560
gggagaggcc agtcagggac aaagccaaag ttaatataga gaatggagct tccagggtat    1620
aggggttggg tctgggctag ggagctggaa acctaggttt tacgcttgtc ccagttttga    1680
tgttagccct gagcagtgct gtttctcatc agcctctgcc tgctccaggg gtcacagggc    1740
caagccagat agagggctgc tagcgtcact ggacacaaga ttgctttccc acagctgtcc    1800
ttcctccagc ccctctgctc cccatccgga aacctgggta cccttcaccc acctagctct    1860
gtcccgcagt gagatttatt gctgactgcc ctgccatcta ccccagggta ataaatcagg    1920
gcagagcaga attgcaatca ccccatgcat ggagtgtata aaaggggaag ggctaaggga    1980
gccacagaac ctcagtggat ctcagagaga gccccagact gagggaagca tggatggatg    2040
gagaaggatg cctcgctggg gactgctgct gctgctctgg ggctcctgta cctttggtct    2100
cccgacagac accaccacct ttaaacggta attggtaact caggcagaga aggggtggga    2160
ggggtgcagg gttcccacct tcccaacacc ctggcttttc cacatgcggt gtcattcagt    2220
ccttacgatc agctggacag ggaagtatgg acctgttcag agaggtcaag tgacttgccc    2280
aataaatgac actagtagtc aggtctagaa gctgtgactt tgcttcctg cccagagcac     2340 catgctaact aagcactgta gagaactcag aagtattagg acatgcccct tgcacttgag    2400
gagctcacag cctgaatatt aagaagggca tgggtggttg ggcgcggtgg ctcctgcctg    2460
taatcccagc actttgggag gctgagacgg atcacttgag gtcaggagtt tgagaccagc    2520
ctggccaaca tggggaaacc ccatctctac taaaaataca aaaattagcc gggcatggtg    2580
gcaggcactt gtaatcccca gctactcggg aagctgaggc aggagaatcg tttgagcccg    2640
gaaggtggag attgctgagc caagatcgtg ccactgcact ccagcctgag tgacagaaca    2700
agactccatc tcaaaaaaaa aaaagacggg ggtcggggca tgggtacagt taactgtacc    2760
agggaagcag cttgatatcg tggttaaatg caaggcttat agagttagat tgccttcatt    2820
taaattttgc ttcactagca gaacaaacta ggtctggaat catgggcaag ttatttaacc    2880
tctccaagtc tcagtttatc attttaaaca ggtatgataa taacagtacc tacttgatgg    2940
ggctgctttg gggatttag gagataaggc atagaaagct gggcacgttg taagagccca     3000
gctactgtta gtactacagg atagattctt acaaatatca aaagcaaggt ttggccggga    3060
gcagtggctc acgcctataa tcccaacact ttgggaggcc gagggggca gatcacccga     3120 ggtcaggagt tcaagaccag cctgaccaac atggagaaac cctgtctcta ctaaaaatac    3180
aaaattagcc gggcgtggtg gcacatgcct gtaattccag ctacttggga ggctgaggca    3240
ggagaatcgc ttgaacctgg gaggctgagg ttgcagtgag ccgacatagc gccattgcac    3300
tccagcctgg tcaacaagag caaaactcag tctaaaaaaa aaaagaaag aaaaaaacaa     3360 ggctttaggt agcccacaat tagaaggaga aaaccttagc atcccctagg tgccaggcct    3420
tgtgggaaca agtgattcat taagactgta gaaggaagct gggcacgcgg ctcatgcttg    3480
taattccagc actttgagag gctgaggtgg gcagatcgct tgagctcacg agttcaagac    3540
cagcctaggc aacatggtga aaccttgtct gtacaaatac aaaaattagc taggtgtggt    3600
ggtgcaaatc tgtagtccca gctactcggg aggctgaggt gggagcatca cttcagcctg    3660
ggaggtggag gctgcagtga gcagagactg acccactgtg ctctagcctg ggtgatagag    3720
ccagacctta tgtaaaaaaa aaaaaaaaaa aaaaaagac tgaagaaggg gaagagacag     3780
```

```
catttgagaa aaggcctcac agagaaaggg gttttcaatc tggggacagc agatatgacc    3840
agcagtcctg aaggtaggga ggcacacttt aataatggta atagttgcta agcctataaa    3900
atgcttaggg tgtcacagga tcttttcaca tgtctcatct caagtcatgc ccccaacaac    3960
tcagcattcc cactttgcag atgaggacac tgaggctcag ggaggtgata tgtaagaggc    4020
taagcctcaa cacacactgg gccttttgct tccgaaactg ctttcccttg ctctgaggct    4080
ctcggagagt aattgctggg ttgtgagcac tgggtaagag gatgggtgct tcaaagcagc    4140
tgcactccag gataaaggta gaggaaagta aaaacatctt ccctgctgt tatccaaaag    4200
agaaaaagaa tggaattggg caaggggtgg aggggga atc cagcttttga aacagtatta    4260
taggaatttt gctacccgct atgtgcagag catcatgcga ggcacttggg acagctgaat    4320
gaatgagctc cattctcaag gtgaacatgt acatatacac acctacaatt tacatttatt    4380
gagcagtggt cgcatggttt catctgcaca gtgactctga ggtaggtact accattaggc    4440
ccattgttag agaggggtta atggagactt agaagaggcc cagagaggtt aggtagcttt    4500
ctcagaatca cataagtggt aaggggattc aggcatgccc cctgcaacca ctgtcttcac    4560
caccgtacgg caccagttcc acaagctgta cagtgtgggc tgtgagaccc aaggaaaaac    4620
agagctgagg cccacgggaa ggtgaggccg gtgtgggctg gaggccttgg ggtaagcttc    4680
ctggaggtgg gggtacatgt tgggccttgg aggactaaag aactgggggg aaaaggaagg    4740
gaagaaggaa aggattttct gaaaaggaaa tggcaagaag taaaggtcca agcataggc    4800
tgttgtgagt aaacagtggg aaatgcaacc tctttgggc caaacctctg accctccacg    4860
ttcccagctg tgaagtggga gtaataaaat catccacctt atgagagcaa ataaaataat    4920
gattgtgaaa atattttggt aacagtaacc tgtgatagga agataacaaa tcatttctgt    4980
tacaatacca tgctgatagg cataaaagtt gcattcatgt tcatgggcaa aatgggggta    5040
agtagaatgc atgggacgca agaaggatgt aggaaggaaa gggtagtgtg agtataggag    5100
gactagccac tgagaagaaa gtagaagaaa gagggaatct ttgtgtgtat gggaaagtct    5160
attgcagagt caacttgggc ttccatcctg ggaccttccc gtgaacagct agagacatct    5220
tcctctgggc tttggcagcc tttatgtcgg gacccagggg accctatatg ggaaataggg    5280
ccagacacat gctctgaatc cctgcttcaa catttctgag tcacctttgt ccctgtgagc    5340
cttcatttt ctcatctata aaatggatga cagctagctt gttggtgtga tttcagtagc    5400
ggctcagtag agtcagtttc ctaggtctct ttaattctgc ctctcaaagg tgatgggaaa    5460
acatctagac aagaagccaa gggaccggga cacatctctc caaggacgag gtgcatggcg    5520
ctctgaagat gctggcatct tctaggccc aacccagctc aggggtcca ctccaccaca    5580
gccctggctg ggtgcctgtc ccctggtatc ctggagacct tgcagctgct gtgggcatct    5640
gctgccacct agcggcctcc catggcactg tctccccgcc agcccctagt tttgacaggg    5700
gcactccctg gcattaatct cttcagaggg aatgtctgtg cctgtttcct gtctgtcctc    5760
ccgccaggtg gagttcctta aaggcagtca tgatcattat ctttctagct ccagtgtcca    5820
gcacagtgag gcacaaagta gttgttcagc aggtgattac ggaataaatg aatgaacgga    5880
ccaataaaca aatagccttg tctaatcaaa attaggcaac agaaggaagt cacttcaggg    5940
ttatttaatc cccgggcagc tgactcctct aaattgactc ttgacaagaa gtaactctta    6000
taaatgctcc agaggccctc agcgacagag gtgatttcca ggtggctggg ctaacgttaa    6060
aggtggttgt actaaaagca ggggtttggc ctcaggagact ccaccactgt ggtggaggta    6120
cagcactttt ctattttttgc ttcctccacc ctgggccagg atcttcctca agagaatgcc    6180
```

```
ctcaatccga gaaagcctga aggaacgagg tgtggacatg gccaggcttg gtcccgagtg    6240
gagccaaccc atgaagaggc tgacacttgg caacaccacc tcctccgtga tcctcaccaa    6300
ctacatggac gtgagtgctt ggctcagccc ctcgctccct ccctgtctcc tttccctcat    6360
ggacctaggg ctttctttgc tgcaagactc acccctttcca agctgtgttt gacgaaggcg   6420
ctgagtagca cgtgagcacc ctagaaaatt cccattttcc agctggaaag cctgagcaca    6480
gaagacagga aggcatccag gggccattca ggggcagggt taggtttgga actcagccca    6540
ggcctcaagc caggtgtcac aggtgggtgg aagggggtgt gtgactcagg tgggggtttc    6600
tgtgacctgg cccagcacaa cctgatggct tcctgcccca gaggatcctc aagagtcaag    6660
tttgcttcct gcttcattct caatgttttg attttgccct cttgtcttac tgagactccc    6720
actttctggg atgccatggg gagatgctaa gcctcctacc agttcctgca ggaaaatgga    6780
aaccccgaga ggctatagga cctcgcctgg gccaagtctc acaccgagag ccaagagtga    6840
agccaggcaa gaccccaaga cccaaggtcc cctgagcccc tccagccctc tcttttttacc   6900
cccacagacc cagtactatg gcgagattgg catcggcacc ccaccccaga ccttcaaagt    6960
cgtctttgac actggttcgt ccaatgtttg ggtgccctcc tccaagtgca gccgtctcta    7020
cactgcctgt ggtgagacct aagacccaca gtgcctctcc tccatccccc tgccctactg    7080
tgcatgagca atcctgccca cacccagct cccatccctc ttgccaccaa gggagtggct     7140
tcctctctgc ctctgtgccc actgacatgt aggggagagg ggaagatgtc tcccgttttt    7200
ctgatacagc caccaaggtt aaaaacaaaa aaggtccaa gaacccctga gcacccagaa     7260
ggccacttcc cagtcttcct gagattgaga caggactgaa ttctcaaacc catcccaggc    7320
actcggaact cttccatccc tagtcttaat caacaacctc ttactaggca cttactctgt    7380
gcctggcatc ttctctggtg ttatcagtgt tagtgattac tttaaattcc ttcatttagg    7440
acaaaattct cgatgtatgg gcacattagg agagcccaag aaacccagtc cttgattgat    7500
gaagcacata ttccaagccc cctgacccta gggccactca tccctgcacc taagctaacc    7560
agccataccc acaatgcacc ctgcctctga gtccccctgt ctgggccact cttggacaaa    7620
cctgagcctc tgtcccctg ccagtgtatc acaagctctt cgatgcttcg gattcctcca    7680
gctacaagca caatggaaca gaactcaccc tccgctattc aacagggaca gtcagtggct    7740
ttctcagcca ggacatcatc accgtaagtt gggccgccct aggtcatctg ccccggaccc    7800
cttctgtccc caggcctctc ctgaccctcc agggcccaca cctgcgggga ggtacactgc    7860
agcccacttg gagcctgggg agctgaggaa caccctactc tgccacatct ggctgttgct    7920
gcaaagcagc agtacctatg ggggagcaag cctgggctac gggctcaccg ttgggtggtt    7980
tgtggatgtt tttgcatcta acttgcatgt agggcttgtc ctgagcccg tggctgcagt     8040
caagtaactc gtccaagttc accagctctg actgggctac accctagact gaaatccagg    8100
gtcagagtca ggctgagttt tagggtcagg cataggtttt aaggtcacag ttgaggttga    8160
ctctgggact caggtcaagg cctgcttttc ttttccatgt ggcccatgtc tgaccgtttc    8220
ctcatcctgg agtttctcag gccctgctcc atcagagtta ggggaggggc acacgtggca    8280
cctgagagga aatcagggtg attcctgcct cccttccttt ttctgtgaac tcagatataa    8340
aggagggaga agggcaagct tgtctgtgct aaagaaaccc ttcgcccatg ataagggtgg    8400
gggccaagac ccagtcctgc caggcacgaa agtctggcca ctggggaggg gaggagctct    8460
tggcagcttt tcttttgctg cttggcagga ccacccctctc agcctctgct ctccgatccc   8520
tggtcaactc tagctctctc tgggctccgc agcagagatg tgtattggca cagagtgtgt    8580
```

```
gcgtgcaggg ttgaggaaat actcttaccc cgatttctgt accctggagc atgtgtgccc    8640
ctgggatccc tagtgtggaa gcccagacca gactccaacc aaggagtggg cagtgggctt    8700
ggtctcctct ggtccttcct cccacaggtg ggtggaatca cggtgacaca gatgtttgga    8760
gaggtcacgg agatgcccgc cttacccttc atgctggccg agtttgatgg ggttgtgggc    8820
atgggcttca ttgaacaggc cattggcagg gtcaccccta tcttcgacaa catcatctcc    8880
caagggggtgc taaaagagga cgtcttctct ttctactaca acaggtgggg actgggactc    8940
caagggctga ggtgggggga caggagggga gaagagatgg ggagtggaag gagagtctgg    9000
gccagaattg taaagtgttt gtaattaggt gacagccaat caatatctag agctgtacta    9060
gccaatatgg aaggcactat tgaaatttaa attaattaaa tacagttaag catcaattaa    9120
gcattcaact ggtggctctt agttgtacta gccacacgtc aaatgcctgg cagccacggt    9180
ggctagtaac tacagtctta tgacagtgca gatagagaat attcccagca tgacaggaca    9240
ttctaataga cagcgccact ctggagcaag aggagatgca aggtggggc gatggtaaat    9300
aagggattac tgtgacctgt agccctgcct gttagggcca tggctcctcc cacacagaga    9360
cagccaactt cagtcatcca ttagatcctt cattcgtttg tttgctcact catcagttca    9420
gtaaatgcta tgtgccaagc actgtggtag gctctggggg tgcagcagtg aacacagtga    9480
acaaggcaga atctgtactc ccctacccac atagagctta caggctaaca gggaagacaa    9540
gacatattcc aacataaaga gtgtcacagg caggcagcaa gtgtggtgct gaaaaccatg    9600
gatgcttttc aattctaggc tgagcttata tgcagctcag ccagccttgg ggaagctctt    9660
gagcagggtt gggctctact ccaaactgct gggcttagaa agatggcatg agttggagac    9720
aagagagctg gaggcaaaag gggctgggtg cagtggctca tgcctgtaat cccagcactt    9780
tgggaggcca aggcgagagg atcgcatgag cccaggagtt aaggcttcag tgagcagtga    9840
ttgtgccact gcactccagc taaggcaaca gagtgagatc cagtctcaaa aaaaaaaaa    9900
aaaaaaaaaa agtcacaagg gtaagaacat gaggccagtg gcaaaagaa tagaggagag    9960
gatcagagtt cagagaaatc tcacagtaaa atggagagga gtctccggtt tggtgataga   10020
aagtgaggcc ttgagaaaag gccaattggc ggctctgcat tcagggtggg tctttagaag   10080
aactgtttta gaggangtgg gggcaaggcc agatggcaag aagttaagag gtggacgacg   10140
tgggtgtcag gaagtggagg tcatgagatg taggctgccc tgggacattc aacagggaag   10200
ggaatggggg gtggcgtggg gggtgagatc cagaagcaga agaggaaggg tgggtgtttt   10260
taaatgctag aggatgctcg agtgatgcct gtaggtggag gaagaagcca atggaaagaa   10320
agagattaaa aatgtggaaa gaagaggagc taaatggggg cactggagtt tggaggcctt   10380
gaaagagatg aggttccagc agacaggaag aagccaggtt ttgcagagga gagggctggc   10440
ctcttctttt atcttgggat gggaaggagg gaacatccag agagatactg aagtgttgag   10500
agacaggcag gagggaattt gtgctagcat atacacatac attccgaatt tataaaaaca   10560
caagtagttt gcagttgcac aaaataacat atgcacacct acacacccat gcacacatgt   10620
gcatgtgtga attctagtat gaattctgga aaaacacatc acacacacag gcatgccctg   10680
gagactaggc ctacagtagt ccctgagcca agtgcagtga ggaggaaagg aaggtgaggg   10740
gaatcagctc cagacggggc accaggagcc tggctccagt cccccacttg ttcactcatg   10800
gactgggtaa cttcaggcaa gtgacttcgc ctcttggtga ctccattgcc tgaagggcaa   10860
agagagtaca taacacccac cctgccaaac agcagggctg atgaggctgg catgaaatga   10920
agcttccttt ctgctgtctc tctttctctg cagagattcc gagtaaggag acaaaacccc   10980
```

```
cacatggctg tgaccttcca gtactccccg agcacctgac ctagaattac acacgccacc   11040
ggcccaaaac tcacatcagc aagcccagcc tccgctagat gccgaagttc tctgtctctc   11100
cttcctgctc tctccatgcc acctgccac cccatacccca atagcctccc cagggtcccc   11160
tcccatgcac ctgctcaatc agcagcaacc caagagtgag gggtgtccat ttgtgtcttg   11220
ttcacatcca ctcactgtcc ttgtacctgc tccttttctg tgacctctct ggggatgctt   11280
tttgggggaa cagctggact accctggaac aacctctggt tggtcttggg gaggggaaga   11340
aaggcagaga agcagtatgt tctgcatgct tcccaacgac agctccgagc ctggctgtct   11400
gtcccacatt cctctgctct agagccctct gtcctcccct gcacccttgt gcaaccttcc   11460
ccaattgcct gagttgctgg gtcctggagg ttatgggttt ccaagagctt ctgatctttc   11520
ctttaggaat tcccaatcgc tgggaggaca gattgtgctg ggaggcagcg accccccagca   11580
ttacgaaggg aatttccact atatcaacct catcaagact ggtgtctggc agattcaaat   11640
gaaggggtca gaaatcctca accctccccg ggctccaaaa aatgctgccg tcactggggt   11700
tggggagggt ggggaaggac tgcattacca tcctgccctc tttccaaatg cagccacttc   11760
ttaagcacag ccaccatttg ctctctgcct gctctgtcca ggctggggaa cagagaaggg   11820
aggggcctgg ggagaagtgg tggagggtga cagtaccttc cctcctctac tcactgcctc   11880
aacaggccac cagcgtggcc tccacccacc cacccacact caggaaggac atgcagcctg   11940
gaggtgcccc atcagccttc tgtctgtctg tctgtctgtc tgtctgactg tggcctcccc   12000
cagggtgtct gtgggtcat ccaccttgct ctgtgaagac ggctgcctgg cattggtaga   12060
caccggtgca tcctacatct caggttctac cagctccata gagaagctca tggaggcctt   12120
gggagccaag aagaggctgt ttgatgtaag aagccaaaga gggaaggtgc tgtgggtggg   12180
gggagcgcca cctggtatcg gctcacaaat cccccaggca aatgaggcca tctcaggcct   12240
tcgcttgttc acctcacact ctccacacat gtggctggtc acccatgggg cggggcactg   12300
tccccagccc tctccagcag agagaccagg ccaccagcgc aggactcctt gtctgctgag   12360
acgtcttcca tactcaagaa ggctctcttt gccccccacc ccagtatgtc gtgaagtgta   12420
acgagggccc tacactcccc gacatctctt tccacctggg aggcaaagaa tacacgctca   12480
ccagcgcgga ctatgtattt caggtgaggt tcgagtcggc cccctcggtg cagggagaa   12540
aggctggaca gagaccctca aagagtgaca gattacaatg cacagntcat gttagaactg   12600
tagttctcaa acttggctgt gcatgtcacc tggagagctt tgaaaaatcc tggtacctgg   12660
gccacatccc atacctatta aatcagaacc tctagaagtg gcacctgggg ttcagtttcc   12720
ccaggtgatt ccaatgtgtg gccatgtttg ggcatcacta tgcctgttcc ctcatctcca   12780
ttttctcatc aaatactccc aagaatccta tgctcctata ttcttaccct cttttcataa   12840
tcaataggct tagagaagtt gaataacttg tctaggatca gaagctaagg caaactgtaa   12900
gctcctgaag gaagcacggt gcctgatgca ttgtttgcct gggatctagc acaggggcta   12960
aacataggag tggtgcagtc cacgatgggg caaaatggcc atgatgtgag ggaggcccag   13020
tgtggctagg ggagagatgg gggcgagagg gggaatgttg ctgaagacag ttgctngggg   13080
tcaggcaagg tgaaaggaga atgctcatgt gctgggtatg gagaaactct cccccttcct   13140
gccaggaatc ctacagtagt aaaaagctgt gcacactggc catccacgcc atggatatcc   13200
cgccacccac tggacccacc tgggccctgg gggccacctt catccgaaag ttctacacag   13260
agtttgatcg gcgtaacaac cgcattggct tcgccttggc ccgctgaggc cctctgccac   13320
ccaggcaggc cctgccttca gccctggccc agagctggaa cactctctga gatgcccctc   13380
```

```
tgcctgggct tatgccctca gatggagaca ttggatgtgg agctcctgct ggatgcgtgc    13440
cctgacccct gcaccagccc ttccctgctt tgaggacaaa gagaataaag acttcatgtt    13500
cacagcctgt tgcatctggg ttcactaggg tttagaacag agggaggggc tgcgtgatca    13560
tgtgtggaca ggaatgtgac acagacaagc tacacattcg cctagcgcac aggttcttgc    13620
gtgcagggat gatgccatcc atctgccatc aacgggactc aggtggagct gtttacacaa    13680
cctcaggtgg gaagtctgaa aagagccgga accaagctcc ctctagtccc tcagggacca    13740
aggctaatgc tgtggcagta gactgtgggt cagaaagttc tcccagctca cagaagccag    13800
ctctgagttc agactctgct ctgctgagct agtcagccct gtctcttgtc cctgcaaaac    13860
tcccctcagc tgtccttatc cactgcagat gccccgccc tgcccatgt agccatttac      13920 acaggcattc taaggcacta ccacctaaaa tcatagaaca ccagagatcc aggcaatact    13980
tccactttac aggtggggaa actgaggccc agagaatgga aggccttgcc caagattact    14040
cggtcaagaa tcaagtagtg aagaatactg aaagatagtg aagaatcaag actggaaccc    14100
agcccgtctg acttgggtcc tgggggtttc caccttatca taagcagttg gtaccgtcat    14160
aagtacagtg cttcacgcac gctggtacag ggccacgtgc acaagcacac aggtgcacac    14220
acacactgct atcctccatc ccatccacct gggactcgtc aggctgaagt ctcttctccc    14280
actctcactc cttgggctgt cttcaggca catgtaactt ggggaatgag aaattagcat     14340
ccacctggag ccactgaagc catccctctt caccatagtt gctcacctct cttttgacag    14400
aaagtcgtga ggcactgaat ggcccaacca ggccctcagt acctctggga gccatctgca    14460
agagtccctg tgtagcgcca agagccggag cctgggcttc agg                      14503

<210> SEQ ID NO 8
<211> LENGTH: 1461
<212> TYPE: DNA
<213> ORGANISM: Homo sapiens

<400> SEQUENCE: 8
agaacctcag tggatctcag agagagcccc agactgaggg aagcatggat ggatggagaa      60
ggatgcctcg ctggggactg ctgctgctgc tctggggctc ctgtaccttt ggtctcccga     120
cagacaccac cacctttaaa cggatcttcc tcaagagaat gccctcaatc cgagaaagcc     180
tgaaggaacg aggtgtggac atggccaggc ttggtcccga gtggagccaa cccatgaaga     240
ggctgacact tggcaacacc acctcctccg tgatcctcac caactacatg gacacccagt     300
actatggcga gattgggatc gggacccac cccaaacctt caaagtcgtc tttgacactg      360
gttcgtccaa tgtttgggtg ccctcctcca gtgcagccg tctctacact gcctgtgtgt      420
atcacaagct cttcgatgct tcggattcct ccagctacag gcacaatgga acagaactca     480
ccctccgcta ttcaacaggg acagtcagtg gctttctcag ccaggacatc atcaccgtgg     540
gtggaatcac ggtgacacag atgtttgag aggtcacgga gatgcccgcc ttacccttca      600
tgctggccga gtttgatggg gttgtgggca tgggcttcat tgaacaggcc attggcaggg     660 tcaccccctat cttcgacaac atcatctccc aaggggtgct aaaagaggac gtcttctctt    720
tctactacaa cagagattcc gagaattccc aatcgctggg aggacagatt gtgctgggag     780
gcagcgaccc ccagcattac gaagggaatt tccactatat caacctcatc aagactggtg     840
tctggcagat tcaaatgaag gggggtgtctg tggggtcatc caccttgctc tgtgaagacg     900
gctgcctggc attggtagac accggtgcat cctacatctc aggttctacc agctccatag     960
agaagctcat ggaggccttg ggagccaaga agaggctgtt tgattatgtc gtgaagtgta    1020
```

-continued

```
acgagggccc tacactcccc gacatctctt tccacctggg aggcaaagaa tacacgctca   1080
ccagcgcgga ctatgtattt caggaatcct acagtagtaa aaagctgtgc acactggcca   1140
tccacgccat ggatatcccg ccacccactg gacccacctg ggccctgggg gccaccttca   1200
tccgaaagtt ctacacagag tttgatcggc gtaacaaccg cattggcttc gccttggccc   1260
gctgaggccc tctgccaccc aggcaggccc tgccttcagc cctggcccag agctggaaca   1320
ctctctgaga tgcccctctg cctgggctta tgccctcaga tggagacatt ggatgtggag   1380
ctcctgctgg atgcgtgccc tgaccctgc accagcccct ccctgctttg aggacaaaga   1440
gaataaagac ttcatgttca c                                             1461

<210> SEQ ID NO 9
<211> LENGTH: 406
<212> TYPE: PRT
<213> ORGANISM: Homo sapiens

<400> SEQUENCE: 9

Met Asp Gly Trp Arg Met Pro Arg Trp Gly Leu Leu Leu Leu Leu
1               5                   10                  15

Trp Gly Ser Cys Thr Phe Gly Leu Pro Thr Asp Thr Thr Thr Phe Lys
            20                  25                  30

Arg Ile Phe Leu Lys Arg Met Pro Ser Ile Arg Glu Ser Leu Lys Glu
        35                  40                  45

Arg Gly Val Asp Met Ala Arg Leu Gly Pro Glu Trp Ser Gln Pro Met
    50                  55                  60

Lys Arg Leu Thr Leu Gly Asn Thr Thr Ser Ser Val Ile Leu Thr Asn
65                  70                  75                  80

Tyr Met Asp Thr Gln Tyr Tyr Gly Glu Ile Gly Ile Gly Thr Pro Pro
                85                  90                  95

Gln Thr Phe Lys Val Val Phe Asp Thr Gly Ser Ser Asn Val Trp Val
            100                 105                 110

Pro Ser Ser Lys Cys Ser Arg Leu Tyr Thr Ala Cys Val Tyr His Lys
        115                 120                 125

Leu Phe Asp Ala Ser Asp Ser Ser Tyr Lys His Asn Gly Thr Glu
    130                 135                 140

Leu Thr Leu Arg Tyr Ser Thr Gly Thr Val Ser Gly Phe Leu Ser Gln
145                 150                 155                 160

Asp Ile Ile Thr Val Gly Gly Ile Thr Val Thr Gln Met Phe Gly Glu
                165                 170                 175

Val Thr Glu Met Pro Ala Leu Pro Phe Met Leu Ala Glu Phe Asp Gly
            180                 185                 190

Val Val Gly Met Gly Phe Ile Glu Gln Ala Ile Gly Arg Val Thr Pro
        195                 200                 205

Ile Phe Asp Asn Ile Ile Ser Gln Gly Val Leu Lys Glu Asp Val Phe
    210                 215                 220

Ser Phe Tyr Tyr Asn Arg Asp Ser Glu Asn Ser Gln Ser Leu Gly Gly
225                 230                 235                 240

Gln Ile Val Leu Gly Gly Ser Asp Pro Gln His Tyr Glu Gly Asn Phe
                245                 250                 255

His Tyr Ile Asn Leu Ile Lys Thr Gly Val Trp Gln Ile Gln Met Lys
            260                 265                 270

Gly Val Ser Val Gly Ser Ser Thr Leu Leu Cys Glu Asp Gly Cys Leu
        275                 280                 285
```

```
Ala Leu Val Asp Thr Gly Ala Ser Tyr Ile Ser Gly Ser Thr Ser Ser
    290                 295                 300

Ile Glu Lys Leu Met Glu Ala Leu Gly Ala Lys Lys Arg Leu Phe Asp
305                 310                 315                 320

Tyr Val Val Lys Cys Asn Glu Gly Pro Thr Leu Pro Asp Ile Ser Phe
                325                 330                 335

His Leu Gly Gly Lys Glu Tyr Thr Leu Thr Ser Ala Asp Tyr Val Phe
            340                 345                 350

Gln Glu Ser Tyr Ser Ser Lys Lys Leu Cys Thr Leu Ala Ile His Ala
        355                 360                 365

Met Asp Ile Pro Pro Thr Gly Pro Thr Trp Ala Leu Gly Ala Thr
    370                 375                 380

Phe Ile Arg Lys Phe Tyr Thr Glu Phe Asp Arg Arg Asn Asn Arg Ile
385                 390                 395                 400

Gly Phe Ala Leu Ala Arg
            405

<210> SEQ ID NO 10
<211> LENGTH: 11518
<212> TYPE: DNA
<213> ORGANISM: Homo sapiens

<400> SEQUENCE: 10
agaacctcag tggatctcag agagagcccc agactgaggg aagcatggat ggatggagaa      60
ggatgcctcg ctggggactg ctgctgctgc tctggggctc ctgtaccttt ggtctcccga     120
cagacaccac cacctttaaa cggtaattgg taactcaggc agagaagggg tgggagggt     180 gcagggttcc caccttccca acaccctggc ttttccacat gcggtgtcat tcagtcctta     240
cgatcagctg gacagggaag tatggacctg ttcagagagg tcaagtgact tgcccaataa     300
atgacactag tagtcaggtc tagaagctgt gacttttgct tcctgcccag agcaccatgc     360
taactaagca ctgtagagaa ctcagaagta ttaggacatg ccccttgcac ttgaggagct     420
cacagcctga atattaagaa gggcatgggt ggttgggcgc ggtggctcct gcctgtaatc     480
ccagcacttt gggaggctga gacggatcac ttgaggtcag gagtttgaga ccagcctggc     540
caacatgggg aaaccccatc tctactaaaa atacaaaaat tagccgggca tggtggcagg     600
cacttgtaat ccccagctac tcgggaagct gaggcaggag aatcgtttga gcccggaagg     660
tggagattgc tgagccaaga tcgtgccact gcactccagc ctgagtgaca gaacaagact     720
ccatctcaaa aaaaaaaaag acggggtcg gggcatgggt acagttaact gtaccaggga     780
agcagcttga tatcgtggtt aaatgcaagg cttatagagt tagattgcct tcatttaaat     840
tttgcttcac tagcagaaca aactaggtct ggaatcatgg gcaagttatt taacctctcc     900
aagtctcagt ttatcatttt aaacaggtat gataataaca gtacctactt gatgggctg     960 ctttggggat tttaggagat aaggcataga agctgggca cgttgtaaga gcccagctac    1020
tgttagtact acaggataga ttcttacaaa tatcaaaagc aaggtttggc cgggagcagt    1080
ggctcacgcc tataatccca cactttggg aggccgaggg gggcagatca cccgaggtca    1140
ggagttcaag accagcctga ccaacatgga gaaaccctgt ctctactaaa aatacaaaat    1200
tagccgggcg tggtggcaca tgcctgtaat tccagctact tgggaggctg aggcaggaga    1260
atcgcttgaa cctgggaggc tgaggttgca gtgagccgac atagcgccat tgcactccag    1320
cctggtcaac aagagcaaaa ctcagtctaa aaaaaaaaaa gaaagaaaaa acaaggctt    1380 taggtagccc acaattagaa ggagaaaacc ttagcatccc ctaggtgcca ggccttgtgg    1440
```

```
gaacaagtga ttcattaaga ctgtagaagg aagctgggca cgcggctcat gcttgtaatt   1500
ccagcacttt gagaggctga ggtgggcaga tcgcttgagc tcacgagttc aagaccagcc   1560
taggcaacat ggtgaaacct tgtctgtaca aatacaaaaa ttagctaggt gtggtggtgc   1620
aaatctgtag tcccagctac tcgggaggct gaggtgggag catcacttca gcctgggagg   1680
tggaggctgc agtgagcaga gactgaccca ctgtgctcta gcctgggtga tagagccaga   1740
ccttatgtaa aaaaaaaaa aaaaaaaaa aagactgaag aaggggaaga gacagcattt   1800
gagaaaaggc ctcacagaga aaggggtttt caatctgggg acagcagata tgaccagcag   1860
tcctgaaggt agggaggcac actttaataa tggtaatagt tgctaagcct ataaaatgct   1920
tagggtgtca caggatcttt tcacatgtct catctcaagt catgccccca acaactcagc   1980
attcccactt tgcagatgag gacactgagg ctcaggaggg tgatatgtaa gaggctaagc   2040
ctcaacacac actgggcctt ttgcttccga aactgctttc ccttgctctg aggctctcgg   2100
agagtaattg ctgggttgtg agcactgggt aagaggatgg gtgcttcaaa gcagctgcac   2160
tccaggataa aggtagagga aagtaaaaac atcttcccct gctgttatcc aaaagagaaa   2220
aagaatggaa ttgggcaagg ggtggagggg gaatccagct tttgaaacag tattatagga   2280
attttgctac ccgctatgtg cagagcatca tgcgaggcac ttgggacagc tgaatgaatg   2340
agctccattc tcaaggtgaa catgtacata tacacaccta caatttacat ttattgagca   2400
gtggtcgcat ggtttcatct gcacagtgac tctgaggtag gtactaccat taggcccatt   2460
gttagagagg ggttaatgga gacttagaag aggcccagag aggttaggta gctttctcag   2520
aatcacataa gtggtaaggg gattcaggca tgcccctgc aaccactgtc ttcaccaccg   2580
tacggcacca gttccacaag ctgtacagtg tgggctgtga gacccaagga aaaacagagc   2640
tgaggcccac gggaaggtga ggccggtgtg ggctggaggc cttggggtaa gcttcctgga   2700
ggtgggggta catgttgggc cttggaggac taaagaactg gggggaaaag gaagggaaga   2760
aggaaaggat tttctgaaaa ggaaatggca agaagtaaag gtccaaagca taggctgttg   2820
tgagtaaaca gtgggaaatg caacctcttt ggggccaaac ctctgaccct ccacgttccc   2880
agctgtgaag tgggagtaat aaaatcatcc accttatgag agcaaataaa ataatgattg   2940
tgaaaatatt ttggtaacag taacctgtga taggaagata acaaatcatt tctgttacaa   3000
taccatgctg ataggcataa aagttgcatt catgttcatg ggcaaaatgg gggtaagtag   3060
aatgcatggg acgcaagaag gatgtaggaa ggaaagggta gtgtgagtat aggaggacta   3120
gccactgaga agaaagtaga agaaagaggg aatctttgtg tgtatgggaa agtctattgc   3180
agagtcaact tgggcttcca tcctgggacc ttcccgtgaa cagctagaga catcttcctc   3240
tgggctttgg cagcctttat gtcgggaccc aggggaccct atatgggaaa tagggccaga   3300
cacatgctct gaatccctgc ttcaacattt ctgagtcacc tttgtccctg tgagccttca   3360
tttttctcat ctataaaatg gatgcagct agcttgttgg tgtgatttca gtagcggctc   3420
agtagagtca gtttcctagg tctctttaat tctgcctctc aaaggtgatg ggaaaacatc   3480
tagacaagaa gccaagggac cgggacacat ctctccaagg acgaggtgca tggcgctctg   3540
aagatgctgg catctctcta ggcccaaccc agctcagggg gtccactcca ccacagccct   3600
ggctgggtgc ctgtccctg gtatcctgga gaccttgcag ctgctgtggg catctgctgc   3660
cacctagcgg cctcccatgg cactgtctcc ccgccagccc ctagttttga caggggcact   3720
ccctggcatt aatctcttca gagggaatgt ctgtgcctgt ttcctgtctg tcctcccgcc   3780
aggtggagtt ccttaaaggc agtcatgatc attatctttc tagctccagt gtccagcaca   3840
```

```
gtgaggcaca aagtagttgt tcagcaggtg attacggaat aaatgaatga acggaccaat    3900
aaacaaatag ccttgtctaa tcaaaattag gcaacagaag gaagtcactt cagggttatt    3960
taatccccgg gcagctgact cctctaaatt gactcttgac aagaagtaac tcttataaat    4020
gctccagagg ccctcagcga cagaggtgat ttccaggtgg ctgggctaac gttaaaggtg    4080
gttgtactaa aagcaggggt ttggcctcag ggactccacc actgtggtgg aggtacagca    4140
cttttctatt tttgcttcct ccaccctggg ccaggatctt cctcaagaga atgccctcaa    4200
tccgagaaag cctgaaggaa cgaggtgtgg acatggccag gcttggtccc gagtggagcc    4260
aacccatgaa gaggctgaca cttggcaaca ccacctcctc cgtgatcctc accaactaca    4320
tggacgtgag tgcttggctc agcccctcgc tccctccctg tctccttttcc ctcatggacc    4380
tagggctttc tttgctgcaa gactcaccct ttccaagctg tgtttgacga aggcgctgag    4440
tagcacgtga gcaccctaga aaattcccat tttccagctg gaaagcctga gcacagaaga    4500
caggaaggca tccaggggcc attcaggggc agggttaggt ttggaactca gcccaggcct    4560
caagccaggt gtcacaggtg ggtgggaagg ggtgtgtgac tcaggtgggg gtttctgtga    4620
cctggcccag cacaacctga tggcttcctg ccccagagga tcctcaagag tcaagtttgc    4680
ttcctgcttc attctcaatg ttttgatttt gccctcttgt cttactgaga ctcccacttt    4740
ctgggatgcc atggggagat gctaagcctc ctaccagttc ctgcaggaaa atggaaaccc    4800
cgagaggcta taggacctcg cctgggccaa gtctcacacc gagagccaag agtgaagcca    4860
ggcaagaccc caagacccaa ggtccccctga gcccctccag ccctctcttt ttaccccccac   4920
agacccagta ctatggcgag attggcatcg gcaccccacc ccagaccttc aaagtcgtct    4980
ttgacactgg ttcgtccaat gtttgggtgc cctcctccaa gtgcagccgt tctctacactg    5040
cctgtggtga gacctaagac ccacagtgcc tctcctccat ccccctgccc tactgtgcat    5100
gagcaatcct gcccaacacc cagctcccat ccctcttgcc accaagggag tggcttcctc    5160
tctgcctctg tgcccactga catgtagggg agaggggaag atgtctcccg tttttctgat    5220
acagccacca aggttaaaaa caaaaaaagg tccaagaacc cctgagcacc cagaaggcca    5280
cttcccagtc ttcctgagat tgagacagga ctgaattctc aaacccatcc caggcactcg    5340
gaactcttcc atccctagtc ttaatcaaca acctcttact aggcacttac tctgtgcctg    5400
gcatcttctc tggtgttatc agtgttagtg attactttaa attccttcat ttaggacaaa    5460
attctcgatg tatgggcaca ttaggagagc ccaagaaacc cagtccttga ttgatgaagc    5520
acatattcca agccccctga ccctagggcc actcatccct gcacctaagc taaccagcca    5580
tacccacaat gcaccctgcc tctgagtccc cctgtctggg ccactcttgg acaaacctga    5640
gcctctgtcc ccctgccagt gtatcacaag ctcttcgatg cttcggattc ctccagctac    5700
aagcacaatg gaacagaact caccctccgc tattcaacag ggacagtcag tggctttctc    5760
agccaggaca tcatcaccgt aagttgggcc gccctaggtc atctgccccg gacccttct    5820
gtccccaggc ctctcctgac cctccagggc ccacacctgc ggggaggtac actgcagccc    5880
acttggagcc tggggagctg aggaacaccc tactctgcca catctggctg ttgctgcaaa    5940
gcagcagtac ctatggggga gcaagcctgg gctacgggct caccgttggg tggtttgtgg    6000
atgttttgc atctaacttg catgtagggc ttgtcctgag ccccgtggct gcagtcaagt    6060
aactcgtcca agttcaccag ctctgactgg gctacaccct agactgaaat ccagggtcag    6120
agtcaggctg agtttaggg tcaggcatag gttttaaggt cacagttgag gttgactctg    6180
ggactcaggt caaggcctgc ttttcttttc catgtggccc atgtctgacc gtttcctcat    6240
```

```
cctggagttt ctcaggccct gctccatcag agttagggga gggcacacg tggcacctga      6300 gaggaaatca gggtgattcc tgcctccctt ccttttctg tgaactcaga tataaaggag      6360
ggagaagggc aagcttgtct gtgctaaaga aaccccttcgc ccatgataag ggtgggggcc    6420
aagacccagt cctgccaggc acgaaagtct ggccactggg gaggggagga gctcttggca    6480
gcttttcttt tgctgcttgg caggaccacc ctctcagcct ctgctctccg atccctggtc    6540
aactctagct ctctctgggc tccgcagcag agatgtgtat tggcacagag tgtgtgcgtg    6600
cagggttgag gaaatactct taccccgatt tctgtaccct ggagcatgtg tgcccctggg    6660
atccctagtg tggaagccca gaccagactc caaccaagga gtgggcagtg ggcttggtct    6720
cctctggtcc ttcctcccac aggtgggtgg aatcacggtg acacagatgt ttggagaggt    6780 cacgagatg cccgccttac ccttcatgct ggccgagttt gatggggttg tgggcatggg    6840
cttcattgaa caggccattg gcagggtcac ccctatcttc gacaacatca tctcccaagg    6900
ggtgctaaaa gaggacgtct tctctttcta ctacaacagg tggggactgg gactccaagg    6960
gctgaggtgg ggggacagga ggggagaaga gatggggagt ggaaggagag tctgggccag    7020
aattgtaaag tgtttgtaat taggtgacag ccaatcaata tctagagctg tactagccaa    7080
tatggaaggc actattgaaa tttaaattaa ttaaatacag ttaagcatca attaagcatt      7140
caactggtgg ctcttagttg tactagccac acgtcaaatg cctggcagcc acggtggcta    7200
gtaactacag tcttatgaca gtgcagatag agaatattcc cagcatgaca ggacattcta    7260
atagacagcg ccactctgga gcaagaggag atgcaaggtg ggggcgatgg taaataaggg    7320
attactgtga cctgtagccc tgcctgttag ggccatggct cctcccacac agagacagcc    7380
aacttcagtc atccattaga tccttcattc gtttgtttgc tcactcatca gttcagtaaa    7440
tgctatgtgc caagcactgt ggtaggctct gggggtgcag cagtgaacac agtgaacaag    7500
gcagaatctg tactccccta cccacataga gcttacaggc taacagggaa gacaagacat    7560
attccaacat aaagagtgtc acaggcaggc agcaagtgtg gtgctgaaaa ccatggatgc    7620 tttttcaattc taggctgagc ttatatgcag ctcagccagc cttggggaag ctcttgagca    7680
gggttgggct ctactccaaa ctgctgggct tagaaagatg gcatgagttg gagacaagag    7740
agctggaggc aaaaggggct gggtgcagtg gctcatgcct gtaatcccag cactttggga    7800
ggccaaggcg agaggatcgc atgagcccag gagttaaggc ttcagtgagc agtgattgtg    7860
ccactgcact ccagctaagg caacagagtg agatccagtc tcaaaaaaaa aaaaaaaaa    7920 aaaaaagtca aagggtaag aacatgaggc cagtggcaaa aagaatagag gagaggatca    7980
gagttcagag aaatctcaca gtaaaatgga gaggagtctc cggtttggtg atagaaagtg    8040
aggccttgag aaaaggccaa ttggcggctc tgcattcagg ggtggtcttt agaagaactg    8100
ttttagagga agtgggggca aggccagatg gcaagaagtt aagaggtgga cgacgtgggt    8160
gtcaggaagt ggaggtcatg agatgtaggc tgccctggga cattcaacag ggaagggaat    8220
ggggggtggc gtgggggtg agatccagaa gcagaagagg aagggtgggt gtttttaaat    8280
gctagaggat gctcgagtga tgcctgtagg tggaggaaga agccaatgga agaaagagaa    8340
ttaaaaatgt ggaaagaaga ggagctaaat gggggcactg gagtttggag gccttgaaag    8400
agatgaggtt ccagcagaca ggaagaagcc aggttttgca gaggagaggg ctggcctctt    8460 ctttttatctt gggatgggaa ggagggaaca tccagagaga tactgaagtg ttgagagaca    8520
ggcaggaggg aatttgtgct agcatataca catacattcc gaatttataa aaacacaagt    8580
agtttgcagt tgcacaaaat aacatatgca cacctacaca cccatgcaca catgtgcatg    8640
```

```
tgtgaattct agtatgaatt ctggaaaaac acatcacaca cacaggcatg ccctggagac   8700
taggcctaca gtagtccctg agccaagtgc agtgaggagg aaaggaaggt gagggggaatc   8760 agctccagac ggggcaccag gagcctggct ccagtccccc acttgttcac tcatggactg   8820
ggtaacttca ggcaagtgac ttcgcctctt ggtgactcca ttgcctgaag ggcaaagaga   8880
gtacataaca cccaccctgc caaacagcag ggctgatgag gctggcatga aatgaagctt   8940
cctttctgct gtctctcttt ctctgcagag attccgagta aggagacaaa acccccacat   9000
ggctgtgacc ttccagtact cccgagcac ctgacctaga attacacacg ccaccggccc   9060
aaaactcaca tcagcaagcc cagcctccgc tagatgccga agttctctgt ctctccttcc   9120
tgctctctcc atgccacctg cccaccccat acccaatagc ctccccaggg tcccctccca   9180
tgcacctgct caatcagcag caacccaaga gtgaggggtg tccatttgtg tcttgttcac   9240
atccactcac tgtccttgta cctgctcctt ttctgtgacc tctctgggga tgcttttttgg  9300 gggaacagct ggactaccct ggaacaacct ctggttggtc ttggggaggg gaagaaaggc   9360
agagaagcag tatgttctgc atgcttccca acgacagctc cgagcctggc tgtctgtccc   9420
acattcctct gctctagagc cctctgtcct ccctgcacc cttgtgcaac cttccccaat    9480
tgcctgagtt gctgggtcct ggaggttatg ggtttccaag agcttctgat ctttccttta   9540
ggaattccca atcgctggga ggacagattg tgctgggagg cagcgacccc cagcattacg   9600
aagggaattt ccactatatc aacctcatca agactggtgt ctggcagatt caaatgaagg   9660
ggtcagaaat cctcaaccct ccccgggctc caaaaaatgc tgccgtcact ggggttgggg   9720
agggtgggga aggactgcat taccatcctg ccctcttcc aaatgcagcc acttcttaag     9780
cacagccacc atttgctctc tgcctgctct gtccaggctg gggaacagag aagggagggg   9840
cctggggaga agtggtggag ggtgacagta ccttccctcc tctactcact gcctcaacag   9900
gccaccagcg tggcctccac ccacccaccc acactcagga aggacatgca gcctggaggt   9960
gccccatcag ccttctgtct gtctgtctgt ctgtctgtct gactgtggcc tcccccaggg  10020
tgtctgtggg gtcatccacc ttgctctgtg aagacggctg cctggcattg gtagacaccg  10080
gtgcatccta catctcaggt tctaccagct ccatagaaga gctcatggag gccttgggag  10140
ccaagaagag gctgtttgat gtaagaagcc aaagagggaa ggtgctgtgg gtgggggag   10200 cgccacctgg tatcggctca caaatccccc aggcaaatga ggccatctca ggccttcgct  10260
tgttcacctc acactctcca cacatgtggc tggtcaccca tggggcgggg cactgtcccc  10320
agccctctcc agcagagaga ccaggccacc agcgcaggac tccttgtctg ctgagacgtc  10380
ttccatactc aagaaggctc tctttgcccc ccaccccagt atgtcgtgaa gtgtaacgag  10440
ggccctacac tccccgacat ctctttccac ctggaggca aagaatacac gctcaccagc  10500
gcggactatg tatttcaggt gaggttcgag tcggccccct cggtggcagg gagaaaggct  10560
ggacagagac cctcaaagag tgacagatta caatgcacag gtcatgttag aactgtagtt  10620
ctcaaacttg gctgtgcatg tcacctggag agctttgaaa aatcctggta cctgggccac  10680
atcccatacc tattaaatca gaacctctag aagtggcacc tggggttcag tttccccagg  10740
tgattccaat gtgtggccat gtttgggcat cactatgcct gttccctcat ctccattttc  10800
tcatcaaata ctcccaagaa tcctatgctc ctatattctt accctctttt cataatcaat  10860
aggcttagag aagttgaata acttgtctag gatcagaagc taaggcaaac tgtaagctcc  10920
tgaaggaagc acggtgcctg atgcattgtt tgcctgggat ctagcacagg gctaaacat   10980 aggagtggtg cagtccacga tggggcaaaa tggccatgat gtgagggagg cccagtgtgg  11040
```

```
ctaggggaga gatgggggcg agagggggaa tgttgctgaa gacagttgct ggggtcagg   11100 caaggtgaaa ggagaatgct catgtgctgg gtatggagaa actctccccc ttcctgccag   11160
gaatcctaca gtagtaaaaa gctgtgcaca ctggccatcc acgccatgga tatcccgcca   11220
cccactggac ccacctgggc cctgggggcc accttcatcc gaaagttcta cacagagttt   11280
gatcggcgta acaaccgcat tggcttcgcc ttggcccgct gaggccctct gccacccagg   11340
caggccctgc cttcagccct ggcccagagc tggaacactc tctgagatgc ccctctgcct   11400
gggcttatgc cctcagatgg agacattgga tgtggagctc ctgctggatg cgtgccctga   11460
cccctgcacc agcccttccc tgctttgagg acaaagagaa taaagacttc atgttcac    11518
```

```
<210> SEQ ID NO 11
<211> LENGTH: 38
<212> TYPE: DNA
<213> ORGANISM: Homo sapiens

<400> SEQUENCE: 11
tgtaaaacga cggccagttt cgcttgttca cctcacac                          38

<210> SEQ ID NO 12
<211> LENGTH: 38
<212> TYPE: DNA
<213> ORGANISM: Homo sapiens

<400> SEQUENCE: 12
caggaaacag ctatgaccgc ccaggtacca ggattttt                          38

<210> SEQ ID NO 13
<211> LENGTH: 39
<212> TYPE: DNA
<213> ORGANISM: Homo sapiens

<400> SEQUENCE: 13
tgtaaaacga cggccagtgg gtaagaacat gaggccagt                         39

<210> SEQ ID NO 14
<211> LENGTH: 38
<212> TYPE: DNA
<213> ORGANISM: Homo sapiens

<400> SEQUENCE: 14
caggaaacag ctatgaccaa aaacacccac ccttcctc                          38

<210> SEQ ID NO 15
<211> LENGTH: 38
<212> TYPE: DNA
<213> ORGANISM: Homo sapiens

<400> SEQUENCE: 15
tgtaaaacga cggccagttt gtttgcctgg gatctagc                          38

<210> SEQ ID NO 16
<211> LENGTH: 38
<212> TYPE: DNA
<213> ORGANISM: Homo sapiens

<400> SEQUENCE: 16
caggaaacag ctatgaccgg ggcatctcag agagtgtt                          38
```

```
<210> SEQ ID NO 17
<211> LENGTH: 25
<212> TYPE: DNA
<213> ORGANISM: Homo sapiens

<400> SEQUENCE: 17
acagagaccc tcaaagagtg acaga                                        25

<210> SEQ ID NO 18
<211> LENGTH: 22
<212> TYPE: DNA
<213> ORGANISM: Homo sapiens

<400> SEQUENCE: 18
acatgcacag ccaagtttga ga                                           22

<210> SEQ ID NO 19
<211> LENGTH: 21
<212> TYPE: DNA
<213> ORGANISM: Homo sapiens

<400> SEQUENCE: 19
ttctaacatg acctgtgcat t                                            21

<210> SEQ ID NO 20
<211> LENGTH: 21
<212> TYPE: DNA
<213> ORGANISM: Homo sapiens

<400> SEQUENCE: 20
ctaacatgat ctgtgcattg t                                            21

<210> SEQ ID NO 21
<211> LENGTH: 25
<212> TYPE: DNA
<213> ORGANISM: Homo sapiens

<400> SEQUENCE: 21
tgatagaaag tgaggccttg agaaa                                        25

<210> SEQ ID NO 22
<211> LENGTH: 24
<212> TYPE: DNA
<213> ORGANISM: Homo sapiens

<400> SEQUENCE: 22
cacgtcgtcc acctcttaac ttct                                         24

<210> SEQ ID NO 23
<211> LENGTH: 28
<212> TYPE: DNA
<213> ORGANISM: Homo sapiens

<400> SEQUENCE: 23
ccttgccccc acttcctcta aaacagtt                                     28

<210> SEQ ID NO 24
<211> LENGTH: 27
<212> TYPE: DNA
<213> ORGANISM: Homo sapiens

<400> SEQUENCE: 24
ccttgccccc acctcctcta aaacagt                                      27
```

```
<210> SEQ ID NO 25
<211> LENGTH: 20
<212> TYPE: DNA
<213> ORGANISM: Homo sapiens

<400> SEQUENCE: 25
aatggccatg atgtgaggga                                           20

<210> SEQ ID NO 26
<211> LENGTH: 21
<212> TYPE: DNA
<213> ORGANISM: Homo sapiens

<400> SEQUENCE: 26
ccatacccag cacatgagca t                                         21

<210> SEQ ID NO 27
<211> LENGTH: 24
<212> TYPE: DNA
<213> ORGANISM: Homo sapiens

<400> SEQUENCE: 27
ttgcctgacc cccagcaact gtct                                      24

<210> SEQ ID NO 28
<211> LENGTH: 24
<212> TYPE: DNA
<213> ORGANISM: Homo sapiens

<400> SEQUENCE: 28
ccttgcctga ccccagcaac tgtc                                      24

<210> SEQ ID NO 29
<211> LENGTH: 24
<212> TYPE: DNA
<213> ORGANISM: Bacteriophage M13

<400> SEQUENCE: 29
cgccagggtt ttcccagtca cgac                                      24

<210> SEQ ID NO 30
<211> LENGTH: 24
<212> TYPE: DNA
<213> ORGANISM: Bacteriophage M13

<400> SEQUENCE: 30
agcggataac aatttcacac agga                                      24

<210> SEQ ID NO 31
<211> LENGTH: 40
<212> TYPE: DNA
<213> ORGANISM: Homo sapiens

<400> SEQUENCE: 31
gacagattac aatgcacaga tcatgttaga actgtagttc                     40

<210> SEQ ID NO 32
<211> LENGTH: 40
<212> TYPE: DNA
<213> ORGANISM: Homo sapiens

<400> SEQUENCE: 32
gaactacagt tctaacatga tctgtgcatt gtaatctgtc                     40
```

```
<210> SEQ ID NO 33
<211> LENGTH: 47
<212> TYPE: DNA
<213> ORGANISM: Homo sapiens

<400> SEQUENCE: 33
gtctttagaa gaactgtttt agaggaggtg ggggcaaggc cagatgg          47

<210> SEQ ID NO 34
<211> LENGTH: 47
<212> TYPE: DNA
<213> ORGANISM: Homo sapiens

<400> SEQUENCE: 34
ccatctggcc ttgccccac ctcctctaaa acagttcttc taaagac            47

<210> SEQ ID NO 35
<211> LENGTH: 40
<212> TYPE: DNA
<213> ORGANISM: Homo sapiens

<400> SEQUENCE: 35
gttgctgaag acagttgctg gggtcaggca aggtgaaagg                    40

<210> SEQ ID NO 36
<211> LENGTH: 40
<212> TYPE: DNA
<213> ORGANISM: Homo sapiens

<400> SEQUENCE: 36
cctttcacct tgcctgaccc cagcaactgt cttcagcaac                    40

<210> SEQ ID NO 37
<211> LENGTH: 1334
<212> TYPE: DNA
<213> ORGANISM: Homo sapiens

<400> SEQUENCE: 37
cgccgcgtgc gcctgcagac gctccgctcg ctgccttctc tcctggcagg cgctgccttt    60
tctccccgtt aaagggcact tgggctgaag gatcgctttg agatctgagg aacccgcagc   120
gctttgaggg acctgaagct gttttttcttc gttttccttt gggttcagtt tgaacgggag   180
gtttttgatc cctttttttc agaatggatt atttgctcat gattttctct ctgctgtttg   240
tggcttgcca aggagctcca gaaacagcag tcttaggcgc tgagctcagc gcggtgggtg   300
agaacggcgg ggagaaaccc actcccagtc caccctggcg gctccgccgg tccaagcgct   360
gctcctgctc gtccctgatg gataaagagt gtgtctactt ctgccacctg gacatcattt   420
gggtcaacac tcccgagcac gttgttccgt atggacttgg aagccctagg tccaagagag   480
ccttggagaa tttacttccc acaaaggcaa cagaccgtga aatagatgc caatgtgcta   540 gccaaaaaga caagaagtgc tggaattttt gccaagcagg aaaagaactc agggctgaag   600
acattatgga gaaagactgg aataatcata gaaaggaaa agactgttcc aagcttggga   660
aaaagtgtat ttatcagcag ttagtgagag gaagaaaaat cagaagaagt tcagaggaac   720
acctaagaca aaccaggtcg gagaccatga aaacagcgt caaatcatct tttcatgatc   780
ccaagctgaa aggcaagccc tccagagagc gttatgtgac ccacaaccga gcacattggt   840
gacagacctt cggggcctgt ctgaagccat agcctcacg gagagccctg tggccgactc   900
tgcactctcc accctggctg ggatcagagc aggagcatcc tctgctggtt cctgactggc   960
```

```
aaaggaccag cgtcctcgtt caaaacattc caagaaaggt taaggagttc ccccaaccat    1020
cttcactggc ttccatcagt ggtaactgct ttggtctctt ctttcatctg gggatgacaa    1080
tggacctctc agcagaaaca cacagtcaca ttcgaattcg ggtggcatcc tccggagaga    1140
gagagaggaa ggagattcca cacaggggtg gagtttctga cgaaggtcct aagggagtgt    1200
ttgtgtctga ctcaggcgcc tggcacattt cagggagaaa ctccaaagtc cacacaaaga    1260
ttttctaagg aatgcacaaa ttgaaaacac actcaaaaga caaacatgca agtaaagaaa    1320
aaaaaaaaaa aaaa                                                      1334
```

<210> SEQ ID NO 38
<211> LENGTH: 212
<212> TYPE: PRT
<213> ORGANISM: Homo sapiens

<400> SEQUENCE: 38

```
Met Asp Tyr Leu Leu Met Ile Phe Ser Leu Leu Phe Val Ala Cys Gln
 1               5                  10                  15

Gly Ala Pro Glu Thr Ala Val Leu Gly Ala Glu Leu Ser Ala Val Gly
             20                  25                  30

Glu Asn Gly Gly Glu Lys Pro Thr Pro Ser Pro Pro Trp Arg Leu Arg
         35                  40                  45

Arg Ser Lys Arg Cys Ser Cys Ser Ser Leu Met Asp Lys Glu Cys Val
     50                  55                  60

Tyr Phe Cys His Leu Asp Ile Ile Trp Val Asn Thr Pro Glu His Val
 65                  70                  75                  80

Val Pro Tyr Gly Leu Gly Ser Pro Arg Ser Lys Arg Ala Leu Glu Asn
                 85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
        115                 120                 125

Leu Arg Ala Glu Asp Ile Met Glu Lys Asp Trp Asn Asn His Lys Lys
    130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu Glu His Leu Arg Gln
                165                 170                 175

Thr Arg Ser Glu Thr Met Arg Asn Ser Val Lys Ser Ser Phe His Asp
            180                 185                 190

Pro Lys Leu Lys Gly Lys Pro Ser Arg Glu Arg Tyr Val Thr His Asn
        195                 200                 205

Arg Ala His Trp
    210
```

<210> SEQ ID NO 39
<211> LENGTH: 1334
<212> TYPE: DNA
<213> ORGANISM: Homo sapiens

<400> SEQUENCE: 39

```
cgccgcgtgc gcctgcagac gctccgctcg ctgccttctc tcctggcagg cgctgccttt      60
tctccccgtt aaagggcact tgggctgaag gatcgctttg agatctgagg aacccgcagc     120
gctttgaggg acctgaagct gttttttcttc gttttccttt gggttcagtt tgaacgggag    180 gttttttgatc cctttttttc agaatggatt atttgctcat gattttctct ctgctgtttg    240
```

-continued

```
tggcttgcca aggagctcca gaaacagcag tcttaggcgc tgagctcagc gcggtgggtg    300
agaacggcgg ggagaaaccc actcccagtc caccctggcg gctccgccgg tccaagcgct    360
gctcctgctc gtccctgatg gataaagagt gtgtctactt ctgccacctg gacatcattt    420
gggtcaacac tcccgagcac gttgttccgt atggacttgg aagccctagg tccaagagag    480
ccttggagaa tttacttccc acaaaggcaa cagaccgtga gaatagatgc caatgtgcta    540
gccaaaaaga caagaagtgc tggaattttt gccaagcagg aaaagaactc agggctgaag    600
acattatgga gaaagactgg aataatcata gaaaggaaa agactgttcc aagcttggga    660
aaaagtgtat ttatcagcag ttagtgagag gaagaaaaat cagaagaagt tcagaggaac    720
acctaagaca aaccaggtcg gagaccatga gaaacagcgt caaatcatct tttcatgatc    780
ccaagctgaa aggcaatccc tccagagagc gttatgtgac ccacaaccga gcacattggt    840
gacagacctt cggggcctgt ctgaagccat agcctccacg gagagccctg tggccgactc    900
tgcactctcc accctggctg ggatcagagc aggagcatcc tctgctggtt cctgactggc    960
aaaggaccag cgtcctcgtt caaaacattc aagaaaggt taaggagttc ccccaaccat    1020
cttcactggc ttccatcagt ggtaactgct ttggtctctt ctttcatctg gggatgacaa    1080
tggacctctc agcagaaaca cacagtcaca ttcgaattcg ggtggcatcc tccggagaga    1140
gagagaggaa ggagattcca cacaggggtg gagtttctga cgaaggtcct aagggagtgt    1200
ttgtgtctga ctcaggcgcc tggcacattt cagggagaaa ctccaaagtc cacacaaaga    1260
ttttctaagg aatgcacaaa ttgaaaacac actcaaaaga caaacatgca agtaaagaaa    1320
aaaaaaaaaa aaaa                                                      1334
```

<210> SEQ ID NO 40
<211> LENGTH: 212
<212> TYPE: PRT
<213> ORGANISM: Homo sapiens

<400> SEQUENCE: 40

```
Met Asp Tyr Leu Leu Met Ile Phe Ser Leu Leu Phe Val Ala Cys Gln
1               5                   10                  15

Gly Ala Pro Glu Thr Ala Val Leu Gly Ala Glu Leu Ser Ala Val Gly
            20                  25                  30

Glu Asn Gly Gly Glu Lys Pro Thr Pro Ser Pro Trp Arg Leu Arg
        35                  40                  45

Arg Ser Lys Arg Cys Ser Cys Ser Ser Leu Met Asp Lys Glu Cys Val
50                  55                  60

Tyr Phe Cys His Leu Asp Ile Ile Trp Val Asn Thr Pro Glu His Val
65                  70                  75                  80

Val Pro Tyr Gly Leu Gly Ser Pro Arg Ser Lys Arg Ala Leu Glu Asn
                85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
        115                 120                 125

Leu Arg Ala Glu Asp Ile Met Glu Lys Asp Trp Asn Asn His Lys Lys
    130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu Glu His Leu Arg Gln
                165                 170                 175
```

```
Thr Arg Ser Glu Thr Met Arg Asn Ser Val Lys Ser Ser Phe His Asp
        180                 185                 190

Pro Lys Leu Lys Gly Asn Pro Ser Arg Glu Arg Tyr Val Thr His Asn
    195                 200                 205

Arg Ala His Trp
    210

<210> SEQ ID NO 41
<211> LENGTH: 26
<212> TYPE: DNA
<213> ORGANISM: Homo sapiens

<400> SEQUENCE: 41
acagcgtcaa atcatctttt catgat                                           26

<210> SEQ ID NO 42
<211> LENGTH: 22
<212> TYPE: DNA
<213> ORGANISM: Homo sapiens

<400> SEQUENCE: 42
tctgtcacca atgtgctcgg tt                                               22

<210> SEQ ID NO 43
<211> LENGTH: 25
<212> TYPE: DNA
<213> ORGANISM: Homo sapiens

<400> SEQUENCE: 43
ctgaaaggca agccctccag agagc                                            25

<210> SEQ ID NO 44
<211> LENGTH: 25
<212> TYPE: DNA
<213> ORGANISM: Homo sapiens

<400> SEQUENCE: 44
tgaaaggcaa tccctccaga gagcg                                            25

<210> SEQ ID NO 45
<211> LENGTH: 24
<212> TYPE: DNA
<213> ORGANISM: Bacteriophage M13

<400> SEQUENCE: 45
cgccagggtt ttcccagtca cgac                                             24

<210> SEQ ID NO 46
<211> LENGTH: 24
<212> TYPE: DNA
<213> ORGANISM: Bacteriophage M13

<400> SEQUENCE: 46
agcggataac aatttcacac agga                                             24

<210> SEQ ID NO 47
<211> LENGTH: 40
<212> TYPE: DNA
<213> ORGANISM: Homo sapiens

<400> SEQUENCE: 47
gatcccaagc tgaaaggcaa tccctccaga gagcgttatg                            40
```

```
<210> SEQ ID NO 48
<211> LENGTH: 40
<212> TYPE: DNA
<213> ORGANISM: Homo sapiens

<400> SEQUENCE: 48
cataacgctc tctggaggga ttgcctttca gcttgggatc                              40

<210> SEQ ID NO 49
<211> LENGTH: 8127
<212> TYPE: DNA
<213> ORGANISM: Homo sapiens

<400> SEQUENCE: 49
gcccccaagc caggttgcgt ttttttctgc catttagaag ggttttcctt tttgtcctag        60
taaaacatca gccctgtag  ctcttcatct cccctggtg  ttcttctccc gccatgtctt        120
aagattggtg gcaccgacca atcttaagat ttaagttctg tgtgaaaaac acctttgctt       180
ttcaatcagt ttatcagcct cctccgcagg ggaagtgtgg acacacaaaa gaacttatcg       240
gggcttctca tcagtgatag ggaaaagact gggcatgtgc ctaaacgagc tctgatgtta       300
tttttaagct ccctttcttg ccaatccctc acggatcttt ctccgataga tgcaaagaac       360
ttcagcaaaa aagacccgca ggaaggggct tgaagagaaa agtacgttga tctgccaaaa       420
tagtctgacc cccagtagtg gggcagtgac gagggagagc attcccttgt ttgactgaga       480
ctagaatcgg agagacataa aaggaaaatg aagcgagcaa caattaaaaa aaattccccg       540
cacacaacaa tacaatctat ttaaactgtg gctcatactt tcataccaa  tggtatgact       600 tttttttctgg agtcccctct tctgattctt gaactccggg gctggcagct tgcaagggg       660 aagcggactc cagcactgca cgggcaggtt tagcaaaggt ctctaatggg tattttcttt       720
ttcttagccc tgcccccgaa ttgtcagacg gcgggcgtct gcctctgaag ttagcagtga       780
tttcctttcg ggcctggcct tatctccggc tgcacgttgc ctgttggtga ctaataacac       840
aataacattg tctggggctg gaataaagtc ggagctgttt accccactc  taatagggt        900 tcaatataaa aagccggcag agagctgtcc aagtcagacg cgcctctgca tctgcgccag       960
gcgaacgggt cctgcgcctc ctgcagtccc agctctccac cgccgcgtgc gcctgcagac      1020
gctccgctcg ctgccttctc tcctggcagg cgctgccttt tctccccgtt aaaagggcac      1080
ttgggctgaa ggatcgcttt gagatctgag gaacccgcag cgctttgagg gacctgaagc      1140 tgttttctt  cgttttcctt tgggttcagt ttgaacggga ggttttgat  ccctttttt       1200 cagaatggat tatttgctca tgattttctc tctgctgttt gtggcttgcc aaggagctcc      1260
agaaacaggt aggcacgctc gttgacttgt aagtctcgga attacaagtt agtgtgttct      1320
tatccacctt catgcttttc ttgcttctat tttccccgt  tctttttatg actgcagctt      1380
agagagcaag tgtctgagaa ttattgctga aagctacttt aagtcttcta gtgtaaaatg      1440
taaaattcct ctattgaata caattaggtg caattgacta aacatgaca  ttaaaataac      1500 ttatcgtttt attattatta ttccattatg tgtttccttg gcttttaaaa aatgagaaga      1560
gtatggacat atacaattta gtcaaatgta tgtttgtaat atatgtgttt atacaggtac      1620
acaggccata taggaactta aatcttattt aaacactatt ttaatagtgt gttaacgtgt      1680 aaaatatttta agcattccag cttgaagcca aggaattgta tccagtcgtt caagcaatgt      1740
atgttcagta aaatcacctg cagagcaaaa gtctgttgac taactaccgc ctccccccc      1800 ccccgccacc accccccgca ggcggtttct gggtgaagca gatgttttct ttaaaatttg      1860
```

```
tcatcattga ctttaggttt cttttggcag gttttttggca cccaaaacag tgtgagctct    1920
cttttcagct ttattcacct gtgctgggag gggagctagg ataattcttg ctgccgaag     1980
gatttaggca gtgcgtgtgc atctgcccgg gtccccccg tttttagggt cagtgcactt     2040
tttttgtctt ttcgtgaccc tgactaaaga gaaaggatgt caagggaatg aaaatcctgg    2100
aatgtgtctg atcatttgaa atgtacaaaa ttgggcagat aagctgcatg ctaaattgt     2160
taggaggaag aggcaaggca gtagtggaga aggggaggc agtggatccc acacaagcct     2220
gatgcccagg gattcggaat tcaaaatccc cccagcctac cttcagtccc ctgacctgct    2280
tctcagcccc accttaggtc actggtttct atggagttac cctcctgaat tgaatattga    2340
atagttaatt tctctctcca atcatttccc ccacctaatt ttgaaagata tacatcatct    2400
ggggtaccct gtgccctaca cagcatgtga agtggatggg taccccctaa agagagggtc    2460
atcctgaatg gggaagtggc cccaaagcta ggaataactg tgatttcttg tctttagtca    2520
tgtgccaatg ttaagtaagc ttcagtggat agtgctgtcc taccaagttc cttgtagaag    2580
ccagccggat tttcaacagg cagcattcca cagcatttcc ctgagcctgc ttcaagaggg    2640
gtggggaag tccctttttca ggtgtttatc tcctctgcat ttgtgtaatc tccctgaagg    2700
tggataagcc aagggcatga gggggaggca aaaggtgaac tcatgttaag gagggaaaaa    2760
aataaagagc cctttttttct gtgtttcttg ctgatggcag gctgtgtgct tcatctgctt    2820
ttatctgctc tgctagctct gactctactg tgatccagca tgtctctcgg cgtttgagga    2880
gacatccccc actgacctgc tctttctctc cccagcagtc ttaggcgctg agctcagcgc    2940
ggtgggtgag aacggcgggg agaaacccac tcccagtcca ccctggcggc tccgccggtc    3000
caagcgctgc tcctgctcgt ccctgatgga taaagagtgt gtctacttct gccacctgga    3060
catcatttgg gtcaacactc ccgagtaagt ctctagaggg cattgtaacc ctagtcattc    3120
attagcgctg gctccactgg agcccagttt tagagtttct tttctaggga ctctgaaggt    3180
agtccttcta acaccatcca agtgcctcag tggggacagt ttccctctat tcctgaaaat    3240
aacgacagct tcgttcttag caaccaaggg gagggtcttc tgaggccccg tagctcaggc    3300
tactcatgat gggacaagca ggaggccact gcacgtttca aatgaggaac tttcagtgag    3360
agggcctcag ggggacactc tcacagtggc atctgatggg gtttcgggaa taattgccga    3420
ggtcagatgt gggttagtgc aacctgtgct tctcatggga gggtggagac tgagaggcag    3480
aagtgatgat atagagggtt agaatcactt aattttactt acagaaaaac ctaggctcaa    3540
agtgttgaag ccatttgtgc aggagtgagt ttgtagcaga gctagaactg gagcccggat    3600
ttcctttgct gctatatttt ccctttagaa atgcccattt cagaactgaa atagaaatac    3660
tgtccatagg cttctctttc acctacagag aagaaaagca gatttcctcc ttctgccctg    3720
gacactagtt catcatctgt cggaagcagt cataaacaag cacacattta ctatgcatac    3780
aatgtaccgt tatgacaaag gaggaccaaa atccaaacaa tatcaaacca caccaaaaac    3840
cacaaggagc ctaataatta ctaaggtgat acttccaaag ggaggacttt atttcttaga    3900
tgagaatgaa aatggacaca ttggaaatta ttggagagcc ctctggctat gagtccttcc    3960
acaaccatat ggtaccaccg actggcagga gaaatgtgtg aacatgtgcc tcctcctccc    4020
ccaaccactg gggtcggtgg ggtgacggtg gcacttttag cagtatcctc cgtggtttga    4080
gttgaaaata agttttaaaa atcctgtgag tcatggtttt gcattgaaac ctcttcccac    4140
tgtgtaccca caaatagtta actaaatag ccattagaaa aggaagaaaa tataaagcag    4200
atgccaagca gagatgtcct aattttttgac aaaaaaagcaa tgttgcttgt gtcaagaaga    4260
```

```
aactgaactt tgtgaagagt tgaaatggaa ttccactgaa ttagaaaaac ttgttttctc    4320
ctgcctggat acatacagtc agggccattg atgcacaggt gttcctggct gttgttacac    4380
tttaccctct gaaatgatgc tcccaagtgc tatgtgatga gctccttgtg tgcccagtgg    4440
aataggtgtg tccatgtgtc attttaaaga ctattaatta cactaatata gtttctttct    4500
ctctttggat aataggcacg ttgttccgta tggacttgga agccctaggt ccaagagagc    4560
cttggagaat ttacttccca caaaggcaac agaccgtgaa aatagatgcc aatgtgctag    4620
ccaaaaagac aagaagtgct ggaattttttg ccaagcagga aaagaactca ggtgagcaga    4680
aacacctttg cttttcaatc agtttaacag cctcctgaac tccttcctat catggtactg    4740
ccttcctgtt ttagagagac taacagagac attgaaagtc agggtaaagc tgaatataac    4800
attgctgaaa tgttttttcct tgtgtatttt aacagggctg aagacattat ggagaaagac    4860
tggaataatc ataagaaagg aaaagactgt tccaagcttg ggaaaagtg tatttatcag    4920 cagttagtga gaggaagaaa aatcagaaga agttcagagg aacacctaag acaaaccagg    4980
taagagggaa ggaagaaaaa ttaggtaaga ggttcacaag aacaactagc cccagtcagt    5040
gatgccagca gcctgttcct ccagcccttc ttacccgggc aggtgaaaga cttagaaaac    5100
agtagcagag gagatctatg catcctatag attaaaagga gcaaagaat ccctcttaaa    5160 tatttccatg aagctctgga atgcaaaccg atgtcctctg tacttttagc acataccatt    5220
tcatctacag gtagatttcc caaccaaaat atatccagag atgcctttgt cattgggtta    5280
tatacagcct ttgcctctct gagtcaatgt atttaccact ttccctgaga aatcgaaaat    5340
cattttgggg agcggacatt tagaaaaaga atcaaagtgt catggataat caaattcttc    5400
aataagttgc agttattcag atggccaaag gaaaaataaa gtcattagat agggttggta    5460
gaatttagaa catgctgttt ttcaggttta tggtcttttt tttttttttt ttttttaaata    5520 gggaaatgtg tttggtgcag agccaatgtc attccaaaaa gctctctctt ttcctggtca    5580
gtcatgtgct gggacagaga agggatctgg attaggcaac atcatagagt tgctctgagc    5640
tgctctttgg tgataaccct tccaaatcct aaacttttttg gaattcacaa gctcaaagga    5700
ggaaacctac tctctgatct accacatgtt ctgcattttt ctatcatggt ctatggaaac    5760
ttctcttaga aatccagtgg caagaagttc tatgattaaa gtgttctgag ctcaggccag    5820
gcagtcatga actacttctg agttatttac tactgatttg tggggcagcc tcagctatcg    5880
gtttcttcac acctgcttat gagagtatcc atatttatgg tcgcaggcca gtaatgctcc    5940
ccacgagatc agtttctgaa ctaacctgga attttttatg ggttttttatt atgccaacta    6000 ttaaatcaac attacagttc ttccctctgt atttctcctg taaaacatta ggcctgcaaa    6060
aaaaaaaaat cttttttaaaa ataattgcca taaagtattt gctctgggcc tactgtatgc    6120
ttcttttctt tttctctctt ttcaactaag tcaccgtcaa tttattaaga tggccataac    6180
tattcaaaac ctatgctgag ttcctcaagg cagggtcaca tagtgatgaa ggttgggatg    6240
gggctacgga agaaaccaga acaactctag tttatttaaa acctgtattt actgccccact    6300 tccccttaga cttgaccata tgaccctcg ctcccattct aagcataggg gcaggcttta    6360
tttttacaat ggtaatagat atcacttgag gttttatcaa agagttgcgg cgggtggtga    6420
aagttcacaa ccagattcag gttttgtttg tgccagattc taattttaca tgtttctttt    6480
gccaaagggt gattttttta aaataacatt tgttttctct tatcttgctt tattaggtcg    6540
gagaccatga gaaacagcgt caaatcatct tttcatgatc ccaagctgaa aggcaagccc    6600
tccagagagc gttatgtgac ccacaaccga gcacattggt gacagacctt cggggcctgt    6660
```

-continued

| | |
|---|---|
| ctgaagccat agcctccacg gagagccctg tggccgactc tgcactctcc accctggctg | 6720 |
| ggatcagagc aggagcatcc tctgctggtt cctgactggc aaaggaccag cgtcctcgtt | 6780 |
| caaaacattc aagaaaggt taaggagttc ccccaaccat cttcactggc ttccatcagt | 6840 |
| ggtaactgct ttggtctctt ctttcatctg gggatgacaa tggacctctc agcagaaaca | 6900 |
| cacagtcaca ttcgaattcg ggtggcatcc tccggagaga gagagaggaa ggagattcca | 6960 |
| cacaggggtg gagtttctga cgaaggtcct aagggagtgt ttgtgtctga ctcaggcgcc | 7020 |
| tggcacattt cagggagaaa ctccaaagtc cacacaaaga ttttctaagg aatgcacaaa | 7080 |
| ttgaaaacac actcaaaaga caaacatgca agtaaagaaa aaaaaaagaa agacttttgt | 7140 |
| ttaaatttgt aaaatgcaaa actgaatgaa actgttacta ccataaatca ggatatgttt | 7200 |
| catgaatatg agtctaccte acctatattg cactctggca gaagtatttc ccacatttaa | 7260 |
| ttattgcctc cccaaactct tcccacccct gctgcccctt cctccatccc ccatactaaa | 7320 |
| tcctagcctc gtagaagtct ggtctaatgt gtcagcagta gatataatat tttcatggta | 7380 |
| atctactagc tctgatccat aagaaaaaaa agatcattaa atcaggagat tccctgtcct | 7440 |
| tgattttttgg agacacaatg gtatagggtt gtttatgaaa tatattgaaa agtaagtgtt | 7500 |
| tgttacgctt taaagcagta aaattatttt cctttatata accggctaat gaaagaggtt | 7560 |
| ggattgaatt ttgatgtact tattttttta tagatattta tattcaaaca atttattcct | 7620 |
| tatatttacc atgttaaata tctgtttggg caggccatat tggtctatgt attttttaaaa | 7680 |
| tatgtatttc taaatgaaat tgagaacatg ctttgttttg cctgtcaagg taatgacttt | 7740 |
| agaaaataaa tattttttttc cttactgtac tgatttggaa tcattactga aatttgtaag | 7800 |
| gagtgggcca acgtgattaa gtaccataaa ggcaaataaa tggttaaaga cggtttcata | 7860 |
| gaaaagtgac aattagaagg atattacggt ctaagctaat tatataaaga attttatctg | 7920 |
| tatcttaaat gttgattta tactgcattg aggtaaaaac acaaaacaaa aaagcagctt | 7980 |
| taacacctct gtcttctctt gggtagcagc ctcctgcttc tccttcacct gaaaaattct | 8040 |
| ccagggactt catccattaa cttggctcag gctattaggc aggattcaac agtttaagct | 8100 |
| gatggtgtgg tgagagatgc tttatcc | 8127 |

<210> SEQ ID NO 50
<211> LENGTH: 1723
<212> TYPE: DNA
<213> ORGANISM: Homo sapiens

<400> SEQUENCE: 50

| | |
|---|---|
| tgctacccgc gcccgggctt ctggggtgtt ccccaaccac ggcccagccc tgccacaccc | 60 |
| cccgccccccg gcctccgcag ctcggcatgg gcgcgggggt gctcgtcctg ggcgcctccg | 120 |
| agcccggtaa cctgtcgtcg gccgcaccgc tccccgacgg cgcggccacc gcggcgcggc | 180 |
| tgctggtgcc cgcgtcgccg cccgcctcgt tgctgcctcc cgccagcgaa agccccgagc | 240 |
| cgctgtctca gcagtggaca gcgggcatgg gtctgctgat ggcgctcatc gtgctgctca | 300 |
| tcgtggcggg caatgtgctg gtgatcgtgg ccatcgccaa gacgccgcgg ctgcagacgc | 360 |
| tcaccaacct cttcatcatg tccctggcca gcgccgacct ggtcatgggg ctgctggtgg | 420 |
| tgccgttcgg ggccaccatc gtggtgtggg gccgctggga gtacggctcc ttcttctgcg | 480 |
| agctgtggac ctcagtggac gtgctgtgcg tgacggccag catcgagacc ctgtgtgtca | 540 |
| ttgccctgga ccgctacctc gccatcacct cgccttccg ctaccagagc ctgctgacgc | 600 |
| gcgcgcgggc gcggggcctc gtgtgcaccg tgtgggccat ctcggccctg gtgtccttcc | 660 |

-continued

```
tgcccatcct catgcactgg tggcgggcgg agagcgacga ggcgcgccgc tgctacaacg      720
accccaagtg ctgcgacttc gtcaccaacc gggcctacgc catcgcctcg tccgtagtct      780
ccttctacgt gccctgtgc atcatggcct tcgtgtacct gcgggtgttc cgcgaggccc       840
agaagcaggt gaagaagatc gacagctgcg agcgccgttt cctcggcggc ccagcgcggc      900
cgccctcgcc ctcgcccctcg cccgtccccg cgcccgcgcc gcgcccggga ccccgcgcc      960 ccgccgccgc cgccgccacc gccccgctgg ccaacgggcg tgcgggtaag cggcggccct     1020
cgcgcctcgt ggcctacgc gagcagaagg cgctcaagac gctgggcatc atcatgggcg     1080
tcttcacgct ctgctggctg cccttcttcc tggccaacgt ggtgaaggcc ttccaccgcg     1140
agctggtgcc cgaccgcctc ttcgtcttct caactggct gggctacgcc aactcggcct      1200
tcaaccccat catctactgc cgcagccccg acttccgcaa ggccttccag cgactgctct     1260
gctgcgcgcg cagggctgcc cgccggcgcc acgcgaccca cggagaccgg ccgcgcgcct     1320
cgggctgtct ggcccggccc ggaccccgc catcgcccgg ggccgcctcg gacgacgacg     1380
acgacgatgt cgtcggggcc acgccgcccg cgcgcctgct ggagccctgg gccggctgca     1440 acggcgggc ggcggcggac agcgactcga gcctggacga gccgtgccgc cccggcttcg      1500
cctcggaatc caaggtgtag ggcccggcgc ggggcgcgga ctccgggcac ggcttcccag    1560
gggaacgagg agatctgtgt ttacttaaga ccgatagcag gtgaactcga gcccacaat      1620 cctcgtctga atcatccgag gcaaagagaa aagccacgga ccgttgcaca aaaaggaaag    1680
tttgggaagg gatgggagag tggcttgctg atgttccttg ttg                     1723
```

<210> SEQ ID NO 51
<211> LENGTH: 477
<212> TYPE: PRT
<213> ORGANISM: Homo sapiens

<400> SEQUENCE: 51

```
Met Gly Ala Gly Val Leu Val Leu Gly Ala Ser Glu Pro Gly Asn Leu
1               5                   10                  15

Ser Ser Ala Ala Pro Leu Pro Asp Gly Ala Ala Thr Ala Ala Arg Leu
            20                  25                  30

Leu Val Pro Ala Ser Pro Pro Ala Ser Leu Leu Pro Pro Ala Ser Glu
        35                  40                  45

Ser Pro Glu Pro Leu Ser Gln Gln Trp Thr Ala Gly Met Gly Leu Leu
    50                  55                  60

Met Ala Leu Ile Val Leu Leu Ile Val Ala Gly Asn Val Leu Val Ile
65                  70                  75                  80

Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
        115                 120                 125

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
                165                 170                 175

Gly Leu Val Cys Thr Val Trp Ala Ile Ser Ala Leu Val Ser Phe Leu
            180                 185                 190
```

```
Pro Ile Leu Met His Trp Trp Arg Ala Glu Ser Asp Glu Ala Arg Arg
        195                 200                 205

Cys Tyr Asn Asp Pro Lys Cys Cys Asp Phe Val Thr Asn Arg Ala Tyr
        210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255

Lys Ile Asp Ser Cys Glu Arg Arg Phe Leu Gly Gly Pro Ala Arg Pro
            260                 265                 270

Pro Ser Pro Ser Pro Ser Pro Val Pro Ala Pro Ala Pro Pro Pro Gly
        275                 280                 285

Pro Pro Arg Pro Ala Ala Ala Ala Thr Ala Pro Leu Ala Asn Gly
290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
                325                 330                 335

Trp Leu Pro Phe Phe Leu Ala Asn Val Val Lys Ala Phe His Arg Glu
            340                 345                 350

Leu Val Pro Asp Arg Leu Phe Val Phe Phe Asn Trp Leu Gly Tyr Ala
        355                 360                 365

Asn Ser Ala Phe Asn Pro Ile Ile Tyr Cys Arg Ser Pro Asp Phe Arg
370                 375                 380

Lys Ala Phe Gln Arg Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
                405                 410                 415

Arg Pro Gly Pro Pro Pro Ser Pro Gly Ala Ala Ser Asp Asp Asp Asp
            420                 425                 430

Asp Asp Val Val Gly Ala Thr Pro Pro Ala Arg Leu Leu Glu Pro Trp
        435                 440                 445

Ala Gly Cys Asn Gly Gly Ala Ala Ala Asp Ser Asp Ser Ser Leu Asp
450                 455                 460

Glu Pro Cys Arg Pro Gly Phe Ala Ser Glu Ser Lys Val
465                 470                 475

<210> SEQ ID NO 52
<211> LENGTH: 1723
<212> TYPE: DNA
<213> ORGANISM: Homo sapiens

<400> SEQUENCE: 52
tgctacccgc gcccgggctt ctggggtgtt ccccaaccac ggcccagccc tgccacaccc      60 cccgccccg  gcctccgcag ctcggcatgg gcgcgggggt gctcgtcctg ggcgcctccg     120
agcccggtaa cctgtcgtcg gccgcaccgc tccccgacgg cgcggccacc gcggcgcggc     180
tgctggtgcc cgcgtcgccg cccgcctcgt tgctgcctcc cgccagcgaa agccccgagc     240
cgctgtctca gcagtggaca gcgggcatgg gtctgctgat ggcgctcatc gtgctgctca     300
tcgtggcggg caatgtgctg gtgatcgtgg ccatcgccaa gacgccgcgg ctgcagacgc     360
tcaccaacct cttcatcatg tccctggcca cgccgacct  ggtcatgggg ctgctggtgg     420
tgccgttcgg ggccaccatc gtggtgtggg gccgctggga gtacggctcc ttcttctgcg     480
agctgtggac ctcagtggac gtgctgtgcg tgacggccag catcgagacc ctgtgtgtca     540
```

-continued

```
ttgccctgga ccgctacctc gccatcacct cgcccttccg ctaccagagc ctgctgacgc    600
gcgcgcgggc gcggggcctc gtgtgcaccg tgtgggccat ctcggccctg gtgtccttcc    660
tgcccatcct catgcactgg tggcgggcgg agagcgacga ggcgcgccgc tgctacaacg    720
accccaagtg ctgcgacttc gtcaccaacc gggcctacgc catcgcctcg tccgtagtct    780
ccttctacgt gccctgtgc atcatggcct tcgtgtacct gcgggtgttc cgcgaggccc    840
agaagcaggt gaagaagatc gacagctgcg agcgccgttt cctcggcggc cagcgcggc    900 cgccctcgcc ctcgccctcg cccgtccccg cgcccgcgcc gccgcccgga ccccgcgcc    960 ccgccgccgc cgccgccacc gccccgctgg ccaacgggcg tgcgggtaag cggcggcccc    1020
cgcgcctcgt ggccctacgc gagcagaagg cgctcaagac gctgggcatc atcatgggcg    1080
tcttcacgct ctgctggctg cccttcttcc tggccaacgt ggtgaaggcc ttccaccgcg    1140
agctggtgcc cgaccgcctc ttcgtcttct tcaactggct gggctacgcc aactcggcct    1200
tcaaccccat catctactgc cgcagccccg acttccgcaa ggccttccag ggactgctct    1260
gctgcgcgcg cagggctgcc cgccggcgcc acgcgaccca cggagaccgg ccgcgcgcct    1320
cgggctgtct ggcccggccc ggaccccgc catcgcccgg ggccgcctcg acgacgacg    1380 acgacgatgt cgtcggggcc acgccgcccg cgcgcctgct ggagccctgg gccggctgca    1440 acggcgggc ggcggcggac agcgactcga gcctggacga gccgtgccgc cccggcttcg    1500
cctcggaatc caaggtgtag ggcccggcgc ggggcgcgga ctccgggcac ggcttcccag    1560
gggaacgagg agatctgtgt ttacttaaga ccgatagcag gtgaactcga agcccacaat    1620
cctcgtctga atcatccgag gcaaagagaa aagccacgga ccgttgcaca aaaaggaaag    1680
tttgggaagg gatgggagag tggcttgctg atgttccttg ttg                     1723
```

<210> SEQ ID NO 53
<211> LENGTH: 477
<212> TYPE: PRT
<213> ORGANISM: Homo sapiens

<400> SEQUENCE: 53

```
Met Gly Ala Gly Val Leu Val Leu Gly Ala Ser Glu Pro Gly Asn Leu
1               5                   10                  15

Ser Ser Ala Ala Pro Leu Pro Asp Gly Ala Ala Thr Ala Ala Arg Leu
            20                  25                  30

Leu Val Pro Ala Ser Pro Pro Ala Ser Leu Leu Pro Pro Ala Ser Glu
        35                  40                  45

Ser Pro Glu Pro Leu Ser Gln Gln Trp Thr Ala Gly Met Gly Leu Leu
    50                  55                  60

Met Ala Leu Ile Val Leu Leu Ile Val Ala Gly Asn Val Leu Val Ile
65                  70                  75                  80

Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
        115                 120                 125

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160
```

```
Thr Ser Pro Phe Arg Tyr Gln Ser Leu Leu Thr Arg Ala Arg Ala Arg
            165                 170                 175

Gly Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
            195                 200                 205

Cys Tyr Asn Asp Pro Lys Cys Cys Asp Phe Val Thr Asn Arg Ala Tyr
210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
            245                 250                 255

Lys Ile Asp Ser Cys Glu Arg Arg Phe Leu Gly Gly Pro Ala Arg Pro
            260                 265                 270

Pro Ser Pro Ser Pro Ser Pro Val Pro Ala Pro Ala Pro Pro Pro Gly
            275                 280                 285

Pro Pro Arg Pro Ala Ala Ala Ala Thr Ala Pro Leu Ala Asn Gly
            290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
            325                 330                 335

Trp Leu Pro Phe Phe Leu Ala Asn Val Val Lys Ala Phe His Arg Glu
            340                 345                 350

Leu Val Pro Asp Arg Leu Phe Val Phe Phe Asn Trp Leu Gly Tyr Ala
            355                 360                 365

Asn Ser Ala Phe Asn Pro Ile Ile Tyr Cys Arg Ser Pro Asp Phe Arg
            370                 375                 380

Lys Ala Phe Gln Gly Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
            405                 410                 415

Arg Pro Gly Pro Pro Ser Pro Gly Ala Ala Ser Asp Asp Asp Asp
            420                 425                 430

Asp Asp Val Val Gly Ala Thr Pro Pro Ala Arg Leu Leu Glu Pro Trp
            435                 440                 445

Ala Gly Cys Asn Gly Gly Ala Ala Ala Asp Ser Asp Ser Ser Leu Asp
            450                 455                 460

Glu Pro Cys Arg Pro Gly Phe Ala Ser Glu Ser Lys Val
465                 470                 475

<210> SEQ ID NO 54
<211> LENGTH: 21
<212> TYPE: DNA
<213> ORGANISM: Homo sapiens

<400> SEQUENCE: 54
ggccttcaac cccatcatct a                                              21

<210> SEQ ID NO 55
<211> LENGTH: 20
<212> TYPE: DNA
<213> ORGANISM: Homo sapiens

<400> SEQUENCE: 55
ccggtctccg tgggtcgcgt                                                20
```

-continued

```
<210> SEQ ID NO 56
<211> LENGTH: 23
<212> TYPE: DNA
<213> ORGANISM: Homo sapiens

<400> SEQUENCE: 56
aggccttcca gcgactgctc tgc                                              23

<210> SEQ ID NO 57
<211> LENGTH: 24
<212> TYPE: DNA
<213> ORGANISM: Homo sapiens

<400> SEQUENCE: 57
aggccttcca gggactgctc tgct                                             24

<210> SEQ ID NO 58
<211> LENGTH: 24
<212> TYPE: DNA
<213> ORGANISM: Bacteriophage M13

<400> SEQUENCE: 58
cgccagggtt ttcccagtca cgac                                             24

<210> SEQ ID NO 59
<211> LENGTH: 24
<212> TYPE: DNA
<213> ORGANISM: Bacteriophage M13

<400> SEQUENCE: 59
agcggataac aatttcacac agga                                             24

<210> SEQ ID NO 60
<211> LENGTH: 44
<212> TYPE: DNA
<213> ORGANISM: Homo sapiens

<400> SEQUENCE: 60
ccgacttccg caaggccttc cagggactgc tctgctgcgc gcgc                       44

<210> SEQ ID NO 61
<211> LENGTH: 44
<212> TYPE: DNA
<213> ORGANISM: Homo sapiens

<400> SEQUENCE: 61
gcgcgcgcag cagagcagtc cctggaaggc cttgcggaag tcgg                       44
```